US012110557B2

(12) United States Patent
Kida et al.

(10) Patent No.: US 12,110,557 B2
(45) Date of Patent: Oct. 8, 2024

(54) KIT, DEVICE, AND METHOD FOR DETECTING OVARIAN TUMOR

(71) Applicants: TORAY INDUSTRIES, INC., Tokyo (JP); NATIONAL CANCER CENTER, Tokyo (JP)

(72) Inventors: Yuho Kida, Kamakura (JP); Satoko Kozono, Kamakura (JP); Hiroko Sudo, Kamakura (JP); Satoshi Kondou, Kamakura (JP); Junpei Kawauchi, Kamakura (JP); Hitoshi Nobumasa, Kamakura (JP); Takahiro Ochiya, Tokyo (JP); Tomoyasu Kato, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 630 days.

(21) Appl. No.: 17/219,000

(22) Filed: Mar. 31, 2021

(65) Prior Publication Data

US 2021/0230706 A1 Jul. 29, 2021

Related U.S. Application Data

(62) Division of application No. 16/608,673, filed as application No. PCT/JP2018/017125 on Apr. 27, 2018, now Pat. No. 10,975,444.

(30) Foreign Application Priority Data

Apr. 28, 2017 (JP) ................................ 2017-090799

(51) Int. Cl.
*C12Q 1/6886* (2018.01)
*B01L 7/00* (2006.01)
*C12Q 1/6869* (2018.01)

(52) U.S. Cl.
CPC .............. *C12Q 1/6886* (2013.01); *B01L 7/52* (2013.01); *C12Q 1/6869* (2013.01); *C12Q 2600/112* (2013.01); *C12Q 2600/178* (2013.01); *G01N 2800/7028* (2013.01)

(58) Field of Classification Search
CPC ............ C12Q 1/6886; C12Q 2600/112; C12Q 2600/178; C12Q 1/6813
USPC .... 435/6.1, 91.1, 91.31, 455, 458; 536/23.1, 536/24.5
See application file for complete search history.

(56) References Cited

U.S. PATENT DOCUMENTS

2010/0249213 A1 9/2010 Croce
2011/0166041 A1 7/2011 Zama et al.
2012/0309645 A1 12/2012 Keller et al.
2016/0312301 A1 10/2016 Lee et al.
2017/0130274 A1 5/2017 Kozono et al.
2017/0130276 A1 5/2017 Kozono et al.
2017/0166975 A1 6/2017 Kondou et al.
2017/0218454 A1* 8/2017 Plaisier .................. G16B 25/00
2019/0290742 A1 9/2019 Chakraborty
2020/0147156 A1 5/2020 Greenberg

FOREIGN PATENT DOCUMENTS

CN 106459867 A 2/2017
CN 106460068 A 2/2017
JP 2010-154843 A 7/2010
JP 2010-538610 A 12/2010
WO WO 2009/033140 A1 3/2009
WO WO 2011/095623 A2 8/2011
WO WO 2013/148151 A1 10/2013
WO WO 2015/095862 A2 6/2015
WO WO 2015/190586 A1 12/2015
WO WO 2015/194535 A1 12/2015
WO WO 2015/194615 A1 12/2015

OTHER PUBLICATIONS

Chinese Office Action and Search Report for corresponding Chinese Application No. 201880027774.X, dated Nov. 22, 2022.
Japanese Office Action dated Sep. 5, 2023 for Application No. 2022-164429.
Katz et al., "MicroRNAs in Ovarian Cancer," Human Pathology (2015), vol. 46, pp. 1245-1256.
Japanese Office Action for Japanese Application No. 2019-514645, dated May 10, 2022.
Bauer et al., "Diagnosis of Pancreatic Ductal Adenocarcinoma and Chronic Pancreatitis by Measurement of microRNA Abundance in Blood and Tissue," PLoS One (2012), vol. 7, Issue 4, e34151, 6 pages.
Office Action issued Nov. 30, 2023, in European Patent Application No. 18 790 377.8.
Giusti et al., "Microvesicles as Potential Ovarian Cancer Biomarkers", BioMed Research International, 2013, vol. 2013, Article ID 703048, 12 pages.
International Search Report, issued in PCT/JP2018/017125, dated Jul. 31, 2018.
Ji et al., "Differential microRNA Expression by Solexa Sequencing in the Sera of Ovarian Cancer Patients", Asian Pacific Journal of Cancer Prevention. 2014, vol. 15, No. 4, pp. 1739-1743.
Kim et al., "Development of Multiplexed Bead-Based Immunoassays for the Detection of Early Stage Ovarian Cancer Using a Combination of Serum Biomarkers", PLoS One, 2012, vol. 7, Issue 9, e44960, 9 pages.
Li et al., "Characterization of microRNA expression in serous ovarian carcinoma," International Journal of Molecular Medicine (2014), vol. 34, pp. 491-498.

(Continued)

*Primary Examiner* — Jane J Zara
(74) *Attorney, Agent, or Firm* — Birch, Stewart, Kolasch & Birch, LLP

(57) ABSTRACT

This application provides a kit or a device for detection of ovarian tumor, comprising a nucleic acid(s) for detecting a miRNA(s) in a sample from a subject, and a method for detecting ovarian tumor, comprising measuring the miRNA (s) in vitro.

7 Claims, 3 Drawing Sheets

Specification includes a Sequence Listing.

(56) References Cited

OTHER PUBLICATIONS

Nakamura et al., "Clinical relevance of circulating cell-free microRNAs in ovarian cancer", Molecular Cancer, 2016, vol. 15:48, 10 pages.
Partial Supplementary European Search Report issued Feb. 8, 2021, in European Patent Application No. 18790377.8.
Written Opinion of the International Searching Authority, issued in PCT/JP2018/017125, dated Jul. 31, 2018.

* cited by examiner

KIT, DEVICE, AND METHOD FOR DETECTING OVARIAN TUMOR

CROSS-CITE TO RELATED APPLICATIONS

This application is a Divisional of copending application Ser. No. 16/608,673, filed on Oct. 25, 2019, which is the National Phase under 35 U.S.C. § 371 of International Application No. PCT/JP2018/017125, filed on Apr. 27, 2018, which claims the benefit under 35 U.S.C. § 119(a) to Patent Application No. 2017-090799, filed in Japan on Apr. 28, 2017, all of which are hereby expressly incorporated by reference into the present application.

TECHNICAL FIELD

The present invention relates to a kit or a device for detection of ovarian tumor, comprising a nucleic acid capable of specifically binding to a particular miRNA or a complementary strand thereof, which is used for examining the presence or absence of ovarian tumor in a subject, and a method for detecting ovarian tumor, comprising measuring an expression level of the miRNA using the nucleic acid.

BACKGROUND ART

The ovary is the female reproductive organ that produces an ovum and one each is found on both sides of the uterus. Fallopian tube is a tube through which an ovum, when released from the ovary, travels down into the uterus in which the fertilized ovum is implanted and grows into the fetus. The ovary further functions to secrete female hormones such as estrogen and progesterone. The ovary is considered an organ prone to develop tumors, which are roughly classified into surface epithelial-stromal tumors, sex cord-stromal tumor, and germ cell tumor based on the origin of tumorigenesis. The ovarian tumors are categorized into benign, borderline malignant, and malignant, and borderline malignant and malignant ovarian tumors are called ovarian cancers. Ovarian cancer incidence rate of 2012 in Japan disclosed by the Center for Cancer Control and Information Services, National Cancer Center was 9,384 people, in other words, 1 out of every 87 Japanese women had the cancer, causing the number of ovarian cancer deaths to climb to 4,840 people in 2014. In the United States, it is said that one in every 75 women develops ovarian cancer and the estimated number of people affected by ovarian cancer in 2017 climbed to 22,440 people, out of which about 14,080 people are expected to die.

A stage of progression of ovarian cancer and fallopian tube cancer is defined according to a tumor being unilateral or bilateral, the presence or absence of peritoneal dissemination, lymph node metastasis and distant metastasis, the size, and the like, and is classified into stages IA, IB, IC (IC1, IC2, IC3), IIA, IIB, IIIA1, IIIA2, IIIB, IIIC, IVA, and IVB. Five-year relative survival rate in ovarian cancer depends largely on a stage of progression of the cancer, and it is reported that the rate is 92% in the case of a localized cancer, 73% in the case of a peripheral region cancer, and 29% in the case of a distant metastatic cancer. Thus, early detection of ovarian cancer leads to improvement in survival rate and the provision of means for enabling the early detection is strongly required.

Treatment of ovarian cancer is surgical therapy in principal but drug therapy is concurrently used depending on a stage of progression, metastasis, systemic conditions, and the classification of ovarian cancer. Particularly, in the case that an ovarian cancer is detected early as stage I, a removal operation of an ovary or fallopian tube only on the side at which the cancer is detected may be sufficient instead of the total removal of the uterus, ovaries or fallopian tubes, whereby women can save a chance for future childbirth.

Early ovarian cancer and benign ovarian tumor are often asymptomatic, and even progressive ovarian cancer often only involves general symptoms which could be caused by other reasons such as abdominal bloating sensation and pains, because of which it is difficult to detect ovarian tumor based on subjective symptoms. Extensive studies on the screening test for ovarian cancer have been conducted but no substantial achievement is accomplished, and only two methods are actually usable: transvaginal ultrasound test and a CA-125 blood marker test. The secondary test for ovarian cancer includes imaging tests such as ultrasonography, CT scanning test, MRI, and PET/CT test.

As shown in Patent Literatures 1 to 4 and Non-Patent Literatures 1 to 3, there are reports, albeit at a research stage, on the detection of ovarian tumor using the expression levels of microRNAs (miRNAs) in biological samples including blood.

Specifically, Patent Literature 1 discloses a method for detecting ovarian cancer or predicting prognosis using miR-191, miR-24, miR-320, miR-328, miR-625-3p, miR-483-5p, miR-92a, miR-1290 and the like in plasma.

Patent Literature 2 discloses miR-135a-3 and the like in blood as biomarkers for gynecologic cancers.

Patent Literature 3 discloses miR-125a-3p, miR-211-3 and the like as biomarkers for ovarian cancers using human sample tissues.

Patent Literature 4 discloses a method for discriminating endometriosis-derived ovarian cancer and serous ovarian cancer from endometriosis using miR-191-5p, miR-652-5p, miR-744-5p, miR-1246 and the like in plasma.

Non-Patent Literature 1 discloses miR-92a, miR-128, miR-191-5p, miR-296-5p, miR-320a, miR-625-3p and the like in blood as circulating extracellular miRNAs involved in ovarian cancer.

Non-Patent Literature 2 discloses that there are differences in expression levels of miR-22, miR-45 and the like as a result of analyzing miRNAs from serum samples of ovarian cancer patients, benign disease patients and healthy subjects, using a next generation sequencer.

Non-Patent Literature 3 discloses that miR-23a/b, miR-92, miR-125a, miR-296-5p, miR-320, miR-422a, miR-663a and the like are present in the body fluid endoplasmic reticulum of ovarian cancer patients.

Non-Patent Literature 4 reports that the CA-125 blood marker had a sensitivity of 77.4% and a specificity of 70.8% for detecting ovarian cancer.

PRIOR ART LITERATURE

Patent Literature

Patent Literature 1: Published U.S. Patent Application No. 2016/0312301

Patent Literature 2: JP Patent Publication (Kokai) No. 2010-154843 A (2010)

Patent Literature 3: JP Patent Publication (Kohyo) No. 2010-538610 A (2010)

Patent Literature 4: International Publication No. WO 2013/148151

Non-Patent Literature

Non-Patent Literature 1: Nakamura K. et al., 2016, Molecular Cancer. Vol. 15, (1):48

Non-Patent Literature 2: Ji T. et al., 2014, Asian Pacific Journal of Cancer Prevention. Vol. 15, (4):1739

Non-Patent Literature 3: Giusti I. et al., 2013, BioMed Research International. Vol. 2013, 703048

Non-Patent Literature 4: Kim Y W. et al., 2012, PLoS One. Vol. 7, (9): e44960

SUMMARY OF INVENTION

Problem to be Solved by Invention

An object of the present invention is to find novel tumor markers for ovarian tumor and to provide a method that can effectively detect ovarian tumor using nucleic acids for detecting the markers.

It is difficult to detect ovarian tumor based on subjective symptoms and the screening test method for ovarian tumor is said to be only two, transvaginal ultrasound test and a CA-125 tumor marker test. However, the transvaginal ultrasound test can detect a tumor using ultrasound from within the vagina but the ultrasound has a limited reachable range and thus may fail to detect a tumor present distant from the vagina. Additionally, CA-125 is a protein in blood and is said to increase in ovarian tumor patients but more often increases for different reasons from ovarian tumor, while a CA-125 level does not increase in some ovarian tumor patients thus making the CA-125 test not an effective screening test. Further, as described above, Non-Patent Literature 4 reports that the CA-125 had a sensitivity of 77.4% and a specificity of 70.8% for detecting ovarian cancer.

Additionally, it is known that the transvaginal ultrasound test and CA-125 tumor marker test, even when carried out, do not lead to the reduction in mortality by ovarian cancer.

Further, as described below, there are reports, albeit at a research stage, on the determination of ovarian tumor using the expression levels of miRNAs in biological samples including blood, none of which, however, have yet been brought into practical use.

Patent Literature 1 discloses a method for detecting ovarian cancer or predicting prognosis using miR-191, miR-24, miR-320, miR-328, miR-625-3p, miR-483-5p, miR-92a, miR-1290 and the like in plasma, but these miRNAs are expressed also in control groups and unsuitable for the method for detecting the presence or absence of ovarian cancer. Additionally, the number of samples subjected to the test is as few as several tens of cases and thus the marker has low reliability.

Patent Literature 2 discloses miRNA such as miR-135a-3 and the like in blood as biomarkers for gynecologic cancers, however, it discloses only miRNA expression differences relevant to uterine cancer and does not describe the specific detection performance, such as accuracy, sensitivity, or specificity, for determining ovarian tumor, making these miRNAs poor in industrially practical use.

Patent Literature 3 discloses miRNAs such as miR-125a-3p, miR-211-3 and the like as biomarkers for ovarian cancers using human sample tissues, however, obtaining tissue samples requires tissue resection by surgery, and this step causes a physical burden on a patient, hence not preferable as a test method. Additionally, the literature does not describe the specific detection performance, such as accuracy, sensitivity, or specificity, for determining ovarian cancer, making these miRNAs poor in industrially practical use.

Patent Literature 4 discloses a method for determining, endometriosis-derived ovarian cancer and serous ovarian cancer from endometriosis using miR-191-5p, miR-652-5p, miR-744-5p, miR-1246 and the like in plasma, however, it does not disclose the distinguishment of ovarian cancer from other cancers, and consequently there is a risk for mistakenly detecting other cancers for ovarian cancer. Additionally, the number of samples subjected to the test is as few as several tens of cases and thus the marker has low reliability.

Non-Patent Literature 1 discloses miR-92a, miR-128, miR-191-5p, miR-296-5p, miR-320a, miR-625-3p and the like in blood as circulating extracellular miRNAs involved in ovarian cancer. However, a detection sensitivity for epithelial ovarian cancer by a combination of miR-205 and let-7f is as low as 62.4%, concerning overlooking ovarian cancer. Additionally, the performance of the discriminant between ovarian cancer and healthy subjects in combination with other miRNAs is also partially disclosed but other cancer patients were not included in the research, risking misjudgment of other cancers for ovarian cancer, possibly leading to needless extra examination and a delay in detection of essential cancer, hence not desirable.

Non-Patent Literature 2 discloses that there are differences in expression levels of miRNAs such as miR-22, miR-45 and the like as a result of analyzing miRNAs from serum samples of ovarian cancer patients, benign disease patients and healthy subjects by a next generation sequencer, however, does not describe the specific detection performance, such as accuracy, sensitivity, or specificity, for determining ovarian cancer, making these miRNAs poor in industrially practical use.

Non-Patent Literature 3 discloses that miRNAs such as miR-23a/b, miR-92, miR-125a, miR-296-5p, miR-320, miR-422a, miR-663a and the like are present in the body fluid endoplasmic reticulum of ovarian cancer patients, however, does not describe the specific detection performance, such as accuracy, sensitivity, or specificity, for determining ovarian tumor, making these miRNAs poor in industrially practical use.

As mentioned above, the existing tumor markers exhibit low performance in the detection of ovarian tumor, or neither performance nor detection methods are specifically shown as to the markers at a research stage. Therefore, use of these markers might lead to carry out needless extra examination due to the false detection of healthy subjects as being ovarian tumor patients, or might waste therapeutic opportunity because of overlooking ovarian tumor patients. Furthermore, the collection of ovarian tissues for measuring the tumor markers is highly invasive to patients and is not favorable. Hence, there is a demand for a highly accurate ovarian cancer marker that is detectable from blood, which can be collected in less invasive manner, and is capable of correctly determining an ovarian tumor patient as an ovarian tumor patient and a healthy subject as a healthy subject. Particularly, a highly sensitive ovarian cancer marker capable of detecting ovarian cancer at an early stage of progression is desired because ovarian cancer can dramatically reduce a recurrence risk when detected and treated early, and women can save a chance for future childbirth if the treatment is only partial resection surgery. Furthermore, when a simpler primary screening test for ovarian tumor is provided, a consultation rate of the secondary test is expected to increase.

Means for Solution of Problem

The present inventors have conducted diligent studies to attain the object and consequently completed the present invention by finding miRNA gene markers usable as markers for detection of ovarian tumor from blood, which can be collected with limited invasiveness, and finding that ovarian tumor can be significantly, preferably specifically, detected by using nucleic acids for detecting such markers, for example, at least one, or at least two, nucleic acids selected from probes capable of specifically binding to any of these markers and primers which amplify these markers.

Summary of Invention

The present invention has the following features:

(1) A kit for detection of ovarian tumor, comprising a nucleic acid(s) capable of specifically binding to at least one polynucleotide selected from the following ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p, or to a complementary strand of the polynucleotide.

(2) The kit according to (1), wherein miR-4675 is hsa-miR-4675, miR-4783-3p is hsa-miR-4783-3p, miR-1228-5p is hsa-miR-1228-5p, miR-4532 is hsa-miR-4532, miR-6802-5p is hsa-miR-6802-5p, miR-6784-5p is hsa-miR-6784-5p, miR-3940-5p is hsa-miR-3940-5p, miR-1307-3p is hsa-miR-1307-3p, miR-8073 is hsa-miR-8073, miR-3184-5p is hsa-miR-3184-5p, miR-1233-5p is hsa-miR-1233-5p, miR-6088 is hsa-miR-6088, miR-5195-3p is hsa-miR-5195-3p, miR-320b is hsa-miR-320b, miR-4649-5p is hsa-miR-4649-5p, miR-6800-5p is hsa-miR-6800-5p, miR-1343-3p is hsa-miR-1343-3p, miR-4730 is hsa-miR-4730, miR-6885-5p is hsa-miR-6885-5p, miR-5100 is hsa-miR-5100, miR-1203 is hsa-miR-1203, miR-6756-5p is hsa-miR-6756-5p, miR-373-5p is hsa-miR-373-5p, miR-1268a is hsa-miR-1268a, miR-1260b is hsa-miR-1260b, miR-4258 is hsa-miR-4258, miR-4697-5p is hsa-miR-4697-5p, miR-1469 is hsa-miR-1469, miR-4515 is hsa-miR-4515, miR-6861-5p is hsa-miR-6861-5p, miR-6821-5p is hsa-miR-6821-5p, miR-575 is hsa-miR-575, miR-6805-5p is hsa-miR-6805-5p, miR-4758-5p is hsa-miR-4758-5p, miR-3663-3p is hsa-miR-3663-3p, miR-4530 is hsa-miR-4530, miR-6798-5p is hsa-miR-6798-5p, miR-6781-5p is hsa-miR-6781-5p, miR-885-3p is hsa-miR-885-3p, miR-1273g-3p is hsa-miR-1273g-3p, miR-4787-3p is hsa-miR-4787-3p, miR-4454 is hsa-miR-4454, miR-4706 is hsa-miR-4706, miR-1249-3p is hsa-miR-1249-3p, miR-887-3p is hsa-miR-887-3p, miR-6786-5p is hsa-miR-6786-5p, miR-1238-5p is hsa-miR-1238-5p, miR-6749-5p is hsa-miR-6749-5p, miR-6729-5p is hsa-miR-6729-5p, miR-6825-5p is hsa-miR-6825-5p, miR-663b is hsa-miR-663b, miR-6858-5p is hsa-miR-6858-5p, miR-4690-5p is hsa-miR-4690-5p, miR-6765-5p is hsa-miR-6765-5p, miR-4710 is hsa-miR-4710, miR-6775-5p is hsa-miR-6775-5p, miR-371a-5p is hsa-miR-371a-5p, miR-6816-5p is hsa-miR-6816-5p, miR-296-3p is hsa-miR-296-3p, miR-7977 is hsa-miR-7977, miR-8069 is hsa-miR-8069, miR-6515-3p is hsa-miR-6515-3p, miR-4687-5p is hsa-miR-4687-5p, miR-1343-5p is hsa-miR-1343-5p, miR-7110-5p is hsa-miR-7110-5p, miR-4525 is hsa-miR-4525, miR-3158-5p is hsa-miR-3158-5p, miR-6787-5p is hsa-miR-6787-5p, miR-614 is hsa-miR-614, miR-4689 is hsa-miR-4689, miR-1185-2-3p is hsa-miR-1185-2-3p, miR-1268b is hsa-miR-1268b, miR-1228-3p is hsa-miR-1228-3p, miR-1185-1-3p is hsa-miR-1185-1-3p, miR-940 is hsa-miR-940, miR-939-5p is hsa-miR-939-5p, miR-6757-5p is hsa-miR-6757-5p, miR-1275 is hsa-miR-1275, miR-5001-5p is hsa-miR-5001-5p, miR-6826-5p is hsa-miR-6826-5p, miR-6765-3p is hsa-miR-6765-3p, miR-3679-3p is hsa-miR-3679-3p, miR-4718 is hsa-miR-4718, miR-4286 is hsa-miR-4286, miR-8059 is hsa-miR-8059, miR-4447 is hsa-miR-4447, miR-4448 is hsa-miR-4448, miR-658 is hsa-miR-658, miR-6766-3p is hsa-miR-6766-3p, miR-197-5p is hsa-miR-197-5p, miR-6887-5p is hsa-miR-6887-5p, miR-6742-5p is hsa-miR-6742-5p, miR-6729-3p is hsa-miR-6729-3p, miR-5090 is hsa-miR-5090, miR-7975 is hsa-miR-7975, miR-4505 is hsa-miR-4505, miR-6889-5p is hsa-miR-6889-5p, miR-4708-3p is hsa-miR-4708-3p, miR-6131 is hsa-miR-6131, miR-1225-3p is hsa-miR-1225-3p, miR-6132 is hsa-miR-6132, miR-4734 is hsa-miR-4734, miR-3194-3p is hsa-miR-3194-3p, miR-638 is hsa-miR-638, miR-2467-3p is hsa-miR-2467-3p, miR-4728-5p is hsa-miR-4728-5p, miR-5572 is hsa-miR-5572, miR-6789-5p is hsa-miR-6789-5p, miR-8063 is hsa-miR-8063, miR-4429 is hsa-miR-4429, miR-6840-3p is hsa-miR-6840-3p, miR-4476 is hsa-miR-4476, miR-675-5p is hsa-miR-675-5p, miR-711 is hsa-miR-711, miR-6875-5p is hsa-miR-6875-5p, miR-3160-5p is hsa-miR-3160-5p, miR-1908-5p is hsa-miR-1908-5p, miR-6726-5p is hsa-miR-6726-5p, miR-1913 is hsa-miR-1913, miR-8071 is hsa-miR-8071, miR-3648 is hsa-miR-3648, miR-4732-5p is hsa-miR-4732-5p, miR-4787-5p is hsa-miR-4787-5p, miR-3917 is hsa-miR-3917, miR-619-5p is hsa-miR-619-5p, miR-1231 is hsa-miR-1231, miR-342-5p is hsa-miR-342-5p, miR-4433a-5p is hsa-miR-4433a-5p, miR-6766-5p is hsa-miR-6766-5p, miR-4707-5p is hsa-miR-4707-5p, miR-7114-5p is hsa-miR-7114-5p, miR-6872-3p is hsa-miR-6872-3p, miR-6780b-5p is hsa-miR-6780b-5p, miR-7845-5p is hsa-miR-7845-5p, miR-6798-3p is hsa-miR-6798-3p, miR-665 is hsa-miR-665, miR-6848-5p is hsa-miR-6848-5p, miR-5008-5p is hsa-miR-5008-5p, miR-4294 is hsa-miR-4294, miR-6511a-5p is hsa-miR-6511a-5p, miR-4435 is hsa-miR-4435, miR-4747-3p is hsa-miR-4747-3p, miR-6880-3p is hsa-miR-6880-3p, miR-6869-5p is hsa-miR-6869-5p, miR-7150 is hsa-miR-7150, miR-1260a is hsa-miR-1260a, miR-6877-5p is hsa-miR-6877-5p, miR-6721-5p is hsa-miR-6721-5p, miR-4656 is hsa-miR-4656, miR-1229-5p is hsa-miR-1229-5p, miR-4433a-3p is hsa-miR-4433a-3p, miR-4274 is hsa-miR-4274, miR-4419b is hsa-miR-4419b, miR-4674 is hsa-miR-4674, miR-6893-5p is hsa-miR-6893-5p, miR-6763-3p is hsa-miR-6763-3p, miR-6762-5p is hsa-miR-6762-5p, miR-6738-5p is hsa-miR-6738-5p, miR-4513 is hsa-miR-4513, miR-6746-5p is hsa-miR-6746-5p, miR-6880-5p is hsa-miR-6880-5p, miR-4736 is hsa-miR-4736, miR-718 is hsa-miR-718, miR-6717-5p is hsa-miR-6717-5p, miR-7847-3p is hsa-miR-7847-3p, miR-760 is hsa-miR-760, miR-1199-5p is hsa-miR-1199-5p, miR-6813-5p is hsa-miR-6813-5p, miR-6769a-5p is hsa-miR-6769a-5p, miR-1193 is hsa-miR-1193, miR-7108-3p is hsa-miR-7108-3p, miR-6741-5p is hsa-miR-6741-5p, miR-4298 is hsa-miR-4298, miR-6796-3p is hsa-miR-6796-3p, miR-4750-5p is hsa-miR-4750-5p, miR-6785-5p is hsa-miR-6785-5p, miR-1292-3p is hsa-miR-1292-3p, miR-4749-3p is hsa-miR-4749-3p, miR-6800-3p is hsa-miR-6800-3p, miR-722-5p is hsa-miR-4722-5p, miR-4746-3p is hsa-miR-4746-3p, miR-4450 is hsa-miR-4450, miR-6795-5p is hsa-miR-6795-5p, miR-365a-5p is hsa-miR-365a-5p, miR-498 is hsa-miR-498, miR-6797-5p is hsa-miR-6797-5p, miR-1470 is hsa-miR-1470, miR-6851-5p is hsa-miR-6851-5p, miR-1247-3p is hsa-miR-1247-3p, miR-5196-5p is hsa-miR-5196-5p, miR-208a-5p is hsa-miR-208a-5p, miR-6842-5p is hsa-miR-6842-5p, miR-150-3p is hsa-miR-150-3p, miR-4534 is hsa-miR-4534, miR-3135b is hsa-miR-3135b, miR-3131 is hsa-miR-3131, miR-4792 is hsa-miR-4792, miR-6510-5p is hsa-miR-6510-5p, miR-504-3p is hsa-miR-504-3p, miR-3619-3p is hsa-miR-3619-3p, miR-671-5p is hsa-miR-671-5p, miR-4667-5p is hsa-miR-4667-5p, miR-4430 is hsa-miR-4430, miR-3195 is hsa-miR-3195, miR-3679-5p is hsa-miR-3679-5p, miR-6076 is hsa-miR-6076, miR-6515-5p is hsa-miR-6515-5p, miR-6820-5p is hsa-miR-6820-5p, miR-4634 is hsa-miR-4634, miR-187-5p is hsa-miR-187-5p, miR-6763-5p is hsa-miR-6763-5p, miR-1908-3p is hsa-miR-1908-3p, miR-1181 is hsa-miR-1181, miR-6782-5p is hsa-miR-6782-5p, miR-5010-5p is hsa-miR-5010-5p, miR-6870-5p is hsa-miR-6870-5p, miR-6124 is hsa-miR-6124, miR-1249-5p is hsa-miR-1249-5p, miR-6511b-5p is hsa-miR-6511b-5p, miR-1254 is hsa-miR-1254, miR-4727-3p is hsa-miR-4727-3p, miR-4259 is hsa-miR-4259, miR-4771 is hsa-miR-4771, miR-3622a-5p is hsa-miR-3622a-5p, miR-4480 is hsa-miR-4480, miR-4740-5p is hsa-miR-4740-5p, miR-6777-5p is hsa-miR-6777-5p, miR-6794-5p is hsa-miR-6794-5p, miR-4687-3p is hsa-miR-4687-3p, miR-6743-5p is hsa-miR-6743-5p, miR-6771-5p is hsa-miR-6771-5p, miR-3141 is hsa-miR-3141, miR-3162-5p is hsa-miR-3162-5p, miR-4271 is hsa-miR-4271, miR-1227-5p is hsa-miR-1227-5p, miR-4257 is hsa-miR-4257, miR-4270 is hsa-miR-4270, miR-4516 is hsa-miR-4516, miR-4651 is hsa-miR-4651, miR-4725-3p is hsa-miR-4725-3p, miR-6125 is hsa-miR-6125, miR-6732-5p is hsa-miR-6732-5p, miR-6791-5p is hsa-miR-6791-5p, miR-6819-5p is hsa-miR-6819-5p, miR-6891-5p is hsa-miR-6891-5p, miR-7108-5p is hsa-miR-7108-5p, miR-7109-5p is hsa-miR-7109-5p, miR-642b-3p is hsa-miR-642b-3p, and miR-642a-3p is hsa-miR-642a-3p.

(3) The kit according to (1) or (2), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 247, 251, and 268;

(c) a polynucleotide consisting of a nucleotide sequence complementary to a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 247, 251, and 268 or a nucleotide sequence derived from the nucleotide sequence by the replacement of u with t; and (e) a polynucleotide hybridizing under stringent conditions to any of the polynucleotides (a) to (d).

(4) The kit according to any of (1) to (3), wherein the kit further comprises a nucleic acid(s) capable of specifically binding to at least one polynucleotide selected from the group consisting of other ovarian tumor markers: miR-320a, miR-663a, miR-328-5p, miR-128-2-5p, miR-125a-3p, miR-191-5p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, and miR-22-3p, or to a complementary strand of the polynucleotide.

(5) The kit according to (4), wherein miR-320a is hsa-miR-320a, miR-663a is hsa-miR-663a, miR-328-5p is hsa-miR-328-5p, miR-128-2-5p is hsa-miR-128-2-5p, miR-125a-3p is hsa-miR-125a-3p, miR-191-5p is hsa-miR-191-5p, miR-92b-5p is hsa-miR-92b-5p, miR-296-5p is hsa-miR-296-5p, miR-1246 is hsa-miR-1246, miR-92a-2-5p is hsa-miR-92a-2-5p, miR-128-1-5p is hsa-miR-128-1-5p, miR-1290 is hsa-miR-1290, miR-211-3p is hsa-miR-211-3p, miR-744-5p is hsa-miR-744-5p, miR-135a-3p is hsa-miR-135a-3p, miR-451a is hsa-miR-451a, miR-625-3p is hsa-miR-625-3p, miR-92a-3p is hsa-miR-92a-3p, miR-422a is hsa-miR-422a, miR-483-5p is hsa-miR-483-5p, miR-652-5p is hsa-miR-652-5p, miR-24-3p is hsa-miR-24-3p, miR-23b-3p is hsa-miR-23b-3p, miR-23a-3p is hsa-miR-23a-3p, miR-92b-3p is hsa-miR-92b-3p, and miR-22-3p is hsa-miR-22-3p.

(6) The kit according to (4) or (5), wherein the nucleic acid(s) is a polynucleotide(s) selected from the group consisting of the following polynucleotides (f) to (j): (f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

(7) The kit according to any of (1) to (6), wherein the kit comprises at least two nucleic acids capable of specifically binding to at least two polynucleotides selected from all of the ovarian tumor markers according to (1) or (2), or complementary strands of the polynucleotides, respectively.

(8) A device for detection of ovarian tumor, comprising a nucleic acid(s) capable of specifically binding to at least one polynucleotide selected from the following ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p, or to a complementary strand of the polynucleotide.

(9) The device according to (8), wherein miR-4675 is hsa-miR-4675, miR-4783-3p is hsa-miR-4783-3p, miR-1228-5p is hsa-miR-1228-5p, miR-4532 is hsa-miR-4532, miR-6802-5p is hsa-miR-6802-5p, miR-6784-5p is hsa-miR-6784-5p, miR-3940-5p is hsa-miR-3940-5p, miR-1307-3p is hsa-miR-1307-3p, miR-8073 is hsa-miR-8073, miR-3184-5p is hsa-miR-3184-5p, miR-1233-5p is hsa-miR-1233-5p, miR-6088 is hsa-miR-6088, miR-5195-3p is hsa-miR-5195-3p, miR-320b is hsa-miR-320b, miR-4649-5p is hsa-miR-4649-5p, miR-6800-5p is hsa-miR-6800-5p, miR-1343-3p is hsa-miR-1343-3p, miR-4730 is hsa-miR-4730, miR-6885-5p is hsa-miR-6885-5p, miR-5100 is hsa-miR-5100, miR-1203 is hsa-miR-1203, miR-6756-5p is hsa-miR-6756-5p, miR-373-5p is hsa-miR-373-5p, miR-1268a is hsa-miR-1268a, miR-1260b is hsa-miR-1260b, miR-4258 is hsa-miR-4258, miR-4697-5p is hsa-miR-4697-5p, miR-1469 is hsa-miR-1469, miR-4515 is hsa-miR-4515, miR-6861-5p is hsa-miR-6861-5p, miR-6821-5p is hsa-miR-6821-5p, miR-575 is hsa-miR-575, miR-6805-5p is hsa-miR-6805-5p, miR-4758-5p is hsa-miR-4758-5p, miR-3663-3p is hsa-miR-3663-3p, miR-4530 is hsa-miR-4530, miR-6798-5p is hsa-miR-6798-5p, miR-6781-5p is hsa-miR-6781-5p, miR-885-3p is hsa-miR-885-3p, miR-1273g-3p is hsa-miR-1273g-3p, miR-4787-3p is hsa-miR-4787-3p, miR-4454 is hsa-miR-4454, miR-4706 is hsa-miR-4706, miR-1249-3p is hsa-miR-1249-3p, miR-887-3p is hsa-miR-887-3p, miR-6786-5p is hsa-miR-6786-5p, miR-1238-5p is hsa-miR-1238-5p, miR-6749-5p is hsa-miR-6749-5p, miR-6729-5p is hsa-miR-6729-5p, miR-6825-5p is hsa-miR-6825-5p, miR-663b is hsa-miR-663b, miR-6858-5p is hsa-miR-6858-5p, miR-4690-5p is hsa-miR-4690-5p, miR-6765-5p is hsa-miR-6765-5p, miR-4710 is hsa-miR-4710, miR-6775-5p is hsa-miR-6775-5p, miR-371a-5p is hsa-miR-371a-5p, miR-6816-5p is hsa-miR-6816-5p, miR-296-3p is hsa-miR-296-3p, miR-7977 is hsa-miR-7977, miR- 8069 is hsa-miR-8069, miR-6515-3p is hsa-miR-6515-3p, miR-4687-5p is hsa-miR-4687-5p, miR-1343-5p is hsa-miR-1343-5p, miR-7110-5p is hsa-miR-7110-5p, miR-4525 is hsa-miR-4525, miR-3158-5p is hsa-miR-3158-5p, miR-6787-5p is hsa-miR-6787-5p, miR-614 is hsa-miR-614, miR-4689 is hsa-miR-4689, miR-1185-2-3p is hsa-miR-1185-2-3p, miR-1268b is hsa-miR-1268b, miR-1228-3p is hsa-miR-1228-3p, miR-1185-1-3p is hsa-miR-1185-1-3p, miR-940 is hsa-miR-940, miR-939-5p is hsa-miR-939-5p, miR-6757-5p is hsa-miR-6757-5p, miR-1275 is hsa-miR-1275, miR-5001-5p is hsa-miR-5001-5p, miR-6826-5p is hsa-miR-6826-5p, miR-6765-3p is hsa-miR-6765-3p, miR-3679-3p is hsa-miR-3679-3p, miR-4718 is hsa-miR-4718, miR-4286 is hsa-miR-4286, miR-8059 is hsa-miR-8059, miR-4447 is hsa-miR-4447, miR-4448 is hsa-miR-4448, miR-658 is hsa-miR-658, miR-6766-3p is hsa-miR-6766-3p, miR-197-5p is hsa-miR-197-5p, miR-6887-5p is hsa-miR-6887-5p, miR-6742-5p is hsa-miR-6742-5p, miR-6729-3p is hsa-miR-6729-3p, miR-5090 is hsa-miR-5090, miR-7975 is hsa-miR-7975, miR-4505 is hsa-miR-4505, miR-6889-5p is hsa-miR-6889-5p, miR-4708-3p is hsa-miR-4708-3p, miR-6131 is hsa-miR-6131, miR-1225-3p is hsa-miR-1225-3p, miR-6132 is hsa-miR-6132, miR-4734 is hsa-miR-4734, miR-3194-3p is hsa-miR-3194-3p, miR-638 is hsa-miR-638, miR-2467-3p is hsa-miR-2467-3p, miR-4728-5p is hsa-miR-4728-5p, miR-5572 is hsa-miR-5572, miR-6789-5p is hsa-miR-6789-5p, miR-8063 is hsa-miR-8063, miR-4429 is hsa-miR-4429, miR-6840-3p is hsa-miR-6840-3p, miR-4476 is hsa-miR-4476, miR-675-5p is hsa-miR-675-5p, miR-711 is hsa-miR-711, miR-6875-5p is hsa-miR-6875-5p, miR-3160-5p is hsa-miR-3160-5p, miR-1908-5p is hsa-miR-1908-5p, miR-6726-5p is hsa-miR-6726-5p, miR-1913 is hsa-miR-1913, miR-8071 is hsa-miR-8071, miR-3648 is hsa-miR-3648, miR-4732-5p is hsa-miR-4732-5p, miR-4787-5p is hsa-miR-4787-5p, miR-3917 is hsa-miR-3917, miR-619-5p is hsa-miR-619-5p, miR-1231 is hsa-miR-1231, miR-342-5p is hsa-miR-342-5p, miR-4433a-5p is hsa-miR-4433a-5p, miR-6766-5p is hsa-miR-6766-5p, miR-4707-5p is hsa-miR-4707-5p, miR-7114-5p is hsa-miR-7114-5p, miR-6872-3p is hsa-miR-6872-3p, miR-6780b-5p is hsa-miR-6780b-5p, miR-7845-5p is hsa-miR-7845-5p, miR-6798-3p is hsa-miR-6798-3p, miR-665 is hsa-miR-665, miR-6848-5p is hsa-miR-6848-5p, miR-5008-5p is hsa-miR-5008-5p, miR-4294 is hsa-miR-4294, miR-6511a-5p is hsa-miR-6511a-5p, miR-4435 is hsa-miR-4435, miR-4747-3p is hsa-miR-4747-3p, miR-6880-3p is hsa-miR-6880-3p, miR-6869-5p is hsa-miR-6869-5p, miR-7150 is hsa-miR-7150, miR-1260a is hsa-miR-1260a, miR-6877-5p is hsa-miR-6877-5p, miR-6721-5p is hsa-miR-6721-5p, miR-4656 is hsa-miR-4656, miR-1229-5p is hsa-miR-1229-5p, miR-4433a-3p is hsa-miR-4433a-3p, miR-4274 is hsa-miR-4274, miR-4419b is hsa-miR-4419b, miR-4674 is hsa-miR-4674, miR-6893-5p is hsa-miR-6893-5p, miR-6763-3p is hsa-miR-6763-3p, miR-6762-5p is hsa-miR-6762-5p, miR-6738-5p is hsa-miR-6738-5p, miR-4513 is hsa-miR-4513, miR-6746-5p is hsa-miR-6746-5p, miR-6880-5p is hsa-miR-6880-5p, miR-4736 is hsa-miR-4736, miR-718 is hsa-miR-718, miR-6717-5p is hsa-miR-6717-5p, miR-7847-3p is hsa-miR-7847-3p, miR-760 is hsa-miR-760, miR-1199-5p is hsa-miR-1199-5p, miR-6813-5p is hsa-miR-6813-5p, miR-6769a-5p is hsa-miR-6769a-5p, miR-1193 is hsa-miR-1193, miR-7108-3p is hsa-miR-7108-3p, miR-6741-5p is hsa-miR-6741-5p, miR-4298 is hsa-miR-4298, miR-6796-3p is hsa-miR-6796-3p, miR-4750-5p is hsa-miR-4750-5p, miR-6785-5p is hsa-miR-6785-5p, miR-1292-3p is hsa-miR-1292-3p, miR-4749-3p is hsa-miR-4749-3p, miR-6800-3p is hsa-miR-6800-3p, miR-722-5p is hsa-miR-4722-5p, miR-4746-3p is hsa-miR-4746-3p, miR-4450 is hsa-miR-4450, miR-6795-5p is hsa-miR-6795-5p, miR-365a-5p is hsa-miR-365a-5p, miR-498 is hsa-miR-498, miR-6797-5p is hsa-miR-6797-5p, miR-1470 is hsa-miR-1470, miR-6851-5p is hsa-miR-6851-5p, miR-1247-3p is hsa-miR-1247-3p, miR-5196-5p is hsa-miR-5196-5p, miR-208a-5p is hsa-miR-208a-5p, miR-6842-5p is hsa-miR-6842-5p, miR-150-3p is hsa-miR-150-3p, miR-4534 is hsa-miR-4534, miR-3135b is hsa-miR-3135b, miR-3131 is hsa-miR-3131, miR-4792 is hsa-miR-4792, miR-6510-5p is hsa-miR-6510-5p, miR-504-3p is hsa-miR-504-3p, miR-3619-3p is hsa-miR-3619-3p, miR-671-5p is hsa-miR-671-5p, miR-4667-5p is hsa-miR-4667-5p, miR-4430 is hsa-miR-4430, miR-3195 is hsa-miR-3195, miR-3679-5p is hsa-miR-3679-5p, miR-6076 is hsa-miR-6076, miR-6515-5p is hsa-miR-6515-5p, miR-6820-5p is hsa-miR-6820-5p, miR-4634 is hsa-miR-4634, miR-187-5p is hsa-miR-187-5p, miR-6763-5p is hsa-miR-6763-5p, miR-1908-3p is hsa-miR-1908-3p, miR-1181 is hsa-miR-1181, miR-6782-5p is hsa-miR-6782-5p, miR-5010-5p is hsa-miR-5010-5p, miR-6870-5p is hsa-miR-6870-5p, miR-6124 is hsa-miR-6124, miR-1249-5p is hsa-miR-1249-5p, miR-6511b-5p is hsa-miR-6511b-5p, miR-1254 is hsa-miR-1254, miR-4727-3p is hsa-miR-4727-3p, miR-4259 is hsa-miR-4259, miR-4771 is hsa-miR-4771, miR-3622a-5p is hsa-miR-3622a-5p, miR-4480 is hsa-miR-4480, miR-4740-5p is hsa-miR-4740-5p, miR-6777-5p is hsa-miR-6777-5p, miR-6794-5p is hsa-miR-6794-5p, miR-4687-3p is hsa-miR-4687-3p, miR-6743-5p is hsa-miR-6743-5p, miR-6771-5p is hsa-miR-6771-5p, miR-3141 is hsa-miR-3141, miR-3162-5p is hsa-miR-3162-5p, miR-4271 is hsa-miR-4271, miR-1227-5p is hsa-miR-1227-5p, miR-4257 is hsa-miR-4257, miR-4270 is hsa-miR-4270, miR-4516 is hsa-miR-4516, miR-4651 is hsa-miR-4651, miR-4725-3p is hsa-miR-4725-3p, miR-6125 is hsa-miR-6125, miR-6732-5p is hsa-miR-6732-5p, miR-6791-5p is hsa-miR-6791-5p, miR-6819-5p is hsa-miR-6819-5p, miR-6891-5p is hsa-miR-6891-5p, miR-7108-5p is hsa-miR-7108-5p, miR-7109-5p is hsa-miR-7109-5p, miR-642b-3p is hsa-miR-642b-3p, and miR-642a-3p is hsa-miR-642a-3p.

(10) The device according to (8) or (9), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 247, 251, and 268;

(c) a polynucleotide consisting of a nucleotide sequence complementary to a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 247, 251, and 268 or a nucleotide sequence derived from the nucleotide sequence by the replacement of u with t; and (e) a polynucleotide hybridizing under stringent conditions to any of the polynucleotides (a) to (d).

(11) The device according to any of (8) to (10), wherein the device further comprises a nucleic acid(s) capable of specifically binding to at least one polynucleotide selected from the group consisting of other ovarian tumor markers: miR-320a, miR-663a, miR-328-5p, miR-128-2-5p, miR-125a-3p, miR-191-5p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, and miR-22-3p, or to a complementary strand of the polynucleotide.

(12) The device according to (11), wherein miR-320a is hsa-miR-320a, miR-663a is hsa-miR-663a, miR-328-5p is hsa-miR-328-5p, miR-128-2-5p is hsa-miR-128-2-5p, miR-125a-3p is hsa-miR-125a-3p, miR-191-5p is hsa-miR-191-5p, miR-92b-5p is hsa-miR-92b-5p, miR-296-5p is hsa-miR-296-5p, miR-1246 is hsa-miR-1246, miR-92a-2-5p is hsa-miR-92a-2-5p, miR-128-1-5p is hsa-miR-128-1-5p, miR-1290 is hsa-miR-1290, miR-211-3p is hsa-miR-211-3p, miR-744-5p is hsa-miR-744-5p, miR-135a-3p is hsa-miR-135a-3p, miR-451a is hsa-miR-451a, miR-625-3p is hsa-miR-625-3p, miR-92a-3p is hsa-miR-92a-3p, miR-422a is hsa-miR-422a, miR-483-5p is hsa-miR-483-5p, miR-652-5p is hsa-miR-652-5p, miR-24-3p is hsa-miR-24-3p, miR-23b-3p is hsa-miR-23b-3p, miR-23a-3p is hsa-miR-23a-3p, miR-92b-3p is hsa-miR-92b-3p, and miR-22-3p is hsa-miR-22-3p.

(13) The device according to (11) or (12), wherein the nucleic acid(s) is a polynucleotide(s) selected from the group consisting of the following polynucleotides (f) to (j):

(f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

(14) The device according to any of (8) to (13), wherein the device is for measurement based on a hybridization technique.

(15) The device according to (14), wherein the hybridization technique is a nucleic acid array technique.

(16) The device according to any of (8) to (15), wherein the device comprises at least two polynucleotides selected from all of the ovarian tumor markers according to (8) or (9), or at least two nucleic acids capable of specifically binding to a complementary strand of the polynucleotide, respectively.

(17) A method for detecting ovarian tumor, comprising: measuring an expression level(s) of at least one polynucleotide selected from the following ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p in a sample from a subject; and evaluating in vitro whether or not the subject has ovarian tumor using the measured expression level(s).

(18) A method for detecting ovarian tumor, comprising: measuring an expression level(s) of a target nucleic acid(s) in a sample from a subject using a kit according to any of (1) to (7) or a device according to any of (8) to (16), comprising a nucleic acid(s) capable of specifically binding to at least one or at least two polynucleotides selected from the following ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p, or to a complementary strand(s) of the polynucleotide(s), respectively; and evaluating in vitro whether or not the subject has ovarian tumor using both of the measured expression level(s) and a control expression level(s) from a healthy subject measured in the same way.

(19) A method for detecting ovarian tumor, comprising: measuring an expression level(s) of a target gene(s) in a sample from a subject using a kit according to any of (1) to (7) or a device according to any of (8) to (16), comprising a nucleic acid(s) capable of specifically binding to at least one or at least two polynucleotides selected from the following ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p, or to a complementary strand(s) of the polynucleotide(s), respectively; and assigning the expression level(s) of the target gene(s) in the sample from the subject to a discriminant, which is capable of discriminatorily determining the presence or absence of ovarian tumor and is prepared with gene expression levels in a sample(s) from a subject(s) known to have ovarian tumor and a sample(s) from a subject(s) without ovarian tumor as a training sample(s), and thereby evaluating in vitro the presence or absence of ovarian tumor.

(20) The method according to any of (17) to (19), wherein miR-4675 is hsa-miR-4675, miR-4783-3p is hsa-miR-4783-3p, miR-1228-5p is hsa-miR-1228-5p, miR-4532 is hsa-miR-4532, miR-6802-5p is hsa-miR-6802-5p, miR-6784-5p is hsa-miR-6784-5p, miR-3940-5p is hsa-miR-3940-5p, miR-1307-3p is hsa-miR-1307-3p, miR-8073 is hsa-miR-8073, miR-3184-5p is hsa-miR-3184-5p, miR-1233-5p is hsa-miR-1233-5p, miR-6088 is hsa-miR-6088, miR-5195-3p is hsa-miR-5195-3p, miR-320b is hsa-miR-320b, miR-4649-5p is hsa-miR-4649-5p, miR-6800-5p is hsa-miR-6800-5p, miR-1343-3p is hsa-miR-1343-3p, miR-4730 is hsa-miR-4730, miR-6885-5p is hsa-miR-6885-5p, miR-5100 is hsa-miR-5100, miR-1203 is hsa-miR-1203, miR-6756-5p is hsa-miR-6756-5p, miR-373-5p is hsa-miR-373-5p, miR-1268a is hsa-miR-1268a, miR-1260b is hsa-miR-1260b, miR-4258 is hsa-miR-4258, miR-4697-5p is hsa-miR-4697-5p, miR-1469 is hsa-miR-1469, miR-4515 is hsa-miR-4515, miR-6861-5p is hsa-miR-6861-5p, miR-6821-5p is hsa-miR-6821-5p, miR-575 is hsa-miR-575, miR-6805-5p is hsa-miR-6805-5p, miR-4758-5p is hsa-miR-4758-5p, miR-3663-3p is hsa-miR-3663-3p, miR-4530 is hsa-miR-4530, miR-6798-5p is hsa-miR-6798-5p, miR-6781-5p is hsa-miR-6781-5p, miR-885-3p is hsa-miR-885-3p, miR-1273g-3p is hsa-miR-1273g-3p, miR-4787-3p is hsa-miR-4787-3p, miR-4454 is hsa-miR-4454, miR-4706 is hsa-miR-4706, miR-1249-3p is hsa-miR-1249-3p, miR-887-3p is hsa-miR-887-3p, miR-6786-5p is hsa-miR-6786-5p, miR-1238-5p is hsa-miR-1238-5p, miR-6749-5p is hsa-miR-6749-5p, miR-6729-5p is hsa-miR-6729-5p, miR-6825-5p is hsa-miR-6825-5p, miR-663b is hsa-miR-663b, miR-6858-5p is hsa-miR-6858-5p, miR-4690-5p is hsa-miR-4690-5p, miR-6765-5p is hsa-miR-6765-5p, miR-4710 is hsa-miR-4710, miR-6775-5p is hsa-miR-6775-5p, miR-371a-5p is hsa-miR-371a-5p, miR-6816-5p is hsa-miR-6816-5p, miR-296-3p is hsa-miR-296-3p, miR-7977 is hsa-miR-7977, miR-8069 is hsa-miR-8069, miR-6515-3p is hsa-miR-6515-3p, miR-4687-5p is hsa-miR-4687-5p, miR-1343-5p is hsa-miR-1343-5p, miR-7110-5p is hsa-miR-7110-5p, miR-4525 is hsa-miR-4525, miR-3158-5p is hsa-miR-3158-5p, miR-6787-5p is hsa-miR-6787-5p, miR-614 is hsa-miR-614, miR-4689 is hsa-miR-4689, miR-1185-2-3p is hsa-miR-1185-2-3p, miR-1268b is hsa-miR-1268b, miR-1228-3p is hsa-miR-1228-3p, miR-1185-1-3p is hsa-miR-1185-1-3p, miR-940 is hsa-miR-940, miR-939-5p is hsa-miR-939-5p, miR-6757-5p is hsa-miR-6757-5p, miR-1275 is hsa-miR-1275, miR-5001-5p is hsa-miR-5001-5p, miR-6826-5p is hsa-miR-6826-5p, miR-6765-3p is hsa-miR-6765-3p, miR-3679-3p is hsa-miR-3679-3p, miR-4718 is hsa-miR-4718, miR-4286 is hsa-miR-4286, miR-8059 is hsa-miR-8059, miR-4447 is hsa-miR-4447, miR-4448 is hsa-miR-4448, miR-658 is hsa-miR-658, miR-6766-3p is hsa-miR-6766-3p, miR-197-5p is hsa-miR-197-5p, miR-6887-5p is hsa-miR-6887-5p, miR-6742-5p is hsa-miR-6742-5p, miR-6729-3p is hsa-miR-6729-3p, miR-5090 is hsa-miR-5090, miR-7975 is hsa-miR-7975, miR-4505 is hsa-miR-4505, miR-6889-5p is hsa-miR-6889-5p, miR-4708-3p is hsa-miR-4708-3p, miR-6131 is hsa-miR-6131, miR-1225-3p is hsa-miR-1225-3p, miR-6132 is hsa-miR-6132, miR-4734 is hsa-miR-4734, miR-3194-3p is hsa-miR-3194-3p, miR-638 is hsa-miR-638, miR-2467-3p is hsa-miR-2467-3p, miR-4728-5p is hsa-miR-4728-5p, miR-5572 is hsa-miR-5572, miR-6789-5p is hsa-miR-6789-5p, miR-8063 is hsa-miR-8063, miR-4429 is hsa-miR-4429, miR-6840-3p is hsa-miR-6840-3p, miR-4476 is hsa-miR-4476, miR-675-5p is hsa-miR-675-5p, miR-711 is hsa-miR-711, miR-6875-5p is hsa-miR-6875-5p, miR-3160-5p is hsa-miR-3160-5p, miR-1908-5p is hsa-miR-1908-5p, miR-6726-5p is hsa-miR-6726-5p, miR-1913 is hsa-miR-1913, miR-8071 is hsa-miR-8071, miR-3648 is hsa-miR-3648, miR-4732-5p is hsa-miR-4732-5p, miR-4787-5p is hsa-miR-4787-5p, miR-3917 is hsa-miR-3917, miR-619-5p is hsa-miR-619-5p, miR-1231 is hsa-miR-1231, miR-342-5p is hsa-miR-342-5p, miR-4433a-5p is hsa-miR-4433a-5p, miR-6766-5p is hsa-miR-6766-5p, miR-4707-5p is hsa-miR-4707-5p, miR-7114-5p is hsa-miR-7114-5p, miR-6872-3p is hsa-miR-6872-3p, miR-6780b-5p is hsa-miR-6780b-5p, miR-7845-5p is hsa-miR-7845-5p, miR-6798-3p is hsa-miR-6798-3p, miR-665 is hsa-miR-665, miR-6848-5p is hsa-miR-6848-5p, miR-5008-5p is hsa-miR-5008-5p, miR-4294 is hsa-miR-4294, miR-6511a-5p is hsa-miR-6511a-5p, miR-4435 is hsa-miR-4435, miR-4747-3p is hsa-miR-4747-3p, miR-6880-3p is hsa-miR-6880-3p, miR-6869-5p is hsa-miR-6869-5p, miR-7150 is hsa-miR-7150, miR-1260a is hsa-miR-1260a, miR-6877-5p is hsa-miR-6877-5p, miR-6721-5p is hsa-miR-6721-5p, miR-4656 is hsa-miR-4656, miR-1229-5p is hsa-miR-1229-5p, miR-4433a-3p is hsa-miR-4433a-3p, miR-4274 is hsa-miR-4274, miR-4419b is hsa-miR-4419b, miR-4674 is hsa-miR-4674, miR-6893-5p is hsa-miR-6893-5p, miR-6763-3p is hsa-miR-6763-3p, miR-6762-5p is hsa-miR-6762-5p, miR-6738-5p is hsa-miR-6738-5p, miR-4513 is hsa-miR-4513, miR-6746-5p is hsa-miR-6746-5p, miR-6880-5p is hsa-miR-6880-5p, miR-4736 is hsa-miR-4736, miR-718 is hsa-miR-718, miR-6717-5p is hsa-miR-6717-5p, miR-7847-3p is hsa-miR-7847-3p, miR-760 is hsa-miR-760, miR-1199-5p is hsa-miR-1199-5p, miR-6813-5p is hsa-miR-6813-5p, miR-6769a-5p is hsa-miR-6769a-5p, miR-1193 is hsa-miR-1193, miR-7108-3p is hsa-miR-7108-3p, miR-6741-5p is hsa-miR-6741-5p, miR-4298 is hsa-miR-4298, miR-6796-3p is hsa-miR-6796-3p, miR-4750-5p is hsa-miR-4750-5p, miR-6785-5p is hsa-miR-6785-5p, miR-1292-3p is hsa-miR-1292-3p, miR-4749-3p is hsa-miR-4749-3p, miR-6800-3p is hsa-miR-6800-3p, miR-722-5p is hsa-miR-4722-5p, miR-4746-3p is hsa-miR-4746-3p, miR-4450 is hsa-miR-4450, miR-6795-5p is hsa-miR-6795-5p, miR-365a-5p is hsa-miR-365a-5p, miR-498 is hsa-miR-498, miR-6797-5p is hsa-miR-6797-5p, miR-1470 is hsa-miR-1470, miR-6851-5p is hsa-miR-6851-5p, miR-1247-3p is hsa-miR-1247-3p, miR-5196-5p is hsa-miR-5196-5p, miR-208a-5p is hsa-miR-208a-5p, miR-6842-5p is hsa-miR-6842-5p, miR-150-3p is hsa-miR-150-3p, miR-4534 is hsa-miR-4534, miR-3135b is hsa-miR-3135b, miR-3131 is hsa-miR-3131, miR-4792 is hsa-miR-4792, miR-6510-5p is hsa-miR-6510-5p, miR-504-3p is hsa-miR-504-3p, miR-3619-3p is hsa-miR-3619-3p, miR-671-5p is hsa-miR-671-5p, miR-4667-5p is hsa-miR-4667-5p, miR-4430 is hsa-miR-4430, miR-3195 is hsa-miR-3195, miR-3679-5p is hsa-miR-3679-5p, miR-6076 is hsa-miR-6076, miR-6515-5p is hsa-miR-6515-5p, miR-6820-5p is hsa-miR-6820-5p, miR-4634 is hsa-miR-4634, miR-187-5p is hsa-miR-187-5p, miR-6763-5p is hsa-miR-6763-5p, miR-1908-3p is hsa-miR-1908-3p, miR-1181 is hsa-miR-1181, miR-6782-5p is hsa-miR-6782-5p, miR-5010-5p is hsa-miR-5010-5p, miR-6870-5p is hsa-miR-6870-5p, miR-6124 is hsa-miR-6124, miR-1249-5p is hsa-miR-1249-5p, miR-6511b-5p is hsa-miR-6511b-5p, miR-1254 is hsa-miR-1254, miR-4727-3p is hsa-miR-4727-3p, miR-4259 is hsa-miR-4259, miR-4771 is hsa-miR-4771, miR-3622a-5p is hsa-miR-3622a-5p, miR-4480 is hsa-miR- 4480, miR-4740-5p is hsa-miR-4740-5p, miR-6777-5p is hsa-miR-6777-5p, miR-6794-5p is hsa-miR-6794-5p, miR-4687-3p is hsa-miR-4687-3p, miR-6743-5p is hsa-miR-6743-5p, miR-6771-5p is hsa-miR-6771-5p, miR-3141 is hsa-miR-3141, miR-3162-5p is hsa-miR-3162-5p, miR-4271 is hsa-miR-4271, miR-1227-5p is hsa-miR-1227-5p, miR-4257 is hsa-miR-4257, miR-4270 is hsa-miR-4270, miR-4516 is hsa-miR-4516, miR-4651 is hsa-miR-4651, miR-4725-3p is hsa-miR-4725-3p, miR-6125 is hsa-miR-6125, miR-6732-5p is hsa-miR-6732-5p, miR-6791-5p is hsa-miR-6791-5p, miR-6819-5p is hsa-miR-6819-5p, miR-6891-5p is hsa-miR-6891-5p, miR-7108-5p is hsa-miR-7108-5p, miR-7109-5p is hsa-miR-7109-5p, miR-642b-3p is hsa-miR-642b-3p, and miR-642a-3p is hsa-miR-642a-3p.

(21) The method according to any of (17) to (19), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 247, 251, and 268;

(c) a polynucleotide consisting of a nucleotide sequence complementary to a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 247, 251, and 268 or a nucleotide sequence derived from the nucleotide sequence by the replacement of u with t; and (e) a polynucleotide hybridizing under stringent conditions to any of the polynucleotides (a) to (d).

(22) The method according to any of (17) to (21), wherein the kit or device further comprises a nucleic acid(s) capable of specifically binding to at least one polynucleotide selected from the following other ovarian tumor markers: miR-320a, miR-663a, miR-328-5p, miR-128-2-5p, miR-125a-3p, miR-191-5p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, and miR-22-3p, or to a complementary strand of the polynucleotide.

(23) The method according to (22), wherein miR-320a is hsa-miR-320a, miR-663a is hsa-miR-663a, miR-328-5p is hsa-miR-328-5p, miR-128-2-5p is hsa-miR-128-2-5p, miR-125a-3p is hsa-miR-125a-3p, miR-191-5p is hsa-miR-191-5p, miR-92b-5p is hsa-miR-92b-5p, miR-296-5p is hsa-miR-296-5p, miR-1246 is hsa-miR-1246, miR-92a-2-5p is hsa-miR-92a-2-5p, miR-128-1-5p is hsa-miR-128-1-5p, miR-1290 is hsa-miR-1290, miR-211-3p is hsa-miR-211-3p, miR-744-5p is hsa-miR-744-5p, miR-135a-3p is hsa-miR-135a-3p, miR-451a is hsa-miR-451a, miR-625-3p is hsa-miR-625-3p, miR-92a-3p is hsa-miR-92a-3p, miR-422a is hsa-miR-422a, miR-483-5p is hsa-miR-483-5p, miR-652-5p is hsa-miR-652-5p, miR-24-3p is hsa-miR-24-3p, miR-23b-3p is hsa-miR-23b-3p, miR-23a-3p is hsa-miR-23a-3p, miR-92b-3p is hsa-miR-92b-3p, and miR-22-3p is hsa-miR-22-3p.

(24) The method according to (22) or (23), wherein the nucleic acid(s) is a polynucleotide(s) selected from the group consisting of the following polynucleotides (f) to (j):

(f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

(25) The method according to any one of (17) to (24), wherein the subject is a human.

(26) The method according to any one of (17) to (25), wherein the sample is blood, serum, or plasma.

Definition of Terms

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA and synthetic RNA. Here the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length. Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID NO) but "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 842 or a nucleotide sequence derived from the nucleotide sequence by the replacement of u with t. Regardless whether or not there is a difference in functional region, the "gene" can comprise, for example, expression control regions, coding region, exons, or introns. The "gene" may be contained in a cell or may exist alone after being released from a cell. Alternatively, the "gene" may be in a state enclosed in a vesicle called exosome.

The term "exosome" used herein is a vesicle that is encapsulated by lipid bilayer and secreted from a cell. The exosome is derived from a multivesicular endosome and may incorporate biomaterials such as "genes" (e.g., RNA or DNA) or proteins when released into an extracellular environment. The exosome is known to be contained in a body fluid such as blood, serum, plasma, serum or lymph.

The term "transcript" used herein refers to an RNA synthesized from the DNA sequence of a gene as a template. RNA polymerase binds to a site called promoter located upstream of the gene and adds ribonucleotides complementary to the nucleotide sequence of the DNA to the 3' end to synthesize an RNA. This RNA contains not only the gene itself but the whole sequence from a transcription initiation site to the end of a polyA sequence, including expression control regions, coding region, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, and integrated into a protein complex called RISC, and that is involved in the suppression of translation of mRNA. The term "miRNA" used herein includes not only a "miRNA" represented by a particular nucleotide sequence (or SEQ ID NO) but a "miRNA" comprising a precursor of the "miRNA" (pre-miRNA or pri-miRNA) and having biological functions equivalent to miRNAs encoded by these, for example, a "miRNA" encoding a congener (i.e., a homolog or an ortholog), a variant such as a genetic polymorph, and a derivative. Such a "miRNA" encoding a precursor, a congener, a variant, or a derivative can be specifically identified using miRBase Release 21 (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 842. The term "miRNA" used herein may be a gene product of a miR gene. Such a gene product includes a mature miRNA (e.g., a 15- to 25-nucleotide or 19- to 25-nucleotide non-coding RNA involved in the suppression of translation of mRNA as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

In this context, the complementary polynucleotide (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 842 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID NO or a nucleotide sequence derived from the nucleotide sequence by the replacement of u with t, or a partial sequence thereof; a variant containing the deletion, substitution, addition, or insertion of 1 or 2 or more nucleotides in a nucleotide sequence of a premature miRNA of the sequence of any of SEQ ID NOs 1 to 275 or a nucleotide sequence derived from the nucleotide sequence by the replacement of u with t, or a partial sequence thereof; a variant that exhibits percent (%) identity of approximately 90% or higher, approximately 95% or higher, approximately 97% or higher, approximately 98% or higher, approximately 99% or higher to each of these nucleotide sequences or the partial sequences thereof; or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by use of a well-known technique such as site-directed mutagenesis or mutagenesis using PCR.

The term "percent (%) identity" used herein can be determined with or without an introduced gap, using a protein or gene search system based on BLAST (https://blast.nebi.nlm.nih.gov/Blast.cgi) or FASTA (http://www.genome.jp/tools/fasta/) (Zheng Zhang et al., 2000, J. Comput. Biol., Vol. 7, p. 203-214; Altschul, S. F. et al., 1990, Journal of Molecular Biology, Vol. 215, p. 403-410; and Pearson, W. R. et al., 1988, Proc. Natl. Acad. Sci. U.S.A, Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur atom, etc.), PNA (peptide nucleic acid; Nielsen, P. E. et al., 1991, Science, Vol. 254, p. 1497-500), and LNA (locked nucleic acid; Obika, S. et al., 1998, Tetrahedron Lett., Vol. 39, p. 5401-5404).

As used herein, the "nucleic acid" capable of specifically binding to a polynucleotide selected from the ovarian tumor marker miRNAs described above or to a complementary strand of the polynucleotide, or the "nucleic acid" capable of detecting the polynucleotide, is a synthesized or prepared nucleic acid and, for example, includes a "nucleic acid probe" or a "primer", and is utilized directly or indirectly for detecting the presence or absence of ovarian tumor in a subject, for diagnosing the presence or absence or the severity of ovarian tumor, the presence or absence or the degree of amelioration of ovarian tumor, or the therapeutic sensitivity of ovarian tumor, or for screening for a candidate substance useful in the prevention, amelioration, or treatment of ovarian tumor. The "nucleic acid" includes a nucleotide, an oligonucleotide, and a polynucleotide capable of specifically recognizing and binding to a transcript represented by any of SEQ ID NOs: 1 to 842 or a synthetic cDNA nucleic acid thereof in vivo, particularly, in a sample such as a body fluid (e.g., blood or urine), in relation to the development of ovarian tumor. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosing- or evaluation-supporting on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. The term "subject" herein may be optionally referred to as "test subject". The term "healthy subject" also means such a mammal, which is an animal or a subject without the cancer to be detected. The healthy subject is preferably a human.

The term "ovarian cancer" used herein is a malignant tumor which develops in the ovary and includes, for example, epithelial ovarian cancer which develops from the mucosal epithelium, and germ cell stromal ovarian cancers.

The term "ovarian benign tumor" used herein is a benign tumor which develops in the ovary and includes, for example, mucinous cystadenoma, serous cystadenoma, mature teratoma and fibroma.

The term "ovarian tumor" used herein is a term including the above "ovarian cancers" and "ovarian benign tumors".

The term "P" or "P value" used herein refers to a probability at which a more extreme statistic than that actually calculated from data under null hypothesis is observed in a statistical test. Thus, smaller "P" or "P value" is regarded as being a more significant difference between subjects to be compared.

The term "sensitivity" used herein means a value of (the number of true positives)/(the number of true positives+the number of false negatives). High sensitivity allows ovarian tumor to be detected early, leading to the complete resection of cancer sites and reduction in the rate of recurrence.

The term "specificity" used herein means a value of (the number of true negatives)/(the number of true negatives+the number of false positives). High specificity prevents needless extra examination for healthy subjects misjudged as being ovarian tumor patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as ovarian tumor develops, as ovarian tumor progresses, or as therapeutic effects on ovarian tumor are exerted. Specifically, the sample refers to an ovarian tissue and fallopian tube, lymph node and a surrounding organ thereof, an organ suspected of having metastasis, the skin, a body fluid such as blood, urine, saliva, sweat, or tissue exudates, serum or plasma prepared from blood, feces, hair, and the like. The "sample" further refers to a biological sample extracted therefrom, specifically, a gene such as RNA or miRNA.

The term "hsa-miR-4675 gene" or "hsa-miR-4675" used herein includes the hsa-miR-4675 gene (miRBase Accession No. MIMAT0019757) described in SEQ ID NO: 1, a homolog or an ortholog of a different organism species, and the like. The hsa-miR-4675 gene can be obtained by a method described in Persson H et al., 2011, Cancer Res, Vol. 71, p. 78-86. Also, "hsa-mir-4675" (miRBase Accession No. MI0017306, SEQ ID NO: 276) having a hairpin-like structure is known as a precursor of "hsa-miR-4675".

The term "hsa-miR-4783-3p gene" or "hsa-miR-4783-3p" used herein includes the hsa-miR-4783-3p gene (miRBase Accession No. MIMAT0019947) described in SEQ ID NO: 2, a homolog or an ortholog of a different organism species, and the like. The hsa-miR-4783-3p gene can be obtained by a method described in Persson H et al., 2011, Cancer Res, Vol. 71, p. 78-86. Also, "hsa-mir-4783" (miRBase Accession No. MI0017428, SEQ ID NO: 277) having a hairpin-like structure is known as a precursor of "hsa-miR-4783-3p".

The term "hsa-miR-1228-5p gene" or "hsa-miR-1228-5p" used herein includes the hsa-miR-1228-5p gene (miRBase Accession No. MIMAT0005582) described in SEQ ID NO: 3, a homolog or an ortholog of a different organism species, and the like. The hsa-miR-1228-5p gene can be obtained by a method described in Berezikov E et al., 2007, Mol Cell, Vol. 28, p. 328-336. Also, "hsa-mir-1228" (miRBase Accession No. MI0006318, SEQ ID NO: 278) having a hairpin-like structure is known as a precursor of "hsa-miR-1228-5p".

The term "hsa-miR-4532 gene" or "hsa-miR-4532" used herein includes the hsa-miR-4532 gene (miRBase Accession No. MIMAT0019071) described in SEQ ID NO: 4, a homolog or an ortholog of a different organism species, and the like. The hsa-miR-4532 gene can be obtained by a method described in Jima D D et al., 2010, Blood, Vol. 116, e118-e127. Also, "hsa-mir-4532" (miRBase Accession No. MI0016899, SEQ ID NO: 279) having a hairpin-like structure is known as a precursor of "hsa-miR-4532".

The term "hsa-miR-6802-5p gene" or "hsa-miR-6802-5p" used herein includes the hsa-miR-6802-5p gene (miRBase Accession No. MIMAT0027504) described in SEQ ID NO: 5, a homolog or an ortholog of a different organism species, and the like. The hsa-miR-6802-5p gene can be obtained by a method described in Ladewig E et al., 2012, Genome Res, Vol. 22, p. 1634-1645. Also, "hsa-mir-6802" (miRBase Accession No. MI0022647, SEQ ID NO: 280) having a hairpin-like structure is known as a precursor of "hsa-miR-6802-5p".

The term "hsa-miR-6784-5p gene" or "hsa-miR-6784-5p" used herein includes the hsa-miR-6784-5p gene (miRBase Accession No. MIMAT0027468) described in SEQ ID NO: 6, a homolog or an ortholog of a different organism species, and the like. The hsa-miR-6784-5p gene can be obtained by a method described in Ladewig E et al., 2012, Genome Res, Vol. 22, p. 1634-1645. Also, "hsa-mir-6784" (miRBase Accession No. MI0022629, SEQ ID NO: 281) having a hairpin-like structure is known as a precursor of "hsa-miR-6784-5p".

The term "hsa-miR-3940-5p gene" or "hsa-miR-3940-5p" used herein includes the hsa-miR-3940-5p gene (miRBase Accession No. MIMAT0019229) described in SEQ ID NO: 7, a homolog or an ortholog of a different organism species, and the like. The hsa-miR-3940-5p gene can be obtained by a method described in Liao J Y et al., 2010, PLoS One, Vol. 5, e10563. Also, "hsa-mir-3940" (miRBase Accession No. MI0016597, SEQ ID NO: 282) having a hairpin-like structure is known as a precursor of "hsa-miR-3940-5p".

The term "hsa-miR-1307-3p gene" or "hsa-miR-1307-3p" used herein includes the hsa-miR-1307-3p gene (miRBase Accession No. MIMAT0005951) described in SEQ ID NO: 8, a homolog or an ortholog of a different organism species, and the like. The hsa-miR-1307-3p gene can be obtained by a method described in Morin R D et al., 2008, Genome Res, Vol. 18, p. 610-621. Also, "hsa-mir-1307" (miRBase Accession No. MI0006444, SEQ ID NO: 283) having a hairpin-like structure is known as a precursor of "hsa-miR-1307-3p".

The term "hsa-miR-8073 gene" or "hsa-miR-8073" used herein includes the hsa-miR-8073 gene (miRBase Accession No. MIMAT0031000) described in SEQ ID NO: 9, a homolog or an ortholog of a different organism species, and the like. The hsa-miR-8073 gene can be obtained by a method described in Wang H J et al., 2013, Shock, Vol. 39, p. 480-487. Also, "hsa-mir-8073" (miRBase Accession No. MI0025909, SEQ ID NO: 284) having a hairpin-like structure is known as a precursor of "hsa-miR-8073".

The term "hsa-miR-3184-5p gene" or "hsa-miR-3184-5p" used herein includes the hsa-miR-3184-5p gene (miRBase Accession No. MIMAT0015064) described in SEQ ID NO: 10, a homolog or an ortholog of a different organism species, and the like. The hsa-miR-3184-5p gene can be obtained by a method described in Stark M S et al., 2010, PLoS One, Vol. 5, e9685. Also, "hsa-mir-3184" (miRBase Accession No. MI0014226, SEQ ID NO: 285) having a hairpin-like structure is known as a precursor of "hsa-miR-3184-5p".

The term "hsa-miR-1233-5p gene" or "hsa-miR-1233-5p" used herein includes the hsa-miR-1233-5p gene (miRBase Accession No. MIMAT0022943) described in SEQ ID NO: 11, a homolog or an ortholog of a different organism species, and the like. The hsa-miR-1233-5p gene can be obtained by a method described in Berezikov E et al., 2007, Mol Cell, Vol. 28, p. 328-336. Also, "hsa-mir-1233-1 and hsa-mir-1233-2" (miRBase Accession Nos. MI10006323 and MI0015973, SEQ ID NOs: 286 and 287) having a hairpin-like structure are known as precursors of "hsa-miR-1233-5p".

The term "hsa-miR-6088 gene" or "hsa-miR-6088" used herein includes the hsa-miR-6088 gene (miRBase Accession No. MIMAT0023713) described in SEQ ID NO: 12, a homolog or an ortholog of a different organism species, and the like. The hsa-miR-6088 gene can be obtained by a method described in Yoo J K et al., 2012, Stem Cells Dev, Vol. 21, p. 2049-2057. Also, "hsa-mir-6088" (miRBase Accession No. MI0020365, SEQ ID NO: 288) having a hairpin-like structure is known as a precursor of "hsa-miR-6088".

The term "hsa-miR-5195-3p gene" or "hsa-miR-5195-3p" used herein includes the hsa-miR-5195-3p gene (miRBase Accession No. MIMAT0021127) described in SEQ ID NO: 13, a homolog or an ortholog of a different organism species, and the like. The hsa-miR-5195-3p gene can be obtained by a method described in Schotte D et al., 2011, Leukemia, Vol. 25, p. 1389-1399. Also, "hsa-mir-5195" (miRBase Accession No. MI0018174, SEQ ID NO: 289) having a hairpin-like structure is known as a precursor of "hsa-miR-5195-3p".

The term "hsa-miR-320b gene" or "hsa-miR-320b" used herein includes the hsa-miR-320b gene (miRBase Accession No. MIMAT0005792) described in SEQ ID NO: 14, a homolog or an ortholog of a different organism species, and the like. The hsa-miR-320b gene can be obtained by a method described in Berezikov E et al., 2006, Genome Res, Vol. 16, p. 1289-1298. Also, "hsa-mir-320b-1 and hsa-mir-320b-2" (miRBase Accession Nos. MI0003776 and MI0003839, SEQ ID NOs: 290 and 291) having a hairpin-like structure are known as precursors of "hsa-miR-320b".

The term "hsa-miR-4649-5p gene" or "hsa-miR-4649-5p" used herein includes the hsa-miR-4649-5p gene (miRBase Accession No. MIMAT0019711) described in SEQ ID NO: 15, a homolog or an ortholog of a different organism species, and the like. The hsa-miR-4649-5p gene can be obtained by a method described in Persson H et al., 2011, Cancer Res, Vol. 71, p. 78-86. Also, "hsa-mir-4649" (miRBase Accession No. MI10017276, SEQ ID NO: 292) having a hairpin-like structure is known as a precursor of "hsa-miR-4649-5p".

The term "hsa-miR-6800-5p gene" or "hsa-miR-6800-5p" used herein includes the hsa-miR-6800-5p gene (miRBase Accession No. MIMAT0027500) described in SEQ ID NO: 16, a homolog or an ortholog of a different organism species, and the like. The hsa-miR-6800-5p gene can be obtained by a method described in Ladewig E et al., 2012, Genome Res, Vol. 22, p. 1634-1645. Also, "hsa-mir-6800" (miRBase Accession No. MI0022645, SEQ ID NO: 293) having a hairpin-like structure is known as a precursor of "hsa-miR-6800-5p".

The term "hsa-miR-1343-3p gene" or "hsa-miR-1343-3p" used herein includes the hsa-miR-1343-3p gene (miRBase Accession No. MIMAT0019776) described in SEQ ID NO:

17, a homolog or an ortholog of a different organism species, and the like. The hsa-miR-1343-3p gene can be obtained by a method described in Persson H et al., 2011, Cancer Res, Vol. 71, p. 78-86. Also, “hsa-mir-1343” (miRBase Accession No. MI0017320, SEQ ID NO: 294) having a hairpin-like structure is known as a precursor of “hsa-miR-1343-3p”.

The term “hsa-miR-4730 gene” or “hsa-miR-4730” used herein includes the hsa-miR-4730 gene (miRBase Accession No. MIMAT0019852) described in SEQ ID NO: 18, a homolog or an ortholog of a different organism species, and the like. The hsa-miR-4730 gene can be obtained by a method described in Persson H et al., 2011, Cancer Res, Vol. 71, p. 78-86. Also, “hsa-mir-4730” (miRBase Accession No. MI0017367, SEQ ID NO: 295) having a hairpin-like structure is known as a precursor of “hsa-miR-4730”.

The term “hsa-miR-6885-5p gene” or “hsa-miR-6885-5p” used herein includes the hsa-miR-6885-5p gene (miRBase Accession No. MIMAT0027670) described in SEQ ID NO: 19, a homolog or an ortholog of a different organism species, and the like. The hsa-miR-6885-5p gene can be obtained by a method described in Ladewig E et al., 2012, Genome Res, Vol. 22, p. 1634-1645. Also, “hsa-mir-6885” (miRBase Accession No. MI0022732, SEQ ID NO: 296) having a hairpin-like structure is known as a precursor of “hsa-miR-6885-5p”.

The term “hsa-miR-5100 gene” or “hsa-miR-5100” used herein includes the hsa-miR-5100 gene (miRBase Accession No. MIMAT0022259) described in SEQ ID NO: 20, a homolog or an ortholog of a different organism species, and the like. The hsa-miR-5100 gene can be obtained by a method described in Tandon M et al., 2012, Oral Dis, Vol. 18, p. 127-131. Also, “hsa-mir-5100” (miRBase Accession No. MI0019116, SEQ ID NO: 297) having a hairpin-like structure is known as a precursor of “hsa-miR-5100”.

The term “hsa-miR-1203 gene” or “hsa-miR-1203” used herein includes the hsa-miR-1203 gene (miRBase Accession No. MIMAT0005866) described in SEQ ID NO: 21, a homolog or an ortholog of a different organism species, and the like. The hsa-miR-1203 gene can be obtained by a method described in Marton S et al., 2008, Leukemia, Vol. 22, p. 330-338. Also, “hsa-mir-1203” (miRBase Accession No. MI0006335, SEQ ID NO: 298) having a hairpin-like structure is known as a precursor of “hsa-miR-1203”.

The term “hsa-miR-6756-5p gene” or “hsa-miR-6756-5p” used herein includes the hsa-miR-6756-5p gene (miRBase Accession No. MIMAT0027412) described in SEQ ID NO: 22, a homolog or an ortholog of a different organism species, and the like. The hsa-miR-6756-5p gene can be obtained by a method described in Ladewig E et al., 2012, Genome Res, Vol. 22, p. 1634-1645. Also, “hsa-mir-6756” (miRBase Accession No. MI0022601, SEQ ID NO: 299) having a hairpin-like structure is known as a precursor of “hsa-miR-6756-5p”.

The term “hsa-miR-373-5p gene” or “hsa-miR-373-5p” used herein includes the hsa-miR-373-5p gene (miRBase Accession No. MIMAT0000725) described in SEQ ID NO: 23, a homolog or an ortholog of a different organism species, and the like. The hsa-miR-373-5p gene can be obtained by a method described in Suh M R et al., 2004, Dev Biol, Vol. 270, p. 488-498. Also, “hsa-mir-373” (miRBase Accession No. MI0000781, SEQ ID NO: 300) having a hairpin-like structure is known as a precursor of “hsa-miR-373-5p”.

The term “hsa-miR-1268a gene” or “hsa-miR-1268a” used herein includes the hsa-miR-1268a gene (miRBase Accession No. MIMAT0005922) described in SEQ ID NO: 24, a homolog or an ortholog of a different organism species, and the like. The hsa-miR-1268a gene can be obtained by a method described in Morin R D et al., 2008, Genome Res, Vol. 18, p. 610-621. Also, “hsa-mir-1268a” (miRBase Accession No. MI0006405, SEQ ID NO: 301) having a hairpin-like structure is known as a precursor of “hsa-miR-1268a”.

The term “hsa-miR-1260b gene” or “hsa-miR-1260b” used herein includes the hsa-miR-1260b gene (miRBase Accession No. MIMAT0015041) described in SEQ ID NO: 25, a homolog or an ortholog of a different organism species, and the like. The hsa-miR-1260b gene can be obtained by a method described in Stark M S et al., 2010, PLoS One, Vol. 5, e9685. Also, “hsa-mir-1260b” (miRBase Accession No. MI0014197, SEQ ID NO: 302) having a hairpin-like structure is known as a precursor of “hsa-miR-1260b”.

The term “hsa-miR-4258 gene” or “hsa-miR-4258” used herein includes the hsa-miR-4258 gene (miRBase Accession No. MIMAT0016879) described in SEQ ID NO: 26, a homolog or an ortholog of a different organism species, and the like. The hsa-miR-4258 gene can be obtained by a method described in Goff L A et al., 2009, PLoS One, Vol. 4, e7192. Also, “hsa-mir-4258” (miRBase Accession No. MI0015857, SEQ ID NO: 303) having a hairpin-like structure is known as a precursor of “hsa-miR-4258”.

The term “hsa-miR-4697-5p gene” or “hsa-miR-4697-5p” used herein includes the hsa-miR-4697-5p gene (miRBase Accession No. MIMAT0019791) described in SEQ ID NO: 27, a homolog or an ortholog of a different organism species, and the like. The hsa-miR-4697-5p gene can be obtained by a method described in Persson H et al., 2011, Cancer Res, Vol. 71, p. 78-86. Also, “hsa-mir-4697” (miRBase Accession No. MI10017330, SEQ ID NO: 304) having a hairpin-like structure is known as a precursor of “hsa-miR-4697-5p”.

The term “hsa-miR-1469 gene” or “hsa-miR-1469” used herein includes the hsa-miR-1469 gene (miRBase Accession No. MIMAT0007347) described in SEQ ID NO: 28, a homolog or an ortholog of a different organism species, and the like. The hsa-miR-1469 gene can be obtained by a method described in Kawaji H et al., 2008, BMC Genomics, Vol. 9, p. 157. Also, “hsa-mir-1469” (miRBase Accession No. MI0007074, SEQ ID NO: 305) having a hairpin-like structure is known as a precursor of “hsa-miR-1469”.

The term “hsa-miR-4515 gene” or “hsa-miR-4515” used herein includes the hsa-miR-4515 gene (miRBase Accession No. MIMAT0019052) described in SEQ ID NO: 29, a homolog or an ortholog of a different organism species, and the like. The hsa-miR-4515 gene can be obtained by a method described in Jima D D et al., 2010, Blood, Vol. 116, e118-e127. Also, “hsa-mir-4515” (miRBase Accession No. MI0016881, SEQ ID NO: 306) having a hairpin-like structure is known as a precursor of “hsa-miR-4515”.

The term “hsa-miR-6861-5p gene” or “hsa-miR-6861-5p” used herein includes the hsa-miR-6861-5p gene (miRBase Accession No. MIMAT0027623) described in SEQ ID NO: 30, a homolog or an ortholog of a different organism species, and the like. The hsa-miR-6861-5p gene can be obtained by a method described in Ladewig E et al., 2012, Genome Res, Vol. 22, p. 1634-1645. Also, “hsa-mir-6861” (miRBase Accession No. MI0022708, SEQ ID NO: 307) having a hairpin-like structure is known as a precursor of “hsa-miR-6861-5p”.

The term “hsa-miR-6821-5p gene” or “hsa-miR-6821-5p” used herein includes the hsa-miR-6821-5p gene (miRBase Accession No. MIMAT0027542) described in SEQ ID NO: 31, a homolog or an ortholog of a different organism species, and the like. The hsa-miR-6821-5p gene can be obtained by a method described in Ladewig E et al., 2012, Genome Res, Vol. 22, p. 1634-1645. Also, “hsa-mir-6821” (miRBase Accession No. MI0022666, SEQ ID NO: 308) having a hairpin-like structure is known as a precursor of "hsa-miR-6821-5p".

The term "hsa-miR-575 gene" or "hsa-miR-575" used herein includes the hsa-miR-575 gene (miRBase Accession No. MIMAT0003240) described in SEQ ID NO: 32, a homolog or an ortholog of a different organism species, and the like. The hsa-miR-575 gene can be obtained by a method described in Cummins J M et al., 2006, Proc Natl Acad Sci US A, Vol. 103, p. 3687-3692. Also, "hsa-mir-575" (miRBase Accession No. MI0003582, SEQ ID NO: 309) having a hairpin-like structure is known as a precursor of "hsa-miR-575".

The term "hsa-miR-6805-5p gene" or "hsa-miR-6805-5p" used herein includes the hsa-miR-6805-5p gene (miRBase Accession No. MIMAT0027510) described in SEQ ID NO: 33, a homolog or an ortholog of a different organism species, and the like. The hsa-miR-6805-5p gene can be obtained by a method described in Ladewig E et al., 2012, Genome Res, Vol. 22, p. 1634-1645. Also, "hsa-mir-6805" (miRBase Accession No. MI0022650, SEQ ID NO: 310) having a hairpin-like structure is known as a precursor of "hsa-miR-6805-5p".

The term "hsa-miR-4758-5p gene" or "hsa-miR-4758-5p" used herein includes the hsa-miR-4758-5p gene (miRBase Accession No. MIMAT0019903) described in SEQ ID NO: 34, a homolog or an ortholog of a different organism species, and the like. The hsa-miR-4758-5p gene can be obtained by a method described in Persson H et al., 2011, Cancer Res, Vol. 71, p. 78-86. Also, "hsa-mir-4758" (miRBase Accession No. MI0017399, SEQ ID NO: 311) having a hairpin-like structure is known as a precursor of "hsa-miR-4758-5p".

The term "hsa-miR-3663-3p gene" or "hsa-miR-3663-3p" used herein includes the hsa-miR-3663-3p gene (miRBase Accession No. MIMAT0018085) described in SEQ ID NO: 35, a homolog or an ortholog of a different organism species, and the like. The hsa-miR-3663-3p gene can be obtained by a method described in Liao J Y et al., 2010, PLoS One, Vol. 5, e10563. Also, "hsa-mir-3663" (miRBase Accession No. MI0016064, SEQ ID NO: 312) having a hairpin-like structure is known as a precursor of "hsa-miR-3663-3p".

The term "hsa-miR-4530 gene" or "hsa-miR-4530" used herein includes the hsa-miR-4530 gene (miRBase Accession No. MIMAT0019069) described in SEQ ID NO: 36, a homolog or an ortholog of a different organism species, and the like. The hsa-miR-4530 gene can be obtained by a method described in Jima D D et al., 2010, Blood, Vol. 116, e118-e127. Also, "hsa-mir-4530" (miRBase Accession No. MI0016897, SEQ ID NO: 313) having a hairpin-like structure is known as a precursor of "hsa-miR-4530".

The term "hsa-miR-6798-5p gene" or "hsa-miR-6798-5p" used herein includes the hsa-miR-6798-5p gene (miRBase Accession No. MIMAT0027496) described in SEQ ID NO: 37, a homolog or an ortholog of a different organism species, and the like. The hsa-miR-6798-5p gene can be obtained by a method described in Ladewig E et al., 2012, Genome Res, Vol. 22, p. 1634-1645. Also, "hsa-mir-6798" (miRBase Accession No. MI0022643, SEQ ID NO: 314) having a hairpin-like structure is known as a precursor of "hsa-miR-6798-5p".

The term "hsa-miR-6781-5p gene" or "hsa-miR-6781-5p" used herein includes the hsa-miR-6781-5p gene (miRBase Accession No. MIMAT0027462) described in SEQ ID NO: 38, a homolog or an ortholog of a different organism species, and the like. The hsa-miR-6781-5p gene can be obtained by a method described in Ladewig E et al., 2012, Genome Res, Vol. 22, p. 1634-1645. Also, "hsa-mir-6781" (miRBase Accession No. MI0022626, SEQ ID NO: 315) having a hairpin-like structure is known as a precursor of "hsa-miR-6781-5p".

The term "hsa-miR-885-3p gene" or "hsa-miR-885-3p" used herein includes the hsa-miR-885-3p gene (miRBase Accession No. MIMAT0004948) described in SEQ ID NO: 39, a homolog or an ortholog of a different organism species, and the like. The hsa-miR-885-3p gene can be obtained by a method described in Berezikov E et al., 2006, Genome Res, Vol. 16, p. 1289-1298. Also, "hsa-mir-885" (miRBase Accession No. MI0005560, SEQ ID NO: 316) having a hairpin-like structure is known as a precursor of "hsa-miR-885-3p".

The term "hsa-miR-1273g-3p gene" or "hsa-miR-1273g-3p" used herein includes the hsa-miR-1273g-3p gene (miRBase Accession No. MIMAT0022742) described in SEQ ID NO: 40, a homolog or an ortholog of a different organism species, and the like. The hsa-miR-1273g-3p gene can be obtained by a method described in Reshmi G et al., 2011, Genomics, Vol. 97, p. 333-340. Also, "hsa-mir-1273g" (miRBase Accession No. MI0018003, SEQ ID NO: 317) having a hairpin-like structure is known as a precursor of "hsa-miR-1273g-3p".

The term "hsa-miR-4787-3p gene" or "hsa-miR-4787-3p" used herein includes the hsa-miR-4787-3p gene (miRBase Accession No. MIMAT0019957) described in SEQ ID NO: 41, a homolog or an ortholog of a different organism species, and the like. The hsa-miR-4787-3p gene can be obtained by a method described in Persson H et al., 2011, Cancer Res, Vol. 71, p. 78-86. Also, "hsa-mir-4787" (miRBase Accession No. MI0017434, SEQ ID NO: 318) having a hairpin-like structure is known as a precursor of "hsa-miR-4787-3p".

The term "hsa-miR-4454 gene" or "hsa-miR-4454" used herein includes the hsa-miR-4454 gene (miRBase Accession No. MIMAT0018976) described in SEQ ID NO: 42, a homolog or an ortholog of a different organism species, and the like. The hsa-miR-4454 gene can be obtained by a method described in Jima D D et al., 2010, Blood, Vol. 116, e118-e127. Also, "hsa-mir-4454" (miRBase Accession No. MI0016800, SEQ ID NO: 319) having a hairpin-like structure is known as a precursor of "hsa-miR-4454".

The term "hsa-miR-4706 gene" or "hsa-miR-4706" used herein includes the hsa-miR-4706 gene (miRBase Accession No. MIMAT0019806) described in SEQ ID NO: 43, a homolog or an ortholog of a different organism species, and the like. The hsa-miR-4706 gene can be obtained by a method described in Persson H et al., 2011, Cancer Res, Vol. 71, p. 78-86. Also, "hsa-mir-4706" (miRBase Accession No. MI0017339, SEQ ID NO: 320) having a hairpin-like structure is known as a precursor of "hsa-miR-4706".

The term "hsa-miR-1249-3p gene" or "hsa-miR-1249-3p" used herein includes the hsa-miR-1249-3p gene (miRBase Accession No. MIMAT0005901) described in SEQ ID NO: 44, a homolog or an ortholog of a different organism species, and the like. The hsa-miR-1249-3p gene can be obtained by a method described in Morin R D et al., 2008, Genome Res, Vol. 18, p. 610-621. Also, "hsa-mir-1249" (miRBase Accession No. MI0006384, SEQ ID NO: 321) having a hairpin-like structure is known as a precursor of "hsa-miR-1249-3p".

The term "hsa-miR-887-3p gene" or "hsa-miR-887-3p" used herein includes the hsa-miR-887-3p gene (miRBase Accession No. MIMAT0004951) described in SEQ ID NO: 45, a homolog or an ortholog of a different organism species, and the like. The hsa-miR-887-3p gene can be obtained by a method described in Berezikov E et al., 2006, Genome Res, Vol. 16, p. 1289-1298. Also, "hsa-mir-887" (miRBase Accession No. MI0005562, SEQ ID NO: 322) having a hairpin-like structure is known as a precursor of "hsa-miR-887-3p".

The term "hsa-miR-6786-5p gene" or "hsa-miR-6786-5p" used herein includes the hsa-miR-6786-5p gene (miRBase Accession No. MIMAT0027472) described in SEQ ID NO: 46, a homolog or an ortholog of a different organism species, and the like. The hsa-miR-6786-5p gene can be obtained by a method described in Ladewig E et al., 2012, Genome Res, Vol. 22, p. 1634-1645. Also, "hsa-mir-6786" (miRBase Accession No. MI0022631, SEQ ID NO: 323) having a hairpin-like structure is known as a precursor of "hsa-miR-6786-5p".

The term "hsa-miR-1238-5p gene" or "hsa-miR-1238-5p" used herein includes the hsa-miR-1238-5p gene (miRBase Accession No. MIMAT0022947) described in SEQ ID NO: 47, a homolog or an ortholog of a different organism species, and the like. The hsa-miR-1238-5p gene can be obtained by a method described in Berezikov E et al., 2007, Mol Cell, Vol. 28, p. 328-336. Also, "hsa-mir-1238" (miRBase Accession No. MI0006328, SEQ ID NO: 324) having a hairpin-like structure is known as a precursor of "hsa-miR-1238-5p".

The term "hsa-miR-6749-5p gene" or "hsa-miR-6749-5p" used herein includes the hsa-miR-6749-5p gene (miRBase Accession No. MIMAT0027398) described in SEQ ID NO: 48, a homolog or an ortholog of a different organism species, and the like. The hsa-miR-6749-5p gene can be obtained by a method described in Ladewig E et al., 2012, Genome Res, Vol. 22, p. 1634-1645. Also, "hsa-mir-6749" (miRBase Accession No. MI0022594, SEQ ID NO: 325) having a hairpin-like structure is known as a precursor of "hsa-miR-6749-5p".

The term "hsa-miR-6729-5p gene" or "hsa-miR-6729-5p" used herein includes the hsa-miR-6729-5p gene (miRBase Accession No. MIMAT0027359) described in SEQ ID NO: 49, a homolog or an ortholog of a different organism species, and the like. The hsa-miR-6729-5p gene can be obtained by a method described in Ladewig E et al., 2012, Genome Res, Vol. 22, p. 1634-1645. Also, "hsa-mir-6729" (miRBase Accession No. MI0022574, SEQ ID NO: 326) having a hairpin-like structure is known as a precursor of "hsa-miR-6729-5p".

The term "hsa-miR-6825-5p gene" or "hsa-miR-6825-5p" used herein includes the hsa-miR-6825-5p gene (miRBase Accession No. MIMAT0027550) described in SEQ ID NO: 50, a homolog or an ortholog of a different organism species, and the like. The hsa-miR-6825-5p gene can be obtained by a method described in Ladewig E et al., 2012, Genome Res, Vol. 22, p. 1634-1645. Also, "hsa-mir-6825" (miRBase Accession No. MI0022670, SEQ ID NO: 327) having a hairpin-like structure is known as a precursor of "hsa-miR-6825-5p".

The term "hsa-miR-663b gene" or "hsa-miR-663b" used herein includes the hsa-miR-663b gene (miRBase Accession No. MIMAT0005867) described in SEQ ID NO: 51, a homolog or an ortholog of a different organism species, and the like. The hsa-miR-663b gene can be obtained by a method described in Takada S et al., 2008, Leukemia, Vol. 22, p. 1274-1278. Also, "hsa-mir-663b" (miRBase Accession No. MI0006336, SEQ ID NO: 328) having a hairpin-like structure is known as a precursor of "hsa-miR-663b".

The term "hsa-miR-6858-5p gene" or "hsa-miR-6858-5p" used herein includes the hsa-miR-6858-5p gene (miRBase Accession No. MIMAT0027616) described in SEQ ID NO: 52, a homolog or an ortholog of a different organism species, and the like. The hsa-miR-6858-5p gene can be obtained by a method described in Ladewig E et al., 2012, Genome Res, Vol. 22, p. 1634-1645. Also, "hsa-mir-6858" (miRBase Accession No. MI0022704, SEQ ID NO: 329) having a hairpin-like structure is known as a precursor of "hsa-miR-6858-5p".

The term "hsa-miR-4690-5p gene" or "hsa-miR-4690-5p" used herein includes the hsa-miR-4690-5p gene (miRBase Accession No. MIMAT0019779) described in SEQ ID NO: 53, a homolog or an ortholog of a different organism species, and the like. The hsa-miR-4690-5p gene can be obtained by a method described in Persson H et al., 2011, Cancer Res, Vol. 71, p. 78-86. Also, "hsa-mir-4690" (miRBase Accession No. MI0017323, SEQ ID NO: 330) having a hairpin-like structure is known as a precursor of "hsa-miR-4690-5p".

The term "hsa-miR-6765-5p gene" or "hsa-miR-6765-5p" used herein includes the hsa-miR-6765-5p gene (miRBase Accession No. MIMAT0027430) described in SEQ ID NO: 54, a homolog or an ortholog of a different organism species, and the like. The hsa-miR-6765-5p gene can be obtained by a method described in Ladewig E et al., 2012, Genome Res, Vol. 22, p. 1634-1645. Also, "hsa-mir-6765" (miRBase Accession No. MI0022610, SEQ ID NO: 331) having a hairpin-like structure is known as a precursor of "hsa-miR-6765-5p".

The term "hsa-miR-4710 gene" or "hsa-miR-4710" used herein includes the hsa-miR-4710 gene (miRBase Accession No. MIMAT0019815) described in SEQ ID NO: 55, a homolog or an ortholog of a different organism species, and the like. The hsa-miR-4710 gene can be obtained by a method described in Persson H et al., 2011, Cancer Res, Vol. 71, p. 78-86. Also, "hsa-mir-4710" (miRBase Accession No. MI0017344, SEQ ID NO: 332) having a hairpin-like structure is known as a precursor of "hsa-miR-4710".

The term "hsa-miR-6775-5p gene" or "hsa-miR-6775-5p" used herein includes the hsa-miR-6775-5p gene (miRBase Accession No. MIMAT0027450) described in SEQ ID NO: 56, a homolog or an ortholog of a different organism species, and the like. The hsa-miR-6775-5p gene can be obtained by a method described in Ladewig E et al., 2012, Genome Res, Vol. 22, p. 1634-1645. Also, "hsa-mir-6775" (miRBase Accession No. MI0022620, SEQ ID NO: 333) having a hairpin-like structure is known as a precursor of "hsa-miR-6775-5p".

The term "hsa-miR-371a-5p gene" or "hsa-miR-371a-5p" used herein includes the hsa-miR-371a-5p gene (miRBase Accession No. MIMAT0004687) described in SEQ ID NO: 57, a homolog or an ortholog of a different organism species, and the like. The hsa-miR-371a-5p gene can be obtained by a method described in Suh M R et al., 2004, Dev Biol, Vol. 270, p. 488-498. Also, "hsa-mir-371a" (miRBase Accession No. MI0000779, SEQ ID NO: 334) having a hairpin-like structure is known as a precursor of "hsa-miR-371a-5p".

The term "hsa-miR-6816-5p gene" or "hsa-miR-6816-5p" used herein includes the hsa-miR-6816-5p gene (miRBase Accession No. MIMAT0027532) described in SEQ ID NO: 58, a homolog or an ortholog of a different organism species, and the like. The hsa-miR-6816-5p gene can be obtained by a method described in Ladewig E et al., 2012, Genome Res, Vol. 22, p. 1634-1645. Also, "hsa-mir-6816" (miRBase Accession No. MI0022661, SEQ ID NO: 335) having a hairpin-like structure is known as a precursor of "hsa-miR-6816-5p".

The term "hsa-miR-296-3p gene" or "hsa-miR-296-3p" used herein includes the hsa-miR-296-3p gene (miRBase Accession No. MIMAT0004679) described in SEQ ID NO: 59, a homolog or an ortholog of a different organism species, and the like. The hsa-miR-296-3p gene can be obtained by a method described in Houbaviy H B et al., 2003, Dev Cell, Vol. 5, p. 351-358. Also, "hsa-mir-296" (miRBase Accession No. MI0000747, SEQ ID NO: 336) having a hairpin-like structure is known as a precursor of "hsa-miR-296-3p".

The term "hsa-miR-7977 gene" or "hsa-miR-7977" used herein includes the hsa-miR-7977 gene (miRBase Accession No. MIMAT0031180) described in SEQ ID NO: 60, a homolog or an ortholog of a different organism species, and the like. The hsa-miR-7977 gene can be obtained by a method described in Velthut-Meikas A et al., 2013, Mol Endocrinol, Vol. 27, p. 1128-1141. Also, "hsa-mir-7977" (miRBase Accession No. MI0025753, SEQ ID NO: 337) having a hairpin-like structure is known as a precursor of "hsa-miR-7977".

The term "hsa-miR-8069 gene" or "hsa-miR-8069" used herein includes the hsa-miR-8069 gene (miRBase Accession No. MIMAT0030996) described in SEQ ID NO: 61, a homolog or an ortholog of a different organism species, and the like. The hsa-miR-8069 gene can be obtained by a method described in Wang H J et al., 2013, Shock, Vol. 39, p. 480-487. Also, "hsa-mir-8069-1 and hsa-mir-8069-2" (miRBase Accession Nos. MI0025905 and MI0031519, SEQ ID NOs: 338 and 339) having a hairpin-like structure are known as precursors of "hsa-miR-8069".

The term "hsa-miR-6515-3p gene" or "hsa-miR-6515-3p" used herein includes the hsa-miR-6515-3p gene (miRBase Accession No. MIMAT0025487) described in SEQ ID NO: 62, a homolog or an ortholog of a different organism species, and the like. The hsa-miR-6515-3p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 340) having a hairpin-like structure is known as a precursor of "hsa-miR-6515-3p".

The term "hsa-miR-4687-5p gene" or "hsa-miR-4687-5p" used herein includes the hsa-miR-4687-5p gene (miRBase Accession No. MIMAT0019774) described in SEQ ID NO: 63, a homolog or an ortholog of a different organism species, and the like. The hsa-miR-4687-5p gene can be obtained by a method described in Persson H et al., 2011, Cancer Res, Vol. 71, p. 78-86. Also, "hsa-mir-4687" (miRBase Accession No. MI0017319, SEQ ID NO: 341) having a hairpin-like structure is known as a precursor of "hsa-miR-4687-5p".

The term "hsa-miR-1343-5p gene" or "hsa-miR-1343-5p" used herein includes the hsa-miR-1343-5p gene (miRBase Accession No. MIMAT0027038) described in SEQ ID NO: 64, a homolog or an ortholog of a different organism species, and the like. The hsa-miR-1343-5p gene can be obtained by a method described in Persson H et al., 2011, Cancer Res, Vol. 71, p. 78-86. Also, "hsa-mir-1343" (miRBase Accession No. MI0017320, SEQ ID NO: 294) having a hairpin-like structure is known as a precursor of "hsa-miR-1343-5p".

The term "hsa-miR-7110-5p gene" or "hsa-miR-7110-5p" used herein includes the hsa-miR-7110-5p gene (miRBase Accession No. MIMAT0028117) described in SEQ ID NO: 65, a homolog or an ortholog of a different organism species, and the like. The hsa-miR-7110-5p gene can be obtained by a method described in Ladewig E et al., 2012, Genome Res, Vol. 22, p. 1634-1645. Also, "hsa-mir-7110" (miRBase Accession No. MI0022961, SEQ ID NO: 342) having a hairpin-like structure is known as a precursor of "hsa-miR-7110-5p".

The term "hsa-miR-4525 gene" or "hsa-miR-4525" used herein includes the hsa-miR-4525 gene (miRBase Accession No. MIMAT0019064) described in SEQ ID NO: 66, a homolog or an ortholog of a different organism species, and the like. The hsa-miR-4525 gene can be obtained by a method described in Jima D D et al., 2010, Blood, Vol. 116, e118-e127. Also, "hsa-mir-4525" (miRBase Accession No. MI0016892, SEQ ID NO: 343) having a hairpin-like structure is known as a precursor of "hsa-miR-4525".

The term "hsa-miR-3158-5p gene" or "hsa-miR-3158-5p" used herein includes the hsa-miR-3158-5p gene (miRBase Accession No. MIMAT0019211) described in SEQ ID NO: 67, a homolog or an ortholog of a different organism species, and the like. The hsa-miR-3158-5p gene can be obtained by a method described in Creighton C J et al., 2010, PLoS One, Vol. 5, e9637. Also, "hsa-mir-3158-1 and hsa-mir-3158-2" (miRBase Accession Nos. MI0014186 and MI0014187, SEQ ID NOs: 344 and 345) having a hairpin-like structure are known as precursors of "hsa-miR-3158-5p".

The term "hsa-miR-6787-5p gene" or "hsa-miR-6787-5p" used herein includes the hsa-miR-6787-5p gene (miRBase Accession No. MIMAT0027474) described in SEQ ID NO: 68, a homolog or an ortholog of a different organism species, and the like. The hsa-miR-6787-5p gene can be obtained by a method described in Ladewig E et al., 2012, Genome Res, Vol. 22, p. 1634-1645. Also, "hsa-mir-6787" (miRBase Accession No. MI0022632, SEQ ID NO: 346) having a hairpin-like structure is known as a precursor of "hsa-miR-6787-5p".

The term "hsa-miR-614 gene" or "hsa-miR-614" used herein includes the hsa-miR-614 gene (miRBase Accession No. MIMAT0003282) described in SEQ ID NO: 69, a homolog or an ortholog of a different organism species, and the like. The hsa-miR-614 gene can be obtained by a method described in Cummins J M et al., 2006, Proc Natl Acad Sci US A, Vol. 103, p. 3687-3692. Also, "hsa-mir-614" (miRBase Accession No. MI0003627, SEQ ID NO: 347) having a hairpin-like structure is known as a precursor of "hsa-miR-614".

The term "hsa-miR-4689 gene" or "hsa-miR-4689" used herein includes the hsa-miR-4689 gene (miRBase Accession No. MIMAT0019778) described in SEQ ID NO: 70, a homolog or an ortholog of a different organism species, and the like. The hsa-miR-4689 gene can be obtained by a method described in Persson H et al., 2011, Cancer Res, Vol. 71, p. 78-86. Also, "hsa-mir-4689" (miRBase Accession No. MI0017322, SEQ ID NO: 348) having a hairpin-like structure is known as a precursor of "hsa-miR-4689".

The term "hsa-miR-1185-2-3p gene" or "hsa-miR-1185-2-3p" used herein includes the hsa-miR-1185-2-3p gene (miRBase Accession No. MIMAT0022713) described in SEQ ID NO: 71, a homolog or an ortholog of a different organism species, and the like. The hsa-miR-1185-2-3p gene can be obtained by a method described in Berezikov E et al., 2006, Genome Res, Vol. 16, p. 1289-1298. Also, "hsa-mir-1185-2" (miRBase Accession No. MI0003821, SEQ ID NO: 349) having a hairpin-like structure is known as a precursor of "hsa-miR-1185-2-3p".

The term "hsa-miR-1268b gene" or "hsa-miR-1268b" used herein includes the hsa-miR-1268b gene (miRBase Accession No. MIMAT0018925) described in SEQ ID NO: 72, a homolog or an ortholog of a different organism species, and the like. The hsa-miR-1268b gene can be obtained by a method described in Jima D D et al., 2010, Blood, Vol. 116, e118-e127. Also, "hsa-mir-1268b" (miRBase Accession No. MI0016748, SEQ ID NO: 350) having a hairpin-like structure is known as a precursor of "hsa-miR-1268b".

The term "hsa-miR-1228-3p gene" or "hsa-miR-1228-3p" used herein includes the hsa-miR-1228-3p gene (miRBase Accession No. MIMAT0005583) described in SEQ ID NO: 73, a homolog or an ortholog of a different organism species, and the like. The hsa-miR-1228-3p gene can be obtained by a method described in Berezikov E et al., 2007, Mol Cell, Vol. 28, p. 328-336. Also, "hsa-mir-1228" (miRBase Accession No. MI0006318, SEQ ID NO: 278) having a hairpin-like structure is known as a precursor of "hsa-miR-1228-3p".

The term "hsa-miR-1185-1-3p gene" or "hsa-miR-1185-1-3p" used herein includes the hsa-miR-1185-1-3p gene (miRBase Accession No. MIMAT0022838) described in SEQ ID NO: 74, a homolog or an ortholog of a different organism species, and the like. The hsa-miR-1185-1-3p gene can be obtained by a method described in Berezikov E et al., 2006, Genome Res, Vol. 16, p. 1289-1298. Also, "hsa-mir-1185-1" (miRBase Accession No. MI0003844, SEQ ID NO: 351) having a hairpin-like structure is known as a precursor of "hsa-miR-1185-1-3p".

The term "hsa-miR-940 gene" or "hsa-miR-940" used herein includes the hsa-miR-940 gene (miRBase Accession No. MIMAT0004983) described in SEQ ID NO: 75, a homolog or an ortholog of a different organism species, and the like. The hsa-miR-940 gene can be obtained by a method described in Lui W O et al., 2007, Cancer Res, Vol. 67, p. 6031-6043. Also, "hsa-mir-940" (miRBase Accession No. MI0005762, SEQ ID NO: 352) having a hairpin-like structure is known as a precursor of "hsa-miR-940".

The term "hsa-miR-939-5p gene" or "hsa-miR-939-5p" used herein includes the hsa-miR-939-5p gene (miRBase Accession No. MIMAT0004982) described in SEQ ID NO: 76, a homolog or an ortholog of a different organism species, and the like. The hsa-miR-939-5p gene can be obtained by a method described in Lui W O et al., 2007, Cancer Res, Vol. 67, p. 6031-6043. Also, "hsa-mir-939" (miRBase Accession No. MI0005761, SEQ ID NO: 353) having a hairpin-like structure is known as a precursor of "hsa-miR-939-5p".

The term "hsa-miR-6757-5p gene" or "hsa-miR-6757-5p" used herein includes the hsa-miR-6757-5p gene (miRBase Accession No. MIMAT0027414) described in SEQ ID NO: 77, a homolog or an ortholog of a different organism species, and the like. The hsa-miR-6757-5p gene can be obtained by a method described in Ladewig E et al., 2012, Genome Res, Vol. 22, p. 1634-1645. Also, "hsa-mir-6757" (miRBase Accession No. MI0022602, SEQ ID NO: 354) having a hairpin-like structure is known as a precursor of "hsa-miR-6757-5p".

The term "hsa-miR-1275 gene" or "hsa-miR-1275" used herein includes the hsa-miR-1275 gene (miRBase Accession No. MIMAT0005929) described in SEQ ID NO: 78, a homolog or an ortholog of a different organism species, and the like. The hsa-miR-1275 gene can be obtained by a method described in Morin R D et al., 2008, Genome Res, Vol. 18, p. 610-621. Also, "hsa-mir-1275" (miRBase Accession No. MI0006415, SEQ ID NO: 355) having a hairpin-like structure is known as a precursor of "hsa-miR-1275".

The term "hsa-miR-5001-5p gene" or "hsa-miR-5001-5p" used herein includes the hsa-miR-5001-5p gene (miRBase Accession No. MIMAT0021021) described in SEQ ID NO: 79, a homolog or an ortholog of a different organism species, and the like. The hsa-miR-5001-5p gene can be obtained by a method described in Hansen T B et al., 2011, RNA Biol, Vol. 8, p. 378-383. Also, "hsa-mir-5001" (miRBase Accession No. MI0017867, SEQ ID NO: 356) having a hairpin-like structure is known as a precursor of "hsa-miR-5001-5p".

The term "hsa-miR-6826-5p gene" or "hsa-miR-6826-5p" used herein includes the hsa-miR-6826-5p gene (miRBase Accession No. MIMAT0027552) described in SEQ ID NO: 80, a homolog or an ortholog of a different organism species, and the like. The hsa-miR-6826-5p gene can be obtained by a method described in Ladewig E et al., 2012, Genome Res, Vol. 22, p. 1634-1645. Also, "hsa-mir-6826" (miRBase Accession No. MI0022671, SEQ ID NO: 357) having a hairpin-like structure is known as a precursor of "hsa-miR-6826-5p".

The term "hsa-miR-6765-3p gene" or "hsa-miR-6765-3p" used herein includes the hsa-miR-6765-3p gene (miRBase Accession No. MIMAT0027431) described in SEQ ID NO: 81, a homolog or an ortholog of a different organism species, and the like. The hsa-miR-6765-3p gene can be obtained by a method described in Ladewig E et al., 2012, Genome Res, Vol. 22, p. 1634-1645. Also, "hsa-mir-6765" (miRBase Accession No. MI0022610, SEQ ID NO: 331) having a hairpin-like structure is known as a precursor of "hsa-miR-6765-3p".

The term "hsa-miR-3679-3p gene" or "hsa-miR-3679-3p" used herein includes the hsa-miR-3679-3p gene (miRBase Accession No. MIMAT0018105) described in SEQ ID NO: 82, a homolog or an ortholog of a different organism species, and the like. The hsa-miR-3679-3p gene can be obtained by a method described in Creighton C J et al., 2010, PLoS One, Vol. 5, e9637. Also, "hsa-mir-3679" (miRBase Accession No. MI0016080, SEQ ID NO: 358) having a hairpin-like structure is known as a precursor of "hsa-miR-3679-3p".

The term "hsa-miR-4718 gene" or "hsa-miR-4718" used herein includes the hsa-miR-4718 gene (miRBase Accession No. MIMAT0019831) described in SEQ ID NO: 83, a homolog or an ortholog of a different organism species, and the like. The hsa-miR-4718 gene can be obtained by a method described in Persson H et al., 2011, Cancer Res, Vol. 71, p. 78-86. Also, "hsa-mir-4718" (miRBase Accession No. MI0017353, SEQ ID NO: 359) having a hairpin-like structure is known as a precursor of "hsa-miR-4718".

The term "hsa-miR-4286 gene" or "hsa-miR-4286" used herein includes the hsa-miR-4286 gene (miRBase Accession No. MIMAT0016916) described in SEQ ID NO: 84, a homolog or an ortholog of a different organism species, and the like. The hsa-miR-4286 gene can be obtained by a method described in Goff L A et al., 2009, PLoS One, Vol. 4, e7192. Also, "hsa-mir-4286" (miRBase Accession No. MI0015894, SEQ ID NO: 360) having a hairpin-like structure is known as a precursor of "hsa-miR-4286".

The term "hsa-miR-8059 gene" or "hsa-miR-8059" used herein includes the hsa-miR-8059 gene (miRBase Accession No. MIMAT0030986) described in SEQ ID NO: 85, a homolog or an ortholog of a different organism species, and the like. The hsa-miR-8059 gene can be obtained by a method described in Wang H J et al., 2013, Shock, Vol. 39, p. 480-487. Also, "hsa-mir-8059" (miRBase Accession No. MI0025895, SEQ ID NO: 361) having a hairpin-like structure is known as a precursor of "hsa-miR-8059".

The term "hsa-miR-4447 gene" or "hsa-miR-4447" used herein includes the hsa-miR-4447 gene (miRBase Accession No. MIMAT0018966) described in SEQ ID NO: 86, a homolog or an ortholog of a different organism species, and the like. The hsa-miR-4447 gene can be obtained by a method described in Jima D D et al., 2010, Blood, Vol. 116, e118-e127. Also, "hsa-mir-4447" (miRBase Accession No. MI0016790, SEQ ID NO: 362) having a hairpin-like structure is known as a precursor of "hsa-miR-4447".

The term "hsa-miR-4448 gene" or "hsa-miR-4448" used herein includes the hsa-miR-4448 gene (miRBase Accession No. MIMAT0018967) described in SEQ ID NO: 87, a homolog or an ortholog of a different organism species, and the like. The hsa-miR-4448 gene can be obtained by a method described in Jima D D et al., 2010, Blood, Vol. 116, e118-e127. Also, "hsa-mir-4448" (miRBase Accession No.

MI0016791, SEQ ID NO: 363) having a hairpin-like structure is known as a precursor of "hsa-miR-4448".

The term "hsa-miR-658 gene" or "hsa-miR-658" used herein includes the hsa-miR-658 gene (miRBase Accession No. MIMAT0003336) described in SEQ ID NO: 88, a homolog or an ortholog of a different organism species, and the like. The hsa-miR-658 gene can be obtained by a method described in Cummins J M et al., 2006, Proc Natl Acad Sci US A, Vol. 103, p. 3687-3692. Also, "hsa-mir-658" (miRBase Accession No. MI0003682, SEQ ID NO: 364) having a hairpin-like structure is known as a precursor of "hsa-miR-658".

The term "hsa-miR-6766-3p gene" or "hsa-miR-6766-3p" used herein includes the hsa-miR-6766-3p gene (miRBase Accession No. MIMAT0027433) described in SEQ ID NO: 89, a homolog or an ortholog of a different organism species, and the like. The hsa-miR-6766-3p gene can be obtained by a method described in Ladewig E et al., 2012, Genome Res, Vol. 22, p. 1634-1645. Also, "hsa-mir-6766" (miRBase Accession No. MI0022611, SEQ ID NO: 365) having a hairpin-like structure is known as a precursor of "hsa-miR-6766-3p".

The term "hsa-miR-197-5p gene" or "hsa-miR-197-5p" used herein includes the hsa-miR-197-5p gene (miRBase Accession No. MIMAT0022691) described in SEQ ID NO: 90, a homolog or an ortholog of a different organism species, and the like. The hsa-miR-197-5p gene can be obtained by a method described in Lagos-Quintana M et al., 2003, RNA, Vol. 9, p. 175-179. Also, "hsa-mir-197" (miRBase Accession No. MI0000239, SEQ ID NO: 366) having a hairpin-like structure is known as a precursor of "hsa-miR-197-5p".

The term "hsa-miR-6887-5p gene" or "hsa-miR-6887-5p" used herein includes the hsa-miR-6887-5p gene (miRBase Accession No. MIMAT0027674) described in SEQ ID NO: 91, a homolog or an ortholog of a different organism species, and the like. The hsa-miR-6887-5p gene can be obtained by a method described in Ladewig E et al., 2012, Genome Res, Vol. 22, p. 1634-1645. Also, "hsa-mir-6887" (miRBase Accession No. MI0022734, SEQ ID NO: 367) having a hairpin-like structure is known as a precursor of "hsa-miR-6887-5p".

The term "hsa-miR-6742-5p gene" or "hsa-miR-6742-5p" used herein includes the hsa-miR-6742-5p gene (miRBase Accession No. MIMAT0027385) described in SEQ ID NO: 92, a homolog or an ortholog of a different organism species, and the like. The hsa-miR-6742-5p gene can be obtained by a method described in Ladewig E et al., 2012, Genome Res, Vol. 22, p. 1634-1645. Also, "hsa-mir-6742" (miRBase Accession No. MI0022587, SEQ ID NO: 368) having a hairpin-like structure is known as a precursor of "hsa-miR-6742-5p".

The term "hsa-miR-6729-3p gene" or "hsa-miR-6729-3p" used herein includes the hsa-miR-6729-3p gene (miRBase Accession No. MIMAT0027360) described in SEQ ID NO: 93, a homolog or an ortholog of a different organism species, and the like. The hsa-miR-6729-3p gene can be obtained by a method described in Ladewig E et al., 2012, Genome Res, Vol. 22, p. 1634-1645. Also, "hsa-mir-6729" (miRBase Accession No. MI0022574, SEQ ID NO: 326) having a hairpin-like structure is known as a precursor of "hsa-miR-6729-3p".

The term "hsa-miR-5090 gene" or "hsa-miR-5090" used herein includes the hsa-miR-5090 gene (miRBase Accession No. MIMAT0021082) described in SEQ ID NO: 94, a homolog or an ortholog of a different organism species, and the like. The hsa-miR-5090 gene can be obtained by a method described in Ding N et al., 2011, J Radiat Res, Vol. 52, p. 425-432. Also, "hsa-mir-5090" (miRBase Accession No. MI0017979, SEQ ID NO: 369) having a hairpin-like structure is known as a precursor of "hsa-miR-5090".

The term "hsa-miR-7975 gene" or "hsa-miR-7975" used herein includes the hsa-miR-7975 gene (miRBase Accession No. MIMAT0031178) described in SEQ ID NO: 95, a homolog or an ortholog of a different organism species, and the like. The hsa-miR-7975 gene can be obtained by a method described in Velthut-Meikas A et al., 2013, Mol Endocrinol, Vol. 27, p. 1128-1141. Also, "hsa-mir-7975" (miRBase Accession No. MI0025751, SEQ ID NO: 370) having a hairpin-like structure is known as a precursor of "hsa-miR-7975".

The term "hsa-miR-4505 gene" or "hsa-miR-4505" used herein includes the hsa-miR-4505 gene (miRBase Accession No. MIMAT0019041) described in SEQ ID NO: 96, a homolog or an ortholog of a different organism species, and the like. The hsa-miR-4505 gene can be obtained by a method described in Jima D D et al., 2010, Blood, Vol. 116, e118-e127. Also, "hsa-mir-4505" (miRBase Accession No. MI0016868, SEQ ID NO: 371) having a hairpin-like structure is known as a precursor of "hsa-miR-4505".

The term "hsa-miR-6889-5p gene" or "hsa-miR-6889-5p" used herein includes the hsa-miR-6889-5p gene (miRBase Accession No. MIMAT0027678) described in SEQ ID NO: 97, a homolog or an ortholog of a different organism species, and the like. The hsa-miR-6889-5p gene can be obtained by a method described in Ladewig E et al., 2012, Genome Res, Vol. 22, p. 1634-1645. Also, "hsa-mir-6889" (miRBase Accession No. MI0022736, SEQ ID NO: 372) having a hairpin-like structure is known as a precursor of "hsa-miR-6889-5p".

The term "hsa-miR-4708-3p gene" or "hsa-miR-4708-3p" used herein includes the hsa-miR-4708-3p gene (miRBase Accession No. MIMAT0019810) described in SEQ ID NO: 98, a homolog or an ortholog of a different organism species, and the like. The hsa-miR-4708-3p gene can be obtained by a method described in Persson H et al., 2011, Cancer Res, Vol. 71, p. 78-86. Also, "hsa-mir-4708" (miRBase Accession No. MI0017341, SEQ ID NO: 373) having a hairpin-like structure is known as a precursor of "hsa-miR-4708-3p".

The term "hsa-miR-6131 gene" or "hsa-miR-6131" used herein includes the hsa-miR-6131 gene (miRBase Accession No. MIMAT0024615) described in SEQ ID NO: 99, a homolog or an ortholog of a different organism species, and the like. The hsa-miR-6131 gene can be obtained by a method described in Dannemann M et al., 2012, Genome Biol Evol, Vol. 4, p. 552-564. Also, "hsa-mir-6131" (miRBase Accession No. MI0021276, SEQ ID NO: 374) having a hairpin-like structure is known as a precursor of "hsa-miR-6131".

The term "hsa-miR-1225-3p gene" or "hsa-miR-1225-3p" used herein includes the hsa-miR-1225-3p gene (miRBase Accession No. MIMAT0005573) described in SEQ ID NO: 100, a homolog or an ortholog of a different organism species, and the like. The hsa-miR-1225-3p gene can be obtained by a method described in Berezikov E et al., 2007, Mol Cell, Vol. 28, p. 328-336. Also, "hsa-mir-1225" (miRBase Accession No. MI0006311, SEQ ID NO: 375) having a hairpin-like structure is known as a precursor of "hsa-miR-1225-3p".

The term "hsa-miR-6132 gene" or "hsa-miR-6132" used herein includes the hsa-miR-6132 gene (miRBase Accession No. MIMAT0024616) described in SEQ ID NO: 101, a homolog or an ortholog of a different organism species, and the like. The hsa-miR-6132 gene can be obtained by a method described in Dannemann M et al., 2012, Genome Biol Evol, Vol. 4, p. 552-564. Also, "hsa-mir-6132" (miRBase Accession No. MI0021277, SEQ ID NO: 376) having a hairpin-like structure is known as a precursor of "hsa-miR-6132".

The term "hsa-miR-4734 gene" or "hsa-miR-4734" used herein includes the hsa-miR-4734 gene (miRBase Accession No. MIMAT0019859) described in SEQ ID NO: 102, a homolog or an ortholog of a different organism species, and the like. The hsa-miR-4734 gene can be obtained by a method described in Persson H et al., 2011, Cancer Res, Vol. 71, p. 78-86. Also, "hsa-mir-4734" (miRBase Accession No. MI0017371, SEQ ID NO: 377) having a hairpin-like structure is known as a precursor of "hsa-miR-4734".

The term "hsa-miR-3194-3p gene" or "hsa-miR-3194-3p" used herein includes the hsa-miR-3194-3p gene (miRBase Accession No. MIMAT0019218) described in SEQ ID NO: 103, a homolog or an ortholog of a different organism species, and the like. The hsa-miR-3194-3p gene can be obtained by a method described in Stark M S et al., 2010, PLoS One, Vol. 5, e9685. Also, "hsa-mir-3194" (miRBase Accession No. MI0014239, SEQ ID NO: 378) having a hairpin-like structure is known as a precursor of "hsa-miR-3194-3p".

The term "hsa-miR-638 gene" or "hsa-miR-638" used herein includes the hsa-miR-638 gene (miRBase Accession No. MIMAT0003308) described in SEQ ID NO: 104, a homolog or an ortholog of a different organism species, and the like. The hsa-miR-638 gene can be obtained by a method described in Cummins J M et al., 2006, Proc Natl Acad Sci US A, Vol. 103, p. 3687-3692. Also, "hsa-mir-638" (miRBase Accession No. MI0003653, SEQ ID NO: 379) having a hairpin-like structure is known as a precursor of "hsa-miR-638".

The term "hsa-miR-2467-3p gene" or "hsa-miR-2467-3p" used herein includes the hsa-miR-2467-3p gene (miRBase Accession No. MIMAT0019953) described in SEQ ID NO: 105, a homolog or an ortholog of a different organism species, and the like. The hsa-miR-2467-3p gene can be obtained by a method described in Persson H et al., 2011, Cancer Res, Vol. 71, p. 78-86. Also, "hsa-mir-2467" (miRBase Accession No. MI0017432, SEQ ID NO: 380) having a hairpin-like structure is known as a precursor of "hsa-miR-2467-3p".

The term "hsa-miR-4728-5p gene" or "hsa-miR-4728-5p" used herein includes the hsa-miR-4728-5p gene (miRBase Accession No. MIMAT0019849) described in SEQ ID NO: 106, a homolog or an ortholog of a different organism species, and the like. The hsa-miR-4728-5p gene can be obtained by a method described in Persson H et al., 2011, Cancer Res, Vol. 71, p. 78-86. Also, "hsa-mir-4728" (miRBase Accession No. MI10017365, SEQ ID NO: 381) having a hairpin-like structure is known as a precursor of "hsa-miR-4728-5p".

The term "hsa-miR-5572 gene" or "hsa-miR-5572" used herein includes the hsa-miR-5572 gene (miRBase Accession No. MIMAT0022260) described in SEQ ID NO: 107, a homolog or an ortholog of a different organism species, and the like. The hsa-miR-5572 gene can be obtained by a method described in Tandon M et al., 2012, Oral Dis, Vol. 18, p. 127-131. Also, "hsa-mir-5572" (miRBase Accession No. MI0019117, SEQ ID NO: 382) having a hairpin-like structure is known as a precursor of "hsa-miR-5572".

The term "hsa-miR-6789-5p gene" or "hsa-miR-6789-5p" used herein includes the hsa-miR-6789-5p gene (miRBase Accession No. MIMAT0027478) described in SEQ ID NO: 108, a homolog or an ortholog of a different organism species, and the like. The hsa-miR-6789-5p gene can be obtained by a method described in Ladewig E et al., 2012, Genome Res, Vol. 22, p. 1634-1645. Also, "hsa-mir-6789" (miRBase Accession No. MI0022634, SEQ ID NO: 383) having a hairpin-like structure is known as a precursor of "hsa-miR-6789-5p".

The term "hsa-miR-8063 gene" or "hsa-miR-8063" used herein includes the hsa-miR-8063 gene (miRBase Accession No. MIMAT0030990) described in SEQ ID NO: 109, a homolog or an ortholog of a different organism species, and the like. The hsa-miR-8063 gene can be obtained by a method described in Wang H J et al., 2013, Shock, Vol. 39, p. 480-487. Also, "hsa-mir-8063" (miRBase Accession No. MI0025899, SEQ ID NO: 384) having a hairpin-like structure is known as a precursor of "hsa-miR-8063".

The term "hsa-miR-4429 gene" or "hsa-miR-4429" used herein includes the hsa-miR-4429 gene (miRBase Accession No. MIMAT0018944) described in SEQ ID NO: 110, a homolog or an ortholog of a different organism species, and the like. The hsa-miR-4429 gene can be obtained by a method described in Jima D D et al., 2010, Blood, Vol. 116, e118-e127. Also, "hsa-mir-4429" (miRBase Accession No. MI0016768, SEQ ID NO: 385) having a hairpin-like structure is known as a precursor of "hsa-miR-4429".

The term "hsa-miR-6840-3p gene" or "hsa-miR-6840-3p" used herein includes the hsa-miR-6840-3p gene (miRBase Accession No. MIMAT0027583) described in SEQ ID NO: 111, a homolog or an ortholog of a different organism species, and the like. The hsa-miR-6840-3p gene can be obtained by a method described in Ladewig E et al., 2012, Genome Res, Vol. 22, p. 1634-1645. Also, "hsa-mir-6840" (miRBase Accession No. MI0022686, SEQ ID NO: 386) having a hairpin-like structure is known as a precursor of "hsa-miR-6840-3p".

The term "hsa-miR-4476 gene" or "hsa-miR-4476" used herein includes the hsa-miR-4476 gene (miRBase Accession No. MIMAT0019003) described in SEQ ID NO: 112, a homolog or an ortholog of a different organism species, and the like. The hsa-miR-4476 gene can be obtained by a method described in Jima D D et al., 2010, Blood, Vol. 116, e118-e127. Also, "hsa-mir-4476" (miRBase Accession No. MI0016828, SEQ ID NO: 387) having a hairpin-like structure is known as a precursor of "hsa-miR-4476".

The term "hsa-miR-675-5p gene" or "hsa-miR-675-5p" used herein includes the hsa-miR-675-5p gene (miRBase Accession No. MIMAT0004284) described in SEQ ID NO: 113, a homolog or an ortholog of a different organism species, and the like. The hsa-miR-675-5p gene can be obtained by a method described in Cai X et al., 2007, RNA, Vol. 13, p. 313-316. Also, "hsa-mir-675" (miRBase Accession No. MI0005416, SEQ ID NO: 388) having a hairpin-like structure is known as a precursor of "hsa-miR-675-5p".

The term "hsa-miR-711 gene" or "hsa-miR-711" used herein includes the hsa-miR-711 gene (miRBase Accession No. MIMAT0012734) described in SEQ ID NO: 114, a homolog or an ortholog of a different organism species, and the like. The hsa-miR-711 gene can be obtained by a method described in Artzi S et al., 2008, BMC Bioinformatics, Vol. 9, p. 39. Also, "hsa-mir-711" (miRBase Accession No. MI0012488, SEQ ID NO: 389) having a hairpin-like structure is known as a precursor of "hsa-miR-711".

The term "hsa-miR-6875-5p gene" or "hsa-miR-6875-5p" used herein includes the hsa-miR-6875-5p gene (miRBase Accession No. MIMAT0027650) described in SEQ ID NO: 115, a homolog or an ortholog of a different organism species, and the like. The hsa-miR-6875-5p gene can be obtained by a method described in Ladewig E et al., 2012, Genome Res, Vol. 22, p. 1634-1645. Also, "hsa-mir-6875"

(miRBase Accession No. MI0022722, SEQ ID NO: 390) having a hairpin-like structure is known as a precursor of "hsa-miR-6875-5p".

The term "hsa-miR-3160-5p gene" or "hsa-miR-3160-5p" used herein includes the hsa-miR-3160-5p gene (miRBase Accession No. MIMAT0019212) described in SEQ ID NO: 116, a homolog or an ortholog of a different organism species, and the like. The hsa-miR-3160-5p gene can be obtained by a method described in Stark M S et al., 2010, PLoS One, Vol. 5, e9685. Also, "hsa-mir-3160-1 and hsa-mir-3160-2" (miRBase Accession Nos. MI0014189 and MI0014190, SEQ ID NOs: 391 and 392) having a hairpin-like structure are known as precursors of "hsa-miR-3160-5p".

The term "hsa-miR-1908-5p gene" or "hsa-miR-1908-5p" used herein includes the hsa-miR-1908-5p gene (miRBase Accession No. MIMAT0007881) described in SEQ ID NO: 117, a homolog or an ortholog of a different organism species, and the like. The hsa-miR-1908-5p gene can be obtained by a method described in Bar M et al., 2008, Stem Cells, Vol. 26, p. 2496-2505. Also, "hsa-mir-1908" (miRBase Accession No. MI10008329, SEQ ID NO: 393) having a hairpin-like structure is known as a precursor of "hsa-miR-1908-5p".

The term "hsa-miR-6726-5p gene" or "hsa-miR-6726-5p" used herein includes the hsa-miR-6726-5p gene (miRBase Accession No. MIMAT0027353) described in SEQ ID NO: 118, a homolog or an ortholog of a different organism species, and the like. The hsa-miR-6726-5p gene can be obtained by a method described in Ladewig E et al., 2012, Genome Res, Vol. 22, p. 1634-1645. Also, "hsa-mir-6726" (miRBase Accession No. MI0022571, SEQ ID NO: 394) having a hairpin-like structure is known as a precursor of "hsa-miR-6726-5p".

The term "hsa-miR-1913 gene" or "hsa-miR-1913" used herein includes the hsa-miR-1913 gene (miRBase Accession No. MIMAT0007888) described in SEQ ID NO: 119, a homolog or an ortholog of a different organism species, and the like. The hsa-miR-1913 gene can be obtained by a method described in Bar M et al., 2008, Stem Cells, Vol. 26, p. 2496-2505. Also, "hsa-mir-1913" (miRBase Accession No. MI0008334, SEQ ID NO: 395) having a hairpin-like structure is known as a precursor of "hsa-miR-1913".

The term "hsa-miR-8071 gene" or "hsa-miR-8071" used herein includes the hsa-miR-8071 gene (miRBase Accession No. MIMAT0030998) described in SEQ ID NO: 120, a homolog or an ortholog of a different organism species, and the like. The hsa-miR-8071 gene can be obtained by a method described in Wang H J et al., 2013, Shock, Vol. 39, p. 480-487. Also, "hsa-mir-8071-1 and hsa-mir-8071-2" (miRBase Accession Nos. MI0025907 and MI10026417, SEQ ID NOs: 396 and 397) having a hairpin-like structure are known as precursors of "hsa-miR-8071".

The term "hsa-miR-3648 gene" or "hsa-miR-3648" used herein includes the hsa-miR-3648 gene (miRBase Accession No. MIMAT0018068) described in SEQ ID NO: 121, a homolog or an ortholog of a different organism species, and the like. The hsa-miR-3648 gene can be obtained by a method described in Meiri E et al., 2010, Nucleic Acids Res, Vol. 38, p. 6234-6246. Also, "hsa-mir-3648-1 and hsa-mir-3648-2" (miRBase Accession Nos. MI10016048 and MI0031512, SEQ ID NOs: 398 and 399) having a hairpin-like structure are known as precursors of "hsa-miR-3648".

The term "hsa-miR-4732-5p gene" or "hsa-miR-4732-5p" used herein includes the hsa-miR-4732-5p gene (miRBase Accession No. MIMAT0019855) described in SEQ ID NO: 122, a homolog or an ortholog of a different organism species, and the like. The hsa-miR-4732-5p gene can be obtained by a method described in Persson H et al., 2011, Cancer Res, Vol. 71, p. 78-86. Also, "hsa-mir-4732" (miRBase Accession No. MI0017369, SEQ ID NO: 400) having a hairpin-like structure is known as a precursor of "hsa-miR-4732-5p".

The term "hsa-miR-4787-5p gene" or "hsa-miR-4787-5p" used herein includes the hsa-miR-4787-5p gene (miRBase Accession No. MIMAT0019956) described in SEQ ID NO: 123, a homolog or an ortholog of a different organism species, and the like. The hsa-miR-4787-5p gene can be obtained by a method described in Persson H et al., 2011, Cancer Res, Vol. 71, p. 78-86. Also, "hsa-mir-4787" (miRBase Accession No. MI0017434, SEQ ID NO: 318) having a hairpin-like structure is known as a precursor of "hsa-miR-4787-5p".

The term "hsa-miR-3917 gene" or "hsa-miR-3917" used herein includes the hsa-miR-3917 gene (miRBase Accession No. MIMAT0018191) described in SEQ ID NO: 124, a homolog or an ortholog of a different organism species, and the like. The hsa-miR-3917 gene can be obtained by a method described in Creighton C J et al., 2010, PLoS One, Vol. 5, e9637. Also, "hsa-mir-3917" (miRBase Accession No. MI0016423, SEQ ID NO: 401) having a hairpin-like structure is known as a precursor of "hsa-miR-3917".

The term "hsa-miR-619-5p gene" or "hsa-miR-619-5p" used herein includes the hsa-miR-619-5p gene (miRBase Accession No. MIMAT0026622) described in SEQ ID NO: 125, a homolog or an ortholog of a different organism species, and the like. The hsa-miR-619-5p gene can be obtained by a method described in Cummins J M et al., 2006, Proc Natl Acad Sci USA, Vol. 103, p. 3687-3692. Also, "hsa-mir-619" (miRBase Accession No. MI0003633, SEQ ID NO: 402) having a hairpin-like structure is known as a precursor of "hsa-miR-619-5p".

The term "hsa-miR-1231 gene" or "hsa-miR-1231" used herein includes the hsa-miR-1231 gene (miRBase Accession No. MIMAT0005586) described in SEQ ID NO: 126, a homolog or an ortholog of a different organism species, and the like. The hsa-miR-1231 gene can be obtained by a method described in Berezikov E et al., 2007, Mol Cell, Vol. 28, p. 328-336. Also, "hsa-mir-1231" (miRBase Accession No. MI0006321, SEQ ID NO: 403) having a hairpin-like structure is known as a precursor of "hsa-miR-1231".

The term "hsa-miR-342-5p gene" or "hsa-miR-342-5p" used herein includes the hsa-miR-342-5p gene (miRBase Accession No. MIMAT0004694) described in SEQ ID NO: 127, a homolog or an ortholog of a different organism species, and the like. The hsa-miR-342-5p gene can be obtained by a method described in Kim J et al., 2004, Proc Natl Acad Sci USA, Vol. 101, p. 360-365. Also, "hsa-mir-342" (miRBase Accession No. MI0000805, SEQ ID NO: 404) having a hairpin-like structure is known as a precursor of "hsa-miR-342-5p".

The term "hsa-miR-4433a-5p gene" or "hsa-miR-4433a-5p" used herein includes the hsa-miR-4433a-5p gene (miRBase Accession No. MIMAT0020956) described in SEQ ID NO: 128, a homolog or an ortholog of a different organism species, and the like. The hsa-miR-4433a-5p gene can be obtained by a method described in Jima D D et al., 2010, Blood, Vol. 116, e118-e127. Also, "hsa-mir-4433a" (miRBase Accession No. MI0016773, SEQ ID NO: 405) having a hairpin-like structure is known as a precursor of "hsa-miR-4433a-5p".

The term "hsa-miR-6766-5p gene" or "hsa-miR-6766-5p" used herein includes the hsa-miR-6766-5p gene (miRBase Accession No. MIMAT0027432) described in SEQ ID NO:

129, a homolog or an ortholog of a different organism species, and the like. The hsa-miR-6766-5p gene can be obtained by a method described in Ladewig E et al., 2012, Genome Res, Vol. 22, p. 1634-1645. Also, “hsa-mir-6766” (miRBase Accession No. MI0022611, SEQ ID NO: 365) having a hairpin-like structure is known as a precursor of “hsa-miR-6766-5p”.

The term “hsa-miR-4707-5p gene” or “hsa-miR-4707-5p” used herein includes the hsa-miR-4707-5p gene (miRBase Accession No. MIMAT0019807) described in SEQ ID NO: 130, a homolog or an ortholog of a different organism species, and the like. The hsa-miR-4707-5p gene can be obtained by a method described in Persson H et al., 2011, Cancer Res, Vol. 71, p. 78-86. Also, “hsa-mir-4707” (miRBase Accession No. MI0017340, SEQ ID NO: 406) having a hairpin-like structure is known as a precursor of “hsa-miR-4707-5p”.

The term “hsa-miR-7114-5p gene” or “hsa-miR-7114-5p” used herein includes the hsa-miR-7114-5p gene (miRBase Accession No. MIMAT0028125) described in SEQ ID NO: 131, a homolog or an ortholog of a different organism species, and the like. The hsa-miR-7114-5p gene can be obtained by a method described in Ladewig E et al., 2012, Genome Res, Vol. 22, p. 1634-1645. Also, “hsa-mir-7114” (miRBase Accession No. MI0022965, SEQ ID NO: 407) having a hairpin-like structure is known as a precursor of “hsa-miR-7114-5p”.

The term “hsa-miR-6872-3p gene” or “hsa-miR-6872-3p” used herein includes the hsa-miR-6872-3p gene (miRBase Accession No. MIMAT0027645) described in SEQ ID NO: 132, a homolog or an ortholog of a different organism species, and the like. The hsa-miR-6872-3p gene can be obtained by a method described in Ladewig E et al., 2012, Genome Res, Vol. 22, p. 1634-1645. Also, “hsa-mir-6872” (miRBase Accession No. MI0022719, SEQ ID NO: 408) having a hairpin-like structure is known as a precursor of “hsa-miR-6872-3p”.

The term “hsa-miR-6780b-5p gene” or “hsa-miR-6780b-5p” used herein includes the hsa-miR-6780b-5p gene (miRBase Accession No. MIMAT0027572) described in SEQ ID NO: 133, a homolog or an ortholog of a different organism species, and the like. The hsa-miR-6780b-5p gene can be obtained by a method described in Ladewig E et al., 2012, Genome Res, Vol. 22, p. 1634-1645. Also, “hsa-mir-6780b” (miRBase Accession No. MI10022681, SEQ ID NO: 409) having a hairpin-like structure is known as a precursor of “hsa-miR-6780b-5p”.

The term “hsa-miR-7845-5p gene” or “hsa-miR-7845-5p” used herein includes the hsa-miR-7845-5p gene (miRBase Accession No. MIMAT0030420) described in SEQ ID NO: 134, a homolog or an ortholog of a different organism species, and the like. The hsa-miR-7845-5p gene can be obtained by a method described in Ple H et al., 2012, PLoS One, Vol. 7, e50746. Also, “hsa-mir-7845” (miRBase Accession No. MI0025515, SEQ ID NO: 410) having a hairpin-like structure is known as a precursor of “hsa-miR-7845-5p”.

The term “hsa-miR-6798-3p gene” or “hsa-miR-6798-3p” used herein includes the hsa-miR-6798-3p gene (miRBase Accession No. MIMAT0027497) described in SEQ ID NO: 135, a homolog or an ortholog of a different organism species, and the like. The hsa-miR-6798-3p gene can be obtained by a method described in Ladewig E et al., 2012, Genome Res, Vol. 22, p. 1634-1645. Also, “hsa-mir-6798” (miRBase Accession No. MI0022643, SEQ ID NO: 314) having a hairpin-like structure is known as a precursor of “hsa-miR-6798-3p”.

The term “hsa-miR-665 gene” or “hsa-miR-665” used herein includes the hsa-miR-665 gene (miRBase Accession No. MIMAT0004952) described in SEQ ID NO: 136, a homolog or an ortholog of a different organism species, and the like. The hsa-miR-665 gene can be obtained by a method described in Berezikov E et al., 2006, Genome Res, Vol. 16, p. 1289-1298. Also, “hsa-mir-665” (miRBase Accession No. MI0005563, SEQ ID NO: 411) having a hairpin-like structure is known as a precursor of “hsa-miR-665”.

The term “hsa-miR-6848-5p gene” or “hsa-miR-6848-5p” used herein includes the hsa-miR-6848-5p gene (miRBase Accession No. MIMAT0027596) described in SEQ ID NO: 137, a homolog or an ortholog of a different organism species, and the like. The hsa-miR-6848-5p gene can be obtained by a method described in Ladewig E et al., 2012, Genome Res, Vol. 22, p. 1634-1645. Also, “hsa-mir-6848” (miRBase Accession No. MI0022694, SEQ ID NO: 412) having a hairpin-like structure is known as a precursor of “hsa-miR-6848-5p”.

The term “hsa-miR-5008-5p gene” or “hsa-miR-5008-5p” used herein includes the hsa-miR-5008-5p gene (miRBase Accession No. MIMAT0021039) described in SEQ ID NO: 138, a homolog or an ortholog of a different organism species, and the like. The hsa-miR-5008-5p gene can be obtained by a method described in Hansen T B et al., 2011, RNA Biol, Vol. 8, p. 378-383. Also, “hsa-mir-5008” (miRBase Accession No. MI0017876, SEQ ID NO: 413) having a hairpin-like structure is known as a precursor of “hsa-miR-5008-5p”.

The term “hsa-miR-4294 gene” or “hsa-miR-4294” used herein includes the hsa-miR-4294 gene (miRBase Accession No. MIMAT0016849) described in SEQ ID NO: 139, a homolog or an ortholog of a different organism species, and the like. The hsa-miR-4294 gene can be obtained by a method described in Goff L A et al., 2009, PLoS One, Vol. 4, e7192. Also, “hsa-mir-4294” (miRBase Accession No. MI0015827, SEQ ID NO: 414) having a hairpin-like structure is known as a precursor of “hsa-miR-4294”.

The term “hsa-miR-6511a-5p gene” or “hsa-miR-6511a-5p” used herein includes the hsa-miR-6511a-5p gene (miRBase Accession No. MIMAT0025478) described in SEQ ID NO: 140, a homolog or an ortholog of a different organism species, and the like. The hsa-miR-6511a-5p gene can be obtained by a method described in Joyce C E et al., 2011, Hum Mol Genet, Vol. 20, p. 4025-4040. Also, “hsa-mir-6511a-1, hsa-mir-6511a-2, hsa-mir-6511a-3 and hsa-mir-6511a-4” (miRBase Accession Nos. MI0022223, MI0023564, MI0023565 and MI0023566, SEQ ID NOs: 415, 416, 417 and 418) having a hairpin-like structure are known as precursors of “hsa-miR-6511a-5p”.

The term “hsa-miR-4435 gene” or “hsa-miR-4435” used herein includes the hsa-miR-4435 gene (miRBase Accession No. MIMAT0018951) described in SEQ ID NO: 141, a homolog or an ortholog of a different organism species, and the like. The hsa-miR-4435 gene can be obtained by a method described in Jima D D et al., 2010, Blood, Vol. 116, e118-e127. Also, “hsa-mir-4435-1 and hsa-mir-4435-2” (miRBase Accession Nos. MI0016775 and MI0016777, SEQ ID NOs: 419 and 420) having a hairpin-like structure are known as precursors of “hsa-miR-4435”.

The term “hsa-miR-4747-3p gene” or “hsa-miR-4747-3p” used herein includes the hsa-miR-4747-3p gene (miRBase Accession No. MIMAT0019883) described in SEQ ID NO: 142, a homolog or an ortholog of a different organism species, and the like. The hsa-miR-4747-3p gene can be obtained by a method described in Persson H et al., 2011, Cancer Res, Vol. 71, p. 78-86. Also, “hsa-mir-4747” (miR- Base Accession No. MI0017386, SEQ ID NO: 421) having a hairpin-like structure is known as a precursor of "hsa-miR-4747-3p".

The term "hsa-miR-6880-3p gene" or "hsa-miR-6880-3p" used herein includes the hsa-miR-6880-3p gene (miRBase Accession No. MIMAT0027661) described in SEQ ID NO: 143, a homolog or an ortholog of a different organism species, and the like. The hsa-miR-6880-3p gene can be obtained by a method described in Ladewig E et al., 2012, Genome Res, Vol. 22, p. 1634-1645. Also, "hsa-mir-6880" (miRBase Accession No. MI0022727, SEQ ID NO: 422) having a hairpin-like structure is known as a precursor of "hsa-miR-6880-3p".

The term "hsa-miR-6869-5p gene" or "hsa-miR-6869-5p" used herein includes the hsa-miR-6869-5p gene (miRBase Accession No. MIMAT0027638) described in SEQ ID NO: 144, a homolog or an ortholog of a different organism species, and the like. The hsa-miR-6869-5p gene can be obtained by a method described in Ladewig E et al., 2012, Genome Res, Vol. 22, p. 1634-1645. Also, "hsa-mir-6869" (miRBase Accession No. MI0022716, SEQ ID NO: 423) having a hairpin-like structure is known as a precursor of "hsa-miR-6869-5p".

The term "hsa-miR-7150 gene" or "hsa-miR-7150" used herein includes the hsa-miR-7150 gene (miRBase Accession No. MIMAT0028211) described in SEQ ID NO: 145, a homolog or an ortholog of a different organism species, and the like. The hsa-miR-7150 gene can be obtained by a method described in Oulas A et al., 2009, Nucleic Acids Res, Vol. 37, p. 3276-3287. Also, "hsa-mir-7150" (miRBase Accession No. MI0023610, SEQ ID NO: 424) having a hairpin-like structure is known as a precursor of "hsa-miR-7150".

The term "hsa-miR-1260a gene" or "hsa-miR-1260a" used herein includes the hsa-miR-1260a gene (miRBase Accession No. MIMAT0005911) described in SEQ ID NO: 146, a homolog or an ortholog of a different organism species, and the like. The hsa-miR-1260a gene can be obtained by a method described in Morin R D et al., 2008, Genome Res, Vol. 18, p. 610-621. Also, "hsa-mir-1260a" (miRBase Accession No. MI0006394, SEQ ID NO: 425) having a hairpin-like structure is known as a precursor of "hsa-miR-1260a".

The term "hsa-miR-6877-5p gene" or "hsa-miR-6877-5p" used herein includes the hsa-miR-6877-5p gene (miRBase Accession No. MIMAT0027654) described in SEQ ID NO: 147, a homolog or an ortholog of a different organism species, and the like. The hsa-miR-6877-5p gene can be obtained by a method described in Ladewig E et al., 2012, Genome Res, Vol. 22, p. 1634-1645. Also, "hsa-mir-6877" (miRBase Accession No. MI0022724, SEQ ID NO: 426) having a hairpin-like structure is known as a precursor of "hsa-miR-6877-5p".

The term "hsa-miR-6721-5p gene" or "hsa-miR-6721-5p" used herein includes the hsa-miR-6721-5p gene (miRBase Accession No. MIMAT0025852) described in SEQ ID NO: 148, a homolog or an ortholog of a different organism species, and the like. The hsa-miR-6721-5p gene can be obtained by a method described in Li Y et al., 2012, Gene, Vol. 497, p. 330-335. Also, "hsa-mir-6721" (miRBase Accession No. MI0022556, SEQ ID NO: 427) having a hairpin-like structure is known as a precursor of "hsa-miR-6721-5p".

The term "hsa-miR-4656 gene" or "hsa-miR-4656" used herein includes the hsa-miR-4656 gene (miRBase Accession No. MIMAT0019723) described in SEQ ID NO: 149, a homolog or an ortholog of a different organism species, and the like. The hsa-miR-4656 gene can be obtained by a method described in Persson H et al., 2011, Cancer Res, Vol. 71, p. 78-86. Also, "hsa-mir-4656" (miRBase Accession No. MI0017284, SEQ ID NO: 428) having a hairpin-like structure is known as a precursor of "hsa-miR-4656".

The term "hsa-miR-1229-5p gene" or "hsa-miR-1229-5p" used herein includes the hsa-miR-1229-5p gene (miRBase Accession No. MIMAT0022942) described in SEQ ID NO: 150, a homolog or an ortholog of a different organism species, and the like. The hsa-miR-1229-5p gene can be obtained by a method described in Berezikov E et al., 2007, Mol Cell, Vol. 28, p. 328-336. Also, "hsa-mir-1229" (miRBase Accession No. MI0006319, SEQ ID NO: 429) having a hairpin-like structure is known as a precursor of "hsa-miR-1229-5p".

The term "hsa-miR-4433a-3p gene" or "hsa-miR-4433a-3p" used herein includes the hsa-miR-4433a-3p gene (miRBase Accession No. MIMAT0018949) described in SEQ ID NO: 151, a homolog or an ortholog of a different organism species, and the like. The hsa-miR-4433a-3p gene can be obtained by a method described in Jima D D et al., 2010, Blood, Vol. 116, e118-e127. Also, "hsa-mir-4433a" (miRBase Accession No. MI0016773, SEQ ID NO: 405) having a hairpin-like structure is known as a precursor of "hsa-miR-4433a-3p".

The term "hsa-miR-4274 gene" or "hsa-miR-4274" used herein includes the hsa-miR-4274 gene (miRBase Accession No. MIMAT0016906) described in SEQ ID NO: 152, a homolog or an ortholog of a different organism species, and the like. The hsa-miR-4274 gene can be obtained by a method described in Goff L A et al., 2009, PLoS One, Vol. 4, e7192. Also, "hsa-mir-4274" (miRBase Accession No. MI0015884, SEQ ID NO: 430) having a hairpin-like structure is known as a precursor of "hsa-miR-4274".

The term "hsa-miR-4419b gene" or "hsa-miR-4419b" used herein includes the hsa-miR-4419b gene (miRBase Accession No. MIMAT0019034) described in SEQ ID NO: 153, a homolog or an ortholog of a different organism species, and the like. The hsa-miR-4419b gene can be obtained by a method described in Jima D D et al., 2010, Blood, Vol. 116, e118-e127. Also, "hsa-mir-4419b" (miRBase Accession No. MI0016861, SEQ ID NO: 431) having a hairpin-like structure is known as a precursor of "hsa-miR-4419b".

The term "hsa-miR-4674 gene" or "hsa-miR-4674" used herein includes the hsa-miR-4674 gene (miRBase Accession No. MIMAT0019756) described in SEQ ID NO: 154, a homolog or an ortholog of a different organism species, and the like. The hsa-miR-4674 gene can be obtained by a method described in Persson H et al., 2011, Cancer Res, Vol. 71, p. 78-86. Also, "hsa-mir-4674" (miRBase Accession No. MI0017305, SEQ ID NO: 432) having a hairpin-like structure is known as a precursor of "hsa-miR-4674".

The term "hsa-miR-6893-5p gene" or "hsa-miR-6893-5p" used herein includes the hsa-miR-6893-5p gene (miRBase Accession No. MIMAT0027686) described in SEQ ID NO: 155, a homolog or an ortholog of a different organism species, and the like. The hsa-miR-6893-5p gene can be obtained by a method described in Ladewig E et al., 2012, Genome Res, Vol. 22, p. 1634-1645. Also, "hsa-mir-6893" (miRBase Accession No. MI0022740, SEQ ID NO: 433) having a hairpin-like structure is known as a precursor of "hsa-miR-6893-5p".

The term "hsa-miR-6763-3p gene" or "hsa-miR-6763-3p" used herein includes the hsa-miR-6763-3p gene (miRBase Accession No. MIMAT0027427) described in SEQ ID NO: 156, a homolog or an ortholog of a different organism species, and the like. The hsa-miR-6763-3p gene can be obtained by a method described in Ladewig E et al., 2012, Genome Res, Vol. 22, p. 1634-1645. Also, “hsa-mir-6763” (miRBase Accession No. MI0022608, SEQ ID NO: 434) having a hairpin-like structure is known as a precursor of “hsa-miR-6763-3p”.

The term “hsa-miR-6762-5p gene” or “hsa-miR-6762-5p” used herein includes the hsa-miR-6762-5p gene (miRBase Accession No. MIMAT0027424) described in SEQ ID NO: 157, a homolog or an ortholog of a different organism species, and the like. The hsa-miR-6762-5p gene can be obtained by a method described in Ladewig E et al., 2012, Genome Res, Vol. 22, p. 1634-1645. Also, “hsa-mir-6762” (miRBase Accession No. MI0022607, SEQ ID NO: 435) having a hairpin-like structure is known as a precursor of “hsa-miR-6762-5p”.

The term “hsa-miR-6738-5p gene” or “hsa-miR-6738-5p” used herein includes the hsa-miR-6738-5p gene (miRBase Accession No. MIMAT0027377) described in SEQ ID NO: 158, a homolog or an ortholog of a different organism species, and the like. The hsa-miR-6738-5p gene can be obtained by a method described in Ladewig E et al., 2012, Genome Res, Vol. 22, p. 1634-1645. Also, “hsa-mir-6738” (miRBase Accession No. MI0022583, SEQ ID NO: 436) having a hairpin-like structure is known as a precursor of “hsa-miR-6738-5p”.

The term “hsa-miR-4513 gene” or “hsa-miR-4513” used herein includes the hsa-miR-4513 gene (miRBase Accession No. MIMAT0019050) described in SEQ ID NO: 159, a homolog or an ortholog of a different organism species, and the like. The hsa-miR-4513 gene can be obtained by a method described in Jima D D et al., 2010, Blood, Vol. 116, e118-e127. Also, “hsa-mir-4513” (miRBase Accession No. MI0016879, SEQ ID NO: 437) having a hairpin-like structure is known as a precursor of “hsa-miR-4513”.

The term “hsa-miR-6746-5p gene” or “hsa-miR-6746-5p” used herein includes the hsa-miR-6746-5p gene (miRBase Accession No. MIMAT0027392) described in SEQ ID NO: 160, a homolog or an ortholog of a different organism species, and the like. The hsa-miR-6746-5p gene can be obtained by a method described in Ladewig E et al., 2012, Genome Res, Vol. 22, p. 1634-1645. Also, “hsa-mir-6746” (miRBase Accession No. MI0022591, SEQ ID NO: 438) having a hairpin-like structure is known as a precursor of “hsa-miR-6746-5p”.

The term “hsa-miR-6880-5p gene” or “hsa-miR-6880-5p” used herein includes the hsa-miR-6880-5p gene (miRBase Accession No. MIMAT0027660) described in SEQ ID NO: 161, a homolog or an ortholog of a different organism species, and the like. The hsa-miR-6880-5p gene can be obtained by a method described in Ladewig E et al., 2012, Genome Res, Vol. 22, p. 1634-1645. Also, “hsa-mir-6880” (miRBase Accession No. MI0022727, SEQ ID NO: 422) having a hairpin-like structure is known as a precursor of “hsa-miR-6880-5p”.

The term “hsa-miR-4736 gene” or “hsa-miR-4736” used herein includes the hsa-miR-4736 gene (miRBase Accession No. MIMAT0019862) described in SEQ ID NO: 162, a homolog or an ortholog of a different organism species, and the like. The hsa-miR-4736 gene can be obtained by a method described in Persson H et al., 2011, Cancer Res, Vol. 71, p. 78-86. Also, “hsa-mir-4736” (miRBase Accession No. MI0017373, SEQ ID NO: 439) having a hairpin-like structure is known as a precursor of “hsa-miR-4736”.

The term “hsa-miR-718 gene” or “hsa-miR-718” used herein includes the hsa-miR-718 gene (miRBase Accession No. MIMAT0012735) described in SEQ ID NO: 163, a homolog or an ortholog of a different organism species, and the like. The hsa-miR-718 gene can be obtained by a method described in Artzi S et al., 2008, BMC Bioinformatics, Vol. 9, p. 39. Also, “hsa-mir-718” (miRBase Accession No. MI0012489, SEQ ID NO: 440) having a hairpin-like structure is known as a precursor of “hsa-miR-718”.

The term “hsa-miR-6717-5p gene” or “hsa-miR-6717-5p” used herein includes the hsa-miR-6717-5p gene (miRBase Accession No. MIMAT0025846) described in SEQ ID NO: 164, a homolog or an ortholog of a different organism species, and the like. The hsa-miR-6717-5p gene can be obtained by a method described in Li Y et al., 2012, Gene, Vol. 497, p. 330-335. Also, “hsa-mir-6717” (miRBase Accession No. MI0022551, SEQ ID NO: 441) having a hairpin-like structure is known as a precursor of “hsa-miR-6717-5p”.

The term “hsa-miR-7847-3p gene” or “hsa-miR-7847-3p” used herein includes the hsa-miR-7847-3p gene (miRBase Accession No. MIMAT0030422) described in SEQ ID NO: 165, a homolog or an ortholog of a different organism species, and the like. The hsa-miR-7847-3p gene can be obtained by a method described in Ple H et al., 2012, PLoS One, Vol. 7, e50746. Also, “hsa-mir-7847” (miRBase Accession No. MI0025517, SEQ ID NO: 442) having a hairpin-like structure is known as a precursor of “hsa-miR-7847-3p”.

The term “hsa-miR-760 gene” or “hsa-miR-760” used herein includes the hsa-miR-760 gene (miRBase Accession No. MIMAT0004957) described in SEQ ID NO: 166, a homolog or an ortholog of a different organism species, and the like. The hsa-miR-760 gene can be obtained by a method described in Berezikov E et al., 2006, Genome Res, Vol. 16, p. 1289-1298. Also, “hsa-mir-760” (miRBase Accession No. MI0005567, SEQ ID NO: 443) having a hairpin-like structure is known as a precursor of “hsa-miR-760”.

The term “hsa-miR-1199-5p gene” or “hsa-miR-1199-5p” used herein includes the hsa-miR-1199-5p gene (miRBase Accession No. MIMAT0031119) described in SEQ ID NO: 167, a homolog or an ortholog of a different organism species, and the like. The hsa-miR-1199-5p gene can be obtained by a method described in Salvi A et al., 2013, Int J Oncol, Vol. 42, p. 391-402. Also, “hsa-mir-1199” (miRBase Accession No. MI0020340, SEQ ID NO: 444) having a hairpin-like structure is known as a precursor of “hsa-miR-1199-5p”.

The term “hsa-miR-6813-5p gene” or “hsa-miR-6813-5p” used herein includes the hsa-miR-6813-5p gene (miRBase Accession No. MIMAT0027526) described in SEQ ID NO: 168, a homolog or an ortholog of a different organism species, and the like. The hsa-miR-6813-5p gene can be obtained by a method described in Ladewig E et al., 2012, Genome Res, Vol. 22, p. 1634-1645. Also, “hsa-mir-6813” (miRBase Accession No. MI0022658, SEQ ID NO: 445) having a hairpin-like structure is known as a precursor of “hsa-miR-6813-5p”.

The term “hsa-miR-6769a-5p gene” or “hsa-miR-6769a-5p” used herein includes the hsa-miR-6769a-5p gene (miRBase Accession No. MIMAT0027438) described in SEQ ID NO: 169, a homolog or an ortholog of a different organism species, and the like. The hsa-miR-6769a-5p gene can be obtained by a method described in Ladewig E et al., 2012, Genome Res, Vol. 22, p. 1634-1645. Also, “hsa-mir-6769a” (miRBase Accession No. MI0022614, SEQ ID NO: 446) having a hairpin-like structure is known as a precursor of “hsa-miR-6769a-5p”.

The term “hsa-miR-1193 gene” or “hsa-miR-1193” used herein includes the hsa-miR-1193 gene (miRBase Accession No. MIMAT0015049) described in SEQ ID NO: 170, a homolog or an ortholog of a different organism species, and the like. The hsa-miR-1193 gene can be obtained by a method described in Stark M S et al., 2010, PLoS One, Vol. 5, e9685. Also, "hsa-mir-1193" (miRBase Accession No. MI0014205, SEQ ID NO: 447) having a hairpin-like structure is known as a precursor of "hsa-miR-1193".

The term "hsa-miR-7108-3p gene" or "hsa-miR-7108-3p" used herein includes the hsa-miR-7108-3p gene (miRBase Accession No. MIMAT0028114) described in SEQ ID NO: 171, a homolog or an ortholog of a different organism species, and the like. The hsa-miR-7108-3p gene can be obtained by a method described in Ladewig E et al., 2012, Genome Res, Vol. 22, p. 1634-1645. Also, "hsa-mir-7108" (miRBase Accession No. MI0022959, SEQ ID NO: 448) having a hairpin-like structure is known as a precursor of "hsa-miR-7108-3p".

The term "hsa-miR-6741-5p gene" or "hsa-miR-6741-5p" used herein includes the hsa-miR-6741-5p gene (miRBase Accession No. MIMAT0027383) described in SEQ ID NO: 172, a homolog or an ortholog of a different organism species, and the like. The hsa-miR-6741-5p gene can be obtained by a method described in Ladewig E et al., 2012, Genome Res, Vol. 22, p. 1634-1645. Also, "hsa-mir-6741" (miRBase Accession No. MI0022586, SEQ ID NO: 449) having a hairpin-like structure is known as a precursor of "hsa-miR-6741-5p".

The term "hsa-miR-4298 gene" or "hsa-miR-4298" used herein includes the hsa-miR-4298 gene (miRBase Accession No. MIMAT0016852) described in SEQ ID NO: 173, a homolog or an ortholog of a different organism species, and the like. The hsa-miR-4298 gene can be obtained by a method described in Goff L A et al., 2009, PLoS One, Vol. 4, e7192. Also, "hsa-mir-4298" (miRBase Accession No. MI0015830, SEQ ID NO: 450) having a hairpin-like structure is known as a precursor of "hsa-miR-4298".

The term "hsa-miR-6796-3p gene" or "hsa-miR-6796-3p" used herein includes the hsa-miR-6796-3p gene (miRBase Accession No. MIMAT0027493) described in SEQ ID NO: 174, a homolog or an ortholog of a different organism species, and the like. The hsa-miR-6796-3p gene can be obtained by a method described in Ladewig E et al., 2012, Genome Res, Vol. 22, p. 1634-1645. Also, "hsa-mir-6796" (miRBase Accession No. MI0022641, SEQ ID NO: 451) having a hairpin-like structure is known as a precursor of "hsa-miR-6796-3p".

The term "hsa-miR-4750-5p gene" or "hsa-miR-4750-5p" used herein includes the hsa-miR-4750-5p gene (miRBase Accession No. MIMAT0019887) described in SEQ ID NO: 175, a homolog or an ortholog of a different organism species, and the like. The hsa-miR-4750-5p gene can be obtained by a method described in Persson H et al., 2011, Cancer Res, Vol. 71, p. 78-86. Also, "hsa-mir-4750" (miRBase Accession No. MI10017389, SEQ ID NO: 452) having a hairpin-like structure is known as a precursor of "hsa-miR-4750-5p".

The term "hsa-miR-6785-5p gene" or "hsa-miR-6785-5p" used herein includes the hsa-miR-6785-5p gene (miRBase Accession No. MIMAT0027470) described in SEQ ID NO: 176, a homolog or an ortholog of a different organism species, and the like. The hsa-miR-6785-5p gene can be obtained by a method described in Ladewig E et al., 2012, Genome Res, Vol. 22, p. 1634-1645. Also, "hsa-mir-6785" (miRBase Accession No. MI0022630, SEQ ID NO: 453) having a hairpin-like structure is known as a precursor of "hsa-miR-6785-5p".

The term "hsa-miR-1292-3p gene" or "hsa-miR-1292-3p" used herein includes the hsa-miR-1292-3p gene (miRBase Accession No. MIMAT0022948) described in SEQ ID NO: 177, a homolog or an ortholog of a different organism species, and the like. The hsa-miR-1292-3p gene can be obtained by a method described in Morin R D et al., 2008, Genome Res, Vol. 18, p. 610-621. Also, "hsa-mir-1292" (miRBase Accession No. MI0006433, SEQ ID NO: 454) having a hairpin-like structure is known as a precursor of "hsa-miR-1292-3p".

The term "hsa-miR-4749-3p gene" or "hsa-miR-4749-3p" used herein includes the hsa-miR-4749-3p gene (miRBase Accession No. MIMAT0019886) described in SEQ ID NO: 178, a homolog or an ortholog of a different organism species, and the like. The hsa-miR-4749-3p gene can be obtained by a method described in Persson H et al., 2011, Cancer Res, Vol. 71, p. 78-86. Also, "hsa-mir-4749" (miRBase Accession No. MI10017388, SEQ ID NO: 455) having a hairpin-like structure is known as a precursor of "hsa-miR-4749-3p".

The term "hsa-miR-6800-3p gene" or "hsa-miR-6800-3p" used herein includes the hsa-miR-6800-3p gene (miRBase Accession No. MIMAT0027501) described in SEQ ID NO: 179, a homolog or an ortholog of a different organism species, and the like. The hsa-miR-6800-3p gene can be obtained by a method described in Ladewig E et al., 2012, Genome Res, Vol. 22, p. 1634-1645. Also, "hsa-mir-6800" (miRBase Accession No. MI0022645, SEQ ID NO: 293) having a hairpin-like structure is known as a precursor of "hsa-miR-6800-3p".

The term "hsa-miR-4722-5p gene" or "hsa-miR-4722-5p" used herein includes the hsa-miR-4722-5p gene (miRBase Accession No. MIMAT0019836) described in SEQ ID NO: 180, a homolog or an ortholog of a different organism species, and the like. The hsa-miR-4722-5p gene can be obtained by a method described in Persson H et al., 2011, Cancer Res, Vol. 71, p. 78-86. Also, "hsa-mir-4722" (miRBase Accession No. MI0017357, SEQ ID NO: 456) having a hairpin-like structure is known as a precursor of "hsa-miR-4722-5p".

The term "hsa-miR-4746-3p gene" or "hsa-miR-4746-3p" used herein includes the hsa-miR-4746-3p gene (miRBase Accession No. MIMAT0019881) described in SEQ ID NO: 181, a homolog or an ortholog of a different organism species, and the like. The hsa-miR-4746-3p gene can be obtained by a method described in Persson H et al., 2011, Cancer Res, Vol. 71, p. 78-86. Also, "hsa-mir-4746" (miRBase Accession No. MI0017385, SEQ ID NO: 457) having a hairpin-like structure is known as a precursor of "hsa-miR-4746-3p".

The term "hsa-miR-4450 gene" or "hsa-miR-4450" used herein includes the hsa-miR-4450 gene (miRBase Accession No. MIMAT0018971) described in SEQ ID NO: 182, a homolog or an ortholog of a different organism species, and the like. The hsa-miR-4450 gene can be obtained by a method described in Jima D D et al., 2010, Blood, Vol. 116, e118-e127. Also, "hsa-mir-4450" (miRBase Accession No. MI0016795, SEQ ID NO: 458) having a hairpin-like structure is known as a precursor of "hsa-miR-4450".

The term "hsa-miR-6795-5p gene" or "hsa-miR-6795-5p" used herein includes the hsa-miR-6795-5p gene (miRBase Accession No. MIMAT0027490) described in SEQ ID NO: 183, a homolog or an ortholog of a different organism species, and the like. The hsa-miR-6795-5p gene can be obtained by a method described in Ladewig E et al., 2012, Genome Res, Vol. 22, p. 1634-1645. Also, "hsa-mir-6795"

(miRBase Accession No. MI0022640, SEQ ID NO: 459) having a hairpin-like structure is known as a precursor of "hsa-miR-6795-5p".

The term "hsa-miR-365a-5p gene" or "hsa-miR-365a-5p" used herein includes the hsa-miR-365a-5p gene (miRBase Accession No. MIMAT0009199) described in SEQ ID NO: 184, a homolog or an ortholog of a different organism species, and the like. The hsa-miR-365a-5p gene can be obtained by a method described in Xie X et al., 2005, Nature, Vol. 434, p. 338-345. Also, "hsa-mir-365a" (miRBase Accession No. MI0000767, SEQ ID NO: 460) having a hairpin-like structure is known as a precursor of "hsa-miR-365a-5p".

The term "hsa-miR-498 gene" or "hsa-miR-498" used herein includes the hsa-miR-498 gene (miRBase Accession No. MIMAT0002824) described in SEQ ID NO: 185, a homolog or an ortholog of a different organism species, and the like. The hsa-miR-498 gene can be obtained by a method described in Bentwich I et al., 2005, Nat Genet, Vol. 37, p. 766-770. Also, "hsa-mir-498" (miRBase Accession No. MI0003142, SEQ ID NO: 461) having a hairpin-like structure is known as a precursor of "hsa-miR-498".

The term "hsa-miR-6797-5p gene" or "hsa-miR-6797-5p" used herein includes the hsa-miR-6797-5p gene (miRBase Accession No. MIMAT0027494) described in SEQ ID NO: 186, a homolog or an ortholog of a different organism species, and the like. The hsa-miR-6797-5p gene can be obtained by a method described in Ladewig E et al., 2012, Genome Res, Vol. 22, p. 1634-1645. Also, "hsa-mir-6797" (miRBase Accession No. MI0022642, SEQ ID NO: 462) having a hairpin-like structure is known as a precursor of "hsa-miR-6797-5p".

The term "hsa-miR-1470 gene" or "hsa-miR-1470" used herein includes the hsa-miR-1470 gene (miRBase Accession No. MIMAT0007348) described in SEQ ID NO: 187, a homolog or an ortholog of a different organism species, and the like. The hsa-miR-1470 gene can be obtained by a method described in Kawaji H et al., 2008, BMC Genomics, Vol. 9, p. 157. Also, "hsa-mir-1470" (miRBase Accession No. MI0007075, SEQ ID NO: 463) having a hairpin-like structure is known as a precursor of "hsa-miR-1470".

The term "hsa-miR-6851-5p gene" or "hsa-miR-6851-5p" used herein includes the hsa-miR-6851-5p gene (miRBase Accession No. MIMAT0027602) described in SEQ ID NO: 188, a homolog or an ortholog of a different organism species, and the like. The hsa-miR-6851-5p gene can be obtained by a method described in Ladewig E et al., 2012, Genome Res, Vol. 22, p. 1634-1645. Also, "hsa-mir-6851" (miRBase Accession No. MI0022697, SEQ ID NO: 464) having a hairpin-like structure is known as a precursor of "hsa-miR-6851-5p".

The term "hsa-miR-1247-3p gene" or "hsa-miR-1247-3p" used herein includes the hsa-miR-1247-3p gene (miRBase Accession No. MIMAT0022721) described in SEQ ID NO: 189, a homolog or an ortholog of a different organism species, and the like. The hsa-miR-1247-3p gene can be obtained by a method described in Morin R D et al., 2008, Genome Res, Vol. 18, p. 610-621. Also, "hsa-mir-1247" (miRBase Accession No. MI0006382, SEQ ID NO: 465) having a hairpin-like structure is known as a precursor of "hsa-miR-1247-3p".

The term "hsa-miR-5196-5p gene" or "hsa-miR-5196-5p" used herein includes the hsa-miR-5196-5p gene (miRBase Accession No. MIMAT0021128) described in SEQ ID NO: 190, a homolog or an ortholog of a different organism species, and the like. The hsa-miR-5196-5p gene can be obtained by a method described in Schotte D et al., 2011, Leukemia, Vol. 25, p. 1389-1399. Also, "hsa-mir-5196" (miRBase Accession No. MI0018175, SEQ ID NO: 466) having a hairpin-like structure is known as a precursor of "hsa-miR-5196-5p".

The term "hsa-miR-208a-5p gene" or "hsa-miR-208a-5p" used herein includes the hsa-miR-208a-5p gene (miRBase Accession No. MIMAT0026474) described in SEQ ID NO: 191, a homolog or an ortholog of a different organism species, and the like. The hsa-miR-208a-5p gene can be obtained by a method described in Lagos-Quintana M et al., 2003, RNA, Vol. 9, p. 175-179. Also, "hsa-mir-208a" (miRBase Accession No. MI0000251, SEQ ID NO: 467) having a hairpin-like structure is known as a precursor of "hsa-miR-208a-5p".

The term "hsa-miR-6842-5p gene" or "hsa-miR-6842-5p" used herein includes the hsa-miR-6842-5p gene (miRBase Accession No. MIMAT0027586) described in SEQ ID NO: 192, a homolog or an ortholog of a different organism species, and the like. The hsa-miR-6842-5p gene can be obtained by a method described in Ladewig E et al., 2012, Genome Res, Vol. 22, p. 1634-1645. Also, "hsa-mir-6842" (miRBase Accession No. MI0022688, SEQ ID NO: 468) having a hairpin-like structure is known as a precursor of "hsa-miR-6842-5p".

The term "hsa-miR-150-3p gene" or "hsa-miR-150-3p" used herein includes the hsa-miR-150-3p gene (miRBase Accession No. MIMAT0004610) described in SEQ ID NO: 193, a homolog or an ortholog of a different organism species, and the like. The hsa-miR-150-3p gene can be obtained by a method described in Lagos-Quintana M et al., 2002, Curr Biol, Vol. 12, p. 735-739. Also, "hsa-mir-150" (miRBase Accession No. MI10000479, SEQ ID NO: 469) having a hairpin-like structure is known as a precursor of "hsa-miR-150-3p".

The term "hsa-miR-4534 gene" or "hsa-miR-4534" used herein includes the hsa-miR-4534 gene (miRBase Accession No. MIMAT0019073) described in SEQ ID NO: 194, a homolog or an ortholog of a different organism species, and the like. The hsa-miR-4534 gene can be obtained by a method described in Jima D D et al., 2010, Blood, Vol. 116, e118-e127. Also, "hsa-mir-4534" (miRBase Accession No. MI0016901, SEQ ID NO: 470) having a hairpin-like structure is known as a precursor of "hsa-miR-4534".

The term "hsa-miR-3135b gene" or "hsa-miR-3135b" used herein includes the hsa-miR-3135b gene (miRBase Accession No. MIMAT0018985) described in SEQ ID NO: 195, a homolog or an ortholog of a different organism species, and the like. The hsa-miR-3135b gene can be obtained by a method described in Jima D D et al., 2010, Blood, Vol. 116, e118-e127. Also, "hsa-mir-3135b" (miRBase Accession No. MI0016809, SEQ ID NO: 471) having a hairpin-like structure is known as a precursor of "hsa-miR-3135b".

The term "hsa-miR-3131 gene" or "hsa-miR-3131" used herein includes the hsa-miR-3131 gene (miRBase Accession No. MIMAT0014996) described in SEQ ID NO: 196, a homolog or an ortholog of a different organism species, and the like. The hsa-miR-3131 gene can be obtained by a method described in Stark M S et al., 2010, PLoS One, Vol. 5, e9685. Also, "hsa-mir-3131" (miRBase Accession No. MI0014151, SEQ ID NO: 472) having a hairpin-like structure is known as a precursor of "hsa-miR-3131".

The term "hsa-miR-4792 gene" or "hsa-miR-4792" used herein includes the hsa-miR-4792 gene (miRBase Accession No. MIMAT0019964) described in SEQ ID NO: 197, a homolog or an ortholog of a different organism species, and the like. The hsa-miR-4792 gene can be obtained by a method described in Persson H et al., 2011, Cancer Res, Vol. 71, p. 78-86. Also, "hsa-mir-4792" (miRBase Accession No. MI0017439, SEQ ID NO: 473) having a hairpin-like structure is known as a precursor of "hsa-miR-4792".

The term "hsa-miR-6510-5p gene" or "hsa-miR-6510-5p" used herein includes the hsa-miR-6510-5p gene (miRBase Accession No. MIMAT0025476) described in SEQ ID NO: 198, a homolog or an ortholog of a different organism species, and the like. The hsa-miR-6510-5p gene can be obtained by a method described in Joyce C E et al., 2011, Hum Mol Genet, Vol. 20, p. 4025-4040. Also, "hsa-mir-6510" (miRBase Accession No. MI0022222, SEQ ID NO: 474) having a hairpin-like structure is known as a precursor of "hsa-miR-6510-5p".

The term "hsa-miR-504-3p gene" or "hsa-miR-504-3p" used herein includes the hsa-miR-504-3p gene (miRBase Accession No. MIMAT0026612) described in SEQ ID NO: 199, a homolog or an ortholog of a different organism species, and the like. The hsa-miR-504-3p gene can be obtained by a method described in Bentwich I et al., 2005, Nat Genet, Vol. 37, p. 766-770. Also, "hsa-mir-504" (miRBase Accession No. MI0003189, SEQ ID NO: 475) having a hairpin-like structure is known as a precursor of "hsa-miR-504-3p".

The term "hsa-miR-3619-3p gene" or "hsa-miR-3619-3p" used herein includes the hsa-miR-3619-3p gene (miRBase Accession No. MIMAT0019219) described in SEQ ID NO: 200, a homolog or an ortholog of a different organism species, and the like. The hsa-miR-3619-3p gene can be obtained by a method described in Witten D et al., 2010, BMC Biol, Vol. 8, p. 58. Also, "hsa-mir-3619" (miRBase Accession No. MI0016009, SEQ ID NO: 476) having a hairpin-like structure is known as a precursor of "hsa-miR-3619-3p".

The term "hsa-miR-671-5p gene" or "hsa-miR-671-5p" used herein includes the hsa-miR-671-5p gene (miRBase Accession No. MIMAT0003880) described in SEQ ID NO: 201, a homolog or an ortholog of a different organism species, and the like. The hsa-miR-671-5p gene can be obtained by a method described in Berezikov E et al., 2006, Genome Res, Vol. 16, p. 1289-1298. Also, "hsa-mir-671" (miRBase Accession No. MI0003760, SEQ ID NO: 477) having a hairpin-like structure is known as a precursor of "hsa-miR-671-5p".

The term "hsa-miR-4667-5p gene" or "hsa-miR-4667-5p" used herein includes the hsa-miR-4667-5p gene (miRBase Accession No. MIMAT0019743) described in SEQ ID NO: 202, a homolog or an ortholog of a different organism species, and the like. The hsa-miR-4667-5p gene can be obtained by a method described in Persson H et al., 2011, Cancer Res, Vol. 71, p. 78-86. Also, "hsa-mir-4667" (miRBase Accession No. MI0017297, SEQ ID NO: 478) having a hairpin-like structure is known as a precursor of "hsa-miR-4667-5p".

The term "hsa-miR-4430 gene" or "hsa-miR-4430" used herein includes the hsa-miR-4430 gene (miRBase Accession No. MIMAT0018945) described in SEQ ID NO: 203, a homolog or an ortholog of a different organism species, and the like. The hsa-miR-4430 gene can be obtained by a method described in Jima D D et al., 2010, Blood, Vol. 116, e118-e127. Also, "hsa-mir-4430" (miRBase Accession No. MI0016769, SEQ ID NO: 479) having a hairpin-like structure is known as a precursor of "hsa-miR-4430".

The term "hsa-miR-3195 gene" or "hsa-miR-3195" used herein includes the hsa-miR-3195 gene (miRBase Accession No. MIMAT0015079) described in SEQ ID NO: 204, a homolog or an ortholog of a different organism species, and the like. The hsa-miR-3195 gene can be obtained by a method described in Stark M S et al., 2010, PLoS One, Vol. 5, e9685. Also, "hsa-mir-3195" (miRBase Accession No. MI0014240, SEQ ID NO: 480) having a hairpin-like structure is known as a precursor of "hsa-miR-3195".

The term "hsa-miR-3679-5p gene" or "hsa-miR-3679-5p" used herein includes the hsa-miR-3679-5p gene (miRBase Accession No. MIMAT0018104) described in SEQ ID NO: 205, a homolog or an ortholog of a different organism species, and the like. The hsa-miR-3679-5p gene can be obtained by a method described in Creighton C J et al., 2010, PLoS One, Vol. 5, e9637. Also, "hsa-mir-3679" (miRBase Accession No. MI0016080, SEQ ID NO: 358) having a hairpin-like structure is known as a precursor of "hsa-miR-3679-5p".

The term "hsa-miR-6076 gene" or "hsa-miR-6076" used herein includes the hsa-miR-6076 gene (miRBase Accession No. MIMAT0023701) described in SEQ ID NO: 206, a homolog or an ortholog of a different organism species, and the like. The hsa-miR-6076 gene can be obtained by a method described in Voellenkle C et al., 2012, RNA, Vol. 18, p. 472-484. Also, "hsa-mir-6076" (miRBase Accession No. MI0020353, SEQ ID NO: 481) having a hairpin-like structure is known as a precursor of "hsa-miR-6076".

The term "hsa-miR-6515-5p gene" or "hsa-miR-6515-5p" used herein includes the hsa-miR-6515-5p gene (miRBase Accession No. MIMAT0025486) described in SEQ ID NO: 207, a homolog or an ortholog of a different organism species, and the like. The hsa-miR-6515-5p gene can be obtained by a method described in Joyce C E et al., 2011, Hum Mol Genet, Vol. 20, p. 4025-4040. Also, "hsa-mir-6515" (miRBase Accession No. MI0022227, SEQ ID NO: 340) having a hairpin-like structure is known as a precursor of "hsa-miR-6515-5p".

The term "hsa-miR-6820-5p gene" or "hsa-miR-6820-5p" used herein includes the hsa-miR-6820-5p gene (miRBase Accession No. MIMAT0027540) described in SEQ ID NO: 208, a homolog or an ortholog of a different organism species, and the like. The hsa-miR-6820-5p gene can be obtained by a method described in Ladewig E et al., 2012, Genome Res, Vol. 22, p. 1634-1645. Also, "hsa-mir-6820" (miRBase Accession No. MI0022665, SEQ ID NO: 482) having a hairpin-like structure is known as a precursor of "hsa-miR-6820-5p".

The term "hsa-miR-4634 gene" or "hsa-miR-4634" used herein includes the hsa-miR-4634 gene (miRBase Accession No. MIMAT0019691) described in SEQ ID NO: 209, a homolog or an ortholog of a different organism species, and the like. The hsa-miR-4634 gene can be obtained by a method described in Persson H et al., 2011, Cancer Res, Vol. 71, p. 78-86. Also, "hsa-mir-4634" (miRBase Accession No. MI0017261, SEQ ID NO: 483) having a hairpin-like structure is known as a precursor of "hsa-miR-4634".

The term "hsa-miR-187-5p gene" or "hsa-miR-187-5p" used herein includes the hsa-miR-187-5p gene (miRBase Accession No. MIMAT0004561) described in SEQ ID NO: 210, a homolog or an ortholog of a different organism species, and the like. The hsa-miR-187-5p gene can be obtained by a method described in Lim L P et al., 2003, Science, Vol. 299, p. 1540. Also, "hsa-mir-187" (miRBase Accession No. MI0000274, SEQ ID NO: 484) having a hairpin-like structure is known as a precursor of "hsa-miR-187-5p".

The term "hsa-miR-6763-5p gene" or "hsa-miR-6763-5p" used herein includes the hsa-miR-6763-5p gene (miRBase Accession No. MIMAT0027426) described in SEQ ID NO: 211, a homolog or an ortholog of a different organism species, and the like. The hsa-miR-6763-5p gene can be obtained by a method described in Ladewig E et al., 2012, Genome Res, Vol. 22, p. 1634-1645. Also, "hsa-mir-6763" (miRBase Accession No. MI0022608, SEQ ID NO: 434) having a hairpin-like structure is known as a precursor of "hsa-miR-6763-5p".

The term "hsa-miR-1908-3p gene" or "hsa-miR-1908-3p" used herein includes the hsa-miR-1908-3p gene (miRBase Accession No. MIMAT0026916) described in SEQ ID NO: 212, a homolog or an ortholog of a different organism species, and the like. The hsa-miR-1908-3p gene can be obtained by a method described in Bar M et al., 2008, Stem Cells, Vol. 26, p. 2496-2505. Also, "hsa-mir-1908" (miRBase Accession No. MI10008329, SEQ ID NO: 393) having a hairpin-like structure is known as a precursor of "hsa-miR-1908-3p".

The term "hsa-miR-1181 gene" or "hsa-miR-1181" used herein includes the hsa-miR-1181 gene (miRBase Accession No. MIMAT0005826) described in SEQ ID NO: 213, a homolog or an ortholog of a different organism species, and the like. The hsa-miR-1181 gene can be obtained by a method described in Subramanian S et al., 2008, Oncogene, Vol. 27, p. 2015-2026. Also, "hsa-mir-1181" (miRBase Accession No. MI0006274, SEQ ID NO: 485) having a hairpin-like structure is known as a precursor of "hsa-miR-1181".

The term "hsa-miR-6782-5p gene" or "hsa-miR-6782-5p" used herein includes the hsa-miR-6782-5p gene (miRBase Accession No. MIMAT0027464) described in SEQ ID NO: 214, a homolog or an ortholog of a different organism species, and the like. The hsa-miR-6782-5p gene can be obtained by a method described in Ladewig E et al., 2012, Genome Res, Vol. 22, p. 1634-1645. Also, "hsa-mir-6782" (miRBase Accession No. MI0022627, SEQ ID NO: 486) having a hairpin-like structure is known as a precursor of "hsa-miR-6782-5p".

The term "hsa-miR-5010-5p gene" or "hsa-miR-5010-5p" used herein includes the hsa-miR-5010-5p gene (miRBase Accession No. MIMAT0021043) described in SEQ ID NO: 215, a homolog or an ortholog of a different organism species, and the like. The hsa-miR-5010-5p gene can be obtained by a method described in Hansen T B et al., 2011, RNA Biol, Vol. 8, p. 378-383. Also, "hsa-mir-5010" (miRBase Accession No. MI0017878, SEQ ID NO: 487) having a hairpin-like structure is known as a precursor of "hsa-miR-5010-5p".

The term "hsa-miR-6870-5p gene" or "hsa-miR-6870-5p" used herein includes the hsa-miR-6870-5p gene (miRBase Accession No. MIMAT0027640) described in SEQ ID NO: 216, a homolog or an ortholog of a different organism species, and the like. The hsa-miR-6870-5p gene can be obtained by a method described in Ladewig E et al., 2012, Genome Res, Vol. 22, p. 1634-1645. Also, "hsa-mir-6870" (miRBase Accession No. MI0022717, SEQ ID NO: 488) having a hairpin-like structure is known as a precursor of "hsa-miR-6870-5p".

The term "hsa-miR-6124 gene" or "hsa-miR-6124" used herein includes the hsa-miR-6124 gene (miRBase Accession No. MIMAT0024597) described in SEQ ID NO: 217, a homolog or an ortholog of a different organism species, and the like. The hsa-miR-6124 gene can be obtained by a method described in Smith J L et al., 2012, J Virol, Vol. 86, p. 5278-5287. Also, "hsa-mir-6124" (miRBase Accession No. MI0021258, SEQ ID NO: 489) having a hairpin-like structure is known as a precursor of "hsa-miR-6124".

The term "hsa-miR-1249-5p gene" or "hsa-miR-1249-5p" used herein includes the hsa-miR-1249-5p gene (miRBase Accession No. MIMAT0032029) described in SEQ ID NO: 218, a homolog or an ortholog of a different organism species, and the like. The hsa-miR-1249-5p gene can be obtained by a method described in Morin R D et al., 2008, Genome Res, Vol. 18, p. 610-621. Also, "hsa-mir-1249" (miRBase Accession No. MI0006384, SEQ ID NO: 321) having a hairpin-like structure is known as a precursor of "hsa-miR-1249-5p".

The term "hsa-miR-6511b-5p gene" or "hsa-miR-6511b-5p" used herein includes the hsa-miR-6511b-5p gene (miRBase Accession No. MIMAT0025847) described in SEQ ID NO: 219, a homolog or an ortholog of a different organism species, and the like. The hsa-miR-6511b-5p gene can be obtained by a method described in Li Y et al., 2012, Gene, Vol. 497, p. 330-335. Also, "hsa-mir-6511b-1 and hsa-mir-6511b-2" (miRBase Accession Nos. MI0022552 and MI0023431, SEQ ID NOs: 490 and 491) having a hairpin-like structure are known as precursors of "hsa-miR-6511b-5p".

The term "hsa-miR-1254 gene" or "hsa-miR-1254" used herein includes the hsa-miR-1254 gene (miRBase Accession No. MIMAT0005905) described in SEQ ID NO: 220, a homolog or an ortholog of a different organism species, and the like. The hsa-miR-1254 gene can be obtained by a method described in Morin R D et al., 2008, Genome Res, Vol. 18, p. 610-621. Also, "hsa-mir-1254-1 and hsa-mir-1254-2" (miRBase Accession Nos. MI0006388 and MI0016747, SEQ ID NOs: 492 and 493) having a hairpin-like structure are known as precursors of "hsa-miR-1254".

The term "hsa-miR-4727-3p gene" or "hsa-miR-4727-3p" used herein includes the hsa-miR-4727-3p gene (miRBase Accession No. MIMAT0019848) described in SEQ ID NO: 221, a homolog or an ortholog of a different organism species, and the like. The hsa-miR-4727-3p gene can be obtained by a method described in Persson H et al., 2011, Cancer Res, Vol. 71, p. 78-86. Also, "hsa-mir-4727" (miRBase Accession No. MI0017364, SEQ ID NO: 494) having a hairpin-like structure is known as a precursor of "hsa-miR-4727-3p".

The term "hsa-miR-4259 gene" or "hsa-miR-4259" used herein includes the hsa-miR-4259 gene (miRBase Accession No. MIMAT0016880) described in SEQ ID NO: 222, a homolog or an ortholog of a different organism species, and the like. The hsa-miR-4259 gene can be obtained by a method described in Goff L A et al., 2009, PLoS One, Vol. 4, e7192. Also, "hsa-mir-4259" (miRBase Accession No. MI0015858, SEQ ID NO: 495) having a hairpin-like structure is known as a precursor of "hsa-miR-4259".

The term "hsa-miR-4771 gene" or "hsa-miR-4771" used herein includes the hsa-miR-4771 gene (miRBase Accession No. MIMAT0019925) described in SEQ ID NO: 223, a homolog or an ortholog of a different organism species, and the like. The hsa-miR-4771 gene can be obtained by a method described in Persson H et al., 2011, Cancer Res, Vol. 71, p. 78-86. Also, "hsa-mir-4771-1 and hsa-mir-4771-2" (miRBase Accession Nos. MI0017412 and MI0017413, SEQ ID NOs: 496 and 497) having a hairpin-like structure are known as precursors of "hsa-miR-4771".

The term "hsa-miR-3622a-5p gene" or "hsa-miR-3622a-5p" used herein includes the hsa-miR-3622a-5p gene (miRBase Accession No. MIMAT0018003) described in SEQ ID NO: 224, a homolog or an ortholog of a different organism species, and the like. The hsa-miR-3622a-5p gene can be obtained by a method described in Witten D et al., 2010, BMC Biol, Vol. 8, p. 58. Also, "hsa-mir-3622a" (miRBase Accession No. MI0016013, SEQ ID NO: 498) having a hairpin-like structure is known as a precursor of “hsa-miR-3622a-5p”.

The term “hsa-miR-4480 gene” or “hsa-miR-4480” used herein includes the hsa-miR-4480 gene (miRBase Accession No. MIMAT0019014) described in SEQ ID NO: 225, a homolog or an ortholog of a different organism species, and the like. The hsa-miR-4480 gene can be obtained by a method described in Jima D D et al., 2010, Blood, Vol. 116, e118-e127. Also, “hsa-mir-4480” (miRBase Accession No. MI0016841, SEQ ID NO: 499) having a hairpin-like structure is known as a precursor of “hsa-miR-4480”.

The term “hsa-miR-4740-5p gene” or “hsa-miR-4740-5p” used herein includes the hsa-miR-4740-5p gene (miRBase Accession No. MIMAT0019869) described in SEQ ID NO: 226, a homolog or an ortholog of a different organism species, and the like. The hsa-miR-4740-5p gene can be obtained by a method described in Persson H et al., 2011, Cancer Res, Vol. 71, p. 78-86. Also, “hsa-mir-4740” (miRBase Accession No. MI0017378, SEQ ID NO: 500) having a hairpin-like structure is known as a precursor of “hsa-miR-4740-5p”.

The term “hsa-miR-6777-5p gene” or “hsa-miR-6777-5p” used herein includes the hsa-miR-6777-5p gene (miRBase Accession No. MIMAT0027454) described in SEQ ID NO: 227, a homolog or an ortholog of a different organism species, and the like. The hsa-miR-6777-5p gene can be obtained by a method described in Ladewig E et al., 2012, Genome Res, Vol. 22, p. 1634-1645. Also, “hsa-mir-6777” (miRBase Accession No. MI0022622, SEQ ID NO: 501) having a hairpin-like structure is known as a precursor of “hsa-miR-6777-5p”.

The term “hsa-miR-6794-5p gene” or “hsa-miR-6794-5p” used herein includes the hsa-miR-6794-5p gene (miRBase Accession No. MIMAT0027488) described in SEQ ID NO: 228, a homolog or an ortholog of a different organism species, and the like. The hsa-miR-6794-5p gene can be obtained by a method described in Ladewig E et al., 2012, Genome Res, Vol. 22, p. 1634-1645. Also, “hsa-mir-6794” (miRBase Accession No. MI0022639, SEQ ID NO: 502) having a hairpin-like structure is known as a precursor of “hsa-miR-6794-5p”.

The term “hsa-miR-4687-3p gene” or “hsa-miR-4687-3p” used herein includes the hsa-miR-4687-3p gene (miRBase Accession No. MIMAT0019775) described in SEQ ID NO: 229, a homolog or an ortholog of a different organism species, and the like. The hsa-miR-4687-3p gene can be obtained by a method described in Persson H et al., 2011, Cancer Res, Vol. 71, p. 78-86. Also, “hsa-mir-4687” (miRBase Accession No. MI0017319, SEQ ID NO: 341) having a hairpin-like structure is known as a precursor of “hsa-miR-4687-3p”.

The term “hsa-miR-6743-5p gene” or “hsa-miR-6743-5p” used herein includes the hsa-miR-6743-5p gene (miRBase Accession No. MIMAT0027387) described in SEQ ID NO: 230, a homolog or an ortholog of a different organism species, and the like. The hsa-miR-6743-5p gene can be obtained by a method described in Ladewig E et al., 2012, Genome Res, Vol. 22, p. 1634-1645. Also, “hsa-mir-6743” (miRBase Accession No. MI0022588, SEQ ID NO: 503) having a hairpin-like structure is known as a precursor of “hsa-miR-6743-5p”.

The term “hsa-miR-6771-5p gene” or “hsa-miR-6771-5p” used herein includes the hsa-miR-6771-5p gene (miRBase Accession No. MIMAT0027442) described in SEQ ID NO: 231, a homolog or an ortholog of a different organism species, and the like. The hsa-miR-6771-5p gene can be obtained by a method described in Ladewig E et al., 2012, Genome Res, Vol. 22, p. 1634-1645. Also, “hsa-mir-6771” (miRBase Accession No. MI0022616, SEQ ID NO: 504) having a hairpin-like structure is known as a precursor of “hsa-miR-6771-5p”.

The term “hsa-miR-3141 gene” or “hsa-miR-3141” used herein includes the hsa-miR-3141 gene (miRBase Accession No. MIMAT0015010) described in SEQ ID NO: 232, a homolog or an ortholog of a different organism species, and the like. The hsa-miR-3141 gene can be obtained by a method described in Stark M S et al., 2010, PLoS One, Vol. 5, e9685. Also, “hsa-mir-3141” (miRBase Accession No. MI0014165, SEQ ID NO: 505) having a hairpin-like structure is known as a precursor of “hsa-miR-3141”.

The term “hsa-miR-3162-5p gene” or “hsa-miR-3162-5p” used herein includes the hsa-miR-3162-5p gene (miRBase Accession No. MIMAT0015036) described in SEQ ID NO: 233, a homolog or an ortholog of a different organism species, and the like. The hsa-miR-3162-5p gene can be obtained by a method described in Stark M S et al., 2010, PLoS One, Vol. 5, e9685. Also, “hsa-mir-3162” (miRBase Accession No. MI0014192, SEQ ID NO: 506) having a hairpin-like structure is known as a precursor of “hsa-miR-3162-5p”.

The term “hsa-miR-4271 gene” or “hsa-miR-4271” used herein includes the hsa-miR-4271 gene (miRBase Accession No. MIMAT0016901) described in SEQ ID NO: 234, a homolog or an ortholog of a different organism species, and the like. The hsa-miR-4271 gene can be obtained by a method described in Goff L A et al., 2009, PLoS One, Vol. 4, e7192. Also, “hsa-mir-4271” (miRBase Accession No. MI0015879, SEQ ID NO: 507) having a hairpin-like structure is known as a precursor of “hsa-miR-4271”.

The term “hsa-miR-1227-5p gene” or “hsa-miR-1227-5p” used herein includes the hsa-miR-1227-5p gene (miRBase Accession No. MIMAT0022941) described in SEQ ID NO: 235, a homolog or an ortholog of a different organism species, and the like. The hsa-miR-1227-5p gene can be obtained by a method described in Berezikov E et al., 2007, Mol Cell, Vol. 28, p. 328-336. Also, “hsa-mir-1227” (miRBase Accession No. MI0006316, SEQ ID NO: 508) having a hairpin-like structure is known as a precursor of “hsa-miR-1227-5p”.

The term “hsa-miR-4257 gene” or “hsa-miR-4257” used herein includes the hsa-miR-4257 gene (miRBase Accession No. MIMAT0016878) described in SEQ ID NO: 236, a homolog or an ortholog of a different organism species, and the like. The hsa-miR-4257 gene can be obtained by a method described in Goff L A et al., 2009, PLoS One, Vol. 4, e7192. Also, “hsa-mir-4257” (miRBase Accession No. MI0015856, SEQ ID NO: 509) having a hairpin-like structure is known as a precursor of “hsa-miR-4257”.

The term “hsa-miR-4270 gene” or “hsa-miR-4270” used herein includes the hsa-miR-4270 gene (miRBase Accession No. MIMAT0016900) described in SEQ ID NO: 237, a homolog or an ortholog of a different organism species, and the like. The hsa-miR-4270 gene can be obtained by a method described in Goff L A et al., 2009, PLoS One, Vol. 4, e7192. Also, “hsa-mir-4270” (miRBase Accession No. MI0015878, SEQ ID NO: 510) having a hairpin-like structure is known as a precursor of “hsa-miR-4270”.

The term “hsa-miR-4516 gene” or “hsa-miR-4516” used herein includes the hsa-miR-4516 gene (miRBase Accession No. MIMAT0019053) described in SEQ ID NO: 238, a homolog or an ortholog of a different organism species, and the like. The hsa-miR-4516 gene can be obtained by a method described in Jima D D et al., 2010, Blood, Vol. 116, e118-e127. Also, "hsa-mir-4516" (miRBase Accession No. MI0016882, SEQ ID NO: 511) having a hairpin-like structure is known as a precursor of "hsa-miR-4516".

The term "hsa-miR-4651 gene" or "hsa-miR-4651" used herein includes the hsa-miR-4651 gene (miRBase Accession No. MIMAT0019715) described in SEQ ID NO: 239, a homolog or an ortholog of a different organism species, and the like. The hsa-miR-4651 gene can be obtained by a method described in Persson H et al., 2011, Cancer Res, Vol. 71, p. 78-86. Also, "hsa-mir-4651" (miRBase Accession No. MI0017279, SEQ ID NO: 512) having a hairpin-like structure is known as a precursor of "hsa-miR-4651".

The term "hsa-miR-4725-3p gene" or "hsa-miR-4725-3p" used herein includes the hsa-miR-4725-3p gene (miRBase Accession No. MIMAT0019844) described in SEQ ID NO: 240, a homolog or an ortholog of a different organism species, and the like. The hsa-miR-4725-3p gene can be obtained by a method described in Persson H et al., 2011, Cancer Res, Vol. 71, p. 78-86. Also, "hsa-mir-4725" (miRBase Accession No. MI0017362, SEQ ID NO: 513) having a hairpin-like structure is known as a precursor of "hsa-miR-4725-3p".

The term "hsa-miR-6125 gene" or "hsa-miR-6125" used herein includes the hsa-miR-6125 gene (miRBase Accession No. MIMAT0024598) described in SEQ ID NO: 241, a homolog or an ortholog of a different organism species, and the like. The hsa-miR-6125 gene can be obtained by a method described in Smith J L et al., 2012, J Virol, Vol. 86, p. 5278-5287. Also, "hsa-mir-6125" (miRBase Accession No. MI0021259, SEQ ID NO: 514) having a hairpin-like structure is known as a precursor of "hsa-miR-6125".

The term "hsa-miR-6732-5p gene" or "hsa-miR-6732-5p" used herein includes the hsa-miR-6732-5p gene (miRBase Accession No. MIMAT0027365) described in SEQ ID NO: 242, a homolog or an ortholog of a different organism species, and the like. The hsa-miR-6732-5p gene can be obtained by a method described in Ladewig E et al., 2012, Genome Res, Vol. 22, p. 1634-1645. Also, "hsa-mir-6732" (miRBase Accession No. MI0022577, SEQ ID NO: 515) having a hairpin-like structure is known as a precursor of "hsa-miR-6732-5p".

The term "hsa-miR-6791-5p gene" or "hsa-miR-6791-5p" used herein includes the hsa-miR-6791-5p gene (miRBase Accession No. MIMAT0027482) described in SEQ ID NO: 243, a homolog or an ortholog of a different organism species, and the like. The hsa-miR-6791-5p gene can be obtained by a method described in Ladewig E et al., 2012, Genome Res, Vol. 22, p. 1634-1645. Also, "hsa-mir-6791" (miRBase Accession No. MI0022636, SEQ ID NO: 516) having a hairpin-like structure is known as a precursor of "hsa-miR-6791-5p".

The term "hsa-miR-6819-5p gene" or "hsa-miR-6819-5p" used herein includes the hsa-miR-6819-5p gene (miRBase Accession No. MIMAT0027538) described in SEQ ID NO: 244, a homolog or an ortholog of a different organism species, and the like. The hsa-miR-6819-5p gene can be obtained by a method described in Ladewig E et al., 2012, Genome Res, Vol. 22, p. 1634-1645. Also, "hsa-mir-6819" (miRBase Accession No. MI0022664, SEQ ID NO: 517) having a hairpin-like structure is known as a precursor of "hsa-miR-6819-5p".

The term "hsa-miR-6891-5p gene" or "hsa-miR-6891-5p" used herein includes the hsa-miR-6891-5p gene (miRBase Accession No. MIMAT0027682) described in SEQ ID NO: 245, a homolog or an ortholog of a different organism species, and the like. The hsa-miR-6891-5p gene can be obtained by a method described in Ladewig E et al., 2012, Genome Res, Vol. 22, p. 1634-1645. Also, "hsa-mir-6891" (miRBase Accession No. MI0022738, SEQ ID NO: 518) having a hairpin-like structure is known as a precursor of "hsa-miR-6891-5p".

The term "hsa-miR-7108-5p gene" or "hsa-miR-7108-5p" used herein includes the hsa-miR-7108-5p gene (miRBase Accession No. MIMAT0028113) described in SEQ ID NO: 246, a homolog or an ortholog of a different organism species, and the like. The hsa-miR-7108-5p gene can be obtained by a method described in Ladewig E et al., 2012, Genome Res, Vol. 22, p. 1634-1645. Also, "hsa-mir-7108" (miRBase Accession No. MI0022959, SEQ ID NO: 448) having a hairpin-like structure is known as a precursor of "hsa-miR-7108-5p".

The term "hsa-miR-7109-5p gene" or "hsa-miR-7109-5p" used herein includes the hsa-miR-7109-5p gene (miRBase Accession No. MIMAT0028115) described in SEQ ID NO: 247, a homolog or an ortholog of a different organism species, and the like. The hsa-miR-7109-5p gene can be obtained by a method described in Ladewig E et al., 2012, Genome Res, Vol. 22, p. 1634-1645. Also, "hsa-mir-7109" (miRBase Accession No. MI0022960, SEQ ID NO: 519) having a hairpin-like structure is known as a precursor of "hsa-miR-7109-5p".

The term "hsa-miR-320a gene" or "hsa-miR-320a" used herein includes the hsa-miR-320a gene (miRBase Accession No. MIMAT0000510) described in SEQ ID NO: 248, a homolog or an ortholog of a different organism species, and the like. The hsa-miR-320a gene can be obtained by a method described in Michael M Z et al., 2003, Mol Cancer Res, Vol. 1, p. 882-891. Also, "hsa-mir-320a" (miRBase Accession No. MI0000542, SEQ ID NO: 520) having a hairpin-like structure is known as a precursor of "hsa-miR-320a".

The term "hsa-miR-663a gene" or "hsa-miR-663a" used herein includes the hsa-miR-663a gene (miRBase Accession No. MIMAT0003326) described in SEQ ID NO: 249, a homolog or an ortholog of a different organism species, and the like. The hsa-miR-663a gene can be obtained by a method described in Cummins J M et al., 2006, Proc Natl Acad Sci US A, Vol. 103, p. 3687-3692. Also, "hsa-mir-663a" (miRBase Accession No. MI0003672, SEQ ID NO: 521) having a hairpin-like structure is known as a precursor of "hsa-miR-663a".

The term "hsa-miR-328-5p gene" or "hsa-miR-328-5p" used herein includes the hsa-miR-328-5p gene (miRBase Accession No. MIMAT0026486) described in SEQ ID NO: 250, a homolog or an ortholog of a different organism species, and the like. The hsa-miR-328-5p gene can be obtained by a method described in Kim J et al., 2004, Proc Natl Acad Sci USA, Vol. 101, p. 360-365. Also, "hsa-mir-328" (miRBase Accession No. MI0000804, SEQ ID NO: 522) having a hairpin-like structure is known as a precursor of "hsa-miR-328-5p".

The term "hsa-miR-642b-3p gene" or "hsa-miR-642b-3p" used herein includes the hsa-miR-642b-3p gene (miRBase Accession No. MIMAT0018444) described in SEQ ID NO: 251, a homolog or an ortholog of a different organism species, and the like. The hsa-miR-642b-3p gene can be obtained by a method described in Witten D et al., 2010, BMC Biol, Vol. 8, p. 58. Also, "hsa-mir-642b" (miRBase Accession No. MI0016685, SEQ ID NO: 523) having a hairpin-like structure is known as a precursor of "hsa-miR-642b-3p".

The term "hsa-miR-128-2-5p gene" or "hsa-miR-128-2-5p" used herein includes the hsa-miR-128-2-5p gene (miRBase Accession No. MIMAT0031095) described in SEQ ID NO: 252, a homolog or an ortholog of a different organism species, and the like. The hsa-miR-128-2-5p gene can be obtained by a method described in Lagos-Quintana M et al., 2002, Curr Biol, Vol. 12, p. 735-739. Also, "hsa-mir-128-2" (miRBase Accession No. MI0000727, SEQ ID NO: 524) having a hairpin-like structure is known as a precursor of "hsa-miR-128-2-5p".

The term "hsa-miR-125a-3p gene" or "hsa-miR-125a-3p" used herein includes the hsa-miR-125a-3p gene (miRBase Accession No. MIMAT0004602) described in SEQ ID NO: 253, a homolog or an ortholog of a different organism species, and the like. The hsa-miR-125a-3p gene can be obtained by a method described in Lagos-Quintana M et al., 2002, Curr Biol, Vol. 12, p. 735-739. Also, "hsa-mir-125a" (miRBase Accession No. MI0000469, SEQ ID NO: 525) having a hairpin-like structure is known as a precursor of "hsa-miR-125a-3p".

The term "hsa-miR-191-5p gene" or "hsa-miR-191-5p" used herein includes the hsa-miR-191-5p gene (miRBase Accession No. MIMAT0000440) described in SEQ ID NO: 254, a homolog or an ortholog of a different organism species, and the like. The hsa-miR-191-5p gene can be obtained by a method described in Lagos-Quintana M et al., 2003, RNA, Vol. 9, p. 175-179. Also, "hsa-mir-191" (miRBase Accession No. MI0000465, SEQ ID NO: 526) having a hairpin-like structure is known as a precursor of "hsa-miR-191-5p".

The term "hsa-miR-92b-5p gene" or "hsa-miR-92b-5p" used herein includes the hsa-miR-92b-5p gene (miRBase Accession No. MIMAT0004792) described in SEQ ID NO: 255, a homolog or an ortholog of a different organism species, and the like. The hsa-miR-92b-5p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 527) having a hairpin-like structure is known as a precursor of "hsa-miR-92b-5p".

The term "hsa-miR-296-5p gene" or "hsa-miR-296-5p" used herein includes the hsa-miR-296-5p gene (miRBase Accession No. MIMAT0000690) described in SEQ ID NO: 256, a homolog or an ortholog of a different organism species, and the like. The hsa-miR-296-5p gene can be obtained by a method described in Houbaviy H B et al., 2003, Dev Cell, Vol. 5, p. 351-358. Also, "hsa-mir-296" (miRBase Accession No. MI0000747, SEQ ID NO: 336) having a hairpin-like structure is known as a precursor of "hsa-miR-296-5p".

The term "hsa-miR-1246 gene" or "hsa-miR-1246" used herein includes the hsa-miR-1246 gene (miRBase Accession No. MIMAT0005898) described in SEQ ID NO: 257, a homolog or an ortholog of a different organism species, and the like. The hsa-miR-1246 gene can be obtained by a method described in Morin R D et al., 2008, Genome Res, Vol. 18, p. 610-621. Also, "hsa-mir-1246" (miRBase Accession No. MI0006381, SEQ ID NO: 528) having a hairpin-like structure is known as a precursor of "hsa-miR-1246".

The term "hsa-miR-92a-2-5p gene" or "hsa-miR-92a-2-5p" used herein includes the hsa-miR-92a-2-5p gene (miRBase Accession No. MIMAT0004508) described in SEQ ID NO: 258, a homolog or an ortholog of a different organism species, and the like. The hsa-miR-92a-2-5p gene can be obtained by a method described in Mourelatos Z et al., 2002, Genes Dev, Vol. 16, p. 720-728. Also, "hsa-mir-92a-2" (miRBase Accession No. MI0000094, SEQ ID NO: 529) having a hairpin-like structure is known as a precursor of "hsa-miR-92a-2-5p".

The term "hsa-miR-128-1-5p gene" or "hsa-miR-128-1-5p" used herein includes the hsa-miR-128-1-5p gene (miRBase Accession No. MIMAT0026477) described in SEQ ID NO: 259, a homolog or an ortholog of a different organism species, and the like. The hsa-miR-128-1-5p gene can be obtained by a method described in Lagos-Quintana M et al., 2002, Curr Biol, Vol. 12, p. 735-739. Also, "hsa-mir-128-1" (miRBase Accession No. MI0000447, SEQ ID NO: 530) having a hairpin-like structure is known as a precursor of "hsa-miR-128-1-5p".

The term "hsa-miR-1290 gene" or "hsa-miR-1290" used herein includes the hsa-miR-1290 gene (miRBase Accession No. MIMAT0005880) described in SEQ ID NO: 260, a homolog or an ortholog of a different organism species, and the like. The hsa-miR-1290 gene can be obtained by a method described in Morin R D et al., 2008, Genome Res, Vol. 18, p. 610-621. Also, "hsa-mir-1290" (miRBase Accession No. MI0006352, SEQ ID NO: 531) having a hairpin-like structure is known as a precursor of "hsa-miR-1290".

The term "hsa-miR-211-3p gene" or "hsa-miR-211-3p" used herein includes the hsa-miR-211-3p gene (miRBase Accession No. MIMAT0022694) described in SEQ ID NO: 261, a homolog or an ortholog of a different organism species, and the like. The hsa-miR-211-3p gene can be obtained by a method described in Lim L P et al., 2003, Science, Vol. 299, p. 1540. Also, "hsa-mir-211" (miRBase Accession No. MI0000287, SEQ ID NO: 532) having a hairpin-like structure is known as a precursor of "hsa-miR-211-3p".

The term "hsa-miR-744-5p gene" or "hsa-miR-744-5p" used herein includes the hsa-miR-744-5p gene (miRBase Accession No. MIMAT0004945) described in SEQ ID NO: 262, a homolog or an ortholog of a different organism species, and the like. The hsa-miR-744-5p gene can be obtained by a method described in Berezikov E et al., 2006, Genome Res, Vol. 16, p. 1289-1298. Also, "hsa-mir-744" (miRBase Accession No. MI0005559, SEQ ID NO: 533) having a hairpin-like structure is known as a precursor of "hsa-miR-744-5p".

The term "hsa-miR-135a-3p gene" or "hsa-miR-135a-3p" used herein includes the hsa-miR-135a-3p gene (miRBase Accession No. MIMAT0004595) described in SEQ ID NO: 263, a homolog or an ortholog of a different organism species, and the like. The hsa-miR-135a-3p gene can be obtained by a method described in Lagos-Quintana M et al., 2002, Curr Biol, Vol. 12, p. 735-739. Also, "hsa-mir-135a-1" (miRBase Accession No. MI0000452, SEQ ID NO: 534) having a hairpin-like structure is known as a precursor of "hsa-miR-135a-3p".

The term "hsa-miR-451a gene" or "hsa-miR-451a" used herein includes the hsa-miR-451a gene (miRBase Accession No. MIMAT0001631) described in SEQ ID NO: 264, a homolog or an ortholog of a different organism species, and the like. The hsa-miR-451a gene can be obtained by a method described in Altuvia Y et al., 2005, Nucleic Acids Res, Vol. 33, p. 2697-2706. Also, "hsa-mir-451a" (miRBase Accession No. MI0001729, SEQ ID NO: 535) having a hairpin-like structure is known as a precursor of "hsa-miR-451a".

The term "hsa-miR-625-3p gene" or "hsa-miR-625-3p" used herein includes the hsa-miR-625-3p gene (miRBase Accession No. MIMAT0004808) described in SEQ ID NO: 265, a homolog or an ortholog of a different organism species, and the like. The hsa-miR-625-3p gene can be obtained by a method described in Cummins J M et al., 2006, Proc Natl Acad Sci USA, Vol. 103, p. 3687-3692. Also, "hsa-mir-625" (miRBase Accession No. MI0003639, SEQ ID NO: 536) having a hairpin-like structure is known as a precursor of "hsa-miR-625-3p".

The term "hsa-miR-92a-3p gene" or "hsa-miR-92a-3p" used herein includes the hsa-miR-92a-3p gene (miRBase Accession No. MIMAT0000092) described in SEQ ID NO: 266, a homolog or an ortholog of a different organism species, and the like. The hsa-miR-92a-3p gene can be obtained by a method described in Mourelatos Z et al., 2002, Genes Dev, Vol. 16, p. 720-728. Also, "hsa-mir-92a-1 and hsa-mir-92a-2" (miRBase Accession Nos. MI0000093 and MI0000094, SEQ ID NOs: 537 and 529) having a hairpin-like structure are known as precursors of "hsa-miR-92a-3p".

The term "hsa-miR-422a gene" or "hsa-miR-422a" used herein includes the hsa-miR-422a gene (miRBase Accession No. MIMAT0001339) described in SEQ ID NO: 267, a homolog or an ortholog of a different organism species, and the like. The hsa-miR-422a gene can be obtained by a method described in Kasashima K et al., 2004, Biochem Biophys Res Commun, Vol. 322, p. 403-410. Also, "hsa-mir-422a" (miRBase Accession No. MI0001444, SEQ ID NO: 538) having a hairpin-like structure is known as a precursor of "hsa-miR-422a".

The term "hsa-miR-642a-3p gene" or "hsa-miR-642a-3p" used herein includes the hsa-miR-642a-3p gene (miRBase Accession No. MIMAT0020924) described in SEQ ID NO: 268, a homolog or an ortholog of a different organism species, and the like. The hsa-miR-642a-3p gene can be obtained by a method described in Cummins J M et al., 2006, Proc Natl Acad Sci USA, Vol. 103, p. 3687-3692. Also, "hsa-mir-642a" (miRBase Accession No. MI0003657, SEQ ID NO: 539) having a hairpin-like structure is known as a precursor of "hsa-miR-642a-3p".

The term "hsa-miR-483-5p gene" or "hsa-miR-483-5p" used herein includes the hsa-miR-483-5p gene (miRBase Accession No. MIMAT0004761) described in SEQ ID NO: 269, a homolog or an ortholog of a different organism species, and the like. The hsa-miR-483-5p gene can be obtained by a method described in Fu H et al., 2005, FEBS Lett, Vol. 579, p. 3849-3854. Also, "hsa-mir-483" (miRBase Accession No. MI0002467, SEQ ID NO: 540) having a hairpin-like structure is known as a precursor of "hsa-miR-483-5p".

The term "hsa-miR-652-5p gene" or "hsa-miR-652-5p" used herein includes the hsa-miR-652-5p gene (miRBase Accession No. MIMAT0022709) described in SEQ ID NO: 270, a homolog or an ortholog of a different organism species, and the like. The hsa-miR-652-5p gene can be obtained by a method described in Cummins J M et al., 2006, Proc Natl Acad Sci USA, Vol. 103, p. 3687-3692. Also, "hsa-mir-652" (miRBase Accession No. MI0003667, SEQ ID NO: 541) having a hairpin-like structure is known as a precursor of "hsa-miR-652-5p".

The term "hsa-miR-24-3p gene" or "hsa-miR-24-3p" used herein includes the hsa-miR-24-3p gene (miRBase Accession No. MIMAT0000080) described in SEQ ID NO: 271, a homolog or an ortholog of a different organism species, and the like. The hsa-miR-24-3p gene can be obtained by a method described in Lagos-Quintana M et al., 2001, Science, Vol. 294, p. 853-858. Also, "hsa-mir-24-1 and hsa-mir-24-2" (miRBase Accession Nos. MI0000080 and MI0000081, SEQ ID NOs: 542 and 543) having a hairpin-like structure are known as precursors of "hsa-miR-24-3p".

The term "hsa-miR-23b-3p gene" or "hsa-miR-23b-3p" used herein includes the hsa-miR-23b-3p gene (miRBase Accession No. MIMAT0000418) described in SEQ ID NO: 272, a homolog or an ortholog of a different organism species, and the like. The hsa-miR-23b-3p gene can be obtained by a method described in Lagos-Quintana M et al., 2002, Curr Biol, Vol. 12, p. 735-739. Also, "hsa-mir-23b" (miRBase Accession No. MI10000439, SEQ ID NO: 544) having a hairpin-like structure is known as a precursor of "hsa-miR-23b-3p".

The term "hsa-miR-23a-3p gene" or "hsa-miR-23a-3p" used herein includes the hsa-miR-23a-3p gene (miRBase Accession No. MIMAT0000078) described in SEQ ID NO: 273, a homolog or an ortholog of a different organism species, and the like. The hsa-miR-23a-3p gene can be obtained by a method described in Lagos-Quintana M et al., 2001, Science, Vol. 294, p. 853-858. Also, "hsa-mir-23a" (miRBase Accession No. MI0000079, SEQ ID NO: 545) having a hairpin-like structure is known as a precursor of "hsa-miR-23a-3p".

The term "hsa-miR-92b-3p gene" or "hsa-miR-92b-3p" used herein includes the hsa-miR-92b-3p gene (miRBase Accession No. MIMAT0003218) described in SEQ ID NO: 274, a homolog or an ortholog of a different organism species, and the like. The hsa-miR-92b-3p gene can be obtained by a method described in Cummins J M et al., 2006, Proc Natl Acad Sci USA, Vol. 103, p. 3687-3692. Also, "hsa-mir-92b" (miRBase Accession No. MI0003560, SEQ ID NO: 527) having a hairpin-like structure is known as a precursor of "hsa-miR-92b-3p".

The term "hsa-miR-22-3p gene" or "hsa-miR-22-3p" used herein includes the hsa-miR-22-3p gene (miRBase Accession No. MIMAT0000077) described in SEQ ID NO: 275, a homolog or an ortholog of a different organism species, and the like. The hsa-miR-22-3p gene can be obtained by a method described in Lagos-Quintana M et al., 2001, Science, Vol. 294, p. 853-858. Also, "hsa-mir-22" (miRBase Accession No. MI0000078, SEQ ID NO: 546) having a hairpin-like structure is known as a precursor of "hsa-miR-22-3p".

A mature miRNA may become a variant due to the sequence cleaved shorter or longer by one to several flanking nucleotides, or due to substitution of nucleotides, when cut out as the mature miRNA from its RNA precursor having a hairpin-like structure. This variant is called isomiR (Morin R D. et al., 2008, Genome Res., Vol. 18, p. 610-621). The miRBase Release 21 shows the nucleotide sequences represented by SEQ ID NOs: 1 to 275 as well as a large number of the nucleotide sequence variants and fragments represented by SEQ ID NOs: 547 to 842, called isomiRs. These variants can also be obtained as miRNAs having a nucleotide sequence represented by any of SEQ ID NOs: 1 to 275. Specifically, among the variants of polynucleotides consisting of the nucleotide sequence represented by any of SEQ ID NOs: 2, 3, 4, 8, 11, 14, 17, 18, 20, 24, 25, 29, 34, 36, 39, 40, 41, 42, 43, 44, 45, 51, 53, 55, 57, 59, 62, 63, 66, 67, 69, 70, 71, 72, 73, 75, 76, 78, 79, 84, 87, 88, 90, 94, 96, 98, 101, 102, 103, 104, 105, 110, 112, 113, 117, 119, 121, 122, 123, 124, 125, 127, 130, 136, 140, 141, 146, 148, 151, 153, 154, 159, 164, 166, 170, 175, 180, 184, 185, 189, 190, 193, 195, 196, 197, 198, 199, 201, 202, 203, 204, 205, 207, 210, 212, 213, 215, 217, 218, 219, 220, 221, 223, 224, 229, 232, 233, 238, 239, 240, 241, 248, 249, 250, 251, 252, 253, 254, 255, 256, 257, 258, 259, 260, 261, 262, 263, 264, 265, 266, 269, 270, 271, 272, 274, and 275 or a nucleotide sequence derived from the nucleotide sequence by the replacement of u with t according to the present invention, examples of the longest variants registered in miRBase Release 21 include polynucleotides represented by SEQ ID NOs: 547, 549, 551, 554, 556, 560, 563, 565, 567, 570, 572, 574, 576, 578, 580, 582, 584, 586, 588, 590, 592, 594, 596, 598, 600, 602, 604, 606, 608, 610, 612, 614, 616, 618, 620, 623, 625, 627, 629, 632, 634, 636, 638, 641, 644, 646, 649, 651, 653, 655, 657, 661, 663, 665, 668, 670, 672, 674, 676, 678, 680, 682, 685, 687, 689, 691, 694, 696, 698, 700, 702, 704, 707, 709, 711, 714, 717, 720, 722, 725, 727, 729, 731, 733, 735, 737, 739, 741, 743, 745, 747, 749, 751, 754, 756, 758, 760, 762, 764, 766, 768, 770, 772, 774, 776, 778, 780, 783, 785, 787, 789, 791, 793, 795, 797, 799, 801, 803, 805, 807, 809, 811, 813, 815, 817, 819, 821, 823, 825, 827, 830, 832, 834, 836, 839, and 841, respectively. Also, among the variants of polynucleotides consisting of a nucleotide sequence represented by any of SEQ ID NOs: 2, 3, 4, 8, 11, 14, 17, 18, 20, 24, 25, 29, 34, 36, 39, 40, 41, 42, 43, 44, 45, 51, 53, 55, 57, 59, 62, 63, 66, 67, 69, 70, 71, 72, 73, 75, 76, 78, 79, 84, 87, 88, 90, 94, 96, 98, 101, 102, 103, 104, 105, 110, 112, 113, 117, 119, 121, 122, 123, 124, 125, 127, 130, 136, 140, 141, 146, 148, 151, 153, 154, 159, 164, 166, 170, 175, 180, 184, 185, 189, 190, 193, 195, 196, 197, 198, 199, 201, 202, 203, 204, 205, 207, 210, 212, 213, 215, 217, 218, 219, 220, 221, 223, 224, 229, 232, 233, 238, 239, 240, 241, 248, 249, 250, 251, 252, 253, 254, 255, 256, 257, 258, 259, 260, 261, 262, 263, 264, 265, 266, 269, 270, 271, 272, 274, and 275 or a nucleotide sequence derived from the nucleotide sequence by the replacement of u with t according to the present invention, examples of shortest variants registered in the miRBase Release 21 include polynucleotides having sequences represented by SEQ ID NOs: 548, 550, 552, 555, 557, 561, 564, 566, 568, 571, 573, 575, 577, 579, 581, 583, 585, 587, 589, 591, 593, 595, 597, 599, 601, 603, 605, 607, 609, 611, 613, 615, 617, 619, 621, 624, 626, 628, 630, 633, 635, 637, 639, 642, 645, 647, 650, 652, 654, 656, 658, 662, 664, 666, 669, 671, 673, 675, 677, 679, 681, 683, 686, 688, 690, 692, 695, 697, 699, 701, 703, 705, 708, 710, 712, 715, 718, 721, 723, 726, 728, 730, 732, 734, 736, 738, 740, 742, 744, 746, 748, 750, 752, 755, 757, 759, 761, 763, 765, 767, 769, 771, 773, 775, 777, 779, 781, 784, 786, 788, 790, 792, 794, 796, 798, 800, 802, 804, 806, 808, 810, 812, 814, 816, 818, 820, 822, 824, 826, 828, 831, 833, 835, 837, 840, and 842, respectively. In addition to these variants and fragments, examples thereof include a large number of isomiR polynucleotides of SEQ ID NOs: 1 to 275 registered in the miRBase. Examples of the polynucleotide comprising a nucleotide sequence represented by any of SEQ ID NOs: 1 to 275 include a polynucleotide represented by any of SEQ ID NOs: 276 to 546, which are their respective precursors.

The names and miRBase Accession Nos. (registration numbers) of the genes represented by SEQ ID NOs: 1 to 842 are shown in Table 1.

As used herein, the term "capable of specifically binding" means that nucleic acids such as the nucleic acid probe or the primer used in the present invention binds to a particular target nucleic acid and cannot substantially bind to other nucleic acids.

TABLE 1

| SEQ ID NO. | Name of gene | Accession No. of miRBase |
|---|---|---|
| 1 | hsa-miR-4675 | MIMAT0019757 |
| 2 | hsa-miR-4783-3p | MIMAT0019947 |
| 3 | hsa-miR-1228-5p | MIMAT0005582 |
| 4 | hsa-miR-4532 | MIMAT0019071 |
| 5 | hsa-miR-6802-5p | MIMAT0027504 |
| 6 | hsa-miR-6784-5p | MIMAT0027468 |
| 7 | hsa-miR-3940-5p | MIMAT0019229 |
| 8 | hsa-miR-1307-3p | MIMAT0005951 |

TABLE 1-continued

| SEQ ID NO. | Name of gene | Accession No. of miRBase |
|---|---|---|
| 9 | hsa-miR-8073 | MIMAT0031000 |
| 10 | hsa-miR-3184-5p | MIMAT0015064 |
| 11 | hsa-miR-1233-5p | MIMAT0022943 |
| 12 | hsa-miR-6088 | MIMAT0023713 |
| 13 | hsa-miR-5195-3p | MIMAT0021127 |
| 14 | hsa-miR-320b | MIMAT0005792 |
| 15 | hsa-miR-4649-5p | MIMAT0019711 |
| 16 | hsa-miR-6800-5p | MIMAT0027500 |
| 17 | hsa-miR-1343-3p | MIMAT0019776 |
| 18 | hsa-miR-4730 | MIMAT0019852 |
| 19 | hsa-miR-6885-5p | MIMAT0027670 |
| 20 | hsa-miR-5100 | MIMAT0022259 |
| 21 | hsa-miR-1203 | MIMAT0005866 |
| 22 | hsa-miR-6756-5p | MIMAT0027412 |
| 23 | hsa-miR-373-5p | MIMAT0000725 |
| 24 | hsa-miR-1268a | MIMAT0005922 |
| 25 | hsa-miR-1260b | MIMAT0015041 |
| 26 | hsa-miR-4258 | MIMAT0016879 |
| 27 | hsa-miR-4697-5p | MIMAT0019791 |
| 28 | hsa-miR-1469 | MIMAT0007347 |
| 29 | hsa-miR-4515 | MIMAT0019052 |
| 30 | hsa-miR-6861-5p | MIMAT0027623 |
| 31 | hsa-miR-6821-5p | MIMAT0027542 |
| 32 | hsa-miR-575 | MIMAT0003240 |
| 33 | hsa-miR-6805-5p | MIMAT0027510 |
| 34 | hsa-miR-4758-5p | MIMAT0019903 |
| 35 | hsa-miR-3663-3p | MIMAT0018085 |
| 36 | hsa-miR-4530 | MIMAT0019069 |
| 37 | hsa-miR-6798-5p | MIMAT0027496 |
| 38 | hsa-miR-6781-5p | MIMAT0027462 |
| 39 | hsa-miR-885-3p | MIMAT0004948 |
| 40 | hsa-miR-1273g-3p | MIMAT0022742 |
| 41 | hsa-miR-4787-3p | MIMAT0019957 |
| 42 | hsa-miR-4454 | MIMAT0018976 |
| 43 | hsa-miR-4706 | MIMAT0019806 |
| 44 | hsa-miR-1249-3p | MIMAT0005901 |
| 45 | hsa-miR-887-3p | MIMAT0004951 |
| 46 | hsa-miR-6786-5p | MIMAT0027472 |
| 47 | hsa-miR-1238-5p | MIMAT0022947 |
| 48 | hsa-miR-6749-5p | MIMAT0027398 |
| 49 | hsa-miR-6729-5p | MIMAT0027359 |
| 50 | hsa-miR-6825-5p | MIMAT0027550 |
| 51 | hsa-miR-663b | MIMAT0005867 |
| 52 | hsa-miR-6858-5p | MIMAT0027616 |
| 53 | hsa-miR-4690-5p | MIMAT0019779 |
| 54 | hsa-miR-6765-5p | MIMAT0027430 |
| 55 | hsa-miR-4710 | MIMAT0019815 |
| 56 | hsa-miR-6775-5p | MIMAT0027450 |
| 57 | hsa-miR-371a-5p | MIMAT0004687 |
| 58 | hsa-miR-6816-5p | MIMAT0027532 |
| 59 | hsa-miR-296-3p | MIMAT0004679 |
| 60 | hsa-miR-7977 | MIMAT0031180 |
| 61 | hsa-miR-8069 | MIMAT0030996 |
| 62 | hsa-miR-6515-3p | MIMAT0025487 |
| 63 | hsa-miR-4687-5p | MIMAT0019774 |
| 64 | hsa-miR-1343-5p | MIMAT0027038 |
| 65 | hsa-miR-7110-5p | MIMAT0028117 |
| 66 | hsa-miR-4525 | MIMAT0019064 |
| 67 | hsa-miR-3158-5p | MIMAT0019211 |
| 68 | hsa-miR-6787-5p | MIMAT0027474 |
| 69 | hsa-miR-614 | MIMAT0003282 |
| 70 | hsa-miR-4689 | MIMAT0019778 |
| 71 | hsa-miR-1185-2-3p | MIMAT0022713 |
| 72 | hsa-miR-1268b | MIMAT0018925 |
| 73 | hsa-miR-1228-3p | MIMAT0005583 |
| 74 | hsa-miR-1185-1-3p | MIMAT0022838 |
| 75 | hsa-miR-940 | MIMAT0004983 |
| 76 | hsa-miR-939-5p | MIMAT0004982 |
| 77 | hsa-miR-6757-5p | MIMAT0027414 |
| 78 | hsa-miR-1275 | MIMAT0005929 |
| 79 | hsa-miR-5001-5p | MIMAT0021021 |
| 80 | hsa-miR-6826-5p | MIMAT0027552 |
| 81 | hsa-miR-6765-3p | MIMAT0027431 |
| 82 | hsa-miR-3679-3p | MIMAT0018105 |
| 83 | hsa-miR-4718 | MIMAT0019831 |
| 84 | hsa-miR-4286 | MIMAT0016916 |

TABLE 1-continued

| SEQ ID NO. | Name of gene | Accession No. of miRBase |
|---|---|---|
| 85 | hsa-miR-8059 | MIMAT0030986 |
| 86 | hsa-miR-4447 | MIMAT0018966 |
| 87 | hsa-miR-4448 | MIMAT0018967 |
| 88 | hsa-miR-658 | MIMAT0003336 |
| 89 | hsa-miR-6766-3p | MIMAT0027433 |
| 90 | hsa-miR-197-5p | MIMAT0022691 |
| 91 | hsa-miR-6887-5p | MIMAT0027674 |
| 92 | hsa-miR-6742-5p | MIMAT0027385 |
| 93 | hsa-miR-6729-3p | MIMAT0027360 |
| 94 | hsa-miR-5090 | MIMAT0021082 |
| 95 | hsa-miR-7975 | MIMAT0031178 |
| 96 | hsa-miR-4505 | MIMAT0019041 |
| 97 | hsa-miR-6889-5p | MIMAT0027678 |
| 98 | hsa-miR-4708-3p | MIMAT0019810 |
| 99 | hsa-miR-6131 | MIMAT0024615 |
| 100 | hsa-miR-1225-3p | MIMAT0005573 |
| 101 | hsa-miR-6132 | MIMAT0024616 |
| 102 | hsa-miR-4734 | MIMAT0019859 |
| 103 | hsa-miR-3194-3p | MIMAT0019218 |
| 104 | hsa-miR-638 | MIMAT0003308 |
| 105 | hsa-miR-2467-3p | MIMAT0019953 |
| 106 | hsa-miR-4728-5p | MIMAT0019849 |
| 107 | hsa-miR-5572 | MIMAT0022260 |
| 108 | hsa-miR-6789-5p | MIMAT0027478 |
| 109 | hsa-miR-8063 | MIMAT0030990 |
| 110 | hsa-miR-4429 | MIMAT0018944 |
| 111 | hsa-miR-6840-3p | MIMAT0027583 |
| 112 | hsa-miR-4476 | MIMAT0019003 |
| 113 | hsa-miR-675-5p | MIMAT0004284 |
| 114 | hsa-miR-711 | MIMAT0012734 |
| 115 | hsa-miR-6875-5p | MIMAT0027650 |
| 116 | hsa-miR-3160-5p | MIMAT0019212 |
| 117 | hsa-miR-1908-5p | MIMAT0007881 |
| 118 | hsa-miR-6726-5p | MIMAT0027353 |
| 119 | hsa-miR-1913 | MIMAT0007888 |
| 120 | hsa-miR-8071 | MIMAT0030998 |
| 121 | hsa-miR-3648 | MIMAT0018068 |
| 122 | hsa-miR-4732-5p | MIMAT0019855 |
| 123 | hsa-miR-4787-5p | MIMAT0019956 |
| 124 | hsa-miR-3917 | MIMAT0018191 |
| 125 | hsa-miR-619-5p | MIMAT0026622 |
| 126 | hsa-miR-1231 | MIMAT0005586 |
| 127 | hsa-miR-342-5p | MIMAT0004694 |
| 128 | hsa-miR-4433a-5p | MIMAT0020956 |
| 129 | hsa-miR-6766-5p | MIMAT0027432 |
| 130 | hsa-miR-4707-5p | MIMAT0019807 |
| 131 | hsa-miR-7114-5p | MIMAT0028125 |
| 132 | hsa-miR-6872-3p | MIMAT0027645 |
| 133 | hsa-miR-6780b-5p | MIMAT0027572 |
| 134 | hsa-miR-7845-5p | MIMAT0030420 |
| 135 | hsa-miR-6798-3p | MIMAT0027497 |
| 136 | hsa-miR-665 | MIMAT0004952 |
| 137 | hsa-miR-6848-5p | MIMAT0027596 |
| 138 | hsa-miR-5008-5p | MIMAT0021039 |
| 139 | hsa-miR-4294 | MIMAT0016849 |
| 140 | hsa-miR-6511a-5p | MIMAT0025478 |
| 141 | hsa-miR-4435 | MIMAT0018951 |
| 142 | hsa-miR-4747-3p | MIMAT0019883 |
| 143 | hsa-miR-6880-3p | MIMAT0027661 |
| 144 | hsa-miR-6869-5p | MIMAT0027638 |
| 145 | hsa-miR-7150 | MIMAT0028211 |
| 146 | hsa-miR-1260a | MIMAT0005911 |
| 147 | hsa-miR-6877-5p | MIMAT0027654 |
| 148 | hsa-miR-6721-5p | MIMAT0025852 |
| 149 | hsa-miR-4656 | MIMAT0019723 |
| 150 | hsa-miR-1229-5p | MIMAT0022942 |
| 151 | hsa-miR-4433a-3p | MIMAT0018949 |
| 152 | hsa-miR-4274 | MIMAT0016906 |
| 153 | hsa-miR-4419b | MIMAT0019034 |
| 154 | hsa-miR-4674 | MIMAT0019756 |
| 155 | hsa-miR-6893-5p | MIMAT0027686 |
| 156 | hsa-miR-6763-3p | MIMAT0027427 |
| 157 | hsa-miR-6762-5p | MIMAT0027424 |
| 158 | hsa-miR-6738-5p | MIMAT0027377 |
| 159 | hsa-miR-4513 | MIMAT0019050 |
| 160 | hsa-miR-6746-5p | MIMAT0027392 |

TABLE 1-continued

| SEQ ID NO. | Name of gene | Accession No. of miRBase |
|---|---|---|
| 161 | hsa-miR-6880-5p | MIMAT0027660 |
| 162 | hsa-miR-4736 | MIMAT0019862 |
| 163 | hsa-miR-718 | MIMAT0012735 |
| 164 | hsa-miR-6717-5p | MIMAT0025846 |
| 165 | hsa-miR-7847-3p | MIMAT0030422 |
| 166 | hsa-miR-760 | MIMAT0004957 |
| 167 | hsa-miR-1199-5p | MIMAT0031119 |
| 168 | hsa-miR-6813-5p | MIMAT0027526 |
| 169 | hsa-miR-6769a-5p | MIMAT0027438 |
| 170 | hsa-miR-1193 | MIMAT0015049 |
| 171 | hsa-miR-7108-3p | MIMAT0028114 |
| 172 | hsa-miR-6741-5p | MIMAT0027383 |
| 173 | hsa-miR-4298 | MIMAT0016852 |
| 174 | hsa-miR-6796-3p | MIMAT0027493 |
| 175 | hsa-miR-4750-5p | MIMAT0019887 |
| 176 | hsa-miR-6785-5p | MIMAT0027470 |
| 177 | hsa-miR-1292-3p | MIMAT0022948 |
| 178 | hsa-miR-4749-3p | MIMAT0019886 |
| 179 | hsa-miR-6800-3p | MIMAT0027501 |
| 180 | hsa-miR-4722-5p | MIMAT0019836 |
| 181 | hsa-miR-4746-3p | MIMAT0019881 |
| 182 | hsa-miR-4450 | MIMAT0018971 |
| 183 | hsa-miR-6795-5p | MIMAT0027490 |
| 184 | hsa-miR-365a-5p | MIMAT0009199 |
| 185 | hsa-miR-498 | MIMAT0002824 |
| 186 | hsa-miR-6797-5p | MIMAT0027494 |
| 187 | hsa-miR-1470 | MIMAT0007348 |
| 188 | hsa-miR-6851-5p | MIMAT0027602 |
| 189 | hsa-miR-1247-3p | MIMAT0022721 |
| 190 | hsa-miR-5196-5p | MIMAT0021128 |
| 191 | hsa-miR-208a-5p | MIMAT0026474 |
| 192 | hsa-miR-6842-5p | MIMAT0027586 |
| 193 | hsa-miR-150-3p | MIMAT0004610 |
| 194 | hsa-miR-4534 | MIMAT0019073 |
| 195 | hsa-miR-3135b | MIMAT0018985 |
| 196 | hsa-miR-3131 | MIMAT0014996 |
| 197 | hsa-miR-4792 | MIMAT0019964 |
| 198 | hsa-miR-6510-5p | MIMAT0025476 |
| 199 | hsa-miR-504-3p | MIMAT0026612 |
| 200 | hsa-miR-3619-3p | MIMAT0019219 |
| 201 | hsa-miR-671-5p | MIMAT0003880 |
| 202 | hsa-miR-4667-5p | MIMAT0019743 |
| 203 | hsa-miR-4430 | MIMAT0018945 |
| 204 | hsa-miR-3195 | MIMAT0015079 |
| 205 | hsa-miR-3679-5p | MIMAT0018104 |
| 206 | hsa-miR-6076 | MIMAT0023701 |
| 207 | hsa-miR-6515-5p | MIMAT0025486 |
| 208 | hsa-miR-6820-5p | MIMAT0027540 |
| 209 | hsa-miR-4634 | MIMAT0019691 |
| 210 | hsa-miR-187-5p | MIMAT0004561 |
| 211 | hsa-miR-6763-5p | MIMAT0027426 |
| 212 | hsa-miR-1908-3p | MIMAT0026916 |
| 213 | hsa-miR-1181 | MIMAT0005826 |
| 214 | hsa-miR-6782-5p | MIMAT0027464 |
| 215 | hsa-miR-5010-5p | MIMAT0021043 |
| 216 | hsa-miR-6870-5p | MIMAT0027640 |
| 217 | hsa-miR-6124 | MIMAT0024597 |
| 218 | hsa-miR-1249-5p | MIMAT0032029 |
| 219 | hsa-miR-6511b-5p | MIMAT0025847 |
| 220 | hsa-miR-1254 | MIMAT0005905 |
| 221 | hsa-miR-4727-3p | MIMAT0019848 |
| 222 | hsa-miR-4259 | MIMAT0016880 |
| 223 | hsa-miR-4771 | MIMAT0019925 |
| 224 | hsa-miR-3622a-5p | MIMAT0018003 |
| 225 | hsa-miR-4480 | MIMAT0019014 |
| 226 | hsa-miR-4740-5p | MIMAT0019869 |
| 227 | hsa-miR-6777-5p | MIMAT0027454 |
| 228 | hsa-miR-6794-5p | MIMAT0027488 |
| 229 | hsa-miR-4687-3p | MIMAT0019775 |
| 230 | hsa-miR-6743-5p | MIMAT0027387 |
| 231 | hsa-miR-6771-5p | MIMAT0027442 |
| 232 | hsa-miR-3141 | MIMAT0015010 |
| 233 | hsa-miR-3162-5p | MIMAT0015036 |
| 234 | hsa-miR-4271 | MIMAT0016901 |
| 235 | hsa-miR-1227-5p | MIMAT0022941 |
| 236 | hsa-miR-4257 | MIMAT0016878 |

TABLE 1-continued

| SEQ ID NO. | Name of gene | Accession No. of miRBase |
|---|---|---|
| 237 | hsa-miR-4270 | MIMAT0016900 |
| 238 | hsa-miR-4516 | MIMAT0019053 |
| 239 | hsa-miR-4651 | MIMAT0019715 |
| 240 | hsa-miR-4725-3p | MIMAT0019844 |
| 241 | hsa-miR-6125 | MIMAT0024598 |
| 242 | hsa-miR-6732-5p | MIMAT0027365 |
| 243 | hsa-miR-6791-5p | MIMAT0027482 |
| 244 | hsa-miR-6819-5p | MIMAT0027538 |
| 245 | hsa-miR-6891-5p | MIMAT0027682 |
| 246 | hsa-miR-7108-5p | MIMAT0028113 |
| 247 | hsa-miR-7109-5p | MIMAT0028115 |
| 248 | hsa-miR-320a | MIMAT0000510 |
| 249 | hsa-miR-663a | MIMAT0003326 |
| 250 | hsa-miR-328-5p | MIMAT0026486 |
| 251 | hsa-miR-642b-3p | MIMAT0018444 |
| 252 | hsa-miR-128-2-5p | MIMAT0031095 |
| 253 | hsa-miR-125a-3p | MIMAT0004602 |
| 254 | hsa-miR-191-5p | MIMAT0000440 |
| 255 | hsa-miR-92b-5p | MIMAT0004792 |
| 256 | hsa-miR-296-5p | MIMAT0000690 |
| 257 | hsa-miR-1246 | MIMAT0005898 |
| 258 | hsa-miR-92a-2-5p | MIMAT0004508 |
| 259 | hsa-miR-128-1-5p | MIMAT0026477 |
| 260 | hsa-miR-1290 | MIMAT0005880 |
| 261 | hsa-miR-211-3p | MIMAT0022694 |
| 262 | hsa-miR-744-5p | MIMAT0004945 |
| 263 | hsa-miR-135a-3p | MIMAT0004595 |
| 264 | hsa-miR-451a | MIMAT0001631 |
| 265 | hsa-miR-625-3p | MIMAT0004808 |
| 266 | hsa-miR-92a-3p | MIMAT0000092 |
| 267 | hsa-miR-422a | MIMAT0001339 |
| 268 | hsa-miR-642a-3p | MIMAT0020924 |
| 269 | hsa-miR-483-5p | MIMAT0004761 |
| 270 | hsa-miR-652-5p | MIMAT0022709 |
| 271 | hsa-miR-24-3p | MIMAT0000080 |
| 272 | hsa-miR-23b-3p | MIMAT0000418 |
| 273 | hsa-miR-23a-3p | MIMAT0000078 |
| 274 | hsa-miR-92b-3p | MIMAT0003218 |
| 275 | hsa-miR-22-3p | MIMAT0000077 |
| 276 | hsa-mir-4675 | MI0017306 |
| 277 | hsa-mir-4783 | MI0017428 |
| 278 | hsa-mir-1228 | MI0006318 |
| 279 | hsa-mir-4532 | MI0016899 |
| 280 | hsa-mir-6802 | MI0022647 |
| 281 | hsa-mir-6784 | MI0022629 |
| 282 | hsa-mir-3940 | MI0016597 |
| 283 | hsa-mir-1307 | MI0006444 |
| 284 | hsa-mir-8073 | MI0025909 |
| 285 | hsa-mir-3184 | MI0014226 |
| 286 | hsa-mir-1233-1 | MI0006323 |
| 287 | hsa-mir-1233-2 | MI0015973 |
| 288 | hsa-mir-6088 | MI0020365 |
| 289 | hsa-mir-5195 | MI0018174 |
| 290 | hsa-mir-320b-1 | MI0003776 |
| 291 | hsa-mir-320b-2 | MI0003839 |
| 292 | hsa-mir-4649 | MI0017276 |
| 293 | hsa-mir-6800 | MI0022645 |
| 294 | hsa-mir-1343 | MI0017320 |
| 295 | hsa-mir-4730 | MI0017367 |
| 296 | hsa-mir-6885 | MI0022732 |
| 297 | hsa-mir-5100 | MI0019116 |
| 298 | hsa-mir-1203 | MI0006335 |
| 299 | hsa-mir-6756 | MI0022601 |
| 300 | hsa-mir-373 | MI0000781 |
| 301 | hsa-mir-1268a | MI0006405 |
| 302 | hsa-mir-1260b | MI0014197 |
| 303 | hsa-mir-4258 | MI0015857 |
| 304 | hsa-mir-4697 | MI0017330 |
| 305 | hsa-mir-1469 | MI0007074 |
| 306 | hsa-mir-4515 | MI0016881 |
| 307 | hsa-mir-6861 | MI0022708 |
| 308 | hsa-mir-6821 | MI0022666 |
| 309 | hsa-mir-575 | MI0003582 |
| 310 | hsa-mir-6805 | MI0022650 |
| 311 | hsa-mir-4758 | MI0017399 |
| 312 | hsa-mir-3663 | MI0016064 |

TABLE 1-continued

| SEQ ID NO. | Name of gene | Accession No. of miRBase |
|---|---|---|
| 313 | hsa-mir-4530 | MI0016897 |
| 314 | hsa-mir-6798 | MI0022643 |
| 315 | hsa-mir-6781 | MI0022626 |
| 316 | hsa-mir-885 | MI0005560 |
| 317 | hsa-mir-1273g | MI0018003 |
| 318 | hsa-mir-4787 | MI0017434 |
| 319 | hsa-mir-4454 | MI0016800 |
| 320 | hsa-mir-4706 | MI0017339 |
| 321 | hsa-mir-1249 | MI0006384 |
| 322 | hsa-mir-887 | MI0005562 |
| 323 | hsa-mir-6786 | MI0022631 |
| 324 | hsa-mir-1238 | MI0006328 |
| 325 | hsa-mir-6749 | MI0022594 |
| 326 | hsa-mir-6729 | MI0022574 |
| 327 | hsa-mir-6825 | MI0022670 |
| 328 | hsa-mir-663b | MI0006336 |
| 329 | hsa-mir-6858 | MI0022704 |
| 330 | hsa-mir-4690 | MI0017323 |
| 331 | hsa-mir-6765 | MI0022610 |
| 332 | hsa-mir-4710 | MI0017344 |
| 333 | hsa-mir-6775 | MI0022620 |
| 334 | hsa-mir-371a | MI0000779 |
| 335 | hsa-mir-6816 | MI0022661 |
| 336 | hsa-mir-296 | MI0000747 |
| 337 | hsa-mir-7977 | MI0025753 |
| 338 | hsa-mir-8069-1 | MI0025905 |
| 339 | hsa-mir-8069-2 | MI0031519 |
| 340 | hsa-mir-6515 | MI0022227 |
| 341 | hsa-mir-4687 | MI0017319 |
| 342 | hsa-mir-7110 | MI0022961 |
| 343 | hsa-mir-4525 | MI0016892 |
| 344 | hsa-mir-3158-1 | MI0014186 |
| 345 | hsa-mir-3158-2 | MI0014187 |
| 346 | hsa-mir-6787 | MI0022632 |
| 347 | hsa-mir-614 | MI0003627 |
| 348 | hsa-mir-4689 | MI0017322 |
| 349 | hsa-mir-1185-2 | MI0003821 |
| 350 | hsa-mir-1268b | MI0016748 |
| 351 | hsa-mir-1185-1 | MI0003844 |
| 352 | hsa-mir-940 | MI0005762 |
| 353 | hsa-mir-939 | MI0005761 |
| 354 | hsa-mir-6757 | MI0022602 |
| 355 | hsa-mir-1275 | MI0006415 |
| 356 | hsa-mir-5001 | MI0017867 |
| 357 | hsa-mir-6826 | MI0022671 |
| 358 | hsa-mir-3679 | MI0016080 |
| 359 | hsa-mir-4718 | MI0017353 |
| 360 | hsa-mir-4286 | MI0015894 |
| 361 | hsa-mir-8059 | MI0025895 |
| 362 | hsa-mir-4447 | MI0016790 |
| 363 | hsa-mir-4448 | MI0016791 |
| 364 | hsa-mir-658 | MI0003682 |
| 365 | hsa-mir-6766 | MI0022611 |
| 366 | hsa-mir-197 | MI0000239 |
| 367 | hsa-mir-6887 | MI0022734 |
| 368 | hsa-mir-6742 | MI0022587 |
| 369 | hsa-mir-5090 | MI0017979 |
| 370 | hsa-mir-7975 | MI0025751 |
| 371 | hsa-mir-4505 | MI0016868 |
| 372 | hsa-mir-6889 | MI0022736 |
| 373 | hsa-mir-4708 | MI0017341 |
| 374 | hsa-mir-6131 | MI0021276 |
| 375 | hsa-mir-1225 | MI0006311 |
| 376 | hsa-mir-6132 | MI0021277 |
| 377 | hsa-mir-4734 | MI0017371 |
| 378 | hsa-mir-3194 | MI0014239 |
| 379 | hsa-mir-638 | MI0003653 |
| 380 | hsa-mir-2467 | MI0017432 |
| 381 | hsa-mir-4728 | MI0017365 |
| 382 | hsa-mir-5572 | MI0019117 |
| 383 | hsa-mir-6789 | MI0022634 |
| 384 | hsa-mir-8063 | MI0025899 |
| 385 | hsa-mir-4429 | MI0016768 |
| 386 | hsa-mir-6840 | MI0022686 |
| 387 | hsa-mir-4476 | MI0016828 |
| 388 | hsa-mir-675 | MI0005416 |

TABLE 1-continued

| SEQ ID NO. | Name of gene | Accession No. of miRBase |
|---|---|---|
| 389 | hsa-mir-711 | MI0012488 |
| 390 | hsa-mir-6875 | MI0022722 |
| 391 | hsa-mir-3160-1 | MI0014189 |
| 392 | hsa-mir-3160-2 | MI0014190 |
| 393 | hsa-mir-1908 | MI0008329 |
| 394 | hsa-mir-6726 | MI0022571 |
| 395 | hsa-mir-1913 | MI0008334 |
| 396 | hsa-mir-8071-1 | MI0025907 |
| 397 | hsa-mir-8071-2 | MI0026417 |
| 398 | hsa-mir-3648-1 | MI0016048 |
| 399 | hsa-mir-3648-2 | MI0031512 |
| 400 | hsa-mir-4732 | MI0017369 |
| 401 | hsa-mir-3917 | MI0016423 |
| 402 | hsa-mir-619 | MI0003633 |
| 403 | hsa-mir-1231 | MI0006321 |
| 404 | hsa-mir-342 | MI0000805 |
| 405 | hsa-mir-4433a | MI0016773 |
| 406 | hsa-mir-4707 | MI0017340 |
| 407 | hsa-mir-7114 | MI0022965 |
| 408 | hsa-mir-6872 | MI0022719 |
| 409 | hsa-mir-6780b | MI0022681 |
| 410 | hsa-mir-7845 | MI0025515 |
| 411 | hsa-mir-665 | MI0005563 |
| 412 | hsa-mir-6848 | MI0022694 |
| 413 | hsa-mir-5008 | MI0017876 |
| 414 | hsa-mir-4294 | MI0015827 |
| 415 | hsa-mir-6511a-1 | MI0022223 |
| 416 | hsa-mir-6511a-2 | MI0023564 |
| 417 | hsa-mir-6511a-3 | MI0023565 |
| 418 | hsa-mir-6511a-4 | MI0023566 |
| 419 | hsa-mir-4435-1 | MI0016775 |
| 420 | hsa-mir-4435-2 | MI0016777 |
| 421 | hsa-mir-4747 | MI0017386 |
| 422 | hsa-mir-6880 | MI0022727 |
| 423 | hsa-mir-6869 | MI0022716 |
| 424 | hsa-mir-7150 | MI0023610 |
| 425 | hsa-mir-1260a | MI0006394 |
| 426 | hsa-mir-6877 | MI0022724 |
| 427 | hsa-mir-6721 | MI0022556 |
| 428 | hsa-mir-4656 | MI0017284 |
| 429 | hsa-mir-1229 | MI0006319 |
| 430 | hsa-mir-4274 | MI0015884 |
| 431 | hsa-mir-4419b | MI0016861 |
| 432 | hsa-mir-4674 | MI0017305 |
| 433 | hsa-mir-6893 | MI0022740 |
| 434 | hsa-mir-6763 | MI0022608 |
| 435 | hsa-mir-6762 | MI0022607 |
| 436 | hsa-mir-6738 | MI0022583 |
| 437 | hsa-mir-4513 | MI0016879 |
| 438 | hsa-mir-6746 | MI0022591 |
| 439 | hsa-mir-4736 | MI0017373 |
| 440 | hsa-mir-718 | MI0012489 |
| 441 | hsa-mir-6717 | MI0022551 |
| 442 | hsa-mir-7847 | MI0025517 |
| 443 | hsa-mir-760 | MI0005567 |
| 444 | hsa-mir-1199 | MI0020340 |
| 445 | hsa-mir-6813 | MI0022658 |
| 446 | hsa-mir-6769a | MI0022614 |
| 447 | hsa-mir-1193 | MI0014205 |
| 448 | hsa-mir-7108 | MI0022959 |
| 449 | hsa-mir-6741 | MI0022586 |
| 450 | hsa-mir-4298 | MI0015830 |
| 451 | hsa-mir-6796 | MI0022641 |
| 452 | hsa-mir-4750 | MI0017389 |
| 453 | hsa-mir-6785 | MI0022630 |
| 454 | hsa-mir-1292 | MI0006433 |
| 455 | hsa-mir-4749 | MI0017388 |
| 456 | hsa-mir-4722 | MI0017357 |
| 457 | hsa-mir-4746 | MI0017385 |
| 458 | hsa-mir-4450 | MI0016795 |
| 459 | hsa-mir-6795 | MI0022640 |
| 460 | hsa-mir-365a | MI0000767 |
| 461 | hsa-mir-498 | MI0003142 |
| 462 | hsa-mir-6797 | MI0022642 |
| 463 | hsa-mir-1470 | MI0007075 |
| 464 | hsa-mir-6851 | MI0022697 |

TABLE 1-continued

| SEQ ID NO. | Name of gene | Accession No. of miRBase |
|---|---|---|
| 465 | hsa-mir-1247 | MI0006382 |
| 466 | hsa-mir-5196 | MI0018175 |
| 467 | hsa-mir-208a | MI0000251 |
| 468 | hsa-mir-6842 | MI0022688 |
| 469 | hsa-mir-150 | MI0000479 |
| 470 | hsa-mir-4534 | MI0016901 |
| 471 | hsa-mir-3135b | MI0016809 |
| 472 | hsa-mir-3131 | MI0014151 |
| 473 | hsa-mir-4792 | MI0017439 |
| 474 | hsa-mir-6510 | MI0022222 |
| 475 | hsa-mir-504 | MI0003189 |
| 476 | hsa-mir-3619 | MI0016009 |
| 477 | hsa-mir-671 | MI0003760 |
| 478 | hsa-mir-4667 | MI0017297 |
| 479 | hsa-mir-4430 | MI0016769 |
| 480 | hsa-mir-3195 | MI0014240 |
| 481 | hsa-mir-6076 | MI0020353 |
| 482 | hsa-mir-6820 | MI0022665 |
| 483 | hsa-mir-4634 | MI0017261 |
| 484 | hsa-mir-187 | MI0000274 |
| 485 | hsa-mir-1181 | MI0006274 |
| 486 | hsa-mir-6782 | MI0022627 |
| 487 | hsa-mir-5010 | MI0017878 |
| 488 | hsa-mir-6870 | MI0022717 |
| 489 | hsa-mir-6124 | MI0021258 |
| 490 | hsa-mir-6511b-1 | MI0022552 |
| 491 | hsa-mir-6511b-2 | MI0023431 |
| 492 | hsa-mir-1254-1 | MI0006388 |
| 493 | hsa-mir-1254-2 | MI0016747 |
| 494 | hsa-mir-4727 | MI0017364 |
| 495 | hsa-mir-4259 | MI0015858 |
| 496 | hsa-mir-4771-1 | MI0017412 |
| 497 | hsa-mir-4771-2 | MI0017413 |
| 498 | hsa-mir-3622a | MI0016013 |
| 499 | hsa-mir-4480 | MI0016841 |
| 500 | hsa-mir-4740 | MI0017378 |
| 501 | hsa-mir-6777 | MI0022622 |
| 502 | hsa-mir-6794 | MI0022639 |
| 503 | hsa-mir-6743 | MI0022588 |
| 504 | hsa-mir-6771 | MI0022616 |
| 505 | hsa-mir-3141 | MI0014165 |
| 506 | hsa-mir-3162 | MI0014192 |
| 507 | hsa-mir-4271 | MI0015879 |
| 508 | hsa-mir-1227 | MI0006316 |
| 509 | hsa-mir-4257 | MI0015856 |
| 510 | hsa-mir-4270 | MI0015878 |
| 511 | hsa-mir-4516 | MI0016882 |
| 512 | hsa-mir-4651 | MI0017279 |
| 513 | hsa-mir-4725 | MI0017362 |
| 514 | hsa-mir-6125 | MI0021259 |
| 515 | hsa-mir-6732 | MI0022577 |
| 516 | hsa-mir-6791 | MI0022636 |
| 517 | hsa-mir-6819 | MI0022664 |
| 518 | hsa-mir-6891 | MI0022738 |
| 519 | hsa-mir-7109 | MI0022960 |
| 520 | hsa-mir-320a | MI0000542 |
| 521 | hsa-mir-663a | MI0003672 |
| 522 | hsa-mir-328 | MI0000804 |
| 523 | hsa-mir-642b | MI0016685 |
| 524 | hsa-mir-128-2 | MI0000727 |
| 525 | hsa-mir-125a | MI0000469 |
| 526 | hsa-mir-191 | MI0000465 |
| 527 | hsa-mir-92b | MI0003560 |
| 528 | hsa-mir-1246 | MI0006381 |
| 529 | hsa-mir-92a-2 | MI0000094 |
| 530 | hsa-mir-128-1 | MI0000447 |
| 531 | hsa-mir-1290 | MI0006352 |
| 532 | hsa-mir-211 | MI0000287 |
| 533 | hsa-mir-744 | MI0005559 |
| 534 | hsa-mir-135a-1 | MI0000452 |
| 535 | hsa-mir-451a | MI0001729 |
| 536 | hsa-mir-625 | MI0003639 |
| 537 | hsa-mir-92a-1 | MI0000093 |
| 538 | hsa-mir-422a | MI0001444 |
| 539 | hsa-mir-642a | MI0003657 |
| 540 | hsa-mir-483 | MI0002467 |

TABLE 1-continued

| SEQ ID NO. | Name of gene | Accession No. of miRBase |
|---|---|---|
| 541 | hsa-mir-652 | MI0003667 |
| 542 | hsa-mir-24-1 | MI0000080 |
| 543 | hsa-mir-24-2 | MI0000081 |
| 544 | hsa-mir-23b | MI0000439 |
| 545 | hsa-mir-23a | MI0000079 |
| 546 | hsa-mir-22 | MI0000078 |
| 547 | isomiR Example 1 of SEQ ID NO: 2 | — |
| 548 | isomiR Example 2 of SEQ ID NO: 2 | — |
| 549 | isomiR Example 1 of SEQ ID NO: 3 | — |
| 550 | isomiR Example 2 of SEQ ID NO: 3 | — |
| 551 | isomiR Example 1 of SEQ ID NO: 4 | — |
| 552 | isomiR Example 2 of SEQ ID NO: 4 | — |
| 553 | isomiR Example 1 of SEQ ID NO: 7 | — |
| 554 | isomiR Example 1 of SEQ ID NO: 8 | — |
| 555 | isomiR Example 2 of SEQ ID NO: 8 | — |
| 556 | isomiR Example 1 of SEQ ID NO: 11 | — |
| 557 | isomiR Example 2 of SEQ ID NO: 11 | — |
| 558 | isomiR Example 1 of SEQ ID NO: 12 | — |
| 559 | isomiR Example 1 of SEQ ID NO: 13 | — |
| 560 | isomiR Example 1 of SEQ ID NO: 14 | — |
| 561 | isomiR Example 2 of SEQ ID NO: 14 | — |
| 562 | isomiR Example 1 of SEQ ID NO: 15 | — |
| 563 | isomiR Example 1 of SEQ ID NO: 17 | — |
| 564 | isomiR Example 2 of SEQ ID NO: 17 | — |
| 565 | isomiR Example 1 of SEQ ID NO: 18 | — |
| 566 | isomiR Example 2 of SEQ ID NO: 18 | — |
| 567 | isomiR Example 1 of SEQ ID NO: 20 | — |
| 568 | isomiR Example 2 of SEQ ID NO: 20 | — |
| 569 | isomiR Example 1 of SEQ ID NO: 23 | — |
| 570 | isomiR Example 1 of SEQ ID NO: 24 | — |
| 571 | isomiR Example 2 of SEQ ID NO: 24 | — |
| 572 | isomiR Example 1 of SEQ ID NO: 25 | — |
| 573 | isomiR Example 2 of SEQ ID NO: 25 | — |
| 574 | isomiR Example 1 of SEQ ID NO: 29 | — |
| 575 | isomiR Example 2 of SEQ ID NO: 29 | — |
| 576 | isomiR Example 1 of SEQ ID NO: 34 | — |
| 577 | isomiR Example 2 of SEQ ID NO: 34 | — |
| 578 | isomiR Example 1 of SEQ ID NO: 36 | — |
| 579 | isomiR Example 2 of SEQ ID NO: 36 | — |
| 580 | isomiR Example 1 of SEQ ID NO: 39 | — |
| 581 | isomiR Example 2 of SEQ ID NO: 39 | — |
| 582 | isomiR Example 1 of SEQ ID NO: 40 | — |
| 583 | isomiR Example 2 of SEQ ID NO: 40 | — |
| 584 | isomiR Example 1 of SEQ ID NO: 41 | — |
| 585 | isomiR Example 2 of SEQ ID NO: 41 | — |
| 586 | isomiR Example 1 of SEQ ID NO: 42 | — |
| 587 | isomiR Example 2 of SEQ ID NO: 42 | — |
| 588 | isomiR Example 1 of SEQ ID NO: 43 | — |
| 589 | isomiR Example 2 of SEQ ID NO: 43 | — |
| 590 | isomiR Example 1 of SEQ ID NO: 44 | — |
| 591 | isomiR Example 2 of SEQ ID NO: 44 | — |
| 592 | isomiR Example 1 of SEQ ID NO: 45 | — |
| 593 | isomiR Example 2 of SEQ ID NO: 45 | — |
| 594 | isomiR Example 1 of SEQ ID NO: 51 | — |
| 595 | isomiR Example 2 of SEQ ID NO: 51 | — |
| 596 | isomiR Example 1 of SEQ ID NO: 53 | — |
| 597 | isomiR Example 2 of SEQ ID NO: 53 | — |
| 598 | isomiR Example 1 of SEQ ID NO: 55 | — |
| 599 | isomiR Example 2 of SEQ ID NO: 55 | — |
| 600 | isomiR Example 1 of SEQ ID NO: 57 | — |
| 601 | isomiR Example 2 of SEQ ID NO: 57 | — |
| 602 | isomiR Example 1 of SEQ ID NO: 59 | — |
| 603 | isomiR Example 2 of SEQ ID NO: 59 | — |
| 604 | isomiR Example 1 of SEQ ID NO: 62 | — |
| 605 | isomiR Example 2 of SEQ ID NO: 62 | — |
| 606 | isomiR Example 1 of SEQ ID NO: 63 | — |
| 607 | isomiR Example 2 of SEQ ID NO: 63 | — |
| 608 | isomiR Example 1 of SEQ ID NO: 66 | — |
| 609 | isomiR Example 2 of SEQ ID NO: 66 | — |
| 610 | isomiR Example 1 of SEQ ID NO: 67 | — |
| 611 | isomiR Example 2 of SEQ ID NO: 67 | — |
| 612 | isomiR Example 1 of SEQ ID NO: 69 | — |
| 613 | isomiR Example 2 of SEQ ID NO: 69 | — |
| 614 | isomiR Example 1 of SEQ ID NO: 70 | — |
| 615 | isomiR Example 2 of SEQ ID NO: 70 | — |
| 616 | isomiR Example 1 of SEQ ID NO: 71 | — |

TABLE 1-continued

| SEQ ID NO. | Name of gene | Accession No. of miRBase |
|---|---|---|
| 617 | isomiR Example 2 of SEQ ID NO: 71 | — |
| 618 | isomiR Example 1 of SEQ ID NO: 72 | — |
| 619 | isomiR Example 2 of SEQ ID NO: 72 | — |
| 620 | isomiR Example 1 of SEQ ID NO: 73 | — |
| 621 | isomiR Example 2 of SEQ ID NO: 73 | — |
| 622 | isomiR Example 1 of SEQ ID NO: 74 | — |
| 623 | isomiR Example 1 of SEQ ID NO: 75 | — |
| 624 | isomiR Example 2 of SEQ ID NO: 75 | — |
| 625 | isomiR Example 1 of SEQ ID NO: 76 | — |
| 626 | isomiR Example 2 of SEQ ID NO: 76 | — |
| 627 | isomiR Example 1 of SEQ ID NO: 78 | — |
| 628 | isomiR Example 2 of SEQ ID NO: 78 | — |
| 629 | isomiR Example 1 of SEQ ID NO: 79 | — |
| 630 | isomiR Example 2 of SEQ ID NO: 79 | — |
| 631 | isomiR Example 1 of SEQ ID NO: 82 | — |
| 632 | isomiR Example 1 of SEQ ID NO: 84 | — |
| 633 | isomiR Example 2 of SEQ ID NO: 84 | — |
| 634 | isomiR Example 1 of SEQ ID NO: 87 | — |
| 635 | isomiR Example 2 of SEQ ID NO: 87 | — |
| 636 | isomiR Example 1 of SEQ ID NO: 88 | — |
| 637 | isomiR Example 2 of SEQ ID NO: 88 | — |
| 638 | isomiR Example 1 of SEQ ID NO: 90 | — |
| 639 | isomiR Example 2 of SEQ ID NO: 90 | — |
| 640 | isomiR Example 1 of SEQ ID NO: 93 | — |
| 641 | isomiR Example 1 of SEQ ID NO: 94 | — |
| 642 | isomiR Example 2 of SEQ ID NO: 94 | — |
| 643 | isomiR Example 1 of SEQ ID NO: 95 | — |
| 644 | isomiR Example 1 of SEQ ID NO: 96 | — |
| 645 | isomiR Example 2 of SEQ ID NO: 96 | — |
| 646 | isomiR Example 1 of SEQ ID NO: 98 | — |
| 647 | isomiR Example 2 of SEQ ID NO: 98 | — |
| 648 | isomiR Example 1 of SEQ ID NO: 99 | — |
| 649 | isomiR Example 1 of SEQ ID NO: 101 | — |
| 650 | isomiR Example 2 of SEQ ID NO: 101 | — |
| 651 | isomiR Example 1 of SEQ ID NO: 102 | — |
| 652 | isomiR Example 2 of SEQ ID NO: 102 | — |
| 653 | isomiR Example 1 of SEQ ID NO: 103 | — |
| 654 | isomiR Example 2 of SEQ ID NO: 103 | — |
| 655 | isomiR Example 1 of SEQ ID NO: 104 | — |
| 656 | isomiR Example 2 of SEQ ID NO: 104 | — |
| 657 | isomiR Example 1 of SEQ ID NO: 105 | — |
| 658 | isomiR Example 2 of SEQ ID NO: 105 | — |
| 659 | isomiR Example 1 of SEQ ID NO: 106 | — |
| 660 | isomiR Example 1 of SEQ ID NO: 107 | — |
| 661 | isomiR Example 1 of SEQ ID NO: 110 | — |
| 662 | isomiR Example 2 of SEQ ID NO: 110 | — |
| 663 | isomiR Example 1 of SEQ ID NO: 112 | — |
| 664 | isomiR Example 2 of SEQ ID NO: 112 | — |
| 665 | isomiR Example 1 of SEQ ID NO: 113 | — |
| 666 | isomiR Example 2 of SEQ ID NO: 113 | — |
| 667 | isomiR Example 1 of SEQ ID NO: 114 | — |
| 668 | isomiR Example 1 of SEQ ID NO: 117 | — |
| 669 | isomiR Example 2 of SEQ ID NO: 117 | — |
| 670 | isomiR Example 1 of SEQ ID NO: 119 | — |
| 671 | isomiR Example 2 of SEQ ID NO: 119 | — |
| 672 | isomiR Example 1 of SEQ ID NO: 121 | — |
| 673 | isomiR Example 2 of SEQ ID NO: 121 | — |
| 674 | isomiR Example 1 of SEQ ID NO: 122 | — |
| 675 | isomiR Example 2 of SEQ ID NO: 122 | — |
| 676 | isomiR Example 1 of SEQ ID NO: 123 | — |
| 677 | isomiR Example 2 of SEQ ID NO: 123 | — |
| 678 | isomiR Example 1 of SEQ ID NO: 124 | — |
| 679 | isomiR Example 2 of SEQ ID NO: 124 | — |
| 680 | isomiR Example 1 of SEQ ID NO: 125 | — |
| 681 | isomiR Example 2 of SEQ ID NO: 125 | — |
| 682 | isomiR Example 1 of SEQ ID NO: 127 | — |
| 683 | isomiR Example 2 of SEQ ID NO: 127 | — |
| 684 | isomiR Example 1 of SEQ ID NO: 128 | — |
| 685 | isomiR Example 1 of SEQ ID NO: 130 | — |
| 686 | isomiR Example 2 of SEQ ID NO: 130 | — |
| 687 | isomiR Example 1 of SEQ ID NO: 136 | — |
| 688 | isomiR Example 2 of SEQ ID NO: 136 | — |
| 689 | isomiR Example 1 of SEQ ID NO: 140 | — |
| 690 | isomiR Example 2 of SEQ ID NO: 140 | — |
| 691 | isomiR Example 1 of SEQ ID NO: 141 | — |
| 692 | isomiR Example 2 of SEQ ID NO: 141 | — |

TABLE 1-continued

| SEQ ID NO. | Name of gene | Accession No. of miRBase |
|---|---|---|
| 693 | isomiR Example 1 of SEQ ID NO: 144 | — |
| 694 | isomiR Example 1 of SEQ ID NO: 146 | — |
| 695 | isomiR Example 2 of SEQ ID NO: 146 | — |
| 696 | isomiR Example 1 of SEQ ID NO: 148 | — |
| 697 | isomiR Example 2 of SEQ ID NO: 148 | — |
| 698 | isomiR Example 1 of SEQ ID NO: 151 | — |
| 699 | isomiR Example 2 of SEQ ID NO: 151 | — |
| 700 | isomiR Example 1 of SEQ ID NO: 153 | — |
| 701 | isomiR Example 2 of SEQ ID NO: 153 | — |
| 702 | isomiR Example 1 of SEQ ID NO: 154 | — |
| 703 | isomiR Example 2 of SEQ ID NO: 154 | — |
| 704 | isomiR Example 1 of SEQ ID NO: 159 | — |
| 705 | isomiR Example 2 of SEQ ID NO: 159 | — |
| 706 | isomiR Example 1 of SEQ ID NO: 163 | — |
| 707 | isomiR Example 1 of SEQ ID NO: 164 | — |
| 708 | isomiR Example 2 of SEQ ID NO: 164 | — |
| 709 | isomiR Example 1 of SEQ ID NO: 166 | — |
| 710 | isomiR Example 2 of SEQ ID NO: 166 | — |
| 711 | isomiR Example 1 of SEQ ID NO: 170 | — |
| 712 | isomiR Example 2 of SEQ ID NO: 170 | — |
| 713 | isomiR Example 1 of SEQ ID NO: 173 | — |
| 714 | isomiR Example 1 of SEQ ID NO: 175 | — |
| 715 | isomiR Example 2 of SEQ ID NO: 175 | — |
| 716 | isomiR Example 1 of SEQ ID NO: 179 | — |
| 717 | isomiR Example 1 of SEQ ID NO: 180 | — |
| 718 | isomiR Example 2 of SEQ ID NO: 180 | — |
| 719 | isomiR Example 1 of SEQ ID NO: 182 | — |
| 720 | isomiR Example 1 of SEQ ID NO: 184 | — |
| 721 | isomiR Example 2 of SEQ ID NO: 184 | — |
| 722 | isomiR Example 1 of SEQ ID NO: 185 | — |
| 723 | isomiR Example 2 of SEQ ID NO: 185 | — |
| 724 | isomiR Example 1 of SEQ ID NO: 187 | — |
| 725 | isomiR Example 1 of SEQ ID NO: 189 | — |
| 726 | isomiR Example 2 of SEQ ID NO: 189 | — |
| 727 | isomiR Example 1 of SEQ ID NO: 190 | — |
| 728 | isomiR Example 2 of SEQ ID NO: 190 | — |
| 729 | isomiR Example 1 of SEQ ID NO: 193 | — |
| 730 | isomiR Example 2 of SEQ ID NO: 193 | — |
| 731 | isomiR Example 1 of SEQ ID NO: 195 | — |
| 732 | isomiR Example 2 of SEQ ID NO: 195 | — |
| 733 | isomiR Example 1 of SEQ ID NO: 196 | — |
| 734 | isomiR Example 2 of SEQ ID NO: 196 | — |
| 735 | isomiR Example 1 of SEQ ID NO: 197 | — |
| 736 | isomiR Example 2 of SEQ ID NO: 197 | — |
| 737 | isomiR Example 1 of SEQ ID NO: 198 | — |
| 738 | isomiR Example 2 of SEQ ID NO: 198 | — |
| 739 | isomiR Example 1 of SEQ ID NO: 199 | — |
| 740 | isomiR Example 2 of SEQ ID NO: 199 | — |
| 741 | isomiR Example 1 of SEQ ID NO: 201 | — |
| 742 | isomiR Example 2 of SEQ ID NO: 201 | — |
| 743 | isomiR Example 1 of SEQ ID NO: 202 | — |
| 744 | isomiR Example 2 of SEQ ID NO: 202 | — |
| 745 | isomiR Example 1 of SEQ ID NO: 203 | — |
| 746 | isomiR Example 2 of SEQ ID NO: 203 | — |
| 747 | isomiR Example 1 of SEQ ID NO: 204 | — |
| 748 | isomiR Example 2 of SEQ ID NO: 204 | — |
| 749 | isomiR Example 1 of SEQ ID NO: 205 | — |
| 750 | isomiR Example 2 of SEQ ID NO: 205 | — |
| 751 | isomiR Example 1 of SEQ ID NO: 207 | — |
| 752 | isomiR Example 2 of SEQ ID NO: 207 | — |
| 753 | isomiR Example 1 of SEQ ID NO: 209 | — |
| 754 | isomiR Example 1 of SEQ ID NO: 210 | — |
| 755 | isomiR Example 2 of SEQ ID NO: 210 | — |
| 756 | isomiR Example 1 of SEQ ID NO: 212 | — |
| 757 | isomiR Example 2 of SEQ ID NO: 212 | — |
| 758 | isomiR Example 1 of SEQ ID NO: 213 | — |
| 759 | isomiR Example 2 of SEQ ID NO: 213 | — |
| 760 | isomiR Example 1 of SEQ ID NO: 215 | — |
| 761 | isomiR Example 2 of SEQ ID NO: 215 | — |
| 762 | isomiR Example 1 of SEQ ID NO: 217 | — |
| 763 | isomiR Example 2 of SEQ ID NO: 217 | — |
| 764 | isomiR Example 1 of SEQ ID NO: 218 | — |
| 765 | isomiR Example 2 of SEQ ID NO: 218 | — |
| 766 | isomiR Example 1 of SEQ ID NO: 219 | — |
| 767 | isomiR Example 2 of SEQ ID NO: 219 | — |
| 768 | isomiR Example 1 of SEQ ID NO: 220 | — |

TABLE 1-continued

| SEQ ID NO. | Name of gene | Accession No. of miRBase |
|---|---|---|
| 769 | isomiR Example 2 of SEQ ID NO: 220 | — |
| 770 | isomiR Example 1 of SEQ ID NO: 221 | — |
| 771 | isomiR Example 2 of SEQ ID NO: 221 | — |
| 772 | isomiR Example 1 of SEQ ID NO: 223 | — |
| 773 | isomiR Example 2 of SEQ ID NO: 223 | — |
| 774 | isomiR Example 1 of SEQ ID NO: 224 | — |
| 775 | isomiR Example 2 of SEQ ID NO: 224 | — |
| 776 | isomiR Example 1 of SEQ ID NO: 229 | — |
| 777 | isomiR Example 2 of SEQ ID NO: 229 | — |
| 778 | isomiR Example 1 of SEQ ID NO: 232 | — |
| 779 | isomiR Example 2 of SEQ ID NO: 232 | — |
| 780 | isomiR Example 1 of SEQ ID NO: 233 | — |
| 781 | isomiR Example 2 of SEQ ID NO: 233 | — |
| 782 | isomiR Example 1 of SEQ ID NO: 234 | — |
| 783 | isomiR Example 1 of SEQ ID NO: 238 | — |
| 784 | isomiR Example 2 of SEQ ID NO: 238 | — |
| 785 | isomiR Example 1 of SEQ ID NO: 239 | — |
| 786 | isomiR Example 2 of SEQ ID NO: 239 | — |
| 787 | isomiR Example 1 of SEQ ID NO: 240 | — |
| 788 | isomiR Example 2 of SEQ ID NO: 240 | — |
| 789 | isomiR Example 1 of SEQ ID NO: 241 | — |
| 790 | isomiR Example 2 of SEQ ID NO: 241 | — |
| 791 | isomiR Example 1 of SEQ ID NO: 248 | — |
| 792 | isomiR Example 2 of SEQ ID NO: 248 | — |
| 793 | isomiR Example 1 of SEQ ID NO: 249 | — |
| 794 | isomiR Example 2 of SEQ ID NO: 249 | — |
| 795 | isomiR Example 1 of SEQ ID NO: 250 | — |
| 796 | isomiR Example 2 of SEQ ID NO: 250 | — |
| 797 | isomiR Example 1 of SEQ ID NO: 251 | — |
| 798 | isomiR Example 2 of SEQ ID NO: 251 | — |
| 799 | isomiR Example 1 of SEQ ID NO: 252 | — |
| 800 | isomiR Example 2 of SEQ ID NO: 252 | — |
| 801 | isomiR Example 1 of SEQ ID NO: 253 | — |
| 802 | isomiR Example 2 of SEQ ID NO: 253 | — |
| 803 | isomiR Example 1 of SEQ ID NO: 254 | — |
| 804 | isomiR Example 2 of SEQ ID NO: 254 | — |
| 805 | isomiR Example 1 of SEQ ID NO: 255 | — |
| 806 | isomiR Example 2 of SEQ ID NO: 255 | — |
| 807 | isomiR Example 1 of SEQ ID NO: 256 | — |
| 808 | isomiR Example 2 of SEQ ID NO: 256 | — |
| 809 | isomiR Example 1 of SEQ ID NO: 257 | — |
| 810 | isomiR Example 2 of SEQ ID NO: 257 | — |
| 811 | isomiR Example 1 of SEQ ID NO: 258 | — |
| 812 | isomiR Example 2 of SEQ ID NO: 258 | — |
| 813 | isomiR Example 1 of SEQ ID NO: 259 | — |
| 814 | isomiR Example 2 of SEQ ID NO: 259 | — |
| 815 | isomiR Example 1 of SEQ ID NO: 260 | — |
| 816 | isomiR Example 2 of SEQ ID NO: 260 | — |
| 817 | isomiR Example 1 of SEQ ID NO: 261 | — |
| 818 | isomiR Example 2 of SEQ ID NO: 261 | — |
| 819 | isomiR Example 1 of SEQ ID NO: 262 | — |
| 820 | isomiR Example 2 of SEQ ID NO: 262 | — |
| 821 | isomiR Example 1 of SEQ ID NO: 263 | — |
| 822 | isomiR Example 2 of SEQ ID NO: 263 | — |
| 823 | isomiR Example 1 of SEQ ID NO: 264 | — |
| 824 | isomiR Example 2 of SEQ ID NO: 264 | — |
| 825 | isomiR Example 1 of SEQ ID NO: 265 | — |
| 826 | isomiR Example 2 of SEQ ID NO: 265 | — |
| 827 | isomiR Example 1 of SEQ ID NO: 266 | — |
| 828 | isomiR Example 2 of SEQ ID NO: 266 | — |
| 829 | isomiR Example 1 of SEQ ID NO: 268 | — |
| 830 | isomiR Example 1 of SEQ ID NO: 269 | — |
| 831 | isomiR Example 2 of SEQ ID NO: 269 | — |
| 832 | isomiR Example 1 of SEQ ID NO: 270 | — |
| 833 | isomiR Example 2 of SEQ ID NO: 270 | — |
| 834 | isomiR Example 1 of SEQ ID NO: 271 | — |
| 835 | isomiR Example 2 of SEQ ID NO: 271 | — |
| 836 | isomiR Example 1 of SEQ ID NO: 272 | — |
| 837 | isomiR Example 2 of SEQ ID NO: 272 | — |
| 838 | isomiR Example 1 of SEQ ID NO: 273 | — |
| 839 | isomiR Example 1 of SEQ ID NO: 274 | — |
| 840 | isomiR Example 2 of SEQ ID NO: 274 | — |
| 841 | isomiR Example 1 of SEQ ID NO: 275 | — |
| 842 | isomiR Example 2 of SEQ ID NO: 275 | — |

Advantageous Effect of Invention

According to the present invention, ovarian tumor can be detected easily and in high accuracy. For example, the presence or absence of ovarian tumor in patients can be easily detected by using, as indicators, the determined expression levels of one to several miRNAs in blood, serum, and/or plasma of the patients, which can be collected with limited invasiveness.

The present specification encompasses the contents disclosed in Japanese Patent Application No. 2017-090799 from which the present application claims priority.

MODES FOR CARRYING OUT THE INVENTION

Figure 1:
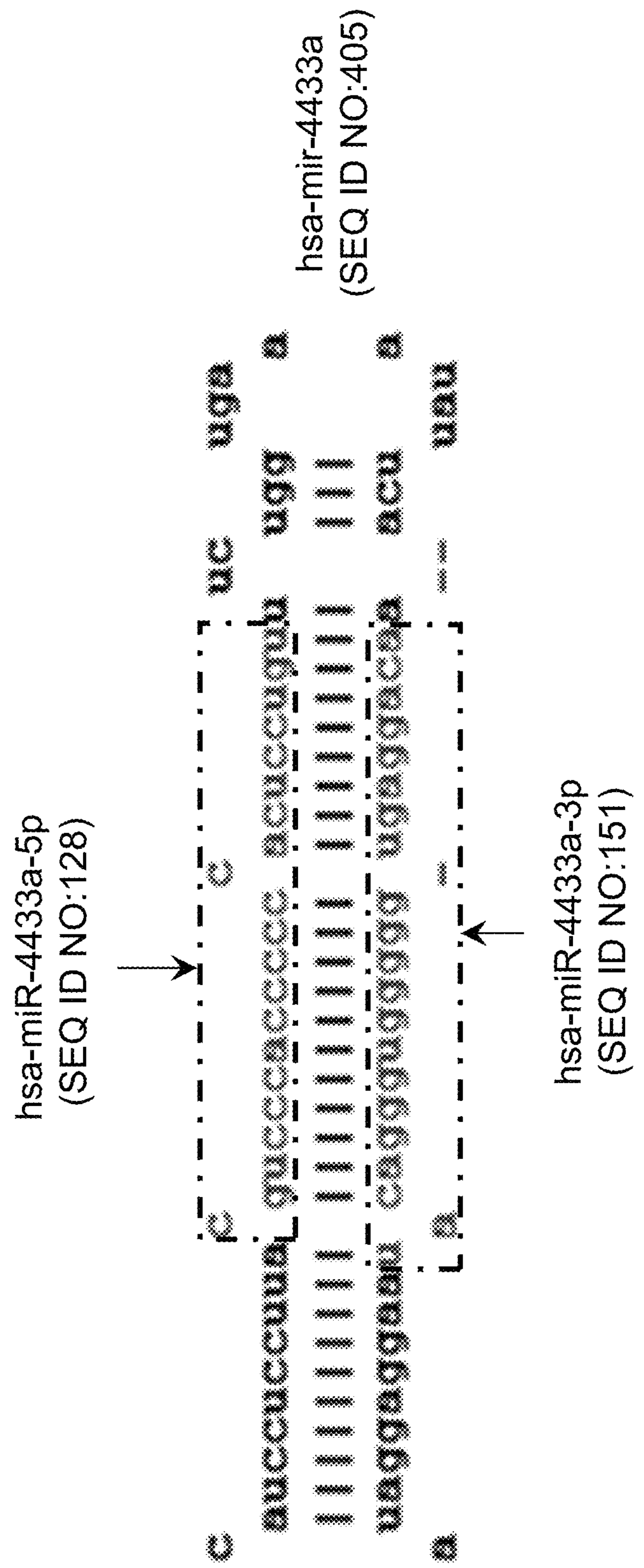
FIG. 1 This figure shows the relationship between the nucleotide sequences of hsa-miR-4433a-5p represented by SEQ ID NO: 128 and hsa-miR-4433a-3p represented by SEQ ID NO: 151, which are produced from the precursor hsa-mir-4433a represented by SEQ ID NO: 405.
Figure 2:
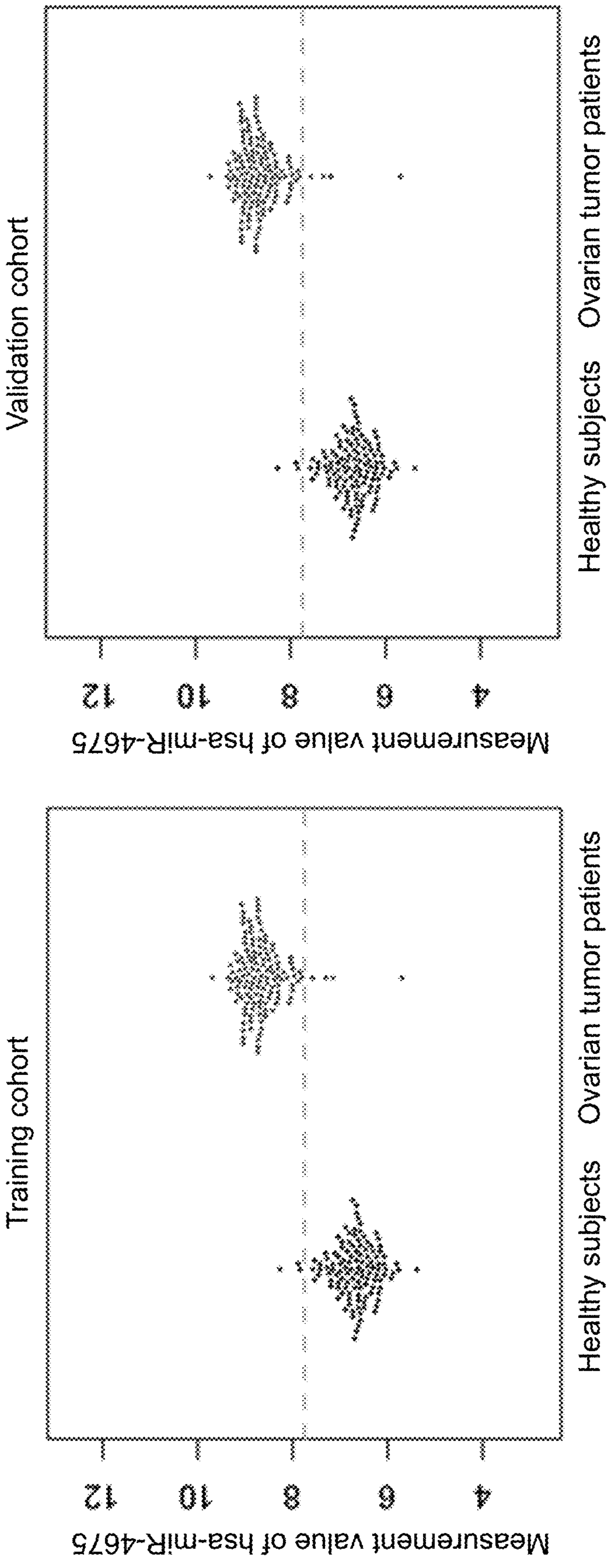
FIG. 2 Left panel: the measured expression level values of hsa-miR-4675 (SEQ ID NO: 1) in sera from healthy subjects (280 people) and ovarian tumor patients (303 people) selected as a training cohort were each plotted on the ordinate. The horizontal line in the panel depicts a threshold (7.75) that was optimized by Fisher's discriminant analysis and discriminated between the two groups. Right panel: the measured expression level values of hsa-miR-4675 (SEQ ID NO: 1) in healthy subjects (120 people) and ovarian tumor patients (131 people) selected as a validation cohort were each plotted on the ordinate. The horizontal line in the panel depicts the threshold (7.75) that was set in the training cohort and discriminated between the two groups.

Hereinafter, the present invention will be further described in detail.

1. Target Nucleic Acid for Ovarian Tumor

Primary target nucleic acids, as ovarian tumor markers, for detecting the presence and/or absence of ovarian tumor or ovarian tumor cells using the nucleic acids such as the nucleic acid probes or the primers for the detection of ovarian tumor defined above according to the present invention comprise at least one miRNA selected from the group consisting of the following miRNAs: hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR- 6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-7109-5p, hsa-miR-642b-3p, and hsa-miR-642a-3p. Furthermore, at least one miRNA selected from the group consisting of the following other ovarian tumor markers that can be combined with these miRNAs, i.e., hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p, and hsa-miR-22-3p can also be preferably used as target nucleic acids.

These miRNAs include, for example, a human gene comprising a nucleotide sequence represented by any of SEQ ID NOs: 1 to 275 (i.e., hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-642b-3p, hsa-miR-642a-3p, hsa-miR-7109-5p, hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p and hsa-miR-22-3p respectively), a congener thereof, a transcript thereof, or/and a variant or a derivative thereof. In this context, the gene, the congener, the transcript, the variant, and the derivative are as defined above.

The target nucleic acid is preferably a human gene comprising a nucleotide sequence represented by any of SEQ ID NOs: 1 to 842 or a transcript thereof, more preferably the transcript, i.e., a miRNA or its precursor RNA, pri-miRNA or pre-miRNA.

The first target gene is the hsa-miR-4675 gene, a congener thereof, a transcript thereof, or a variant or a derivative thereof. None of the previously known report shows that change in the expression of the gene or the transcript thereof can serve as a marker for ovarian tumor.

The second target gene is the hsa-miR-4783-3p gene, a congener thereof, a transcript thereof, or a variant or a derivative thereof. None of the previously known report shows that change in the expression of the gene or the transcript thereof can serve as a marker for ovarian tumor.

The third target gene is the hsa-miR-1228-5p gene, a congener thereof, a transcript thereof, or a variant or a derivative thereof. None of the previously known report shows that change in the expression of the gene or the transcript thereof can serve as a marker for ovarian tumor.

The fourth target gene is the hsa-miR-4532 gene, a congener thereof, a transcript thereof, or a variant or a derivative thereof. None of the previously known report shows that change in the expression of the gene or the transcript thereof can serve as a marker for ovarian tumor.

The fifth target gene is the hsa-miR-6802-5p gene, a congener thereof, a transcript thereof, or a variant or a derivative thereof. None of the previously known report shows that change in the expression of the gene or the transcript thereof can serve as a marker for ovarian tumor.

The sixth target gene is the hsa-miR-6784-5p gene, a congener thereof, a transcript thereof, or a variant or a derivative thereof. None of the previously known report shows that change in the expression of the gene or the transcript thereof can serve as a marker for ovarian tumor.

The seventh target gene is the hsa-miR-3940-5p gene, a congener thereof, a transcript thereof, or a variant or a derivative thereof. None of the previously known report shows that change in the expression of the gene or the transcript thereof can serve as a marker for ovarian tumor.

The eighth target gene is the hsa-miR-1307-3p gene, a congener thereof, a transcript thereof, or a variant or a derivative thereof. None of the previously known report shows that change in the expression of the gene or the transcript thereof can serve as a marker for ovarian tumor.

The ninth target gene is the hsa-miR-8073 gene, a congener thereof, a transcript thereof, or a variant or a derivative thereof. None of the previously known report shows that change in the expression of the gene or the transcript thereof can serve as a marker for ovarian tumor.

The 10th target gene is the hsa-miR-3184-5p gene, a congener thereof, a transcript thereof, or a variant or a derivative thereof. None of the previously known report shows that change in the expression of the gene or the transcript thereof can serve as a marker for ovarian tumor.

The 11th target gene is the hsa-miR-1233-5p gene, a congener thereof, a transcript thereof, or a variant or a derivative thereof. None of the previously known report shows that change in the expression of the gene or the transcript thereof can serve as a marker for ovarian tumor.

The 12th target gene is the hsa-miR-6088 gene, a congener thereof, a transcript thereof, or a variant or a derivative thereof. None of the previously known report shows that change in the expression of the gene or the transcript thereof can serve as a marker for ovarian tumor.

The 13th target gene is the hsa-miR-5195-3p gene, a congener thereof, a transcript thereof, or a variant or a derivative thereof. None of the previously known report shows that change in the expression of the gene or the transcript thereof can serve as a marker for ovarian tumor.

The 14th target gene is the hsa-miR-320b gene, a congener thereof, a transcript thereof, or a variant or a derivative thereof. None of the previously known report shows that change in the expression of the gene or the transcript thereof can serve as a marker for ovarian tumor.

The 15th target gene is the hsa-miR-4649-5p gene, a congener thereof, a transcript thereof, or a variant or a derivative thereof. None of the previously known report shows that change in the expression of the gene or the transcript thereof can serve as a marker for ovarian tumor.

The 16th target gene is the hsa-miR-6800-5p gene, a congener thereof, a transcript thereof, or a variant or a derivative thereof. None of the previously known report shows that change in the expression of the gene or the transcript thereof can serve as a marker for ovarian tumor.

The 17th target gene is the hsa-miR-1343-3p gene, a congener thereof, a transcript thereof, or a variant or a derivative thereof. None of the previously known report shows that change in the expression of the gene or the transcript thereof can serve as a marker for ovarian tumor.

The 18th target gene is the hsa-miR-4730 gene, a congener thereof, a transcript thereof, or a variant or a derivative thereof. None of the previously known report shows that change in the expression of the gene or the transcript thereof can serve as a marker for ovarian tumor.

The 19th target gene is the hsa-miR-6885-5p gene, a congener thereof, a transcript thereof, or a variant or a derivative thereof. None of the previously known report shows that change in the expression of the gene or the transcript thereof can serve as a marker for ovarian tumor.

The 20th target gene is the hsa-miR-5100 gene, a congener thereof, a transcript thereof, or a variant or a derivative thereof. None of the previously known report shows that change in the expression of the gene or the transcript thereof can serve as a marker for ovarian tumor.

The 21st target gene is the hsa-miR-1203 gene, a congener thereof, a transcript thereof, or a variant or a derivative thereof. None of the previously known report shows that change in the expression of the gene or the transcript thereof can serve as a marker for ovarian tumor.

The 22nd target gene is the hsa-miR-6756-5p gene, a congener thereof, a transcript thereof, or a variant or a derivative thereof. None of the previously known report shows that change in the expression of the gene or the transcript thereof can serve as a marker for ovarian tumor.

The 23rd target gene is the hsa-miR-373-5p gene, a congener thereof, a transcript thereof, or a variant or a derivative thereof. None of the previously known report shows that change in the expression of the gene or the transcript thereof can serve as a marker for ovarian tumor.

The 24th target gene is the hsa-miR-1268a gene, a congener thereof, a transcript thereof, or a variant or a derivative thereof. None of the previously known report shows that change in the expression of the gene or the transcript thereof can serve as a marker for ovarian tumor.

The 25th target gene is the hsa-miR-1260b gene, a congener thereof, a transcript thereof, or a variant or a derivative thereof. None of the previously known report shows that change in the expression of the gene or the transcript thereof can serve as a marker for ovarian tumor.

The 26th target gene is the hsa-miR-4258 gene, a congener thereof, a transcript thereof, or a variant or a derivative thereof. None of the previously known report shows that change in the expression of the gene or the transcript thereof can serve as a marker for ovarian tumor.

The 27th target gene is the hsa-miR-4697-5p gene, a congener thereof, a transcript thereof, or a variant or a derivative thereof. None of the previously known report shows that change in the expression of the gene or the transcript thereof can serve as a marker for ovarian tumor.

The 28th target gene is the hsa-miR-1469 gene, a congener thereof, a transcript thereof, or a variant or a derivative thereof. None of the previously known report shows that change in the expression of the gene or the transcript thereof can serve as a marker for ovarian tumor.

The 29th target gene is the hsa-miR-4515 gene, a congener thereof, a transcript thereof, or a variant or a derivative thereof. None of the previously known report shows that change in the expression of the gene or the transcript thereof can serve as a marker for ovarian tumor.

The 30th target gene is the hsa-miR-6861-5p gene, a congener thereof, a transcript thereof, or a variant or a derivative thereof. None of the previously known report shows that change in the expression of the gene or the transcript thereof can serve as a marker for ovarian tumor.

The 31st target gene is the hsa-miR-6821-5p gene, a congener thereof, a transcript thereof, or a variant or a derivative thereof. None of the previously known report shows that change in the expression of the gene or the transcript thereof can serve as a marker for ovarian tumor.

The 32nd target gene is the hsa-miR-575 gene, a congener thereof, a transcript thereof, or a variant or a derivative thereof. None of the previously known report shows that change in the expression of the gene or the transcript thereof can serve as a marker for ovarian tumor.

The 33rd target gene is the hsa-miR-6805-5p gene, a congener thereof, a transcript thereof, or a variant or a derivative thereof. None of the previously known report shows that change in the expression of the gene or the transcript thereof can serve as a marker for ovarian tumor.

The 34th target gene is the hsa-miR-4758-5p gene, a congener thereof, a transcript thereof, or a variant or a derivative thereof. None of the previously known report shows that change in the expression of the gene or the transcript thereof can serve as a marker for ovarian tumor.

The 35th target gene is the hsa-miR-3663-3p gene, a congener thereof, a transcript thereof, or a variant or a derivative thereof. None of the previously known report shows that change in the expression of the gene or the transcript thereof can serve as a marker for ovarian tumor.

The 36th target gene is the hsa-miR-4530 gene, a congener thereof, a transcript thereof, or a variant or a derivative thereof. None of the previously known report shows that change in the expression of the gene or the transcript thereof can serve as a marker for ovarian tumor.

The 37th target gene is the hsa-miR-6798-5p gene, a congener thereof, a transcript thereof, or a variant or a derivative thereof. None of the previously known report shows that change in the expression of the gene or the transcript thereof can serve as a marker for ovarian tumor.

The 38th target gene is the hsa-miR-6781-5p gene, a congener thereof, a transcript thereof, or a variant or a derivative thereof. None of the previously known report shows that change in the expression of the gene or the transcript thereof can serve as a marker for ovarian tumor.

The 39th target gene is the hsa-miR-885-3p gene, a congener thereof, a transcript thereof, or a variant or a derivative thereof. None of the previously known report shows that change in the expression of the gene or the transcript thereof can serve as a marker for ovarian tumor.

The 40th target gene is the hsa-miR-1273g-3p gene, a congener thereof, a transcript thereof, or a variant or a derivative thereof. None of the previously known report shows that change in the expression of the gene or the transcript thereof can serve as a marker for ovarian tumor.

The 41st target gene is the hsa-miR-4787-3p gene, a congener thereof, a transcript thereof, or a variant or a derivative thereof. None of the previously known report shows that change in the expression of the gene or the transcript thereof can serve as a marker for ovarian tumor.

The 42nd target gene is the hsa-miR-4454 gene, a congener thereof, a transcript thereof, or a variant or a derivative thereof. None of the previously known report shows that change in the expression of the gene or the transcript thereof can serve as a marker for ovarian tumor.

The 43rd target gene is the hsa-miR-4706 gene, a congener thereof, a transcript thereof, or a variant or a derivative thereof. None of the previously known report shows that change in the expression of the gene or the transcript thereof can serve as a marker for ovarian tumor.

The 44th target gene is the hsa-miR-1249-3p gene, a congener thereof, a transcript thereof, or a variant or a derivative thereof. None of the previously known report shows that change in the expression of the gene or the transcript thereof can serve as a marker for ovarian tumor.

The 45th target gene is the hsa-miR-887-3p gene, a congener thereof, a transcript thereof, or a variant or a derivative thereof. None of the previously known report shows that change in the expression of the gene or the transcript thereof can serve as a marker for ovarian tumor.

The 46th target gene is the hsa-miR-6786-5p gene, a congener thereof, a transcript thereof, or a variant or a derivative thereof. None of the previously known report shows that change in the expression of the gene or the transcript thereof can serve as a marker for ovarian tumor.

The 47th target gene is the hsa-miR-1238-5p gene, a congener thereof, a transcript thereof, or a variant or a derivative thereof. None of the previously known report shows that change in the expression of the gene or the transcript thereof can serve as a marker for ovarian tumor.

The 48th target gene is the hsa-miR-6749-5p gene, a congener thereof, a transcript thereof, or a variant or a derivative thereof. None of the previously known report shows that change in the expression of the gene or the transcript thereof can serve as a marker for ovarian tumor.

The 49th target gene is the hsa-miR-6729-5p gene, a congener thereof, a transcript thereof, or a variant or a derivative thereof. None of the previously known report shows that change in the expression of the gene or the transcript thereof can serve as a marker for ovarian tumor.

The 50th target gene is the hsa-miR-6825-5p gene, a congener thereof, a transcript thereof, or a variant or a derivative thereof. None of the previously known report shows that change in the expression of the gene or the transcript thereof can serve as a marker for ovarian tumor.

The 51st target gene is the hsa-miR-663b gene, a congener thereof, a transcript thereof, or a variant or a derivative thereof. None of the previously known report shows that change in the expression of the gene or the transcript thereof can serve as a marker for ovarian tumor.

The 52nd target gene is the hsa-miR-6858-5p gene, a congener thereof, a transcript thereof, or a variant or a derivative thereof. None of the previously known report shows that change in the expression of the gene or the transcript thereof can serve as a marker for ovarian tumor.

The 53rd target gene is the hsa-miR-4690-5p gene, a congener thereof, a transcript thereof, or a variant or a derivative thereof. None of the previously known report shows that change in the expression of the gene or the transcript thereof can serve as a marker for ovarian tumor.

The 54th target gene is the hsa-miR-6765-5p gene, a congener thereof, a transcript thereof, or a variant or a derivative thereof. None of the previously known report shows that change in the expression of the gene or the transcript thereof can serve as a marker for ovarian tumor.

The 55th target gene is the hsa-miR-4710 gene, a congener thereof, a transcript thereof, or a variant or a derivative thereof. None of the previously known report shows that change in the expression of the gene or the transcript thereof can serve as a marker for ovarian tumor.

The 56th target gene is the hsa-miR-6775-5p gene, a congener thereof, a transcript thereof, or a variant or a derivative thereof. None of the previously known report shows that change in the expression of the gene or the transcript thereof can serve as a marker for ovarian tumor.

The 57th target gene is the hsa-miR-371a-5p gene, a congener thereof, a transcript thereof, or a variant or a derivative thereof. None of the previously known report shows that change in the expression of the gene or the transcript thereof can serve as a marker for ovarian tumor.

The 58th target gene is the hsa-miR-6816-5p gene, a congener thereof, a transcript thereof, or a variant or a derivative thereof. None of the previously known report shows that change in the expression of the gene or the transcript thereof can serve as a marker for ovarian tumor.

The 59th target gene is the hsa-miR-296-3p gene, a congener thereof, a transcript thereof, or a variant or a derivative thereof. None of the previously known report shows that change in the expression of the gene or the transcript thereof can serve as a marker for ovarian tumor.

The 60th target gene is the hsa-miR-7977 gene, a congener thereof, a transcript thereof, or a variant or a derivative thereof. None of the previously known report shows that change in the expression of the gene or the transcript thereof can serve as a marker for ovarian tumor.

The 61st target gene is the hsa-miR-8069 gene, a congener thereof, a transcript thereof, or a variant or a derivative thereof. None of the previously known report shows that change in the expression of the gene or the transcript thereof can serve as a marker for ovarian tumor.

The 62nd target gene is the hsa-miR-6515-3p gene, a congener thereof, a transcript thereof, or a variant or a derivative thereof. None of the previously known report shows that change in the expression of the gene or the transcript thereof can serve as a marker for ovarian tumor.

The 63rd target gene is the hsa-miR-4687-5p gene, a congener thereof, a transcript thereof, or a variant or a derivative thereof. None of the previously known report shows that change in the expression of the gene or the transcript thereof can serve as a marker for ovarian tumor.

The 64th target gene is the hsa-miR-1343-5p gene, a congener thereof, a transcript thereof, or a variant or a derivative thereof. None of the previously known report shows that change in the expression of the gene or the transcript thereof can serve as a marker for ovarian tumor.

The 65th target gene is the hsa-miR-7110-5p gene, a congener thereof, a transcript thereof, or a variant or a derivative thereof. None of the previously known report shows that change in the expression of the gene or the transcript thereof can serve as a marker for ovarian tumor.

The 66th target gene is the hsa-miR-4525 gene, a congener thereof, a transcript thereof, or a variant or a derivative thereof. None of the previously known report shows that change in the expression of the gene or the transcript thereof can serve as a marker for ovarian tumor.

The 67th target gene is the hsa-miR-3158-5p gene, a congener thereof, a transcript thereof, or a variant or a derivative thereof. None of the previously known report shows that change in the expression of the gene or the transcript thereof can serve as a marker for ovarian tumor.

The 68th target gene is the hsa-miR-6787-5p gene, a congener thereof, a transcript thereof, or a variant or a derivative thereof. None of the previously known report shows that change in the expression of the gene or the transcript thereof can serve as a marker for ovarian tumor.

The 69th target gene is the hsa-miR-614 gene, a congener thereof, a transcript thereof, or a variant or a derivative thereof. None of the previously known report shows that change in the expression of the gene or the transcript thereof can serve as a marker for ovarian tumor.

The 70th target gene is the hsa-miR-4689 gene, a congener thereof, a transcript thereof, or a variant or a derivative thereof. None of the previously known report shows that change in the expression of the gene or the transcript thereof can serve as a marker for ovarian tumor.

The 71st target gene is the hsa-miR-1185-2-3p gene, a congener thereof, a transcript thereof, or a variant or a derivative thereof. None of the previously known report shows that change in the expression of the gene or the transcript thereof can serve as a marker for ovarian tumor.

The 72nd target gene is the hsa-miR-1268b gene, a congener thereof, a transcript thereof, or a variant or a derivative thereof. None of the previously known report shows that change in the expression of the gene or the transcript thereof can serve as a marker for ovarian tumor.

The 73rd target gene is the hsa-miR-1228-3p gene, a congener thereof, a transcript thereof, or a variant or a derivative thereof. None of the previously known report shows that change in the expression of the gene or the transcript thereof can serve as a marker for ovarian tumor.

The 74th target gene is the hsa-miR-1185-1-3p gene, a congener thereof, a transcript thereof, or a variant or a derivative thereof. None of the previously known report shows that change in the expression of the gene or the transcript thereof can serve as a marker for ovarian tumor.

The 75th target gene is the hsa-miR-940 gene, a congener thereof, a transcript thereof, or a variant or a derivative thereof. None of the previously known report shows that change in the expression of the gene or the transcript thereof can serve as a marker for ovarian tumor.

The 76th target gene is the hsa-miR-939-5p gene, a congener thereof, a transcript thereof, or a variant or a derivative thereof. None of the previously known report shows that change in the expression of the gene or the transcript thereof can serve as a marker for ovarian tumor.

The 77th target gene is the hsa-miR-6757-5p gene, a congener thereof, a transcript thereof, or a variant or a derivative thereof. None of the previously known report shows that change in the expression of the gene or the transcript thereof can serve as a marker for ovarian tumor.

The 78th target gene is the hsa-miR-1275 gene, a congener thereof, a transcript thereof, or a variant or a derivative thereof. None of the previously known report shows that change in the expression of the gene or the transcript thereof can serve as a marker for ovarian tumor.

The 79th target gene is the hsa-miR-5001-5p gene, a congener thereof, a transcript thereof, or a variant or a derivative thereof. None of the previously known report shows that change in the expression of the gene or the transcript thereof can serve as a marker for ovarian tumor.

The 80th target gene is the hsa-miR-6826-5p gene, a congener thereof, a transcript thereof, or a variant or a derivative thereof. None of the previously known report shows that change in the expression of the gene or the transcript thereof can serve as a marker for ovarian tumor.

The 81st target gene is the hsa-miR-6765-3p gene, a congener thereof, a transcript thereof, or a variant or a derivative thereof. None of the previously known report shows that change in the expression of the gene or the transcript thereof can serve as a marker for ovarian tumor.

The 82nd target gene is the hsa-miR-3679-3p gene, a congener thereof, a transcript thereof, or a variant or a derivative thereof. None of the previously known report shows that change in the expression of the gene or the transcript thereof can serve as a marker for ovarian tumor.

The 83rd target gene is the hsa-miR-4718 gene, a congener thereof, a transcript thereof, or a variant or a derivative thereof. None of the previously known report shows that change in the expression of the gene or the transcript thereof can serve as a marker for ovarian tumor.

The 84th target gene is the hsa-miR-4286 gene, a congener thereof, a transcript thereof, or a variant or a derivative thereof. None of the previously known report shows that change in the expression of the gene or the transcript thereof can serve as a marker for ovarian tumor.

The 85th target gene is the hsa-miR-8059 gene, a congener thereof, a transcript thereof, or a variant or a derivative thereof. None of the previously known report shows that change in the expression of the gene or the transcript thereof can serve as a marker for ovarian tumor.

The 86th target gene is the hsa-miR-4447 gene, a congener thereof, a transcript thereof, or a variant or a derivative thereof. None of the previously known report shows that change in the expression of the gene or the transcript thereof can serve as a marker for ovarian tumor.

The 87th target gene is the hsa-miR-4448 gene, a congener thereof, a transcript thereof, or a variant or a derivative thereof. None of the previously known report shows that change in the expression of the gene or the transcript thereof can serve as a marker for ovarian tumor.

The 88th target gene is the hsa-miR-658 gene, a congener thereof, a transcript thereof, or a variant or a derivative thereof. None of the previously known report shows that change in the expression of the gene or the transcript thereof can serve as a marker for ovarian tumor.

The 89th target gene is the hsa-miR-6766-3p gene, a congener thereof, a transcript thereof, or a variant or a derivative thereof. None of the previously known report shows that change in the expression of the gene or the transcript thereof can serve as a marker for ovarian tumor.

The 90th target gene is the hsa-miR-197-5p gene, a congener thereof, a transcript thereof, or a variant or a derivative thereof. None of the previously known report shows that change in the expression of the gene or the transcript thereof can serve as a marker for ovarian tumor.

The 91st target gene is the hsa-miR-6887-5p gene, a congener thereof, a transcript thereof, or a variant or a derivative thereof. None of the previously known report shows that change in the expression of the gene or the transcript thereof can serve as a marker for ovarian tumor.

The 92nd target gene is the hsa-miR-6742-5p gene, a congener thereof, a transcript thereof, or a variant or a derivative thereof. None of the previously known report shows that change in the expression of the gene or the transcript thereof can serve as a marker for ovarian tumor.

The 93rd target gene is the hsa-miR-6729-3p gene, a congener thereof, a transcript thereof, or a variant or a derivative thereof. None of the previously known report shows that change in the expression of the gene or the transcript thereof can serve as a marker for ovarian tumor.

The 94th target gene is the hsa-miR-5090 gene, a congener thereof, a transcript thereof, or a variant or a derivative thereof. None of the previously known report shows that change in the expression of the gene or the transcript thereof can serve as a marker for ovarian tumor.

The 95th target gene is the hsa-miR-7975 gene, a congener thereof, a transcript thereof, or a variant or a derivative thereof. None of the previously known report shows that change in the expression of the gene or the transcript thereof can serve as a marker for ovarian tumor.

The 96th target gene is the hsa-miR-4505 gene, a congener thereof, a transcript thereof, or a variant or a derivative thereof. None of the previously known report shows that change in the expression of the gene or the transcript thereof can serve as a marker for ovarian tumor.

The 97th target gene is the hsa-miR-6889-5p gene, a congener thereof, a transcript thereof, or a variant or a derivative thereof. None of the previously known report shows that change in the expression of the gene or the transcript thereof can serve as a marker for ovarian tumor.

The 98th target gene is the hsa-miR-4708-3p gene, a congener thereof, a transcript thereof, or a variant or a derivative thereof. None of the previously known report shows that change in the expression of the gene or the transcript thereof can serve as a marker for ovarian tumor.

The 99th target gene is the hsa-miR-6131 gene, a congener thereof, a transcript thereof, or a variant or a derivative thereof. None of the previously known report shows that change in the expression of the gene or the transcript thereof can serve as a marker for ovarian tumor.

The 100th target gene is the hsa-miR-1225-3p gene, a congener thereof, a transcript thereof, or a variant or a derivative thereof. None of the previously known report shows that change in the expression of the gene or the transcript thereof can serve as a marker for ovarian tumor.

The 101st target gene is the hsa-miR-6132 gene, a congener thereof, a transcript thereof, or a variant or a derivative thereof. None of the previously known report shows that change in the expression of the gene or the transcript thereof can serve as a marker for ovarian tumor.

The 102nd target gene is the hsa-miR-4734 gene, a congener thereof, a transcript thereof, or a variant or a derivative thereof. None of the previously known report shows that change in the expression of the gene or the transcript thereof can serve as a marker for ovarian tumor.

The 103rd target gene is the hsa-miR-3194-3p gene, a congener thereof, a transcript thereof, or a variant or a derivative thereof. None of the previously known report shows that change in the expression of the gene or the transcript thereof can serve as a marker for ovarian tumor.

The 104th target gene is the hsa-miR-638 gene, a congener thereof, a transcript thereof, or a variant or a derivative thereof. None of the previously known report shows that change in the expression of the gene or the transcript thereof can serve as a marker for ovarian tumor.

The 105th target gene is the hsa-miR-2467-3p gene, a congener thereof, a transcript thereof, or a variant or a derivative thereof. None of the previously known report shows that change in the expression of the gene or the transcript thereof can serve as a marker for ovarian tumor.

The 106th target gene is the hsa-miR-4728-5p gene, a congener thereof, a transcript thereof, or a variant or a derivative thereof. None of the previously known report shows that change in the expression of the gene or the transcript thereof can serve as a marker for ovarian tumor.

The 107th target gene is the hsa-miR-5572 gene, a congener thereof, a transcript thereof, or a variant or a derivative thereof. None of the previously known report shows that change in the expression of the gene or the transcript thereof can serve as a marker for ovarian tumor.

The 108th target gene is the hsa-miR-6789-5p gene, a congener thereof, a transcript thereof, or a variant or a derivative thereof. None of the previously known report shows that change in the expression of the gene or the transcript thereof can serve as a marker for ovarian tumor.

The 109th target gene is the hsa-miR-8063 gene, a congener thereof, a transcript thereof, or a variant or a derivative thereof. None of the previously known report shows that change in the expression of the gene or the transcript thereof can serve as a marker for ovarian tumor.

The 110th target gene is the hsa-miR-4429 gene, a congener thereof, a transcript thereof, or a variant or a derivative thereof. None of the previously known report shows that change in the expression of the gene or the transcript thereof can serve as a marker for ovarian tumor.

The 111th target gene is the hsa-miR-6840-3p gene, a congener thereof, a transcript thereof, or a variant or a derivative thereof. None of the previously known report shows that change in the expression of the gene or the transcript thereof can serve as a marker for ovarian tumor.

The 112th target gene is the hsa-miR-4476 gene, a congener thereof, a transcript thereof, or a variant or a derivative thereof. None of the previously known report shows that change in the expression of the gene or the transcript thereof can serve as a marker for ovarian tumor.

The 113th target gene is the hsa-miR-675-5p gene, a congener thereof, a transcript thereof, or a variant or a derivative thereof. None of the previously known report shows that change in the expression of the gene or the transcript thereof can serve as a marker for ovarian tumor.

The 114th target gene is the hsa-miR-711 gene, a congener thereof, a transcript thereof, or a variant or a derivative thereof. None of the previously known report shows that change in the expression of the gene or the transcript thereof can serve as a marker for ovarian tumor.

The 115th target gene is the hsa-miR-6875-5p gene, a congener thereof, a transcript thereof, or a variant or a derivative thereof. None of the previously known report shows that change in the expression of the gene or the transcript thereof can serve as a marker for ovarian tumor.

The 116th target gene is the hsa-miR-3160-5p gene, a congener thereof, a transcript thereof, or a variant or a derivative thereof. None of the previously known report shows that change in the expression of the gene or the transcript thereof can serve as a marker for ovarian tumor.

The 117th target gene is the hsa-miR-1908-5p gene, a congener thereof, a transcript thereof, or a variant or a derivative thereof. None of the previously known report shows that change in the expression of the gene or the transcript thereof can serve as a marker for ovarian tumor.

The 118th target gene is the hsa-miR-6726-5p gene, a congener thereof, a transcript thereof, or a variant or a derivative thereof. None of the previously known report shows that change in the expression of the gene or the transcript thereof can serve as a marker for ovarian tumor.

The 119th target gene is the hsa-miR-1913 gene, a congener thereof, a transcript thereof, or a variant or a derivative thereof. None of the previously known report shows that change in the expression of the gene or the transcript thereof can serve as a marker for ovarian tumor.

The 120th target gene is the hsa-miR-8071 gene, a congener thereof, a transcript thereof, or a variant or a derivative thereof. None of the previously known report shows that change in the expression of the gene or the transcript thereof can serve as a marker for ovarian tumor.

The 121st target gene is the hsa-miR-3648 gene, a congener thereof, a transcript thereof, or a variant or a derivative thereof. None of the previously known report shows that change in the expression of the gene or the transcript thereof can serve as a marker for ovarian tumor.

The 122nd target gene is the hsa-miR-4732-5p gene, a congener thereof, a transcript thereof, or a variant or a derivative thereof. None of the previously known report shows that change in the expression of the gene or the transcript thereof can serve as a marker for ovarian tumor.

The 123rd target gene is the hsa-miR-4787-5p gene, a congener thereof, a transcript thereof, or a variant or a derivative thereof. None of the previously known report shows that change in the expression of the gene or the transcript thereof can serve as a marker for ovarian tumor.

The 124th target gene is the hsa-miR-3917 gene, a congener thereof, a transcript thereof, or a variant or a derivative thereof. None of the previously known report shows that change in the expression of the gene or the transcript thereof can serve as a marker for ovarian tumor.

The 125th target gene is the hsa-miR-619-5p gene, a congener thereof, a transcript thereof, or a variant or a derivative thereof. None of the previously known report shows that change in the expression of the gene or the transcript thereof can serve as a marker for ovarian tumor.

The 126th target gene is the hsa-miR-1231 gene, a congener thereof, a transcript thereof, or a variant or a derivative thereof. None of the previously known report shows that change in the expression of the gene or the transcript thereof can serve as a marker for ovarian tumor.

The 127th target gene is the hsa-miR-342-5p gene, a congener thereof, a transcript thereof, or a variant or a derivative thereof. None of the previously known report shows that change in the expression of the gene or the transcript thereof can serve as a marker for ovarian tumor.

The 128th target gene is the hsa-miR-4433a-5p gene, a congener thereof, a transcript thereof, or a variant or a derivative thereof. None of the previously known report shows that change in the expression of the gene or the transcript thereof can serve as a marker for ovarian tumor.

The 129th target gene is the hsa-miR-6766-5p gene, a congener thereof, a transcript thereof, or a variant or a derivative thereof. None of the previously known report shows that change in the expression of the gene or the transcript thereof can serve as a marker for ovarian tumor.

The 130th target gene is the hsa-miR-4707-5p gene, a congener thereof, a transcript thereof, or a variant or a derivative thereof. None of the previously known report shows that change in the expression of the gene or the transcript thereof can serve as a marker for ovarian tumor.

The 131st target gene is the hsa-miR-7114-5p gene, a congener thereof, a transcript thereof, or a variant or a derivative thereof. None of the previously known report shows that change in the expression of the gene or the transcript thereof can serve as a marker for ovarian tumor.

The 132nd target gene is the hsa-miR-6872-3p gene, a congener thereof, a transcript thereof, or a variant or a derivative thereof. None of the previously known report shows that change in the expression of the gene or the transcript thereof can serve as a marker for ovarian tumor.

The 133rd target gene is the hsa-miR-6780b-5p gene, a congener thereof, a transcript thereof, or a variant or a derivative thereof. None of the previously known report shows that change in the expression of the gene or the transcript thereof can serve as a marker for ovarian tumor.

The 134th target gene is the hsa-miR-7845-5p gene, a congener thereof, a transcript thereof, or a variant or a derivative thereof. None of the previously known report shows that change in the expression of the gene or the transcript thereof can serve as a marker for ovarian tumor.

The 135th target gene is the hsa-miR-6798-3p gene, a congener thereof, a transcript thereof, or a variant or a derivative thereof. None of the previously known report shows that change in the expression of the gene or the transcript thereof can serve as a marker for ovarian tumor.

The 136th target gene is the hsa-miR-665 gene, a congener thereof, a transcript thereof, or a variant or a derivative thereof. None of the previously known report shows that change in the expression of the gene or the transcript thereof can serve as a marker for ovarian tumor.

The 137th target gene is the hsa-miR-6848-5p gene, a congener thereof, a transcript thereof, or a variant or a derivative thereof. None of the previously known report shows that change in the expression of the gene or the transcript thereof can serve as a marker for ovarian tumor.

The 138th target gene is the hsa-miR-5008-5p gene, a congener thereof, a transcript thereof, or a variant or a derivative thereof. None of the previously known report shows that change in the expression of the gene or the transcript thereof can serve as a marker for ovarian tumor.

The 139th target gene is the hsa-miR-4294 gene, a congener thereof, a transcript thereof, or a variant or a derivative thereof. None of the previously known report shows that change in the expression of the gene or the transcript thereof can serve as a marker for ovarian tumor.

The 140th target gene is the hsa-miR-6511a-5p gene, a congener thereof, a transcript thereof, or a variant or a derivative thereof. None of the previously known report shows that change in the expression of the gene or the transcript thereof can serve as a marker for ovarian tumor.

The 141st target gene is the hsa-miR-4435 gene, a congener thereof, a transcript thereof, or a variant or a derivative thereof. None of the previously known report shows that change in the expression of the gene or the transcript thereof can serve as a marker for ovarian tumor.

The 142nd target gene is the hsa-miR-4747-3p gene, a congener thereof, a transcript thereof, or a variant or a derivative thereof. None of the previously known report shows that change in the expression of the gene or the transcript thereof can serve as a marker for ovarian tumor.

The 143rd target gene is the hsa-miR-6880-3p gene, a congener thereof, a transcript thereof, or a variant or a derivative thereof. None of the previously known report shows that change in the expression of the gene or the transcript thereof can serve as a marker for ovarian tumor.

The 144th target gene is the hsa-miR-6869-5p gene, a congener thereof, a transcript thereof, or a variant or a derivative thereof. None of the previously known report shows that change in the expression of the gene or the transcript thereof can serve as a marker for ovarian tumor.

The 145th target gene is the hsa-miR-7150 gene, a congener thereof, a transcript thereof, or a variant or a derivative thereof. None of the previously known report shows that change in the expression of the gene or the transcript thereof can serve as a marker for ovarian tumor.

The 146th target gene is the hsa-miR-1260a gene, a congener thereof, a transcript thereof, or a variant or a derivative thereof. None of the previously known report shows that change in the expression of the gene or the transcript thereof can serve as a marker for ovarian tumor.

The 147th target gene is the hsa-miR-6877-5p gene, a congener thereof, a transcript thereof, or a variant or a derivative thereof. None of the previously known report shows that change in the expression of the gene or the transcript thereof can serve as a marker for ovarian tumor.

The 148th target gene is the hsa-miR-6721-5p gene, a congener thereof, a transcript thereof, or a variant or a derivative thereof. None of the previously known report shows that change in the expression of the gene or the transcript thereof can serve as a marker for ovarian tumor.

The 149th target gene is the hsa-miR-4656 gene, a congener thereof, a transcript thereof, or a variant or a derivative thereof. None of the previously known report shows that change in the expression of the gene or the transcript thereof can serve as a marker for ovarian tumor.

The 150th target gene is the hsa-miR-1229-5p gene, a congener thereof, a transcript thereof, or a variant or a derivative thereof. None of the previously known report shows that change in the expression of the gene or the transcript thereof can serve as a marker for ovarian tumor.

The 151st target gene is the hsa-miR-4433a-3p gene, a congener thereof, a transcript thereof, or a variant or a derivative thereof. None of the previously known report shows that change in the expression of the gene or the transcript thereof can serve as a marker for ovarian tumor.

The 152nd target gene is the hsa-miR-4274 gene, a congener thereof, a transcript thereof, or a variant or a derivative thereof. None of the previously known report shows that change in the expression of the gene or the transcript thereof can serve as a marker for ovarian tumor.

The 153rd target gene is the hsa-miR-4419b gene, a congener thereof, a transcript thereof, or a variant or a derivative thereof. None of the previously known report shows that change in the expression of the gene or the transcript thereof can serve as a marker for ovarian tumor.

The 154th target gene is the hsa-miR-4674 gene, a congener thereof, a transcript thereof, or a variant or a derivative thereof. None of the previously known report shows that change in the expression of the gene or the transcript thereof can serve as a marker for ovarian tumor.

The 155th target gene is the hsa-miR-6893-5p gene, a congener thereof, a transcript thereof, or a variant or a derivative thereof. None of the previously known report shows that change in the expression of the gene or the transcript thereof can serve as a marker for ovarian tumor.

The 156th target gene is the hsa-miR-6763-3p gene, a congener thereof, a transcript thereof, or a variant or a derivative thereof. None of the previously known report shows that change in the expression of the gene or the transcript thereof can serve as a marker for ovarian tumor.

The 157th target gene is the hsa-miR-6762-5p gene, a congener thereof, a transcript thereof, or a variant or a derivative thereof. None of the previously known report shows that change in the expression of the gene or the transcript thereof can serve as a marker for ovarian tumor.

The 158th target gene is the hsa-miR-6738-5p gene, a congener thereof, a transcript thereof, or a variant or a derivative thereof. None of the previously known report shows that change in the expression of the gene or the transcript thereof can serve as a marker for ovarian tumor.

The 159th target gene is the hsa-miR-4513 gene, a congener thereof, a transcript thereof, or a variant or a derivative thereof. None of the previously known report shows that change in the expression of the gene or the transcript thereof can serve as a marker for ovarian tumor.

The 160th target gene is the hsa-miR-6746-5p gene, a congener thereof, a transcript thereof, or a variant or a derivative thereof. None of the previously known report shows that change in the expression of the gene or the transcript thereof can serve as a marker for ovarian tumor.

The 161st target gene is the hsa-miR-6880-5p gene, a congener thereof, a transcript thereof, or a variant or a derivative thereof. None of the previously known report shows that change in the expression of the gene or the transcript thereof can serve as a marker for ovarian tumor.

The 162nd target gene is the hsa-miR-4736 gene, a congener thereof, a transcript thereof, or a variant or a derivative thereof. None of the previously known report shows that change in the expression of the gene or the transcript thereof can serve as a marker for ovarian tumor.

The 163rd target gene is the hsa-miR-718 gene, a congener thereof, a transcript thereof, or a variant or a derivative thereof. None of the previously known report shows that change in the expression of the gene or the transcript thereof can serve as a marker for ovarian tumor.

The 164th target gene is the hsa-miR-6717-5p gene, a congener thereof, a transcript thereof, or a variant or a derivative thereof. None of the previously known report shows that change in the expression of the gene or the transcript thereof can serve as a marker for ovarian tumor.

The 165th target gene is the hsa-miR-7847-3p gene, a congener thereof, a transcript thereof, or a variant or a derivative thereof. None of the previously known report shows that change in the expression of the gene or the transcript thereof can serve as a marker for ovarian tumor.

The 166th target gene is the hsa-miR-760 gene, a congener thereof, a transcript thereof, or a variant or a derivative thereof. None of the previously known report shows that change in the expression of the gene or the transcript thereof can serve as a marker for ovarian tumor.

The 167th target gene is the hsa-miR-1199-5p gene, a congener thereof, a transcript thereof, or a variant or a derivative thereof. None of the previously known report shows that change in the expression of the gene or the transcript thereof can serve as a marker for ovarian tumor.

The 168th target gene is the hsa-miR-6813-5p gene, a congener thereof, a transcript thereof, or a variant or a derivative thereof. None of the previously known report shows that change in the expression of the gene or the transcript thereof can serve as a marker for ovarian tumor.

The 169th target gene is the hsa-miR-6769a-5p gene, a congener thereof, a transcript thereof, or a variant or a derivative thereof. None of the previously known report shows that change in the expression of the gene or the transcript thereof can serve as a marker for ovarian tumor.

The 170th target gene is the hsa-miR-1193 gene, a congener thereof, a transcript thereof, or a variant or a derivative thereof. None of the previously known report shows that change in the expression of the gene or the transcript thereof can serve as a marker for ovarian tumor.

The 171st target gene is the hsa-miR-7108-3p gene, a congener thereof, a transcript thereof, or a variant or a derivative thereof. None of the previously known report shows that change in the expression of the gene or the transcript thereof can serve as a marker for ovarian tumor.

The 172nd target gene is the hsa-miR-6741-5p gene, a congener thereof, a transcript thereof, or a variant or a derivative thereof. None of the previously known report shows that change in the expression of the gene or the transcript thereof can serve as a marker for ovarian tumor.

The 173rd target gene is the hsa-miR-4298 gene, a congener thereof, a transcript thereof, or a variant or a derivative thereof. None of the previously known report shows that change in the expression of the gene or the transcript thereof can serve as a marker for ovarian tumor.

The 174th target gene is the hsa-miR-6796-3p gene, a congener thereof, a transcript thereof, or a variant or a derivative thereof. None of the previously known report shows that change in the expression of the gene or the transcript thereof can serve as a marker for ovarian tumor.

The 175th target gene is the hsa-miR-4750-5p gene, a congener thereof, a transcript thereof, or a variant or a derivative thereof. None of the previously known report shows that change in the expression of the gene or the transcript thereof can serve as a marker for ovarian tumor.

The 176th target gene is the hsa-miR-6785-5p gene, a congener thereof, a transcript thereof, or a variant or a derivative thereof. None of the previously known report shows that change in the expression of the gene or the transcript thereof can serve as a marker for ovarian tumor.

The 177th target gene is the hsa-miR-1292-3p gene, a congener thereof, a transcript thereof, or a variant or a derivative thereof. None of the previously known report shows that change in the expression of the gene or the transcript thereof can serve as a marker for ovarian tumor.

The 178th target gene is the hsa-miR-4749-3p gene, a congener thereof, a transcript thereof, or a variant or a derivative thereof. None of the previously known report shows that change in the expression of the gene or the transcript thereof can serve as a marker for ovarian tumor.

The 179th target gene is the hsa-miR-6800-3p gene, a congener thereof, a transcript thereof, or a variant or a derivative thereof. None of the previously known report shows that change in the expression of the gene or the transcript thereof can serve as a marker for ovarian tumor.

The 180th target gene is the hsa-miR-4722-5p gene, a congener thereof, a transcript thereof, or a variant or a derivative thereof. None of the previously known report shows that change in the expression of the gene or the transcript thereof can serve as a marker for ovarian tumor.

The 181st target gene is the hsa-miR-4746-3p gene, a congener thereof, a transcript thereof, or a variant or a derivative thereof. None of the previously known report shows that change in the expression of the gene or the transcript thereof can serve as a marker for ovarian tumor.

The 182nd target gene is the hsa-miR-4450 gene, a congener thereof, a transcript thereof, or a variant or a derivative thereof. None of the previously known report shows that change in the expression of the gene or the transcript thereof can serve as a marker for ovarian tumor.

The 183rd target gene is the hsa-miR-6795-5p gene, a congener thereof, a transcript thereof, or a variant or a derivative thereof. None of the previously known report shows that change in the expression of the gene or the transcript thereof can serve as a marker for ovarian tumor.

The 184th target gene is the hsa-miR-365a-5p gene, a congener thereof, a transcript thereof, or a variant or a derivative thereof. None of the previously known report shows that change in the expression of the gene or the transcript thereof can serve as a marker for ovarian tumor.

The 185th target gene is the hsa-miR-498 gene, a congener thereof, a transcript thereof, or a variant or a derivative thereof. None of the previously known report shows that change in the expression of the gene or the transcript thereof can serve as a marker for ovarian tumor.

The 186th target gene is the hsa-miR-6797-5p gene, a congener thereof, a transcript thereof, or a variant or a derivative thereof. None of the previously known report shows that change in the expression of the gene or the transcript thereof can serve as a marker for ovarian tumor.

The 187th target gene is the hsa-miR-1470 gene, a congener thereof, a transcript thereof, or a variant or a derivative thereof. None of the previously known report shows that change in the expression of the gene or the transcript thereof can serve as a marker for ovarian tumor.

The 188th target gene is the hsa-miR-6851-5p gene, a congener thereof, a transcript thereof, or a variant or a derivative thereof. None of the previously known report shows that change in the expression of the gene or the transcript thereof can serve as a marker for ovarian tumor.

The 189th target gene is the hsa-miR-1247-3p gene, a congener thereof, a transcript thereof, or a variant or a derivative thereof. None of the previously known report shows that change in the expression of the gene or the transcript thereof can serve as a marker for ovarian tumor.

The 190th target gene is the hsa-miR-5196-5p gene, a congener thereof, a transcript thereof, or a variant or a derivative thereof. None of the previously known report shows that change in the expression of the gene or the transcript thereof can serve as a marker for ovarian tumor.

The 191st target gene is the hsa-miR-208a-5p gene, a congener thereof, a transcript thereof, or a variant or a derivative thereof. None of the previously known report shows that change in the expression of the gene or the transcript thereof can serve as a marker for ovarian tumor.

The 192nd target gene is the hsa-miR-6842-5p gene, a congener thereof, a transcript thereof, or a variant or a derivative thereof. None of the previously known report shows that change in the expression of the gene or the transcript thereof can serve as a marker for ovarian tumor.

The 193rd target gene is the hsa-miR-150-3p gene, a congener thereof, a transcript thereof, or a variant or a derivative thereof. None of the previously known report shows that change in the expression of the gene or the transcript thereof can serve as a marker for ovarian tumor.

The 194th target gene is the hsa-miR-4534 gene, a congener thereof, a transcript thereof, or a variant or a derivative thereof. None of the previously known report shows that change in the expression of the gene or the transcript thereof can serve as a marker for ovarian tumor.

The 195th target gene is the hsa-miR-3135b gene, a congener thereof, a transcript thereof, or a variant or a derivative thereof. None of the previously known report shows that change in the expression of the gene or the transcript thereof can serve as a marker for ovarian tumor.

The 196th target gene is the hsa-miR-3131 gene, a congener thereof, a transcript thereof, or a variant or a derivative thereof. None of the previously known report shows that change in the expression of the gene or the transcript thereof can serve as a marker for ovarian tumor.

The 197th target gene is the hsa-miR-4792 gene, a congener thereof, a transcript thereof, or a variant or a derivative thereof. None of the previously known report shows that change in the expression of the gene or the transcript thereof can serve as a marker for ovarian tumor.

The 198th target gene is the hsa-miR-6510-5p gene, a congener thereof, a transcript thereof, or a variant or a derivative thereof. None of the previously known report shows that change in the expression of the gene or the transcript thereof can serve as a marker for ovarian tumor.

The 199th target gene is the hsa-miR-504-3p gene, a congener thereof, a transcript thereof, or a variant or a derivative thereof. None of the previously known report shows that change in the expression of the gene or the transcript thereof can serve as a marker for ovarian tumor.

The 200th target gene is the hsa-miR-3619-3p gene, a congener thereof, a transcript thereof, or a variant or a derivative thereof. None of the previously known report shows that change in the expression of the gene or the transcript thereof can serve as a marker for ovarian tumor.

The 201st target gene is the hsa-miR-671-5p gene, a congener thereof, a transcript thereof, or a variant or a derivative thereof. None of the previously known report shows that change in the expression of the gene or the transcript thereof can serve as a marker for ovarian tumor.

The 202nd target gene is the hsa-miR-4667-5p gene, a congener thereof, a transcript thereof, or a variant or a derivative thereof. None of the previously known report shows that change in the expression of the gene or the transcript thereof can serve as a marker for ovarian tumor.

The 203rd target gene is the hsa-miR-4430 gene, a congener thereof, a transcript thereof, or a variant or a derivative thereof. None of the previously known report shows that change in the expression of the gene or the transcript thereof can serve as a marker for ovarian tumor.

The 204th target gene is the hsa-miR-3195 gene, a congener thereof, a transcript thereof, or a variant or a derivative thereof. None of the previously known report shows that change in the expression of the gene or the transcript thereof can serve as a marker for ovarian tumor.

The 205th target gene is the hsa-miR-3679-5p gene, a congener thereof, a transcript thereof, or a variant or a derivative thereof. None of the previously known report shows that change in the expression of the gene or the transcript thereof can serve as a marker for ovarian tumor.

The 206th target gene is the hsa-miR-6076 gene, a congener thereof, a transcript thereof, or a variant or a derivative thereof. None of the previously known report shows that change in the expression of the gene or the transcript thereof can serve as a marker for ovarian tumor.

The 207th target gene is the hsa-miR-6515-5p gene, a congener thereof, a transcript thereof, or a variant or a derivative thereof. None of the previously known report shows that change in the expression of the gene or the transcript thereof can serve as a marker for ovarian tumor.

The 208th target gene is the hsa-miR-6820-5p gene, a congener thereof, a transcript thereof, or a variant or a derivative thereof. None of the previously known report shows that change in the expression of the gene or the transcript thereof can serve as a marker for ovarian tumor.

The 209th target gene is the hsa-miR-4634 gene, a congener thereof, a transcript thereof, or a variant or a derivative thereof. None of the previously known report shows that change in the expression of the gene or the transcript thereof can serve as a marker for ovarian tumor.

The 210th target gene is the hsa-miR-187-5p gene, a congener thereof, a transcript thereof, or a variant or a derivative thereof. None of the previously known report shows that change in the expression of the gene or the transcript thereof can serve as a marker for ovarian tumor.

The 211th target gene is the hsa-miR-6763-5p gene, a congener thereof, a transcript thereof, or a variant or a derivative thereof. None of the previously known report shows that change in the expression of the gene or the transcript thereof can serve as a marker for ovarian tumor.

The 212th target gene is the hsa-miR-1908-3p gene, a congener thereof, a transcript thereof, or a variant or a derivative thereof. None of the previously known report shows that change in the expression of the gene or the transcript thereof can serve as a marker for ovarian tumor.

The 213th target gene is the hsa-miR-1181 gene, a congener thereof, a transcript thereof, or a variant or a derivative thereof. None of the previously known report shows that change in the expression of the gene or the transcript thereof can serve as a marker for ovarian tumor.

The 214th target gene is the hsa-miR-6782-5p gene, a congener thereof, a transcript thereof, or a variant or a derivative thereof. None of the previously known report shows that change in the expression of the gene or the transcript thereof can serve as a marker for ovarian tumor.

The 215th target gene is the hsa-miR-5010-5p gene, a congener thereof, a transcript thereof, or a variant or a derivative thereof. None of the previously known report shows that change in the expression of the gene or the transcript thereof can serve as a marker for ovarian tumor.

The 216th target gene is the hsa-miR-6870-5p gene, a congener thereof, a transcript thereof, or a variant or a derivative thereof. None of the previously known report shows that change in the expression of the gene or the transcript thereof can serve as a marker for ovarian tumor.

The 217th target gene is the hsa-miR-6124 gene, a congener thereof, a transcript thereof, or a variant or a derivative thereof. None of the previously known report shows that change in the expression of the gene or the transcript thereof can serve as a marker for ovarian tumor.

The 218th target gene is the hsa-miR-1249-5p gene, a congener thereof, a transcript thereof, or a variant or a derivative thereof. None of the previously known report shows that change in the expression of the gene or the transcript thereof can serve as a marker for ovarian tumor.

The 219th target gene is the hsa-miR-6511b-5p gene, a congener thereof, a transcript thereof, or a variant or a derivative thereof. None of the previously known report shows that change in the expression of the gene or the transcript thereof can serve as a marker for ovarian tumor.

The 220th target gene is the hsa-miR-1254 gene, a congener thereof, a transcript thereof, or a variant or a derivative thereof. None of the previously known report shows that change in the expression of the gene or the transcript thereof can serve as a marker for ovarian tumor.

The 221st target gene is the hsa-miR-4727-3p gene, a congener thereof, a transcript thereof, or a variant or a derivative thereof. None of the previously known report shows that change in the expression of the gene or the transcript thereof can serve as a marker for ovarian tumor.

The 222nd target gene is the hsa-miR-4259 gene, a congener thereof, a transcript thereof, or a variant or a derivative thereof. None of the previously known report shows that change in the expression of the gene or the transcript thereof can serve as a marker for ovarian tumor.

The 223rd target gene is the hsa-miR-4771 gene, a congener thereof, a transcript thereof, or a variant or a derivative thereof. None of the previously known report shows that change in the expression of the gene or the transcript thereof can serve as a marker for ovarian tumor.

The 224th target gene is the hsa-miR-3622a-5p gene, a congener thereof, a transcript thereof, or a variant or a derivative thereof. None of the previously known report shows that change in the expression of the gene or the transcript thereof can serve as a marker for ovarian tumor.

The 225th target gene is the hsa-miR-4480 gene, a congener thereof, a transcript thereof, or a variant or a derivative thereof. None of the previously known report shows that change in the expression of the gene or the transcript thereof can serve as a marker for ovarian tumor.

The 226th target gene is the hsa-miR-4740-5p gene, a congener thereof, a transcript thereof, or a variant or a derivative thereof. None of the previously known report shows that change in the expression of the gene or the transcript thereof can serve as a marker for ovarian tumor.

The 227th target gene is the hsa-miR-6777-5p gene, a congener thereof, a transcript thereof, or a variant or a derivative thereof. None of the previously known report shows that change in the expression of the gene or the transcript thereof can serve as a marker for ovarian tumor.

The 228th target gene is the hsa-miR-6794-5p gene, a congener thereof, a transcript thereof, or a variant or a derivative thereof. None of the previously known report shows that change in the expression of the gene or the transcript thereof can serve as a marker for ovarian tumor.

The 229th target gene is the hsa-miR-4687-3p gene, a congener thereof, a transcript thereof, or a variant or a derivative thereof. None of the previously known report shows that change in the expression of the gene or the transcript thereof can serve as a marker for ovarian tumor.

The 230th target gene is the hsa-miR-6743-5p gene, a congener thereof, a transcript thereof, or a variant or a derivative thereof. None of the previously known report shows that change in the expression of the gene or the transcript thereof can serve as a marker for ovarian tumor.

The 231st target gene is the hsa-miR-6771-5p gene, a congener thereof, a transcript thereof, or a variant or a derivative thereof. None of the previously known report shows that change in the expression of the gene or the transcript thereof can serve as a marker for ovarian tumor.

The 232nd target gene is the hsa-miR-3141 gene, a congener thereof, a transcript thereof, or a variant or a derivative thereof. None of the previously known report shows that change in the expression of the gene or the transcript thereof can serve as a marker for ovarian tumor.

The 233rd target gene is the hsa-miR-3162-5p gene, a congener thereof, a transcript thereof, or a variant or a derivative thereof. None of the previously known report shows that change in the expression of the gene or the transcript thereof can serve as a marker for ovarian tumor.

The 234th target gene is the hsa-miR-4271 gene, a congener thereof, a transcript thereof, or a variant or a derivative thereof. None of the previously known report shows that change in the expression of the gene or the transcript thereof can serve as a marker for ovarian tumor.

The 235th target gene is the hsa-miR-1227-5p gene, a congener thereof, a transcript thereof, or a variant or a derivative thereof. None of the previously known report shows that change in the expression of the gene or the transcript thereof can serve as a marker for ovarian tumor.

The 236th target gene is the hsa-miR-4257 gene, a congener thereof, a transcript thereof, or a variant or a derivative thereof. None of the previously known report shows that change in the expression of the gene or the transcript thereof can serve as a marker for ovarian tumor.

The 237th target gene is the hsa-miR-4270 gene, a congener thereof, a transcript thereof, or a variant or a derivative thereof. None of the previously known report shows that change in the expression of the gene or the transcript thereof can serve as a marker for ovarian tumor.

The 238th target gene is the hsa-miR-4516 gene, a congener thereof, a transcript thereof, or a variant or a derivative thereof. None of the previously known report shows that change in the expression of the gene or the transcript thereof can serve as a marker for ovarian tumor.

The 239th target gene is the hsa-miR-4651 gene, a congener thereof, a transcript thereof, or a variant or a derivative thereof. None of the previously known report shows that change in the expression of the gene or the transcript thereof can serve as a marker for ovarian tumor.

The 240th target gene is the hsa-miR-4725-3p gene, a congener thereof, a transcript thereof, or a variant or a derivative thereof. None of the previously known report shows that change in the expression of the gene or the transcript thereof can serve as a marker for ovarian tumor.

The 241st target gene is the hsa-miR-6125 gene, a congener thereof, a transcript thereof, or a variant or a derivative thereof. None of the previously known report shows that change in the expression of the gene or the transcript thereof can serve as a marker for ovarian tumor.

The 242nd target gene is the hsa-miR-6732-5p gene, a congener thereof, a transcript thereof, or a variant or a derivative thereof. None of the previously known report shows that change in the expression of the gene or the transcript thereof can serve as a marker for ovarian tumor.

The 243rd target gene is the hsa-miR-6791-5p gene, a congener thereof, a transcript thereof, or a variant or a derivative thereof. None of the previously known report shows that change in the expression of the gene or the transcript thereof can serve as a marker for ovarian tumor.

The 244th target gene is the hsa-miR-6819-5p gene, a congener thereof, a transcript thereof, or a variant or a derivative thereof. None of the previously known report shows that change in the expression of the gene or the transcript thereof can serve as a marker for ovarian tumor.

The 245th target gene is the hsa-miR-6891-5p gene, a congener thereof, a transcript thereof, or a variant or a derivative thereof. None of the previously known report shows that change in the expression of the gene or the transcript thereof can serve as a marker for ovarian tumor.

The 246th target gene is the hsa-miR-7108-5p gene, a congener thereof, a transcript thereof, or a variant or a derivative thereof. None of the previously known report shows that change in the expression of the gene or the transcript thereof can serve as a marker for ovarian tumor.

The 247th target gene is the hsa-miR-7109-5p gene, a congener thereof, a transcript thereof, or a variant or a derivative thereof. None of the previously known report shows that change in the expression of the gene or the transcript thereof can serve as a marker for ovarian tumor.

The 248th target gene is the hsa-miR-320a gene, a congener thereof, a transcript thereof, or a variant or a derivative thereof. The previously known report shows that change in the expression of the gene or the transcript thereof can serve as a marker for ovarian tumor (Patent Literature 1).

The 249th target gene is the hsa-miR-663a gene, a congener thereof, a transcript thereof, or a variant or a derivative thereof. The previously known report shows that change in the expression of the gene or the transcript thereof can serve as a marker for ovarian tumor (Non-Patent Literature 3).

The 250th target gene is the hsa-miR-328-5p gene, a congener thereof, a transcript thereof, or a variant or a derivative thereof. The previously known report shows that change in the expression of the gene or the transcript thereof can serve as a marker for ovarian tumor (Patent Literature 1).

The 251st target gene is the hsa-miR-642b-3p gene, a congener thereof, a transcript thereof, or a variant or a derivative thereof. None of the previously known report shows that change in the expression of the gene or the transcript thereof can serve as a marker for ovarian tumor.

The 252nd target gene is the hsa-miR-128-2-5p gene, a congener thereof, a transcript thereof, or a variant or a derivative thereof. The previously known report shows that change in the expression of the gene or the transcript thereof can serve as a marker for ovarian tumor (Non-Patent Literature 1).

The 253rd target gene is the hsa-miR-125a-3p gene, a congener thereof, a transcript thereof, or a variant or a derivative thereof. The previously known report shows that change in the expression of the gene or the transcript thereof can serve as a marker for ovarian tumor (Patent Literature 3).

The 254th target gene is the hsa-miR-191-5p gene, a congener thereof, a transcript thereof, or a variant or a derivative thereof. The previously known report shows that change in the expression of the gene or the transcript thereof can serve as a marker for ovarian tumor (Patent Literature 1).

The 255th target gene is the hsa-miR-92b-5p gene, a congener thereof, a transcript thereof, or a variant or a derivative thereof. The previously known report shows that change in the expression of the gene or the transcript thereof can serve as a marker for ovarian tumor (Non-Patent Literature 3).

The 256th target gene is the hsa-miR-296-5p gene, a congener thereof, a transcript thereof, or a variant or a derivative thereof. The previously known report shows that change in the expression of the gene or the transcript thereof can serve as a marker for ovarian tumor (Non-Patent Literature 3).

The 257th target gene is the hsa-miR-1246 gene, a congener thereof, a transcript thereof, or a variant or a derivative thereof. The previously known report shows that change in the expression of the gene or the transcript thereof can serve as a marker for ovarian tumor (Patent Literature 4).

The 258th target gene is the hsa-miR-92a-2-5p gene, a congener thereof, a transcript thereof, or a variant or a derivative thereof. The previously known report shows that change in the expression of the gene or the transcript thereof can serve as a marker for ovarian tumor (Non-Patent Literature 1).

The 259th target gene is the hsa-miR-128-1-5p gene, a congener thereof, a transcript thereof, or a variant or a derivative thereof. The previously known report shows that change in the expression of the gene or the transcript thereof can serve as a marker for ovarian tumor (Non-Patent Literature 1).

The 260th target gene is the hsa-miR-1290 gene, a congener thereof, a transcript thereof, or a variant or a derivative thereof. The previously known report shows that change in the expression of the gene or the transcript thereof can serve as a marker for ovarian tumor (Patent Literature 1).

The 261st target gene is the hsa-miR-211-3p gene, a congener thereof, a transcript thereof, or a variant or a derivative thereof. The previously known report shows that change in the expression of the gene or the transcript thereof can serve as a marker for ovarian tumor (Patent Literature 3).

The 262nd target gene is the hsa-miR-744-5p gene, a congener thereof, a transcript thereof, or a variant or a derivative thereof. The previously known report shows that change in the expression of the gene or the transcript thereof can serve as a marker for ovarian tumor (Patent Literature 4).

The 263rd target gene is the hsa-miR-135a-3p gene, a congener thereof, a transcript thereof, or a variant or a derivative thereof. The previously known report shows that change in the expression of the gene or the transcript thereof can serve as a marker for ovarian tumor (Patent Literature 2).

The 264th target gene is the hsa-miR-451a gene, a congener thereof, a transcript thereof, or a variant or a derivative thereof. The previously known report shows that change in the expression of the gene or the transcript thereof can serve as a marker for ovarian tumor (Non-Patent Literature 2).

The 265th target gene is the hsa-miR-625-3p gene, a congener thereof, a transcript thereof, or a variant or a derivative thereof. The previously known report shows that change in the expression of the gene or the transcript thereof can serve as a marker for ovarian tumor (Patent Literature 1).

The 266th target gene is the hsa-miR-92a-3p gene, a congener thereof, a transcript thereof, or a variant or a derivative thereof. The previously known report shows that change in the expression of the gene or the transcript thereof can serve as a marker for ovarian tumor (Patent Literature 1).

The 267th target gene is the hsa-miR-422a gene, a congener thereof, a transcript thereof, or a variant or a derivative thereof. The previously known report shows that change in the expression of the gene or the transcript thereof can serve as a marker for ovarian tumor (Non-Patent Literature 3).

The 268th target gene is the hsa-miR-642a-3p gene, a congener thereof, a transcript thereof, or a variant or a derivative thereof. None of the previously known report shows that change in the expression of the gene or the transcript thereof can serve as a marker for ovarian tumor.

The 269th target gene is the hsa-miR-483-5p gene, a congener thereof, a transcript thereof, or a variant or a derivative thereof. The previously known report shows that change in the expression of the gene or the transcript thereof can serve as a marker for ovarian tumor (Patent Literature 1).

The 270th target gene is the hsa-miR-652-5p gene, a congener thereof, a transcript thereof, or a variant or a derivative thereof. The previously known report shows that change in the expression of the gene or the transcript thereof can serve as a marker for ovarian tumor (Patent Literature 4).

The 271st target gene is the hsa-miR-24-3p gene, a congener thereof, a transcript thereof, or a variant or a derivative thereof. The previously known report shows that change in the expression of the gene or the transcript thereof can serve as a marker for ovarian tumor (Patent Literature 1).

The 272nd target gene is the hsa-miR-23b-3p gene, a congener thereof, a transcript thereof, or a variant or a derivative thereof. The previously known report shows that change in the expression of the gene or the transcript thereof can serve as a marker for ovarian tumor (Non-Patent Literature 3).

The 273rd target gene is the hsa-miR-23a-3p gene, a congener thereof, a transcript thereof, or a variant or a derivative thereof. The previously known report shows that change in the expression of the gene or the transcript thereof can serve as a marker for ovarian tumor (Non-Patent Literature 3).

The 274th target gene is the hsa-miR-92b-3p gene, a congener thereof, a transcript thereof, or a variant or a derivative thereof. The previously known report shows that change in the expression of the gene or the transcript thereof can serve as a marker for ovarian tumor (Non-Patent Literature 3).

The 275th target gene is the hsa-miR-22-3p gene, a congener thereof, a transcript thereof, or a variant or a derivative thereof. The previously known report shows that change in the expression of the gene or the transcript thereof can serve as a marker for ovarian tumor (Non-Patent Literature 2).

In one aspect, the present invention relates to a marker containing at least one of the target nucleic acids described above for detecting ovarian tumor or for diagnosing ovarian tumor.

In one aspect, the present invention relates to use of at least one of the target nucleic acids described above for detecting ovarian tumor or for diagnosing ovarian tumor.

2. Nucleic Acid for Detection of Ovarian Tumor

In the present invention, the nucleic acids for detecting ovarian tumor, e.g., nucleic acid probes or primers that can be used for diagnosing ovarian tumor enable qualitative and/or quantitative measurement of the presence, expression levels, or existing amounts (abundance) of: human-derived hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-7109-5p, hsa-miR-642b-3p and hsa-miR-642a-3p, as target nucleic acids for ovarian tumor, or a combination thereof; and hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p, hsa-miR-22-3p, or combinations thereof; congeners thereof: transcripts thereof: or variants or derivatives thereof.

The expression levels of the target nucleic acids described above are increased or decreased (hereinafter, referred to as "increased/decreased") depending on the types of the target nucleic acids in subjects having ovarian tumor as compared with healthy subjects, benign bone and soft tissue tumor patients and benign breast disease patients (or diseased animals), and subjects having a cancer other than ovarian cancer. Hence, the kit or device of the present invention can be effectively used for measuring expression levels of the target nucleic acids in body fluids from subjects (e.g., humans) suspected of having ovarian tumor and body fluids from healthy subjects, benign bone and soft tissue tumor patients and benign breast disease patients (or diseased animals), and patients (or cancer animals) having a cancer other than ovarian cancer, and thereby detecting ovarian tumor through the comparison thereof.

The nucleic acid probe or primer(s) that can be used in the present invention is, for example, a nucleic acid probe capable of specifically binding to a polynucleotide consisting of a nucleotide sequence represented by at least one of SEQ ID NOs: 1 to 247, 251, and 268, or to a complementary strand of the polynucleotide; or a primer(s) for amplifying a polynucleotide consisting of a nucleotide sequence represented by at least one of SEQ ID NOs: 1 to 247, 251, and 268.

The nucleic acid probe or primer(s) that can be used in the present invention may further comprise, for example, a nucleic acid probe capable of specifically binding to a polynucleotide consisting of a nucleotide sequence represented by at least one of SEQ ID NOs: 248 to 250, 252 to 267, and 269 to 275, or to a complementary strand of the polynucleotide; or a primer(s) for amplifying a polynucleotide consisting of a nucleotide sequence represented by at least one of SEQ ID NOs: 248 to 250, 252 to 267, and 269 to 275.

In a preferred embodiment of the present invention, specifically, these nucleic acid probes or primers comprise a combination of one or more polynucleotides selected from: a group of polynucleotides comprising nucleotide sequences represented by any of SEQ ID NOs: 1 to 842 or nucleotide sequences derived from the nucleotide sequences by the replacement of u with t, and a group of complementary polynucleotides thereof; a group of polynucleotides respectively hybridizing under stringent conditions (mentioned later) to DNAs consisting of nucleotide sequences complementary to these nucleotide sequences, and a group of complementary polynucleotides thereof; and a group of polynucleotides comprising 15 or more, preferably 17 or more consecutive nucleotides and being from the nucleotide sequences of these polynucleotide groups. These polynucleotides can be used as nucleic acid probes and primers for detecting the ovarian tumor markers as target nucleic acids.

More specifically, examples of the nucleic acid probes or the primers that can be used in the present invention include one or more polynucleotides selected from the group consisting of the following polynucleotides (a) to (e):

(a) a polynucleotide consisting of a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 247, 251, and 268;

(c) a polynucleotide consisting of a nucleotide sequence complementary to a nucleotide sequence represented by any of SEQ ID NOs: 1 to 247, 251, and 268 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 247, 251, and 268 or a nucleotide sequence derived from the nucleotide sequence by the replacement of u with t; and (e) a polynucleotide hybridizing under stringent conditions to any of the polynucleotides (a) to (d).

In addition to at least one polynucleotide selected from any of the polynucleotides (a) to (e), the nucleic acid probes or the primers that can be used in the present invention may further comprise any of the following polynucleotides (f) to (j):

(f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

These polynucleotides or fragments thereof used in the present invention may each be DNA or may each be RNA.

The polynucleotides that can be used in the present invention can be prepared by use of a general technique such as a DNA recombination technique, a PCR method, or a method using an automatic DNA/RNA synthesizer.

The DNA recombination technique and the PCR method may employ techniques described in, for example, Ausubel et al., Current Protocols in Molecular Biology, John Willey & Sons, US (1993); and Sambrook et al., Molecular Cloning—A Laboratory Manual, Cold Spring Harbor Laboratory Press, US (1989).

The human-derived hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-642b-3p, hsa-miR-642a-3p, hsa-miR-7109-5p, hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p, and hsa-miR-22-3p represented by SEQ ID NOs: 1 to 275 are known in the art, and their obtainment methods are also known as mentioned above. Therefore, each polynucleotide that can be used as a nucleic acid probe or a primer in the present invention can be prepared by cloning the gene.

Such nucleic acid probes or primers can be chemically synthesized using an automatic DNA synthesizer. In general, the phosphoramidite method is used in this synthesis, and single-stranded DNA up to approximately 100 nucleotides can be automatically synthesized by this method. The automatic DNA synthesizer is commercially available from, for example, Polygen GmbH, ABI, or Applied Biosystems, Inc.

Alternatively, the polynucleotides of the present invention can also be prepared by cDNA cloning methods. The cDNA cloning technique may employ, for example, microRNA Cloning Kit Wako.

In this context, the sequences of the nucleic acid probes and the primers for detecting the polynucleotide consisting of a nucleotide sequence represented by any of SEQ ID NOs: 1 to 275 do not exist as miRNAs or precursors thereof in the living body or in vivo. For example, the nucleotide sequences represented by SEQ ID NO: 128 and SEQ ID NO: 151 are produced from the precursor represented by SEQ ID NO: 405. This precursor has a hairpin-like structure as shown in FIG. 1, and the nucleotide sequences represented by SEQ ID NO: 128 and SEQ ID NO: 151 have mismatch sequences with each other. As such, a nucleotide sequence completely complementary to the nucleotide sequence represented by SEQ ID NO: 121 or SEQ ID NO: 151 does not naturally occur in vivo. Therefore, the nucleic acid probes and the primers for detecting the nucleotide sequence represented by any of SEQ ID NOs: 1 to 275 can have artificial nucleotide sequences that do not exist in the living body or in vivo.

3. Kit or Device for Detection of Ovarian Tumor

The present invention also provides a kit or a device for detection of ovarian tumor, comprising one or more polynucleotides (which may include a variant, a fragment, or a derivative thereof) that can be used as nucleic acid probes or primers in the present invention for measuring target nucleic acids as ovarian tumor markers.

The target nucleic acids as ovarian tumor markers according to the present invention are preferably selected from the following group A:

Group A:

hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-7109-5p, hsa-miR-642b-3p, and hsa-miR-642a-3p.

Additional target nucleic acids that may be optionally used in the measurement are preferably selected from the following group B:

Group B:

hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p, hsa-miR-22-3p.

The kit or the device of the present invention comprises one or more nucleic acids capable of specifically binding to any of the target nucleic acids as the ovarian tumor markers described above or nucleic acids for detecting the target nucleic acids, preferably one or more polynucleotides selected from the polynucleotides described in the preceding Section 2, or variants thereof.

Specifically, the kit or the device of the present invention can comprise at least one polynucleotide comprising (or consisting of), for example, a nucleotide sequence represented by any of SEQ ID NOs: 1 to 247, 251, and 268 or a nucleotide sequence derived from the nucleotide sequence by the replacement of u with t, polynucleotide(s) comprising (or consisting of) a complementary sequence thereof, a polynucleotide(s) hybridizing under stringent conditions to any of these polynucleotides, or a variant(s) or a fragment(s) comprising 15 or more consecutive nucleotides of any of these polynucleotide sequences.

The kit or the device of the present invention can further comprise one or more polynucleotides comprising (or consisting of), for example, a nucleotide sequence represented by any of SEQ ID NOs: 248 to 250, 252 to 267, and 269 to 275 or a nucleotide sequence derived from the nucleotide sequence by the replacement of u with t, a polynucleotide(s) comprising (or consisting of) a complementary sequence thereof, a polynucleotide(s) hybridizing under stringent conditions to any of these polynucleotides, a variant(s), or a fragment(s) comprising 15 or more consecutive nucleotides of any of these polynucleotide sequences.

The fragment or fragments that can be comprised in the kit or the device of the present invention is/are, for example, one or more polynucleotides, preferably two or more polynucleotides, selected from the group consisting of the following polynucleotides (1) and (2):

(1) a polynucleotide comprising 15 or more consecutive nucleotides that are from a nucleotide sequence derived from a nucleotide sequence represented by any of SEQ ID NOs: 1 to 247, 251, and 268 by the replacement of u with t, or a complementary sequence thereof; and (2) a polynucleotide comprising 15 or more consecutive nucleotides that are from a nucleotide sequence derived from a nucleotide sequence represented by any of SEQ ID NOs: 248 to 250, 252 to 267, and 269 to 275 by the replacement of u with t, or a complementary sequence thereof.

In a preferred embodiment, the polynucleotide is a polynucleotide consisting of a nucleotide sequence represented by any of SEQ ID NOs: 1 to 247, 251, and 268 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the polynucleotide is a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a polynucleotide consisting of a complementary sequence thereof, a polynucleotide hybridizing under stringent conditions to any of these polynucleotides, or a variant thereof comprising 15 or more, preferably 17 or more, more preferably 19 or more consecutive nucleotides.

In a preferred embodiment, the fragment can be a polynucleotide comprising 15 or more, preferably 17 or more, more preferably 19 or more consecutive nucleotides.

In the present invention, the size of the polynucleotide fragment is the number of nucleotides in the range from, for example, 15 consecutive nucleotides to less than the total number of nucleotides of the sequence, from 17 consecutive nucleotides to less than the total number of nucleotides of the sequence, or from 19 consecutive nucleotides to less than the total number of nucleotides of the sequence, in the nucleotide sequence of each polynucleotide.

Examples of the combination of the above-mentioned polynucleotides as target nucleic acids in the kit or the device of the present invention can include a single (one) polynucleotide or combinations of 2, 3, 4, 5, 6, 7, 8, 9, 10 or more of the above-mentioned polynucleotides consisting of the nucleotide sequences represented by SEQ ID NOs: 1 to 275 as shown in Table 1 above. However, these are given merely for illustrative purposes, and all of various other possible combinations are included in the present invention.

Examples of the combinations of target nucleic acids in the kit or the device for discriminating ovarian tumor patients from healthy subjects according to the present invention can include, for example, combinations of two or more of the above-mentioned polynucleotides consisting of the nucleotide sequences represented by SEQ ID NOs shown in Table 1. More preferably, the examples can include combination of two or more of the above-mentioned polynucleotides consisting of the nucleotide sequences represented by SEQ ID NOs as shown in Table 2. For example, any two or more of the above-mentioned polynucleotides consisting of nucleotide sequences represented by SEQ ID NOs: 1 to 203 and 248 to 268 can be combined. Among them, at least one polynucleotide of the newly found polynucleotides consisting of the nucleotide sequences represented by SEQ ID NOs: 1 to 203, 251, and 268 is preferably selected.

Additionally, examples of the combinations of target nucleic acids in the kit or the device for discriminating ovarian tumor patients from benign bone and soft tissue tumor patients and benign breast disease patients according to the present invention can include combinations of two or more of the above-mentioned polynucleotides consisting of the nucleotide sequences represented by SEQ ID NOs as shown in Table 1. More preferably, the examples can include combinations of two or more of the above-mentioned polynucleotides consisting of the nucleotide sequences represented by SEQ ID NOs as shown in Table 6. For example, any two of the polynucleotides selected from the group consisting of the nucleotide sequences represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269, and 270 can be combined. Among them, at least one polynucleotide of the newly found polynucleotides consisting of the nucleotide sequences represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, and 268 is preferably selected.

Moreover, examples of the combinations of target nucleic acids in the kit or the device for discriminating ovarian tumor patients from patients having a cancer other than ovarian cancer according to the present invention can include combinations of two or more of the above-mentioned polynucleotides consisting of the nucleotide sequences represented by SEQ ID NOs as shown in Table 1. More preferably, two or more of the above-mentioned polynucleotides consisting of the nucleotide sequences represented by SEQ ID NOs as shown in Table 10 can be combined. For example, any two of the polynucleotides selected from the group consisting of the nucleotide sequences represented by SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, 264, 266, 267, 268, 271, 272, 273, 274, and 275 can be combined. Among them, at least one polynucleotide of the newly found polynucleotides selected from the group consisting of the nucleotide sequences represented by SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, and 268 is preferably selected.

Besides, the combination of polynucleotides as target nucleic acids with specificity capable of discriminating an ovarian tumor patient from subjects such as healthy subjects, benign bone and soft tissue tumor patients and benign breast disease patients, and patients having a cancer other than ovarian cancer is preferably, for example, a combination of multiple polynucleotides comprising: at least one polynucleotide selected from the group consisting of polynucleotides consisting of the nucleotide sequences represented by SEQ ID NOs: 2, 3, 4, 9, 11, 13, 15, 20, 33, 34, 38, 40, 44, 47, 56, 62, 68, 77, 78, 80, 82, 86, 89, 90, 91, 102, 104, 109, 117, 118, 135, 136, 145, 150, 157, 160, 161, 164, 169, 172, 196, 199, 211, 216, 217, 218, 220, 228, 229, 230, 231, 232, 233, 234, 235, 236, 237, 238, 239, 240, 241, 242, 243, 244, 245, 246, 247, 250, 252, 256, 260, 267, 268 (hereinafter, this group is referred to as "specific polynucleotide group 1"); and any of the polynucleotides consisting of the nucleotide sequences represented by the other SEQ ID NOs.

Furthermore, all of the combinations of polynucleotides as target nucleic acids with cancer type specificity capable of discriminating an ovarian tumor patient not only from a healthy subject but also from a cancer patient other than ovarian cancer are more preferably combinations of multiple polynucleotides (i.e., two or more) selected from the specific polynucleotide group 1.

Moreover, the combination of polynucleotides as target nucleic acids with cancer type specificity capable of discriminating a ovarian tumor patient not only from a healthy subject but also from a cancer patient other than ovarian cancer is more preferably a combination comprising at least one polynucleotide selected from, for example, the group consisting of polynucleotides of SEQ ID NOs: 228, 9, 196, 229, 145, and 164 (hereinafter, this group is referred to as "specific polynucleotide group 2"), among the combinations of multiple polynucleotides selected from the specific polynucleotide group 1.

1. The number of the polynucleotides as target nucleic acids, with cancer type specificity may be s single polynucleotide or any one of 2, 3, 4, 5, 6, 7, 8, 9, 10 or more in the combination. It is preferably 2 or more in the combination.

Non-limiting examples of the combination of the polynucleotide consisting of the nucleotide sequence represented by SEQ ID NO: 228 or a complementary sequence thereof, with polynucleotides selected from the specific polynucleotide group 1 or polynucleotides consisting of complementary sequences thereof are listed below as combinations of target nucleic acids:

(1) a combination of SEQ ID NOs: 256, and 228;
(2) a combination of SEQ ID NOs: 47, and 228;
(3) a combination of SEQ ID NOs: 228, 9, and 229;
(4) a combination of SEQ ID NOs: 228, 9, and 78;
(5) a combination of SEQ ID NOs: 228, 9, and 82;
(6) a combination of SEQ ID NOs: 228, 9, and 268;
(7) a combination of SEQ ID NOs: 229, 260, and 228;
(8) a combination of SEQ ID NOs: 228, 9, and 247;
(9) a combination of SEQ ID NOs: 228, 9, and 62;
(10) a combination of SEQ ID NOs: 228, 9, and 217;
(11) a combination of SEQ ID NOs: 256, 228, and 9;
(12) a combination of SEQ ID NOs: 256, 228, and 260;
(13) a combination of SEQ ID NOs: 228, 9, and 234;
(14) a combination of SEQ ID NOs: 229, 20, and 228;
(15) a combination of SEQ ID NOs: 47, 228, and 82;
(16) a combination of SEQ ID NOs: 145, 260, and 228;
(17) a combination of SEQ ID NOs: 228, 9, and 145;
(18) a combination of SEQ ID NOs: 228, 9, 268, and 160;
(19) a combination of SEQ ID NOs: 228, 9, 82, and 268;
(20) a combination of SEQ ID NOs: 228, 9, 268, and 196;
(21) a combination of SEQ ID NOs: 145, 260, 228, and 250;
(22) a combination of SEQ ID NOs: 145, 260, 228, and 62;
(23) a combination of SEQ ID NOs: 228, 9, 268, and 230;
(24) a combination of SEQ ID NOs: 229, 260, 228, and 2;
(25) a combination of SEQ ID NOs: 228, 9, 268, and 62;
(26) a combination of SEQ ID NOs: 229, 260, 228, and 172;
(27) a combination of SEQ ID NOs: 229, 260, 228, and 4;
(28) a combination of SEQ ID NOs: 229, 260, 228, and 34;
(29) a combination of SEQ ID NOs: 229, 260, 228, and 56;
(30) a combination of SEQ ID NOs: 229, 20, 228, and 4;
(31) a combination of SEQ ID NOs: 229, 20, 228, and 102;
(32) a combination of SEQ ID NOs: 145, 260, 228, and 89;
(33) a combination of SEQ ID NOs: 228, 9, 229, and 82;
(34) a combination of SEQ ID NOs: 228, 9, 78, and 62;
(35) a combination of SEQ ID NOs: 229, 260, 228, and 157;
(36) a combination of SEQ ID NOs: 229, 260, 228, and 231;
(37) a combination of SEQ ID NOs: 256, 228, 260, and 232;
(38) a combination of SEQ ID NOs: 228, 9, 229, and 117;
(39) a combination of SEQ ID NOs: 228, 9, 229, and 62;
(40) a combination of SEQ ID NOs: 228, 9, 78, and 172;
(41) a combination of SEQ ID NOs: 228, 9, 78, and 3;
(42) a combination of SEQ ID NOs: 228, 9, 82, 268, and 196;
(43) a combination of SEQ ID NOs: 229, 20, 228, 4, and 172;
(44) a combination of SEQ ID NOs: 228, 9, 82, 268, and 233;
(45) a combination of SEQ ID NOs: 228, 9, 268, 196, and 89;
(46) a combination of SEQ ID NOs: 228, 9, 268, 160, and 82;
(47) a combination of SEQ ID NOs: 228, 9, 268, 196, and 256;
(48) a combination of SEQ ID NOs: 228, 9, 78, 62, and 238;
(49) a combination of SEQ ID NOs: 228, 9, 268, 196, and 172;
(50) a combination of SEQ ID NOs: 256, 228, 260, 232, and 196;
(51) a combination of SEQ ID NOs: 228, 9, 268, 160, and 230;
(52) a combination of SEQ ID NOs: 256, 196, 260, 268, and 228;
(53) a combination of SEQ ID NOs: 228, 9, 268, 196, and 62;
(54) a combination of SEQ ID NOs: 228, 9, 268, 196, and 244;
(55) a combination of SEQ ID NOs: 228, 9, 268, 196, and 135;
(56) a combination of SEQ ID NOs: 229, 260, 228, 2, and 217;
(57) a combination of SEQ ID NOs: 228, 9, 268, 62, and 233;
(58) a combination of SEQ ID NOs: 229, 260, 228, 172, and 230;
(59) a combination of SEQ ID NOs: 229, 260, 228, 56, and 33;
(60) a combination of SEQ ID NOs: 229, 260, 228, 56, and 231;
(61) a combination of SEQ ID NOs: 229, 260, 228, 231, and 91;
(62) a combination of SEQ ID NOs: 228, 9, 268, 160, and 245;
(63) a combination of SEQ ID NOs: 228, 9, 82, 268, and 237; and
(64) a combination of SEQ ID NOs: 228, 9, 82, 268, and 236.

Non-limiting examples of the combination of, for example, the polynucleotide consisting of the nucleotide sequence represented by SEQ ID NO: 9 or a polynucleotide consisting of a complementary sequence thereof, with polynucleotides selected from the specific polynucleotide group 1 or polynucleotides consisting of complementary sequences thereof are further listed below as combinations of target nucleic acids:

(1) a combination of SEQ ID NOs: 228, 9, and 229;
(2) a combination of SEQ ID NOs: 228, 9, and 78;
(3) a combination of SEQ ID NOs: 228, 9, and 82;
(4) a combination of SEQ ID NOs: 228, 9, and 268;
(5) a combination of SEQ ID NOs: 228, 9, and 247;
(6) a combination of SEQ ID NOs: 228, 9, and 62;
(7) a combination of SEQ ID NOs: 228, 9, and 217;
(8) a combination of SEQ ID NOs: 256, 228, and 9;
(9) a combination of SEQ ID NOs: 228, 9, and 234;
(10) a combination of SEQ ID NOs: 228, 9, and 145;
(11) a combination of SEQ ID NOs: 256, 196, and 9;
(12) a combination of SEQ ID NOs: 228, 9, 268, and 160;
(13) a combination of SEQ ID NOs: 256, 196, 9, and 68;
(14) a combination of SEQ ID NOs: 228, 9, 82, and 268;
(15) a combination of SEQ ID NOs: 228, 9, 268, and 196;
(16) a combination of SEQ ID NOs: 228, 9, 268, and 230;
(17) a combination of SEQ ID NOs: 228, 9, 268, and 62;
(18) a combination of SEQ ID NOs: 228, 9, 229, and 82;
(19) a combination of SEQ ID NOs: 228, 9, 78, and 62;
(20) a combination of SEQ ID NOs: 228, 9, 229, and 117;
(21) a combination of SEQ ID NOs: 228, 9, 229, and 62;
(22) a combination of SEQ ID NOs: 228, 9, 78, and 172;
(23) a combination of SEQ ID NOs: 228, 9, 78, and 3;
(24) a combination of SEQ ID NOs: 228, 9, 82, 268, and 196;
(25) a combination of SEQ ID NOs: 228, 9, 82, 268, and 233;
(26) a combination of SEQ ID NOs: 228, 9, 268, 196, and 89;
(27) a combination of SEQ ID NOs: 228, 9, 268, 160, and 82;
(28) a combination of SEQ ID NOs: 256, 196, 9, 68, and 86;
(29) a combination of SEQ ID NOs: 228, 9, 268, 196, and 256;
(30) a combination of SEQ ID NOs: 228, 9, 78, 62, and 238;
(31) a combination of SEQ ID NOs: 228, 9, 268, 196, and 172;
(32) a combination of SEQ ID NOs: 228, 9, 268, 160, and 230;
(33) a combination of SEQ ID NOs: 228, 9, 268, 196, and 62;
(34) a combination of SEQ ID NOs: 228, 9, 268, 196, and 244;
(35) a combination of SEQ ID NOs: 228, 9, 268, 196, and 135;
(36) a combination of SEQ ID NOs: 228, 9, 268, 62, and 233;
(37) a combination of SEQ ID NOs: 228, 9, 268, 160, and 245;
(38) a combination of SEQ ID NOs: 256, 196, 9, 68, and 268;
(39) a combination of SEQ ID NOs: 228, 9, 82, 268, and 237; and
(40) a combination of SEQ ID NOs: 228, 9, 82, 268, and 236.

Non-limiting examples of the combination of, for example, the polynucleotide consisting of the nucleotide sequence represented by SEQ ID NO: 196 or a complementary sequence thereof, with polynucleotides selected from the specific polynucleotide group 1 or polynucleotides consisting of complementary sequences thereof are further listed below as combinations of target nucleic acids:

(1) a combination of SEQ ID NOs: 256, and 196;
(2) a combination of SEQ ID NOs: 256, 196, and 260;
(3) a combination of SEQ ID NOs: 256, 196, and 172;
(4) a combination of SEQ ID NOs: 256, 196, and 47;
(5) a combination of SEQ ID NOs: 256, 196, and 11;
(6) a combination of SEQ ID NOs: 256, 196, and 136;
(7) a combination of SEQ ID NOs: 256, 196, and 80;
(8) a combination of SEQ ID NOs: 256, 196, and 9;
(9) a combination of SEQ ID NOs: 256, 196, 260, and 268;
(10) a combination of SEQ ID NOs: 256, 196, 9, and 68;
(11) a combination of SEQ ID NOs: 256, 196, 260, and 216;
(12) a combination of SEQ ID NOs: 256, 196, 260, and 11;
(13) a combination of SEQ ID NOs: 228, 9, 268, and 196;
(14) a combination of SEQ ID NOs: 256, 196, 260, and 217;
(15) a combination of SEQ ID NOs: 228, 9, 82, 268, and 196;
(16) a combination of SEQ ID NOs: 228, 9, 268, 196, and 89;
(17) a combination of SEQ ID NOs: 256, 196, 9, 68, and 86;
(18) a combination of SEQ ID NOs: 228, 9, 268, 196, and 256;
(19) a combination of SEQ ID NOs: 256, 196, 260, 268, and 252;
(20) a combination of SEQ ID NOs: 228, 9, 268, 196, and 172;
(21) a combination of SEQ ID NOs: 256, 228, 260, 232, and 196;
(22) a combination of SEQ ID NOs: 256, 196, 260, 268, and 228;
(23) a combination of SEQ ID NOs: 256, 196, 260, 268, and 218;
(24) a combination of SEQ ID NOs: 256, 196, 260, 268, and 267;
(25) a combination of SEQ ID NOs: 228, 9, 268, 196, and 62;
(26) a combination of SEQ ID NOs: 228, 9, 268, 196, and 244;
(27) a combination of SEQ ID NOs: 228, 9, 268, 196, and 135;
(28) a combination of SEQ ID NOs: 256, 196, 260, 217, and 199;
(29) a combination of SEQ ID NOs: 256, 196, 260, 268, and 161; and
(30) a combination of SEQ ID NOs: 256, 196, 9, 68, and 268.

Non-limiting examples of the combination of, for example, the polynucleotide consisting of the nucleotide sequence represented by SEQ ID NO: 229 or a complementary sequence thereof, with polynucleotides selected from the specific polynucleotide group 1 or polynucleotides consisting of complementary sequences thereof are further listed below as combinations of target nucleic acids:

(1) a combination of SEQ ID NOs: 228, 9, and 229;
(2) a combination of SEQ ID NOs: 229, 260, and 228;
(3) a combination of SEQ ID NOs: 229, 260, and 230;
(4) a combination of SEQ ID NOs: 229, 260, and 169;
(5) a combination of SEQ ID NOs: 229, 260, and 160;

(6) a combination of SEQ ID NOs: 229, 20, and 228;
(7) a combination of SEQ ID NOs: 229, 260, 228, and 2;
(8) a combination of SEQ ID NOs: 229, 260, 169, and 2;
(9) a combination of SEQ ID NOs: 229, 260, 228, and 172;
(10) a combination of SEQ ID NOs: 229, 260, 228, and 4;
(11) a combination of SEQ ID NOs: 229, 260, 228, and 34;
(12) a combination of SEQ ID NOs: 229, 260, 228, and 56;
(13) a combination of SEQ ID NOs: 229, 20, 228, and 4;
(14) a combination of SEQ ID NOs: 229, 20, 228, and 102;
(15) a combination of SEQ ID NOs: 228, 9, 229, and 82;
(16) a combination of SEQ ID NOs: 229, 260, 228, and 157;
(17) a combination of SEQ ID NOs: 229, 260, 228, and 231;
(18) a combination of SEQ ID NOs: 228, 9, 229, and 117;
(19) a combination of SEQ ID NOs: 228, 9, 229, and 62;
(20) a combination of SEQ ID NOs: 229, 20, 228, 4, and 172;
(21) a combination of SEQ ID NOs: 229, 260, 228, 2, and 217;
(22) a combination of SEQ ID NOs: 229, 260, 228, 172, and 230;
(23) a combination of SEQ ID NOs: 229, 260, 228, 56, and 33;
(24) a combination of SEQ ID NOs: 229, 260, 228, 56, and 231; and
(25) a combination of SEQ ID NOs: 229, 260, 228, 231, and 91.

Non-limiting examples of the combination of, for example, the polynucleotide consisting of the nucleotide sequence represented by SEQ ID NO: 145 or a complementary sequence thereof, with polynucleotides selected from the specific polynucleotide group 1 or polynucleotides consisting of complementary sequences thereof are further listed below as combinations of target nucleic acids:

(1) a combination of SEQ ID NOs: 145, 260, and 164;
(2) a combination of SEQ ID NOs: 145, 260, and 230;
(3) a combination of SEQ ID NOs: 145, 260, and 211;
(4) a combination of SEQ ID NOs: 145, 260, and 228;
(5) a combination of SEQ ID NOs: 228, 9, and 145;
(6) a combination of SEQ ID NOs: 145, 260, 228, and 250;
(7) a combination of SEQ ID NOs: 145, 260, 228, and 62; and
(8) a combination of SEQ ID NOs: 145, 260, 228, and 89.

Non-limiting examples of the combination of, for example, the polynucleotide consisting of the nucleotide sequence represented by SEQ ID NO: 164 or a complementary sequence thereof, with polynucleotides selected from the specific polynucleotide group 1 or polynucleotides consisting of complementary sequences thereof are further listed below as combinations of target nucleic acids:

(1) a combination of SEQ ID NOs: 11, 164, and 260;
(2) a combination of SEQ ID NOs: 11, 164, and 20; and
(3) a combination of SEQ ID NOs: 145, 260, and 164.

The kit or device of the present invention can also comprise polynucleotide(s) which can detect ovarian tumor and are known in the art or will be found in the future in addition to the polynucleotide(s) (that can comprise variant(s), fragments, or derivative(s)) according to the present invention as described above.

The kit or device of the present invention can also comprise an antibody for measuring a marker or markers for ovarian tumor examination known in the art, such as CA-125, in addition to the polynucleotide(s) according to the present invention as described above, and a variant or variants thereof or a fragment or fragments thereof.

These polynucleotides and variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention is a device for measurement of cancer markers in which nucleic acids such as the polynucleotides according to the present invention described above, variants thereof, derivatives thereof, or fragments thereof are bonded or attached to, for example, a solid phase. Examples of the material for the solid phase include plastics, paper, glass, and silicon. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or the device of the present invention comprises nucleic acids capable of specifically binding to the polynucleotides of at least one, preferably at least two, more preferably at least three, most preferably at least five to all of the ovarian tumor marker miRNAs, respectively, of the group A described above, or to a complementary strand(s) of the polynucleotide(s). The kit or the device of the present invention can optionally further comprise nucleic acids capable of specifically binding to the polynucleotides of at least one, preferably at least two, more preferably at least three, most preferably at least five to all of the ovarian tumor marker miRNAs, respectively, of the group B described above, or to a complementary strand(s) of the polynucleotide(s).

The kit or the device of the present invention can be used for detecting ovarian tumor as described in Section 4 below.

4. Method for Detecting Ovarian Tumor

The present invention further provides a method for detecting ovarian tumor, comprising using the above-mentioned nucleic acid(s) that can be used in the present invention (alternatively, e.g., the kit or the device of the present invention as described in Section 3 above) to measure: one or more expression levels of ovarian tumor-derived genes represented by: hsa-miR-4675, hsa-miR- 4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, hsa-miR-7109-5p, hsa-miR-642b-3p, and hsa-miR-642a-3p; and optionally one or more expression levels of ovarian tumor-derived genes represented by: hsa-miR-320a, hsa-miR-663a, hsa-miR-328-5p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a, hsa-miR-483-5p, hsa-miR-652-5p, hsa-miR-24-3p, hsa-miR-23b-3p, hsa-miR-23a-3p, hsa-miR-92b-3p, hsa-miR-22-3p, in a sample in vitro (e.g., expression profiles), and evaluating in vitro whether the subject has ovarian tumor or not with the expression levels measured (and control expression levels of healthy subjects optionally measured in the same way as above). In the method, for example, the expression levels of the genes in the sample, such as blood, serum, or plasma, collected from a subject suspected of having ovarian tumor and subjects without ovarian tumor, and control expression levels in the samples collected from subjects without ovarian tumor can be used (e.g., for comparing both expression levels) to evaluate the subject as having ovarian tumor when the expression level(s) of the target nucleic acid(s) is different between the samples.

This method of the present invention enables a limitedly invasive, early diagnosis of the cancer with high sensitivity and high specificity and thereby brings about early treatment and improved prognosis. In addition, exacerbation of the disease or the effectiveness of surgical, radiotherapeutic, and chemotherapeutic treatments can be monitored by the present invention.

The method for extracting the ovarian tumor-derived gene(s) from the sample such as blood, serum, or plasma according to the present invention is particularly preferably prepared by the addition of a reagent for RNA extraction in 3D-Gene™ RNA extraction reagent from liquid sample kit (Toray Industries, Inc., Japan). A general acidic phenol method (acid guanidinium-phenol-chloroform (AGPC)) may be used, or Trizol™ (Life Technologies Corp.) may be used. The ovarian tumor-derived gene(s) may be prepared by the addition of a reagent for RNA extraction containing acidic phenol, such as Trizol (Life Technologies Corp.) or Isogen (Nippon Gene Co., Ltd., Japan). Alternatively, a kit such as miRNeasy™ Mini Kit (Qiagen N.V.) may be used, though the method is not limited thereto.

The present invention also provides use of the kit or the device of the present invention for detecting in vitro an expression product(s) of an ovarian tumor-derived miRNA gene(s) in a sample from a subject.

In the method of the present invention, the kit or the device described above comprises a single polynucleotide or any possible combination of polynucleotides that can be used in the present invention as described above.

In the detection or (genetic) diagnosis of ovarian tumor according to the present invention, each polynucleotide contained in the kit or the device of the present invention can be used as a probe or a primer. In the case of using the polynucleotides as primers, TaqMan™ MicroRNA Assays from Life Technologies Corp., miScript PCR System from Qiagen N.V., or the like can be used, though the method is not limited thereto.

In the method of the present invention, measurement of the gene expression levels can be performed using the above-mentioned primers or probes according to a routine method in a method known in the art for specifically detecting the particular genes, for example, a hybridization technique such as Northern blot, Southern blot, in situ hybridization, Northern hybridization, or Southern hybridization, a quantitative amplification technique such as quantitative RT-PCR, or a method with a next-generation sequencer. A body fluid such as blood, serum, plasma, or urine from a subject is collected as a sample to be assayed according to the type of the detection method used. Alternatively, total RNA prepared from such a body fluid by the method described above may be used, and various polynucleotides including cDNA prepared on the basis of the RNA may be used.

The method, the kit or the device of the present invention is useful for the diagnosis of ovarian tumor or the detection of the presence or absence of ovarian tumor. Specifically, the detection of ovarian tumor using the method, the kit or the device can be performed by detecting in vitro an expression level(s) of a gene(s) which is detected by the method or detected using the nucleic acid probe(s) or the primer(s) contained in the kit or the device, in a sample such as blood, serum, plasma, or urine from a subject suspected of having ovarian tumor. The subject suspected of having ovarian tumor can be evaluated as having ovarian tumor when the expression level(s) of a polynucleotide(s) consisting of a nucleotide sequence(s) represented by at least one of, for example, SEQ ID NOs: 1 to 247, 251, and 268 and optionally a nucleotide sequence(s) represented by one or more of, for example, SEQ ID NOs: 248 to 250, 252 to 267, and 269 to 275, as target nucleic acids, in the sample such as blood, serum, plasma, or urine of the subject, is statistically significantly high compared to an expression level(s) thereof in the sample such as blood, serum, or plasma, or urine of a subject without ovarian tumor (i.e., also referred to as a control animal).

In the method of the present invention, or the method using the kit or the device of the present invention, the method for detecting the absence of ovarian tumor or the presence of ovarian tumor in a sample from a subject comprises collecting a body fluid such as blood, serum, plasma, or urine of a subject, and measuring the expression level(s) of the target gene(s) (or target nucleic acid(s)) contained therein using one or more polynucleotides (including a variant(s), a fragment(s), or a derivative(s)) selected from the groups of polynucleotides of the present invention, to evaluate the presence or absence of ovarian tumor or to detect ovarian tumor. The method for detecting ovarian tumor according to the present invention can also be used to evaluate or diagnose, for example, the presence or absence of amelioration of the disease or the degree of amelioration thereof in a ovarian tumor patient in the case that an ovarian cancer-related therapeutic drug which is known in the art or on a development stage (including cisplatin, cyclophosphamide, doxorubicin, etoposide, carboplatin, paclitaxel, and combination drugs thereof as non-limiting examples) is administered to the patient for treatment or amelioration of the disease.

The method of the present invention can comprise, for example, the following steps (a), (b), and (c):

(a) a step of contacting in vitro a sample from a subject with a polynucleotide(s) contained in the kit or the device of the present invention;

(b) a step of measuring an expression level(s) of the target nucleic acid(s) in the sample using the polynucleotide(s) as a nucleic acid probe(s) or primer(s); and (c) a step of evaluating the presence or absence of ovarian tumor (cells) in the subject on the basis of the measurement results in the step (b).

In one embodiment, the present invention provides a method for detecting ovarian tumor, comprising: measuring an expression level(s) of a target nucleic acid(s) in a sample of a subject using a nucleic acid(s) capable of specifically binding to at least one, preferably at least two polynucleotides selected from the following miRNAs: miR-4675, miR-4783-3p, miR-1228-5p, miR-4532, miR-6802-5p, miR-6784-5p, miR-3940-5p, miR-1307-3p, miR-8073, miR-3184-5p, miR-1233-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1185-2-3p, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR- 3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, and miR-642a-3p, or to a complementary strand(s) of the polynucleotide(s); or a nucleic acid(s) for detecting the polynucleotide(s); and evaluating in vitro whether or not the subject has ovarian tumor using the above-measured expression levels and control expression levels of a healthy subject(s) (see the definition described above) measured in the same way as above.

As used herein, the term “evaluating” is evaluation support based on results of in vitro examination, not physician’s judgment.

As described above, in the method of the present invention, specifically, miR-4675 is hsa-miR-4675, miR-4783-3p is hsa-miR-4783-3p, miR-1228-5p is hsa-miR-1228-5p, miR-4532 is hsa-miR-4532, miR-6802-5p is hsa-miR-6802-5p, miR-6784-5p is hsa-miR-6784-5p, miR-3940-5p is hsa-miR-3940-5p, miR-1307-3p is hsa-miR-1307-3p, miR-8073 is hsa-miR-8073, miR-3184-5p is hsa-miR-3184-5p, miR-1233-5p is hsa-miR-1233-5p, miR-6088 is hsa-miR-6088, miR-5195-3p is hsa-miR-5195-3p, miR-320b is hsa-miR-320b, miR-4649-5p is hsa-miR-4649-5p, miR-6800-5p is hsa-miR-6800-5p, miR-1343-3p is hsa-miR-1343-3p, miR-4730 is hsa-miR-4730, miR-6885-5p is hsa-miR-6885-5p, miR-5100 is hsa-miR-5100, miR-1203 is hsa-miR-1203, miR-6756-5p is hsa-miR-6756-5p, miR-373-5p is hsa-miR-373-5p, miR-1268a is hsa-miR-1268a, miR-1260b is hsa-miR-1260b, miR-4258 is hsa-miR-4258, miR-4697-5p is hsa-miR-4697-5p, miR-1469 is hsa-miR-1469, miR-4515 is hsa-miR-4515, miR-6861-5p is hsa-miR-6861-5p, miR-6821-5p is hsa-miR-6821-5p, miR-575 is hsa-miR-575, miR-6805-5p is hsa-miR-6805-5p, miR-4758-5p is hsa-miR-4758-5p, miR-3663-3p is hsa-miR-3663-3p, miR-4530 is hsa-miR-4530, miR-6798-5p is hsa-miR-6798-5p, miR-6781-5p is hsa-miR-6781-5p, miR-885-3p is hsa-miR-885-3p, miR-1273g-3p is hsa-miR-1273g-3p, miR-4787-3p is hsa-miR-4787-3p, miR-4454 is hsa-miR-4454, miR-4706 is hsa-miR-4706, miR-1249-3p is hsa-miR-1249-3p, miR-887-3p is hsa-miR-887-3p, miR-6786-5p is hsa-miR-6786-5p, miR-1238-5p is hsa-miR-1238-5p, miR-6749-5p is hsa-miR-6749-5p, miR-6729-5p is hsa-miR-6729-5p, miR-6825-5p is hsa-miR-6825-5p, miR-663b is hsa-miR-663b, miR-6858-5p is hsa-miR-6858-5p, miR-4690-5p is hsa-miR-4690-5p, miR-6765-5p is hsa-miR-6765-5p, miR-4710 is hsa-miR-4710, miR-6775-5p is hsa-miR-6775-5p, miR-371a-5p is hsa-miR-371a-5p, miR-6816-5p is hsa-miR-6816-5p, miR-296-3p is hsa-miR-296-3p, miR-7977 is hsa-miR-7977, miR-8069 is hsa-miR-8069, miR-6515-3p is hsa-miR-6515-3p, miR-4687-5p is hsa-miR-4687-5p, miR-1343-5p is hsa-miR-1343-5p, miR-7110-5p is hsa-miR-7110-5p, miR-4525 is hsa-miR-4525, miR-3158-5p is hsa-miR-3158-5p, miR-6787-5p is hsa-miR-6787-5p, miR-614 is hsa-miR-614, miR-4689 is hsa-miR-4689, miR-1185-2-3p is hsa-miR-1185-2-3p, miR-1268b is hsa-miR-1268b, miR-1228-3p is hsa-miR-1228-3p, miR-1185-1-3p is hsa-miR-1185-1-3p, miR-940 is hsa-miR-940, miR-939-5p is hsa-miR-939-5p, miR-6757-5p is hsa-miR-6757-5p, miR-1275 is hsa-miR-1275, miR-5001-5p is hsa-miR-5001-5p, miR-6826-5p is hsa-miR-6826-5p, miR-6765-3p is hsa-miR-6765-3p, miR-3679-3p is hsa-miR-3679-3p, miR-4718 is hsa-miR-4718, miR-4286 is hsa-miR-4286, miR-8059 is hsa-miR-8059, miR-4447 is hsa-miR-4447, miR-4448 is hsa-miR-4448, miR-658 is hsa-miR-658, miR-6766-3p is hsa-miR-6766-3p, miR-197-5p is hsa-miR-197-5p, miR-6887-5p is hsa-miR-6887-5p, miR-6742-5p is hsa-miR-6742-5p, miR-6729-3p is hsa-miR-6729-3p, miR-5090 is hsa-miR-5090, miR-7975 is hsa-miR-7975, miR-4505 is hsa-miR-4505, miR-6889-5p is hsa-miR-6889-5p, miR-4708-3p is hsa-miR-4708-3p, miR-6131 is hsa-miR-6131, miR-1225-3p is hsa-miR-1225-3p, miR-6132 is hsa-miR-6132, miR-4734 is hsa-miR-4734, miR-3194-3p is hsa-miR-3194-3p, miR-638 is hsa-miR-638, miR-2467-3p is hsa-miR-2467-3p, miR-4728-5p is hsa-miR-4728-5p, miR-5572 is hsa-miR-5572, miR-6789-5p is hsa-miR-6789-5p, miR-8063 is hsa-miR-8063, miR-4429 is hsa-miR-4429, miR-6840-3p is hsa-miR-6840-3p, miR-4476 is hsa-miR-4476, miR-675-5p is hsa-miR-675-5p, miR-711 is hsa-miR-711, miR-6875-5p is hsa-miR-6875-5p, miR-3160-5p is hsa-miR-3160-5p, miR-1908-5p is hsa-miR-1908-5p, miR-6726-5p is hsa-miR-6726-5p, miR-1913 is hsa-miR-1913, miR-8071 is hsa-miR-8071, miR-3648 is hsa-miR-3648, miR-4732-5p is hsa-miR-4732-5p, miR-4787-5p is hsa-miR-4787-5p, miR-3917 is hsa-miR-3917, miR-619-5p is hsa-miR-619-5p, miR-1231 is hsa-miR-1231, miR-342-5p is hsa-miR-342-5p, miR-4433a-5p is hsa-miR-4433a-5p, miR-6766-5p is hsa-miR-6766-5p, miR-4707-5p is hsa-miR-4707-5p, miR-7114-5p is hsa-miR-7114-5p, miR-6872-3p is hsa-miR-6872-3p, miR-6780b-5p is hsa-miR-6780b-5p, miR-7845-5p is hsa-miR-7845-5p, miR-6798-3p is hsa-miR-6798-3p, miR-665 is hsa-miR-665, miR-6848-5p is hsa-miR-6848-5p, miR-5008-5p is hsa-miR-5008-5p, miR-4294 is hsa-miR-4294, miR-6511a-5p is hsa-miR-6511a-5p, miR-4435 is hsa-miR-4435, miR-4747-3p is hsa-miR-4747-3p, miR-6880-3p is hsa-miR-6880-3p, miR-6869-5p is hsa-miR-6869-5p, miR-7150 is hsa-miR-7150, miR-1260a is hsa-miR-1260a, miR-6877-5p is hsa-miR-6877-5p, miR-6721-5p is hsa-miR-6721-5p, miR-4656 is hsa-miR-4656, miR-1229-5p is hsa-miR-1229-5p, miR-4433a-3p is hsa-miR-4433a-3p, miR-4274 is hsa-miR-4274, miR-4419b is hsa-miR-4419b, miR-4674 is hsa-miR-4674, miR-6893-5p is hsa-miR-6893-5p, miR-6763-3p is hsa-miR-6763-3p, miR-6762-5p is hsa-miR-6762-5p, miR-6738-5p is hsa-miR-6738-5p, miR-4513 is hsa-miR-4513, miR-6746-5p is hsa-miR-6746-5p, miR-6880-5p is hsa-miR-6880-5p, miR-4736 is hsa-miR-4736, miR-718 is hsa-miR-718, miR-6717-5p is hsa-miR-6717-5p, miR-7847-3p is hsa-miR-7847-3p, miR-760 is hsa-miR-760, miR-1199-5p is hsa-miR-1199-5p, miR-6813-5p is hsa-miR-6813-5p, miR-6769a-5p is hsa-miR-6769a-5p, miR-1193 is hsa-miR-1193, miR-7108-3p is hsa-miR-7108-3p, miR-6741-5p is hsa-miR-6741-5p, miR-4298 is hsa-miR-4298, miR-6796-3p is hsa-miR-6796-3p, miR-4750-5p is hsa-miR-4750-5p, miR-6785-5p is hsa-miR-6785-5p, miR-1292-3p is hsa-miR-1292-3p, miR-4749-3p is hsa-miR-4749-3p, miR-6800-3p is hsa-miR-6800-3p, miR-4722-5p is hsa-miR-4722-5p, miR-4746-3p is hsa-miR-4746-3p, miR-4450 is hsa-miR-4450, miR-6795-5p is hsa-miR-6795-5p, miR-365a-5p is hsa-miR-365a-5p, miR-498 is hsa-miR-498, miR-6797-5p is hsa-miR-6797-5p, miR-1470 is hsa-miR-1470, miR-6851-5p is hsa-miR-6851-5p, miR-1247-3p is hsa-miR-1247-3p, miR-5196-5p is hsa-miR-5196-5p, miR-208a-5p is hsa-miR-208a-5p, miR-6842-5p is hsa-miR-6842-5p, miR-150-3p is hsa-miR-150-3p, miR-4534 is hsa-miR-4534, miR-3135b is hsa-miR-3135b, miR-3131 is hsa-miR-3131, miR-4792 is hsa-miR-4792, miR-6510-5p is hsa-miR-6510-5p, miR-504-3p is hsa-miR-504-3p, miR-3619-3p is hsa-miR-3619-3p, miR-671-5p is hsa-miR-671-5p, miR-4667-5p is hsa-miR-4667-5p, miR-4430 is hsa-miR-4430, miR-3195 is hsa-miR-3195, miR-3679-5p is hsa-miR-3679-5p, miR-6076 is hsa-miR-6076, miR-6515-5p is hsa-miR-6515-5p, miR-6820-5p is hsa-miR-6820-5p, miR-4634 is hsa-miR-4634, miR-187-5p is hsa-miR-187-5p, miR-6763-5p is hsa-miR-6763-5p, miR-1908-3p is hsa-miR-1908-3p, miR-1181 is hsa-miR-1181, miR-6782-5p is hsa-miR-6782-5p, miR-5010-5p is hsa-miR-5010-5p, miR-6870-5p is hsa-miR-6870-5p, miR-6124 is hsa-miR-6124, miR-1249-5p is hsa-miR-1249-5p, miR-6511b-5p is hsa-miR-6511b-5p, miR-1254 is hsa-miR-1254, miR-4727-3p is hsa-miR-4727-3p, miR-4259 is hsa-miR-4259, miR-4771 is hsa-miR-4771, miR-3622a-5p is hsa-miR-3622a-5p, miR-4480 is hsa-miR-4480, miR-4740-5p is hsa-miR-4740-5p, miR-6777-5p is hsa-miR-6777-5p, miR-6794-5p is hsa-miR-6794-5p, miR-4687-3p is hsa-miR-4687-3p, miR-6743-5p is hsa-miR-6743-5p, miR-6771-5p is hsa-miR-6771-5p, miR-3141 is hsa-miR-3141, miR-3162-5p is hsa-miR-3162-5p, miR-4271 is hsa-miR-4271, miR-1227-5p is hsa-miR-1227-5p, miR-4257 is hsa-miR-4257, miR-4270 is hsa-miR-4270, miR-4516 is hsa-miR-4516, miR-4651 is hsa-miR-4651, miR-4725-3p is hsa-miR-4725-3p, miR-6125 is hsa-miR-6125, miR-6732-5p is hsa-miR-6732-5p, miR-6791-5p is hsa-miR-6791-5p, miR-6819-5p is hsa-miR-6819-5p, miR-6891-5p is hsa-miR-6891-5p, miR-7108-5p is hsa-miR-7108-5p, miR-7109-5p is hsa-miR-7109-5p, miR-642b-3p is hsa-miR-642b-3p, and miR-642a-3p is hsa-miR-642a-3p.

Additionally, in one embodiment, the nucleic acid(s) (e.g., a probe(s) or a primer(s)) in the method of the present invention is selected from the group consisting of, for example, the following polynucleotides (a) to (e):

(a) a polynucleotide consisting of a nucleotide sequence represented by any of SEQ ID NOs: 1 to 247, 251 and 268 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 247, 251 and 268;

(c) a polynucleotide consisting of a nucleotide sequence complementary to a nucleotide sequence represented by any of SEQ ID NOs: 1 to 247, 251 and 268 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 247, 251 and 268 or a nucleotide sequence derived from the nucleotide sequence by the replacement of u with t; and (e) a polynucleotide hybridizing under stringent conditions to any of the polynucleotides (a) to (d).

The nucleic acid(s) used in the method of the present invention can further comprise a nucleic acid(s) capable of specifically binding to at least one polynucleotide selected from the following miRNAs: miR-320a, miR-663a, miR-328-5p, miR-128-2-5p, miR-125a-3p, miR-191-5p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, miR-22-3p, or to a complementary strand of the polynucleotide.

Specifically, miR-320a is hsa-miR-320a, miR-663a is hsa-miR-663a, miR-328-5p is hsa-miR-328-5p, miR-128-2-5p is hsa-miR-128-2-5p, miR-125a-3p is hsa-miR-125a-3p, miR-191-5p is hsa-miR-191-5p, miR-92b-5p is hsa-miR-92b-5p, miR-296-5p is hsa-miR-296-5p, miR-1246 is hsa-miR-1246, miR-92a-2-5p is hsa-miR-92a-2-5p, miR-128-1-5p is hsa-miR-128-1-5p, miR-1290 is hsa-miR-1290, miR-211-3p is hsa-miR-211-3p, miR-744-5p is hsa-miR-744-5p, miR-135a-3p is hsa-miR-135a-3p, miR-451a is hsa-miR-451a, miR-625-3p is hsa-miR-625-3p, miR-92a-3p is hsa-miR-92a-3p, miR-422a is hsa-miR-422a, miR-483-5p is hsa-miR-483-5p, miR-652-5p is hsa-miR-652-5p, miR-24-3p is hsa-miR-24-3p, miR-23b-3p is hsa-miR-23b-3p, miR-23a-3p is hsa-miR-23a-3p, miR-92b-3p is hsa-miR-92b-3p, and miR-22-3p is hsa-miR-22-3.

In one embodiment, the nucleic acid(s) may further be selected from, for example, the group consisting of the following polynucleotides (f) to (j):

(f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

Examples of the sample used in the method of the present invention can include samples prepared from living tissues (preferably ovarian tissues or fallopian tube tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed according to the type of the sample to be measured.

In the case of using RNA as an analyte, the method for detecting ovarian tumor (cells) can comprise, for example, the following steps (a), (b), and (c):

(a) a step of binding RNA prepared from a sample from a subject (wherein, for example, the 3' end of the RNA may be polyadenylated for quantitative RT-PCR in step (b)) or complementary polynucleotides (cDNAs) transcribed from the RNA to a polynucleotide(s) in the kit of the present invention;

(b) a step of measuring the sample-derived RNA or the eDNAs synthesized from the RNA, which is/are bound to the polynucleotide(s), by hybridization using the polynucleotide(s) as a nucleic acid probe(s) or by quantitative RT-PCR using the polynucleotide(s) as a primer(s); and (c) a step of evaluating the presence or absence of ovarian tumor (or ovarian tumor-derived gene) on the basis of the measurement results of the step (b).

For example, various hybridization methods can be used for measuring the expression level(s) of a target gene(s), or detecting, examining, evaluating, or diagnosing ovarian tumor (or ovarian tumor-derived gene) in vitro according to the present invention. For example, Northern blot, Southern blot, DNA chip analysis, in situ hybridization, Northern hybridization, or Southern hybridization can be used as such a hybridization method. PCR such as quantitative RT-PCR can also be used in combination with hybridization method, or as an alternative thereof.

In the case of using the Northern blot, the presence or absence of expression of each gene or the expression level thereof in the RNA can be detected or measured by use of, for example, the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by use of, for example, the primer that can be used in the present invention. Specific examples thereof can include a method which comprises recovering the tissue-derived RNA from a subject, preparing eDNAs according to reverse transcription using 3'-end polyadenylation treatment, specific primers, and the like, hybridizing a pair of primers (consisting of a plus strand and a reverse strand binding to the cDNA) prepared from the kit for detection of the present invention with the cDNA such that the region of each target gene marker can be amplified with the cDNA as a template, and performing PCR according to a routine method to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA to a labeled nucleic acid probe for detection.

In the case of using the nucleic acid array analysis, an RNA chip or a DNA chip in which the kit or device for detection of the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene™ Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene™ scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2)") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% identity to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCL, and 1 to 2 mM $MgCl_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan™ MicroRNA Assays (Life Technologies Corp.), LNA™- based MicroRNA PCR (Exiqon), or Ncode™ miRNA qRT-PCT kit (Invitrogen Corp.) may be used.

In the method of the present invention, measurement of the gene expression level(s) may be performed with a sequencer, in addition to hybridization methods described above. In use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specifically designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p. 308 and Int. Neurourol. J., 2016, 20 (Suppl.2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be enriched or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene having a gene expression level of $2^6$, preferably 2', more preferably $2^{10}$ or larger in 20% or more, preferably 50% or more, more preferably 80% or more of the number of measurement samples can be selected as the analyte. Examples of the normalization of the gene expression level include, but are not limited to, global normalization and quantile normalization (Bolstad, B. M. et al., 2003, Bioinformatics, Vol. 19, p. 185-193).

The present invention also provides a method of detecting an ovarian tumor (or assisting detection thereof) in a subject, comprising measuring target genes or gene expression levels in a sample from the subject using the gene markers (or target nucleic acids) of the present invention, the nucleic acids (or polynucleotides for detection or diagnosis), the kit, or the device (e.g., chip) for detecting the gene marker or a combination thereof; and assigning the expression levels of the target genes in a sample from the subject to a discriminant (discriminant function), which is prepared using gene expression levels of a sample(s) from a subject(s) (for example, a patient(s)) known to have an ovarian tumor and a sample(s) from a subject(s) (also referred to as control animal) having no ovarian tumor, as a training sample(s), and which can distinguishably discriminate the presence or absence of an ovarian tumor, thereby evaluating the presence or absence of the ovarian tumor, for example.

Specifically, the present invention further provides the method comprising a first step of measuring in vitro expression levels of target genes, which are known to determine or evaluate that a subject has an ovarian tumor and/or not, in a plurality of samples, using the gene marker (or target nucleic acid) of the present invention, the nucleic acids (or polynucleotides for detection or diagnosis), the kit, the device (e.g., chip) for detecting the gene marker or a combination thereof; a second step of preparing a discriminant with the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether the subject has an ovarian tumor or not on the basis of the results obtained from the discriminant, for example. The above target genes are those that can be detected, for example, by the polynucleotides for detection or diagnosis, the polynucleotides contained in the kit or device, and variants thereof or fragments thereof.

The discriminant herein can be prepared by use of any discriminant analysis method, based on which a discriminant that distinguishably discriminates the presence or absence of an ovarian tumor can be prepared, such as Fisher's discriminant analysis, nonlinear discriminant analysis based on the Mahalanobis' distance, neural network or Support Vector Machine (SVM), though the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and wo represents a constant term.

$$f(x) = w_0 + \sum_{i=1}^{n} w_i x_i \quad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, μ represents an average input, ng represents the number of data belonging to class g, and μg represents an average input of the data belonging to class g. The numerator and the denominator are the interclass variance and the intraclass variance, respectively, when each of data is projected in the direction of the vector w. Discriminant coefficient $w_i$ is determined by maximizing this ratio (Takafumi Kanamori et al., "Pattern Recognition", KYORITSUSHUPPAN CO., LTD. (Tokyo, Japan) (2009); Richard O. et al., Pattern Classification, Second Edition., Wiley-Interscience, 2000).

Formula 2

$$J(w) = \frac{\sum_{g=1}^{G} n_g (w^T\mu_g - w^T\mu)(w^T\mu_g - w^T\mu)^T}{\sum_{g=1}^{G} \sum_{i:y_i=g} (w^T x_i - w^T\mu_g)(w^T x_i - w^T\mu_g)}$$

$$\text{subject to } \mu = \sum_{i=1}^{n} \frac{x_i}{n}, \mu_g = \sum_{i:u_i=g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

Formula 3

$$D(x, \mu) = \{(x-\mu)^t S^{-1} (x-\mu)\}^{\frac{1}{2}}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, a RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of ovarian tumor patients and a group of test subjects having no ovarian tumor. For example, ovarian tissue examination can be used for a reference under which each subject is confirmed to have an ovarian tumor or not.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

Formula 4

$$\min_a \frac{1}{2} a^T Q a - e^T a$$

$$\text{subject to } y^T a = 0, 0 \le a_i, \le C, i = 1, \dots, l$$

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

Formula 5

$$f(x) = \mathrm{sgn}\left(\sum_{i=1}^{l} y_i a_i K(x_i, x) + b\right)$$

For example, a RBF kernel defined by Formula 6 can be used as the kernel function. In this formula, x represents a support vector, and y represents a kernel parameter for adjusting the complexity of the hyperplane.

$$K(x_i, x_j) = \exp\{-r\|x_i - x_j\|^2\}, r < 0 \quad \text{Formula 6}$$

In addition, an approach such as neural network, k-nearest neighbor algorithms, decision trees, or logistic regression analysis can be selected as a method for determining or evaluating the presence or absence of ovarian tumor in a sample from a subject.

In an embodiment, the method of the present invention can comprise, for example, the following steps (a), (b) and (c):

(a) a step of measuring an expression level(s) of a target gene(s) in samples already known to be from ovarian tumor patients and to be subjects having no ovarian tumor, using the polynucleotide(s), the kit, or the device (e.g., DNA chip) for detection or diagnosis according to the present invention;

(b) a step of preparing the discriminants of Formulas 1 to 3, 5 and 6 described above from the measurement values of the expression level determined in the step (a), and (c) a step of measuring an expression level(s) of the target gene(s) in a sample from a subject using the polynucleotide(s), the kit, or the device (e.g., DNA chip) for detection or diagnosis according to the present invention, and assigning the obtained measurement value(s) to the discriminants prepared in the step (b), and determining or evaluating that the subject has an ovarian tumor or not on the basis of the obtained results, or evaluating the expression level derived from an ovarian tumor by comparison with a control from a subject having no ovarian tumor (including, e.g., a healthy subject).

In this context, in the discriminants of Formulas 1 to 3, 5 and 6, x represents an explanatory variable and includes a value obtained by measuring a polynucleotide(s) selected from the polynucleotides serving as a target nucleic acid described in Section 2 above or a fragment thereof. Specifically, the explanatory variable of the present invention for discriminating the presence or absence of an ovarian tumor is a gene expression level(s) selected from, for example, the following expression level (1) or (2).

(1) a gene expression level(s) in the serum of an ovarian tumor patient and a test subject having no ovarian tumor measured by any nucleic acid (e.g., DNA or RNA) comprising 15 or more consecutive nucleotides in the nucleotide sequence represented by any of SEQ ID NOs: 1 to 247, 251 and 268 or a complementary sequence thereof; and (2) a gene expression level(s) in the serum of an ovarian tumor patient and a test subject having no ovarian tumor measured by any nucleic acid (e.g., DNA or RNA) comprising 15 or more consecutive nucleotides in the nucleotide sequence represented by any of SEQ ID NOs: 248 to 250, 252 to 267 and 269 to 275 or a complementary sequence thereof.

As described above, as the method for determining or evaluating whether a subject has an ovarian tumor or not in a sample from the subject, it is necessary to use a discriminant employing one or more gene expression levels as an explanatory variable(s). In particular, for enhancing the accuracy of the discriminant using a single gene expression level alone, it is necessary to use a gene having a clear difference in expression level between two groups consisting of a group of ovarian tumor patients and a group of subjects having no ovarian tumor, in a discriminant.

Specifically, the gene that is used for an explanatory variable of a discriminant is preferably determined as follows. First, using comprehensive gene expression levels of a group of ovarian tumor patients and comprehensive gene expression levels of a group of test subjects having no ovarian tumor, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a group of patients having ovarian tumor and gene expression levels of a group of test subjects having no ovarian tumor may be calculated to select a gene that is used for an explanatory variable in a discriminant. Alternatively, ROC curves may be prepared using gene expression levels of a group of patients having ovarian tumor and a group of test subjects having no ovarian tumor, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics., Vol. 16, p. 906-14). To the discriminant, the gene expression level of another independent patient having an ovarian tumor or a test subject having no ovarian tumor is assigned as an explanatory variable to calculate discrimination results of the group to which the independent patient having an ovarian tumor or the test subject having no ovarian tumor belongs. Specifically, the gene set for diagnosis found and the discriminant constructed using the gene set for diagnosis can be evaluated in an independent sample cohort to find more universal gene set for diagnosis that can detect an ovarian tumor and a more universal method for discriminating an ovarian tumor.

In preparing a discriminant using expression levels of a plurality of genes as an explanatory variable, it is not necessary to select a gene having a clear difference in expression level between the group of ovarian tumor patients and the group of test subjects having no ovarian tumor as described above. Specifically, if expression levels of a plurality of genes are used in combination even though the expression levels of individual genes do not clearly differ, a discriminant having high discriminant performance can be obtained, as the case may be. Because of this, it is preferable to search a discriminant having high discriminant performance without selecting the gene to be employed in the discriminant.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for diagnosis or detection of a disease useful for diagnosing and treating an ovarian tumor, a method for detecting an ovarian tumor using the polynucleotide(s), and a kit and device for detecting or diagnosing an ovarian tumor, comprising the polynucleotide(s). Particularly, in order to select a gene(s) for diagnosis and prepare a discriminant so as to exhibit accuracy beyond the ovarian tumor diagnosis method using the existing tumor marker CA-125, a gene set for diagnosis and a discriminant for the method of present invention can be constructed, which exhibit accuracy beyond CA-125, for example, by comparing expressed genes in serum from a patient confirmed to be negative using a known tumor marker such as CA-125 but finally found to have an ovarian tumor by detailed examination such as computed tomography using a contrast medium, with genes expressed in serum from a test subject having no ovarian tumor.

For example, the gene set for diagnosis is set to any combination selected from one or two or more of the polynucleotides based on a nucleotide sequence represented by any of SEQ ID NOs: 1 to 247, 251, and 268 as described above; and optionally one or two or more of the polynucleotides based on a nucleotide sequence represented by any of SEQ ID NOs: 248 to 250, 252 to 267, and 269 to 275. Further, a discriminant is constructed using the expression levels of the gene set for diagnosis in samples from an ovarian tumor patient as a result of tissue diagnosis and samples from a test subject having no ovarian tumor as a result of tissue diagnosis. As a result, whether a subject, from which an unknown sample is provided, has an ovarian tumor or not can be determined with 100% accuracy at the maximum by measuring expression levels of the gene set for diagnosis in an unknown sample.

EXAMPLES

The present invention will be described further specifically with reference to Examples below. However, the scope of the present invention is not intended to be limited by these Examples.

Reference Example

<Collection of Samples>

Sera were collected using VENOJECT II vacuum blood collecting tube VP-AS 109K60 (Terumo Corp. (Japan)) from 400 healthy subjects, 327 benign bone and soft tissue tumor patients, 41 benign breast disease patients, 406 ovarian cancer patients, 28 ovarian benign tumor patients, and 50 respective patients having breast cancer, biliary cancer, pancreatic cancer, colorectal cancer, esophagus cancer, stomach cancer, liver cancer or lung cancer, after obtainment of informed consent. Note that patients having breast cancer, biliary cancer, pancreatic cancer, colorectal cancer, esophagus cancer, stomach cancer, liver cancer or lung cancer will be collectively referred hereinafter to as "patients having a cancer other than ovarian cancer"

<Extraction of Total RNA>

Total RNA was obtained using a reagent for RNA extraction in 3D-Gene™ RNA extraction reagent from liquid sample kit (Toray Industries, Inc. (Japan)) according to the protocol provided by the manufacturer, from 300 μL of the serum sample obtained from each of 1602 persons in total of 400 healthy subjects, 368 benign bone and soft tissue tumor patients and benign breast disease patients, 434 ovarian tumor patients and 400 patients having a cancer other than ovarian cancer.

<Measurement of Gene Expression Level>

First, miRNA in the total RNA, which was obtained from the serum samples of a total of 1602 people consisting of 400 healthy subjects, 368 benign bone and soft tissue tumor patients and benign breast disease patients, 434 ovarian tumor patients and 400 patients having a cancer other than ovarian cancer, was fluorescently labeled by use of 3D-Gene™ miRNA Labeling kit (Toray Industries, Inc.) according to the protocol provided by the manufacturer. The oligo DNA chip used was 3D-Gene™ Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene™ scanner (Toray Industries, Inc.) to obtain images. Fluorescence intensity was digitized using 3D-Gene™ Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for 400 healthy subjects, 368 benign bone and soft tissue tumor patients and benign breast disease patients, 434 ovarian tumor patients, and 400 patients having a cancer other than ovarian cancer. Subsequently, 70% of each sample group was used as a training cohort and 30% thereof as a validation cohort. Specifically, the training cohort consisted of 280 healthy subjects, 257 benign bone and soft tissue tumor patients and benign breast disease patients, 303 ovarian tumor patients and 280 patients having a cancer other than ovarian cancer; while the validation cohort consisted of 120 healthy subjects, 111 benign bone and soft tissue tumor patients and benign breast disease patients, 131 ovarian tumor patients, and 120 patients having a cancer other than ovarian cancer. Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modern Applied Statistics with S. Fourth Edition. Springer, New York. ISBN 0-387-95457-0).

Example 1

<Selection of Ovarian Tumor Gene Marker by Comparison with Healthy Subject and Method for Evaluating Ovarian Tumor Discriminant Performance by Single Gene Marker>

In this Example, miRNAs whose expression level significantly differs between ovarian tumor patients and healthy subjects were selected as ovarian tumor gene markers. A discriminant(s) was prepared using one or two gene markers in the training cohort, and then, the discrimination accuracy in the validation cohort was calculated. Based on the calculation, the performance of the gene marker(s) to distinguish ovarian tumor patients from healthy subjects was evaluated.

Specifically, first, the miRNA expression levels of the training cohort and the validation cohort obtained in the preceding Reference Examples were combined and normalized by global normalization.

Next, genes for diagnosis were selected. Here, in order to acquire diagnostic markers with higher reliability, only genes having the expression level of $2^6$ or higher in 50% or more of the samples in either of the ovarian tumor patient group or the healthy subject group were selected. Subsequently, in order to obtain a gene whose expression level significantly differs in statistics between an ovarian tumor patient group and a healthy subject group, a two-sided t-test assuming equal variance was carried out, and then, a gene having a P value obtained after the Bonferroni correction of less than 0.01 was selected. Furthermore, in order to select a gene rarely affected by noise at the time of measurement, a gene(s) having an absolute value of the difference (hold change) in gene expression level, which is obtained by logarithmic conversion between the ovarian tumor patient group and the healthy group, and which is larger than 0.5, was selected as a diagnostic marker(s) for an ovarian tumor and a healthy subject. The results are shown in Table 2.

In this way, hsa-miR-4675, hsa-miR-4783-3p, hsa-miR-1228-5p, hsa-miR-4532, hsa-miR-6802-5p, hsa-miR-6784-5p, hsa-miR-3940-5p, hsa-miR-1307-3p, hsa-miR-8073, hsa-miR-3184-5p, hsa-miR-1233-5p, hsa-miR-6088, hsa-miR-5195-3p, hsa-miR-320b, hsa-miR-4649-5p, hsa-miR-6800-5p, hsa-miR-1343-3p, hsa-miR-4730, hsa-miR-6885-5p, hsa-miR-5100, hsa-miR-1203, hsa-miR-6756-5p, hsa-miR-373-5p, hsa-miR-1268a, hsa-miR-1260b, hsa-miR-4258, hsa-miR-4697-5p, hsa-miR-1469, hsa-miR-4515, hsa-miR-6861-5p, hsa-miR-6821-5p, hsa-miR-575, hsa-miR-6805-5p, hsa-miR-4758-5p, hsa-miR-3663-3p, hsa-miR-4530, hsa-miR-6798-5p, hsa-miR-6781-5p, hsa-miR-885-3p, hsa-miR-1273g-3p, hsa-miR-4787-3p, hsa-miR-4454, hsa-miR-4706, hsa-miR-1249-3p, hsa-miR-887-3p, hsa-miR-6786-5p, hsa-miR-1238-5p, hsa-miR-6749-5p, hsa-miR-6729-5p, hsa-miR-6825-5p, hsa-miR-663b, hsa-miR-6858-5p, hsa-miR-4690-5p, hsa-miR-6765-5p, hsa-miR-4710, hsa-miR-6775-5p, hsa-miR-371a-5p, hsa-miR-6816-5p, hsa-miR-296-3p, hsa-miR-7977, hsa-miR-8069, hsa-miR-6515-3p, hsa-miR-4687-5p, hsa-miR-1343-5p, hsa-miR-7110-5p, hsa-miR-4525, hsa-miR-3158-5p, hsa-miR-6787-5p, hsa-miR-614, hsa-miR-4689, hsa-miR-1185-2-3p, hsa-miR-1268b, hsa-miR-1228-3p, hsa-miR-1185-1-3p, hsa-miR-940, hsa-miR-939-5p, hsa-miR-6757-5p, hsa-miR-1275, hsa-miR-5001-5p, hsa-miR-6826-5p, hsa-miR-6765-3p, hsa-miR-3679-3p, hsa-miR-4718, hsa-miR-4286, hsa-miR-8059, hsa-miR-4447, hsa-miR-4448, hsa-miR-658, hsa-miR-6766-3p, hsa-miR-197-5p, hsa-miR-6887-5p, hsa-miR-6742-5p, hsa-miR-6729-3p, hsa-miR-5090, hsa-miR-7975, hsa-miR-4505, hsa-miR-6889-5p, hsa-miR-4708-3p, hsa-miR-6131, hsa-miR-1225-3p, hsa-miR-6132, hsa-miR-4734, hsa-miR-3194-3p, hsa-miR-638, hsa-miR-2467-3p, hsa-miR-4728-5p, hsa-miR-5572, hsa-miR-6789-5p, hsa-miR-8063, hsa-miR-4429, hsa-miR-6840-3p, hsa-miR-4476, hsa-miR-675-5p, hsa-miR-711, hsa-miR-6875-5p, hsa-miR-3160-5p, hsa-miR-1908-5p, hsa-miR-6726-5p, hsa-miR-1913, hsa-miR-8071, hsa-miR-3648, hsa-miR-4732-5p, hsa-miR-4787-5p, hsa-miR-3917, hsa-miR-619-5p, hsa-miR-1231, hsa-miR-342-5p, hsa-miR-4433a-5p, hsa-miR-6766-5p, hsa-miR-4707-5p, hsa-miR-7114-5p, hsa-miR-6872-3p, hsa-miR-6780b-5p, hsa-miR-7845-5p, hsa-miR-6798-3p, hsa-miR-665, hsa-miR-6848-5p, hsa-miR-5008-5p, hsa-miR-4294, hsa-miR-6511a-5p, hsa-miR-4435, hsa-miR-4747-3p, hsa-miR-6880-3p, hsa-miR-6869-5p, hsa-miR-7150, hsa-miR-1260a, hsa-miR-6877-5p, hsa-miR-6721-5p, hsa-miR-4656, hsa-miR-1229-5p, hsa-miR-4433a-3p, hsa-miR-4274, hsa-miR-4419b, hsa-miR-4674, hsa-miR-6893-5p, hsa-miR-6763-3p, hsa-miR-6762-5p, hsa-miR-6738-5p, hsa-miR-4513, hsa-miR-6746-5p, hsa-miR-6880-5p, hsa-miR-4736, hsa-miR-718, hsa-miR-6717-5p, hsa-miR-7847-3p, hsa-miR-760, hsa-miR-1199-5p, hsa-miR-6813-5p, hsa-miR-6769a-5p, hsa-miR-1193, hsa-miR-7108-3p, hsa-miR-6741-5p, hsa-miR-4298, hsa-miR-6796-3p, hsa-miR-4750-5p, hsa-miR-6785-5p, hsa-miR-1292-3p, hsa-miR-4749-3p, hsa-miR-6800-3p, hsa-miR-4722-5p, hsa-miR-4746-3p, hsa-miR-4450, hsa-miR-6795-5p, hsa-miR-365a-5p, hsa-miR-498, hsa-miR-6797-5p, hsa-miR-1470, hsa-miR-6851-5p, hsa-miR-1247-3p, hsa-miR-5196-5p, hsa-miR-208a-5p, hsa-miR-6842-5p, hsa-miR-150-3p, hsa-miR-4534, hsa-miR-3135b, hsa-miR-3131, hsa-miR-4792, hsa-miR-6510-5p, hsa-miR-504-3p, hsa-miR-3619-3p, hsa-miR-671-5p, hsa-miR-4667-5p, hsa-miR-4430, hsa-miR-320a, hsa-miR-663a, hsa-miR-328-5p, hsa-miR-642b-3p, hsa-miR-128-2-5p, hsa-miR-125a-3p, hsa-miR-191-5p, hsa-miR-92b-5p, hsa-miR-296-5p, hsa-miR-1246, hsa-miR-92a-2-5p, hsa-miR-128-1-5p, hsa-miR-1290, hsa-miR-211-3p, hsa-miR-744-5p, hsa-miR-135a-3p, hsa-miR-451a, hsa-miR-625-3p, hsa-miR-92a-3p, hsa-miR-422a and hsa-miR-642a-3p genes, and the relevant polynucleotides consisting of nucleotide sequences of SEQ ID NOs: 1 to 203 and 248 to 268 were found.

Of them, the genes newly found as the marker for examining the presence or absence of an ovarian tumor are polynucleotides consisting of the nucleotide sequences represented by SEQ ID NOs: 1 to 203.

A discriminant for determining the presence or absence of an ovarian tumor was further prepared by the Fisher's discriminant analysis with the expression levels of these genes in the training cohort as indicators. Specifically, the gene expression level of a polynucleotide consisting of the nucleotide sequence represented by any of SEQ ID NOs: 1 to 203 and 248 to 268 found above was input to Formula 2 to prepare a discriminant. Calculated accuracy, sensitivity, and specificity in the training cohort are shown in Table 3. In this respect, discriminant coefficients and constant terms are shown in Table 4.

Next, accuracy, sensitivity, and specificity in the validation cohort were calculated using the discriminant prepared above and the discriminant performance of the selected polynucleotides was validated using independent samples (Table 3). For example, the rate of detecting an ovarian tumor was calculated using the threshold value (7.75) of the gene expression level of the nucleotide sequence represented by SEQ ID NO: 1, for use in discriminating both groups set in the training cohort. As a result, 127 true positives, 117 true negatives, 3 false positives and 4 false negatives were obtained in the validation cohort. From these values, 97.2% accuracy, 96.9% sensitivity, and 97.5% specificity were obtained as the detection performance. In this way, the detection performance values of all polynucleotides represented by SEQ ID NOs: 1 to 203 and 248 to 268 were calculated and described in Table 3.

For example, 143 polynucleotides consisting of the nucleotide sequences represented by SEQ ID NOs: 1 to 78, 80 to 90, 92 to 94, 97, 99, 100, 104, 107, 109 to 111, 113, 115, 119, 121 to 125, 128, 129, 135 to 138, 142 to 146, 148 to 150, 152, 153, 156, 158, 159, 248 to 262 and 265 exhibited sensitivities of 97.2%, 94.4%, 98.0%, 94.4%, 94.8%, 97.6%, 94.4%, 93.6%, 92.8%, 95.6%, 92.8%, 93.2%, 90.8%, 94.4%, 90.0%, 97.6%, 91.2%, 92.0%, 88.0%, 88.8%, 90.8%, 89.2%, 90.8%, 86.9%, 86.9%, 89.2%, 88.4%, 89.2%, 88.0%, 88.4%, 90.0%, 86.1%, 89.2%, 87.6%, 90.8%, 86.1%, 85.3%, 91.2%, 89.6%, 86.5%, 89.2%, 84.9%, 86.5%, 88.4%, 88.8%, 86.9%, 90.4%, 85.7%, 85.3%, 84.5%, 83.7%, 83.3%, 88.4%, 86.5%, 80.5%, 84.9%, 87.3%, 83.7%, 87.6%, 79.7%, 85.3%, 84.1%, 90.8%, 82.9%, 84.9%, 79.7%, 89.2%, 83.3%, 78.5%, 83.7%, 82.1%, 81.3%, 88.0%, 81.3%, 79.7%, 84.5%, 82.9%, 83.7%, 80.1%, 77.7%, 84.9%, 79.7%, 81.3%, 77.7%, 83.3%, 78.5%, 86.5%, 78.9%, 79.7%, 82.9%, 86.5%, 87.6%, 80.1%, 80.5%, 78.5%, 79.3%, 78.9%, 80.5%, 78.1%, 80.5%, 86.1%, 78.9%, 82.5%, 80.9%, 82.1%, 78.5%, 80.9%, 78.1%, 82.9%, 80.1%, 79.7%, 78.9%, 80.5%, 78.5%, 80.1%, 81.3%, 77.7%, 78.9%, 80.1%, 79.3%, 79.3%, 77.7%, 80.1%, 78.9%, 80.1%, 77.7%, 77.7% 97.6%, 93.2%, 94.8%, 93.2%, 88.4%, 90.0%, 88.8%, 90.4%, 92.4%, 83.7%, 88.0%, 93.2%, 85.7%, 84.9%, 79.3%, and 79.3%, respectively in the validation cohort (Table 3). Herein, a general sensitivity of the existing marker CA-125 is reported to be 77.4% (Non Patent Literature 4). Accordingly, it was demonstrated that the polynucleotides consisting of these sequences singly discriminate an ovarian tumor with sensitivity beyond CA-125.

Also, a discriminant was constructed using each of all polynucleotides represented by SEQ ID NOs: 1 to 203 and 248 to 268 in combination with another polynucleotide appropriately selected; in other words, discriminants each were constructed using two polynucleotides. The discrimination accuracy of an ovarian tumor in the validation cohort by the discriminants thus constructed increased, compared with the discriminants using individual genes alone. Specifically, discriminants prepared using combinations of SEQ ID NOs: 1 and 3, 2 and 3, 1 and 3, 3 and 4, 3 and 5, 3 and 6, 3 and 7, 6 and 8, 3 and 9, 248 and 10, 11 and 18, 3 and 12, 3 and 13, 14 and 16, 6 and 15, 248 and 16, 6 and 17, 248 and 18, 3 and 19, 3 and 20, 3 and 21, 3 and 22, 3 and 23, 3 and 24, 1 and 25, 3 and 26, 3 and 27, 1 and 28, 3 and 29, 16 and 30, 3 and 31, 3 and 32, 3 and 33, 6 and 34, 3 and 35, 3 and 36, 3 and 37, 11 and 38, 3 and 39, 3 and 40, 3 and 41, 3 and 42, 3 and 43, 3 and 44, 3 and 45, 3 and 46, 248 and 47, 6 and 48, 249 and 49, 3 and 50, 3 and 51, 3 and 52, 16 and 53, 3 and 54, 7 and 55, 248 and 56, 3 and 57, 249 and 58, 3 and 59, 1 and 60, 249 and 61, 3 and 62, 3 and 63, 248 and 64, 3 and 65, 3 and 66, 3 and 67, 16 and 68, 3 and 69, 3 and 70, 248 and 71, 3 and 72, 3 and 73, 3 and 74, 1 and 75, 3 and 76, 3 and 77, 3 and 78, 1 and 79, 18 and 80, 3 and 81, 3 and 82, 3 and 83, 3 and 84, 10 and 85, 16 and 86, 16 and 87, 3 and 88, 3 and 89, 3 and 90, 248 and 91, 249 and 92, 3 and 93, 3 and 94, 3 and 95, 1 and 96, 3 and 97, 16 and 98, 6 and 99, 10 and 100, 1 and 101, 6 and 102, 3 and 103, 249 and 104, 16 and 105, 3 and 106, 3 and 107, 7 and 108, 3 and 109, 10 and 110, 248 and 111, 3 and 112, 248 and 113, 249 and 114, 248 and 115, 3 and 116, 249 and 117, 3 and 118, 3 and 119, 3 and 120, 3 and 121, 3 and 122, 3 and 123, 3 and 124, 3 and 125, 248 and 126, 10 and 127, 248 and 128, 16 and 129, 3 and 130, 3 and 131, 3 and 132, 1 and 133, 3 and 134, 3 and 135, 10 and 136, 3 and 137, 3 and 138, 249 and 139, 10 and 140, 3 and 141, 3 and 142, 3 and 143, 19 and 144, 3 and 145, 3 and 146, 3 and 147, 248 and 148, 3 and 149, 3 and 150, 3 and 151, 3 and 152, 3 and 153, 3 and 154, 3 and 155, 10 and 156, 3 and 157, 248 and 158, 10 and 159, 10 and 160, 6 and 161, 16 and 162, 3 and 163, 248 and 164, 248 and 165, 3 and 166, 3 and 167, 248 and 168, 3 and 169, 3 and 170, 3 and 171, 3 and 172, 3 and 173, 3 and 174, 3 and 175, 3 and 176, 3 and 177, 6 and 178, 3 and 179, 3 and 180, 3 and 181, 3 and 182, 3 and 183, 3 and 184, 3 and 185, 18 and 186, 3 and 187, 1 and 188, 10 and 189, 3 and 190, 3 and 191, 6 and 192, 3 and 193, 3 and 194, 3 and 195, 3 and 196, 3 and 197, 10 and 198, 3 and 199, 3 and 200, 3 and 201, 250 and 202, 248 and 203, 248 and 10, 1 and 249, 3 and 250, 251 and 18, 6 and 252, 248 and 253, 6 and 254, 3 and 255, 3 and 256, 3 and 257, 3 and 258, 3 and 259, 16 and 260, 10 and 261, 3 and 262, 3 and 263, 3 and 264, 3 and 265, 3 and 266, 248 and 267, and 3 and 268 had discrimination accuracies, in the validation cohort, of 100%, 98.8%, 100%, 99.6%, 100%, 99.6%, 99.6%, 99.2%, 99.2%, 100%, 100%, 99.2%, 99.6%, 100%, 99.2%, 100%, 99.2%, 100%, 99.2%, 99.2%, 98.8%, 99.2%, 99.6%, 99.2%, 99.2%, 98.4%, 99.6%, 99.2%, 99.6%, 99.2%, 99.6%, 99.2%, 98.8%, 99.2%, 98.8%, 99.2%, 99.6%, 99.2%, 99.2%, 99.2%, 98.8%, 99.2%, 99.2%, 98.8%, 99.2%, 98.8%, 99.2%, 98.8%, 99.2%, 98.8%, 98.8%, 98.8%, 99.6%, 99.6%, 97.2%, 99.6%, 99.2%, 99.6%, 98.8%, 98.8%, 98.8%, 99.2%, 99.2%, 98%, 99.2%, 99.2%, 98.8%, 99.6%, 98.4%, 99.2%, 98.8%, 99.6%, 98.8%, 99.2%, 98.8%, 98.4%, 99.2%, 99.6%, 99.6%, 99.6%, 98.4%, 98.8%, 99.2%, 98.4%, 98.8%, 99.6%, 99.2%, 98.8%, 98.8%, 98.8%, 98%, 99.2%, 98.8%, 99.2%, 98.4%, 98.4%, 99.2%, 99.2%, 98.8%, 99.2%, 99.2%, 98.8%, 98.4%, 99.6%, 100%, 99.2%, 98.8%, 98.4%, 98.8%, 98.8%, 98.4%, 99.2%, 98.8%, 99.6%, 99.6%, 98.8%, 99.6%, 98.4%, 99.2%, 98.8%, 99.2%, 98.4%, 98.8%, 98.8%, 98.4%, 98.8%, 99.2%, 98%, 98.8%, 98.4%, 98.8%, 98.4%, 99.6%, 98.8%, 98.4%, 98.8%, 99.2%, 98.4%, 98.8%, 99.2%, 98.8%, 99.2%, 98.4%, 99.2%, 99.2%, 98.4%, 98.4%, 980%, 98.8%, 99.2%, 98.8%, 98.8%, 98.4%, 99.2%, 98.8%, 98.8%, 98.4%, 98.4%, 98.4%, 99.6%, 98.4%, 99.6%, 98.4%, 98.8%, 984%, 98.8%, 98.8%, 98%, 98.4%, 98.4%, 98.4%, 98.4%, 98.4%, 98.8%, 98.4%, 98.8%, 98.4%, 98.4%, 98.4%, 98.4%, 98.4%, 98.8%, 98.4%, 98.4%, 98.4%, 95.6%, 98.8%, 98%, 98.4%, 98.4%, 98.4%, 98%, 98.8%, 98.4%, 98.4%, 98.4%, 98.4%, 98.8%, 98.8%, 98.4%, 98.8%, 97.6%, 98.4%, 100%, 99.6%, 100%, 100%, 99.2%, 99.2%, 99.6%, 98.8%, 99.6%, 99.2%, 98.8%, 99.2%, 100%, 98.8%, 99.6%, 98.4%, 98.4%, 98.8%, 98.4%, 98.8%, and 98.8%, respectively (Table 5). These all exceed discriminant performance of the existing marker CA-125. Note that, in Table 5, in the column of "SEQ ID No", the combinations of a plurality of polynucleotides used are described by SEQ ID Nos. (the same applies to the tables later described).

From the above, it was demonstrated that all polynucleotides consisting of the nucleotide sequences represented by SEQ ID NOs: 1 to 203 and 248 to 268 are genes capable of discriminating an ovarian tumor patient and a healthy subject with high accuracy if these are used singly or in combinations of two or more.

TABLE 2

| SEQ ID NO. | Name of gene | P value after Bonferroni correction | Fold change of healthy subject to ovarian tumor patient |
|---|---|---|---|
| 1 | hsa-miR-4675 | 4.96E−307 | −2.00 |
| 2 | hsa-miR-4783-3p | 2.73E−296 | −3.02 |
| 3 | hsa-miR-1228-5p | 2.40E−291 | 0.83 |
| 4 | hsa-miR-4532 | 1.59E−270 | −2.71 |
| 5 | hsa-miR-6802-5p | 1.40E−264 | −1.13 |
| 6 | hsa-miR-6784-5p | 8.08E−257 | 1.35 |
| 7 | hsa-miR-3940-5p | 5.59E−227 | 0.98 |
| 8 | hsa-miR-1307-3p | 1.31E−224 | −2.79 |
| 9 | hsa-miR-8073 | 6.97E−223 | −2.32 |
| 10 | hsa-miR-3184-5p | 2.06E−214 | 2.53 |
| 11 | hsa-miR-1233-5p | 4.37E−211 | −2.33 |
| 12 | hsa-miR-6088 | 5.55E−203 | −1.27 |
| 13 | hsa-miR-5195-3p | 1.21E−200 | −1.61 |
| 14 | hsa-miR-320b | 1.36E−198 | −3.20 |
| 15 | hsa-miR-4649-5p | 2.36E−193 | −1.81 |
| 16 | hsa-miR-6800-5p | 1.67E−188 | 1.31 |
| 17 | hsa-miR-1343-3p | 1.81E−180 | −1.65 |
| 18 | hsa-miR-4730 | 2.00E−178 | 2.35 |
| 19 | hsa-miR-6885-5p | 8.17E−177 | −1.59 |
| 20 | hsa-miR-5100 | 2.57E−176 | −2.85 |
| 21 | hsa-miR-1203 | 1.01E−173 | 2.18 |
| 22 | hsa-miR-6756-5p | 1.89E−168 | −0.88 |
| 23 | hsa-miR-373-5p | 6.84E−164 | −1.60 |
| 24 | hsa-miR-1268a | 9.51E−161 | 0.69 |
| 25 | hsa-miR-1260b | 3.63E−160 | −1.66 |
| 26 | hsa-miR-4258 | 4.68E−160 | −1.77 |
| 27 | hsa-miR-4697-5p | 3.86E−158 | −0.99 |
| 28 | hsa-miR-1469 | 6.86E−158 | −1.19 |
| 29 | hsa-miR-4515 | 1.11E−153 | −3.34 |
| 30 | hsa-miR-6861-5p | 1.34E−150 | −1.05 |
| 31 | hsa-miR-6821-5p | 1.36E−150 | −0.54 |
| 32 | hsa-miR-575 | 2.21E−150 | 2.12 |
| 33 | hsa-miR-6805-5p | 7.36E−150 | 0.84 |
| 34 | hsa-miR-4758-5p | 7.32E−148 | −0.89 |
| 35 | hsa-miR-3663-3p | 1.12E−147 | −1.08 |
| 36 | hsa-miR-4530 | 1.32E−144 | 1.04 |
| 37 | hsa-miR-6798-5p | 1.72E−143 | 0.94 |
| 38 | hsa-miR-6781-5p | 2.15E−142 | 0.83 |
| 39 | hsa-miR-885-3p | 1.27E−139 | −2.10 |
| 40 | hsa-miR-1273g-3p | 5.04E−139 | −1.80 |
| 41 | hsa-miR-4787-3p | 1.23E−136 | −1.73 |
| 42 | hsa-miR-4454 | 1.31E−135 | −2.01 |
| 43 | hsa-miR-4706 | 1.55E−131 | −1.01 |
| 44 | hsa-miR-1249-3p | 1.50E−130 | −0.98 |
| 45 | hsa-miR-887-3p | 1.57E−129 | 1.29 |
| 46 | hsa-miR-6786-5p | 6.98E−129 | 0.54 |
| 47 | hsa-miR-1238-5p | 4.70E−128 | −1.93 |
| 48 | hsa-miR-6749-5p | 2.87E−127 | −0.72 |
| 49 | hsa-miR-6729-5p | 3.83E−124 | 0.82 |
| 50 | hsa-miR-6825-5p | 7.08E−124 | 1.72 |
| 51 | hsa-miR-663b | 1.78E−123 | −1.27 |
| 52 | hsa-miR-6858-5p | 1.20E−122 | −0.82 |
| 53 | hsa-miR-4690-5p | 2.08E−119 | −1.23 |
| 54 | hsa-miR-6765-5p | 1.17E−116 | 0.57 |
| 55 | hsa-miR-4710 | 2.39E−115 | −2.97 |
| 56 | hsa-miR-6775-5p | 5.02E−115 | −0.76 |
| 57 | hsa-miR-371a-5p | 1.87E−114 | −1.02 |
| 58 | hsa-miR-6816-5p | 4.12E−113 | 0.56 |
| 59 | hsa-miR-296-3p | 5.77E−113 | −1.79 |
| 60 | hsa-miR-7977 | 2.70E−111 | −1.57 |
| 61 | hsa-miR-8069 | 3.35E−109 | 0.74 |
| 62 | hsa-miR-6515-3p | 7.14E−108 | −0.90 |
| 63 | hsa-miR-4687-5p | 1.19E−107 | −1.21 |
| 64 | hsa-miR-1343-5p | 1.57E−107 | 0.51 |
| 65 | hsa-miR-7110-5p | 3.09E−106 | 1.30 |
| 66 | hsa-miR-4525 | 8.77E−106 | −2.49 |
| 67 | hsa-miR-3158-5p | 3.78E−105 | −1.90 |
| 68 | hsa-miR-6787-5p | 4.50E−105 | −0.86 |
| 69 | hsa-miR-614 | 4.58E−105 | −1.96 |
| 70 | hsa-miR-4689 | 1.93E−103 | −0.67 |
| 71 | hsa-miR-1185-2-3p | 4.33E−101 | −1.56 |
| 72 | hsa-miR-1268b | 2.66E−95 | 0.53 |
| 73 | hsa-miR-1228-3p | 4.24E−95 | −0.69 |
| 74 | hsa-miR-1185-1-3p | 9.39E−94 | −1.46 |

TABLE 2-continued

| SEQ ID NO. | Name of gene | P value after Bonferroni correction | Fold change of healthy subject to ovarian tumor patient |
|---|---|---|---|
| 75 | hsa-miR-940 | 5.02E−93 | −1.05 |
| 76 | hsa-miR-939-5p | 2.03E−92 | 1.32 |
| 77 | hsa-miR-6757-5p | 3.72E−92 | −1.47 |
| 78 | hsa-miR-1275 | 1.36E−91 | −0.86 |
| 79 | hsa-miR-5001-5p | 8.91E−91 | −0.77 |
| 80 | hsa-miR-6826-5p | 1.03E−90 | −1.30 |
| 81 | hsa-miR-6765-3p | 1.75E−90 | −1.40 |
| 82 | hsa-miR-3679-3p | 9.05E−90 | −0.90 |
| 83 | hsa-miR-4718 | 5.79E−89 | −3.06 |
| 84 | hsa-miR-4286 | 4.60E−88 | −1.51 |
| 85 | hsa-miR-8059 | 3.10E−87 | −1.52 |
| 86 | hsa-miR-4447 | 6.80E−86 | −1.13 |
| 87 | hsa-miR-4448 | 4.46E−83 | −2.39 |
| 88 | hsa-miR-658 | 4.20E−82 | −1.18 |
| 89 | hsa-miR-6766-3p | 3.46E−81 | −0.93 |
| 90 | hsa-miR-197-5p | 5.57E−81 | −1.18 |
| 91 | hsa-miR-6887-5p | 4.12E−80 | −1.24 |
| 92 | hsa-miR-6742-5p | 9.48E−80 | −1.33 |
| 93 | hsa-miR-6729-3p | 1.41E−79 | −0.94 |
| 94 | hsa-miR-5090 | 3.17E−79 | 1.03 |
| 95 | hsa-miR-7975 | 7.82E−79 | −1.52 |
| 96 | hsa-miR-4505 | 4.34E−77 | −0.74 |
| 97 | hsa-miR-6889-5p | 4.87E−76 | 0.88 |
| 98 | hsa-miR-4708-3p | 6.45E−75 | −2.41 |
| 99 | hsa-miR-6131 | 3.49E−72 | −3.15 |
| 100 | hsa-miR-1225-3p | 1.65E−71 | −0.75 |
| 101 | hsa-miR-6132 | 4.26E−71 | −0.83 |
| 102 | hsa-miR-4734 | 7.61E−71 | −0.87 |
| 103 | hsa-miR-3194-3p | 2.18E−70 | −2.78 |
| 104 | hsa-miR-638 | 4.09E−70 | 0.63 |
| 105 | hsa-miR-2467-3p | 5.90E−70 | −2.32 |
| 106 | hsa-miR-4728-5p | 1.30E−69 | −0.83 |
| 107 | hsa-miR-5572 | 1.81E−69 | 1.05 |
| 108 | hsa-miR-6789-5p | 5.37E−69 | −0.56 |
| 109 | hsa-miR-8063 | 9.86E−69 | −1.28 |
| 110 | hsa-miR-4429 | 1.64E−68 | −1.41 |
| 111 | hsa-miR-6840-3p | 4.67E−68 | −0.77 |
| 112 | hsa-miR-4476 | 1.61E−67 | 1.44 |
| 113 | hsa-miR-675-5p | 9.52E−67 | −0.84 |
| 114 | hsa-miR-711 | 2.88E−64 | 0.66 |
| 115 | hsa-miR-6875-5p | 6.25E−64 | 0.99 |
| 116 | hsa-miR-3160-5p | 3.59E−62 | −2.33 |
| 117 | hsa-miR-1908-5p | 4.73E−62 | 0.56 |
| 118 | hsa-miR-6726-5p | 1.03E−61 | −0.77 |
| 119 | hsa-miR-1913 | 3.07E−60 | −0.66 |
| 120 | hsa-miR-8071 | 5.14E−60 | 1.20 |
| 121 | hsa-miR-3648 | 1.35E−59 | −0.87 |
| 122 | hsa-miR-4732-5p | 2.69E−59 | −1.98 |
| 123 | hsa-miR-4787-5p | 3.13E−59 | 0.53 |
| 124 | hsa-miR-3917 | 4.64E−59 | −0.94 |
| 125 | hsa-miR-619-5p | 7.20E−58 | −1.58 |
| 126 | hsa-miR-1231 | 2.21E−57 | 0.98 |
| 127 | hsa-miR-342-5p | 5.05E−57 | −1.66 |
| 128 | hsa-miR-4433a-5p | 5.32E−56 | −0.84 |
| 129 | hsa-miR-6766-5p | 1.42E−53 | −1.03 |
| 130 | hsa-miR-4707-5p | 4.15E−53 | −0.52 |
| 131 | hsa-miR-7114-5p | 1.40E−52 | 0.85 |
| 132 | hsa-miR-6872-3p | 2.48E−52 | −1.01 |
| 133 | hsa-miR-6780b-5p | 4.10E−52 | −0.62 |
| 134 | hsa-miR-7845-5p | 2.32E−51 | 0.91 |
| 135 | hsa-miR-6798-3p | 6.04E−51 | −0.96 |
| 136 | hsa-miR-665 | 9.73E−51 | −0.80 |
| 137 | hsa-miR-6848-5p | 1.70E−50 | 0.73 |
| 138 | hsa-miR-5008-5p | 2.00E−50 | −1.34 |
| 139 | hsa-miR-4294 | 1.56E−49 | 0.58 |
| 140 | hsa-miR-6511a-5p | 3.13E−49 | −0.91 |
| 141 | hsa-miR-4435 | 4.39E−49 | 1.64 |
| 142 | hsa-miR-4747-3p | 7.86E−49 | −1.02 |
| 143 | hsa-miR-6880-3p | 3.19E−48 | −0.76 |
| 144 | hsa-miR-6869-5p | 6.95E−48 | 0.66 |
| 145 | hsa-miR-7150 | 7.08E−48 | −0.57 |
| 146 | hsa-miR-1260a | 1.22E−47 | −0.90 |
| 147 | hsa-miR-6877-5p | 7.53E−47 | −0.67 |
| 148 | hsa-miR-6721-5p | 9.70E−47 | 0.79 |

TABLE 2-continued

| SEQ ID NO. | Name of gene | P value after Bonferroni correction | Fold change of healthy subject to ovarian tumor patient |
|---|---|---|---|
| 149 | hsa-miR-4656 | 1.13E−46 | −0.55 |
| 150 | hsa-miR-1229-5p | 1.72E−46 | −0.57 |
| 151 | hsa-miR-4433a-3p | 2.51E−46 | −0.52 |
| 152 | hsa-miR-4274 | 6.43E−46 | −0.71 |
| 153 | hsa-miR-4419b | 3.59E−44 | −1.11 |
| 154 | hsa-miR-4674 | 1.71E−40 | 0.71 |
| 155 | hsa-miR-6893-5p | 1.48E−38 | 0.69 |
| 156 | hsa-miR-6763-3p | 2.51E−38 | −0.67 |
| 157 | hsa-miR-6762-5p | 1.13E−37 | −0.64 |
| 158 | hsa-miR-6738-5p | 2.42E−37 | −0.73 |
| 159 | hsa-miR-4513 | 2.19E−35 | −0.66 |
| 160 | hsa-miR-6746-5p | 2.84E−35 | −0.76 |
| 161 | hsa-miR-6880-5p | 4.90E−35 | 0.95 |
| 162 | hsa-miR-4736 | 1.07E−34 | −0.89 |
| 163 | hsa-miR-718 | 3.73E−34 | −0.57 |
| 164 | hsa-miR-6717-5p | 2.68E−33 | −1.29 |
| 165 | hsa-miR-7847-3p | 8.51E−33 | −0.78 |
| 166 | hsa-miR-760 | 4.19E−31 | 0.66 |
| 167 | hsa-miR-1199-5p | 5.43E−31 | −0.73 |
| 168 | hsa-miR-6813-5p | 1.37E−30 | 0.76 |
| 169 | hsa-miR-6769a-5p | 2.48E−29 | −0.75 |
| 170 | hsa-miR-1193 | 2.51E−29 | −0.62 |
| 171 | hsa-miR-7108-3p | 6.05E−28 | −0.59 |
| 172 | hsa-miR-6741-5p | 1.26E−27 | −0.64 |
| 173 | hsa-miR-4298 | 1.63E−27 | −0.65 |
| 174 | hsa-miR-6796-3p | 4.73E−27 | −0.59 |
| 175 | hsa-miR-4750-5p | 6.28E−27 | −0.63 |
| 176 | hsa-miR-6785-5p | 4.16E−26 | 0.64 |
| 177 | hsa-miR-1292-3p | 7.45E−26 | −0.60 |
| 178 | hsa-miR-4749-3p | 1.01E−25 | −0.51 |
| 179 | hsa-miR-6800-3p | 9.04E−25 | −0.51 |
| 180 | hsa-miR-4722-5p | 9.15E−25 | −0.55 |
| 181 | hsa-miR-4746-3p | 2.32E−24 | 0.52 |
| 182 | hsa-miR-4450 | 4.34E−24 | 0.89 |
| 183 | hsa-miR-6795-5p | 4.71E−24 | −0.65 |
| 184 | hsa-miR-365a-5p | 1.05E−23 | −0.52 |
| 185 | hsa-miR-498 | 5.72E−22 | −0.51 |
| 186 | hsa-miR-6797-5p | 1.89E−21 | −0.69 |
| 187 | hsa-miR-1470 | 2.34E−21 | −0.56 |

TABLE 2-continued

| SEQ ID NO. | Name of gene | P value after Bonferroni correction | Fold change of healthy subject to ovarian tumor patient |
|---|---|---|---|
| 188 | hsa-miR-6851-5p | 7.59E−21 | 0.55 |
| 189 | hsa-miR-1247-3p | 1.84E−20 | −0.54 |
| 190 | hsa-miR-5196-5p | 1.34E−18 | −0.55 |
| 191 | hsa-miR-208a-5p | 2.20E−18 | −0.79 |
| 192 | hsa-miR-6842-5p | 2.95E−18 | 0.54 |
| 193 | hsa-miR-150-3p | 6.45E−18 | 0.60 |
| 194 | hsa-miR-4534 | 7.92E−18 | −0.66 |
| 195 | hsa-miR-3135b | 3.33E−17 | −0.51 |
| 196 | hsa-miR-3131 | 1.08E−15 | −0.58 |
| 197 | hsa-miR-4792 | 1.21E−15 | 0.60 |
| 198 | hsa-miR-6510-5p | 3.26E−15 | −0.53 |
| 199 | hsa-miR-504-3p | 4.36E−15 | −0.56 |
| 200 | hsa-miR-3619-3p | 4.56E−14 | −0.53 |
| 201 | hsa-miR-671-5p | 8.88E−13 | −0.50 |
| 202 | hsa-miR-4667-5p | 8.26E−12 | 0.50 |
| 203 | hsa-miR-4430 | 1.84E−09 | −0.52 |
| 248 | hsa-miR-320a | 6.45E−226 | −2.63 |
| 249 | hsa-miR-663a | 8.51E−226 | −1.68 |
| 250 | hsa-miR-328-5p | 7.43E−192 | −0.58 |
| 251 | hsa-miR-642b-3p | 2.09E−186 | −1.92 |
| 252 | hsa-miR-128-2-5p | 1.24E−177 | −1.68 |
| 253 | hsa-miR-125a-3p | 7.31E−175 | 2.85 |
| 254 | hsa-miR-191-5p | 1.36E−174 | -4.42 |
| 255 | hsa-miR-92b-5p | 2.93E−156 | −1.19 |
| 256 | hsa-miR-296-5p | 1.66E−155 | −1.02 |
| 257 | hsa-miR-1246 | 5.89E−152 | −5.34 |
| 258 | hsa-miR-92a-2-5p | 1.32E−143 | 1.64 |
| 259 | hsa-miR-128-1-5p | 8.05E−142 | 1.57 |
| 260 | hsa-miR-1290 | 6.57E−134 | −4.66 |
| 261 | hsa-miR-211-3p | 4.84E−106 | −1.24 |
| 262 | hsa-miR-744-5p | 2.06E−94 | −1.08 |
| 263 | hsa-miR-135a-3p | 4.88E−79 | 1.43 |
| 264 | hsa-miR-451a | 1.22E−75 | −3.37 |
| 265 | hsa-miR-625-3p | 1.43E−61 | −1.10 |
| 266 | hsa-miR-92a-3p | 5.16E−53 | −1.61 |
| 267 | hsa-miR-422a | 2.70E−40 | −1.08 |
| 268 | hsa-miR-642a-3p | 4.24E−18 | −0.58 |

TABLE 3

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 1 | 96.9 | 98.3 | 95.4 | 97.2 | 96.9 | 97.5 |
| 2 | 96.1 | 92.4 | 100.0 | 94.4 | 89.3 | 100.0 |
| 3 | 97.6 | 96.7 | 98.6 | 98.0 | 96.9 | 99.2 |
| 4 | 95.2 | 91.4 | 99.3 | 94.4 | 89.3 | 100.0 |
| 5 | 96.6 | 97.0 | 96.1 | 94.8 | 92.4 | 97.5 |
| 6 | 96.2 | 98.0 | 94.3 | 97.6 | 98.5 | 96.7 |
| 7 | 93.3 | 87.8 | 99.3 | 94.4 | 90.8 | 98.3 |
| 8 | 95.9 | 92.1 | 100.0 | 93.6 | 87.8 | 100.0 |
| 9 | 94.5 | 95.4 | 93.6 | 92.8 | 91.6 | 94.2 |
| 10 | 96.7 | 93.7 | 100.0 | 95.6 | 91.6 | 100.0 |
| 11 | 93.8 | 88.8 | 99.3 | 92.8 | 87.0 | 99.2 |
| 12 | 90.9 | 89.1 | 92.9 | 93.2 | 91.6 | 95.0 |
| 13 | 93.5 | 93.4 | 93.6 | 90.8 | 87.8 | 94.2 |
| 14 | 93.1 | 92.1 | 94.3 | 94.4 | 96.9 | 91.7 |
| 15 | 91.6 | 91.4 | 91.8 | 90.0 | 87.8 | 92.5 |
| 16 | 97.1 | 97.4 | 96.8 | 97.6 | 96.2 | 99.2 |
| 17 | 91.1 | 89.4 | 92.9 | 91.2 | 89.3 | 93.3 |
| 18 | 91.4 | 88.8 | 94.3 | 92.0 | 93.9 | 90.0 |
| 19 | 90.6 | 87.8 | 93.6 | 88.0 | 82.4 | 94.2 |
| 20 | 90.9 | 92.7 | 88.9 | 88.8 | 92.4 | 85.0 |
| 21 | 90.7 | 83.8 | 98.2 | 90.8 | 84.0 | 98.3 |
| 22 | 89.2 | 91.1 | 87.1 | 89.2 | 86.3 | 92.5 |
| 23 | 91.4 | 88.1 | 95.0 | 90.8 | 88.5 | 93.3 |
| 24 | 88.3 | 88.8 | 87.9 | 86.9 | 80.9 | 93.3 |
| 25 | 88.5 | 87.5 | 89.6 | 86.9 | 87.0 | 86.7 |

TABLE 3-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 26 | 89.5 | 87.5 | 91.8 | 89.2 | 84.0 | 95.0 |
| 27 | 91.3 | 89.4 | 93.2 | 88.4 | 82.4 | 95.0 |
| 28 | 89.9 | 83.5 | 96.8 | 89.2 | 80.2 | 99.2 |
| 29 | 90.7 | 95.0 | 86.1 | 88.0 | 92.4 | 83.3 |
| 30 | 90.1 | 88.8 | 91.4 | 88.4 | 82.4 | 95.0 |
| 31 | 88.2 | 90.1 | 86.1 | 90.0 | 93.9 | 85.8 |
| 32 | 90.9 | 85.5 | 96.8 | 86.1 | 77.1 | 95.8 |
| 33 | 90.2 | 85.5 | 95.4 | 89.2 | 84.0 | 95.0 |
| 34 | 88.0 | 82.8 | 93.6 | 87.6 | 78.6 | 97.5 |
| 35 | 90.7 | 93.7 | 87.5 | 90.8 | 90.1 | 91.7 |
| 36 | 88.9 | 91.1 | 86.4 | 86.1 | 85.5 | 86.7 |
| 37 | 85.4 | 84.8 | 86.1 | 85.3 | 78.6 | 92.5 |
| 38 | 90.6 | 83.5 | 98.2 | 91.2 | 83.2 | 100.0 |
| 39 | 89.9 | 86.1 | 93.9 | 89.6 | 84.7 | 95.0 |
| 40 | 88.3 | 86.1 | 90.7 | 86.5 | 80.9 | 92.5 |
| 41 | 89.0 | 87.1 | 91.1 | 89.2 | 89.3 | 89.2 |
| 42 | 85.2 | 85.1 | 85.4 | 84.9 | 87.8 | 81.7 |
| 43 | 86.8 | 81.8 | 92.1 | 86.5 | 80.2 | 93.3 |
| 44 | 87.7 | 90.4 | 84.6 | 88.4 | 84.0 | 93.3 |
| 45 | 88.3 | 87.8 | 88.9 | 88.8 | 83.2 | 95.0 |
| 46 | 86.4 | 83.8 | 89.3 | 86.9 | 84.0 | 90.0 |
| 47 | 89.7 | 83.8 | 96.1 | 90.4 | 86.3 | 95.0 |
| 48 | 86.6 | 82.2 | 91.4 | 85.7 | 79.4 | 92.5 |
| 49 | 88.3 | 83.5 | 93.6 | 85.3 | 77.9 | 93.3 |
| 50 | 89.4 | 82.5 | 96.8 | 84.5 | 74.8 | 95.0 |
| 51 | 84.6 | 82.2 | 87.1 | 83.7 | 81.7 | 85.8 |
| 52 | 84.9 | 86.5 | 83.2 | 83.3 | 82.4 | 84.2 |
| 53 | 88.9 | 90.4 | 87.1 | 88.4 | 92.4 | 84.2 |
| 54 | 89.0 | 82.5 | 96.1 | 86.5 | 77.9 | 95.8 |
| 55 | 84.9 | 83.8 | 86.1 | 80.5 | 80.2 | 80.8 |
| 56 | 83.7 | 88.4 | 78.6 | 84.9 | 87.8 | 81.7 |
| 57 | 85.6 | 86.5 | 84.6 | 87.3 | 86.3 | 88.3 |
| 58 | 84.2 | 82.5 | 86.1 | 83.7 | 80.2 | 87.5 |
| 59 | 87.0 | 84.8 | 89.3 | 87.6 | 83.2 | 92.5 |
| 60 | 82.8 | 84.8 | 80.7 | 79.7 | 84.0 | 75.0 |
| 61 | 88.0 | 81.8 | 94.6 | 85.3 | 77.9 | 93.3 |
| 62 | 83.9 | 86.8 | 80.7 | 84.1 | 84.7 | 83.3 |
| 63 | 90.6 | 88.1 | 93.2 | 90.8 | 88.5 | 93.3 |
| 64 | 82.2 | 84.5 | 79.6 | 82.9 | 83.2 | 82.5 |
| 65 | 86.1 | 81.5 | 91.1 | 84.9 | 75.6 | 95.0 |
| 66 | 80.6 | 79.9 | 81.4 | 79.7 | 78.6 | 80.8 |
| 67 | 85.1 | 81.8 | 88.6 | 89.2 | 87.0 | 91.7 |
| 68 | 88.3 | 80.2 | 97.1 | 83.3 | 72.5 | 95.0 |
| 69 | 83.5 | 85.1 | 81.8 | 78.5 | 76.3 | 80.8 |
| 70 | 83.0 | 85.1 | 80.7 | 83.7 | 80.9 | 86.7 |
| 71 | 80.8 | 79.5 | 82.1 | 82.1 | 82.4 | 81.7 |
| 72 | 81.5 | 77.9 | 85.4 | 81.3 | 71.8 | 91.7 |
| 73 | 88.9 | 89.4 | 88.2 | 88.0 | 87.8 | 88.3 |
| 74 | 80.4 | 80.5 | 80.4 | 81.3 | 82.4 | 80.0 |
| 75 | 83.0 | 84.5 | 81.4 | 79.7 | 83.2 | 75.8 |
| 76 | 82.2 | 74.9 | 90.0 | 84.5 | 73.3 | 96.7 |
| 77 | 82.2 | 82.8 | 81.4 | 82.9 | 78.6 | 87.5 |
| 78 | 82.3 | 78.2 | 86.8 | 83.7 | 76.3 | 91.7 |
| 79 | 82.0 | 82.8 | 81.1 | 76.5 | 78.6 | 74.2 |
| 80 | 79.8 | 84.5 | 74.6 | 80.1 | 79.4 | 80.8 |
| 81 | 80.6 | 85.1 | 75.7 | 77.7 | 80.9 | 74.2 |
| 82 | 83.2 | 86.5 | 79.6 | 84.9 | 83.2 | 86.7 |
| 83 | 83.4 | 85.8 | 80.7 | 79.7 | 80.2 | 79.2 |
| 84 | 82.5 | 81.2 | 83.9 | 81.3 | 80.9 | 81.7 |
| 85 | 82.0 | 80.2 | 83.9 | 77.7 | 74.0 | 81.7 |
| 86 | 82.5 | 84.5 | 80.4 | 83.3 | 84.0 | 82.5 |
| 87 | 79.8 | 79.2 | 80.4 | 78.5 | 75.6 | 81.7 |
| 88 | 83.9 | 86.8 | 80.7 | 86.5 | 87.8 | 85.0 |
| 89 | 80.4 | 83.5 | 77.1 | 78.9 | 81.7 | 75.8 |
| 90 | 81.0 | 73.6 | 88.9 | 79.7 | 73.3 | 86.7 |
| 91 | 77.5 | 81.2 | 73.6 | 77.3 | 75.6 | 79.2 |
| 92 | 85.2 | 79.5 | 91.4 | 82.9 | 80.2 | 85.8 |
| 93 | 85.1 | 85.5 | 84.6 | 86.5 | 81.7 | 91.7 |
| 94 | 85.2 | 75.9 | 95.4 | 87.6 | 84.0 | 91.7 |
| 95 | 78.4 | 78.5 | 78.2 | 76.1 | 79.4 | 72.5 |
| 96 | 77.7 | 75.9 | 79.6 | 76.5 | 76.3 | 76.7 |
| 97 | 82.0 | 76.9 | 87.5 | 80.1 | 71.0 | 90.0 |
| 98 | 80.4 | 80.9 | 80.0 | 77.3 | 74.8 | 80.0 |
| 99 | 78.0 | 73.9 | 82.5 | 80.5 | 77.1 | 84.2 |
| 100 | 81.8 | 84.2 | 79.3 | 78.5 | 80.9 | 75.8 |

TABLE 3-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 101 | 76.8 | 77.9 | 75.7 | 75.3 | 76.3 | 74.2 |
| 102 | 83.5 | 73.3 | 94.6 | 77.3 | 58.8 | 97.5 |
| 103 | 78.6 | 82.8 | 73.9 | 76.1 | 79.4 | 72.5 |
| 104 | 82.0 | 76.9 | 87.5 | 79.3 | 72.5 | 86.7 |
| 105 | 77.2 | 77.9 | 76.4 | 75.7 | 76.3 | 75.0 |
| 106 | 75.6 | 75.6 | 75.7 | 76.9 | 74.0 | 80.0 |
| 107 | 80.1 | 71.3 | 89.6 | 78.9 | 67.2 | 91.7 |
| 108 | 77.4 | 74.3 | 80.7 | 76.5 | 73.3 | 80.0 |
| 109 | 79.9 | 78.2 | 81.8 | 80.5 | 74.0 | 87.5 |
| 110 | 78.7 | 78.2 | 79.3 | 78.1 | 78.6 | 77.5 |
| 111 | 75.1 | 76.2 | 73.9 | 80.5 | 78.6 | 82.5 |
| 112 | 77.0 | 73.9 | 80.4 | 74.5 | 67.2 | 82.5 |
| 113 | 81.0 | 80.5 | 81.4 | 86.1 | 84.0 | 88.3 |
| 114 | 78.2 | 75.6 | 81.1 | 69.7 | 64.9 | 75.0 |
| 115 | 81.3 | 75.6 | 87.5 | 78.9 | 70.2 | 88.3 |
| 116 | 76.0 | 76.6 | 75.4 | 76.1 | 78.6 | 73.3 |
| 117 | 73.1 | 72.6 | 73.6 | 69.7 | 66.4 | 73.3 |
| 118 | 75.6 | 72.3 | 79.3 | 75.7 | 72.5 | 79.2 |
| 119 | 79.6 | 81.5 | 77.5 | 82.5 | 84.0 | 80.8 |
| 120 | 76.3 | 75.9 | 76.8 | 75.3 | 73.3 | 77.5 |
| 121 | 74.1 | 80.5 | 67.1 | 80.9 | 86.3 | 75.0 |
| 122 | 79.9 | 71.0 | 89.6 | 82.1 | 73.3 | 91.7 |
| 123 | 77.7 | 75.9 | 79.6 | 78.5 | 75.6 | 81.7 |
| 124 | 80.8 | 80.9 | 80.7 | 80.9 | 79.4 | 82.5 |
| 125 | 76.8 | 77.9 | 75.7 | 78.1 | 81.7 | 74.2 |
| 126 | 79.8 | 71.3 | 88.9 | 75.3 | 61.8 | 90.0 |
| 127 | 76.2 | 76.9 | 75.4 | 76.1 | 80.9 | 70.8 |
| 128 | 81.0 | 81.8 | 80.0 | 82.9 | 84.7 | 80.8 |
| 129 | 79.8 | 79.5 | 80.0 | 80.1 | 80.2 | 80.0 |
| 130 | 74.8 | 74.3 | 75.4 | 74.5 | 74.0 | 75.0 |
| 131 | 76.8 | 77.6 | 76.1 | 74.9 | 73.3 | 76.7 |
| 132 | 79.8 | 80.2 | 79.3 | 76.1 | 77.9 | 74.2 |
| 133 | 73.2 | 75.9 | 70.4 | 75.3 | 75.6 | 75.0 |
| 134 | 76.2 | 65.3 | 87.9 | 76.9 | 62.6 | 92.5 |
| 135 | 81.5 | 84.5 | 78.2 | 79.7 | 81.7 | 77.5 |
| 136 | 77.9 | 78.5 | 77.1 | 78.9 | 75.6 | 82.5 |
| 137 | 83.2 | 74.3 | 92.9 | 80.5 | 67.9 | 94.2 |
| 138 | 84.4 | 77.9 | 91.4 | 78.5 | 68.7 | 89.2 |
| 139 | 73.2 | 70.6 | 76.1 | 72.9 | 72.5 | 73.3 |
| 140 | 76.3 | 81.2 | 71.1 | 73.7 | 77.9 | 69.2 |
| 141 | 71.5 | 71.9 | 71.1 | 68.9 | 67.9 | 70.0 |
| 142 | 77.9 | 84.5 | 70.7 | 80.1 | 82.4 | 77.5 |
| 143 | 82.0 | 81.2 | 82.9 | 81.3 | 81.7 | 80.8 |
| 144 | 75.1 | 69.6 | 81.1 | 77.7 | 74.0 | 81.7 |
| 145 | 73.2 | 70.0 | 76.8 | 78.9 | 74.8 | 83.3 |
| 146 | 77.2 | 76.2 | 78.2 | 80.1 | 81.7 | 78.3 |
| 147 | 71.5 | 69.3 | 73.9 | 69.3 | 71.0 | 67.5 |
| 148 | 78.7 | 65.7 | 92.9 | 79.3 | 64.1 | 95.8 |
| 149 | 74.8 | 71.6 | 78.2 | 79.3 | 74.8 | 84.2 |
| 150 | 75.3 | 71.3 | 79.6 | 77.7 | 77.1 | 78.3 |
| 151 | 76.8 | 76.6 | 77.1 | 76.1 | 74.8 | 77.5 |
| 152 | 78.2 | 79.2 | 77.1 | 80.1 | 74.0 | 86.7 |
| 153 | 75.8 | 71.0 | 81.1 | 78.9 | 74.8 | 83.3 |
| 154 | 71.7 | 69.0 | 74.6 | 69.7 | 74.8 | 64.2 |
| 155 | 69.0 | 67.3 | 70.7 | 69.3 | 68.7 | 70.0 |
| 156 | 77.9 | 81.5 | 73.9 | 80.1 | 87.0 | 72.5 |
| 157 | 69.0 | 72.6 | 65.0 | 66.9 | 67.2 | 66.7 |
| 158 | 76.7 | 83.2 | 69.6 | 77.7 | 81.7 | 73.3 |
| 159 | 76.5 | 80.2 | 72.5 | 77.7 | 79.4 | 75.8 |
| 160 | 73.8 | 73.9 | 73.6 | 75.7 | 75.6 | 75.8 |
| 161 | 65.7 | 63.7 | 67.9 | 59.8 | 56.5 | 63.3 |
| 162 | 73.4 | 73.6 | 73.2 | 73.3 | 71.8 | 75.0 |
| 163 | 80.3 | 84.5 | 75.7 | 74.5 | 80.9 | 67.5 |
| 164 | 71.5 | 72.9 | 70.0 | 66.9 | 65.6 | 68.3 |
| 165 | 69.1 | 74.3 | 63.6 | 67.3 | 70.2 | 64.2 |
| 166 | 65.2 | 70.0 | 60.0 | 62.9 | 65.6 | 60.0 |
| 167 | 70.3 | 73.6 | 66.8 | 71.3 | 76.3 | 65.8 |
| 168 | 71.0 | 57.1 | 86.1 | 72.1 | 58.0 | 87.5 |
| 169 | 70.8 | 69.6 | 72.1 | 73.7 | 71.0 | 76.7 |
| 170 | 72.6 | 74.6 | 70.4 | 74.5 | 80.2 | 68.3 |
| 171 | 72.9 | 77.6 | 67.9 | 66.5 | 75.6 | 56.7 |
| 172 | 61.2 | 64.7 | 57.5 | 61.8 | 61.1 | 62.5 |
| 173 | 70.0 | 76.9 | 62.5 | 72.9 | 77.9 | 67.5 |
| 174 | 73.1 | 79.2 | 66.4 | 73.3 | 80.2 | 65.8 |
| 175 | 72.7 | 75.9 | 69.3 | 69.7 | 75.6 | 63.3 |

TABLE 3-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 176 | 64.3 | 67.3 | 61.1 | 61.8 | 65.6 | 57.5 |
| 177 | 72.7 | 76.6 | 68.6 | 71.3 | 80.9 | 60.8 |
| 178 | 75.1 | 77.2 | 72.9 | 73.3 | 78.6 | 67.5 |
| 179 | 73.8 | 78.2 | 68.9 | 76.9 | 80.9 | 72.5 |
| 180 | 70.7 | 77.6 | 63.2 | 68.1 | 65.6 | 70.8 |
| 181 | 65.9 | 66.7 | 65.0 | 70.1 | 65.6 | 75.0 |
| 182 | 67.2 | 61.7 | 73.2 | 68.1 | 58.8 | 78.3 |
| 183 | 66.7 | 72.9 | 60.0 | 66.5 | 67.9 | 65.0 |
| 184 | 69.3 | 73.6 | 64.6 | 68.9 | 70.2 | 67.5 |
| 185 | 68.4 | 74.9 | 61.4 | 68.5 | 73.3 | 63.3 |
| 186 | 68.8 | 73.6 | 63.6 | 71.3 | 73.3 | 69.2 |
| 187 | 68.8 | 75.6 | 61.4 | 71.3 | 83.2 | 58.3 |
| 188 | 66.0 | 54.8 | 78.2 | 63.3 | 48.1 | 80.0 |
| 189 | 69.6 | 69.6 | 69.6 | 69.7 | 69.5 | 70.0 |
| 190 | 64.0 | 72.6 | 54.6 | 68.5 | 76.3 | 60.0 |
| 191 | 67.9 | 74.3 | 61.1 | 68.5 | 76.3 | 60.0 |
| 192 | 64.3 | 60.7 | 68.2 | 64.5 | 55.7 | 74.2 |
| 193 | 63.5 | 64.7 | 62.1 | 60.6 | 58.0 | 63.3 |
| 194 | 64.0 | 64.0 | 63.9 | 66.5 | 61.8 | 71.7 |
| 195 | 67.6 | 67.3 | 67.9 | 62.2 | 56.5 | 68.3 |
| 196 | 66.7 | 71.6 | 61.4 | 71.3 | 73.3 | 69.2 |
| 197 | 63.0 | 58.7 | 67.5 | 62.2 | 55.0 | 70.0 |
| 198 | 63.0 | 69.3 | 56.1 | 69.7 | 74.8 | 64.2 |
| 199 | 63.5 | 70.6 | 55.7 | 68.1 | 68.7 | 67.5 |
| 200 | 62.4 | 66.0 | 58.6 | 60.2 | 59.5 | 60.8 |
| 201 | 64.7 | 68.3 | 60.7 | 64.1 | 63.4 | 65.0 |
| 202 | 58.3 | 54.1 | 62.9 | 59.4 | 54.2 | 65.0 |
| 203 | 57.1 | 68.6 | 44.6 | 62.9 | 73.3 | 51.7 |
| 248 | 95.5 | 95.7 | 95.4 | 97.6 | 99.2 | 95.8 |
| 249 | 94.3 | 90.8 | 98.2 | 93.2 | 87.8 | 99.2 |
| 250 | 93.1 | 93.7 | 92.5 | 94.8 | 93.1 | 96.7 |
| 251 | 91.3 | 88.4 | 94.3 | 93.2 | 90.8 | 95.8 |
| 252 | 90.2 | 89.1 | 91.4 | 88.4 | 83.2 | 94.2 |
| 253 | 89.5 | 87.5 | 91.8 | 90.0 | 87.8 | 92.5 |
| 254 | 84.9 | 83.8 | 86.1 | 88.8 | 89.3 | 88.3 |
| 255 | 90.2 | 84.8 | 96.1 | 90.4 | 82.4 | 99.2 |
| 256 | 87.3 | 91.4 | 82.9 | 92.4 | 94.7 | 90.0 |
| 257 | 86.1 | 84.5 | 87.9 | 83.7 | 80.2 | 87.5 |
| 258 | 87.8 | 82.8 | 93.2 | 88.0 | 84.7 | 91.7 |
| 259 | 93.8 | 89.4 | 98.6 | 93.2 | 90.8 | 95.8 |
| 260 | 84.6 | 94.4 | 73.9 | 85.7 | 95.4 | 75.0 |
| 261 | 82.2 | 84.5 | 79.6 | 84.9 | 80.9 | 89.2 |
| 262 | 80.4 | 82.5 | 78.2 | 79.3 | 81.7 | 76.7 |
| 263 | 80.1 | 73.3 | 87.5 | 74.5 | 65.6 | 84.2 |
| 264 | 79.2 | 83.5 | 74.6 | 76.9 | 80.2 | 73.3 |
| 265 | 82.2 | 81.8 | 82.5 | 79.3 | 74.8 | 84.2 |
| 266 | 77.0 | 77.6 | 76.4 | 76.9 | 77.9 | 75.8 |
| 267 | 70.2 | 73.9 | 66.1 | 72.5 | 77.1 | 67.5 |
| 268 | 65.5 | 63.0 | 68.2 | 63.3 | 61.8 | 65.0 |

TABLE 4

| SEQ ID NO. | Coefficient | Constant term |
|---|---|---|
| 1 | 2.123 | 16.461 |
| 2 | 1.384 | 9.575 |
| 3 | 4.869 | 56.826 |
| 4 | 1.396 | 17.610 |
| 5 | 3.373 | 29.135 |
| 6 | 2.664 | 32.360 |
| 7 | 3.268 | 38.312 |
| 8 | 1.163 | 7.999 |
| 9 | 1.368 | 9.338 |
| 10 | 1.159 | 7.999 |
| 11 | 1.289 | 15.195 |
| 12 | 2.319 | 25.799 |
| 13 | 1.757 | 12.187 |
| 14 | 0.879 | 4.347 |
| 15 | 1.520 | 15.872 |
| 16 | 1.908 | 15.742 |

TABLE 4-continued

| SEQ ID NO. | Coefficient | Constant term |
|---|---|---|
| 17 | 1.661 | 11.329 |
| 18 | 1.089 | 9.869 |
| 19 | 1.629 | 18.376 |
| 20 | 0.893 | 10.428 |
| 21 | 1.170 | 6.573 |
| 22 | 2.781 | 23.633 |
| 23 | 1.499 | 9.978 |
| 24 | 3.569 | 39.272 |
| 25 | 1.449 | 12.427 |
| 26 | 1.356 | 12.568 |
| 27 | 2.427 | 20.795 |
| 28 | 2.016 | 22.808 |
| 29 | 0.705 | 3.606 |
| 30 | 2.106 | 15.535 |
| 31 | 4.170 | 38.602 |
| 32 | 1.077 | 6.983 |

TABLE 4-continued

| SEQ ID NO. | Coefficient | Constant term |
|---|---|---|
| 33 | 2.681 | 29.153 |
| 34 | 2.551 | 22.591 |
| 35 | 2.124 | 25.916 |
| 36 | 2.250 | 22.402 |
| 37 | 2.375 | 24.609 |
| 38 | 2.812 | 28.525 |
| 39 | 1.058 | 5.677 |
| 40 | 1.194 | 9.320 |
| 41 | 1.227 | 7.549 |
| 42 | 1.044 | 10.432 |
| 43 | 2.130 | 16.511 |
| 44 | 2.163 | 14.618 |
| 45 | 1.545 | 10.595 |
| 46 | 3.952 | 49.258 |
| 47 | 1.061 | 7.156 |
| 48 | 2.814 | 27.273 |
| 49 | 2.491 | 31.077 |
| 50 | 1.162 | 7.912 |
| 51 | 1.595 | 13.403 |
| 52 | 2.381 | 19.963 |
| 53 | 1.479 | 9.318 |
| 54 | 3.435 | 36.734 |
| 55 | 0.662 | 4.595 |
| 56 | 2.481 | 21.976 |
| 57 | 1.778 | 12.553 |
| 58 | 3.391 | 35.584 |
| 59 | 1.051 | 6.829 |
| 60 | 1.161 | 9.868 |
| 61 | 2.574 | 32.431 |
| 62 | 1.991 | 14.191 |
| 63 | 1.457 | 8.857 |
| 64 | 3.740 | 37.811 |
| 65 | 1.321 | 9.518 |
| 66 | 0.742 | 7.056 |
| 67 | 0.934 | 5.001 |
| 68 | 2.165 | 18.275 |
| 69 | 0.924 | 7.932 |
| 70 | 2.595 | 23.645 |
| 71 | 1.101 | 8.477 |
| 72 | 3.198 | 31.760 |
| 73 | 2.473 | 16.893 |
| 74 | 1.157 | 9.485 |
| 75 | 1.585 | 11.119 |
| 76 | 1.212 | 8.366 |
| 77 | 1.082 | 8.518 |
| 78 | 1.893 | 14.755 |
| 79 | 2.213 | 18.358 |
| 80 | 1.235 | 8.533 |
| 81 | 1.182 | 8.574 |
| 82 | 1.723 | 11.225 |
| 83 | 0.541 | 3.403 |
| 84 | 1.024 | 6.335 |
| 85 | 1.054 | 9.531 |
| 86 | 1.358 | 8.692 |
| 87 | 0.647 | 4.678 |
| 88 | 1.240 | 7.612 |
| 89 | 1.568 | 9.448 |
| 90 | 1.250 | 9.664 |
| 91 | 1.205 | 7.983 |
| 92 | 1.149 | 6.022 |
| 93 | 1.556 | 9.561 |
| 94 | 1.388 | 9.969 |
| 95 | 0.968 | 7.612 |
| 96 | 2.008 | 18.975 |
| 97 | 1.616 | 11.918 |
| 98 | 0.618 | 4.008 |
| 99 | 0.445 | 3.689 |
| 100 | 1.881 | 12.492 |
| 101 | 1.709 | 15.312 |
| 102 | 1.633 | 20.622 |
| 103 | 0.498 | 2.830 |
| 104 | 2.266 | 28.614 |
| 105 | 0.604 | 4.325 |
| 106 | 1.675 | 12.286 |
| 107 | 1.282 | 8.167 |
| 108 | 2.394 | 23.435 |

TABLE 4-continued

| SEQ ID NO. | Coefficient | Constant term |
|---|---|---|
| 109 | 1.053 | 8.539 |
| 110 | 0.985 | 6.096 |
| 111 | 1.694 | 14.189 |
| 112 | 0.931 | 6.212 |
| 113 | 1.531 | 10.326 |
| 114 | 2.056 | 16.586 |
| 115 | 1.298 | 11.492 |
| 116 | 0.569 | 3.293 |
| 117 | 2.355 | 27.797 |
| 118 | 1.646 | 15.659 |
| 119 | 1.815 | 11.796 |
| 120 | 1.022 | 7.122 |
| 121 | 1.426 | 18.104 |
| 122 | 0.629 | 3.413 |
| 123 | 2.416 | 32.426 |
| 124 | 1.319 | 7.733 |
| 125 | 0.771 | 5.365 |
| 126 | 1.242 | 8.113 |
| 127 | 0.719 | 3.627 |
| 128 | 1.421 | 7.974 |
| 129 | 1.134 | 6.426 |
| 130 | 2.258 | 18.373 |
| 131 | 1.364 | 10.682 |
| 132 | 1.137 | 6.086 |
| 133 | 1.921 | 19.578 |
| 134 | 1.217 | 7.932 |
| 135 | 1.182 | 6.733 |
| 136 | 1.373 | 10.118 |
| 137 | 1.550 | 11.154 |
| 138 | 0.848 | 5.153 |
| 139 | 2.009 | 21.173 |
| 140 | 1.277 | 9.081 |
| 141 | 0.676 | 3.802 |
| 142 | 1.076 | 6.019 |
| 143 | 1.466 | 8.667 |
| 144 | 1.735 | 23.462 |
| 145 | 1.904 | 15.630 |
| 146 | 1.196 | 7.706 |
| 147 | 1.661 | 12.333 |
| 148 | 1.332 | 9.486 |
| 149 | 1.902 | 14.524 |
| 150 | 1.901 | 15.043 |
| 151 | 2.365 | 17.993 |
| 152 | 1.519 | 8.468 |
| 153 | 0.925 | 5.559 |
| 154 | 1.424 | 14.174 |
| 155 | 1.445 | 11.773 |
| 156 | 1.406 | 7.825 |
| 157 | 1.499 | 11.695 |
| 158 | 1.306 | 8.480 |
| 159 | 1.422 | 8.864 |
| 160 | 1.166 | 7.753 |
| 161 | 0.986 | 7.102 |
| 162 | 1.026 | 6.301 |
| 163 | 1.550 | 10.712 |
| 164 | 0.695 | 3.993 |
| 165 | 1.148 | 7.715 |
| 166 | 1.311 | 10.092 |
| 167 | 1.170 | 6.320 |
| 168 | 1.097 | 6.199 |
| 169 | 1.178 | 7.806 |
| 170 | 1.298 | 7.638 |
| 171 | 1.404 | 8.033 |
| 172 | 1.291 | 9.864 |
| 173 | 1.190 | 7.474 |
| 174 | 1.278 | 7.428 |
| 175 | 1.277 | 8.008 |
| 176 | 1.228 | 10.468 |
| 177 | 1.309 | 7.689 |
| 178 | 1.543 | 8.824 |
| 179 | 1.442 | 8.131 |
| 180 | 1.429 | 8.934 |
| 181 | 1.530 | 10.398 |
| 182 | 0.834 | 4.706 |
| 183 | 1.229 | 7.422 |
| 184 | 1.446 | 9.586 |

TABLE 4-continued

| SEQ ID NO. | Coefficient | Constant term |
|---|---|---|
| 185 | 1.379 | 8.242 |
| 186 | 1.046 | 5.969 |
| 187 | 1.330 | 7.589 |
| 188 | 1.277 | 7.572 |
| 189 | 1.307 | 8.341 |
| 190 | 1.194 | 7.388 |
| 191 | 0.838 | 4.687 |
| 192 | 1.219 | 7.400 |
| 193 | 1.091 | 6.825 |
| 194 | 1.007 | 8.299 |
| 195 | 1.271 | 9.982 |
| 196 | 1.044 | 7.688 |
| 197 | 1.019 | 6.103 |
| 198 | 1.082 | 7.372 |
| 199 | 1.068 | 6.872 |
| 200 | 1.129 | 8.982 |
| 201 | 1.114 | 7.351 |
| 202 | 1.082 | 6.606 |
| 203 | 0.916 | 5.481 |
| 248 | 1.159 | 6.820 |
| 249 | 1.888 | 21.584 |
| 250 | 4.673 | 53.498 |
| 251 | 1.396 | 12.941 |
| 252 | 1.537 | 16.846 |
| 253 | 0.902 | 4.750 |
| 254 | 0.576 | 2.111 |
| 255 | 1.989 | 18.569 |
| 256 | 2.231 | 17.384 |
| 257 | 0.430 | 2.206 |
| 258 | 1.303 | 11.311 |
| 259 | 1.409 | 9.381 |
| 260 | 0.454 | 3.040 |
| 261 | 1.401 | 9.414 |
| 262 | 1.566 | 13.242 |
| 263 | 1.007 | 6.487 |
| 264 | 0.430 | 2.247 |
| 265 | 1.145 | 6.375 |
| 266 | 0.721 | 3.898 |
| 267 | 0.914 | 6.308 |
| 268 | 1.098 | 8.628 |

TABLE 5

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 1_3 | 99.5 | 100.0 | 98.9 | 100.0 | 100.0 | 100.0 |
| 2_3 | 98.3 | 97.0 | 99.6 | 98.8 | 97.7 | 100.0 |
| 1_3 | 99.5 | 100.0 | 98.9 | 100.0 | 100.0 | 100.0 |
| 3_4 | 99.1 | 99.0 | 99.3 | 99.6 | 99.2 | 100.0 |
| 3_5 | 99.5 | 100.0 | 98.9 | 100.0 | 100.0 | 100.0 |
| 3_6 | 99.1 | 99.0 | 99.3 | 99.6 | 99.2 | 100.0 |
| 3_7 | 98.3 | 97.0 | 99.6 | 99.6 | 99.2 | 100.0 |
| 6_8 | 99.3 | 98.7 | 100.0 | 99.2 | 98.5 | 100.0 |
| 3_9 | 98.8 | 98.7 | 98.9 | 99.2 | 98.5 | 100.0 |
| 248_10 | 99.3 | 100.0 | 98.6 | 100.0 | 100.0 | 100.0 |
| 11_18 | 99.7 | 99.3 | 100.0 | 100.0 | 100.0 | 100.0 |
| 3_12 | 98.8 | 98.3 | 99.3 | 99.2 | 98.5 | 100.0 |
| 3_13 | 99.0 | 98.7 | 99.3 | 99.6 | 100.0 | 99.2 |
| 14_16 | 97.6 | 98.0 | 97.1 | 100.0 | 100.0 | 100.0 |
| 6_15 | 97.8 | 99.7 | 95.7 | 99.2 | 99.2 | 99.2 |
| 248_16 | 97.6 | 97.7 | 97.5 | 100.0 | 100.0 | 100.0 |
| 6_17 | 98.8 | 98.7 | 98.9 | 99.2 | 98.5 | 100.0 |
| 248_18 | 97.9 | 97.0 | 98.9 | 100.0 | 100.0 | 100.0 |
| 3_19 | 98.8 | 98.3 | 99.3 | 99.2 | 98.5 | 100.0 |
| 3_20 | 98.3 | 97.7 | 98.9 | 99.2 | 98.5 | 100.0 |
| 3_21 | 98.5 | 98.0 | 98.9 | 98.8 | 98.5 | 99.2 |
| 3_22 | 98.8 | 98.7 | 98.9 | 99.2 | 99.2 | 99.2 |
| 3_23 | 99.1 | 99.0 | 99.3 | 99.6 | 100.0 | 99.2 |
| 3_24 | 99.0 | 99.0 | 98.9 | 99.2 | 99.2 | 99.2 |
| 1_25 | 99.0 | 99.3 | 98.6 | 99.2 | 98.5 | 100.0 |
| 3_26 | 98.3 | 97.4 | 99.3 | 98.4 | 97.7 | 99.2 |
| 3_27 | 99.0 | 98.7 | 99.3 | 99.6 | 99.2 | 100.0 |
| 1_28 | 97.9 | 99.0 | 96.8 | 99.2 | 99.2 | 99.2 |
| 3_29 | 98.8 | 98.3 | 99.3 | 99.6 | 99.2 | 100.0 |
| 16_30 | 97.9 | 98.0 | 97.9 | 99.2 | 98.5 | 100.0 |
| 3_31 | 98.3 | 97.4 | 99.3 | 99.6 | 99.2 | 100.0 |
| 3_32 | 98.8 | 98.3 | 99.3 | 99.2 | 98.5 | 100.0 |
| 3_33 | 97.6 | 96.4 | 98.9 | 98.8 | 97.7 | 100.0 |
| 6_34 | 98.3 | 99.7 | 96.8 | 99.2 | 99.2 | 99.2 |
| 3_35 | 98.8 | 98.3 | 99.3 | 98.8 | 97.7 | 100.0 |
| 3_36 | 98.5 | 98.0 | 98.9 | 99.2 | 99.2 | 99.2 |
| 3_37 | 99.0 | 99.0 | 98.9 | 99.6 | 99.2 | 100.0 |
| 11_38 | 99.7 | 99.3 | 100.0 | 99.2 | 98.5 | 100.0 |
| 3_39 | 97.6 | 96.0 | 99.3 | 99.2 | 98.5 | 100.0 |
| 3_40 | 98.5 | 98.0 | 98.9 | 99.2 | 98.5 | 100.0 |
| 3_41 | 98.1 | 97.4 | 98.9 | 98.8 | 98.5 | 99.2 |
| 3_42 | 97.6 | 96.7 | 98.6 | 99.2 | 98.5 | 100.0 |
| 3_43 | 98.1 | 97.4 | 98.9 | 99.2 | 99.2 | 99.2 |
| 3_44 | 98.6 | 98.3 | 98.9 | 98.8 | 98.5 | 99.2 |
| 3_45 | 99.0 | 98.7 | 99.3 | 99.2 | 98.5 | 100.0 |

TABLE 5-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 3_46 | 98.5 | 97.7 | 99.3 | 98.8 | 97.7 | 100.0 |
| 248_47 | 95.2 | 93.7 | 96.8 | 99.2 | 99.2 | 99.2 |
| 6_48 | 98.1 | 99.0 | 97.1 | 98.8 | 98.5 | 99.2 |
| 249_49 | 99.3 | 99.0 | 99.6 | 99.2 | 98.5 | 100.0 |
| 3_50 | 98.8 | 98.7 | 98.9 | 98.8 | 97.7 | 100.0 |
| 3_51 | 97.8 | 97.0 | 98.6 | 98.8 | 97.7 | 100.0 |
| 3_52 | 99.0 | 99.0 | 98.9 | 98.8 | 98.5 | 99.2 |
| 16_53 | 97.6 | 96.7 | 98.6 | 99.6 | 99.2 | 100.0 |
| 3_54 | 97.4 | 96.0 | 98.9 | 99.6 | 99.2 | 100.0 |
| 7_55 | 96.2 | 93.1 | 99.6 | 97.2 | 94.7 | 100.0 |
| 248_56 | 95.9 | 95.7 | 96.1 | 99.6 | 99.2 | 100.0 |
| 3_57 | 98.6 | 98.0 | 99.3 | 99.2 | 99.2 | 99.2 |
| 249_58 | 99.5 | 100.0 | 98.9 | 99.6 | 100.0 | 99.2 |
| 3_59 | 97.6 | 96.4 | 98.9 | 98.8 | 98.5 | 99.2 |
| 1_60 | 98.1 | 98.7 | 97.5 | 98.8 | 97.7 | 100.0 |
| 249_61 | 99.1 | 98.7 | 99.6 | 98.8 | 97.7 | 100.0 |
| 3_62 | 98.8 | 98.7 | 98.9 | 99.2 | 99.2 | 99.2 |
| 3_63 | 97.6 | 96.7 | 98.6 | 99.2 | 99.2 | 99.2 |
| 248_64 | 96.6 | 95.4 | 97.9 | 98.0 | 97.7 | 98.3 |
| 3_65 | 99.0 | 98.7 | 99.3 | 99.2 | 98.5 | 100.0 |
| 3_66 | 98.3 | 97.7 | 98.9 | 99.2 | 99.2 | 99.2 |
| 3_67 | 98.1 | 97.4 | 98.9 | 98.8 | 98.5 | 99.2 |
| 16_68 | 99.3 | 98.7 | 100.0 | 99.6 | 99.2 | 100.0 |
| 3_69 | 98.3 | 97.7 | 98.9 | 98.4 | 97.7 | 99.2 |
| 3_70 | 99.0 | 99.3 | 98.6 | 99.2 | 99.2 | 99.2 |
| 248_71 | 95.7 | 95.4 | 96.1 | 98.8 | 100.0 | 97.5 |
| 3_72 | 98.6 | 98.3 | 98.9 | 99.6 | 99.2 | 100.0 |
| 3_73 | 97.8 | 97.4 | 98.2 | 98.8 | 98.5 | 99.2 |
| 3_74 | 98.1 | 97.4 | 98.9 | 99.2 | 99.2 | 99.2 |
| 1_75 | 97.3 | 98.7 | 95.7 | 98.8 | 98.5 | 99.2 |
| 3_76 | 98.8 | 98.3 | 99.3 | 98.4 | 96.9 | 100.0 |
| 3_77 | 98.1 | 97.4 | 98.9 | 99.2 | 99.2 | 99.2 |
| 3_78 | 97.9 | 97.0 | 98.9 | 99.6 | 99.2 | 100.0 |
| 1_79 | 97.9 | 99.0 | 96.8 | 99.6 | 99.2 | 100.0 |
| 18_80 | 99.0 | 98.3 | 99.6 | 99.6 | 99.2 | 100.0 |
| 3_81 | 97.9 | 97.4 | 98.6 | 98.4 | 98.5 | 98.3 |
| 3_82 | 98.5 | 98.0 | 98.9 | 98.8 | 98.5 | 99.2 |
| 3_83 | 97.9 | 97.0 | 98.9 | 99.2 | 98.5 | 100.0 |
| 3_84 | 97.4 | 96.4 | 98.6 | 98.4 | 97.7 | 99.2 |
| 10_85 | 98.1 | 97.4 | 98.9 | 98.8 | 97.7 | 100.0 |
| 16_86 | 98.5 | 97.7 | 99.3 | 99.6 | 99.2 | 100.0 |
| 16_87 | 97.1 | 95.4 | 98.9 | 99.2 | 99.2 | 99.2 |
| 3_88 | 98.6 | 98.0 | 99.3 | 98.8 | 98.5 | 99.2 |
| 3_89 | 98.3 | 97.7 | 98.9 | 98.8 | 98.5 | 99.2 |
| 3_90 | 97.8 | 97.0 | 98.6 | 98.8 | 98.5 | 99.2 |
| 248_91 | 95.7 | 95.4 | 96.1 | 98.0 | 99.2 | 96.7 |
| 249_92 | 97.6 | 97.0 | 98.2 | 99.2 | 98.5 | 100.0 |
| 3_93 | 97.9 | 97.0 | 98.9 | 98.8 | 98.5 | 99.2 |
| 3_94 | 98.1 | 97.4 | 98.9 | 99.2 | 98.5 | 100.0 |
| 3_95 | 97.4 | 96.4 | 98.6 | 98.4 | 97.7 | 99.2 |
| 1_96 | 97.3 | 99.0 | 95.4 | 98.4 | 97.7 | 99.2 |
| 3_97 | 98.6 | 98.3 | 98.9 | 99.2 | 98.5 | 100.0 |
| 16_98 | 96.2 | 95.0 | 97.5 | 99.2 | 98.5 | 100.0 |
| 6_99 | 97.9 | 97.4 | 98.6 | 98.8 | 98.5 | 99.2 |
| 10_100 | 98.6 | 97.4 | 100.0 | 99.2 | 98.5 | 100.0 |
| 1_101 | 97.6 | 99.0 | 96.1 | 99.2 | 99.2 | 99.2 |
| 6_102 | 98.8 | 99.0 | 98.6 | 98.8 | 97.7 | 100.0 |
| 3_103 | 98.1 | 97.4 | 98.9 | 98.4 | 98.5 | 98.3 |
| 249_104 | 99.7 | 99.7 | 99.6 | 99.6 | 99.2 | 100.0 |
| 16_105 | 96.1 | 95.0 | 97.1 | 100.0 | 100.0 | 100.0 |
| 3_106 | 98.3 | 97.7 | 98.9 | 99.2 | 99.2 | 99.2 |
| 3_107 | 98.6 | 98.3 | 98.9 | 98.8 | 97.7 | 100.0 |
| 7_108 | 96.4 | 93.4 | 99.6 | 98.4 | 96.9 | 100.0 |
| 3_109 | 97.9 | 97.0 | 98.9 | 98.8 | 98.5 | 99.2 |
| 10_110 | 99.1 | 99.0 | 99.3 | 98.8 | 97.7 | 100.0 |
| 248_111 | 95.5 | 95.7 | 95.4 | 98.4 | 99.2 | 97.5 |
| 3_112 | 98.3 | 97.7 | 98.9 | 99.2 | 98.5 | 100.0 |
| 248_113 | 95.0 | 94.4 | 95.7 | 98.8 | 100.0 | 97.5 |
| 249_114 | 99.3 | 99.3 | 99.3 | 99.6 | 99.2 | 100.0 |
| 248_115 | 96.4 | 96.4 | 96.4 | 99.6 | 100.0 | 99.2 |
| 3_116 | 97.8 | 96.7 | 98.9 | 98.8 | 98.5 | 99.2 |
| 249_117 | 98.8 | 100.0 | 97.5 | 99.6 | 100.0 | 99.2 |
| 3_118 | 97.6 | 96.7 | 98.6 | 98.4 | 96.9 | 100.0 |
| 3_119 | 97.9 | 97.4 | 98.6 | 99.2 | 98.5 | 100.0 |
| 3_120 | 98.5 | 98.0 | 98.9 | 98.8 | 97.7 | 100.0 |

TABLE 5-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 3_121 | 98.6 | 98.3 | 98.9 | 99.2 | 99.2 | 99.2 |
| 3_122 | 97.6 | 96.7 | 98.6 | 98.4 | 97.7 | 99.2 |
| 3_123 | 97.4 | 96.0 | 98.9 | 98.8 | 98.5 | 99.2 |
| 3_124 | 97.4 | 96.4 | 98.6 | 98.8 | 98.5 | 99.2 |
| 3_125 | 97.6 | 96.4 | 98.9 | 98.4 | 97.7 | 99.2 |
| 248_126 | 96.4 | 96.4 | 96.4 | 98.8 | 99.2 | 98.3 |
| 10_127 | 97.9 | 97.0 | 98.9 | 99.2 | 98.5 | 100.0 |
| 248_128 | 95.0 | 94.7 | 95.4 | 98.0 | 98.5 | 97.5 |
| 16_129 | 96.6 | 93.7 | 99.6 | 98.8 | 98.5 | 99.2 |
| 3_130 | 98.3 | 97.4 | 99.3 | 98.4 | 97.7 | 99.2 |
| 3_131 | 98.5 | 98.0 | 98.9 | 98.8 | 98.5 | 99.2 |
| 3_132 | 97.8 | 97.0 | 98.6 | 98.4 | 97.7 | 99.2 |
| 1_133 | 98.1 | 99.0 | 97.1 | 99.6 | 99.2 | 100.0 |
| 3_134 | 98.3 | 97.7 | 98.9 | 98.8 | 97.7 | 100.0 |
| 3_135 | 97.8 | 96.7 | 98.9 | 98.4 | 97.7 | 99.2 |
| 10_136 | 98.8 | 98.3 | 99.3 | 98.8 | 97.7 | 100.0 |
| 3_137 | 98.5 | 98.0 | 98.9 | 99.2 | 98.5 | 100.0 |
| 3_138 | 97.3 | 96.0 | 98.6 | 98.4 | 97.7 | 99.2 |
| 249_139 | 96.6 | 94.1 | 99.3 | 98.8 | 97.7 | 100.0 |
| 10_140 | 97.4 | 97.4 | 97.5 | 99.2 | 98.5 | 100.0 |
| 3_141 | 97.9 | 97.0 | 98.9 | 98.8 | 97.7 | 100.0 |
| 3_142 | 97.8 | 97.0 | 98.6 | 99.2 | 98.5 | 100.0 |
| 3_143 | 97.8 | 97.0 | 98.6 | 98.4 | 97.7 | 99.2 |
| 19_144 | 97.8 | 97.4 | 98.2 | 99.2 | 98.5 | 100.0 |
| 3_145 | 97.8 | 96.7 | 98.9 | 99.2 | 98.5 | 100.0 |
| 3_146 | 97.6 | 96.7 | 98.6 | 98.4 | 97.7 | 99.2 |
| 3_147 | 97.8 | 97.0 | 98.6 | 98.4 | 97.7 | 99.2 |
| 248_148 | 95.5 | 94.7 | 96.4 | 98.0 | 98.5 | 97.5 |
| 3_149 | 97.8 | 96.7 | 98.9 | 98.8 | 98.5 | 99.2 |
| 3_150 | 98.3 | 97.7 | 98.9 | 99.2 | 99.2 | 99.2 |
| 3_151 | 97.4 | 96.4 | 98.6 | 98.8 | 98.5 | 99.2 |
| 3_152 | 97.4 | 96.4 | 98.6 | 98.8 | 98.5 | 99.2 |
| 3_153 | 97.4 | 96.4 | 98.6 | 98.4 | 97.7 | 99.2 |
| 3_154 | 97.8 | 96.7 | 98.9 | 99.2 | 98.5 | 100.0 |
| 3_155 | 98.8 | 98.3 | 99.3 | 98.8 | 98.5 | 99.2 |
| 10_156 | 97.8 | 97.0 | 98.6 | 98.8 | 97.7 | 100.0 |
| 3_157 | 97.9 | 96.7 | 99.3 | 98.4 | 97.7 | 99.2 |
| 248_158 | 95.9 | 96.0 | 95.7 | 98.4 | 100.0 | 96.7 |
| 10_159 | 98.8 | 99.3 | 98.2 | 98.4 | 96.9 | 100.0 |
| 10_160 | 98.5 | 97.4 | 99.6 | 99.6 | 99.2 | 100.0 |
| 6_161 | 97.8 | 97.0 | 98.6 | 98.4 | 97.7 | 99.2 |
| 16_162 | 97.4 | 96.0 | 98.9 | 99.6 | 100.0 | 99.2 |
| 3_163 | 97.8 | 97.0 | 98.6 | 98.4 | 97.7 | 99.2 |
| 248_164 | 95.4 | 96.0 | 94.6 | 98.8 | 100.0 | 97.5 |
| 248_165 | 95.2 | 95.0 | 95.4 | 98.0 | 99.2 | 96.7 |
| 3_166 | 98.3 | 97.7 | 98.9 | 98.8 | 97.7 | 100.0 |
| 3_167 | 98.1 | 97.7 | 98.6 | 98.8 | 98.5 | 99.2 |
| 248_168 | 95.9 | 95.4 | 96.4 | 98.0 | 98.5 | 97.5 |
| 3_169 | 97.6 | 96.7 | 98.6 | 98.4 | 97.7 | 99.2 |
| 3_170 | 97.9 | 97.4 | 98.6 | 98.4 | 97.7 | 99.2 |
| 3_171 | 97.3 | 96.0 | 98.6 | 98.4 | 97.7 | 99.2 |
| 3_172 | 97.6 | 96.7 | 98.6 | 98.4 | 97.7 | 99.2 |
| 3_173 | 97.4 | 96.0 | 98.9 | 98.4 | 97.7 | 99.2 |
| 3_174 | 97.6 | 96.7 | 98.6 | 98.8 | 98.5 | 99.2 |
| 3_175 | 97.4 | 96.4 | 98.6 | 98.4 | 97.7 | 99.2 |
| 3_176 | 98.3 | 97.7 | 98.9 | 98.8 | 97.7 | 100.0 |
| 3_177 | 97.3 | 96.0 | 98.6 | 98.4 | 97.7 | 99.2 |
| 6_178 | 97.3 | 98.0 | 96.4 | 98.4 | 98.5 | 98.3 |
| 3_179 | 98.3 | 98.0 | 98.6 | 98.4 | 97.7 | 99.2 |
| 3_180 | 97.6 | 96.7 | 98.6 | 98.4 | 97.7 | 99.2 |
| 3_181 | 97.8 | 96.7 | 98.9 | 98.4 | 97.7 | 99.2 |
| 3_182 | 98.5 | 98.3 | 98.6 | 98.8 | 97.7 | 100.0 |
| 3_183 | 97.6 | 96.7 | 98.6 | 98.4 | 97.7 | 99.2 |
| 3_184 | 97.6 | 96.7 | 98.6 | 98.4 | 97.7 | 99.2 |
| 3_185 | 97.6 | 96.7 | 98.6 | 98.4 | 97.7 | 99.2 |
| 18_186 | 95.7 | 93.1 | 98.6 | 95.6 | 93.9 | 97.5 |
| 3_187 | 97.6 | 96.7 | 98.6 | 98.8 | 97.7 | 100.0 |
| 1_188 | 97.3 | 98.7 | 95.7 | 98.0 | 97.7 | 98.3 |
| 10_189 | 98.6 | 98.0 | 99.3 | 98.4 | 97.7 | 99.2 |
| 3_190 | 97.6 | 96.7 | 98.6 | 98.4 | 97.7 | 99.2 |
| 3_191 | 97.4 | 96.4 | 98.6 | 98.4 | 97.7 | 99.2 |
| 6_192 | 96.6 | 97.4 | 95.7 | 98.0 | 98.5 | 97.5 |
| 3_193 | 98.3 | 98.0 | 98.6 | 98.8 | 98.5 | 99.2 |
| 3_194 | 97.6 | 96.7 | 98.6 | 98.4 | 97.7 | 99.2 |
| 3_195 | 97.6 | 96.7 | 98.6 | 98.4 | 97.7 | 99.2 |

TABLE 5-continued

| SEQ ID NO. | Training cohort Accuracy (%) | Sensitivity (%) | Specificity (%) | Validation cohort Accuracy (%) | Sensitivity (%) | Specificity (%) |
|---|---|---|---|---|---|---|
| 3_196 | 97.6 | 96.7 | 98.6 | 98.4 | 97.7 | 99.2 |
| 3_197 | 97.9 | 97.0 | 98.9 | 98.4 | 97.7 | 99.2 |
| 10_198 | 98.5 | 99.0 | 97.9 | 98.8 | 98.5 | 99.2 |
| 3_199 | 97.6 | 96.7 | 98.6 | 98.8 | 98.5 | 99.2 |
| 3_200 | 97.4 | 96.4 | 98.6 | 98.4 | 97.7 | 99.2 |
| 3_201 | 97.8 | 96.7 | 98.9 | 98.8 | 98.5 | 99.2 |
| 250_202 | 93.3 | 93.1 | 93.6 | 97.6 | 96.2 | 99.2 |
| 248_203 | 95.5 | 95.7 | 95.4 | 98.4 | 100.0 | 96.7 |
| 248_10 | 99.3 | 100.0 | 98.6 | 100.0 | 100.0 | 100.0 |
| 1_249 | 98.5 | 99.7 | 97.1 | 99.6 | 99.2 | 100.0 |
| 3_250 | 99.7 | 99.7 | 99.6 | 100.0 | 100.0 | 100.0 |
| 251_18 | 99.0 | 98.3 | 99.6 | 100.0 | 100.0 | 100.0 |
| 6_252 | 97.3 | 99.3 | 95.0 | 99.2 | 99.2 | 99.2 |
| 248_253 | 97.6 | 97.0 | 98.2 | 99.2 | 99.2 | 99.2 |
| 6_254 | 99.0 | 98.7 | 99.3 | 99.6 | 99.2 | 100.0 |
| 3_255 | 98.1 | 97.0 | 99.3 | 98.8 | 97.7 | 100.0 |
| 3_256 | 99.3 | 99.7 | 98.9 | 99.6 | 100.0 | 99.2 |
| 3_257 | 98.5 | 97.7 | 99.3 | 99.2 | 98.5 | 100.0 |
| 3_258 | 97.9 | 97.0 | 98.9 | 98.8 | 97.7 | 100.0 |
| 3_259 | 98.5 | 98.0 | 98.9 | 99.2 | 98.5 | 100.0 |
| 16_260 | 98.1 | 98.3 | 97.9 | 100.0 | 100.0 | 100.0 |
| 10_261 | 99.0 | 99.3 | 98.6 | 98.8 | 98.5 | 99.2 |
| 3_262 | 97.8 | 96.7 | 98.9 | 99.6 | 99.2 | 100.0 |
| 3_263 | 98.1 | 98.3 | 97.9 | 98.4 | 97.7 | 99.2 |
| 3_264 | 97.6 | 96.4 | 98.9 | 98.4 | 97.7 | 99.2 |
| 3_265 | 97.6 | 96.4 | 98.9 | 98.8 | 98.5 | 99.2 |
| 3_266 | 97.8 | 97.0 | 98.6 | 98.4 | 97.7 | 99.2 |
| 248_267 | 95.4 | 95.4 | 95.4 | 98.8 | 100.0 | 97.5 |
| 3 268 | 97.8 | 97.0 | 98.6 | 98.8 | 98.5 | 99.2 |

Example 2

<Selection of Ovarian Tumor Gene Marker by Comparison with Benign Bone and Soft Tissue Tumor Patients and Benign Breast Disease Patients and Method for Evaluating Ovarian Tumor Discriminant Performance by Single Gene Marker>

In this Example, miRNAs whose expression levels significantly differ between an ovarian tumor and a set of benign bone and soft tissue tumor and breast benign disease were selected as ovarian tumor gene markers. A discriminant(s) was prepared using one or two gene markers in the training cohort, and then, the discrimination accuracy in the validation cohort was calculated. Based on the calculation, the performance of the gene marker(s) to distinguish an ovarian tumor from benign bone and soft tissue tumor and breast benign disease was evaluated.

Specifically, first, miRNA expression levels in the training cohort and the validation cohort obtained in the Reference Example above were added up and normalized in accordance with global normalization.

Then, a gene for diagnosis was selected. Herein, in order to obtain a more highly reliable diagnostic marker(s), only a gene(s) having a gene expression level of $2^6$ or more in 50% or more samples in either one of a group of ovarian tumor patients or a group of benign bone and soft tissue tumor patients and breast benign disease patients was selected. Next, in order to obtain a gene(s) whose gene expression level significantly differs in statistics between the group of ovarian tumor patients and the group of benign bone and soft tissue tumor patients and breast benign disease patients, a two-sided t-test assuming equal variance was carried out, and then, a gene(s) having a P value obtained after the Bonferroni correction of less than 0.01 was selected. Furthermore, in order to select a gene(s) rarely affected by noise at the time of measurement, a gene(s) having an absolute value of the difference (hold change) in gene expression level, which is obtained by logarithmic conversion between the group of ovarian tumor patients and the group of benign bone and soft tissue tumor patients and breast benign disease patients, and which is larger than 0.5, was selected as diagnostic markers for ovarian tumor and for benign bone and soft tissue tumor and breast benign disease. The results are shown in Table 6.

In this way, hsa-miR-4532, hsa-miR-8073, hsa-miR-320b, hsa-miR-1343-3p, hsa-miR-4730, hsa-miR-5100, hsa-miR-4515, hsa-miR-1273g-3p, hsa-miR-1238-5p, hsa-miR-6515-3p, hsa-miR-4525, hsa-miR-614, hsa-miR-1275, hsa-miR-3679-3p, hsa-miR-4718, hsa-miR-4447, hsa-miR-4448, hsa-miR-6766-3p, hsa-miR-3160-5p, hsa-miR-619-5p, hsa-miR-342-5p, hsa-miR-6872-3p, hsa-miR-6798-3p, hsa-miR-665, hsa-miR-6877-5p, hsa-miR-718, hsa-miR-6717-5p, hsa-miR-1199-5p, hsa-miR-6796-3p, hsa-miR-1292-3p, hsa-miR-365a-5p, hsa-miR-150-3p, hsa-miR-3195, hsa-miR-3679-5p, hsa-miR-6076, hsa-miR-6515-5p, hsa-miR-6820-5p, hsa-miR-4634, hsa-miR-187-5p, hsa-miR-6763-5p, hsa-miR-1908-3p, hsa-miR-1181, hsa-miR-6782-5p, hsa-miR-5010-5p, hsa-miR-320a, hsa-miR-296-5p, hsa-miR-1290, hsa-miR-451a, hsa-miR-625-3p, hsa-miR-642a-3p, hsa-miR-483-5p, and hsa-miR-652-5p genes, and the relevant polynucleotides consisting of the nucleotide sequences of SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269 and 270 were found.

Of them, the genes newly found as a marker for examining the presence or absence of an ovarian tumor are polynucleotides consisting of the nucleotide sequences represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, and 204 to 215.

A discriminant for determining the presence or absence of an ovarian tumor was further prepared by Fisher's discriminant analysis with the expression levels of these genes in the training cohort as indicators. Specifically, the gene expression level of a polynucleotide consisting of the nucleotide sequence represented by any of SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269 and 270 found above was input to Formula 2 to prepare a discriminant. Calculated accuracy, sensitivity, and specificity in the training cohort are shown in Table 7. In this respect, discriminant coefficients and constant terms are shown in Table 8.

Next, accuracy, sensitivity, and specificity in the validation cohort were calculated using the discriminant prepared above and the discriminant performance of the selected polynucleotides was validated using independent samples (Table 7). For example, the rate of detecting an ovarian tumor was calculated using the threshold value (11.59) of the gene expression level of the nucleotide sequence represented by SEQ ID NO: 20, for use in discriminating both groups set in the training cohort. As a result, 122 true positives, 110 true negatives, 1 false positive and 9 false negatives were obtained in the validation cohort. From these values, 95.9% accuracy, 93.1% sensitivity, and 99.1% specificity were obtained as the detection performance. Similarly, the sensitivities of all polynucleotides represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269 and 270 were 69.5%, 76.3%, 89.3%, 73.3%, 71.8%, 93.1%, 70.2%, 73.3%, 78.6%, 81.7%, 62.6%, 71.0%, 75.6%, 78.6%, 74.8%, 81.7%, 68.7%, 82.4%, 72.5%, 81.7%, 64.9%, 81.7%, 84.0%, 80.2%, 77.1%, 87.0%, 64.1%, 80.9%, 89.3%, 87.8%, 68.7%, 77.1%, 84.7%, 66.4%, 75.6%, 61.1%, 68.7%, 73.3%, 79.4%, 61.8%, 81.7%, 84.0%, 60.3%, 80.9%, 80.9%, 87.8%, 96.2%, 69.5%, 76.3%, 71.8%, 66.4% and 79.4%, respectively; and the specificities thereof were 61.3%, 67.6%, 53.2%, 53.2%, 45.9%, 99.1%, 45.0%, 61.3%, 62.2%, 57.7%, 64.0%, 55.0%, 65.8%, 49.5%, 28.8%, 40.5%, 36.0%, 48.6%, 37.8%, 49.5%, 56.8%, 40.5%, 39.6%, 62.2%, 65.8%, 43.2%, 68.5%, 43.2%, 28.8%, 51.4%, 65.8%, 40.5%, 61.3%, 73.0%, 49.5%, 74.8%, 73.0%, 55.0%, 48.6%, 59.5%, 44.1%, 37.8%, 71.2%, 32.4%, 50.5%, 76.6%, 89.2%, 49.5%, 47.7%, 56.8%, 72.1% and 41.4%, respectively (Table 7).

Also, a discriminant was constructed using each of all polynucleotides represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269 and 270 in combination with another polynucleotide appropriately selected; in other words, discriminants each were constructed using two polynucleotides. The discrimination accuracy of an ovarian tumor in the validation cohort by the discriminants thus constructed increased compared with the discriminants using individual genes alone. Specifically, discriminants prepared using combinations of SEQ ID NOs: 256 and 4, 260 and 9, 256 and 14, 20 and 17, 20 and 18, 20 and 69, 20 and 29, 256 and 40, 260 and 47, 20 and 62, 20 and 66, 20 and 69, 20 and 78, 260 and 82, 20 and 83, 207 and 86, 20 and 87, 20 and 89, 20 and 116, 260 and 125, 20 and 127, 20 and 132, 260 and 135, 20 and 136, 147 and 164, 256 and 163, 20 and 164, 260 and 167, 20 and 174, 20 and 177, 260 and 184, 260 and 193, 260 and 204, 260 and 205, 260 and 206, 20 and 207, 260 and 208, 20 and 209, 256 and 210, 260 and 211, 256 and 212, 20 and 213, 20 and 214, 20 and 215, 269 and 248, 260 and 256, 260 and 69, 20 and 264, 20 and 265, 260 and 268, 20 and 269, and 260 and 270 had discrimination accuracies, in the validation cohort, of 83.5%, 93.8%, 86.8%, 97.5%, 96.3%, 99.6%, 96.7%, 83.9%, 93.4%, 96.3%, 97.9%, 99.6%, 97.5%, 94.2%, 97.5%, 77.3%, 97.9%, 96.3%, 96.7%, 93.4%, 98.8%, 96.3%, 93.8%, 97.1%, 90.9%, 83.1%, 97.5%, 93.4%, 96.3%, 96.3%, 96.7%, 93.4%, 93.8%, 93.4%, 93.4%, 98.3%, 95.9%, 96.3%, 84.3%, 95.5%, 85.1%, 96.30, 96.30, 96.30, 87.2%, 97.5%, 98.3%, 96.7%, 96.3%, 93.4%, 96.3% and 93.8%, respectively (Table 9).

From the above, all polynucleotides consisting of the nucleotide sequences represented by SEQ ID NOs: 4, 9, 14, 17, 18, 20, 29, 40, 47, 62, 66, 69, 78, 82, 83, 86, 87, 89, 116, 125, 127, 132, 135, 136, 147, 163, 164, 167, 174, 177, 184, 193, 204 to 215, 248, 256, 260, 264, 265, 268, 269 and 270 are genes or nucleic acids capable of discriminating an ovarian tumor patient from benign bone and soft tissue tumor patients and benign breast disease patients with high accuracy if these are used singly or in combinations of two or more.

TABLE 6

| SEQ ID NO. | Name of gene | P value after Bonferroni correction | Fold change of benign bone and soft tissue tumor patient and benign breast disease patient to ovarian tumor patient |
|---|---|---|---|
| 4 | hsa-miR-4532 | 1.94.E−22 | −0.67 |
| 9 | hsa-miR-8073 | 5.36.E−53 | −0.97 |
| 14 | hsa-miR-320b | 2.63.E−37 | −1.11 |
| 17 | hsa-miR-1343-3p | 2.00.E−20 | −0.53 |
| 18 | hsa-miR-4730 | 1.19.E−11 | −0.60 |
| 20 | hsa-miR-5100 | 4.36.E−235 | −3.07 |
| 29 | hsa-miR-4515 | 8.99.E−13 | −0.69 |
| 40 | hsa-miR-1273g-3p | 1.55.E−30 | −0.91 |
| 47 | hsa-miR-1238-5p | 4.28.E−35 | −1.03 |
| 62 | hsa-miR-6515-3p | 3.65.E−40 | −0.52 |
| 66 | hsa-miR-4525 | 3.74.E−26 | −1.08 |
| 69 | hsa-miR-614 | 2.07.E−10 | 0.52 |
| 78 | hsa-miR-1275 | 7.46.E−34 | −0.59 |
| 82 | hsa-miR-3679-3p | 1.01.E−21 | −0.51 |
| 83 | hsa-miR-4718 | 3.14.E−03 | −0.55 |
| 86 | hsa-miR-4447 | 2.33.E−14 | −0.55 |
| 87 | hsa-miR-4448 | 2.82.E−06 | −0.64 |
| 89 | hsa-miR-6766-3p | 4.01.E−29 | −0.71 |
| 116 | hsa-miR-3160-5p | 4.57.E−09 | −0.84 |
| 125 | hsa-miR-619-5p | 2.81.E−15 | −0.97 |
| 127 | hsa-miR-342-5p | 8.24.E−09 | 0.63 |
| 132 | hsa-miR-6872-3p | 3.39.E−10 | −0.57 |
| 135 | hsa-miR-6798-3p | 7.08.E−28 | −0.88 |
| 136 | hsa-miR-665 | 1.06.E−38 | −0.91 |
| 147 | hsa-miR-6877-5p | 1.32.E−40 | −0.69 |
| 163 | hsa-miR-718 | 1.44.E−14 | −0.55 |
| 164 | hsa-miR-6717-5p | 1.85.E−22 | 1.07 |
| 167 | hsa-miR-1199-5p | 3.54.E−16 | −0.72 |
| 174 | hsa-miR-6796-3p | 7.02.E−13 | −0.53 |
| 177 | hsa-miR-1292-3p | 4.01.E−28 | −0.90 |
| 184 | hsa-miR-365a-5p | 4.94.E−24 | 0.54 |
| 193 | hsa-miR-150-3p | 1.94.E−08 | −0.53 |
| 204 | hsa-miR-3195 | 1.78.E−43 | −0.70 |
| 205 | hsa-miR-3679-5p | 3.16.E−37 | 0.65 |
| 206 | hsa-miR-6076 | 1.67.E−31 | −0.73 |
| 207 | hsa-miR-6515-5p | 2.68.E−28 | 1.21 |
| 208 | hsa-miR-6820-5p | 1.67.E−23 | 0.50 |
| 209 | hsa-miR-4634 | 1.10.E−22 | −0.52 |
| 210 | hsa-miR-187-5p | 1.01.E−17 | −0.55 |
| 211 | hsa-miR-6763-5p | 1.15.E−12 | 0.55 |

TABLE 6-continued

| SEQ ID NO. | Name of gene | P value after Bonferroni correction | Fold change of benign bone and soft tissue tumor patient and benign breast disease patient to ovarian tumor patient |
|---|---|---|---|
| 212 | hsa-miR-1908-3p | 1.07.E−11 | −0.58 |
| 213 | hsa-miR-1181 | 1.31.E−10 | −0.52 |
| 214 | hsa-miR-6782-5p | 1.68.E−09 | 0.53 |
| 215 | hsa-miR-5010-5p | 3.83.E−06 | 0.59 |
| 248 | hsa-miR-320a | 1.60.E−23 | −0.65 |
| 256 | hsa-miR-296-5p | 1.90.E−87 | −0.68 |
| 260 | hsa-miR-1290 | 7.49.E−208 | −4.86 |

TABLE 6-continued

| SEQ ID NO. | Name of gene | P value after Bonferroni correction | Fold change of benign bone and soft tissue tumor patient and benign breast disease patient to ovarian tumor patient |
|---|---|---|---|
| 264 | hsa-miR-451a | 1.06.E−21 | −1.55 |
| 265 | hsa-miR-625-3p | 6.47.E−20 | −0.80 |
| 268 | hsa-miR-642a-3p | 7.46.E−21 | −0.66 |
| 269 | hsa-miR-483-5p | 9.83.E−30 | 1.00 |
| 270 | hsa-miR-652-5p | 1.89.E−12 | −0.69 |

TABLE 7

| | Training cohort | | | Validation cohort | | |
|---|---|---|---|---|---|---|
| SEQ ID NO. | Accuracy (%) | Sensitivity (%) | Specificity (%) | Accuracy (%)) | Sensitivity (%) | Specificity (%) |
| 4 | 66.8 | 78.5 | 52.9 | 65.7 | 69.5 | 61.3 |
| 9 | 73.4 | 78.2 | 67.7 | 72.3 | 76.3 | 67.6 |
| 14 | 69.6 | 82.2 | 54.9 | 72.7 | 89.3 | 53.2 |
| 17 | 63.6 | 71.9 | 53.7 | 64.0 | 73.3 | 53.2 |
| 18 | 66.4 | 78.9 | 51.8 | 59.9 | 71.8 | 45.9 |
| 20 | 95.7 | 93.1 | 98.8 | 95.9 | 93.1 | 99.1 |
| 29 | 58.6 | 70.3 | 44.7 | 58.7 | 70.2 | 45.0 |
| 40 | 69.6 | 76.6 | 61.5 | 67.8 | 73.3 | 61.3 |
| 47 | 68.0 | 75.9 | 58.8 | 71.1 | 78.6 | 62.2 |
| 62 | 73.4 | 80.9 | 64.6 | 70.7 | 81.7 | 57.7 |
| 66 | 64.8 | 66.3 | 63.0 | 63.2 | 62.6 | 64.0 |
| 69 | 59.6 | 71.0 | 46.3 | 63.6 | 71.0 | 55.0 |
| 78 | 70.4 | 73.9 | 66.1 | 71.1 | 75.6 | 65.8 |
| 82 | 67.0 | 80.5 | 51.0 | 65.3 | 78.6 | 49.5 |
| 83 | 56.6 | 78.9 | 30.4 | 53.7 | 74.8 | 28.8 |
| 86 | 61.6 | 81.8 | 37.7 | 62.8 | 81.7 | 40.5 |
| 87 | 57.0 | 71.6 | 39.7 | 53.7 | 68.7 | 36.0 |
| 89 | 70.4 | 83.5 | 54.9 | 66.9 | 82.4 | 48.6 |
| 116 | 55.5 | 70.3 | 38.1 | 56.6 | 72.5 | 37.8 |
| 125 | 64.3 | 78.2 | 47.9 | 66.9 | 81.7 | 49.5 |
| 127 | 59.3 | 65.0 | 52.5 | 61.2 | 64.9 | 56.8 |
| 132 | 61.1 | 82.2 | 36.2 | 62.8 | 81.7 | 40.5 |
| 135 | 73.4 | 88.4 | 55.6 | 63.6 | 84.0 | 39.6 |
| 136 | 74.8 | 84.8 | 63.0 | 71.9 | 80.2 | 62.2 |
| 147 | 71.2 | 73.9 | 68.1 | 71.9 | 77.1 | 65.8 |
| 163 | 70.9 | 89.4 | 49.0 | 66.9 | 87.0 | 43.2 |
| 164 | 63.4 | 62.7 | 64.2 | 66.1 | 64.1 | 68.5 |
| 167 | 63.4 | 78.9 | 45.1 | 63.6 | 80.9 | 43.2 |
| 174 | 63.4 | 85.8 | 37.0 | 61.6 | 89.3 | 28.8 |
| 177 | 68.0 | 85.1 | 47.9 | 71.1 | 87.8 | 51.4 |
| 184 | 65.2 | 67.7 | 62.3 | 67.4 | 68.7 | 65.8 |
| 193 | 60.5 | 82.2 | 35.0 | 60.3 | 77.1 | 40.5 |
| 204 | 77.1 | 88.4 | 63.8 | 74.0 | 84.7 | 61.3 |
| 205 | 72.0 | 73.9 | 69.6 | 69.4 | 66.4 | 73.0 |
| 206 | 69.8 | 77.6 | 60.7 | 63.6 | 75.6 | 49.5 |
| 207 | 68.4 | 66.0 | 71.2 | 67.4 | 61.1 | 74.8 |
| 208 | 68.8 | 70.0 | 67.3 | 70.7 | 68.7 | 73.0 |
| 209 | 70.9 | 79.2 | 61.1 | 64.9 | 73.3 | 55.0 |
| 210 | 69.8 | 82.2 | 55.3 | 65.3 | 79.4 | 48.6 |
| 211 | 60.2 | 67.7 | 51.4 | 60.7 | 61.8 | 59.5 |
| 212 | 64.1 | 82.8 | 42.0 | 64.5 | 81.7 | 44.1 |
| 213 | 62.5 | 84.5 | 36.6 | 62.8 | 84.0 | 37.8 |
| 214 | 66.1 | 67.7 | 64.2 | 65.3 | 60.3 | 71.2 |
| 215 | 57.7 | 81.2 | 30.0 | 58.7 | 80.9 | 32.4 |
| 248 | 64.3 | 75.6 | 51.0 | 66.9 | 80.9 | 50.5 |
| 256 | 79.3 | 83.8 | 73.9 | 82.6 | 87.8 | 76.6 |
| 260 | 93.6 | 94.7 | 92.2 | 93.0 | 96.2 | 89.2 |
| 264 | 65.5 | 77.2 | 51.8 | 60.3 | 69.5 | 49.5 |
| 265 | 67.3 | 82.5 | 49.4 | 63.2 | 76.3 | 47.7 |
| 268 | 64.1 | 69.0 | 58.4 | 64.9 | 71.8 | 56.8 |
| 269 | 69.6 | 70.0 | 69.3 | 69.0 | 66.4 | 72.1 |
| 270 | 61.6 | 78.5 | 41.6 | 62.0 | 79.4 | 41.4 |

TABLE 8

| SEQ ID NO. | Coefficient | Constant term |
|---|---|---|
| 4 | 1.163 | 15.873 |
| 9 | 1.284 | 9.651 |
| 14 | 0.874 | 5.236 |
| 17 | 1.441 | 10.642 |
| 18 | 0.889 | 6.725 |
| 20 | 1.095 | 12.683 |
| 29 | 0.867 | 5.603 |
| 40 | 0.985 | 8.121 |
| 47 | 0.939 | 6.768 |
| 62 | 1.991 | 14.542 |
| 66 | 0.800 | 8.178 |
| 69 | 1.039 | 10.209 |
| 78 | 1.705 | 13.533 |
| 82 | 1.520 | 10.204 |
| 83 | 0.601 | 4.544 |
| 86 | 1.088 | 7.271 |
| 87 | 0.642 | 5.196 |
| 89 | 1.250 | 7.650 |
| 116 | 0.585 | 3.824 |
| 125 | 0.635 | 4.619 |
| 127 | 0.756 | 4.670 |
| 132 | 0.889 | 4.985 |
| 135 | 0.956 | 5.435 |
| 136 | 1.078 | 7.870 |
| 147 | 1.515 | 11.241 |
| 163 | 1.101 | 7.632 |
| 164 | 0.695 | 4.807 |

TABLE 8-continued

| SEQ ID NO. | Coefficient | Constant term |
|---|---|---|
| 167 | 0.894 | 4.845 |
| 174 | 1.038 | 6.049 |
| 177 | 0.942 | 5.418 |
| 184 | 1.423 | 10.156 |
| 193 | 0.891 | 5.086 |
| 204 | 1.598 | 13.356 |
| 205 | 1.574 | 12.205 |
| 206 | 1.283 | 9.375 |
| 207 | 0.712 | 3.814 |
| 208 | 1.578 | 11.937 |
| 209 | 1.474 | 13.007 |
| 210 | 1.184 | 9.382 |
| 211 | 1.069 | 7.298 |
| 212 | 0.963 | 6.212 |
| 213 | 0.992 | 5.528 |
| 214 | 0.956 | 5.581 |
| 215 | 0.681 | 3.993 |
| 248 | 1.158 | 7.969 |
| 256 | 2.371 | 18.848 |
| 260 | 0.629 | 4.171 |
| 264 | 0.481 | 2.967 |
| 265 | 0.895 | 5.115 |
| 268 | 1.077 | 8.405 |
| 269 | 0.861 | 5.053 |
| 270 | 0.831 | 4.838 |

TABLE 9

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 256_4 | 84.1 | 90.1 | 77.0 | 83.5 | 83.2 | 83.8 |
| 260_9 | 93.4 | 95.0 | 91.4 | 93.8 | 96.2 | 91.0 |
| 256_14 | 82.3 | 87.1 | 76.7 | 86.8 | 92.4 | 80.2 |
| 20_17 | 96.1 | 94.4 | 98.1 | 97.5 | 96.9 | 98.2 |
| 20_18 | 95.4 | 92.7 | 98.4 | 96.3 | 93.9 | 99.1 |
| 20_69 | 98.6 | 98.3 | 98.8 | 99.6 | 100.0 | 99.1 |
| 20_29 | 96.4 | 94.4 | 98.8 | 96.7 | 95.4 | 98.2 |
| 256_40 | 80.4 | 85.1 | 74.7 | 83.9 | 87.0 | 80.2 |
| 260_47 | 93.4 | 94.7 | 91.8 | 93.4 | 96.2 | 90.1 |
| 20_62 | 96.4 | 94.4 | 98.8 | 96.3 | 93.9 | 99.1 |
| 20_66 | 96.4 | 94.4 | 98.8 | 97.9 | 96.9 | 99.1 |
| 20_69 | 98.6 | 98.3 | 98.8 | 99.6 | 100.0 | 99.1 |
| 20_78 | 96.4 | 94.4 | 98.8 | 97.5 | 95.4 | 100.0 |
| 260_82 | 93.4 | 95.4 | 91.1 | 94.2 | 96.2 | 91.9 |
| 20_83 | 96.8 | 95.4 | 98.4 | 97.5 | 96.9 | 98.2 |
| 207_86 | 79.1 | 80.9 | 77.0 | 77.3 | 74.0 | 81.1 |
| 20_87 | 96.2 | 93.7 | 99.2 | 97.9 | 96.9 | 99.1 |
| 20_89 | 95.7 | 93.1 | 98.8 | 96.3 | 93.9 | 99.1 |
| 20_116 | 96.2 | 94.1 | 98.8 | 96.7 | 95.4 | 98.2 |
| 260_125 | 93.4 | 94.4 | 92.2 | 93.4 | 96.2 | 90.1 |
| 20_127 | 98.0 | 97.0 | 99.2 | 98.8 | 98.5 | 99.1 |
| 20_132 | 95.9 | 93.1 | 99.2 | 96.3 | 93.9 | 99.1 |
| 260_135 | 94.5 | 95.0 | 93.8 | 93.8 | 95.4 | 91.9 |
| 20_136 | 96.1 | 94.1 | 98.4 | 97.1 | 95.4 | 99.1 |
| 147_164 | 88.4 | 88.8 | 87.9 | 90.9 | 91.6 | 90.1 |
| 256_163 | 80.2 | 85.8 | 73.5 | 83.1 | 88.5 | 76.6 |
| 20_164 | 97.1 | 95.4 | 99.2 | 97.5 | 96.2 | 99.1 |
| 260_167 | 93.4 | 95.0 | 91.4 | 93.4 | 95.4 | 91.0 |
| 20_174 | 95.9 | 93.1 | 99.2 | 96.3 | 93.9 | 99.1 |
| 20_177 | 95.7 | 93.1 | 98.8 | 96.3 | 93.9 | 99.1 |
| 260_184 | 95.7 | 97.0 | 94.2 | 96.7 | 96.9 | 96.4 |
| 260_193 | 93.2 | 94.7 | 91.4 | 93.4 | 96.2 | 90.1 |
| 260_204 | 93.4 | 95.0 | 91.4 | 93.8 | 96.2 | 91.0 |
| 260_205 | 94.5 | 95.4 | 93.4 | 93.4 | 94.7 | 91.9 |
| 260_206 | 93.9 | 95.0 | 92.6 | 93.4 | 96.2 | 90.1 |
| 20_207 | 96.8 | 94.7 | 99.2 | 98.3 | 98.5 | 98.2 |
| 260_208 | 96.1 | 97.0 | 94.9 | 95.9 | 95.4 | 96.4 |
| 20_209 | 95.5 | 92.7 | 98.8 | 96.3 | 93.9 | 99.1 |
| 256_210 | 81.2 | 86.8 | 74.7 | 84.3 | 88.5 | 79.3 |

TABLE 9-continued

| SEQ ID NO. | Training cohort Accuracy (%) | Sensitivity (%) | Specificity (%) | Validation cohort Accuracy (%) | Sensitivity (%) | Specificity (%) |
|---|---|---|---|---|---|---|
| 260_211 | 95.0 | 96.0 | 93.8 | 95.5 | 96.2 | 94.6 |
| 256_212 | 82.3 | 87.5 | 76.3 | 85.1 | 90.1 | 79.3 |
| 20_213 | 95.5 | 92.7 | 98.8 | 96.3 | 93.9 | 99.1 |
| 20_214 | 95.7 | 93.1 | 98.8 | 96.3 | 94.7 | 98.2 |
| 20_215 | 95.5 | 92.7 | 98.8 | 96.3 | 93.9 | 99.1 |
| 269_248 | 78.2 | 79.2 | 77.0 | 87.2 | 86.3 | 88.3 |
| 260_256 | 95.9 | 97.0 | 94.6 | 97.5 | 97.7 | 97.3 |
| 260_69 | 97.7 | 98.3 | 96.9 | 98.3 | 98.5 | 98.2 |
| 20_264 | 95.9 | 93.4 | 98.8 | 96.7 | 94.7 | 99.1 |
| 20_265 | 95.5 | 92.7 | 98.8 | 96.3 | 93.9 | 99.1 |
| 260_268 | 93.8 | 95.0 | 92.2 | 93.4 | 96.2 | 90.1 |
| 20_269 | 95.5 | 92.7 | 98.8 | 96.3 | 93.9 | 99.1 |
| 260_270 | 93.4 | 95.7 | 90.7 | 93.8 | 95.4 | 91.9 |

Example 3

<Selection of Ovarian Tumor Gene Marker by Comparison with Patients Having a Cancer Other than Ovarian Cancer and Method for Evaluating Ovarian Tumor Discriminant Performance by Single Gene Marker>

In this Example, miRNAs whose expression level significantly differs between an ovarian tumor and a cancer other than ovarian cancer, such as breast cancer, biliary cancer, pancreatic cancer, colorectal cancer, esophagus cancer, stomach cancer, liver cancer and lung cancer, were selected as ovarian tumor gene markers. A discriminant(s) was prepared using one or two gene markers in the training cohort, and then, the discrimination accuracy in the validation cohort was calculated. Based on the calculation, the performance of the gene marker(s) to distinguish an ovarian tumor from a cancer other than ovarian cancer was evaluated.

Specifically, first, miRNA expression levels in the training cohort and the validation cohort obtained in the Reference Example above were added up and normalized in accordance with global normalization.

Then, genes for diagnosis were selected. Herein, in order to obtain a more highly reliable diagnostic marker, only a gene having a gene expression level of $2^6$ or more in 50% or more samples in either one of a group of ovarian tumor patients or a group of patients having a cancer other than ovarian cancer was selected. Next, in order to obtain a gene(s) whose gene expression level significantly differs in statistics between the ovarian tumor patient group or the group of patients having a cancer other than ovarian cancer, a two-sided t-test assuming equal variance was carried out and a gene(s) having a P value obtained after the Bonferroni correction of less than 0.01 was selected. Furthermore, in order to select a gene(s) rarely affected by noise at the time of measurement, a gene(s) having an absolute value of the difference (hold change) in gene expression level, which is obtained by logarithmic conversion, between the group of ovarian tumor patients and the group of patients having a cancer other than ovarian cancer, and which is larger than 0.5, was selected as a diagnostic marker(s) for an ovarian tumor and a cancer other than ovarian cancer. The results are shown in Table 10.

In this way, hsa-miR-4532, hsa-miR-1233-5p, hsa-miR-1343-3p, hsa-miR-6787-5p, hsa-miR-614, hsa-miR-939-5p, hsa-miR-1275, hsa-miR-3679-3p, hsa-miR-8059, hsa-miR-6766-3p, hsa-miR-6131, hsa-miR-3194-3p, hsa-miR-2467-3p, hsa-miR-8063, hsa-miR-342-5p, hsa-miR-4433a-5p, hsa-miR-6798-3p, hsa-miR-7150, hsa-miR-6746-5p, hsa-miR-6717-5p, hsa-miR-6769a-5p, hsa-miR-3131, hsa-miR-6510-5p, hsa-miR-6515-5p, hsa-miR-6763-5p, hsa-miR-6870-5p, hsa-miR-6124, hsa-miR-1249-5p, hsa-miR-6511b-5p, hsa-miR-1254, hsa-miR-4727-3p, hsa-miR-4259, hsa-miR-4771, hsa-miR-3622a-5p, hsa-miR-4480, hsa-miR-4740-5p, hsa-miR-6777-5p, hsa-miR-451a, hsa-miR-92a-3p, hsa-miR-422a, hsa-miR-642a-3p, hsa-miR-24-3p, hsa-miR-23b-3p, hsa-miR-23a-3p, hsa-miR-92b-3p and hsa-miR-22-3p genes, and the relevant polynucleotides consisting of the nucleotide sequences of SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, 264, 266, 267, 268, 271, 272, 273, 274 and 275 were found.

Of them, the genes newly found as the marker for examining the presence or absence of an ovarian tumor are polynucleotides consisting of the nucleotide sequences represented by SEQ ID NOs: 4, 11, 17, 68, 69, 76, 78, 82, 85, 89, 99, 103, 105, 109, 127, 128, 135, 145, 160, 164, 169, 196, 198, 207, 211 and 216 to 227.

A discriminant for determining the presence or absence of an ovarian tumor was further prepared by Fisher's discriminant analysis with the expression levels of these genes in the training cohort as indicators. Specifically, the gene expression level of a polynucleotide consisting of the nucleotide sequence represented by any of SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, 264, 266, 267, 268, 271, 272, 273, 274 and 275 found above was input to Formula 2 to prepare a discriminant. Calculated accuracy, sensitivity, and specificity in the training cohort are shown in Table 11. In this respect, discriminant coefficients and constant terms are shown in Table 12.

Next, accuracy, sensitivity, and specificity in the validation cohort were calculated using the discriminant prepared above and the discriminant performance of the selected polynucleotides was validated using independent samples (Table 11). For example, the rate of detecting an ovarian tumor was calculated using the threshold value (8.07) of the gene expression level of the nucleotide sequence represented by SEQ ID NO: 17, for use in discriminating both groups set in the training cohort. As a result, 97 true positives, 74 true negatives, 46 false positives and 34 false negatives were obtained in the validation cohort. From these values, 68.1% accuracy, 74.0% sensitivity, and 61.7% specificity were obtained as the detection performance. Similarly, the sensitivities of all polynucleotides represented by SEQ ID NOs: 4, 11, 17, 68, 69, 76, 78, 82, 85, 89, 99, 103, 105, 109, 127, 128, 135, 145, 160, 164, 169, 196, 198, 207, 211, and 216 to 227 were 65.6%, 62.6%, 74.0%, 74.8%, 67.9%, 63.4%, 74.0%, 77.1%, 67.9%, 80.2%, 61.1%, 65.6%, 68.7%, 64.9%, 60.3%, 80.9%, 80.2%, 74.8%, 54.2%, 64.1%, 63.4%, 58.8%, 77.1%, 57.3%, 61.1%, 80.9%, 78.6%, 71.8%, 58.8%, 59.5%, 71.0%, 54.2%, 66.4%, 55.7%, 65.6%, 66.4%, 48.9%, 70.2%, 62.6%, 77.1%, 63.4%, 62.6%, 65.6%, 67.2%, 61.1% and 63.4%, respectively, and the specificities thereof were 51.7%, 59.2%, 61.7%, 60.0%, 71.7%, 66.7%, 60.0%, 58.3%, 66.7%, 47.5%, 71.7%, 57.5%, 48.3%, 50.0%, 72.5%, 40.0%, 46.7%, 65.0%, 66.7%, 82.5%, 70.0%, 61.7%, 45.0%, 81.7%, 66.7%, 49.2%, 56.7%, 50.0%, 65.8%, 67.5%, 62.5%, 65.8%, 61.7%, 61.7%, 60.8%, 55.0%, 60.0%, 65.0%, 67.5%, 39.2%, 53.3%, 68.3%, 64.2%, 63.3%, 64.2% and 63.3%, respectively (Table 11).

Also, a discriminant was constructed using each of all polynucleotides represented by SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, 264, 266, 267, 268, 271, 272, 273, 274 and 275 in combination with another polynucleotide appropriately selected; in other words, discriminants each were constructed using two polynucleotides. The discrimination accuracy of an ovarian tumor in the validation cohort by the discriminants thus constructed increased, compared with the discriminants using individual genes alone. Specifically, discriminants prepared using combinations of SEQ ID NOs: 164 and 4, 17 and 11, 17 and 82, 82 and 68, 69 and 82, 82 and 76, 164 and 78, 164 and 82, 82 and 85, 164 and 89, 145 and 99, 217 and 103, 164 and 105, 69 and 109, 82 and 127, 164 and 128, 17 and 135, 145 and 164, 82 and 160, 164 and 82, 82 and 169, 82 and 196, 164 and 198, 82 and 207, 82 and 211, 164 and 216, 164 and 217, 164 and 218, 82 and 219, 82 and 220, 82 and 221, 145 and 222, 82 and 223, 78 and 224, 82 and 225, 217 and 226, 82 and 227, 82 and 264, 145 and 266, 145 and 267, 160 and 268, 82 and 271, 82 and 272, 164 and 273, 145 and 274, and 217 and 275 had discrimination accuracies, in the validation cohort, of 73.3%, 74.1%, 80.5%, 76.1%, 79.7%, 80.1%, 78.5%, 83.3%, 79.7%, 82.5%, 73.7%, 72.9%, 74.5%, 71.3%, 79.3%, 77.7%, 77.3% 78.5%, 82.5%, 83.3%, 80.5%, 83.3%, 77.7%, 78.5%, 76.5%, 77.7%, 78.5%, 76.9%, 76.9%, 82.5%, 80.1%, 73.3%, 75.3%, 74.1%, 72.5%, 71.7%, 74.1%, 74.1%, 73.3%, 73.7%, 80.9%, 75.3%, 71.7%, 73.3%, 73.3% and 73.7%, respectively (Table 13).

From the above, all polynucleotides consisting of the nucleotide sequences represented by SEQ ID NOs: 4, 11, 17, 68, 69, 76, 78, 82, 85, 89, 99, 103, 105, 109, 127, 128, 135, 145, 160, 164, 169, 196, 198, 207, 211, 216 to 227, 264, 266, 267, 268, 271, 272, 273, 274 and 275 are genes or nucleic acids capable of discriminating an ovarian tumor patient from patients having a cancer other than ovarian cancer with high accuracy if these are used singly or in combinations of two or more.

TABLE 10

| SEQ ID NO. | Name of gene | P value after Bonferroni correction | Fold change of patient having cancer other than ovarian cancer to ovarian tumor patient |
|---|---|---|---|
| 4 | hsa-miR-4532 | 7.46.E-09 | −0.51 |
| 11 | hsa-miR-1233-5p | 5.68.E-14 | −0.53 |
| 17 | hsa-miR-1343-3p | 1.00.E-30 | 0.90 |
| 68 | hsa-miR-6787-5p | 1.25.E-24 | 0.58 |
| 69 | hsa-miR-614 | 5.61.E-27 | 0.84 |
| 76 | hsa-miR-939-5p | 5.01.E-13 | 0.57 |
| 78 | hsa-miR-1275 | 1.64.E-27 | −0.53 |
| 82 | hsa-miR-3679-3p | 6.03.E-25 | −0.57 |
| 85 | hsa-miR-8059 | 1.86.E-11 | 0.56 |
| 89 | hsa-miR-6766-3p | 1.12.E-22 | −0.65 |
| 99 | hsa-miR-6131 | 5.83.E-09 | 1.24 |
| 103 | hsa-miR-3194-3p | 2.11.E-07 | 0.84 |
| 105 | hsa-miR-2467-3p | 9.35.E-04 | 0.58 |
| 109 | hsa-miR-8063 | 2.24.E-08 | −0.50 |
| 127 | hsa-miR-342-5p | 5.64.E-12 | 0.75 |
| 128 | hsa-miR-4433a-5p | 2.92.E-11 | −0.50 |
| 135 | hsa-miR-6798-3p | 5.26.E-19 | −0.72 |
| 145 | hsa-miR-7150 | 3.07.E-30 | −0.54 |
| 160 | hsa-miR-6746-5p | 7.58.E-15 | 0.63 |
| 164 | hsa-miR-6717-5p | 6.16.E-29 | 1.38 |
| 169 | hsa-miR-6769a-5p | 2.10.E-14 | 0.61 |
| 196 | hsa-miR-3131 | 1.75.E-11 | 0.51 |
| 198 | hsa-miR-6510-5p | 8.28.E-17 | −0.71 |
| 207 | hsa-miR-6515-5p | 4.94.E-24 | 1.18 |
| 211 | hsa-miR-6763-5p | 8.39.E-11 | 0.58 |
| 216 | hsa-miR-6870-5p | 1.33.E-27 | −0.78 |
| 217 | hsa-miR-6124 | 1.25.E-26 | −0.75 |
| 218 | hsa-miR-1249-5p | 1.73.E-21 | −0.78 |
| 219 | hsa-miR-6511b-5p | 1.65.E-15 | 0.87 |
| 220 | hsa-miR-1254 | 8.73.E-14 | 0.69 |
| 221 | hsa-miR-4727-3p | 1.89.E-09 | 0.71 |
| 222 | hsa-miR-4259 | 1.87.E-08 | 0.71 |
| 223 | hsa-miR-4771 | 5.92.E-08 | 0.76 |
| 224 | hsa-miR-3622a-5p | 1.63.E-07 | 0.52 |
| 225 | hsa-miR-4480 | 1.26.E-06 | 0.73 |
| 226 | hsa-miR-4740-5p | 7.43.E-05 | 0.60 |
| 227 | hsa-miR-6777-5p | 1.46.E-04 | 0.50 |
| 264 | hsa-miR-451a | 2.61.E-08 | 0.99 |
| 266 | hsa-miR-92a-3p | 8.20.E-10 | 0.77 |
| 267 | hsa-miR-422a | 2.83.E-08 | −0.67 |
| 268 | hsa-miR-642a-3p | 5.51.E-13 | −0.53 |
| 271 | hsa-miR-24-3p | 5.29.E-14 | 0.91 |
| 272 | hsa-miR-23b-3p | 9.72.E-12 | 1.11 |
| 273 | hsa-miR-23a-3p | 9.52.E-10 | 1.09 |
| 274 | hsa-miR-92b-3p | 2.81.E-09 | 0.73 |
| 275 | hsa-miR-22-3p | 9.10.E-09 | 0.86 |

TABLE 11

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 17 | 65.7 | 77.9 | 52.5 | 68.1 | 74.0 | 61.7 |
| 145 | 65.5 | 70.6 | 60.0 | 70.1 | 74.8 | 65.0 |
| 164 | 67.6 | 61.4 | 74.3 | 72.9 | 64.1 | 82.5 |
| 216 | 69.1 | 79.9 | 57.5 | 65.7 | 80.9 | 49.2 |
| 78 | 66.9 | 71.3 | 62.1 | 67.3 | 74.0 | 60.0 |
| 69 | 67.1 | 68.0 | 66.1 | 69.7 | 67.9 | 71.7 |
| 217 | 65.9 | 75.6 | 55.4 | 68.1 | 78.6 | 56.7 |
| 82 | 67.2 | 78.9 | 54.6 | 68.1 | 77.1 | 58.3 |

TABLE 11-continued

| SEQ ID NO. | Training cohort Accuracy (%) | Training cohort Sensitivity (%) | Training cohort Specificity (%) | Validation cohort Accuracy (%) | Validation cohort Sensitivity (%) | Validation cohort Specificity (%) |
|---|---|---|---|---|---|---|
| 68 | 66.7 | 77.9 | 54.6 | 67.7 | 74.8 | 60.0 |
| 207 | 65.2 | 63.0 | 67.5 | 68.9 | 57.3 | 81.7 |
| 89 | 66.0 | 81.2 | 49.6 | 64.5 | 80.2 | 47.5 |
| 218 | 65.7 | 73.6 | 57.1 | 61.4 | 71.8 | 50.0 |
| 135 | 67.9 | 84.2 | 50.4 | 64.1 | 80.2 | 46.7 |
| 198 | 62.3 | 74.6 | 48.9 | 61.8 | 77.1 | 45.0 |
| 219 | 60.4 | 60.1 | 60.7 | 62.2 | 58.8 | 65.8 |
| 160 | 63.0 | 65.0 | 60.7 | 60.2 | 54.2 | 66.7 |
| 169 | 59.0 | 60.4 | 57.5 | 66.5 | 63.4 | 70.0 |
| 271 | 60.9 | 59.1 | 62.9 | 65.3 | 62.6 | 68.3 |
| 11 | 64.0 | 65.0 | 62.9 | 61.0 | 62.6 | 59.2 |
| 220 | 61.7 | 63.0 | 60.4 | 63.3 | 59.5 | 67.5 |
| 76 | 63.0 | 63.4 | 62.5 | 64.9 | 63.4 | 66.7 |
| 268 | 58.8 | 65.0 | 52.1 | 58.6 | 63.4 | 53.3 |
| 127 | 62.6 | 61.1 | 64.3 | 66.1 | 60.3 | 72.5 |
| 272 | 60.0 | 64.4 | 55.4 | 64.9 | 65.6 | 64.2 |
| 196 | 62.8 | 68.3 | 56.8 | 60.2 | 58.8 | 61.7 |
| 85 | 61.7 | 65.3 | 57.9 | 67.3 | 67.9 | 66.7 |
| 128 | 62.6 | 80.2 | 43.6 | 61.4 | 80.9 | 40.0 |
| 211 | 64.5 | 64.0 | 65.0 | 63.7 | 61.1 | 66.7 |
| 266 | 60.0 | 62.4 | 57.5 | 64.9 | 62.6 | 67.5 |
| 273 | 59.9 | 64.4 | 55.0 | 65.3 | 67.2 | 63.3 |
| 221 | 62.4 | 65.7 | 58.9 | 66.9 | 71.0 | 62.5 |
| 274 | 61.6 | 66.0 | 56.8 | 62.5 | 61.1 | 64.2 |
| 99 | 59.5 | 53.8 | 65.7 | 66.1 | 61.1 | 71.7 |
| 4 | 62.1 | 77.6 | 45.4 | 59.0 | 65.6 | 51.7 |
| 275 | 57.6 | 60.7 | 54.3 | 63.3 | 63.4 | 63.3 |
| 222 | 59.7 | 62.0 | 57.1 | 59.8 | 54.2 | 65.8 |
| 109 | 60.9 | 71.0 | 50.0 | 57.8 | 64.9 | 50.0 |
| 264 | 58.0 | 62.0 | 53.6 | 67.7 | 70.2 | 65.0 |
| 267 | 58.0 | 73.9 | 40.7 | 59.0 | 77.1 | 39.2 |
| 223 | 62.8 | 64.0 | 61.4 | 64.1 | 66.4 | 61.7 |
| 224 | 56.6 | 61.1 | 51.8 | 58.6 | 55.7 | 61.7 |
| 103 | 59.2 | 63.7 | 54.3 | 61.8 | 65.6 | 57.5 |
| 225 | 59.9 | 63.4 | 56.1 | 63.3 | 65.6 | 60.8 |
| 226 | 59.2 | 61.7 | 56.4 | 61.0 | 66.4 | 55.0 |
| 227 | 55.7 | 56.8 | 54.6 | 54.2 | 48.9 | 60.0 |
| 105 | 59.3 | 68.0 | 50.0 | 59.0 | 68.7 | 48.3 |

TABLE 12

| SEQ ID NO. | Coefficient | Constant term |
|---|---|---|
| 4 | 0.922 | 12.664 |
| 11 | 1.105 | 14.004 |
| 17 | 0.960 | 7.747 |
| 68 | 1.375 | 12.584 |
| 69 | 0.985 | 9.816 |
| 76 | 0.965 | 6.289 |
| 78 | 1.556 | 12.359 |
| 82 | 1.331 | 8.889 |
| 85 | 0.947 | 9.520 |
| 89 | 1.112 | 6.837 |
| 99 | 0.380 | 3.958 |
| 103 | 0.509 | 3.812 |
| 105 | 0.585 | 5.043 |
| 109 | 0.897 | 7.611 |
| 127 | 0.695 | 4.323 |
| 128 | 1.011 | 5.816 |
| 135 | 0.904 | 5.237 |
| 145 | 1.582 | 13.004 |
| 160 | 0.891 | 6.528 |
| 164 | 0.601 | 4.237 |
| 169 | 0.977 | 7.088 |
| 196 | 1.000 | 7.867 |
| 198 | 0.884 | 5.915 |
| 207 | 0.644 | 3.437 |
| 211 | 0.882 | 6.012 |
| 216 | 1.037 | 7.417 |
| 217 | 1.063 | 7.712 |
| 218 | 0.904 | 6.645 |
| 219 | 0.688 | 3.697 |

TABLE 12-continued

| SEQ ID NO. | Coefficient | Constant term |
|---|---|---|
| 220 | 0.807 | 4.862 |
| 221 | 0.652 | 3.708 |
| 222 | 0.646 | 3.514 |
| 223 | 0.586 | 3.132 |
| 224 | 0.826 | 4.941 |
| 225 | 0.562 | 3.235 |
| 226 | 0.614 | 3.688 |
| 227 | 0.697 | 4.274 |
| 264 | 0.463 | 3.401 |
| 266 | 0.636 | 4.190 |
| 267 | 0.670 | 4.758 |
| 268 | 1.011 | 7.943 |
| 271 | 0.631 | 3.810 |
| 272 | 0.482 | 2.852 |
| 273 | 0.448 | 2.494 |
| 274 | 0.661 | 3.646 |
| 275 | 0.544 | 3.116 |

TABLE 13

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 164_4 | 71.0 | 69.6 | 72.5 | 73.3 | 67.9 | 79.2 |
| 17_11 | 73.1 | 81.8 | 63.6 | 74.1 | 79.4 | 68.3 |
| 17_82 | 78.9 | 91.4 | 65.4 | 80.5 | 90.1 | 70.0 |
| 82_68 | 76.2 | 85.5 | 66.1 | 76.1 | 79.4 | 72.5 |
| 69_82 | 75.1 | 81.2 | 68.6 | 79.7 | 81.7 | 77.5 |
| 82_76 | 77.0 | 80.9 | 72.9 | 80.1 | 78.6 | 81.7 |
| 164_78 | 75.8 | 76.9 | 74.6 | 78.5 | 77.9 | 79.2 |
| 164_82 | 80.1 | 82.5 | 77.5 | 83.3 | 81.7 | 85.0 |
| 82_85 | 71.9 | 78.5 | 64.6 | 79.7 | 83.2 | 75.8 |
| 164_89 | 80.1 | 82.8 | 77.1 | 82.5 | 84.0 | 80.8 |
| 145_99 | 67.2 | 69.3 | 65.0 | 73.7 | 79.4 | 67.5 |
| 217_103 | 69.3 | 75.6 | 62.5 | 72.9 | 80.9 | 64.2 |
| 164_105 | 68.6 | 63.4 | 74.3 | 74.5 | 64.9 | 85.0 |
| 69_109 | 68.4 | 71.3 | 65.4 | 71.3 | 69.5 | 73.3 |
| 82_127 | 75.0 | 79.2 | 70.4 | 79.3 | 80.2 | 78.3 |
| 164_128 | 78.2 | 82.2 | 73.9 | 77.7 | 77.9 | 77.5 |
| 17_135 | 75.5 | 86.1 | 63.9 | 77.3 | 87.0 | 66.7 |
| 145_164 | 75.3 | 77.2 | 73.2 | 78.5 | 77.1 | 80.0 |
| 82_160 | 81.6 | 86.5 | 76.4 | 82.5 | 83.2 | 81.7 |
| 164_82 | 80.1 | 82.5 | 77.5 | 83.3 | 81.7 | 85.0 |
| 82_169 | 74.6 | 81.2 | 67.5 | 80.5 | 81.7 | 79.2 |
| 82_196 | 78.9 | 87.8 | 69.3 | 83.3 | 85.5 | 80.8 |
| 164_198 | 75.6 | 76.9 | 74.3 | 77.7 | 77.9 | 77.5 |
| 82_207 | 77.7 | 80.2 | 75.0 | 78.5 | 74.8 | 82.5 |
| 82_211 | 76.5 | 80.5 | 72.1 | 76.5 | 76.3 | 76.7 |
| 164_216 | 76.3 | 78.9 | 73.6 | 77.7 | 80.9 | 74.2 |
| 164_217 | 75.3 | 79.2 | 71.1 | 78.5 | 77.9 | 79.2 |
| 164_218 | 77.2 | 78.9 | 75.4 | 76.9 | 77.1 | 76.7 |
| 82_219 | 76.7 | 81.5 | 71.4 | 76.9 | 75.6 | 78.3 |
| 82_220 | 79.4 | 83.5 | 75.0 | 82.5 | 84.0 | 80.8 |
| 82_221 | 75.1 | 81.8 | 67.9 | 80.1 | 84.7 | 75.0 |
| 145_222 | 69.8 | 75.9 | 63.2 | 73.3 | 74.8 | 71.7 |
| 82_223 | 69.0 | 76.6 | 60.7 | 75.3 | 80.9 | 69.2 |
| 78_224 | 68.8 | 71.3 | 66.1 | 74.1 | 79.4 | 68.3 |
| 82_225 | 69.6 | 77.9 | 60.7 | 72.5 | 80.2 | 64.2 |
| 217_226 | 67.9 | 73.6 | 61.8 | 71.7 | 80.9 | 61.7 |
| 82_227 | 73.1 | 80.2 | 65.4 | 74.1 | 74.8 | 73.3 |
| 82_264 | 70.8 | 78.2 | 62.9 | 74.1 | 79.4 | 68.3 |
| 145_266 | 67.9 | 69.6 | 66.1 | 73.3 | 77.9 | 68.3 |
| 145_267 | 69.0 | 74.6 | 62.9 | 73.7 | 83.2 | 63.3 |
| 160_268 | 80.4 | 77.2 | 83.9 | 80.9 | 77.1 | 85.0 |
| 82_271 | 72.4 | 76.6 | 67.9 | 75.3 | 76.3 | 74.2 |
| 82_272 | 67.9 | 74.6 | 60.7 | 71.7 | 71.0 | 72.5 |
| 164_273 | 68.1 | 64.0 | 72.5 | 73.3 | 64.9 | 82.5 |
| 145_274 | 68.8 | 72.6 | 64.6 | 73.3 | 77.9 | 68.3 |
| 217_275 | 68.6 | 75.2 | 61.4 | 73.7 | 80.2 | 66.7 |

Example 4

<Method for Evaluating Ovarian Tumor Discriminant Performance by Combination of a Plurality of Gene Markers>

In this Example, healthy subjects, benign bone and soft tissue tumor patients and benign breast disease patients, and patients having a cancer other than ovarian cancer (i.e., test subjects having no ovarian tumor) used in Examples 1, 2 and 3 were used as a negative sample group; and ovarian tumor patients were used as a positive sample group. The combinations of gene markers having high performance to discriminate an ovarian tumor were searched.

Specifically, miRNA expression levels in sera of 280 healthy subjects, 257 benign bone and soft tissue tumor patients and benign breast disease patients, 303 ovarian tumor patients, and 280 patients having a cancer other than ovarian cancer obtained in the Reference Example above were used as a training cohort; whereas miRNA expression levels in sera of 120 healthy subjects, 111 benign bone and soft tissue tumor patients and benign breast disease patients, 131 ovarian tumor patients and 120 patients having a cancer other than ovarian cancer were used as a validation cohort.

In order to obtain a more highly reliable diagnostic marker(s), only a gene(s) having a gene expression level of $2^6$ or more in 50% or more samples in either one of a group of ovarian tumor patients or a group of test subjects having no ovarian tumor was selected.

Next, using combinations of 1 to 5 of these genes, discriminants were prepared by the Fisher's discriminant analysis and using the training cohort. Of the discriminants, those having the top to 30th ovarian tumor discriminant performance were searched for each of the above combinations of the genes. In the search, a modified greedy algorithm was used. Specifically, 30 genes singly showing satisfactory discriminant performance are used as pivots. Each of the genes used as pivots is used in combination with other genes and the Fisher's discriminant analysis was carried out. Discriminants (constituted of two genes) having the top to 30th discriminant performance are used as new pivots. This operation was repeated until the number of combined genes reached 5. In this manner, 150 discriminants for combined gene numbers having the top-level discriminant performance were obtained. As the genes constituting these discriminants, 73 genes represented by SEQ ID NOs: 2, 3, 4, 9, 11, 13, 15, 20, 33, 34, 38, 40, 44, 47, 56, 62, 68, 77, 78, 80, 82, 86, 89, 90, 91, 102, 104, 109, 117, 118, 135, 136, 145, 150, 157, 160, 161, 164, 169, 172, 196, 199, 211, 216, 217, 218, 220, 228 to 247, 250, 252, 256, 260, 267 and 268 were obtained (Table 14). Specifically, polynucleotides consisting of nucleotide sequences represented by the aforementioned SEQ ID NOs (SEQ ID NOs: 2, 3, 4, 9, 11, 13, 15, 20, 33, 34, 38, 40, 44, 47, 56, 62, 68, 77, 78, 80, 82, 86, 89, 90, 91, 102, 104, 109, 117, 118, 135, 136, 145, 150, 157, 160, 161, 164, 169, 172, 196, 199, 211, 216, 217, 218, 220, 228 to 247, 250, 252, 256, 260, 267 and 268) or complementary sequences thereof were found as target markers (specific polynucleotide group 1) which can specifically discriminate the presence or absence of an ovarian tumor.

The specific polynucleotide group 1 newly contains, in addition to the polynucleotides consisting of SEQ ID NOs: 2, 3, 4, 9, 11, 13, 15, 20, 33, 34, 38, 40, 44, 47, 56, 62, 68, 77, 78, 80, 82, 86, 89, 90, 91, 102, 104, 109, 117, 118, 135, 136, 145, 150, 157, 160, 161, 164, 169, 172, 196, 199, 250, 252, 256, 260, 267 and 268 and obtained in Example 1; the polynucleotide consisting of SEQ ID NO: 211 and obtained in Example 2; and the polynucleotides consisting of SEQ ID NOs: 216 to 218 and 220 and obtained in Example 3, hsa-miR-6794-5p, hsa-miR-4687-3p, hsa-miR-6743-5p, hsa-miR-6771-5p, hsa-miR-3141, hsa-miR-3162-5p, hsa-miR-4271, hsa-miR-1227-5p, hsa-miR-4257, hsa-miR-4270, hsa-miR-4516, hsa-miR-4651, hsa-miR-4725-3p, hsa-miR-6125, hsa-miR-6732-5p, hsa-miR-6791-5p, hsa-miR-6819-5p, hsa-miR-6891-5p, hsa-miR-7108-5p, and hsa-miR-7109-5p genes and the relevant SEQ ID NOs: 228, 229, 230, 231, 232, 233, 234, 235, 236, 237, 238, 239, 240, 241, 242, 243, 244, 245, 246 and 247.

The polynucleotides consisting of the nucleotide sequences represented by SEQ ID NOs: 228, 229, 230, 231, 232, 233, 234, 235, 236, 237, 238, 239, 240, 241, 242, 243, 244, 245, 246 and 247, which were newly found in this Example, are all genes newly found as the markers for examining the presence or absence of an ovarian tumor.

Of the above polynucleotides, four polynucleotides consisting of the nucleotide sequences represented by, for example, SEQ ID NOs: 260, 256, 20 and 89, had sensitivities of 87.0%, 80.9%, 77.9% and 77.9%, respectively in the validation cohort (Table 15). Herein, the general sensitivity of the existing marker CA-125 is reported as 77.4% (Non Patent Literature 4). Accordingly, it was demonstrated that the polynucleotides consisting of these sequences singly discriminate an ovarian tumor with sensitivity beyond CA-125.

These genes, if they are used not only singly but also in combinations of, for example, 2, 3, 4, 5, 6, 7, 8, 9, 10 or more, provide excellent ovarian tumor discriminant performance. For example, if a discriminant was prepared using gene expression level of the nucleotide sequence represented by SEQ ID NO: 256, alone, the discrimination accuracy in the validation cohort was 79.5%; however, if a discriminant was prepared using 2 genes (SEQ ID NOs: 256 and 196) in combination, the discrimination accuracy in the validation cohort was 84.4%, if a discriminant was prepared using 3 genes (SEQ ID NOs: 256, 196 and 260), the discrimination accuracy in the validation cohort was 87.6%, if a discriminant was prepared using 4 genes (SEQ ID NOs: 256, 196, 260 and 268), the discrimination accuracy in the validation cohort was 90.2%, and if a discriminant was prepared using 5 genes (SEQ ID NOs: 256, 196, 260, 268 and 252), the discrimination accuracy in the validation cohort was 92.3%.

Figure 3:
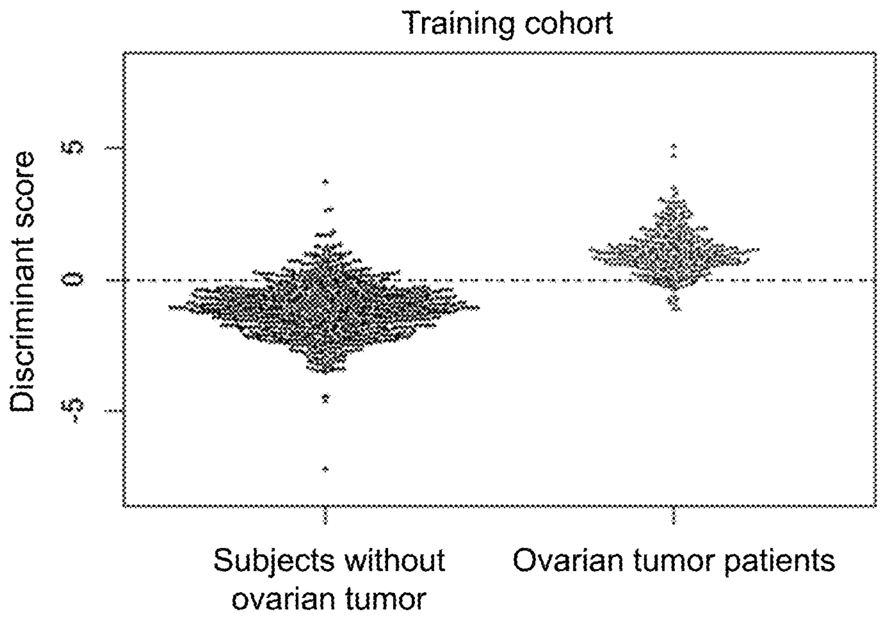
FIG. 3 Upper panel: a discriminant (1.390×hsa-miR-296-5p-1.095×hsa-miR-3131+0.201×hsa-miR-1290+0.695×hsa-miR-642a-3p+0.306×hsa-miR-128-2-5p-13.186) was prepared by use of Fisher's discriminant analysis from the measured expression level values of hsa-miR-296-5p (SEQ ID NO: 256), hsa-miR-3131 (SEQ ID NO: 196), hsa-miR-1290 (SEQ ID NO: 260), hsa-miR-642a-3p (SEQ ID NO: 268), and hsa-miR-128-2-5p (SEQ ID NO: 252) in sera of subjects without ovarian tumor (total 817 people including 280 healthy subjects, 257 benign bone and soft tissue tumor patients and benign breast disease patients, 280 patients having a cancer other than ovarian cancer) and ovarian tumor patients (303 people) selected as a training cohort, and discriminant scores obtained from the discriminant were plotted on the ordinate against the sample groups on the abscissa. The dotted line in the panel depicts a discriminant boundary that offered a discriminant score of 0 and discriminated between the two groups. Lower panel: discriminant scores obtained from assignment to the discriminant (1.390×hsa-miR-296-5p-1.095×hsa-miR-3131+0.201×hsa-miR-1290+0.695×hsa-miR-642a-3p+0.306×hsa-miR-128-2-5p-13.186) prepared from the training cohort as to the expression level measurement values of hsa-miR-296-5p (SEQ ID NO: 256), hsa-miR-3131 (SEQ ID NO: 196), hsa-miR-1290 (SEQ ID NO: 260), hsa-miR-642a-3p (SEQ ID NO: 268), and hsa-miR-128-2-5p (SEQ ID NO: 252) in sera of subjects without ovarian tumor (total 351 people including 120 healthy subjects, 111 benign bone and soft tissue tumor patients and benign breast disease patients, 120 patients having a cancer other than ovarian cancer) and ovarian tumor patients (131 people) selected as a validation cohort were plotted on the ordinate against the sample groups on the abscissa. The dotted line in the panel depicts the discriminant boundary that offered a discriminant score of 0 and discriminated between the two groups.
Figure 3:
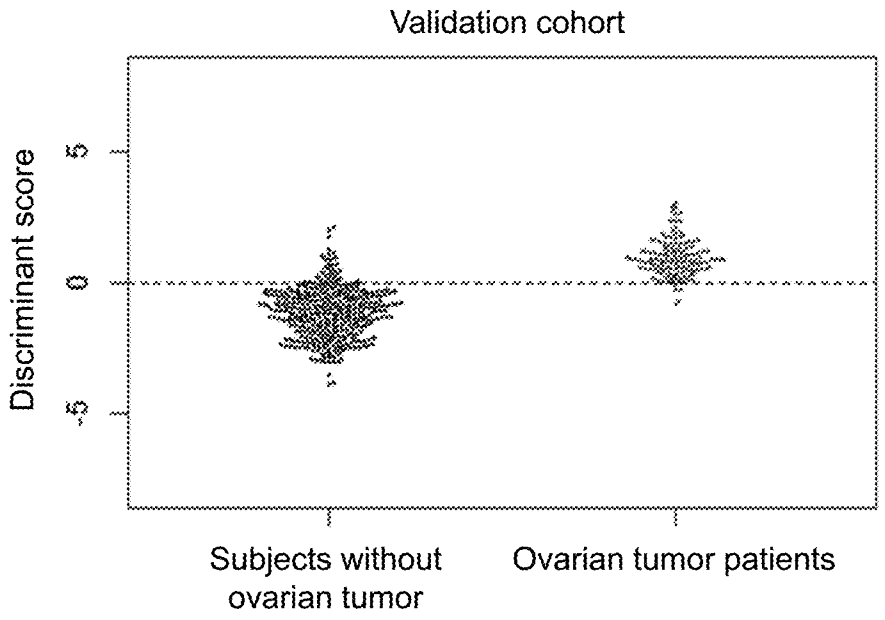

As to the discriminant prepared using measurement values of nucleotide sequences represented by SEQ ID NOs: 256, 196, 260, 268 and 252 in combination, discriminant scores of 303 ovarian tumor patients and 817 test subjects having no ovarian tumor in the training cohort are significantly separated, as shown in the upper panel of FIG. 3. The same results were able to be reproduced also in the validation cohort (FIG. 3, lower panel).

Of the 150 discriminants having the top-level discriminant performance and obtained above, the number of discriminants exhibiting a discrimination accuracy of 80% or more both in the training cohort and verification cohort was 94. Of them, 93 discriminants contained, as an explanatory variance, a target nucleic acid, which is any of polynucleotides consisting of nucleotide sequences represented by SEQ ID NOs: 228, 9, 196, 229, 145 or 164 or a complementary sequence thereof. In other words, of the combinations of a plurality of polynucleotides selected from the specific polynucleotide group 1, a combination containing at least one polynucleotide selected from the group (specific polynucleotide group 2) consisting of a polynucleotide consisting of the nucleotide sequence represented by SEQ ID NO: 228, 9, 196, 229, 145 or 164 or a complementary sequence thereof contained in the specific polynucleotide group 1 was able to specifically discriminate the presence or absence of an ovarian tumor with high accuracy.

Specifically, when measurement was carried out using a polynucleotide consisting of the nucleotide sequence represented by SEQ ID NO: 228 or a complementary sequence thereof as a target nucleic acid, discrimination accuracy is shown in Table 16-1. The measurement using a combination of 1, 2, 3, 4 or 5 genes comprising the polynucleotide consisting of the nucleotide sequence represented by SEQ ID NO: 228 or a complementary sequence thereof exhibited the highest accuracy of 58.9%, 81.7%, 85.5%, 89.8% and 91.3%, respectively, in the validation cohort.

Further, when measurement was carried out using a polynucleotide consisting of the nucleotide sequence represented by SEQ ID NO: 9 or a complementary sequence thereof as a target nucleic acid, discrimination accuracy is shown in Table 16-2. The measurement using a combination of 1, 2, 3, 4 or 5 genes comprising the polynucleotide consisting of the nucleotide sequence represented by SEQ ID NO: 9 or a complementary sequence thereof exhibited the highest accuracy of 66.8%, 79.0%, 85.7%, 89.8% and 91.1%, respectively, in the validation cohort.

Further, when measurement was carried out using a polynucleotide consisting of the nucleotide sequence represented by SEQ ID NO: 196 or a complementary sequence thereof as a target nucleic acid, discrimination accuracy is shown in Table 16-3. The measurement using a combination of 1, 2, 3, 4 or 5 genes comprising the polynucleotide consisting of the nucleotide sequence represented by SEQ ID NO: 196 or a complementary sequence thereof exhibited the highest accuracy of 58.9%, 84.4%, 87.6%, 90.2% and 92.3%, respectively, in the validation cohort.

Further, when measurement was carried out using a polynucleotide consisting of the nucleotide sequence represented by SEQ ID NO: 229 or a complementary sequence thereof as a target nucleic acid, discrimination accuracy is shown in Table 16-4. The measurement using a combination of 1, 2, 3, 4 or 5 genes comprising the polynucleotide consisting of the nucleotide sequence represented by SEQ ID NO: 229 or a complementary sequence thereof exhibited the highest accuracy of 74.9%, 81.5%, 85.9%, 89.4% and 91.3%, respectively, in the validation cohort.

Further, when measurement was carried out using a polynucleotide consisting of the nucleotide sequence represented by SEQ ID NO: 145 or a complementary sequence thereof as a target nucleic acid, discrimination accuracy is shown in Table 16-5. The measurement using a combination of 1, 2, 3, or 4 genes comprising the polynucleotide consisting of the nucleotide sequence represented by SEQ ID NO: 145 or a complementary sequence thereof exhibited the highest accuracy of 70.3%, 82.6%, 87.3% and 89.8%, respectively, in the validation cohort.

Further, when measurement was carried out using a polynucleotide consisting of the nucleotide sequence represented by SEQ ID NO: 164 or a complementary sequence thereof as a target nucleic acid, discrimination accuracy is shown in Table 16-6. The measurement using a combination of 1, 2 or 3 genes comprising the polynucleotide consisting of the nucleotide sequence represented by SEQ ID NO: 164 or a complementary sequence thereof exhibited the highest accuracy of 53.1%, 81.1% and 85.5%, respectively, in the validation cohort.

The specific polynucleotide groups 1 and 2 obtained in this Example can be deemed to be gene groups based on which an ovarian tumor patient can be specifically discriminated from any of healthy subjects, benign bone and soft tissue tumor patients and benign breast disease patients, and patients having a cancer other than ovarian cancer. It was demonstrated that high ovarian tumor discriminant performance can be obtained by using a plurality of polynucleotides in combination as a target nucleic acid rather than using a single polynucleotide or a few polynucleotides in combination. Herein, the combination of the plurality of polynucleotides is not limited to those mentioned above. Even if the polynucleotides are used in any combination, an ovarian tumor can be detected.

TABLE 14

| SEQ ID NO. | Name of gene | ID |
|---|---|---|
| 2 | hsa-miR-4783-3p | MIMAT0019947 |
| 3 | hsa-miR-1228-5p | MIMAT0005582 |
| 4 | hsa-miR-4532 | MIMAT0019071 |
| 9 | hsa-miR-8073 | MIMAT0031000 |
| 11 | hsa-miR-1233-5p | MIMAT0022943 |
| 13 | hsa-miR-5195-3p | MIMAT0021127 |
| 15 | hsa-miR-4649-5p | MIMAT0019711 |
| 20 | hsa-miR-5100 | MIMAT0022259 |
| 33 | hsa-miR-6805-5p | MIMAT0027510 |
| 34 | hsa-miR-4758-5p | MIMAT0019903 |
| 38 | hsa-miR-6781-5p | MIMAT0027462 |
| 40 | hsa-miR-1273g-3p | MIMAT0022742 |
| 44 | hsa-miR-1249-3p | MIMAT0005901 |
| 47 | hsa-miR-1238-5p | MIMAT0022947 |
| 56 | hsa-miR-6775-5p | MIMAT0027450 |
| 62 | hsa-miR-6515-3p | MIMAT0025487 |
| 68 | hsa-miR-6787-5p | MIMAT0027474 |

TABLE 14-continued

| SEQ ID NO. | Name of gene | ID |
|---|---|---|
| 77 | hsa-miR-6757-5p | MIMAT0027414 |
| 78 | hsa-miR-1275 | MIMAT0005929 |
| 80 | hsa-miR-6826-5p | MIMAT0027552 |
| 82 | hsa-miR-3679-3p | MIMAT0018105 |
| 86 | hsa-miR-4447 | MIMAT0018966 |
| 89 | hsa-miR-6766-3p | MIMAT0027433 |
| 90 | hsa-miR-197-5p | MIMAT0022691 |
| 91 | hsa-miR-6887-5p | MIMAT0027674 |
| 102 | hsa-miR-4734 | MIMAT0019859 |
| 104 | hsa-miR-638 | MIMAT0003308 |
| 109 | hsa-miR-8063 | MIMAT0030990 |
| 117 | hsa-miR-1908-5p | MIMAT0007881 |
| 118 | hsa-miR-6726-5p | MIMAT0027353 |
| 135 | hsa-miR-6798-3p | MIMAT0027497 |
| 136 | hsa-miR-665 | MIMAT0004952 |
| 145 | hsa-miR-7150 | MIMAT0028211 |
| 150 | hsa-miR-1229-5p | MIMAT0022942 |
| 157 | hsa-miR-6762-5p | MIMAT0027424 |
| 160 | hsa-miR-6746-5p | MIMAT0027392 |
| 161 | hsa-miR-6880-5p | MIMAT0027660 |
| 164 | hsa-miR-6717-5p | MIMAT0025846 |
| 169 | hsa-miR-6769a-5p | MIMAT0027438 |
| 172 | hsa-miR-6741-5p | MIMAT0027383 |
| 196 | hsa-miR-3131 | MIMAT0014996 |
| 199 | hsa-miR-504-3p | MIMAT0026612 |
| 211 | hsa-miR-6763-5p | MIMAT0027426 |
| 216 | hsa-miR-6870-5p | MIMAT0027640 |
| 217 | hsa-miR-6124 | MIMAT0024597 |
| 218 | hsa-miR-1249-5p | MIMAT0032029 |
| 220 | hsa-miR-1254 | MIMAT0005905 |
| 228 | hsa-miR-6794-5p | MIMAT0027488 |
| 229 | hsa-miR-4687-3p | MIMAT0019775 |
| 230 | hsa-miR-6743-5p | MIMAT0027387 |
| 231 | hsa-miR-6771-5p | MIMAT0027442 |
| 232 | hsa-miR-3141 | MIMAT0015010 |
| 233 | hsa-miR-3162-5p | MIMAT0015036 |
| 234 | hsa-miR-4271 | MIMAT0016901 |
| 235 | hsa-miR-1227-5p | MIMAT0022941 |
| 236 | hsa-miR-4257 | MIMAT0016878 |
| 237 | hsa-miR-4270 | MIMAT0016900 |
| 238 | hsa-miR-4516 | MIMAT0019053 |
| 239 | hsa-miR-4651 | MIMAT0019715 |
| 240 | hsa-miR-4725-3p | MIMAT0019844 |
| 241 | hsa-miR-6125 | MIMAT0024598 |
| 242 | hsa-miR-6732-5p | MIMAT0027365 |
| 243 | hsa-miR-6791-5p | MIMAT0027482 |
| 244 | hsa-miR-6819-5p | MIMAT0027538 |
| 245 | hsa-miR-6891-5p | MIMAT0027682 |
| 246 | hsa-miR-7108-5p | MIMAT0028113 |
| 247 | hsa-miR-7109-5p | MIMAT0028115 |
| 250 | hsa-miR-328-5p | MIMAT0026486 |
| 252 | hsa-miR-128-2-5p | MIMAT0031095 |
| 256 | hsa-miR-296-5p | MIMAT0000690 |
| 260 | hsa-miR-1290 | MIMAT0005880 |
| 267 | hsa-miR-422a | MIMAT0001339 |
| 268 | hsa-miR-642a-3p | MIMAT0020924 |

TABLE 15

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 2 | 61.0 | 81.8 | 53.2 | 61.2 | 74.8 | 56.1 |
| 3 | 50.4 | 62.0 | 46.0 | 55.2 | 71.0 | 49.3 |
| 4 | 69.2 | 82.5 | 64.3 | 64.7 | 72.5 | 61.8 |
| 9 | 66.0 | 73.9 | 63.0 | 66.8 | 73.3 | 64.4 |
| 11 | 68.8 | 72.6 | 67.3 | 66.8 | 66.4 | 67.0 |
| 13 | 65.0 | 75.2 | 61.2 | 66.0 | 64.9 | 66.4 |
| 15 | 66.2 | 74.9 | 63.0 | 66.0 | 62.6 | 67.2 |
| 20 | 73.5 | 82.2 | 70.3 | 74.1 | 77.9 | 72.6 |
| 33 | 61.3 | 68.6 | 58.6 | 64.1 | 70.2 | 61.8 |
| 34 | 63.5 | 67.0 | 62.2 | 61.4 | 61.8 | 61.3 |
| 38 | 63.5 | 66.3 | 62.4 | 65.1 | 65.6 | 65.0 |

TABLE 15-continued

| | Training cohort | | | Validation cohort | | |
|---|---|---|---|---|---|---|
| SEQ ID NO. | Accuracy (%) | Sensitivity (%) | Specificity (%) | Accuracy (%) | Sensitivity (%) | Specificity (%) |
| 40 | 67.0 | 69.0 | 66.2 | 70.3 | 69.5 | 70.7 |
| 44 | 68.1 | 76.9 | 64.9 | 68.9 | 72.5 | 67.5 |
| 47 | 66.4 | 69.6 | 65.2 | 66.6 | 74.0 | 63.8 |
| 56 | 63.4 | 69.3 | 61.2 | 66.2 | 59.5 | 68.7 |
| 62 | 69.6 | 75.2 | 67.6 | 72.8 | 74.8 | 72.1 |
| 68 | 48.7 | 53.5 | 46.9 | 47.3 | 58.8 | 43.0 |
| 77 | 56.8 | 59.4 | 55.8 | 62.7 | 64.9 | 61.8 |
| 78 | 72.7 | 71.3 | 73.2 | 77.8 | 74.0 | 79.2 |
| 80 | 61.9 | 67.7 | 59.7 | 65.4 | 65.6 | 65.2 |
| 82 | 68.8 | 77.6 | 65.5 | 73.0 | 76.3 | 71.8 |
| 86 | 62.3 | 71.6 | 58.9 | 66.6 | 69.5 | 65.5 |
| 89 | 67.9 | 77.6 | 64.3 | 72.4 | 77.9 | 70.4 |
| 90 | 60.0 | 55.1 | 61.8 | 65.6 | 61.8 | 67.0 |
| 91 | 57.4 | 63.7 | 55.1 | 62.4 | 61.1 | 63.0 |
| 102 | 61.2 | 61.4 | 61.2 | 59.3 | 47.3 | 63.8 |
| 104 | 64.6 | 64.4 | 64.7 | 67.2 | 61.8 | 69.2 |
| 109 | 63.3 | 68.6 | 61.3 | 63.9 | 60.3 | 65.2 |
| 117 | 62.6 | 58.7 | 64.0 | 63.9 | 55.0 | 67.2 |
| 118 | 64.1 | 61.7 | 65.0 | 64.9 | 60.3 | 66.7 |
| 135 | 67.6 | 79.9 | 63.0 | 71.8 | 74.8 | 70.7 |
| 136 | 70.8 | 74.6 | 69.4 | 74.9 | 70.2 | 76.6 |
| 145 | 68.8 | 64.4 | 70.5 | 70.3 | 67.2 | 71.5 |
| 150 | 63.5 | 59.4 | 65.0 | 70.3 | 63.4 | 72.9 |
| 157 | 58.8 | 62.7 | 57.4 | 61.0 | 62.6 | 60.4 |
| 160 | 48.8 | 48.5 | 49.0 | 41.3 | 43.5 | 40.5 |
| 161 | 56.2 | 49.2 | 58.8 | 55.2 | 48.9 | 57.5 |
| 164 | 56.1 | 49.2 | 58.6 | 53.1 | 48.9 | 54.7 |
| 169 | 49.2 | 44.2 | 51.0 | 46.9 | 48.1 | 46.4 |
| 172 | 55.7 | 57.1 | 55.2 | 58.5 | 56.5 | 59.3 |
| 196 | 53.9 | 57.4 | 52.6 | 58.9 | 58.0 | 59.3 |
| 199 | 57.9 | 63.4 | 55.8 | 59.1 | 61.8 | 58.1 |
| 211 | 69.1 | 55.1 | 74.3 | 68.0 | 57.3 | 72.1 |
| 216 | 54.8 | 61.4 | 52.4 | 53.9 | 62.6 | 50.7 |
| 217 | 61.7 | 64.4 | 60.7 | 60.0 | 64.1 | 58.4 |
| 218 | 56.1 | 58.7 | 55.1 | 56.0 | 60.3 | 54.4 |
| 220 | 57.4 | 49.8 | 60.2 | 52.3 | 42.0 | 56.1 |
| 228 | 62.9 | 66.7 | 61.6 | 58.9 | 61.1 | 58.1 |
| 229 | 69.2 | 56.4 | 73.9 | 74.9 | 61.1 | 80.1 |
| 230 | 59.8 | 63.7 | 58.4 | 56.4 | 57.3 | 56.1 |
| 231 | 61.5 | 62.7 | 61.1 | 62.0 | 58.8 | 63.2 |
| 232 | 57.5 | 58.4 | 57.2 | 61.8 | 61.1 | 62.1 |
| 233 | 52.4 | 47.5 | 54.2 | 52.1 | 46.6 | 54.1 |
| 234 | 64.9 | 60.7 | 66.5 | 67.2 | 60.3 | 69.8 |
| 235 | 58.4 | 54.1 | 60.0 | 57.7 | 52.7 | 59.5 |
| 236 | 48.7 | 47.5 | 49.1 | 45.2 | 47.3 | 44.4 |
| 237 | 50.5 | 47.5 | 51.7 | 55.0 | 48.1 | 57.5 |
| 238 | 64.4 | 62.7 | 65.0 | 62.7 | 55.7 | 65.2 |
| 239 | 63.0 | 57.1 | 65.2 | 62.9 | 55.0 | 65.8 |
| 240 | 50.9 | 53.8 | 49.8 | 46.5 | 47.3 | 46.2 |
| 241 | 66.0 | 61.4 | 67.7 | 63.7 | 55.0 | 67.0 |
| 242 | 69.9 | 65.7 | 71.5 | 66.2 | 58.0 | 69.2 |
| 243 | 65.1 | 62.7 | 66.0 | 62.4 | 51.9 | 66.4 |
| 244 | 55.3 | 51.5 | 56.7 | 56.6 | 55.7 | 57.0 |
| 245 | 51.6 | 60.4 | 48.3 | 53.5 | 63.4 | 49.9 |
| 246 | 57.1 | 55.8 | 57.6 | 57.5 | 56.5 | 57.8 |
| 247 | 59.0 | 56.8 | 59.9 | 59.5 | 55.0 | 61.3 |
| 250 | 63.6 | 71.9 | 60.5 | 67.8 | 69.5 | 67.2 |
| 252 | 67.5 | 73.6 | 65.2 | 68.5 | 64.9 | 69.8 |
| 256 | 72.5 | 80.5 | 69.5 | 79.5 | 80.9 | 78.9 |
| 260 | 72.5 | 88.4 | 66.6 | 73.4 | 87.0 | 68.4 |
| 267 | 57.3 | 65.0 | 54.5 | 61.8 | 64.1 | 61.0 |
| 268 | 65.4 | 57.1 | 68.4 | 66.4 | 58.8 | 69.2 |

TABLE 16-1

| | Combined | Validation cohort | | |
|---|---|---|---|---|
| SEQ ID NO. | gene number | Accuracy (%) | Sensitivity (%) | Specificity (%) |
| 228 | 1 | 58.9 | 61.1 | 58.1 |
| 256_228 | 2 | 81.7 | 78.6 | 82.9 |

TABLE 16-1-continued

| | Combined | Validation cohort | | |
|---|---|---|---|---|
| SEQ ID NO. | gene number | Accuracy (%) | Sensitivity (%) | Specificity (%) |
| 47_228 | 2 | 80.9 | 83.2 | 80.1 |
| 228_9_229 | 3 | 85.7 | 86.3 | 85.5 |

TABLE 16-1-continued

| SEQ ID NO. | Combined gene number | Validation cohort Accuracy (%) | Sensitivity (%) | Specificity (%) |
|---|---|---|---|---|
| 228_9_78 | 3 | 83.6 | 87.8 | 82.1 |
| 228_9_82 | 3 | 83.0 | 88.5 | 80.9 |
| 228_9_268 | 3 | 83.8 | 87.0 | 82.6 |
| 229_260_228 | 3 | 85.5 | 87.0 | 84.9 |
| 228_9_247 | 3 | 81.3 | 86.3 | 79.5 |
| 228_9_62 | 3 | 84.9 | 89.3 | 83.2 |
| 228_9_217 | 3 | 81.5 | 86.3 | 79.8 |
| 256_228_9 | 3 | 84.4 | 88.5 | 82.9 |
| 256_228_260 | 3 | 83.8 | 90.1 | 81.5 |
| 228_9_234 | 3 | 80.9 | 82.4 | 80.3 |
| 229_20_228 | 3 | 85.3 | 86.3 | 84.9 |
| 47_228_82 | 3 | 83.0 | 87.0 | 81.5 |
| 145_260_228 | 3 | 85.5 | 91.6 | 83.2 |
| 228_9_145 | 3 | 82.6 | 90.1 | 79.8 |
| 228_9_268_160 | 4 | 88.0 | 89.3 | 87.5 |
| 228_9_82_268 | 4 | 85.5 | 88.5 | 84.3 |
| 228_9_268_196 | 4 | 86.7 | 87.8 | 86.3 |
| 145_260_228_250 | 4 | 89.8 | 95.4 | 87.7 |
| 145_260_228_62 | 4 | 88.0 | 93.9 | 85.8 |
| 228_9_268_230 | 4 | 86.1 | 89.3 | 84.9 |
| 229_260_228_2 | 4 | 87.1 | 87.0 | 87.2 |
| 228_9_268_62 | 4 | 86.5 | 90.1 | 85.2 |
| 229_260_228_172 | 4 | 87.1 | 87.0 | 87.2 |
| 229_260_228_4 | 4 | 86.9 | 89.3 | 86.0 |
| 229_260_228_34 | 4 | 85.9 | 84.7 | 86.3 |
| 229_260_228_56 | 4 | 88.4 | 90.8 | 87.5 |
| 229_20_228_4 | 4 | 86.9 | 87.8 | 86.6 |
| 229_20_228_102 | 4 | 85.5 | 81.7 | 86.9 |
| 145_260_228_89 | 4 | 89.6 | 95.4 | 87.5 |
| 228_9_229_82 | 4 | 87.8 | 88.5 | 87.5 |
| 228_9_78_62 | 4 | 86.7 | 90.1 | 85.5 |
| 229_260_228_157 | 4 | 87.1 | 88.5 | 86.6 |
| 229_260_228_231 | 4 | 89.4 | 90.8 | 88.9 |
| 256_228_260_232 | 4 | 87.8 | 91.6 | 86.3 |
| 228_9_229_117 | 4 | 85.3 | 82.4 | 86.3 |
| 228_9_229_62 | 4 | 86.9 | 86.3 | 87.2 |
| 228_9_78_172 | 4 | 84.9 | 87.8 | 83.8 |
| 228_9_78_3 | 4 | 84.0 | 83.2 | 84.3 |
| 228_9_82_268_196 | 5 | 89.0 | 91.6 | 88.0 |
| 229_20_228_4_172 | 5 | 87.3 | 86.3 | 87.7 |
| 228_9_82_268_233 | 5 | 87.8 | 90.8 | 86.6 |
| 228_9_268_196_89 | 5 | 88.0 | 90.8 | 86.9 |
| 228_9_268_160_82 | 5 | 89.8 | 91.6 | 89.2 |
| 228_9_268_196_256 | 5 | 91.1 | 95.4 | 89.5 |
| 228_9_78_62_238 | 5 | 87.1 | 90.1 | 86.0 |
| 228_9_268_196_172 | 5 | 87.1 | 88.5 | 86.6 |
| 256_228_260_232_196 | 5 | 90.0 | 94.7 | 88.3 |
| 228_9_268_160_230 | 5 | 88.6 | 90.1 | 88.0 |
| 256_196_260_268_228 | 5 | 90.9 | 95.4 | 89.2 |
| 228_9_268_196_62 | 5 | 89.8 | 90.8 | 89.5 |
| 228_9_268_196_244 | 5 | 85.7 | 87.8 | 84.9 |
| 228_9_268_196_135 | 5 | 87.8 | 89.3 | 87.2 |
| 229_260_228_2_217 | 5 | 88.6 | 92.4 | 87.2 |
| 228_9_268_62_233 | 5 | 87.6 | 90.8 | 86.3 |
| 229_260_228_172_230 | 5 | 88.8 | 90.1 | 88.3 |
| 229_260_228_56_33 | 5 | 90.2 | 91.6 | 89.7 |
| 229_260_228_56_231 | 5 | 91.3 | 92.4 | 90.9 |
| 229_260_228_231_91 | 5 | 90.2 | 93.9 | 88.9 |
| 228_9_268_160_245 | 5 | 88.6 | 89.3 | 88.3 |
| 228_9_82_268_237 | 5 | 86.1 | 90.1 | 84.6 |
| 228_9_82_268_236 | 5 | 88.2 | 90.1 | 87.5 |

TABLE 16-2

| SEQ ID NO. | Combined gene number | Validation cohort Accuracy (%) | Sensitivity (%) | Specificity (%) |
|---|---|---|---|---|
| 9 | 1 | 66.8 | 73.3 | 64.4 |
| 9_164 | 2 | 79.0 | 88.5 | 75.5 |
| 228_9_229 | 3 | 85.7 | 86.3 | 85.5 |

TABLE 16-2-continued

| SEQ ID NO. | Combined gene number | Validation cohort Accuracy (%) | Sensitivity (%) | Specificity (%) |
|---|---|---|---|---|
| 228_9_78 | 3 | 83.6 | 87.8 | 82.1 |
| 228_9_82 | 3 | 83.0 | 88.5 | 80.9 |
| 228_9_268 | 3 | 83.8 | 87.0 | 82.6 |
| 228_9_247 | 3 | 81.3 | 86.3 | 79.5 |
| 228_9_62 | 3 | 84.9 | 89.3 | 83.2 |
| 228_9_217 | 3 | 81.5 | 86.3 | 79.8 |
| 256_228_9 | 3 | 84.4 | 88.5 | 82.9 |
| 228_9_234 | 3 | 80.9 | 82.4 | 80.3 |
| 228_9_145 | 3 | 82.6 | 90.1 | 79.8 |
| 256_196_9 | 3 | 84.4 | 89.3 | 82.6 |
| 228_9_268_160 | 4 | 88.0 | 89.3 | 87.5 |
| 256_196_9_68 | 4 | 85.9 | 88.5 | 84.9 |
| 228_9_82_268 | 4 | 85.5 | 88.5 | 84.3 |
| 228_9_268_196 | 4 | 86.7 | 87.8 | 86.3 |
| 228_9_268_230 | 4 | 86.1 | 89.3 | 84.9 |
| 228_9_268_62 | 4 | 86.5 | 90.1 | 85.2 |
| 228_9_229_82 | 4 | 87.8 | 88.5 | 87.5 |
| 228_9_78_62 | 4 | 86.7 | 90.1 | 85.5 |
| 228_9_229_117 | 4 | 85.3 | 82.4 | 86.3 |
| 228_9_229_62 | 4 | 86.9 | 86.3 | 87.2 |
| 228_9_78_172 | 4 | 84.9 | 87.8 | 83.8 |
| 228_9_78_3 | 4 | 84.0 | 83.2 | 84.3 |
| 228_9_82_268_196 | 4 | 89.0 | 91.6 | 88.0 |
| 228_9_82_268_233 | 4 | 87.8 | 90.8 | 86.6 |
| 228_9_268_196_89 | 4 | 88.0 | 90.8 | 86.9 |
| 228_9_268_160_82 | 4 | 89.8 | 91.6 | 89.2 |
| 256_196_9_68_86 | 5 | 87.8 | 88.5 | 87.5 |
| 228_9_268_196_256 | 5 | 91.1 | 95.4 | 89.5 |
| 228_9_78_62_238 | 5 | 87.1 | 90.1 | 86.0 |
| 228_9_268_196_172 | 5 | 87.1 | 88.5 | 86.6 |
| 228_9_268_160_230 | 5 | 88.6 | 90.1 | 88.0 |
| 228_9_268_196_62 | 5 | 89.8 | 90.8 | 89.5 |
| 228_9_268_196_244 | 5 | 85.7 | 87.8 | 84.9 |
| 228_9_268_196_135 | 5 | 87.8 | 89.3 | 87.2 |
| 228_9_268_62_233 | 5 | 87.6 | 90.8 | 86.3 |
| 228_9_268_160_245 | 5 | 88.6 | 89.3 | 88.3 |
| 256_196_9_68_268 | 5 | 89.4 | 90.8 | 88.9 |
| 228_9_82_268_237 | 5 | 86.1 | 90.1 | 84.6 |
| 228_9_82_268_236 | 5 | 88.2 | 90.1 | 87.5 |

TABLE 16-3

| SEQ ID NO. | Combined gene number | Validation cohort Accuracy (%) | Sensitivity (%) | Specificity (%) |
|---|---|---|---|---|
| 196 | 1 | 58.9 | 58.0 | 59.3 |
| 256_196 | 2 | 84.4 | 84.7 | 84.3 |
| 256_196_260 | 3 | 87.6 | 93.9 | 85.2 |
| 256_196_172 | 3 | 85.5 | 84.7 | 85.8 |
| 256_196_47 | 3 | 86.7 | 93.1 | 84.3 |
| 256_196_11 | 3 | 85.1 | 88.5 | 83.8 |
| 256_196_136 | 3 | 85.9 | 85.5 | 86.0 |
| 256_196_80 | 3 | 86.9 | 90.1 | 85.8 |
| 256_196_9 | 3 | 84.4 | 89.3 | 82.6 |
| 256_196_260_268 | 4 | 90.2 | 93.9 | 88.9 |
| 256_196_9_68 | 4 | 85.9 | 88.5 | 84.9 |
| 256_196_260_216 | 4 | 90.2 | 96.9 | 87.7 |
| 256_196_260_11 | 4 | 89.0 | 93.1 | 87.5 |
| 228_9_268_196 | 4 | 86.7 | 87.8 | 86.3 |
| 256_196_260_217 | 4 | 89.6 | 93.9 | 88.0 |
| 228_9_82_268_196 | 5 | 89.0 | 91.6 | 88.0 |
| 228_9_268_196_89 | 5 | 88.0 | 90.8 | 86.9 |
| 256_196_9_68_86 | 5 | 87.8 | 88.5 | 87.5 |
| 228_9_268_196_256 | 5 | 91.1 | 95.4 | 89.5 |
| 256_196_260_268_252 | 5 | 92.3 | 96.2 | 90.9 |
| 228_9_268_196_172 | 5 | 87.1 | 88.5 | 86.6 |
| 256_228_260_232_196 | 5 | 90.0 | 94.7 | 88.3 |
| 256_196_260_268_228 | 5 | 90.9 | 95.4 | 89.2 |
| 256_196_260_268_218 | 5 | 90.9 | 94.7 | 89.5 |
| 256_196_260_268_267 | 5 | 90.9 | 96.2 | 88.9 |

TABLE 16-3-continued

| SEQ ID NO. | Combined gene number | Validation cohort Accuracy (%) | Sensitivity (%) | Specificity (%) |
|---|---|---|---|---|
| 228_9_268_196_62 | 5 | 89.8 | 90.8 | 89.5 |
| 228_9_268_196_244 | 5 | 85.7 | 87.8 | 84.9 |
| 228_9_268_196_135 | 5 | 87.8 | 89.3 | 87.2 |
| 256_196_260_217_199 | 5 | 89.2 | 94.7 | 87.2 |
| 256_196_260_268_161 | 5 | 91.5 | 96.2 | 89.7 |
| 256_196_9_68_268 | 5 | 89.4 | 90.8 | 88.9 |

TABLE 16-4

| SEQ ID NO. | Combined gene number | Validation cohort Accuracy (%) | Sensitivity (%) | Specificity (%) |
|---|---|---|---|---|
| 229 | 1 | 74.9 | 61.1 | 80.1 |
| 229_256 | 2 | 81.5 | 74.8 | 84.0 |
| 228_9_229 | 3 | 85.7 | 86.3 | 85.5 |
| 229_260_228 | 3 | 85.5 | 87.0 | 84.9 |
| 229_260_230 | 3 | 85.9 | 88.5 | 84.9 |
| 229_260_169 | 3 | 83.0 | 84.7 | 82.3 |
| 229_260_160 | 3 | 83.0 | 78.6 | 84.6 |
| 229_20_228 | 3 | 85.3 | 86.3 | 84.9 |
| 229_260_228_2 | 4 | 87.1 | 87.0 | 87.2 |
| 229_260_169_2 | 4 | 89.2 | 90.1 | 88.9 |
| 229_260_228_172 | 4 | 87.1 | 87.0 | 87.2 |
| 229_260_228_4 | 4 | 86.9 | 89.3 | 86.0 |
| 229_260_228_34 | 4 | 85.9 | 84.7 | 86.3 |
| 229_260_228_56 | 4 | 88.4 | 90.8 | 87.5 |
| 229_20_228_4 | 4 | 86.9 | 87.8 | 86.6 |
| 229_20_228_102 | 4 | 85.5 | 81.7 | 86.9 |
| 228_9_229_82 | 4 | 87.8 | 88.5 | 87.5 |
| 229_260_228_157 | 4 | 87.1 | 88.5 | 86.6 |
| 229_260_228_231 | 4 | 89.4 | 90.8 | 88.9 |
| 228_9_229_117 | 4 | 85.3 | 82.4 | 86.3 |
| 228_9_229_62 | 4 | 86.9 | 86.3 | 87.2 |
| 229_20_228_4_172 | 5 | 87.3 | 86.3 | 87.7 |
| 229_260_228_2_217 | 5 | 88.6 | 92.4 | 87.2 |
| 229_260_228_172_230 | 5 | 88.8 | 90.1 | 88.3 |
| 229_260_228_56_33 | 5 | 90.2 | 91.6 | 89.7 |
| 229_260_228_56_231 | 5 | 91.3 | 92.4 | 90.9 |
| 229_260_228_231_91 | 5 | 90.2 | 93.9 | 88.9 |

TABLE 16-5

| | Combined gene number | Validation cohort Accuracy (%) | Sensitivity (%) | Specificity (%) |
|---|---|---|---|---|
| 145 | 1 | 70.3 | 67.2 | 71.5 |
| 145_256 | 2 | 82.6 | 84.0 | 82.1 |
| 145_260_164 | 3 | 82.0 | 90.8 | 78.6 |

TABLE 16-5-continued

| | Combined gene number | Validation cohort Accuracy (%) | Sensitivity (%) | Specificity (%) |
|---|---|---|---|---|
| 145_260_230 | 3 | 83.4 | 88.5 | 81.5 |
| 145_260_211 | 3 | 87.3 | 88.5 | 86.9 |
| 145_260_228 | 3 | 85.5 | 91.6 | 83.2 |
| 228_9_145 | 3 | 82.6 | 90.1 | 79.8 |
| 145_260_228_250 | 4 | 89.8 | 95.4 | 87.7 |
| 145_260_228_62 | 4 | 88.0 | 93.9 | 85.8 |
| 145_260_228_89 | 4 | 89.6 | 95.4 | 87.5 |

TABLE 16-6

| SEQ ID NO. | Combined gene number | Validation cohort Accuracy (%) | Sensitivity (%) | Specificity (%) |
|---|---|---|---|---|
| 164 | 1 | 53.1 | 48.9 | 54.7 |
| 164_256 | 2 | 81.1 | 80.9 | 81.2 |
| 11_164_260 | 3 | 85.3 | 86.3 | 84.9 |
| 11_164_20 | 3 | 85.5 | 84.7 | 85.8 |
| 145_260_164 | 3 | 82.0 | 90.8 | 78.6 |

Specifically, as shown in Tables 4 to 16 of Examples 1 to 4, it can be concluded that in all of the polynucleotides consisting of the nucleotide sequences represented by SEQ ID NOs: 1 to 275 or complementary sequences thereof as the target nucleic acid, a combination of 1, 2, 3, 4 or 5 exhibits discriminant performance beyond the existing ovarian tumor markers, and thus, such polynucleotides serve as excellent diagnostic markers.

As shown in the above Examples, the kit, device and method of the present invention can detect an ovarian tumor with higher sensitivity than the existing tumor markers and therefore permit early detection of an ovarian tumor. As a result, a treatment such as a chemotherapy, a radiotherapy, an immunotherapy, a molecular targeted therapy, or surgery with a high degree of probability for complete therapy can be early applied, significantly improving a survival rate.

INDUSTRIAL APPLICABILITY

According to the present invention, an ovarian tumor can be effectively detected by a simple and inexpensive method. This enables early detection, diagnosis and treatment of an ovarian tumor. Also, the method of the present invention enables less-invasive detection of an ovarian tumor using patient's blood and therefore an ovarian tumor can be simply and quickly detected.

All publications, patents, and patent applications cited herein are incorporated herein by reference in their entirety.

The invention claimed is:

1. A method for detecting ovarian tumor, comprising:

1) measuring an expression level of miR-1233-5p in a sample from a subject; and evaluating in vitro whether or not the subject has ovarian tumor using the measured expression level;

2) measuring an expression level of a target gene in a sample from a subject using a kit or device comprising a nucleic acid capable of specifically binding to a polynucleotide of miR-1233-5p or to a complementary strand of the polynucleotide; and evaluating in vitro whether or not the subject has ovarian tumor using both of the measured expression levels and a control expression level from a healthy subject measured in the same way; or 3) Measuring an expression level of a target gene in a sample from a subject using a kit or device comprising a nucleic acid capable of specifically binding a polynucleotide of miR-1233-5p or to a complementary strand of the polynucleotide; and assigning the expression level of the target gene in the sample from the subject to a discriminant, which is capable of discriminatorily determining the presence or absence of ovarian tumor and is prepared with gene expression levels in a sample(s) from a subject(s) known to have ovarian tumor and a sample(s) from a subject(s) without ovarian tumor as a training sample(s), and thereby evaluating in vitro the presence or absence of ovarian tumor.

2. The method according to claim 1, wherein the kit or device further comprises a nucleic acid(s) capable of specifically binding to at least one polynucleotide selected from the following other ovarian tumor markers: miR-320a, miR-663a, miR-328-5p, miR-128-2-5p, miR-125a-3p, miR-191-5p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, and miR-22-3p, or to a complementary strand of the polynucleotide.

3. The method according to claim 1, wherein the nucleic acid is a polynucleotide selected from the group consisting of the following polynucleotides (a) to (e):

(a) a polynucleotide consisting of a nucleotide sequence represented by SEQ ID NO: 11 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by SEQ ID NO: 11 or a nucleotide sequence derived from the nucleotide sequence by the replacement of u with t;

(c) a polynucleotide consisting of a nucleotide sequence complementary to a nucleotide sequence represented by SEQ ID NO: 11 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by SEQ ID NO: 11 or a nucleotide sequence derived from the nucleotide sequence by the replacement of u with t; and (e) a polynucleotide hybridizing under stringent conditions to any of the polynucleotides (a) to (d).

4. The method according to claim 1, wherein the kit or device further comprises a nucleic acid(s) capable of specifically binding to at least one polynucleotide selected from the following other ovarian tumor markers: miR-4675, miR-4783-3p, miR-1228-5p, miR-4532, miR-6802-5p, miR-6784-5p, miR-3940-5p, miR-1307-3p, miR-8073, miR-3184-5p, miR-6088, miR-5195-3p, miR-320b, miR-4649-5p, miR-6800-5p, miR-1343-3p, miR-4730, miR-6885-5p, miR-5100, miR-1203, miR-6756-5p, miR-373-5p, miR-1268a, miR-1260b, miR-4258, miR-4697-5p, miR-1469, miR-4515, miR-6861-5p, miR-6821-5p, miR-575, miR-6805-5p, miR-4758-5p, miR-3663-3p, miR-4530, miR-6798-5p, miR-6781-5p, miR-885-3p, miR-1273g-3p, miR-4787-3p, miR-4454, miR-4706, miR-1249-3p, miR-887-3p, miR-6786-5p, miR-1238-5p, miR-6749-5p, miR-6729-5p, miR-6825-5p, miR-663b, miR-6858-5p, miR-4690-5p, miR-6765-5p, miR-4710, miR-6775-5p, miR-371a-5p, miR-6816-5p, miR-296-3p, miR-7977, miR-8069, miR-6515-3p, miR-4687-5p, miR-1343-5p, miR-7110-5p, miR-4525, miR-3158-5p, miR-6787-5p, miR-614, miR-4689, miR-1268b, miR-1228-3p, miR-1185-1-3p, miR-940, miR-939-5p, miR-6757-5p, miR-1275, miR-5001-5p, miR-6826-5p, miR-6765-3p, miR-3679-3p, miR-4718, miR-4286, miR-8059, miR-4447, miR-4448, miR-658, miR-6766-3p, miR-197-5p, miR-6887-5p, miR-6742-5p, miR-6729-3p, miR-5090, miR-7975, miR-4505, miR-6889-5p, miR-4708-3p, miR-6131, miR-1225-3p, miR-6132, miR-4734, miR-3194-3p, miR-638, miR-2467-3p, miR-4728-5p, miR-5572, miR-6789-5p, miR-8063, miR-4429, miR-6840-3p, miR-4476, miR-675-5p, miR-711, miR-6875-5p, miR-3160-5p, miR-1908-5p, miR-6726-5p, miR-1913, miR-8071, miR-3648, miR-4732-5p, miR-4787-5p, miR-3917, miR-619-5p, miR-1231, miR-342-5p, miR-4433a-5p, miR-6766-5p, miR-4707-5p, miR-7114-5p, miR-6872-3p, miR-6780b-5p, miR-7845-5p, miR-6798-3p, miR-665, miR-6848-5p, miR-5008-5p, miR-4294, miR-6511a-5p, miR-4435, miR-4747-3p, miR-6880-3p, miR-6869-5p, miR-7150, miR-1260a, miR-6877-5p, miR-6721-5p, miR-4656, miR-1229-5p, miR-4433a-3p, miR-4274, miR-4419b, miR-4674, miR-6893-5p, miR-6763-3p, miR-6762-5p, miR-6738-5p, miR-4513, miR-6746-5p, miR-6880-5p, miR-4736, miR-718, miR-6717-5p, miR-7847-3p, miR-760, miR-1199-5p, miR-6813-5p, miR-6769a-5p, miR-1193, miR-7108-3p, miR-6741-5p, miR-4298, miR-6796-3p, miR-4750-5p, miR-6785-5p, miR-1292-3p, miR-4749-3p, miR-6800-3p, miR-4722-5p, miR-4746-3p, miR-4450, miR-6795-5p, miR-365a-5p, miR-498, miR-6797-5p, miR-1470, miR-6851-5p, miR-1247-3p, miR-5196-5p, miR-208a-5p, miR-6842-5p, miR-150-3p, miR-4534, miR-3135b, miR-3131, miR-4792, miR-6510-5p, miR-504-3p, miR-3619-3p, miR-671-5p, miR-4667-5p, miR-4430, miR-3195, miR-3679-5p, miR-6076, miR-6515-5p, miR-6820-5p, miR-4634, miR-187-5p, miR-6763-5p, miR-1908-3p, miR-1181, miR-6782-5p, miR-5010-5p, miR-6870-5p, miR-6124, miR-1249-5p, miR-6511b-5p, miR-1254, miR-4727-3p, miR-4259, miR-4771, miR-3622a-5p, miR-4480, miR-4740-5p, miR-6777-5p, miR-6794-5p, miR-4687-3p, miR-6743-5p, miR-6771-5p, miR-3141, miR-3162-5p, miR-4271, miR-1227-5p, miR-4257, miR-4270, miR-4516, miR-4651, miR-4725-3p, miR-6125, miR-6732-5p, miR-6791-5p, miR-6819-5p, miR-6891-5p, miR-7108-5p, miR-7109-5p, miR-642b-3p, miR-92b-5p, miR-296-5p, miR-1246, miR-92a-2-5p, miR-128-1-5p, miR-1290, miR-211-3p, miR-744-5p, miR-135a-3p, miR-451a, miR-625-3p, miR-92a-3p, miR-422a, miR-483-5p, miR-652-5p, miR-24-3p, miR-23b-3p, miR-23a-3p, miR-92b-3p, and miR-22-3p, or to a complementary strand of the polynucleotide.

5. The method according to claim 4, wherein the nucleic acid(s) is a polynucleotide(s) selected from the group consisting of the following polynucleotides (a)' to (e)':

(a)' a polynucleotide consisting of a nucleotide sequence represented by any of SEQ ID NOs: 1 to 10, 12 to 70, 72 to 247, 251, and 268 or a nucleotide sequence derived from the nucleotide sequence by the replacement of u with t, a variant thereof, a derivative thereof, or a fragment thereof comprising 15 or more consecutive nucleotides;

(b)' a polynucleotide comprising a nucleotide sequence represented by any of SEQ ID NOs: 1 to 10, 12 to 70, 72 to 247, 251, and 268 or a nucleotide sequence derived from the nucleotide sequence by the replacement of u with t;

(c)' a polynucleotide consisting of a nucleotide sequence complementary to a nucleotide sequence represented by any of SEQ ID NOs: 1 to 10, 12 to 70, 72 to 247, 251, and 268 or a nucleotide sequence derived from the nucleotide sequence by the replacement of u with t, a variant thereof, a derivative thereof, or a fragment thereof comprising 15 or more consecutive nucleotides;

(d)' a polynucleotide comprising a nucleotide sequence complementary to a nucleotide sequence represented by any of SEQ ID NOs: 1 to 10, 12 to 70, 72 to 247, 251, and 268 or a nucleotide sequence derived from the nucleotide sequence by the replacement of u with t; and (e)' a polynucleotide hybridizing under stringent conditions to any of the polynucleotides (a)' to (d)'; and/or a polynucleotide(s) selected from the group consisting of the following polynucleotides (f) to (j):

(f) a polynucleotide consisting of a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 248 to 250, 252 to 267, and 269 to 275 or a nucleotide sequence derived from the nucleotide sequence by the replacement of u with t;

(h) a polynucleotide consisting of a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 248 to 250, 252 to 267, and 269 to 275 or a nucleotide sequence derived from the nucleotide sequence by the replacement of u with t; and (j) a polynucleotide hybridizing under stringent conditions to any of the polynucleotides (f) to (i).

6. The method according to claim 1, wherein the subject is a human.

7. The method according to claim 1, wherein the sample is blood, serum, or plasma.

* * * * *

SEQUENCE LISTING

```
<160> NUMBER OF SEQ ID NOS: 842

<210> SEQ ID NO 1
<211> LENGTH: 22
<212> TYPE: RNA
<213> ORGANISM: Homo sapiens

<400> SEQUENCE: 1

ggggcuguga uugaccagca gg                                              22
```

-continued

<210> SEQ ID NO 2
<211> LENGTH: 23
<212> TYPE: RNA
<213> ORGANISM: Homo sapiens

<400> SEQUENCE: 2
ccccgguguu ggggcgcguc ugc 23

<210> SEQ ID NO 3
<211> LENGTH: 21
<212> TYPE: RNA
<213> ORGANISM: Homo sapiens

<400> SEQUENCE: 3
gugggcgggg gcaggugugu g 21

<210> SEQ ID NO 4
<211> LENGTH: 17
<212> TYPE: RNA
<213> ORGANISM: Homo sapiens

<400> SEQUENCE: 4
ccccggggag cccggcg 17

<210> SEQ ID NO 5
<211> LENGTH: 20
<212> TYPE: RNA
<213> ORGANISM: Homo sapiens

<400> SEQUENCE: 5
cuaggugggg ggcuugaagc 20

<210> SEQ ID NO 6
<211> LENGTH: 20
<212> TYPE: RNA
<213> ORGANISM: Homo sapiens

<400> SEQUENCE: 6
gccggggcuu ugggugaggg 20

<210> SEQ ID NO 7
<211> LENGTH: 20
<212> TYPE: RNA
<213> ORGANISM: Homo sapiens

<400> SEQUENCE: 7 gugguuggg gcgggcucug 20

<210> SEQ ID NO 8
<211> LENGTH: 22
<212> TYPE: RNA
<213> ORGANISM: Homo sapiens

<400> SEQUENCE: 8
acucggcgug gcgucggucg ug 22

<210> SEQ ID NO 9
<211> LENGTH: 22
<212> TYPE: RNA
<213> ORGANISM: Homo sapiens

<400> SEQUENCE: 9
accuggcagc agggagcguc gu 22

<210> SEQ ID NO 10
<211> LENGTH: 24
<212> TYPE: RNA
<213> ORGANISM: Homo sapiens

<400> SEQUENCE: 10
ugaggggccu cagaccgagc uuuu 24

<210> SEQ ID NO 11
<211> LENGTH: 22
<212> TYPE: RNA
<213> ORGANISM: Homo sapiens

<400> SEQUENCE: 11
agugggaggc cagggcacgg ca 22

<210> SEQ ID NO 12
<211> LENGTH: 20
<212> TYPE: RNA
<213> ORGANISM: Homo sapiens

<400> SEQUENCE: 12
agagaugaag cggggggcg 20

<210> SEQ ID NO 13
<211> LENGTH: 21
<212> TYPE: RNA
<213> ORGANISM: Homo sapiens

<400> SEQUENCE: 13
auccaguucu cugagggggc u 21

<210> SEQ ID NO 14
<211> LENGTH: 22
<212> TYPE: RNA
<213> ORGANISM: Homo sapiens

<400> SEQUENCE: 14
aaaagcuggg uugagagggc aa 22

<210> SEQ ID NO 15
<211> LENGTH: 24
<212> TYPE: RNA
<213> ORGANISM: Homo sapiens

<400> SEQUENCE: 15
ugggcgaggg gugggcucuc agag 24

<210> SEQ ID NO 16
<211> LENGTH: 21
<212> TYPE: RNA
<213> ORGANISM: Homo sapiens

<400> SEQUENCE: 16
guaggugaca gucaggggcg g 21

<210> SEQ ID NO 17
<211> LENGTH: 22
<212> TYPE: RNA
<213> ORGANISM: Homo sapiens

<400> SEQUENCE: 17
cuccuggggc ccgcacucuc gc                                            22

<210> SEQ ID NO 18
<211> LENGTH: 23
<212> TYPE: RNA
<213> ORGANISM: Homo sapiens

<400> SEQUENCE: 18
cuggcggagc ccauuccaug cca                                           23

<210> SEQ ID NO 19
<211> LENGTH: 25
<212> TYPE: RNA
<213> ORGANISM: Homo sapiens

<400> SEQUENCE: 19
aggggggcac ugcgcaagca aagcc                                         25

<210> SEQ ID NO 20
<211> LENGTH: 22
<212> TYPE: RNA
<213> ORGANISM: Homo sapiens

<400> SEQUENCE: 20
uucagauccc agcggugccu cu                                            22

<210> SEQ ID NO 21
<211> LENGTH: 21
<212> TYPE: RNA
<213> ORGANISM: Homo sapiens

<400> SEQUENCE: 21
cccggagcca ggaugcagcu c                                             21

<210> SEQ ID NO 22
<211> LENGTH: 23
<212> TYPE: RNA
<213> ORGANISM: Homo sapiens

<400> SEQUENCE: 22 agggugggc uggagguggg gcu                                            23

<210> SEQ ID NO 23
<211> LENGTH: 22
<212> TYPE: RNA
<213> ORGANISM: Homo sapiens

<400> SEQUENCE: 23
acucaaaaug ggggcgcuuu cc                                            22

<210> SEQ ID NO 24
<211> LENGTH: 18
<212> TYPE: RNA
<213> ORGANISM: Homo sapiens

<400> SEQUENCE: 24
cgggcguggu ggugggg                                                  18

<210> SEQ ID NO 25
<211> LENGTH: 19
<212> TYPE: RNA
<213> ORGANISM: Homo sapiens

<400> SEQUENCE: 25
aucccaccac ugccaccau 19

<210> SEQ ID NO 26
<211> LENGTH: 17
<212> TYPE: RNA
<213> ORGANISM: Homo sapiens

<400> SEQUENCE: 26
ccccgccacc gccuugg 17

<210> SEQ ID NO 27
<211> LENGTH: 22
<212> TYPE: RNA
<213> ORGANISM: Homo sapiens

<400> SEQUENCE: 27
agggggcgca gucacugacg ug 22

<210> SEQ ID NO 28
<211> LENGTH: 22
<212> TYPE: RNA
<213> ORGANISM: Homo sapiens

<400> SEQUENCE: 28
cucggcgcgg ggcgcgggcu cc 22

<210> SEQ ID NO 29
<211> LENGTH: 22
<212> TYPE: RNA
<213> ORGANISM: Homo sapiens

<400> SEQUENCE: 29
aggacuggac ucccggcagc cc 22

<210> SEQ ID NO 30
<211> LENGTH: 22
<212> TYPE: RNA
<213> ORGANISM: Homo sapiens

<400> SEQUENCE: 30
acuggguagg uggggcucca gg 22

<210> SEQ ID NO 31
<211> LENGTH: 23
<212> TYPE: RNA
<213> ORGANISM: Homo sapiens

<400> SEQUENCE: 31
gugcguggug gcucgaggcg ggg 23

<210> SEQ ID NO 32
<211> LENGTH: 19
<212> TYPE: RNA
<213> ORGANISM: Homo sapiens

<400> SEQUENCE: 32
gagccaguug gacaggagc 19

<210> SEQ ID NO 33
<211> LENGTH: 22
<212> TYPE: RNA
<213> ORGANISM: Homo sapiens

<400> SEQUENCE: 33
uagggggcgg cuuguggagu gu 22

<210> SEQ ID NO 34
<211> LENGTH: 23
<212> TYPE: RNA
<213> ORGANISM: Homo sapiens

<400> SEQUENCE: 34
gugaguggga gccggugggg cug 23

<210> SEQ ID NO 35
<211> LENGTH: 23
<212> TYPE: RNA
<213> ORGANISM: Homo sapiens

<400> SEQUENCE: 35
ugagcaccac acaggccggg cgc 23

<210> SEQ ID NO 36
<211> LENGTH: 18
<212> TYPE: RNA
<213> ORGANISM: Homo sapiens

<400> SEQUENCE: 36
cccagcagga cgggagcg 18

<210> SEQ ID NO 37
<211> LENGTH: 23
<212> TYPE: RNA
<213> ORGANISM: Homo sapiens

<400> SEQUENCE: 37
ccagggggau gggcgagcuu ggg 23

<210> SEQ ID NO 38
<211> LENGTH: 21
<212> TYPE: RNA
<213> ORGANISM: Homo sapiens

<400> SEQUENCE: 38
cgggccggag gucaagggcg u 21

<210> SEQ ID NO 39
<211> LENGTH: 22
<212> TYPE: RNA
<213> ORGANISM: Homo sapiens

<400> SEQUENCE: 39
aggcagcggg guguagugga ua 22

<210> SEQ ID NO 40
<211> LENGTH: 21
<212> TYPE: RNA
<213> ORGANISM: Homo sapiens

<400> SEQUENCE: 40
accacugcac uccagccuga g 21

<210> SEQ ID NO 41
<211> LENGTH: 24
<212> TYPE: RNA
<213> ORGANISM: Homo sapiens

```
<400> SEQUENCE: 41

gaugcgccgc ccacugcccc gcgc                                              24

<210> SEQ ID NO 42
<211> LENGTH: 20
<212> TYPE: RNA
<213> ORGANISM: Homo sapiens

<400> SEQUENCE: 42

ggauccgagu cacggcacca                                                   20

<210> SEQ ID NO 43
<211> LENGTH: 25
<212> TYPE: RNA
<213> ORGANISM: Homo sapiens

<400> SEQUENCE: 43

agcggggagg aagugggcgc ugcuu                                             25

<210> SEQ ID NO 44
<211> LENGTH: 22
<212> TYPE: RNA
<213> ORGANISM: Homo sapiens

<400> SEQUENCE: 44

acgcccuucc ccccuucuu ca                                                 22

<210> SEQ ID NO 45
<211> LENGTH: 22
<212> TYPE: RNA
<213> ORGANISM: Homo sapiens

<400> SEQUENCE: 45

gugaacgggc gccaucccga gg                                                22

<210> SEQ ID NO 46
<211> LENGTH: 21
<212> TYPE: RNA
<213> ORGANISM: Homo sapiens

<400> SEQUENCE: 46

gcgguggggc cggaggggcg u                                                 21

<210> SEQ ID NO 47
<211> LENGTH: 23
<212> TYPE: RNA
<213> ORGANISM: Homo sapiens

<400> SEQUENCE: 47

gugaguggga gccccagugu gug                                               23

<210> SEQ ID NO 48
<211> LENGTH: 22
<212> TYPE: RNA
<213> ORGANISM: Homo sapiens

<400> SEQUENCE: 48

ucgggccugg gguuggggga gc                                                22

<210> SEQ ID NO 49
<211> LENGTH: 22
<212> TYPE: RNA
```

```
<213> ORGANISM: Homo sapiens

<400> SEQUENCE: 49

ugggcgaggg cggcugagcg gc                                              22

<210> SEQ ID NO 50
<211> LENGTH: 22
<212> TYPE: RNA
<213> ORGANISM: Homo sapiens

<400> SEQUENCE: 50

uggggaggug uggagucagc au                                              22

<210> SEQ ID NO 51
<211> LENGTH: 22
<212> TYPE: RNA
<213> ORGANISM: Homo sapiens

<400> SEQUENCE: 51

gguggcccgg ccgugccuga gg                                              22

<210> SEQ ID NO 52
<211> LENGTH: 22
<212> TYPE: RNA
<213> ORGANISM: Homo sapiens

<400> SEQUENCE: 52

gugaggaggg gcuggcaggg ac                                              22

<210> SEQ ID NO 53
<211> LENGTH: 22
<212> TYPE: RNA
<213> ORGANISM: Homo sapiens

<400> SEQUENCE: 53

gagcaggcga ggcugggcug aa                                              22

<210> SEQ ID NO 54
<211> LENGTH: 25
<212> TYPE: RNA
<213> ORGANISM: Homo sapiens

<400> SEQUENCE: 54

gugaggcggg gccaggaggg ugugu                                           25

<210> SEQ ID NO 55
<211> LENGTH: 18
<212> TYPE: RNA
<213> ORGANISM: Homo sapiens

<400> SEQUENCE: 55

gggugagggc aggugguu                                                   18

<210> SEQ ID NO 56
<211> LENGTH: 25
<212> TYPE: RNA
<213> ORGANISM: Homo sapiens

<400> SEQUENCE: 56

ucggggcaug ggggagggag gcugg                                           25

<210> SEQ ID NO 57
<211> LENGTH: 20
```

<212> TYPE: RNA
<213> ORGANISM: Homo sapiens

<400> SEQUENCE: 57
acucaaacug ugggggcacu 20

<210> SEQ ID NO 58
<211> LENGTH: 21
<212> TYPE: RNA
<213> ORGANISM: Homo sapiens

<400> SEQUENCE: 58
uggggcgggg caggucccug c 21

<210> SEQ ID NO 59
<211> LENGTH: 22
<212> TYPE: RNA
<213> ORGANISM: Homo sapiens

<400> SEQUENCE: 59
gaggguuggg uggaggcucu cc 22

<210> SEQ ID NO 60
<211> LENGTH: 18
<212> TYPE: RNA
<213> ORGANISM: Homo sapiens

<400> SEQUENCE: 60
uucccagcca acgcacca 18

<210> SEQ ID NO 61
<211> LENGTH: 23
<212> TYPE: RNA
<213> ORGANISM: Homo sapiens

<400> SEQUENCE: 61
ggaugguugg gggcggucgg cgu 23

<210> SEQ ID NO 62
<211> LENGTH: 20
<212> TYPE: RNA
<213> ORGANISM: Homo sapiens

<400> SEQUENCE: 62
ucucuucauc uaccccccag 20

<210> SEQ ID NO 63
<211> LENGTH: 22
<212> TYPE: RNA
<213> ORGANISM: Homo sapiens

<400> SEQUENCE: 63
cagcccuccu cccgcaccca aa 22

<210> SEQ ID NO 64
<211> LENGTH: 22
<212> TYPE: RNA
<213> ORGANISM: Homo sapiens

<400> SEQUENCE: 64
uggggagcgg cccccgggug gg 22

<210> SEQ ID NO 65

-continued

<211> LENGTH: 21
<212> TYPE: RNA
<213> ORGANISM: Homo sapiens

<400> SEQUENCE: 65
ugggggugug gggagagaga g 21

<210> SEQ ID NO 66
<211> LENGTH: 21
<212> TYPE: RNA
<213> ORGANISM: Homo sapiens

<400> SEQUENCE: 66 gggggaugu gcaugcuggu u 21

<210> SEQ ID NO 67
<211> LENGTH: 21
<212> TYPE: RNA
<213> ORGANISM: Homo sapiens

<400> SEQUENCE: 67
ccugcagaga ggaagcccuu c 21

<210> SEQ ID NO 68
<211> LENGTH: 22
<212> TYPE: RNA
<213> ORGANISM: Homo sapiens

<400> SEQUENCE: 68
uggcgggggu agagcuggcu gc 22

<210> SEQ ID NO 69
<211> LENGTH: 23
<212> TYPE: RNA
<213> ORGANISM: Homo sapiens

<400> SEQUENCE: 69
gaacgccugu ucuugccagg ugg 23

<210> SEQ ID NO 70
<211> LENGTH: 22
<212> TYPE: RNA
<213> ORGANISM: Homo sapiens

<400> SEQUENCE: 70
uugaggagac auggugggg cc 22

<210> SEQ ID NO 71
<211> LENGTH: 22
<212> TYPE: RNA
<213> ORGANISM: Homo sapiens

<400> SEQUENCE: 71
auauacaggg ggagacucuc au 22

<210> SEQ ID NO 72
<211> LENGTH: 20
<212> TYPE: RNA
<213> ORGANISM: Homo sapiens

<400> SEQUENCE: 72
cgggcguggu gguggggug 20

-continued

<210> SEQ ID NO 73
<211> LENGTH: 20
<212> TYPE: RNA
<213> ORGANISM: Homo sapiens

<400> SEQUENCE: 73
ucacaccugc cucgcccccc 20

<210> SEQ ID NO 74
<211> LENGTH: 22
<212> TYPE: RNA
<213> ORGANISM: Homo sapiens

<400> SEQUENCE: 74
auauacaggg ggagacucuu au 22

<210> SEQ ID NO 75
<211> LENGTH: 21
<212> TYPE: RNA
<213> ORGANISM: Homo sapiens

<400> SEQUENCE: 75
aaggcagggc ccccgcuccc c 21

<210> SEQ ID NO 76
<211> LENGTH: 24
<212> TYPE: RNA
<213> ORGANISM: Homo sapiens

<400> SEQUENCE: 76
uggggagcug aggcucuggg ggug 24

<210> SEQ ID NO 77
<211> LENGTH: 22
<212> TYPE: RNA
<213> ORGANISM: Homo sapiens

<400> SEQUENCE: 77
uagggauggg aggccaggau ga 22

<210> SEQ ID NO 78
<211> LENGTH: 17
<212> TYPE: RNA
<213> ORGANISM: Homo sapiens

<400> SEQUENCE: 78
gugggggaga ggcuguc 17

<210> SEQ ID NO 79
<211> LENGTH: 24
<212> TYPE: RNA
<213> ORGANISM: Homo sapiens

<400> SEQUENCE: 79
agggcuggac ucagcggcgg agcu 24

<210> SEQ ID NO 80
<211> LENGTH: 23
<212> TYPE: RNA
<213> ORGANISM: Homo sapiens

<400> SEQUENCE: 80
ucaauaggaa agagguggga ccu 23

<210> SEQ ID NO 81
<211> LENGTH: 21
<212> TYPE: RNA
<213> ORGANISM: Homo sapiens

<400> SEQUENCE: 81
ucaccuggcu ggcccgccca g 21

<210> SEQ ID NO 82
<211> LENGTH: 22
<212> TYPE: RNA
<213> ORGANISM: Homo sapiens

<400> SEQUENCE: 82
cuucccccca guaaucuuca uc 22

<210> SEQ ID NO 83
<211> LENGTH: 21
<212> TYPE: RNA
<213> ORGANISM: Homo sapiens

<400> SEQUENCE: 83
agcuguaccu gaaaccaagc a 21

<210> SEQ ID NO 84
<211> LENGTH: 17
<212> TYPE: RNA
<213> ORGANISM: Homo sapiens

<400> SEQUENCE: 84
accccacucc ugguacc 17

<210> SEQ ID NO 85
<211> LENGTH: 22
<212> TYPE: RNA
<213> ORGANISM: Homo sapiens

<400> SEQUENCE: 85
ggggaacugu agaugaaaag gc 22

<210> SEQ ID NO 86
<211> LENGTH: 17
<212> TYPE: RNA
<213> ORGANISM: Homo sapiens

<400> SEQUENCE: 86
ggugggggcu guuguuu 17

<210> SEQ ID NO 87
<211> LENGTH: 20
<212> TYPE: RNA
<213> ORGANISM: Homo sapiens

<400> SEQUENCE: 87
ggcuccuugg ucuaggggua 20

<210> SEQ ID NO 88
<211> LENGTH: 25
<212> TYPE: RNA
<213> ORGANISM: Homo sapiens

<400> SEQUENCE: 88
ggcggaggga aguagguccg uuggu 25

```
<210> SEQ ID NO 89
<211> LENGTH: 22
<212> TYPE: RNA
<213> ORGANISM: Homo sapiens

<400> SEQUENCE: 89

ugauugucuu cccccacccu ca                                              22

<210> SEQ ID NO 90
<211> LENGTH: 23
<212> TYPE: RNA
<213> ORGANISM: Homo sapiens

<400> SEQUENCE: 90

cggguagaga gggcaguggg agg                                             23

<210> SEQ ID NO 91
<211> LENGTH: 23
<212> TYPE: RNA
<213> ORGANISM: Homo sapiens

<400> SEQUENCE: 91

uggggggaca gauggagagg aca                                             23

<210> SEQ ID NO 92
<211> LENGTH: 22
<212> TYPE: RNA
<213> ORGANISM: Homo sapiens

<400> SEQUENCE: 92

agugggugg gacccagcug uu                                               22

<210> SEQ ID NO 93
<211> LENGTH: 21
<212> TYPE: RNA
<213> ORGANISM: Homo sapiens

<400> SEQUENCE: 93

ucaucccccu cgcccucuca g                                               21

<210> SEQ ID NO 94
<211> LENGTH: 23
<212> TYPE: RNA
<213> ORGANISM: Homo sapiens

<400> SEQUENCE: 94

ccggggcaga uugguguagg gug                                             23

<210> SEQ ID NO 95
<211> LENGTH: 18
<212> TYPE: RNA
<213> ORGANISM: Homo sapiens

<400> SEQUENCE: 95

auccuaguca cggcacca                                                   18

<210> SEQ ID NO 96
<211> LENGTH: 18
<212> TYPE: RNA
<213> ORGANISM: Homo sapiens

<400> SEQUENCE: 96
```

```
aggcugggcu gggacgga                                                 18

<210> SEQ ID NO 97
<211> LENGTH: 23
<212> TYPE: RNA
<213> ORGANISM: Homo sapiens

<400> SEQUENCE: 97

ucggggaguc ugggguccgg aau                                           23

<210> SEQ ID NO 98
<211> LENGTH: 22
<212> TYPE: RNA
<213> ORGANISM: Homo sapiens

<400> SEQUENCE: 98

agcaaggcgg caucucucug au                                            22

<210> SEQ ID NO 99
<211> LENGTH: 19
<212> TYPE: RNA
<213> ORGANISM: Homo sapiens

<400> SEQUENCE: 99

ggcuggucag augggagug                                                19

<210> SEQ ID NO 100
<211> LENGTH: 22
<212> TYPE: RNA
<213> ORGANISM: Homo sapiens

<400> SEQUENCE: 100

ugagccccug ugccgccccc ag                                            22

<210> SEQ ID NO 101
<211> LENGTH: 19
<212> TYPE: RNA
<213> ORGANISM: Homo sapiens

<400> SEQUENCE: 101

agcagggcug gggauugca                                                19

<210> SEQ ID NO 102
<211> LENGTH: 22
<212> TYPE: RNA
<213> ORGANISM: Homo sapiens

<400> SEQUENCE: 102

gcugcgggcu gcggucaggg cg                                            22

<210> SEQ ID NO 103
<211> LENGTH: 22
<212> TYPE: RNA
<213> ORGANISM: Homo sapiens

<400> SEQUENCE: 103

agcucugcug cucacuggca gu                                            22

<210> SEQ ID NO 104
<211> LENGTH: 25
<212> TYPE: RNA
<213> ORGANISM: Homo sapiens

<400> SEQUENCE: 104
```

agggaucgcg ggcggguggc ggccu 25

<210> SEQ ID NO 105
<211> LENGTH: 22
<212> TYPE: RNA
<213> ORGANISM: Homo sapiens

<400> SEQUENCE: 105
agcagaggca gagaggcuca gg 22

<210> SEQ ID NO 106
<211> LENGTH: 23
<212> TYPE: RNA
<213> ORGANISM: Homo sapiens

<400> SEQUENCE: 106
ugggagggga gaggcagcaa gca 23

<210> SEQ ID NO 107
<211> LENGTH: 21
<212> TYPE: RNA
<213> ORGANISM: Homo sapiens

<400> SEQUENCE: 107
guuggggugc aggggucugc u 21

<210> SEQ ID NO 108
<211> LENGTH: 24
<212> TYPE: RNA
<213> ORGANISM: Homo sapiens

<400> SEQUENCE: 108
guaggggcgu cccgggcgcg cggg 24

<210> SEQ ID NO 109
<211> LENGTH: 22
<212> TYPE: RNA
<213> ORGANISM: Homo sapiens

<400> SEQUENCE: 109
ucaaaaucag gagucggggc uu 22

<210> SEQ ID NO 110
<211> LENGTH: 20
<212> TYPE: RNA
<213> ORGANISM: Homo sapiens

<400> SEQUENCE: 110
aaaagcuggg cugagaggcg 20

<210> SEQ ID NO 111
<211> LENGTH: 22
<212> TYPE: RNA
<213> ORGANISM: Homo sapiens

<400> SEQUENCE: 111
gcccaggacu uugugcgggg ug 22

<210> SEQ ID NO 112
<211> LENGTH: 22
<212> TYPE: RNA
<213> ORGANISM: Homo sapiens

```
<400> SEQUENCE: 112

caggaaggau uuagggacag gc                                              22

<210> SEQ ID NO 113
<211> LENGTH: 23
<212> TYPE: RNA
<213> ORGANISM: Homo sapiens

<400> SEQUENCE: 113

uggugcggag agggcccaca gug                                             23

<210> SEQ ID NO 114
<211> LENGTH: 22
<212> TYPE: RNA
<213> ORGANISM: Homo sapiens

<400> SEQUENCE: 114

gggacccagg gagagacgua ag                                              22

<210> SEQ ID NO 115
<211> LENGTH: 21
<212> TYPE: RNA
<213> ORGANISM: Homo sapiens

<400> SEQUENCE: 115

ugagggaccc aggacaggag a                                               21

<210> SEQ ID NO 116
<211> LENGTH: 22
<212> TYPE: RNA
<213> ORGANISM: Homo sapiens

<400> SEQUENCE: 116

ggcuuucuag ucucagcucu cc                                              22

<210> SEQ ID NO 117
<211> LENGTH: 21
<212> TYPE: RNA
<213> ORGANISM: Homo sapiens

<400> SEQUENCE: 117

cggcggggac ggcgauuggu c                                               21

<210> SEQ ID NO 118
<211> LENGTH: 21
<212> TYPE: RNA
<213> ORGANISM: Homo sapiens

<400> SEQUENCE: 118

cgggagcugg ggucugcagg u                                               21

<210> SEQ ID NO 119
<211> LENGTH: 22
<212> TYPE: RNA
<213> ORGANISM: Homo sapiens

<400> SEQUENCE: 119

ucugcccccu ccgcugcugc ca                                              22

<210> SEQ ID NO 120
<211> LENGTH: 20
<212> TYPE: RNA
<213> ORGANISM: Homo sapiens
```

<400> SEQUENCE: 120
cgguggacug gagugggugg 20

<210> SEQ ID NO 121
<211> LENGTH: 21
<212> TYPE: RNA
<213> ORGANISM: Homo sapiens

<400> SEQUENCE: 121
agccgcgggg aucgccgagg g 21

<210> SEQ ID NO 122
<211> LENGTH: 23
<212> TYPE: RNA
<213> ORGANISM: Homo sapiens

<400> SEQUENCE: 122
uguagagcag ggagcaggaa gcu 23

<210> SEQ ID NO 123
<211> LENGTH: 22
<212> TYPE: RNA
<213> ORGANISM: Homo sapiens

<400> SEQUENCE: 123
gcgggggugg cggcggcauc cc 22

<210> SEQ ID NO 124
<211> LENGTH: 20
<212> TYPE: RNA
<213> ORGANISM: Homo sapiens

<400> SEQUENCE: 124
gcucggacug agcaggugg 20

<210> SEQ ID NO 125
<211> LENGTH: 22
<212> TYPE: RNA
<213> ORGANISM: Homo sapiens

<400> SEQUENCE: 125
gcugggauua caggcaugag cc 22

<210> SEQ ID NO 126
<211> LENGTH: 20
<212> TYPE: RNA
<213> ORGANISM: Homo sapiens

<400> SEQUENCE: 126
gugucugggc ggacagcugc 20

<210> SEQ ID NO 127
<211> LENGTH: 21
<212> TYPE: RNA
<213> ORGANISM: Homo sapiens

<400> SEQUENCE: 127
aggggugcua ucugugauug a 21

<210> SEQ ID NO 128
<211> LENGTH: 21
<212> TYPE: RNA

<213> ORGANISM: Homo sapiens

<400> SEQUENCE: 128
cgucccaccc cccacuccug u 21

<210> SEQ ID NO 129
<211> LENGTH: 24
<212> TYPE: RNA
<213> ORGANISM: Homo sapiens

<400> SEQUENCE: 129
cgggugggag cagaucuuau ugag 24

<210> SEQ ID NO 130
<211> LENGTH: 23
<212> TYPE: RNA
<213> ORGANISM: Homo sapiens

<400> SEQUENCE: 130
gccccggcgc gggcggguuc ugg 23

<210> SEQ ID NO 131
<211> LENGTH: 21
<212> TYPE: RNA
<213> ORGANISM: Homo sapiens

<400> SEQUENCE: 131
ucuguggagu ggggugccug u 21

<210> SEQ ID NO 132
<211> LENGTH: 21
<212> TYPE: RNA
<213> ORGANISM: Homo sapiens

<400> SEQUENCE: 132
cccaugccuc cugccgcggu c 21

<210> SEQ ID NO 133
<211> LENGTH: 23
<212> TYPE: RNA
<213> ORGANISM: Homo sapiens

<400> SEQUENCE: 133
uggggaaggc uuggcaggga aga 23

<210> SEQ ID NO 134
<211> LENGTH: 21
<212> TYPE: RNA
<213> ORGANISM: Homo sapiens

<400> SEQUENCE: 134
aagggacagg gagggucgug g 21

<210> SEQ ID NO 135
<211> LENGTH: 21
<212> TYPE: RNA
<213> ORGANISM: Homo sapiens

<400> SEQUENCE: 135
cuacccccca ucccccugua g 21

<210> SEQ ID NO 136
<211> LENGTH: 20

<212> TYPE: RNA
<213> ORGANISM: Homo sapiens

<400> SEQUENCE: 136
accaggaggc ugaggccccu 20

<210> SEQ ID NO 137
<211> LENGTH: 23
<212> TYPE: RNA
<213> ORGANISM: Homo sapiens

<400> SEQUENCE: 137
ugggggcugg gaugggccau ggu 23

<210> SEQ ID NO 138
<211> LENGTH: 22
<212> TYPE: RNA
<213> ORGANISM: Homo sapiens

<400> SEQUENCE: 138
ugaggcccuu ggggcacagu gg 22

<210> SEQ ID NO 139
<211> LENGTH: 17
<212> TYPE: RNA
<213> ORGANISM: Homo sapiens

<400> SEQUENCE: 139
gggagucuac agcaggg 17

<210> SEQ ID NO 140
<211> LENGTH: 23
<212> TYPE: RNA
<213> ORGANISM: Homo sapiens

<400> SEQUENCE: 140
caggcagaag uggggcugac agg 23

<210> SEQ ID NO 141
<211> LENGTH: 22
<212> TYPE: RNA
<213> ORGANISM: Homo sapiens

<400> SEQUENCE: 141
auggccagag cucacacaga gg 22

<210> SEQ ID NO 142
<211> LENGTH: 22
<212> TYPE: RNA
<213> ORGANISM: Homo sapiens

<400> SEQUENCE: 142
aaggcccggg cuuuccuccc ag 22

<210> SEQ ID NO 143
<211> LENGTH: 21
<212> TYPE: RNA
<213> ORGANISM: Homo sapiens

<400> SEQUENCE: 143
ccgccuucuc uccuccccca g 21

<210> SEQ ID NO 144

<211> LENGTH: 22
<212> TYPE: RNA
<213> ORGANISM: Homo sapiens

<400> SEQUENCE: 144
gugaguagug gcgcgcggcg gc 22

<210> SEQ ID NO 145
<211> LENGTH: 18
<212> TYPE: RNA
<213> ORGANISM: Homo sapiens

<400> SEQUENCE: 145
cuggcagggg gagaggua 18

<210> SEQ ID NO 146
<211> LENGTH: 18
<212> TYPE: RNA
<213> ORGANISM: Homo sapiens

<400> SEQUENCE: 146
aucccaccuc ugccacca 18

<210> SEQ ID NO 147
<211> LENGTH: 22
<212> TYPE: RNA
<213> ORGANISM: Homo sapiens

<400> SEQUENCE: 147
agggccgaag gguggaagcu gc 22

<210> SEQ ID NO 148
<211> LENGTH: 23
<212> TYPE: RNA
<213> ORGANISM: Homo sapiens

<400> SEQUENCE: 148
ugggcagggg cuuauuguag gag 23

<210> SEQ ID NO 149
<211> LENGTH: 23
<212> TYPE: RNA
<213> ORGANISM: Homo sapiens

<400> SEQUENCE: 149
ugggcugagg gcaggaggcc ugu 23

<210> SEQ ID NO 150
<211> LENGTH: 24
<212> TYPE: RNA
<213> ORGANISM: Homo sapiens

<400> SEQUENCE: 150
guggguaggg uuuggggag agcg 24

<210> SEQ ID NO 151
<211> LENGTH: 21
<212> TYPE: RNA
<213> ORGANISM: Homo sapiens

<400> SEQUENCE: 151
acaggagugg gggugggaca u 21

<210> SEQ ID NO 152
<211> LENGTH: 18
<212> TYPE: RNA
<213> ORGANISM: Homo sapiens

<400> SEQUENCE: 152
cagcaguccc ucccccug 18

<210> SEQ ID NO 153
<211> LENGTH: 18
<212> TYPE: RNA
<213> ORGANISM: Homo sapiens

<400> SEQUENCE: 153
gaggcugaag gaagaugg 18

<210> SEQ ID NO 154
<211> LENGTH: 21
<212> TYPE: RNA
<213> ORGANISM: Homo sapiens

<400> SEQUENCE: 154
cugggcucgg gacgcgcggc u 21

<210> SEQ ID NO 155
<211> LENGTH: 21
<212> TYPE: RNA
<213> ORGANISM: Homo sapiens

<400> SEQUENCE: 155
caggcaggug uaggguggag c 21

<210> SEQ ID NO 156
<211> LENGTH: 21
<212> TYPE: RNA
<213> ORGANISM: Homo sapiens

<400> SEQUENCE: 156
cuccccggcc ucugccccca g 21

<210> SEQ ID NO 157
<211> LENGTH: 23
<212> TYPE: RNA
<213> ORGANISM: Homo sapiens

<400> SEQUENCE: 157
cggggccaug gagcagccug ugu 23

<210> SEQ ID NO 158
<211> LENGTH: 23
<212> TYPE: RNA
<213> ORGANISM: Homo sapiens

<400> SEQUENCE: 158 cgaggguag aagagcacag ggg 23

<210> SEQ ID NO 159
<211> LENGTH: 22
<212> TYPE: RNA
<213> ORGANISM: Homo sapiens

<400> SEQUENCE: 159
agacugacgg cuggaggccc au 22

<210> SEQ ID NO 160
<211> LENGTH: 22
<212> TYPE: RNA
<213> ORGANISM: Homo sapiens

<400> SEQUENCE: 160
ccgggagaag gagguggccu gg 22

<210> SEQ ID NO 161
<211> LENGTH: 22
<212> TYPE: RNA
<213> ORGANISM: Homo sapiens

<400> SEQUENCE: 161
ugguggagga agagggcagc uc 22

<210> SEQ ID NO 162
<211> LENGTH: 19
<212> TYPE: RNA
<213> ORGANISM: Homo sapiens

<400> SEQUENCE: 162
aggcagguua ucugggcug 19

<210> SEQ ID NO 163
<211> LENGTH: 21
<212> TYPE: RNA
<213> ORGANISM: Homo sapiens

<400> SEQUENCE: 163
cuuccgcccc gccgggcguc g 21

<210> SEQ ID NO 164
<211> LENGTH: 22
<212> TYPE: RNA
<213> ORGANISM: Homo sapiens

<400> SEQUENCE: 164
aggcgaugug gggauguaga ga 22

<210> SEQ ID NO 165
<211> LENGTH: 21
<212> TYPE: RNA
<213> ORGANISM: Homo sapiens

<400> SEQUENCE: 165
cguggaggac gaggaggagg c 21

<210> SEQ ID NO 166
<211> LENGTH: 20
<212> TYPE: RNA
<213> ORGANISM: Homo sapiens

<400> SEQUENCE: 166
cggcucuggg ucugugggga 20

<210> SEQ ID NO 167
<211> LENGTH: 20
<212> TYPE: RNA
<213> ORGANISM: Homo sapiens

<400> SEQUENCE: 167
ccugagcccg ggccgcgcag 20

```
<210> SEQ ID NO 168
<211> LENGTH: 23
<212> TYPE: RNA
<213> ORGANISM: Homo sapiens

<400> SEQUENCE: 168

cagggggcugg gguuucaggu ucu                                              23

<210> SEQ ID NO 169
<211> LENGTH: 21
<212> TYPE: RNA
<213> ORGANISM: Homo sapiens

<400> SEQUENCE: 169

agguggguau ggaggagccc u                                                 21

<210> SEQ ID NO 170
<211> LENGTH: 23
<212> TYPE: RNA
<213> ORGANISM: Homo sapiens

<400> SEQUENCE: 170

gggaugguag accggugacg ugc                                               23

<210> SEQ ID NO 171
<211> LENGTH: 20
<212> TYPE: RNA
<213> ORGANISM: Homo sapiens

<400> SEQUENCE: 171

acccgcccgu cuccccacag                                                   20

<210> SEQ ID NO 172
<211> LENGTH: 22
<212> TYPE: RNA
<213> ORGANISM: Homo sapiens

<400> SEQUENCE: 172

gugggugcug gugggagccg ug                                                22

<210> SEQ ID NO 173
<211> LENGTH: 22
<212> TYPE: RNA
<213> ORGANISM: Homo sapiens

<400> SEQUENCE: 173

cugggacagg aggaggaggc ag                                                22

<210> SEQ ID NO 174
<211> LENGTH: 21
<212> TYPE: RNA
<213> ORGANISM: Homo sapiens

<400> SEQUENCE: 174

gaagcucucc ccuccccgca g                                                 21

<210> SEQ ID NO 175
<211> LENGTH: 22
<212> TYPE: RNA
<213> ORGANISM: Homo sapiens

<400> SEQUENCE: 175
```

cucgggcgga ggugguugag ug 22

<210> SEQ ID NO 176
<211> LENGTH: 22
<212> TYPE: RNA
<213> ORGANISM: Homo sapiens

<400> SEQUENCE: 176
ugggagggcg uggaugaugg ug 22

<210> SEQ ID NO 177
<211> LENGTH: 20
<212> TYPE: RNA
<213> ORGANISM: Homo sapiens

<400> SEQUENCE: 177
ucgcgccccg gcucccguuc 20

<210> SEQ ID NO 178
<211> LENGTH: 20
<212> TYPE: RNA
<213> ORGANISM: Homo sapiens

<400> SEQUENCE: 178
cgccccuccu gcccccacag 20

<210> SEQ ID NO 179
<211> LENGTH: 21
<212> TYPE: RNA
<213> ORGANISM: Homo sapiens

<400> SEQUENCE: 179
caccucuccu ggcaucgccc c 21

<210> SEQ ID NO 180
<211> LENGTH: 23
<212> TYPE: RNA
<213> ORGANISM: Homo sapiens

<400> SEQUENCE: 180
ggcaggaggg cugugccagg uug 23

<210> SEQ ID NO 181
<211> LENGTH: 21
<212> TYPE: RNA
<213> ORGANISM: Homo sapiens

<400> SEQUENCE: 181
agcggugcuc cugcgggccg a 21

<210> SEQ ID NO 182
<211> LENGTH: 22
<212> TYPE: RNA
<213> ORGANISM: Homo sapiens

<400> SEQUENCE: 182
uggggauuug gagaaguggu ga 22

<210> SEQ ID NO 183
<211> LENGTH: 24
<212> TYPE: RNA
<213> ORGANISM: Homo sapiens

<400> SEQUENCE: 183
uggggggaca ggaugagagg cugu 24

<210> SEQ ID NO 184
<211> LENGTH: 23
<212> TYPE: RNA
<213> ORGANISM: Homo sapiens

<400> SEQUENCE: 184
agggacuuuu gggggcagau gug 23

<210> SEQ ID NO 185
<211> LENGTH: 23
<212> TYPE: RNA
<213> ORGANISM: Homo sapiens

<400> SEQUENCE: 185
uuucaagcca gggggcguuu uuc 23

<210> SEQ ID NO 186
<211> LENGTH: 25
<212> TYPE: RNA
<213> ORGANISM: Homo sapiens

<400> SEQUENCE: 186
aggagggaag ggcugagaa cagga 25

<210> SEQ ID NO 187
<211> LENGTH: 21
<212> TYPE: RNA
<213> ORGANISM: Homo sapiens

<400> SEQUENCE: 187
gcccuccgcc cgugcacccc g 21

<210> SEQ ID NO 188
<211> LENGTH: 23
<212> TYPE: RNA
<213> ORGANISM: Homo sapiens

<400> SEQUENCE: 188
aggagguggu acuaggggcc agc 23

<210> SEQ ID NO 189
<211> LENGTH: 24
<212> TYPE: RNA
<213> ORGANISM: Homo sapiens

<400> SEQUENCE: 189
ccccgggaac gucgagacug gagc 24

<210> SEQ ID NO 190
<211> LENGTH: 22
<212> TYPE: RNA
<213> ORGANISM: Homo sapiens

<400> SEQUENCE: 190
agggaagggg acgaggguug gg 22

<210> SEQ ID NO 191
<211> LENGTH: 22
<212> TYPE: RNA
<213> ORGANISM: Homo sapiens

<400> SEQUENCE: 191
gagcuuuugg cccggguuau ac 22

<210> SEQ ID NO 192
<211> LENGTH: 22
<212> TYPE: RNA
<213> ORGANISM: Homo sapiens

<400> SEQUENCE: 192 ugggggguggu cucuagccaa gg 22

<210> SEQ ID NO 193
<211> LENGTH: 22
<212> TYPE: RNA
<213> ORGANISM: Homo sapiens

<400> SEQUENCE: 193
cugguacagg ccugggggac ag 22

<210> SEQ ID NO 194
<211> LENGTH: 17
<212> TYPE: RNA
<213> ORGANISM: Homo sapiens

<400> SEQUENCE: 194
ggauggagga ggggucu 17

<210> SEQ ID NO 195
<211> LENGTH: 22
<212> TYPE: RNA
<213> ORGANISM: Homo sapiens

<400> SEQUENCE: 195
ggcuggagcg agugcagugg ug 22

<210> SEQ ID NO 196
<211> LENGTH: 23
<212> TYPE: RNA
<213> ORGANISM: Homo sapiens

<400> SEQUENCE: 196
ucgaggacug guggaagggc cuu 23

<210> SEQ ID NO 197
<211> LENGTH: 18
<212> TYPE: RNA
<213> ORGANISM: Homo sapiens

<400> SEQUENCE: 197
cggugagcgc ucgcuggc 18

<210> SEQ ID NO 198
<211> LENGTH: 22
<212> TYPE: RNA
<213> ORGANISM: Homo sapiens

<400> SEQUENCE: 198
cagcagggga gagagaggag uc 22

<210> SEQ ID NO 199
<211> LENGTH: 21
<212> TYPE: RNA
<213> ORGANISM: Homo sapiens

<400> SEQUENCE: 199
gggagugcag ggcaggguuu c 21

<210> SEQ ID NO 200
<211> LENGTH: 22
<212> TYPE: RNA
<213> ORGANISM: Homo sapiens

<400> SEQUENCE: 200
gggaccaucc ugccugcugu gg 22

<210> SEQ ID NO 201
<211> LENGTH: 23
<212> TYPE: RNA
<213> ORGANISM: Homo sapiens

<400> SEQUENCE: 201
aggaagcccu ggaggggcug gag 23

<210> SEQ ID NO 202
<211> LENGTH: 22
<212> TYPE: RNA
<213> ORGANISM: Homo sapiens

<400> SEQUENCE: 202
acuggggagc agaaggagaa cc 22

<210> SEQ ID NO 203
<211> LENGTH: 18
<212> TYPE: RNA
<213> ORGANISM: Homo sapiens

<400> SEQUENCE: 203
aggcuggagu gagcggag 18

<210> SEQ ID NO 204
<211> LENGTH: 17
<212> TYPE: RNA
<213> ORGANISM: Homo sapiens

<400> SEQUENCE: 204
cgcgccgggc ccggguu 17

<210> SEQ ID NO 205
<211> LENGTH: 23
<212> TYPE: RNA
<213> ORGANISM: Homo sapiens

<400> SEQUENCE: 205
ugaggauaug gcagggaagg gga 23

<210> SEQ ID NO 206
<211> LENGTH: 21
<212> TYPE: RNA
<213> ORGANISM: Homo sapiens

<400> SEQUENCE: 206
agcaugacag aggagaggug g 21

<210> SEQ ID NO 207
<211> LENGTH: 21
<212> TYPE: RNA

<213> ORGANISM: Homo sapiens

<400> SEQUENCE: 207
uuggagggug uggaagacau c 21

<210> SEQ ID NO 208
<211> LENGTH: 19
<212> TYPE: RNA
<213> ORGANISM: Homo sapiens

<400> SEQUENCE: 208
ugcggcagag cugggguca 19

<210> SEQ ID NO 209
<211> LENGTH: 19
<212> TYPE: RNA
<213> ORGANISM: Homo sapiens

<400> SEQUENCE: 209
cggcgcgacc ggcccgggg 19

<210> SEQ ID NO 210
<211> LENGTH: 22
<212> TYPE: RNA
<213> ORGANISM: Homo sapiens

<400> SEQUENCE: 210
ggcuacaaca caggacccgg gc 22

<210> SEQ ID NO 211
<211> LENGTH: 19
<212> TYPE: RNA
<213> ORGANISM: Homo sapiens

<400> SEQUENCE: 211
cuggggagug gcuggggag 19

<210> SEQ ID NO 212
<211> LENGTH: 21
<212> TYPE: RNA
<213> ORGANISM: Homo sapiens

<400> SEQUENCE: 212
ccggccgccg gcuccgcccc g 21

<210> SEQ ID NO 213
<211> LENGTH: 21
<212> TYPE: RNA
<213> ORGANISM: Homo sapiens

<400> SEQUENCE: 213
ccgucgccgc cacccgagcc g 21

<210> SEQ ID NO 214
<211> LENGTH: 25
<212> TYPE: RNA
<213> ORGANISM: Homo sapiens

<400> SEQUENCE: 214
uaggggaggg ggaauucagg ggugu 25

<210> SEQ ID NO 215
<211> LENGTH: 22

<212> TYPE: RNA
<213> ORGANISM: Homo sapiens

<400> SEQUENCE: 215
agggggaugg cagagcaaaa uu 22

<210> SEQ ID NO 216
<211> LENGTH: 19
<212> TYPE: RNA
<213> ORGANISM: Homo sapiens

<400> SEQUENCE: 216
ugggggagau gggggguuga 19

<210> SEQ ID NO 217
<211> LENGTH: 20
<212> TYPE: RNA
<213> ORGANISM: Homo sapiens

<400> SEQUENCE: 217
gggaaaagga agggggagga 20

<210> SEQ ID NO 218
<211> LENGTH: 24
<212> TYPE: RNA
<213> ORGANISM: Homo sapiens

<400> SEQUENCE: 218
aggagggagg agaugggcca aguu 24

<210> SEQ ID NO 219
<211> LENGTH: 24
<212> TYPE: RNA
<213> ORGANISM: Homo sapiens

<400> SEQUENCE: 219
cugcaggcag aaguggggcu gaca 24

<210> SEQ ID NO 220
<211> LENGTH: 24
<212> TYPE: RNA
<213> ORGANISM: Homo sapiens

<400> SEQUENCE: 220
agccuggaag cuggagccug cagu 24

<210> SEQ ID NO 221
<211> LENGTH: 22
<212> TYPE: RNA
<213> ORGANISM: Homo sapiens

<400> SEQUENCE: 221
auagugggaa gcuggcagau uc 22

<210> SEQ ID NO 222
<211> LENGTH: 22
<212> TYPE: RNA
<213> ORGANISM: Homo sapiens

<400> SEQUENCE: 222 caguugggguc uaggggucag ga 22

<210> SEQ ID NO 223

<211> LENGTH: 21
<212> TYPE: RNA
<213> ORGANISM: Homo sapiens

<400> SEQUENCE: 223
agcagacuug accuacaauu a 21

<210> SEQ ID NO 224
<211> LENGTH: 22
<212> TYPE: RNA
<213> ORGANISM: Homo sapiens

<400> SEQUENCE: 224
caggcacggg agcucaggug ag 22

<210> SEQ ID NO 225
<211> LENGTH: 21
<212> TYPE: RNA
<213> ORGANISM: Homo sapiens

<400> SEQUENCE: 225
agccaagugg aaguuacuuu a 21

<210> SEQ ID NO 226
<211> LENGTH: 22
<212> TYPE: RNA
<213> ORGANISM: Homo sapiens

<400> SEQUENCE: 226
aggacugauc cucucgggca gg 22

<210> SEQ ID NO 227
<211> LENGTH: 23
<212> TYPE: RNA
<213> ORGANISM: Homo sapiens

<400> SEQUENCE: 227
acggggaguc aggcaguggu gga 23

<210> SEQ ID NO 228
<211> LENGTH: 20
<212> TYPE: RNA
<213> ORGANISM: Homo sapiens

<400> SEQUENCE: 228
cagggggacu gggggugagc 20

<210> SEQ ID NO 229
<211> LENGTH: 21
<212> TYPE: RNA
<213> ORGANISM: Homo sapiens

<400> SEQUENCE: 229
uggcuguugg agggggcagg c 21

<210> SEQ ID NO 230
<211> LENGTH: 22
<212> TYPE: RNA
<213> ORGANISM: Homo sapiens

<400> SEQUENCE: 230
aaggggcagg gacggguggc cc 22

<210> SEQ ID NO 231
<211> LENGTH: 22
<212> TYPE: RNA
<213> ORGANISM: Homo sapiens

<400> SEQUENCE: 231
cucgggaggg caugggccag gc 22

<210> SEQ ID NO 232
<211> LENGTH: 19
<212> TYPE: RNA
<213> ORGANISM: Homo sapiens

<400> SEQUENCE: 232
gagggcgggu ggaggagga 19

<210> SEQ ID NO 233
<211> LENGTH: 23
<212> TYPE: RNA
<213> ORGANISM: Homo sapiens

<400> SEQUENCE: 233
uuagggagua gaagggXuggg gag 23

<210> SEQ ID NO 234
<211> LENGTH: 19
<212> TYPE: RNA
<213> ORGANISM: Homo sapiens

<400> SEQUENCE: 234
gggggaagaa aaggugggg 19

<210> SEQ ID NO 235
<211> LENGTH: 17
<212> TYPE: RNA
<213> ORGANISM: Homo sapiens

<400> SEQUENCE: 235
guggggccag gcggugg 17

<210> SEQ ID NO 236
<211> LENGTH: 18
<212> TYPE: RNA
<213> ORGANISM: Homo sapiens

<400> SEQUENCE: 236
ccagaggugg ggacugag 18

<210> SEQ ID NO 237
<211> LENGTH: 20
<212> TYPE: RNA
<213> ORGANISM: Homo sapiens

<400> SEQUENCE: 237
ucagggaguc aggggagggc 20

<210> SEQ ID NO 238
<211> LENGTH: 17
<212> TYPE: RNA
<213> ORGANISM: Homo sapiens

<400> SEQUENCE: 238
gggagaaggg ucggggc 17

<210> SEQ ID NO 239
<211> LENGTH: 20
<212> TYPE: RNA
<213> ORGANISM: Homo sapiens

<400> SEQUENCE: 239
cggggugggu gaggucgggc 20

<210> SEQ ID NO 240
<211> LENGTH: 22
<212> TYPE: RNA
<213> ORGANISM: Homo sapiens

<400> SEQUENCE: 240
uggggaaggc gucagugucg gg 22

<210> SEQ ID NO 241
<211> LENGTH: 20
<212> TYPE: RNA
<213> ORGANISM: Homo sapiens

<400> SEQUENCE: 241
gcggaaggcg gagcggcgga 20

<210> SEQ ID NO 242
<211> LENGTH: 20
<212> TYPE: RNA
<213> ORGANISM: Homo sapiens

<400> SEQUENCE: 242
uagggggugg caggcuggcc 20

<210> SEQ ID NO 243
<211> LENGTH: 22
<212> TYPE: RNA
<213> ORGANISM: Homo sapiens

<400> SEQUENCE: 243
ccccuggggc ugggcaggcg ga 22

<210> SEQ ID NO 244
<211> LENGTH: 22
<212> TYPE: RNA
<213> ORGANISM: Homo sapiens

<400> SEQUENCE: 244
uuggggugga gggccaagga gc 22

<210> SEQ ID NO 245
<211> LENGTH: 19
<212> TYPE: RNA
<213> ORGANISM: Homo sapiens

<400> SEQUENCE: 245
uaaggagggg gaugagggg 19

<210> SEQ ID NO 246
<211> LENGTH: 21
<212> TYPE: RNA
<213> ORGANISM: Homo sapiens

<400> SEQUENCE: 246
guguggccgg caggcgggug g 21

<210> SEQ ID NO 247
<211> LENGTH: 21
<212> TYPE: RNA
<213> ORGANISM: Homo sapiens

<400> SEQUENCE: 247
cuggggggag gagacccugc u 21

<210> SEQ ID NO 248
<211> LENGTH: 22
<212> TYPE: RNA
<213> ORGANISM: Homo sapiens

<400> SEQUENCE: 248
aaaagcuggg uugagagggc ga 22

<210> SEQ ID NO 249
<211> LENGTH: 22
<212> TYPE: RNA
<213> ORGANISM: Homo sapiens

<400> SEQUENCE: 249
aggcggggcg ccgcgggacc gc 22

<210> SEQ ID NO 250
<211> LENGTH: 23
<212> TYPE: RNA
<213> ORGANISM: Homo sapiens

<400> SEQUENCE: 250
gggggggcag gaggggcuca ggg 23

<210> SEQ ID NO 251
<211> LENGTH: 22
<212> TYPE: RNA
<213> ORGANISM: Homo sapiens

<400> SEQUENCE: 251
agacacauuu ggagagggac cc 22

<210> SEQ ID NO 252
<211> LENGTH: 23
<212> TYPE: RNA
<213> ORGANISM: Homo sapiens

<400> SEQUENCE: 252
gggggccgau acacuguacg aga 23

<210> SEQ ID NO 253
<211> LENGTH: 22
<212> TYPE: RNA
<213> ORGANISM: Homo sapiens

<400> SEQUENCE: 253
acaggugagg uucuugggag cc 22

<210> SEQ ID NO 254
<211> LENGTH: 23
<212> TYPE: RNA
<213> ORGANISM: Homo sapiens

<400> SEQUENCE: 254

```
caacggaauc ccaaaagcag cug                                          23

<210> SEQ ID NO 255
<211> LENGTH: 22
<212> TYPE: RNA
<213> ORGANISM: Homo sapiens

<400> SEQUENCE: 255

agggacggga cgcggugcag ug                                           22

<210> SEQ ID NO 256
<211> LENGTH: 21
<212> TYPE: RNA
<213> ORGANISM: Homo sapiens

<400> SEQUENCE: 256

agggccccccc cucaauccug u                                           21

<210> SEQ ID NO 257
<211> LENGTH: 19
<212> TYPE: RNA
<213> ORGANISM: Homo sapiens

<400> SEQUENCE: 257

aauggauuuu uggagcagg                                               19

<210> SEQ ID NO 258
<211> LENGTH: 22
<212> TYPE: RNA
<213> ORGANISM: Homo sapiens

<400> SEQUENCE: 258

ggguggggau uuguugcauu ac                                           22

<210> SEQ ID NO 259
<211> LENGTH: 23
<212> TYPE: RNA
<213> ORGANISM: Homo sapiens

<400> SEQUENCE: 259

cggggccgua gcacugucug aga                                          23

<210> SEQ ID NO 260
<211> LENGTH: 19
<212> TYPE: RNA
<213> ORGANISM: Homo sapiens

<400> SEQUENCE: 260

uggauuuuug gaucaggga                                               19

<210> SEQ ID NO 261
<211> LENGTH: 21
<212> TYPE: RNA
<213> ORGANISM: Homo sapiens

<400> SEQUENCE: 261

gcagggacag caaaggggug c                                            21

<210> SEQ ID NO 262
<211> LENGTH: 22
<212> TYPE: RNA
<213> ORGANISM: Homo sapiens

<400> SEQUENCE: 262
```

ugcggggcua gggcuaacag ca 22

<210> SEQ ID NO 263
<211> LENGTH: 22
<212> TYPE: RNA
<213> ORGANISM: Homo sapiens

<400> SEQUENCE: 263
uauagggauu ggagccgugg cg 22

<210> SEQ ID NO 264
<211> LENGTH: 22
<212> TYPE: RNA
<213> ORGANISM: Homo sapiens

<400> SEQUENCE: 264
aaaccguuac cauuacugag uu 22

<210> SEQ ID NO 265
<211> LENGTH: 22
<212> TYPE: RNA
<213> ORGANISM: Homo sapiens

<400> SEQUENCE: 265
gacuauagaa cuuuccccu ca 22

<210> SEQ ID NO 266
<211> LENGTH: 22
<212> TYPE: RNA
<213> ORGANISM: Homo sapiens

<400> SEQUENCE: 266
uauugcacuu gucccggccu gu 22

<210> SEQ ID NO 267
<211> LENGTH: 22
<212> TYPE: RNA
<213> ORGANISM: Homo sapiens

<400> SEQUENCE: 267
acuggacuua gggucagaag gc 22

<210> SEQ ID NO 268
<211> LENGTH: 22
<212> TYPE: RNA
<213> ORGANISM: Homo sapiens

<400> SEQUENCE: 268
agacacauuu ggagagggaa cc 22

<210> SEQ ID NO 269
<211> LENGTH: 22
<212> TYPE: RNA
<213> ORGANISM: Homo sapiens

<400> SEQUENCE: 269
aagacgggag gaaagaaggg ag 22

<210> SEQ ID NO 270
<211> LENGTH: 25
<212> TYPE: RNA
<213> ORGANISM: Homo sapiens

<400> SEQUENCE: 270
caacccuagg agagggugcc auuca 25

<210> SEQ ID NO 271
<211> LENGTH: 22
<212> TYPE: RNA
<213> ORGANISM: Homo sapiens

<400> SEQUENCE: 271
uggcucaguu cagcaggaac ag 22

<210> SEQ ID NO 272
<211> LENGTH: 21
<212> TYPE: RNA
<213> ORGANISM: Homo sapiens

<400> SEQUENCE: 272
aucacauugc cagggauuac c 21

<210> SEQ ID NO 273
<211> LENGTH: 21
<212> TYPE: RNA
<213> ORGANISM: Homo sapiens

<400> SEQUENCE: 273
aucacauugc cagggauuuc c 21

<210> SEQ ID NO 274
<211> LENGTH: 22
<212> TYPE: RNA
<213> ORGANISM: Homo sapiens

<400> SEQUENCE: 274
uauugcacuc gucccggccu cc 22

<210> SEQ ID NO 275
<211> LENGTH: 22
<212> TYPE: RNA
<213> ORGANISM: Homo sapiens

<400> SEQUENCE: 275
aagcugccag uugaagaacu gu 22

<210> SEQ ID NO 276
<211> LENGTH: 77
<212> TYPE: RNA
<213> ORGANISM: Homo sapiens

<400> SEQUENCE: 276
caugagaaau ccugcugguc aaccauagcc cuggucagac ucuccggggc ugugauugac 60
cagcaggacu ucucaug 77

<210> SEQ ID NO 277
<211> LENGTH: 82
<212> TYPE: RNA
<213> ORGANISM: Homo sapiens

<400> SEQUENCE: 277
gggaaagcgg agggcgcgcc cagcucccgg gcugauugcg cuaacagugg ccccgguguu 60
ggggcgcguc ugccgcugcc cc 82

<210> SEQ ID NO 278
<211> LENGTH: 73
<212> TYPE: RNA
<213> ORGANISM: Homo sapiens

<400> SEQUENCE: 278
gugggcgggg gcaggugugu gguggguggu ggccugcggu gagcagggcc cucacaccug 60
ccucgccccc cag 73

<210> SEQ ID NO 279
<211> LENGTH: 51
<212> TYPE: RNA
<213> ORGANISM: Homo sapiens

<400> SEQUENCE: 279
acagaccccg gggagcccgg cggugaagcu ccugguaucc ugggugucug a 51

<210> SEQ ID NO 280
<211> LENGTH: 65
<212> TYPE: RNA
<213> ORGANISM: Homo sapiens

<400> SEQUENCE: 280
gagggcuagg uggggggcuu gaagccccga gaugccucac gucuucaccc cucucaccua 60
agcag 65

<210> SEQ ID NO 281
<211> LENGTH: 67
<212> TYPE: RNA
<213> ORGANISM: Homo sapiens

<400> SEQUENCE: 281
uacaggccgg ggcuuugggu gagggacccc cggagucugu cacggucuca ccccaacucu 60
gccccag 67

<210> SEQ ID NO 282
<211> LENGTH: 102
<212> TYPE: RNA
<213> ORGANISM: Homo sapiens

<400> SEQUENCE: 282
gcuuaucgag gaaaagaucg aggugggguug gggcgggcuc uggggauuug gucucacagc 60
ccggauccca gcccacuuac cuugguuacu cuccuuccuu cu 102

<210> SEQ ID NO 283
<211> LENGTH: 149
<212> TYPE: RNA
<213> ORGANISM: Homo sapiens

<400> SEQUENCE: 283
caucaagacc cagcugaguc acugucacug ccuaccaauc ucgaccggac cucgaccggc 60
ucgucugugu ugccaaucga cucggcgugg cgucggucgu gguagauagg cggucaugca 120
uacgaauuuu cagcucuugu ucuggugac 149

<210> SEQ ID NO 284
<211> LENGTH: 72
<212> TYPE: RNA
<213> ORGANISM: Homo sapiens

<400> SEQUENCE: 284
gauuucagug accuggcagc agggagcguc gucaguguuu gacuguuuau gguaugucag 60
ggagcugguu cc 72

<210> SEQ ID NO 285
<211> LENGTH: 75
<212> TYPE: RNA
<213> ORGANISM: Homo sapiens

<400> SEQUENCE: 285
aagcaagacu gaggggccuc agaccgagcu uuuggaaaau agaaaagucu cgcucucugc 60
cccucagccu aacuu 75

<210> SEQ ID NO 286
<211> LENGTH: 82
<212> TYPE: RNA
<213> ORGANISM: Homo sapiens

<400> SEQUENCE: 286
gugaguggga ggccagggca cggcaggggg agcugcaggg cuaugggagg ggccccagcg 60
ucugagcccu guccucccgc ag 82

<210> SEQ ID NO 287
<211> LENGTH: 82
<212> TYPE: RNA
<213> ORGANISM: Homo sapiens

<400> SEQUENCE: 287
gugaguggga ggccagggca cggcaggggg agcugcaggg cuaugggagg ggccccagcg 60
ucugagcccu guccucccgc ag 82

<210> SEQ ID NO 288
<211> LENGTH: 51
<212> TYPE: RNA
<213> ORGANISM: Homo sapiens

<400> SEQUENCE: 288
agagaugaag cggggggcg gggucuugcu cuauugccua cgcugaucuc a 51

<210> SEQ ID NO 289
<211> LENGTH: 115
<212> TYPE: RNA
<213> ORGANISM: Homo sapiens

<400> SEQUENCE: 289
gagcaaaaac cagagaacaa caugggagcg uuccuaaccc cuaaggcaac uggaugggag 60
accugaccca uccaguucuc ugagggggcu cuugugugu cuacaagguu guuca 115

<210> SEQ ID NO 290
<211> LENGTH: 79
<212> TYPE: RNA
<213> ORGANISM: Homo sapiens

<400> SEQUENCE: 290
aauuaauccc ucucuuucua guucuuccua gagugaggaa aagcuggguu gagagggcaa 60
acaaauuaac uaauuaauu 79

<210> SEQ ID NO 291
<211> LENGTH: 138
<212> TYPE: RNA
<213> ORGANISM: Homo sapiens

<400> SEQUENCE: 291
uguuauuuuu ugucuucuac cuaagaauuc ugucucuuag gcuuucucuu cccagauuuc 60
ccaaaguugg gaaaagcugg guugagaggg caaaaggaaa aaaaaagaau ucugucucug 120
acauaauuag auagggaa 138

<210> SEQ ID NO 292
<211> LENGTH: 64
<212> TYPE: RNA
<213> ORGANISM: Homo sapiens

<400> SEQUENCE: 292
ucugggcgag gggugggcuc ucagaggggc uggcaguacu gcucugaggc cugccucucc 60
ccag 64

<210> SEQ ID NO 293
<211> LENGTH: 82
<212> TYPE: RNA
<213> ORGANISM: Homo sapiens

<400> SEQUENCE: 293
accuguaggu gacagucagg ggcggggugu ggugggggcug gggcuggccc ccuccucaca 60
ccucuccugg caucgccccc ag 82

<210> SEQ ID NO 294
<211> LENGTH: 84
<212> TYPE: RNA
<213> ORGANISM: Homo sapiens

<400> SEQUENCE: 294
gcuggcgucg gugcugggga gcggcccccg ggugggccuc ugcucuggcc ccuccugggg 60
cccgcacucu cgcucugggc ccgc 84

<210> SEQ ID NO 295
<211> LENGTH: 76
<212> TYPE: RNA
<213> ORGANISM: Homo sapiens

<400> SEQUENCE: 295
cgcaggccuc uggcggagcc cauuccaugc cagaugcuga gcgauggcug gugugugcug 60
cuccacaggc cuggug 76

<210> SEQ ID NO 296
<211> LENGTH: 66
<212> TYPE: RNA
<213> ORGANISM: Homo sapiens

<400> SEQUENCE: 296
ccuggagggg ggcacugcgc aagcaaagcc agggacccug agaggcuuug cuuccugcuc 60
cccuag 66

<210> SEQ ID NO 297
<211> LENGTH: 119
<212> TYPE: RNA
<213> ORGANISM: Homo sapiens

<400> SEQUENCE: 297
ccaugaggag cuggcagugg gauggccugg ggguaggagc guggcuucug gagcuagacc 60
acauggguuc agaucccagc ggugccucua acuggccaca ggaccuuggg cagucagcu 119

<210> SEQ ID NO 298
<211> LENGTH: 85
<212> TYPE: RNA
<213> ORGANISM: Homo sapiens

<400> SEQUENCE: 298
uccuccccgg agccaggaug cagcucaagc cacagcaggg uguuuagcgc ucuucagugg 60
cuccagauug uggcgcuggu gcagg 85

<210> SEQ ID NO 299
<211> LENGTH: 63
<212> TYPE: RNA
<213> ORGANISM: Homo sapiens

<400> SEQUENCE: 299
acccuagggu ggggcuggag gugggggcuga ggcugagucu uccuccccuu ccucccugcc 60
cag 63

<210> SEQ ID NO 300
<211> LENGTH: 69
<212> TYPE: RNA
<213> ORGANISM: Homo sapiens

<400> SEQUENCE: 300
gggauacuca aaaugggggc gcuuuccuuu uugucuguac ugggaagugc uucgauuuug 60
gggugucc 69

<210> SEQ ID NO 301
<211> LENGTH: 52
<212> TYPE: RNA
<213> ORGANISM: Homo sapiens

<400> SEQUENCE: 301
uagccgggcg uggugguggg ggccuguggu cccagcuacu uuggaggcug ag 52

<210> SEQ ID NO 302
<211> LENGTH: 89
<212> TYPE: RNA
<213> ORGANISM: Homo sapiens

<400> SEQUENCE: 302
ucuccguuua ucccaccacu gccaccauua uugcuacugu ucagcaggug cugcuggugg 60
ugauggugau agucuggugg gggcggugg 89

<210> SEQ ID NO 303
<211> LENGTH: 91
<212> TYPE: RNA
<213> ORGANISM: Homo sapiens

<400> SEQUENCE: 303
acgccccccg ccccgccacc gccuuggagg cugaccucuu acuuucgguc ggucuucuuc 60
ccugggcuug guuugggggc gggggagugu c 91

<210> SEQ ID NO 304
<211> LENGTH: 78
<212> TYPE: RNA
<213> ORGANISM: Homo sapiens

<400> SEQUENCE: 304
gggcccagaa gggggcgcag ucacugacgu gaagggacca caucccgcuu caugucagug 60
acuccugccc cuuggucu 78

<210> SEQ ID NO 305
<211> LENGTH: 47
<212> TYPE: RNA
<213> ORGANISM: Homo sapiens

<400> SEQUENCE: 305
cucggcgcgg ggcgcgggcu ccggguuggg gcgagccaac gccgggg 47

<210> SEQ ID NO 306
<211> LENGTH: 81
<212> TYPE: RNA
<213> ORGANISM: Homo sapiens

<400> SEQUENCE: 306
gcgggaggug uaacaggacu ggacucccgg cagccccagg gcaggggcgu ggggagcugg 60
uccuagcuca gcgcucccgg a 81

<210> SEQ ID NO 307
<211> LENGTH: 64
<212> TYPE: RNA
<213> ORGANISM: Homo sapiens

<400> SEQUENCE: 307
gaggcacugg guaggugggg cuccagggcu ccugacaccu ggaccucucc uccccaggcc 60
caca 64

<210> SEQ ID NO 308
<211> LENGTH: 74
<212> TYPE: RNA
<213> ORGANISM: Homo sapiens

<400> SEQUENCE: 308
gugcguggug gcucgaggcg gggguggggg ccucgcccug cuugggcccu cccugaccuc 60
uccgcuccgc acag 74

<210> SEQ ID NO 309
<211> LENGTH: 94
<212> TYPE: RNA
<213> ORGANISM: Homo sapiens

<400> SEQUENCE: 309
aauucagccc ugccacuggc uuaugucaug accuugggcu acucaggcug ucugcacaau 60
gagccaguug gacaggagca gugccacuca acuc 94

<210> SEQ ID NO 310
<211> LENGTH: 62
<212> TYPE: RNA
<213> ORGANISM: Homo sapiens

<400> SEQUENCE: 310
uggccuaggg ggcggcuugu ggaguguaug ggcugagccu ugcucugcuc ccccgccccc 60
ag 62

<210> SEQ ID NO 311
<211> LENGTH: 71
<212> TYPE: RNA

<213> ORGANISM: Homo sapiens

<400> SEQUENCE: 311
ggugaguggg agccgguggg gcuggaguaa gggcacgccc ggggcugccc caccugcuga 60
ccacccuccc c 71

<210> SEQ ID NO 312
<211> LENGTH: 97
<212> TYPE: RNA
<213> ORGANISM: Homo sapiens

<400> SEQUENCE: 312
cccgggaccu ugguccaggc gcuggucugc guggugcucg gguggauaag ucugaucuga 60
gcaccacaca ggccgggcgc cgggaccaag gggggcuc 97

<210> SEQ ID NO 313
<211> LENGTH: 56
<212> TYPE: RNA
<213> ORGANISM: Homo sapiens

<400> SEQUENCE: 313
cgaccgcacc cgcccgaagc ugggucaagg agcccagcag gacgggagcg cggcgc 56

<210> SEQ ID NO 314
<211> LENGTH: 67
<212> TYPE: RNA
<213> ORGANISM: Homo sapiens

<400> SEQUENCE: 314
ggcagccagg gggaugggcg agcuugggcc cauuccuuuc cuuacccuac cccccauccc 60
ccuguag 67

<210> SEQ ID NO 315
<211> LENGTH: 64
<212> TYPE: RNA
<213> ORGANISM: Homo sapiens

<400> SEQUENCE: 315
aaccccgggc cggaggucaa gggcgucgcu ucucccuaau guugccucuu uuccacggcc 60
ucag 64

<210> SEQ ID NO 316
<211> LENGTH: 74
<212> TYPE: RNA
<213> ORGANISM: Homo sapiens

<400> SEQUENCE: 316
ccgcacucuc uccauuacac uacccugccu cuucuccaug agaggcagcg ggguguagug 60
gauagagcac gggu 74

<210> SEQ ID NO 317
<211> LENGTH: 100
<212> TYPE: RNA
<213> ORGANISM: Homo sapiens

<400> SEQUENCE: 317
gaggugggag gauugcuuga gucagggugg uugaggcugc aguaaguugu gaucauacca 60
cugcacucca gccugaguga cagagcaaga ccuugucuca 100

<210> SEQ ID NO 318
<211> LENGTH: 84
<212> TYPE: RNA
<213> ORGANISM: Homo sapiens

<400> SEQUENCE: 318
cgguccagac guggcggggg uggcggcggc aucccggacg gccugugagg gaugcgccgc 60
ccacugcccc gcgccgccug accg 84

<210> SEQ ID NO 319
<211> LENGTH: 55
<212> TYPE: RNA
<213> ORGANISM: Homo sapiens

<400> SEQUENCE: 319
ccggauccga gucacggcac caaauuucau gcguguccgu gugaagagac cacca 55

<210> SEQ ID NO 320
<211> LENGTH: 82
<212> TYPE: RNA
<213> ORGANISM: Homo sapiens

<400> SEQUENCE: 320
gcuacgggga gcggggagga agugggcgcu gcuucugcgu uaucuggaag gagcagccca 60
cuccuguccu gggcucugug gu 82

<210> SEQ ID NO 321
<211> LENGTH: 66
<212> TYPE: RNA
<213> ORGANISM: Homo sapiens

<400> SEQUENCE: 321
gggaggaggg aggagauggg ccaaguuccc ucuggcugga acgcccuucc cccccuucuu 60
caccug 66

<210> SEQ ID NO 322
<211> LENGTH: 79
<212> TYPE: RNA
<213> ORGANISM: Homo sapiens

<400> SEQUENCE: 322
gugcagaucc uugggagccc uguuagacuc uggauuuuac acuuggagug aacgggcgcc 60
aucccgaggc uuugcacag 79

<210> SEQ ID NO 323
<211> LENGTH: 113
<212> TYPE: RNA
<213> ORGANISM: Homo sapiens

<400> SEQUENCE: 323
gccggguggg gcggggcggc cucaggaggg gcccagcucc ccuggaugug cugcggugggg 60 gccggagggg cgucacgugc acccaaguga cgccccuucu gauucugccu cag 113

<210> SEQ ID NO 324
<211> LENGTH: 83
<212> TYPE: RNA
<213> ORGANISM: Homo sapiens

<400> SEQUENCE: 324 gugagugggga gccccagugu gugguugggg ccauggcggg ugggcagccc agccucugag 60
ccuuccucgu cugucugccc cag 83

<210> SEQ ID NO 325
<211> LENGTH: 69
<212> TYPE: RNA
<213> ORGANISM: Homo sapiens

<400> SEQUENCE: 325
ggcccucggg ccugggguug ggggagcucu guccugucuc acucauugcu ccucccccugc 60 cuggcccag 69

<210> SEQ ID NO 326
<211> LENGTH: 65
<212> TYPE: RNA
<213> ORGANISM: Homo sapiens

<400> SEQUENCE: 326 gaggguggc gagggcggcu gagcggcucc aucccccggc cugcucaucc cccucgcccu 60
cucag 65

<210> SEQ ID NO 327
<211> LENGTH: 66
<212> TYPE: RNA
<213> ORGANISM: Homo sapiens

<400> SEQUENCE: 327
gggcaugggg agguguggag ucagcauggg gcuaggaggc cccgcgcuga cccgccuucu 60
ccgcag 66

<210> SEQ ID NO 328
<211> LENGTH: 115
<212> TYPE: RNA
<213> ORGANISM: Homo sapiens

<400> SEQUENCE: 328
ggugccgagg gccguccggc auccuaggcg ggucgcugcg guaccucccu ccugucugug 60
gcggugggau cccguggccg uguuuuccug guggcccggc cgugccugag guuuc 115

<210> SEQ ID NO 329
<211> LENGTH: 67
<212> TYPE: RNA
<213> ORGANISM: Homo sapiens

<400> SEQUENCE: 329
gugaggaggg gcuggcaggg accccuccaa guuggggacg gcagccagcc ccugcucacc 60
ccucgcc 67

<210> SEQ ID NO 330
<211> LENGTH: 60
<212> TYPE: RNA
<213> ORGANISM: Homo sapiens

<400> SEQUENCE: 330
gagcaggcga ggcugggcug aacccguggg ugaggagugc agcccagcug aggccucugc 60

<210> SEQ ID NO 331
<211> LENGTH: 87
<212> TYPE: RNA
<213> ORGANISM: Homo sapiens

<400> SEQUENCE: 331
gugaggcggg gccaggaggg uguguggcgu gggugcugcg gggccgucag ggugccugcg 60
ggacgcucac cuggcuggcc cgcccag 87

<210> SEQ ID NO 332
<211> LENGTH: 56
<212> TYPE: RNA
<213> ORGANISM: Homo sapiens

<400> SEQUENCE: 332
gaccgagugg ggugagggca ggugguucuu cccgaagcag cucucgccuc uucguc 56

<210> SEQ ID NO 333
<211> LENGTH: 69
<212> TYPE: RNA
<213> ORGANISM: Homo sapiens

<400> SEQUENCE: 333
gaaccucggg gcauggggga gggaggcugg acaggagagg gcucacccag gcccuguccu 60
cugccccag 69

<210> SEQ ID NO 334
<211> LENGTH: 67
<212> TYPE: RNA
<213> ORGANISM: Homo sapiens

<400> SEQUENCE: 334
guggcacuca aacugugggg gcacuuucug cucucuggug aaagugccgc caucuuuuga 60
guguuac 67

<210> SEQ ID NO 335
<211> LENGTH: 66
<212> TYPE: RNA
<213> ORGANISM: Homo sapiens

<400> SEQUENCE: 335
ccgagugggg cggggcaggu cccugcaggg acugugacac ugaaggaccu gcaccuucgc 60
ccacag 66

<210> SEQ ID NO 336
<211> LENGTH: 80
<212> TYPE: RNA
<213> ORGANISM: Homo sapiens

<400> SEQUENCE: 336
aggacccuuc cagagggccc ccccucaauc cuguugugcc uaauucagag gguugggugg 60
aggcucuccu gaagggcucu 80

<210> SEQ ID NO 337
<211> LENGTH: 49
<212> TYPE: RNA
<213> ORGANISM: Homo sapiens

<400> SEQUENCE: 337
uucccagcca acgcaccaaa aaugauaugg gucuguuguc uggagaaac 49

<210> SEQ ID NO 338
<211> LENGTH: 86
<212> TYPE: RNA
<213> ORGANISM: Homo sapiens

<400> SEQUENCE: 338
cgccugagcg ugcagcagga caucuuccug accugguaau aauuagguga gaaggauggu 60
ugggggcggu cggcguaacu caggga 86

<210> SEQ ID NO 339
<211> LENGTH: 86
<212> TYPE: RNA
<213> ORGANISM: Homo sapiens

<400> SEQUENCE: 339
cgccugagcg ugcagcagga caucuuccug accugguaau aauuagguga gaaggauggu 60
ugggggcggu cggcguaacu caggga 86

<210> SEQ ID NO 340
<211> LENGTH: 57
<212> TYPE: RNA
<213> ORGANISM: Homo sapiens

<400> SEQUENCE: 340
cauuggaggg uguggaagac aucugggcca acucugaucu cuucaucuac cccccag 57

<210> SEQ ID NO 341
<211> LENGTH: 80
<212> TYPE: RNA
<213> ORGANISM: Homo sapiens

<400> SEQUENCE: 341
accugaggag ccagcccucc ucccgcaccc aaacuuggag cacuugaccu uuggcuguug 60
gagggggcag gcucgcgggu 80

<210> SEQ ID NO 342
<211> LENGTH: 86
<212> TYPE: RNA
<213> ORGANISM: Homo sapiens

<400> SEQUENCE: 342
ggggcugggg gugugggggag agagagugca cagccagcuc agggauuaaa gcucuuucuc 60
ucucucucuc ucccacuucc cugcag 86

<210> SEQ ID NO 343
<211> LENGTH: 75
<212> TYPE: RNA
<213> ORGANISM: Homo sapiens

<400> SEQUENCE: 343
gucagagggg ggaugugcau gcugguuggg gugggcugcc uguggaccaa ucagcgugca 60
cuuccccacc cugaa 75

<210> SEQ ID NO 344
<211> LENGTH: 81
<212> TYPE: RNA
<213> ORGANISM: Homo sapiens

<400> SEQUENCE: 344
auucaggccg guccugcaga gaggaagccc uucugcuuac agguauugga agggcuuccu 60
cucugcagga ccggccugaa u 81

<210> SEQ ID NO 345
<211> LENGTH: 81

<212> TYPE: RNA
<213> ORGANISM: Homo sapiens

<400> SEQUENCE: 345
auucaggccg guccugcaga gaggaagccc uuccaauacc uguaagcaga agggcuuccu 60
cucugcagga ccggccugaa u 81

<210> SEQ ID NO 346
<211> LENGTH: 61
<212> TYPE: RNA
<213> ORGANISM: Homo sapiens

<400> SEQUENCE: 346
ucggcuggcg gggguagagc uggcugcagg cccggccccu cucagcugcu gcccucucca 60
g 61

<210> SEQ ID NO 347
<211> LENGTH: 90
<212> TYPE: RNA
<213> ORGANISM: Homo sapiens

<400> SEQUENCE: 347
ucuaagaaac gcaguggucu cugaagccug caggggcagg ccagcccugc acugaacgcc 60
uguucuugcc agguggcaga agguugcugc 90

<210> SEQ ID NO 348
<211> LENGTH: 70
<212> TYPE: RNA
<213> ORGANISM: Homo sapiens

<400> SEQUENCE: 348
gguuucuccu ugaggagaca ugguggggc cggucaggca gcccaugcca ugugucucca 60
uggagaggcc 70

<210> SEQ ID NO 349
<211> LENGTH: 86
<212> TYPE: RNA
<213> ORGANISM: Homo sapiens

<400> SEQUENCE: 349
uuugguacuu aaagagagga uacccuuugu auguucacuu gauuaauggc gaauauacag 60
ggggagacuc ucauuugcgu aucaaa 86

<210> SEQ ID NO 350
<211> LENGTH: 50
<212> TYPE: RNA
<213> ORGANISM: Homo sapiens

<400> SEQUENCE: 350
acccgggcgu gguggugggg gugggugccu guaauuccag cuaguuggga 50

<210> SEQ ID NO 351
<211> LENGTH: 86
<212> TYPE: RNA
<213> ORGANISM: Homo sapiens

<400> SEQUENCE: 351
uuugguacuu gaagagagga uacccuuugu auguucacuu gauuaauggc gaauauacag 60
ggggagacuc uuauuugcgu aucaaa 86

<210> SEQ ID NO 352
<211> LENGTH: 94
<212> TYPE: RNA
<213> ORGANISM: Homo sapiens

<400> SEQUENCE: 352
gugaggugug ggcccggccc caggagcggg gccugggcag ccccgugugu ugaggaagga 60
aggcagggcc cccgcucccc gggccugacc ccac 94

<210> SEQ ID NO 353
<211> LENGTH: 82
<212> TYPE: RNA
<213> ORGANISM: Homo sapiens

<400> SEQUENCE: 353
ugugggcagg gcccugggga gcugaggcuc ugggggugge cggggcugac ccugggccuc 60
ugcuccccag ugucugaccg cg 82

<210> SEQ ID NO 354
<211> LENGTH: 69
<212> TYPE: RNA
<213> ORGANISM: Homo sapiens

<400> SEQUENCE: 354
gggcuuaggg augggaggcc aggaugaaga uuaaucccua auccccaaca cuggccuugc 60
uauccccag 69

<210> SEQ ID NO 355
<211> LENGTH: 80
<212> TYPE: RNA
<213> ORGANISM: Homo sapiens

<400> SEQUENCE: 355
ccucugugag aaagggugug ggggagaggc ugucuugugu cuguaaguau gccaaacuua 60
uuuuccccaa ggcagaggga 80

<210> SEQ ID NO 356
<211> LENGTH: 100
<212> TYPE: RNA
<213> ORGANISM: Homo sapiens

<400> SEQUENCE: 356
agcucagggc ggcugcgcag agggcuggac ucagcggcgg agcuggcugc uggccucagu 60
ucugccucug uccaggnccu ugugacccgc ccgcucuccu 100

<210> SEQ ID NO 357
<211> LENGTH: 98
<212> TYPE: RNA
<213> ORGANISM: Homo sapiens

<400> SEQUENCE: 357
cuuggucaau aggaaagagg ugggaccucc uggcuuuucc ucugcagcau ggcucggacc 60
uagugcaaug uuuaagcucc ccucucuuuc cuguucag 98

<210> SEQ ID NO 358
<211> LENGTH: 68
<212> TYPE: RNA
<213> ORGANISM: Homo sapiens

<400> SEQUENCE: 358

```
cguggugagg auauggcagg gaaggggagu uucccucuau ucccuucccc ccaguaaucu    60

ucaucaug                                                             68

<210> SEQ ID NO 359
<211> LENGTH: 51
<212> TYPE: RNA
<213> ORGANISM: Homo sapiens

<400> SEQUENCE: 359

agcuguaccu gaaaccaagc accuguuugu gacuuggcuu caguuacuag c              51

<210> SEQ ID NO 360
<211> LENGTH: 93
<212> TYPE: RNA
<213> ORGANISM: Homo sapiens

<400> SEQUENCE: 360

uacuuauggc accccacucc ugguaccaua gucauaaguu aggagauguu agagcuguga    60

guaccaugac uuaagugugg uggcuuaaac aug                                 93

<210> SEQ ID NO 361
<211> LENGTH: 81
<212> TYPE: RNA
<213> ORGANISM: Homo sapiens

<400> SEQUENCE: 361

uacaggugca ggggaacugu agaugaaaag gcuuggcacu ugagggaaag ccucaguuca    60

uucucauuuu gcucaccugu u                                              81

<210> SEQ ID NO 362
<211> LENGTH: 91
<212> TYPE: RNA
<213> ORGANISM: Homo sapiens

<400> SEQUENCE: 362

guucuagagc augguuucuc aucauuugca cuacugauac uuggggucag auaauuguuu    60

gugguggggg cuguuguuug cauuguagga u                                   91

<210> SEQ ID NO 363
<211> LENGTH: 86
<212> TYPE: RNA
<213> ORGANISM: Homo sapiens

<400> SEQUENCE: 363

aggagugacc aaaagacaag agugcgagcc uucuauuaug cccagacagg gccaccagag    60

ggcuccuugg ucuaggggua augcca                                         86

<210> SEQ ID NO 364
<211> LENGTH: 100
<212> TYPE: RNA
<213> ORGANISM: Homo sapiens

<400> SEQUENCE: 364

gcucgguugc cgugguugcg ggcccugccc gcccgccagc ucgcugacag cacgacucag    60

ggcggaggga aguaggguccg uuggucgguc gggaacgagg                        100

<210> SEQ ID NO 365
<211> LENGTH: 72
<212> TYPE: RNA
```

<213> ORGANISM: Homo sapiens

<400> SEQUENCE: 365
augagcgggu gggagcagau cuuauugaga guuccuucuc cugcuccuga uugucuuccc 60
ccacccucac ag 72

<210> SEQ ID NO 366
<211> LENGTH: 75
<212> TYPE: RNA
<213> ORGANISM: Homo sapiens

<400> SEQUENCE: 366
ggcugugccg gguagagagg gcagugggag guaagagcuc uucacccuuc accaccuucu 60
ccacccagca uggcc 75

<210> SEQ ID NO 367
<211> LENGTH: 65
<212> TYPE: RNA
<213> ORGANISM: Homo sapiens

<400> SEQUENCE: 367
gagaaugggg ggacagaugg agaggacaca ggcuggcacu gagguccccu ccacuuuccu 60
ccuag 65

<210> SEQ ID NO 368
<211> LENGTH: 62
<212> TYPE: RNA
<213> ORGANISM: Homo sapiens

<400> SEQUENCE: 368
gagggagugg ggugggaccc agcuguuggc cauggcgaca acaccugggu uguccccucu 60
ag 62

<210> SEQ ID NO 369
<211> LENGTH: 85
<212> TYPE: RNA
<213> ORGANISM: Homo sapiens

<400> SEQUENCE: 369
ucugagguac ccggggcaga uuggguguagg gugcaaagcc ugcccgcccc cuaagccuuc 60
ugcccccaac uccagccugu cagga 85

<210> SEQ ID NO 370
<211> LENGTH: 68
<212> TYPE: RNA
<213> ORGANISM: Homo sapiens

<400> SEQUENCE: 370
gugcaaagag caggaggaca ggggauuuau cucccaaggg agguccccug auccuaguca 60
cggcacca 68

<210> SEQ ID NO 371
<211> LENGTH: 73
<212> TYPE: RNA
<213> ORGANISM: Homo sapiens

<400> SEQUENCE: 371
ggaggcuggg cugggacgga cacccggccu ccacuuucug uggcagguac cuccuccaug 60
ucggcccgcc uug 73

<210> SEQ ID NO 372
<211> LENGTH: 59
<212> TYPE: RNA
<213> ORGANISM: Homo sapiens

<400> SEQUENCE: 372
cugugucggg gagucugggg uccggaauuc uccagagccu cugugccccu acuucccag 59

<210> SEQ ID NO 373
<211> LENGTH: 67
<212> TYPE: RNA
<213> ORGANISM: Homo sapiens

<400> SEQUENCE: 373
uuuaggagag agaugccgcc uugcuccuug aacaggagga gcaaggcggc aucucucuga 60
uacuaaa 67

<210> SEQ ID NO 374
<211> LENGTH: 109
<212> TYPE: RNA
<213> ORGANISM: Homo sapiens

<400> SEQUENCE: 374
ucccgcauuc ccucugcuuu ggucaggugg ugcccuccuu ccaugggguag agccagagau 60 gguggguucu ggcuggucag augggagugg acagagaccc ggggguccuc 109

<210> SEQ ID NO 375
<211> LENGTH: 90
<212> TYPE: RNA
<213> ORGANISM: Homo sapiens

<400> SEQUENCE: 375
guggguacgg cccagugggg gggagaggga cacgcccugg gcucugccca gggugcagcc 60
ggacugacug agccccugug ccgccccag 90

<210> SEQ ID NO 376
<211> LENGTH: 109
<212> TYPE: RNA
<213> ORGANISM: Homo sapiens

<400> SEQUENCE: 376
ugcuauuguc uuacugcuac agcagggcug gggauugcag uauccgcugu ugcugcugcu 60
cccaguccug ccccugcugc uaccuagucc agccucaccg caucccaga 109

<210> SEQ ID NO 377
<211> LENGTH: 70
<212> TYPE: RNA
<213> ORGANISM: Homo sapiens

<400> SEQUENCE: 377
cucgggcccg accgcgccgg cccgcaccuc ccggcccgga gcugcgggcu gcggucaggg 60
cgaucccggg 70

<210> SEQ ID NO 378
<211> LENGTH: 73
<212> TYPE: RNA
<213> ORGANISM: Homo sapiens

<400> SEQUENCE: 378

-continued aggugggcagg gccagccacc aggagggcug cgugccaccc gggcagcucu gcugcucacu 60
ggcaguguca ccu 73

<210> SEQ ID NO 379
<211> LENGTH: 100
<212> TYPE: RNA
<213> ORGANISM: Homo sapiens

<400> SEQUENCE: 379
gugagcgggc gcggcaggga ucgcgggcgg guggcggccu agggcgcgga gggcggaccg 60
ggaauggcgc gccgugcgcc gccggcguaa cugcggcgcu 100

<210> SEQ ID NO 380
<211> LENGTH: 81
<212> TYPE: RNA
<213> ORGANISM: Homo sapiens

<400> SEQUENCE: 380
ggacaggcac cugaggcucu guuagccuug gcucuggguc cugcuccuua gagcagaggc 60
agagaggcuc agggucuguc u 81

<210> SEQ ID NO 381
<211> LENGTH: 67
<212> TYPE: RNA
<213> ORGANISM: Homo sapiens

<400> SEQUENCE: 381
gugggagggg agaggcagca agcacacagg gccugggacu agcaugcuga ccucccuccu 60
gccccag 67

<210> SEQ ID NO 382
<211> LENGTH: 137
<212> TYPE: RNA
<213> ORGANISM: Homo sapiens

<400> SEQUENCE: 382
agccagacaa gagggucaug ggagucacu gucaacccag agcaggcacu gccccugcga 60
ccagccuggg gcaucgguug gggugcaggg gucugcuggu gaugcuuucc aucucuuugc 120
uuuguccuga uuguagc 137

<210> SEQ ID NO 383
<211> LENGTH: 98
<212> TYPE: RNA
<213> ORGANISM: Homo sapiens

<400> SEQUENCE: 383
cgagguaggg gcgucccggg cgcgcgggcg ggucccaggc ugggccccuc ggaggccggg 60
ugcucacugc cccgucccgg cgcccguguc uccuccag 98

<210> SEQ ID NO 384
<211> LENGTH: 81
<212> TYPE: RNA
<213> ORGANISM: Homo sapiens

<400> SEQUENCE: 384
uagaggcagu uucaacagau guguagacuu uugauaugag aaauugguuu caaaaucagg 60
agucggggcu uuacugcuuu u 81

<210> SEQ ID NO 385
<211> LENGTH: 73
<212> TYPE: RNA
<213> ORGANISM: Homo sapiens

<400> SEQUENCE: 385
agggagaaaa gcugggcuga gaggcgacug gugucuaauu uguuugucuc uccaacucag 60
acugccuggc cca 73

<210> SEQ ID NO 386
<211> LENGTH: 71
<212> TYPE: RNA
<213> ORGANISM: Homo sapiens

<400> SEQUENCE: 386
ugaccacccc cgggcaaaga ccugcagauc cccuguuaga gacgggccca ggacuuugug 60
cggggugccc a 71

<210> SEQ ID NO 387
<211> LENGTH: 70
<212> TYPE: RNA
<213> ORGANISM: Homo sapiens

<400> SEQUENCE: 387
aaaagccugu cccuaagucc cucccagccu uccagaguug gugccaggaa ggauuuaggg 60
acaggcuuug 70

<210> SEQ ID NO 388
<211> LENGTH: 73
<212> TYPE: RNA
<213> ORGANISM: Homo sapiens

<400> SEQUENCE: 388
cccagggucu ggugcggaga gggcccacag uggacuuggu gacgcuguau gcccucaccg 60
cucagccccu ggg 73

<210> SEQ ID NO 389
<211> LENGTH: 76
<212> TYPE: RNA
<213> ORGANISM: Homo sapiens

<400> SEQUENCE: 389
acugacuuug agucucuccu cagggugcug caggcaaagc uggggaccca gggagagacg 60
uaagugaggg gagaug 76

<210> SEQ ID NO 390
<211> LENGTH: 72
<212> TYPE: RNA
<213> ORGANISM: Homo sapiens

<400> SEQUENCE: 390
gagucugagg gacccaggac aggagaaggc cuauggugau uugcauucuu ccugcccugg 60
cuccauccuc ag 72

<210> SEQ ID NO 391
<211> LENGTH: 85
<212> TYPE: RNA
<213> ORGANISM: Homo sapiens

<400> SEQUENCE: 391
ggaccugccc ugggcuuucu agucucagcu cuccuccagc ucagcugguc aggagagcug 60
agacuagaaa gcccagggca gguuc 85

<210> SEQ ID NO 392
<211> LENGTH: 81
<212> TYPE: RNA
<213> ORGANISM: Homo sapiens

<400> SEQUENCE: 392
accugcccug ggcuuucuag ucucagcucu ccugaccagc ugagcuggag gagagcugag 60
acuagaaagc ccagggcagg u 81

<210> SEQ ID NO 393
<211> LENGTH: 80
<212> TYPE: RNA
<213> ORGANISM: Homo sapiens

<400> SEQUENCE: 393
cgggaaugcc gcggcgggga cggcgauugg uccguaugug uggugccacc ggccgccggc 60
uccgccccgg cccccgcccc 80

<210> SEQ ID NO 394
<211> LENGTH: 61
<212> TYPE: RNA
<213> ORGANISM: Homo sapiens

<400> SEQUENCE: 394
gggggcggga gcuggggucu gcagguucgc acugaugccu gcucgcccug ucuccccgcua 60 g 61

<210> SEQ ID NO 395
<211> LENGTH: 80
<212> TYPE: RNA
<213> ORGANISM: Homo sapiens

<400> SEQUENCE: 395
accucuaccu cccggcagag gaggcugcag aggcuggcuu uccaaaacuc ugccccccucc 60 gcugcugcca aguggcuggu 80

<210> SEQ ID NO 396
<211> LENGTH: 65
<212> TYPE: RNA
<213> ORGANISM: Homo sapiens

<400> SEQUENCE: 396
cggccacaug gcccaggcuc uucuccgagu gaucucggug gacuggagug ggugguaggu 60
ggcag 65

<210> SEQ ID NO 397
<211> LENGTH: 65
<212> TYPE: RNA
<213> ORGANISM: Homo sapiens

<400> SEQUENCE: 397
cggccacaug gcccaggcuc uucuccgagu gaucucggug gacuggagug ggugguaggu 60
ggcag 65

<210> SEQ ID NO 398
<211> LENGTH: 180

<212> TYPE: RNA
<213> ORGANISM: Homo sapiens

<400> SEQUENCE: 398
cgcgacugcg gcggcggugg uggggggagc cgcggggauc gccgagggcc ggucggccgc 60
cccgggugcc gcgcggugcc gccggcggcg gugaggcccc gcgcgugugu cccggcugcg 120
gucggccgcg cucgaggggu ccccguggcg uccccuuccc cgccggccgc cuuucucgcg 180

<210> SEQ ID NO 399
<211> LENGTH: 180
<212> TYPE: RNA
<213> ORGANISM: Homo sapiens

<400> SEQUENCE: 399
cgcgacugcg gcggcggugg uggggggagc cgcggggauc gccgagggcc ggucggccgc 60
cccgggugcc gcgcggugcc gccggcggcg gugaggcccc gcgcgugugu cccggcugcg 120
gucggccgcg cucgaggggu ccccguggcg uccccuuccc cgccggccgc cuuucucgcg 180

<210> SEQ ID NO 400
<211> LENGTH: 76
<212> TYPE: RNA
<213> ORGANISM: Homo sapiens

<400> SEQUENCE: 400
gagggagcug uagagcaggg agcaggaagc ugugugugucc cagcccugac cuguccuguu 60
cugcccccag ccccuc 76

<210> SEQ ID NO 401
<211> LENGTH: 93
<212> TYPE: RNA
<213> ORGANISM: Homo sapiens

<400> SEQUENCE: 401
ggcgcuuuug ugcgcgcccg ggucuguugg ugcucagagu guggucaggc ggcucggacu 60
gagcaggugg gugcggggcu cggaggaggc ggc 93

<210> SEQ ID NO 402
<211> LENGTH: 99
<212> TYPE: RNA
<213> ORGANISM: Homo sapiens

<400> SEQUENCE: 402
cgcccaccuc agccucccaa aaugcuggga uuacaggcau gagccacugc ggucgaccau 60
gaccuggaca uguuugugcc caguacuguc aguuugcag 99

<210> SEQ ID NO 403
<211> LENGTH: 92
<212> TYPE: RNA
<213> ORGANISM: Homo sapiens

<400> SEQUENCE: 403
gucagugucu gggcggacag cugcaggaaa gggaagacca aggcuugcug ucuguccagu 60
cugccacccu acccugucug uucuugccac ag 92

<210> SEQ ID NO 404
<211> LENGTH: 99
<212> TYPE: RNA
<213> ORGANISM: Homo sapiens

<400> SEQUENCE: 404
gaaacugggc ucaaggugag gggugcuauc ugugauugag ggacaugguu aauggaauug 60
ucucacacag aaaucgcacc cgucaccuug gccuacuua 99

<210> SEQ ID NO 405
<211> LENGTH: 81
<212> TYPE: RNA
<213> ORGANISM: Homo sapiens

<400> SEQUENCE: 405
cauccuccuu acgucccacc ccccacuccu guuucuggug aaauauucaa acaggagugg 60
gggugggaca uaaggaggau a 81

<210> SEQ ID NO 406
<211> LENGTH: 80
<212> TYPE: RNA
<213> ORGANISM: Homo sapiens

<400> SEQUENCE: 406
gguuccggag ccccggcgcg ggcggguucu ggggguguaga cgcugcuggc cagcccgccc 60
cagccgaggu ucucggcacc 80

<210> SEQ ID NO 407
<211> LENGTH: 61
<212> TYPE: RNA
<213> ORGANISM: Homo sapiens

<400> SEQUENCE: 407
uccgcucugu ggaguggggu gccugucccc ugccacuggg ugacccaccc cucuccacca 60
g 61

<210> SEQ ID NO 408
<211> LENGTH: 62
<212> TYPE: RNA
<213> ORGANISM: Homo sapiens

<400> SEQUENCE: 408
gugggucucg caucaggagg caaggccagg acccgcugac ccaugccucc ugccgcgguc 60
ag 62

<210> SEQ ID NO 409
<211> LENGTH: 79
<212> TYPE: RNA
<213> ORGANISM: Homo sapiens

<400> SEQUENCE: 409
cagccugggg aaggcuuggc agggaagaca caugagcagu gccuccacuu cacgccucuc 60
ccuugucucc uuucccuag 79

<210> SEQ ID NO 410
<211> LENGTH: 99
<212> TYPE: RNA
<213> ORGANISM: Homo sapiens

<400> SEQUENCE: 410
gcaagggaca gggagggucg uggcgacacu cgcgccagcu cccgggacgg cugggcucgg 60
gcuggucgcc gaccuccgac ccuccacuag augccuggc 99

<210> SEQ ID NO 411
<211> LENGTH: 72
<212> TYPE: RNA
<213> ORGANISM: Homo sapiens

<400> SEQUENCE: 411
ucuccucgag gggucucugc cucuacccag gacucuuuca ugaccaggag gcugaggccc 60
cucacaggcg gc 72

<210> SEQ ID NO 412
<211> LENGTH: 70
<212> TYPE: RNA
<213> ORGANISM: Homo sapiens

<400> SEQUENCE: 412
gucccugggg gcugggaugg gccauggugu gcucugaucc cccugugguc ucuuggcccc 60
caggaacucc 70

<210> SEQ ID NO 413
<211> LENGTH: 94
<212> TYPE: RNA
<213> ORGANISM: Homo sapiens

<400> SEQUENCE: 413
gggcugaccc cuagggucag gugaggcccu uggggcacag uggugccauc uccccugugc 60
ucccagggcc ucgccugucc cuugaggucg gccc 94

<210> SEQ ID NO 414
<211> LENGTH: 76
<212> TYPE: RNA
<213> ORGANISM: Homo sapiens

<400> SEQUENCE: 414
ccgaugccuc gggagucuac agcagggcca ugucugugag ggcccaaggg ugcauguguc 60
ucccagguuu cggugc 76

<210> SEQ ID NO 415
<211> LENGTH: 67
<212> TYPE: RNA
<213> ORGANISM: Homo sapiens

<400> SEQUENCE: 415
ccugcaggca gaagugggc ugacagggca gaggguugcg cccccucacc aucccuucug 60
ccugcag 67

<210> SEQ ID NO 416
<211> LENGTH: 67
<212> TYPE: RNA
<213> ORGANISM: Homo sapiens

<400> SEQUENCE: 416
ccugcaggca gaagugggc ugacagggca gaggguugcg cccccucacc aucccuucug 60
ccugcag 67

<210> SEQ ID NO 417
<211> LENGTH: 67
<212> TYPE: RNA
<213> ORGANISM: Homo sapiens

<400> SEQUENCE: 417
ccugcaggca gaaguggggc ugacagggca gaggguugcg cccccucacc aucccuucug 60
ccugcag 67

<210> SEQ ID NO 418
<211> LENGTH: 67
<212> TYPE: RNA
<213> ORGANISM: Homo sapiens

<400> SEQUENCE: 418
ccugcaggca gaaguggggc ugacagggca gaggguugcg cccccucacc aucccuucug 60
ccugcag 67

<210> SEQ ID NO 419
<211> LENGTH: 80
<212> TYPE: RNA
<213> ORGANISM: Homo sapiens

<400> SEQUENCE: 419
aggcagcaaa uggccagagc ucacacagag ggaugagugc acuucaccug cagugugacu 60
cagcaggcca acagaugcua 80

<210> SEQ ID NO 420
<211> LENGTH: 74
<212> TYPE: RNA
<213> ORGANISM: Homo sapiens

<400> SEQUENCE: 420
gcaaauggcc agagcucaca cagagggaug agugcacuuc accugcagug ugacucagca 60
ggccaacaga ugcu 74

<210> SEQ ID NO 421
<211> LENGTH: 54
<212> TYPE: RNA
<213> ORGANISM: Homo sapiens

<400> SEQUENCE: 421
agggaaggag gcuuggucuu agcacggggu cuaaggcccg ggcuuuccuc ccag 54

<210> SEQ ID NO 422
<211> LENGTH: 62
<212> TYPE: RNA
<213> ORGANISM: Homo sapiens

<400> SEQUENCE: 422 gagggguggug gaggaagagg gcagcuccca ugacugccug accgccuucu cuccuccccc 60
ag 62

<210> SEQ ID NO 423
<211> LENGTH: 62
<212> TYPE: RNA
<213> ORGANISM: Homo sapiens

<400> SEQUENCE: 423
gugaguagug gcgcgcggcg gcucggagua ccucugccgc cgcgcgcauc ggcucagcau 60
gc 62

<210> SEQ ID NO 424
<211> LENGTH: 94
<212> TYPE: RNA
<213> ORGANISM: Homo sapiens

<400> SEQUENCE: 424
cacggugucc ccugguggaa ccuggcaggg ggagagguaa ggucuuucag ccucuccaaa 60
gcccaugguc agguacucag guggggggagc ccug 94

<210> SEQ ID NO 425
<211> LENGTH: 73
<212> TYPE: RNA
<213> ORGANISM: Homo sapiens

<400> SEQUENCE: 425
accuuuccag cucaucccac cucugccacc aaaacacuca ucgcggggguc agagggagug 60 ccaaaaaagg uaa 73

<210> SEQ ID NO 426
<211> LENGTH: 64
<212> TYPE: RNA
<213> ORGANISM: Homo sapiens

<400> SEQUENCE: 426
aguucagggc cgaagggugg aagcugcugg ugcucaucuc agccucugcc cuuggccucc 60
ccag 64

<210> SEQ ID NO 427
<211> LENGTH: 87
<212> TYPE: RNA
<213> ORGANISM: Homo sapiens

<400> SEQUENCE: 427
cccucaucuc ugggcagggg cuuauuguag gagucucuga agagagcugu ggacugaccu 60
gcuuuaaccc uuccccaggu ucccauu 87

<210> SEQ ID NO 428
<211> LENGTH: 75
<212> TYPE: RNA
<213> ORGANISM: Homo sapiens

<400> SEQUENCE: 428
aggcuggcgu gggcugaggg caggaggccu guggccgguc ccaggccucc ugcuuccugg 60
gcucaggcuc gguuu 75

<210> SEQ ID NO 429
<211> LENGTH: 69
<212> TYPE: RNA
<213> ORGANISM: Homo sapiens

<400> SEQUENCE: 429
guggguaggg uuugggggag agcgugggcu gggguucagg gacacccucu caccacugcc 60
cucccacag 69

<210> SEQ ID NO 430
<211> LENGTH: 91
<212> TYPE: RNA
<213> ORGANISM: Homo sapiens

<400> SEQUENCE: 430
ggggcauuua ggguaacuga gcugcugccg gggccuggcg cuccucuacc uugucaggug 60
acccagcagu cccuccccu gcauggugcc c 91

<210> SEQ ID NO 431
<211> LENGTH: 68
<212> TYPE: RNA
<213> ORGANISM: Homo sapiens

<400> SEQUENCE: 431
cucaggcuca guggugcaug cuuauagucc cagccacucu ggaggcugaa ggaagauggc 60
uugagccu 68

<210> SEQ ID NO 432
<211> LENGTH: 87
<212> TYPE: RNA
<213> ORGANISM: Homo sapiens

<400> SEQUENCE: 432
cccaggcgcc cgcucccgac ccacgccgcg ccgccggguc ccuccucccc ggagaggcug 60
ggcucgggac gcgcggcuca gcucggg 87

<210> SEQ ID NO 433
<211> LENGTH: 69
<212> TYPE: RNA
<213> ORGANISM: Homo sapiens

<400> SEQUENCE: 433
ccgggcaggc agguguaggg uggagcccac uguggcuccu gacucagccc ugcugccuuc 60
accugccag 69

<210> SEQ ID NO 434
<211> LENGTH: 65
<212> TYPE: RNA
<213> ORGANISM: Homo sapiens

<400> SEQUENCE: 434
uucuccuggg gaguggcugg ggagcagaca gacccaaccu caugcucccc ggccucugcc 60
cccag 65

<210> SEQ ID NO 435
<211> LENGTH: 86
<212> TYPE: RNA
<213> ORGANISM: Homo sapiens

<400> SEQUENCE: 435
agagccgggg ccauggagca gccuguguag acggggaccu gcccugcaug ggcacccccu 60
cacuggcugc uucccuuggu cuccag 86

<210> SEQ ID NO 436
<211> LENGTH: 64
<212> TYPE: RNA
<213> ORGANISM: Homo sapiens

<400> SEQUENCE: 436
gaaggcgagg gguagaagag cacaggggguu cugauaaacc cuucugccug cauucuacuc 60
ccag 64

<210> SEQ ID NO 437
<211> LENGTH: 86
<212> TYPE: RNA
<213> ORGANISM: Homo sapiens

<400> SEQUENCE: 437
auucuaggug gggagacuga cggcuggagg cccauaagcu gucuaaaacu ucggcccccca 60 gauuucuggu cuccccacuu cagaac 86

<210> SEQ ID NO 438
<211> LENGTH: 63
<212> TYPE: RNA
<213> ORGANISM: Homo sapiens

<400> SEQUENCE: 438
cuugcccggg agaaggaggu ggccuggaga gcugcugucu ccagccgccg ccugucucca 60
cag 63

<210> SEQ ID NO 439
<211> LENGTH: 47
<212> TYPE: RNA
<213> ORGANISM: Homo sapiens

<400> SEQUENCE: 439
aggcagguua ucugggcugc caucucccac uggcugcuug ccugccu 47

<210> SEQ ID NO 440
<211> LENGTH: 70
<212> TYPE: RNA
<213> ORGANISM: Homo sapiens

<400> SEQUENCE: 440
ggccgcggcg cgcaagaugg cggcgggccc gggcaccgcc ccuuccgccc cgccgggcgu 60
cgcacgaggc 70

<210> SEQ ID NO 441
<211> LENGTH: 73
<212> TYPE: RNA
<213> ORGANISM: Homo sapiens

<400> SEQUENCE: 441 cuggguguuug aggcgaugug gggauguaga gacaacuucc cagucucauu uccucauccu 60
gccaggccac cau 73

<210> SEQ ID NO 442
<211> LENGTH: 103
<212> TYPE: RNA
<213> ORGANISM: Homo sapiens

<400> SEQUENCE: 442
gugucggcug uggcgugacu gucccucugu gucccccacu aggcccacug cucaguggag 60
cguggaggac gaggaggagg ccguccacga gcaaugccag cau 103

<210> SEQ ID NO 443
<211> LENGTH: 80
<212> TYPE: RNA
<213> ORGANISM: Homo sapiens

<400> SEQUENCE: 443
ggcgcgucgc cccccucagu ccaccagagc ccggauaccu cagaaauucg gcucuggguc 60
uguggggagc gaaaugcaac 80

<210> SEQ ID NO 444
<211> LENGTH: 119
<212> TYPE: RNA

<213> ORGANISM: Homo sapiens

<400> SEQUENCE: 444
agccugcgcc ggagccgggg ccugagcccg ggccgcgcag gccgugaacu cgucgagcug 60
cgcgugcggc cggugcucaa ccugccgggu ccuggccccg cgcucccgcg cgcccugga 119

<210> SEQ ID NO 445
<211> LENGTH: 56
<212> TYPE: RNA
<213> ORGANISM: Homo sapiens

<400> SEQUENCE: 445
guaggcaggg gcugggguuu cagguucuca gucagaaccu uggccccucu ccccag 56

<210> SEQ ID NO 446
<211> LENGTH: 73
<212> TYPE: RNA
<213> ORGANISM: Homo sapiens

<400> SEQUENCE: 446
aggccaggug gguauggagg agcccucaua uggcaguugg cgagggccca gugagccccu 60
cucugcucuc cag 73

<210> SEQ ID NO 447
<211> LENGTH: 78
<212> TYPE: RNA
<213> ORGANISM: Homo sapiens

<400> SEQUENCE: 447
guagcugagg ggaugguaga ccggugacgu gcacuucauu uacgauguag gucacccguu 60
ugacuaucca ccagcgcc 78

<210> SEQ ID NO 448
<211> LENGTH: 87
<212> TYPE: RNA
<213> ORGANISM: Homo sapiens

<400> SEQUENCE: 448
guguggccgg caggcgggug ggcgggggcg gccgguggga accccgcccc gccccgcgcc 60
cgcacucacc cgcccgucuc cccacag 87

<210> SEQ ID NO 449
<211> LENGTH: 63
<212> TYPE: RNA
<213> ORGANISM: Homo sapiens

<400> SEQUENCE: 449 aaugggugggg ugcuggugggg agccgugccc uggccacuca uucggcucuc ucccucaccc 60
uag 63

<210> SEQ ID NO 450
<211> LENGTH: 73
<212> TYPE: RNA
<213> ORGANISM: Homo sapiens

<400> SEQUENCE: 450
ggggagguac cugggacagg aggaggaggc agccuugccu cagaaaccaa acugucaaaa 60
guguagguuc cac 73

-continued

<210> SEQ ID NO 451
<211> LENGTH: 62
<212> TYPE: RNA
<213> ORGANISM: Homo sapiens

<400> SEQUENCE: 451
uuaccuugug ggguuggaga gcuggcuggu ccagccccuc agaagcucuc cccucccccgc 60 ag 62

<210> SEQ ID NO 452
<211> LENGTH: 56
<212> TYPE: RNA
<213> ORGANISM: Homo sapiens

<400> SEQUENCE: 452
cgcucgggcg gaggugguug agugccgacu ggcgccugac ccacccccuc ccgcag 56

<210> SEQ ID NO 453
<211> LENGTH: 81
<212> TYPE: RNA
<213> ORGANISM: Homo sapiens

<400> SEQUENCE: 453
cucccuggga gggcguggau gaugguggga gaggagcccc acuguggaag ucugaccccc 60
acaucgcccc accuuccca g 81

<210> SEQ ID NO 454
<211> LENGTH: 66
<212> TYPE: RNA
<213> ORGANISM: Homo sapiens

<400> SEQUENCE: 454
ccugggaacg gguuccggca gacgcugagg uugcguugac gcucgcgccc cggcuccccgu 60 uccagg 66

<210> SEQ ID NO 455
<211> LENGTH: 61
<212> TYPE: RNA
<213> ORGANISM: Homo sapiens

<400> SEQUENCE: 455
ccugcgggga caggccaggg caucuaggcu gugcacagug acgcccccucc ugcccccaca 60 g 61

<210> SEQ ID NO 456
<211> LENGTH: 60
<212> TYPE: RNA
<213> ORGANISM: Homo sapiens

<400> SEQUENCE: 456
ggcaggaggg cugugccagg uuggcugggc caggccugac cugccagcac cucccugcag 60

<210> SEQ ID NO 457
<211> LENGTH: 71
<212> TYPE: RNA
<213> ORGANISM: Homo sapiens

<400> SEQUENCE: 457
gugucugugc cggucccagg agaaccugca gaggcaucgg gucagcggug cuccugcggg 60
ccgacacuca c 71

<210> SEQ ID NO 458
<211> LENGTH: 65
<212> TYPE: RNA
<213> ORGANISM: Homo sapiens

<400> SEQUENCE: 458
ugucugggga uuuggagaag uggugagcgc aggucuuugg caccaucucc ccugguccccu 60 uggcu 65

<210> SEQ ID NO 459
<211> LENGTH: 68
<212> TYPE: RNA
<213> ORGANISM: Homo sapiens

<400> SEQUENCE: 459
aggguugggg ggacaggaug agaggcuguc uucauucccu cuugaccacc ccucguuucu 60
ucccccag 68

<210> SEQ ID NO 460
<211> LENGTH: 87
<212> TYPE: RNA
<213> ORGANISM: Homo sapiens

<400> SEQUENCE: 460
accgcaggga aaaugaggga cuuuuggggg cagauguguu uccauuccac uaucauaaug 60
ccccuaaaaa uccuuauugc ucuugca 87

<210> SEQ ID NO 461
<211> LENGTH: 124
<212> TYPE: RNA
<213> ORGANISM: Homo sapiens

<400> SEQUENCE: 461
aacccuccuu gggaagugaa gcucaggcug ugauuucaag ccaggggggcg uuuuucuaua 60 acuggaugaa aagcaccucc agagcuugaa gcucacaguu ugagagcaau cgucuaagga 120
aguu 124

<210> SEQ ID NO 462
<211> LENGTH: 72
<212> TYPE: RNA
<213> ORGANISM: Homo sapiens

<400> SEQUENCE: 462
cagccaggag ggaaggggcu gagaacagga ccugugcuca cuggggccug caugacccuu 60
cccuccccac ag 72

<210> SEQ ID NO 463
<211> LENGTH: 61
<212> TYPE: RNA
<213> ORGANISM: Homo sapiens

<400> SEQUENCE: 463
gcccuccgcc cgugcacccc ggggcaggag accccgcggg acgcgccgag guagggggga 60
c 61

<210> SEQ ID NO 464
<211> LENGTH: 67
<212> TYPE: RNA
<213> ORGANISM: Homo sapiens

<400> SEQUENCE: 464
cagggaggag gugguacuag gggccagcaa ccugauuacc ccucuuuggc ccuuuguacc 60
ccuccag 67

<210> SEQ ID NO 465
<211> LENGTH: 136
<212> TYPE: RNA
<213> ORGANISM: Homo sapiens

<400> SEQUENCE: 465
ccgcuugccu cgcccagcgc agccccggcc gcugggcgca cccgucccgu ucguccccgg 60
acguugcucu cuaccccggg aacgucgaga cuggagcgcc cgaacugagc caccuucgcg 120
gaccccgaga gcggcg 136

<210> SEQ ID NO 466
<211> LENGTH: 115
<212> TYPE: RNA
<213> ORGANISM: Homo sapiens

<400> SEQUENCE: 466
ucugaggaga ccugggcugu cagaggccag ggaaggggac gaggguuggg gaacaggugg 60
uuagcacuuc auccucgucu cccucccagg uuagaagggc cccccucucu gaagg 115

<210> SEQ ID NO 467
<211> LENGTH: 71
<212> TYPE: RNA
<213> ORGANISM: Homo sapiens

<400> SEQUENCE: 467
ugacgggcga gcuuuuggcc cggguuauac cugaugcuca cguauaagac gagcaaaaag 60
cuuguugguc a 71

<210> SEQ ID NO 468
<211> LENGTH: 65
<212> TYPE: RNA
<213> ORGANISM: Homo sapiens

<400> SEQUENCE: 468
agcccugggg guggucucua gccaaggcuc uggggucuca cccuuggcug gucucugcuc 60
cgcag 65

<210> SEQ ID NO 469
<211> LENGTH: 84
<212> TYPE: RNA
<213> ORGANISM: Homo sapiens

<400> SEQUENCE: 469
cuccccaugg cccugucucc caacccuugu accagugcug ggcucagacc cugguacagg 60
ccugggggac agggaccugg ggac 84

<210> SEQ ID NO 470
<211> LENGTH: 60
<212> TYPE: RNA
<213> ORGANISM: Homo sapiens

<400> SEQUENCE: 470
ugugaaugac ccccuuccag agccaaaauc accagggaug gaggaggggu cuuggguacu 60

<210> SEQ ID NO 471
<211> LENGTH: 68
<212> TYPE: RNA
<213> ORGANISM: Homo sapiens

<400> SEQUENCE: 471
ugcccaggcu ggagcgagug caguggugca gucaguccua gcucacugca gccucgaacu 60
ccugggcu 68

<210> SEQ ID NO 472
<211> LENGTH: 63
<212> TYPE: RNA
<213> ORGANISM: Homo sapiens

<400> SEQUENCE: 472
gagucgagga cugguggaag ggccuuuccc cucagaccaa ggcccuggcc ccagcuucuu 60
cuc 63

<210> SEQ ID NO 473
<211> LENGTH: 74
<212> TYPE: RNA
<213> ORGANISM: Homo sapiens

<400> SEQUENCE: 473
gcagcccggu gagcgcucgc uggccuggca gugcgucgga agaacagggc ggguggggcc 60
gcgcacaucu cugc 74

<210> SEQ ID NO 474
<211> LENGTH: 54
<212> TYPE: RNA
<213> ORGANISM: Homo sapiens

<400> SEQUENCE: 474
agcagcaggg gagagagagg aguccucuag acaccgacuc ugucuccugc agau 54

<210> SEQ ID NO 475
<211> LENGTH: 83
<212> TYPE: RNA
<213> ORGANISM: Homo sapiens

<400> SEQUENCE: 475
gcugcuguug ggagacccug gucugcacuc uaucuguauu cuuacugaag ggagugcagg 60
gcaggguuuc ccauacagag ggc 83

<210> SEQ ID NO 476
<211> LENGTH: 83
<212> TYPE: RNA
<213> ORGANISM: Homo sapiens

<400> SEQUENCE: 476
acggcaucuu ugcacucagc aggcaggcug gugcagcccg uggugggga ccauccugcc 60 ugcugugggg uaaggacggc ugu 83

<210> SEQ ID NO 477
<211> LENGTH: 118
<212> TYPE: RNA
<213> ORGANISM: Homo sapiens

<400> SEQUENCE: 477
gcaggugaac uggcaggcca ggaagaggag gaagcccugg aggggcugga ggugauggau 60
guuuuccucc gguucucagg gcuccaccuc uuucgggccg uagagccagg gcuggugc 118

<210> SEQ ID NO 478
<211> LENGTH: 66
<212> TYPE: RNA
<213> ORGANISM: Homo sapiens

<400> SEQUENCE: 478
ugacugggga gcagaaggag aacccaagaa aagcugacuu ggaggucccu ccuucugucc 60
ccacag 66

<210> SEQ ID NO 479
<211> LENGTH: 49
<212> TYPE: RNA
<213> ORGANISM: Homo sapiens

<400> SEQUENCE: 479
gugaggcugg agugagcgga gaucguacca cugcacucca accugguga 49

<210> SEQ ID NO 480
<211> LENGTH: 84
<212> TYPE: RNA
<213> ORGANISM: Homo sapiens

<400> SEQUENCE: 480
ccgcagccgc cgcgccgggc ccggguuggc cgcugacccc cgcggggccc ccggcggccg 60
gggcgggggc gggggcugcc ccgg 84

<210> SEQ ID NO 481
<211> LENGTH: 113
<212> TYPE: RNA
<213> ORGANISM: Homo sapiens

<400> SEQUENCE: 481
agcaugacag aggagaggug gagguaggcg agaguaauau aauuucucca ggagaacauc 60
ugagagggga aguugcuuuc cugcccuggc ccuuucaccc uccugaguuu ggg 113

<210> SEQ ID NO 482
<211> LENGTH: 62
<212> TYPE: RNA
<213> ORGANISM: Homo sapiens

<400> SEQUENCE: 482
ccuucugcgg cagagcuggg gucaccagcc cucauguacu ugugacuucu ccccugccac 60
ag 62

<210> SEQ ID NO 483
<211> LENGTH: 54
<212> TYPE: RNA
<213> ORGANISM: Homo sapiens

<400> SEQUENCE: 483
ggacaagggc ggcgcgaccg gcccggggcu cuugggcggc cgcguuuccc cucc 54

<210> SEQ ID NO 484
<211> LENGTH: 109
<212> TYPE: RNA
<213> ORGANISM: Homo sapiens

<400> SEQUENCE: 484

-continued

```
ggucgggcuc accaugacac agugugagac cucgggcuac aacacaggac ccgggcgcug     60

cucugacccc ucgugucuug uguugcagcc ggagggacgc agguccgca                109


<210> SEQ ID NO 485
<211> LENGTH: 81
<212> TYPE: RNA
<213> ORGANISM: Homo sapiens

<400> SEQUENCE: 485

uccacugcug ccgccgucgc cgccacccga gccggagcgg gcugggccgc caaggcaaga     60

ugguggacua cagcgugugg g                                               81


<210> SEQ ID NO 486
<211> LENGTH: 69
<212> TYPE: RNA
<213> ORGANISM: Homo sapiens

<400> SEQUENCE: 486

ugggguaggg gugggggaau ucaggggugu cgaacucaug gcugccaccu uugugucccc     60

auccugcag                                                             69


<210> SEQ ID NO 487
<211> LENGTH: 120
<212> TYPE: RNA
<213> ORGANISM: Homo sapiens

<400> SEQUENCE: 487

gauccaggga acccuagagc agggggaugg cagagcaaaa uucauggccu acagcugccu     60

cuugccaaac ugcacuggau uuugugucuc ccauuccccca gagcugucug aggugcuuug   120


<210> SEQ ID NO 488
<211> LENGTH: 60
<212> TYPE: RNA
<213> ORGANISM: Homo sapiens

<400> SEQUENCE: 488

caaggugggg gagaugggg uugaacuuca uuucucaugc ucauccccau cuccuuucag     60


<210> SEQ ID NO 489
<211> LENGTH: 85
<212> TYPE: RNA
<213> ORGANISM: Homo sapiens

<400> SEQUENCE: 489

ggggagguag ggaaaaggaa gggggaggag aaggugagac caauguccug ggugccacuc     60

cugcccagug ccucccuucc ucguu                                           85


<210> SEQ ID NO 490
<211> LENGTH: 85
<212> TYPE: RNA
<213> ORGANISM: Homo sapiens

<400> SEQUENCE: 490

gggacggggc cugcaggcag aaguggggcu gacagggcag aggguugcgc ccccucacca     60

ccccuucugc cugcagcggu gggcu                                           85


<210> SEQ ID NO 491
<211> LENGTH: 71
<212> TYPE: RNA
<213> ORGANISM: Homo sapiens
```

<400> SEQUENCE: 491
ggggccugca ggcagaagug gggcugacag ggcagagggu ugcgcccccu caccaccccu 60
ucugccugca g 71

<210> SEQ ID NO 492
<211> LENGTH: 97
<212> TYPE: RNA
<213> ORGANISM: Homo sapiens

<400> SEQUENCE: 492
ggugggagga uugcuugagc cuggaagcug gagccugcag ugaacuauca uugugccacu 60
guacuccagc cuaggcaaca aaaugaaauc cugucua 97

<210> SEQ ID NO 493
<211> LENGTH: 63
<212> TYPE: RNA
<213> ORGANISM: Homo sapiens

<400> SEQUENCE: 493
cugagccugg aagcuggagc cugcagugag cuaugaucau gucccuguac ucuagccugg 60
gca 63

<210> SEQ ID NO 494
<211> LENGTH: 55
<212> TYPE: RNA
<213> ORGANISM: Homo sapiens

<400> SEQUENCE: 494
aaucugccag cuuccacagu ggcagauuuu cccauagugg gaagcuggca gauuc 55

<210> SEQ ID NO 495
<211> LENGTH: 101
<212> TYPE: RNA
<213> ORGANISM: Homo sapiens

<400> SEQUENCE: 495
gaugggcccc uuguguccug aauugggugg gggcucugag uggggaaagu gggggccuag 60
gggaggucac aguugggucu aggggucagg agggcccagg a 101

<210> SEQ ID NO 496
<211> LENGTH: 74
<212> TYPE: RNA
<213> ORGANISM: Homo sapiens

<400> SEQUENCE: 496
gcucuagccu aauuuuagau cuggucugcu ucaguuucac uccaagcaga cuugaccuac 60
aauuagccua gagc 74

<210> SEQ ID NO 497
<211> LENGTH: 74
<212> TYPE: RNA
<213> ORGANISM: Homo sapiens

<400> SEQUENCE: 497
gcucuagccu aauuuuagau cuggucugcu ucaguuucac uccaagcaga cuugaccuac 60
aauuagccua gagc 74

<210> SEQ ID NO 498

<211> LENGTH: 83
<212> TYPE: RNA
<213> ORGANISM: Homo sapiens

<400> SEQUENCE: 498
aauagagggu gcacaggcac gggagcucag gugaggcagg gagcugagcu caccugaccu 60
cccaugccug ugcacccucu auu 83

<210> SEQ ID NO 499
<211> LENGTH: 71
<212> TYPE: RNA
<213> ORGANISM: Homo sapiens

<400> SEQUENCE: 499
gcagagguga guugaccucc acagggccac ccagggagua aguagccaag uggaaguuac 60
uuuaccucug u 71

<210> SEQ ID NO 500
<211> LENGTH: 63
<212> TYPE: RNA
<213> ORGANISM: Homo sapiens

<400> SEQUENCE: 500
gccaaggacu gauccucucg ggcagggagu cagaggggac cgcccgagag gauccguccc 60
ugc 63

<210> SEQ ID NO 501
<211> LENGTH: 66
<212> TYPE: RNA
<213> ORGANISM: Homo sapiens

<400> SEQUENCE: 501
ucaagacggg gagucaggca gugguggaga uggagagccc ugagccucca cucuccuggc 60
ccccag 66

<210> SEQ ID NO 502
<211> LENGTH: 68
<212> TYPE: RNA
<213> ORGANISM: Homo sapiens

<400> SEQUENCE: 502
gggcgcaggg ggacuggggg ugagcaggcc cagaacccag cucgugcuca cucucagucc 60
cucccuag 68

<210> SEQ ID NO 503
<211> LENGTH: 71
<212> TYPE: RNA
<213> ORGANISM: Homo sapiens

<400> SEQUENCE: 503
ggguaaaggg gcagggacgg guggccccag gaagaagggc cugguggagc cgcucuucuc 60
ccugcccaca g 71

<210> SEQ ID NO 504
<211> LENGTH: 60
<212> TYPE: RNA
<213> ORGANISM: Homo sapiens

<400> SEQUENCE: 504
ggugccucgg gagggcaugg gccaggccac auaaugagcc aaaccccugu cuacccgcag 60

<210> SEQ ID NO 505
<211> LENGTH: 61
<212> TYPE: RNA
<213> ORGANISM: Homo sapiens

<400> SEQUENCE: 505
ucacccggug agggcgggug gaggaggagg guccccacca ucagccuuca cugggacggg 60
a 61

<210> SEQ ID NO 506
<211> LENGTH: 82
<212> TYPE: RNA
<213> ORGANISM: Homo sapiens

<400> SEQUENCE: 506
cugacuuuuu uagggaguag aagggugggg agcaugaaca auguuucuca cucccuaccc 60
cuccacuccc caaaaaaguc ag 82

<210> SEQ ID NO 507
<211> LENGTH: 67
<212> TYPE: RNA
<213> ORGANISM: Homo sapiens

<400> SEQUENCE: 507
aaaucucucu ccauaucuuu ccugcagccc ccaggugggg gggaagaaaa gguggggaau 60
uagauuc 67

<210> SEQ ID NO 508
<211> LENGTH: 88
<212> TYPE: RNA
<213> ORGANISM: Homo sapiens

<400> SEQUENCE: 508
guggggccag gcgguggugg gcacugcugg ggugggcaca gcagccaugc agagcgggca 60
uuugaccccg ugccacccuu uuccccag 88

<210> SEQ ID NO 509
<211> LENGTH: 86
<212> TYPE: RNA
<213> ORGANISM: Homo sapiens

<400> SEQUENCE: 509
ggcuuagaaa caguccuag guaggauuug gggaggagcu aagaagcccc uacagggccc 60
agaggugggg acugagccuu aguugg 86

<210> SEQ ID NO 510
<211> LENGTH: 70
<212> TYPE: RNA
<213> ORGANISM: Homo sapiens

<400> SEQUENCE: 510
acaaauagcu ucagggaguc aggggagggc agaaauagau ggccuucccc ugcugggaag 60
aaaguggguc 70

<210> SEQ ID NO 511
<211> LENGTH: 86
<212> TYPE: RNA
<213> ORGANISM: Homo sapiens

<400> SEQUENCE: 511
agggagaagg gucggggcag ggagggcagg gcaggcucug gggugggggg ucugugaguc 60
agccacggcu cugcccacgu cucccc 86

<210> SEQ ID NO 512
<211> LENGTH: 73
<212> TYPE: RNA
<213> ORGANISM: Homo sapiens

<400> SEQUENCE: 512
cggcgacggc ggggugggug aggucgggcc ccaagacucg ggguuugccg ggcgccucag 60
uucaccgcgg ccg 73

<210> SEQ ID NO 513
<211> LENGTH: 90
<212> TYPE: RNA
<213> ORGANISM: Homo sapiens

<400> SEQUENCE: 513
gugucucucu ggagacccug cagccuuccc acccaccagg gagcuuucca ugggcugugg 60
ggaaggcguc agugucgggu gagggaacac 90

<210> SEQ ID NO 514
<211> LENGTH: 96
<212> TYPE: RNA
<213> ORGANISM: Homo sapiens

<400> SEQUENCE: 514
gcucuggggc gugccgccgc cgucgcugcc accuccccua ccgcuagugg aagaagaugg 60
cggaaggcgg agcggcggau cuggacaccc agcggu 96

<210> SEQ ID NO 515
<211> LENGTH: 60
<212> TYPE: RNA
<213> ORGANISM: Homo sapiens

<400> SEQUENCE: 515
aggccuaggg gguggcaggc uggccaucag ugugggcuaa cccuguccuc ucccucccag 60

<210> SEQ ID NO 516
<211> LENGTH: 67
<212> TYPE: RNA
<213> ORGANISM: Homo sapiens

<400> SEQUENCE: 516
ccagacccca ggggcugggc aggcggaaag aggucugaac ugccucugcc uccuuggucu 60
ccggcag 67

<210> SEQ ID NO 517
<211> LENGTH: 61
<212> TYPE: RNA
<213> ORGANISM: Homo sapiens

<400> SEQUENCE: 517
gaggguuggg guggagggcc aaggagcugg gugggggugcc aagccucugu ccccacccca 60
g 61

<210> SEQ ID NO 518
<211> LENGTH: 93

<212> TYPE: RNA
<213> ORGANISM: Homo sapiens

<400> SEQUENCE: 518
guaaggaggg ggaugagggg ucauaucucu ucucagggaa agcaggagcc cuucagcagg 60
gucagggccc cucaucuucc ccuccuuucc cag 93

<210> SEQ ID NO 519
<211> LENGTH: 65
<212> TYPE: RNA
<213> ORGANISM: Homo sapiens

<400> SEQUENCE: 519
gucuccuggg gggaggagac ccugcucucc cuggcagcaa gccucuccug cccuuccaga 60
uuagc 65

<210> SEQ ID NO 520
<211> LENGTH: 82
<212> TYPE: RNA
<213> ORGANISM: Homo sapiens

<400> SEQUENCE: 520
gcuucgcucc ccuccgccuu cucuucccgg uucuucccgg agucgggaaa agcuggguug 60
agagggcgaa aaaggaugag gu 82

<210> SEQ ID NO 521
<211> LENGTH: 93
<212> TYPE: RNA
<213> ORGANISM: Homo sapiens

<400> SEQUENCE: 521
ccuuccggcg ucccaggcgg ggcgccgcgg gaccgcccuc gugucugugg cgguggggauc 60 ccgcggccgu guuuuccugg uggcccggcc aug 93

<210> SEQ ID NO 522
<211> LENGTH: 75
<212> TYPE: RNA
<213> ORGANISM: Homo sapiens

<400> SEQUENCE: 522
uggagugggg gggcaggagg ggcucaggga gaaagugcau acagccccug gcccucucug 60
cccuuccguc cccug 75

<210> SEQ ID NO 523
<211> LENGTH: 77
<212> TYPE: RNA
<213> ORGANISM: Homo sapiens

<400> SEQUENCE: 523
gaguugggag guucccucuc caaaugugucc uugaucccccc accccaagac acauuuggag 60
agggacccuc ccaacuc 77

<210> SEQ ID NO 524
<211> LENGTH: 84
<212> TYPE: RNA
<213> ORGANISM: Homo sapiens

<400> SEQUENCE: 524
ugugcagugg gaaggggggc cgauacacug uacgagagug aguagcaggu cucacaguga 60
accggucucu uucccuacug uguc 84

<210> SEQ ID NO 525
<211> LENGTH: 86
<212> TYPE: RNA
<213> ORGANISM: Homo sapiens

<400> SEQUENCE: 525
ugccagucuc uaggucccug agacccuuua accugugagg acauccaggg ucacagguga 60
gguucuuggg agccuggcgu cuggcc 86

<210> SEQ ID NO 526
<211> LENGTH: 92
<212> TYPE: RNA
<213> ORGANISM: Homo sapiens

<400> SEQUENCE: 526
cggcuggaca gcgggcaacg gaaucccaaa agcagcuguu gucuccagag cauuccagcu 60
gcgcuuggau uucguccccu gcucuccugc cu 92

<210> SEQ ID NO 527
<211> LENGTH: 96
<212> TYPE: RNA
<213> ORGANISM: Homo sapiens

<400> SEQUENCE: 527
cgggccccgg gcgggcggga gggacgggac gcggugcagu guuguuuuuu cccccgccaa 60
uauugcacuc gucccggccu ccggcccccc cggccc 96

<210> SEQ ID NO 528
<211> LENGTH: 73
<212> TYPE: RNA
<213> ORGANISM: Homo sapiens

<400> SEQUENCE: 528
uguauccuug aauggauuuu uggagcagga guggacaccu gacccaaagg aaaucaaucc 60
auaggcuagc aau 73

<210> SEQ ID NO 529
<211> LENGTH: 75
<212> TYPE: RNA
<213> ORGANISM: Homo sapiens

<400> SEQUENCE: 529
ucaucccugg guggggauuu guugcauuac uuguguucua uauaaaguau ugcacuuguc 60
ccggccugug gaaga 75

<210> SEQ ID NO 530
<211> LENGTH: 82
<212> TYPE: RNA
<213> ORGANISM: Homo sapiens

<400> SEQUENCE: 530
ugagcuguug gauucggggc cguagcacug ucugagaggu uuacauuucu cacagugaac 60
cggucucuuu uucagcugcu uc 82

<210> SEQ ID NO 531
<211> LENGTH: 78
<212> TYPE: RNA
<213> ORGANISM: Homo sapiens

<400> SEQUENCE: 531
gagcgucacg uugacacuca aaaaguuuca gauuuuggaa cauuucggau uuuggauuuu 60
uggaucaggg augcucaa 78

<210> SEQ ID NO 532
<211> LENGTH: 110
<212> TYPE: RNA
<213> ORGANISM: Homo sapiens

<400> SEQUENCE: 532
ucaccuggcc augugacuug ugggcuuccc uuugucaucc uucgccuagg gcucugagca 60
gggcagggac agcaaagggg ugcucaguug ucacuuccca cagcacggag 110

<210> SEQ ID NO 533
<211> LENGTH: 98
<212> TYPE: RNA
<213> ORGANISM: Homo sapiens

<400> SEQUENCE: 533
uugggcaagg ugcggggcua gggcuaacag cagucuuacu gaagguuucc uggaaaccac 60
gcacaugcug uugccacuaa ccucaaccuu acucgguc 98

<210> SEQ ID NO 534
<211> LENGTH: 90
<212> TYPE: RNA
<213> ORGANISM: Homo sapiens

<400> SEQUENCE: 534
aggccucgcu guucucuaug gcuuuuuauu ccuaugugau ucuacugcuc acucauauag 60
ggauuggagc cguggcgcac ggcggggaca 90

<210> SEQ ID NO 535
<211> LENGTH: 72
<212> TYPE: RNA
<213> ORGANISM: Homo sapiens

<400> SEQUENCE: 535
cuugggaaug gcaaggaaac cguuaccauu acugaguuua guaaugguaa ugguucucuu 60
gcuauaccca ga 72

<210> SEQ ID NO 536
<211> LENGTH: 85
<212> TYPE: RNA
<213> ORGANISM: Homo sapiens

<400> SEQUENCE: 536
aggguagagg gaugaggggg aaaguucuau aguccuguaa uuagaucuca ggacuauaga 60
acuuuccccc ucaucccucu gcccu 85

<210> SEQ ID NO 537
<211> LENGTH: 78
<212> TYPE: RNA
<213> ORGANISM: Homo sapiens

<400> SEQUENCE: 537
cuuucuacac agguugggau cgguugcaau gcuguguuuc uguaugguau ugcacuuguc 60
ccggccuguu gaguuugg 78

<210> SEQ ID NO 538
<211> LENGTH: 90
<212> TYPE: RNA
<213> ORGANISM: Homo sapiens

<400> SEQUENCE: 538
gagagaagca cuggacuuag ggucagaagg ccugagucuc ucugcugcag augggcucuc 60
ugucccugag ccaagcuuug uccucccugg 90

<210> SEQ ID NO 539
<211> LENGTH: 97
<212> TYPE: RNA
<213> ORGANISM: Homo sapiens

<400> SEQUENCE: 539
aucugaguug ggagggucc c ucuccaaaug ugucuugggg ugggggauca agacacauuu 60
ggagagggaa ccucccaacu cggccucugc caucauu 97

<210> SEQ ID NO 540
<211> LENGTH: 76
<212> TYPE: RNA
<213> ORGANISM: Homo sapiens

<400> SEQUENCE: 540
gagggggaag acgggaggaa agaagggagu gguuccauca cgccuccuca cuccucuccu 60
cccgucuucu ccucuc 76

<210> SEQ ID NO 541
<211> LENGTH: 98
<212> TYPE: RNA
<213> ORGANISM: Homo sapiens

<400> SEQUENCE: 541
acgaauggcu augcacugca caacccuagg agagggugcc auucacauag acuauaauug 60
aauggcgcca cuaggguugu gcagugcaca accuacac 98

<210> SEQ ID NO 542
<211> LENGTH: 68
<212> TYPE: RNA
<213> ORGANISM: Homo sapiens

<400> SEQUENCE: 542
cuccggugcc uacugagcug auaucaguuc ucauuuuaca cacuggcuca guucagcagg 60
aacaggag 68

<210> SEQ ID NO 543
<211> LENGTH: 73
<212> TYPE: RNA
<213> ORGANISM: Homo sapiens

<400> SEQUENCE: 543
cucugccucc cgugccuacu gagcugaaac acaguugguu uguguacacu ggcucaguuc 60
agcaggaaca ggg 73

<210> SEQ ID NO 544
<211> LENGTH: 97
<212> TYPE: RNA
<213> ORGANISM: Homo sapiens

<400> SEQUENCE: 544
cucaggugcu cuggcugcuu ggguuccugg caugcugauu ugugacuuaa gauuaaaauc 60
acauugccag ggauuaccac gcaaccacga ccuuggc 97

<210> SEQ ID NO 545
<211> LENGTH: 73
<212> TYPE: RNA
<213> ORGANISM: Homo sapiens

<400> SEQUENCE: 545
ggccggcugg gguuccuggg gaugggauuu gcuuccuguc acaaaucaca uugccaggga 60
uuuccaaccg acc 73

<210> SEQ ID NO 546
<211> LENGTH: 85
<212> TYPE: RNA
<213> ORGANISM: Homo sapiens

<400> SEQUENCE: 546
ggcugagccg caguaguucu ucaguggcaa gcuuuauguc cugacccagc uaaagcugcc 60
aguugaagaa cuguugcccu cugcc 85

<210> SEQ ID NO 547
<211> LENGTH: 22
<212> TYPE: RNA
<213> ORGANISM: Homo sapiens

<400> SEQUENCE: 547
ccccgguguu ggggcgcguc ug 22

<210> SEQ ID NO 548
<211> LENGTH: 21
<212> TYPE: RNA
<213> ORGANISM: Homo sapiens

<400> SEQUENCE: 548
cccgguguug gggcgcgucu g 21

<210> SEQ ID NO 549
<211> LENGTH: 22
<212> TYPE: RNA
<213> ORGANISM: Homo sapiens

<400> SEQUENCE: 549
gugggcgggg gcaggugugu gg 22

<210> SEQ ID NO 550
<211> LENGTH: 15
<212> TYPE: RNA
<213> ORGANISM: Homo sapiens

<400> SEQUENCE: 550
cgggggcagg ugugu 15

<210> SEQ ID NO 551
<211> LENGTH: 20
<212> TYPE: RNA
<213> ORGANISM: Homo sapiens

<400> SEQUENCE: 551
ccccggggag cccggcggug 20

<210> SEQ ID NO 552
<211> LENGTH: 15
<212> TYPE: RNA
<213> ORGANISM: Homo sapiens

<400> SEQUENCE: 552
accccgggga gcccg 15

<210> SEQ ID NO 553
<211> LENGTH: 19
<212> TYPE: RNA
<213> ORGANISM: Homo sapiens

<400> SEQUENCE: 553
guggguuggg gcgggcucu 19

<210> SEQ ID NO 554
<211> LENGTH: 25
<212> TYPE: RNA
<213> ORGANISM: Homo sapiens

<400> SEQUENCE: 554
acucggcgug gcgucggucg uggua 25

<210> SEQ ID NO 555
<211> LENGTH: 15
<212> TYPE: RNA
<213> ORGANISM: Homo sapiens

<400> SEQUENCE: 555
acucggcgug gcguc 15

<210> SEQ ID NO 556
<211> LENGTH: 19
<212> TYPE: RNA
<213> ORGANISM: Homo sapiens

<400> SEQUENCE: 556
agugggaggc cagggcacg 19

<210> SEQ ID NO 557
<211> LENGTH: 15
<212> TYPE: RNA
<213> ORGANISM: Homo sapiens

<400> SEQUENCE: 557
agggggagcu gcagg 15

<210> SEQ ID NO 558
<211> LENGTH: 15
<212> TYPE: RNA
<213> ORGANISM: Homo sapiens

<400> SEQUENCE: 558
ugaagcgggg gggcg 15

<210> SEQ ID NO 559
<211> LENGTH: 21
<212> TYPE: RNA
<213> ORGANISM: Homo sapiens

<400> SEQUENCE: 559
auccaguucu cugagggggc u 21

<210> SEQ ID NO 560
<211> LENGTH: 24
<212> TYPE: RNA
<213> ORGANISM: Homo sapiens

<400> SEQUENCE: 560
gaaaagcugg guugagaggg caaa 24

<210> SEQ ID NO 561
<211> LENGTH: 15
<212> TYPE: RNA
<213> ORGANISM: Homo sapiens

<400> SEQUENCE: 561
gaaaagcugg guuga 15

<210> SEQ ID NO 562
<211> LENGTH: 15
<212> TYPE: RNA
<213> ORGANISM: Homo sapiens

<400> SEQUENCE: 562
ucugggcgag gggug 15

<210> SEQ ID NO 563
<211> LENGTH: 23
<212> TYPE: RNA
<213> ORGANISM: Homo sapiens

<400> SEQUENCE: 563
cuccuggggc ccgcacucuc gcu 23

<210> SEQ ID NO 564
<211> LENGTH: 18
<212> TYPE: RNA
<213> ORGANISM: Homo sapiens

<400> SEQUENCE: 564
cuccuggggc ccgcacuc 18

<210> SEQ ID NO 565
<211> LENGTH: 22
<212> TYPE: RNA
<213> ORGANISM: Homo sapiens

<400> SEQUENCE: 565
uggcggagcc cauuccaugc ca 22

<210> SEQ ID NO 566
<211> LENGTH: 21
<212> TYPE: RNA
<213> ORGANISM: Homo sapiens

<400> SEQUENCE: 566
cuggcggagc ccauuccaug c 21

<210> SEQ ID NO 567
<211> LENGTH: 17
<212> TYPE: RNA
<213> ORGANISM: Homo sapiens

<400> SEQUENCE: 567
gaucccagcg gugccuc 17

<210> SEQ ID NO 568
<211> LENGTH: 15
<212> TYPE: RNA
<213> ORGANISM: Homo sapiens

<400> SEQUENCE: 568
gaucccagcg gugcc 15

<210> SEQ ID NO 569
<211> LENGTH: 22
<212> TYPE: RNA
<213> ORGANISM: Homo sapiens

<400> SEQUENCE: 569
acucaaaaug ggggcgcuuu cc 22

<210> SEQ ID NO 570
<211> LENGTH: 21
<212> TYPE: RNA
<213> ORGANISM: Homo sapiens

<400> SEQUENCE: 570
gccgggcgug gugguggggg c 21

<210> SEQ ID NO 571
<211> LENGTH: 15
<212> TYPE: RNA
<213> ORGANISM: Homo sapiens

<400> SEQUENCE: 571
uagccgggcg uggug 15

<210> SEQ ID NO 572
<211> LENGTH: 20
<212> TYPE: RNA
<213> ORGANISM: Homo sapiens

<400> SEQUENCE: 572
aucccaccac ugccaccauu 20

<210> SEQ ID NO 573
<211> LENGTH: 15
<212> TYPE: RNA
<213> ORGANISM: Homo sapiens

<400> SEQUENCE: 573
aucccaccac ugcca 15

<210> SEQ ID NO 574
<211> LENGTH: 23
<212> TYPE: RNA
<213> ORGANISM: Homo sapiens

<400> SEQUENCE: 574
aggacuggac ucccggcagc ccc 23

<210> SEQ ID NO 575
<211> LENGTH: 18
<212> TYPE: RNA
<213> ORGANISM: Homo sapiens

<400> SEQUENCE: 575
gcguggggag cugguccu 18

<210> SEQ ID NO 576
<211> LENGTH: 24
<212> TYPE: RNA
<213> ORGANISM: Homo sapiens

<400> SEQUENCE: 576
gugaguggga gccggugggg cugg 24

<210> SEQ ID NO 577
<211> LENGTH: 15
<212> TYPE: RNA
<213> ORGANISM: Homo sapiens

<400> SEQUENCE: 577
ggggcuggag uaagg 15

<210> SEQ ID NO 578
<211> LENGTH: 21
<212> TYPE: RNA
<213> ORGANISM: Homo sapiens

<400> SEQUENCE: 578
cccagcagga cgggagcgcg g 21

<210> SEQ ID NO 579
<211> LENGTH: 16
<212> TYPE: RNA
<213> ORGANISM: Homo sapiens

<400> SEQUENCE: 579 aagcugguc aaggag 16

<210> SEQ ID NO 580
<211> LENGTH: 22
<212> TYPE: RNA
<213> ORGANISM: Homo sapiens

<400> SEQUENCE: 580
aggcagcggg guguagugga ua 22

<210> SEQ ID NO 581
<211> LENGTH: 21
<212> TYPE: RNA
<213> ORGANISM: Homo sapiens

<400> SEQUENCE: 581
aggcagcggg guguagugga u 21

<210> SEQ ID NO 582
<211> LENGTH: 21
<212> TYPE: RNA
<213> ORGANISM: Homo sapiens

<400> SEQUENCE: 582
cagccugagu gacagagcaa g 21

<210> SEQ ID NO 583
<211> LENGTH: 15
<212> TYPE: RNA
<213> ORGANISM: Homo sapiens

<400> SEQUENCE: 583
acugcacucc agccu 15

<210> SEQ ID NO 584
<211> LENGTH: 24
<212> TYPE: RNA
<213> ORGANISM: Homo sapiens

<400> SEQUENCE: 584
gaugcgccgc ccacugcccc gcgc 24

<210> SEQ ID NO 585
<211> LENGTH: 15
<212> TYPE: RNA
<213> ORGANISM: Homo sapiens

<400> SEQUENCE: 585
gcccacugcc ccgcg 15

<210> SEQ ID NO 586
<211> LENGTH: 21
<212> TYPE: RNA
<213> ORGANISM: Homo sapiens

<400> SEQUENCE: 586
cggauccgag ucacggcacc a 21

<210> SEQ ID NO 587
<211> LENGTH: 15
<212> TYPE: RNA
<213> ORGANISM: Homo sapiens

<400> SEQUENCE: 587
ggauccgagu cacgg 15

<210> SEQ ID NO 588
<211> LENGTH: 25
<212> TYPE: RNA
<213> ORGANISM: Homo sapiens

<400> SEQUENCE: 588
agcggggagg aagugggcgc ugcuu 25

<210> SEQ ID NO 589
<211> LENGTH: 21
<212> TYPE: RNA
<213> ORGANISM: Homo sapiens

<400> SEQUENCE: 589
agcggggagg aagugggcgc u 21

<210> SEQ ID NO 590
<211> LENGTH: 24
<212> TYPE: RNA
<213> ORGANISM: Homo sapiens

<400> SEQUENCE: 590
acgcccuucc cccccuucuu cacc 24

<210> SEQ ID NO 591
<211> LENGTH: 17
<212> TYPE: RNA
<213> ORGANISM: Homo sapiens

<400> SEQUENCE: 591
acgcccuucc cccccuu 17

<210> SEQ ID NO 592
<211> LENGTH: 27
<212> TYPE: RNA
<213> ORGANISM: Homo sapiens

<400> SEQUENCE: 592
gugaacgggc gccaucccga ggcuuug 27

<210> SEQ ID NO 593
<211> LENGTH: 16
<212> TYPE: RNA
<213> ORGANISM: Homo sapiens

<400> SEQUENCE: 593
gugaacgggc gccauc 16

<210> SEQ ID NO 594
<211> LENGTH: 23
<212> TYPE: RNA
<213> ORGANISM: Homo sapiens

<400> SEQUENCE: 594
ggcccggccg ugccugaggu uuc 23

<210> SEQ ID NO 595
<211> LENGTH: 15
<212> TYPE: RNA
<213> ORGANISM: Homo sapiens

<400> SEQUENCE: 595
uguggcggug ggauc 15

<210> SEQ ID NO 596
<211> LENGTH: 19
<212> TYPE: RNA
<213> ORGANISM: Homo sapiens

<400> SEQUENCE: 596
gcaggcgagg cugggcuga 19

<210> SEQ ID NO 597
<211> LENGTH: 16
<212> TYPE: RNA
<213> ORGANISM: Homo sapiens

<400> SEQUENCE: 597
aggcgaggcu gggcug 16

<210> SEQ ID NO 598
<211> LENGTH: 18
<212> TYPE: RNA
<213> ORGANISM: Homo sapiens

<400> SEQUENCE: 598
gggugagggc aggugguu 18

<210> SEQ ID NO 599
<211> LENGTH: 15
<212> TYPE: RNA

<213> ORGANISM: Homo sapiens

<400> SEQUENCE: 599
gggugagggc aggug 15

<210> SEQ ID NO 600
<211> LENGTH: 22
<212> TYPE: RNA
<213> ORGANISM: Homo sapiens

<400> SEQUENCE: 600
acucaaacug ugggggcacu uu 22

<210> SEQ ID NO 601
<211> LENGTH: 19
<212> TYPE: RNA
<213> ORGANISM: Homo sapiens

<400> SEQUENCE: 601
acucaaacug ugggggcac 19

<210> SEQ ID NO 602
<211> LENGTH: 22
<212> TYPE: RNA
<213> ORGANISM: Homo sapiens

<400> SEQUENCE: 602
gaggguuggg uggaggcucu cc 22

<210> SEQ ID NO 603
<211> LENGTH: 15
<212> TYPE: RNA
<213> ORGANISM: Homo sapiens

<400> SEQUENCE: 603
gaggguuggg uggag 15

<210> SEQ ID NO 604
<211> LENGTH: 21
<212> TYPE: RNA
<213> ORGANISM: Homo sapiens

<400> SEQUENCE: 604
caacucugau cucuucaucu a 21

<210> SEQ ID NO 605
<211> LENGTH: 20
<212> TYPE: RNA
<213> ORGANISM: Homo sapiens

<400> SEQUENCE: 605
ucucuucauc uaccccccag 20

<210> SEQ ID NO 606
<211> LENGTH: 22
<212> TYPE: RNA
<213> ORGANISM: Homo sapiens

<400> SEQUENCE: 606
cagcccuccu cccgcaccca aa 22

<210> SEQ ID NO 607
<211> LENGTH: 21

<212> TYPE: RNA
<213> ORGANISM: Homo sapiens

<400> SEQUENCE: 607
cagcccuccu cccgcaccca a 21

<210> SEQ ID NO 608
<211> LENGTH: 23
<212> TYPE: RNA
<213> ORGANISM: Homo sapiens

<400> SEQUENCE: 608
ggggggaugu gcaugcuggu ugg 23

<210> SEQ ID NO 609
<211> LENGTH: 15
<212> TYPE: RNA
<213> ORGANISM: Homo sapiens

<400> SEQUENCE: 609
aucagcgugc acuuc 15

<210> SEQ ID NO 610
<211> LENGTH: 22
<212> TYPE: RNA
<213> ORGANISM: Homo sapiens

<400> SEQUENCE: 610
uccugcagag aggaagcccu uc 22

<210> SEQ ID NO 611
<211> LENGTH: 18
<212> TYPE: RNA
<213> ORGANISM: Homo sapiens

<400> SEQUENCE: 611
ccugcagaga ggaagccc 18

<210> SEQ ID NO 612
<211> LENGTH: 17
<212> TYPE: RNA
<213> ORGANISM: Homo sapiens

<400> SEQUENCE: 612
ugcaggggca ggccagc 17

<210> SEQ ID NO 613
<211> LENGTH: 15
<212> TYPE: RNA
<213> ORGANISM: Homo sapiens

<400> SEQUENCE: 613
ccuguucuug ccagg 15

<210> SEQ ID NO 614
<211> LENGTH: 21
<212> TYPE: RNA
<213> ORGANISM: Homo sapiens

<400> SEQUENCE: 614
uugaggagac augguggggg c 21

<210> SEQ ID NO 615

<211> LENGTH: 15
<212> TYPE: RNA
<213> ORGANISM: Homo sapiens

<400> SEQUENCE: 615
uugaggagac auggu 15

<210> SEQ ID NO 616
<211> LENGTH: 24
<212> TYPE: RNA
<213> ORGANISM: Homo sapiens

<400> SEQUENCE: 616
auauacaggg ggagacucuc auuu 24

<210> SEQ ID NO 617
<211> LENGTH: 15
<212> TYPE: RNA
<213> ORGANISM: Homo sapiens

<400> SEQUENCE: 617
auauacaggg ggaga 15

<210> SEQ ID NO 618
<211> LENGTH: 24
<212> TYPE: RNA
<213> ORGANISM: Homo sapiens

<400> SEQUENCE: 618
cgggcguggu gguggggug ggug 24

<210> SEQ ID NO 619
<211> LENGTH: 15
<212> TYPE: RNA
<213> ORGANISM: Homo sapiens

<400> SEQUENCE: 619
cgggcguggu ggugg 15

<210> SEQ ID NO 620
<211> LENGTH: 22
<212> TYPE: RNA
<213> ORGANISM: Homo sapiens

<400> SEQUENCE: 620
ccucacaccu gccucgcccc cc 22

<210> SEQ ID NO 621
<211> LENGTH: 15
<212> TYPE: RNA
<213> ORGANISM: Homo sapiens

<400> SEQUENCE: 621
ucacaccugc cucgc 15

<210> SEQ ID NO 622
<211> LENGTH: 23
<212> TYPE: RNA
<213> ORGANISM: Homo sapiens

<400> SEQUENCE: 622
aauauacagg gggagacucu uau 23

<210> SEQ ID NO 623
<211> LENGTH: 25
<212> TYPE: RNA
<213> ORGANISM: Homo sapiens

<400> SEQUENCE: 623
aaggcagggc ccccgcuccc cgggc 25

<210> SEQ ID NO 624
<211> LENGTH: 15
<212> TYPE: RNA
<213> ORGANISM: Homo sapiens

<400> SEQUENCE: 624
guguguugag gaagg 15

<210> SEQ ID NO 625
<211> LENGTH: 24
<212> TYPE: RNA
<213> ORGANISM: Homo sapiens

<400> SEQUENCE: 625
uggggagcug aggcucuggg ggug 24

<210> SEQ ID NO 626
<211> LENGTH: 15
<212> TYPE: RNA
<213> ORGANISM: Homo sapiens

<400> SEQUENCE: 626
ggcccugggg agcug 15

<210> SEQ ID NO 627
<211> LENGTH: 23
<212> TYPE: RNA
<213> ORGANISM: Homo sapiens

<400> SEQUENCE: 627
gugggggaga ggcugucuug ugu 23

<210> SEQ ID NO 628
<211> LENGTH: 15
<212> TYPE: RNA
<213> ORGANISM: Homo sapiens

<400> SEQUENCE: 628 gugugggga gaggc 15

<210> SEQ ID NO 629
<211> LENGTH: 26
<212> TYPE: RNA
<213> ORGANISM: Homo sapiens

<400> SEQUENCE: 629
agggcuggac ucagcggcgg agcugg 26

<210> SEQ ID NO 630
<211> LENGTH: 17
<212> TYPE: RNA
<213> ORGANISM: Homo sapiens

<400> SEQUENCE: 630
gcggcggagc uggcugc 17

<210> SEQ ID NO 631
<211> LENGTH: 21
<212> TYPE: RNA
<213> ORGANISM: Homo sapiens

<400> SEQUENCE: 631 cuuccccca guaaucuuca u 21

<210> SEQ ID NO 632
<211> LENGTH: 22
<212> TYPE: RNA
<213> ORGANISM: Homo sapiens

<400> SEQUENCE: 632
accccacucc ugguaccaua gu 22

<210> SEQ ID NO 633
<211> LENGTH: 15
<212> TYPE: RNA
<213> ORGANISM: Homo sapiens

<400> SEQUENCE: 633
accccacucc uggua 15

<210> SEQ ID NO 634
<211> LENGTH: 20
<212> TYPE: RNA
<213> ORGANISM: Homo sapiens

<400> SEQUENCE: 634
ggcuccuugg ucuaggggua 20

<210> SEQ ID NO 635
<211> LENGTH: 15
<212> TYPE: RNA
<213> ORGANISM: Homo sapiens

<400> SEQUENCE: 635
cuuggucuag gggua 15

<210> SEQ ID NO 636
<211> LENGTH: 22
<212> TYPE: RNA
<213> ORGANISM: Homo sapiens

<400> SEQUENCE: 636
gcacgacuca gggcggaggg aa 22

<210> SEQ ID NO 637
<211> LENGTH: 15
<212> TYPE: RNA
<213> ORGANISM: Homo sapiens

<400> SEQUENCE: 637
agggcggagg gaagu 15

<210> SEQ ID NO 638
<211> LENGTH: 26
<212> TYPE: RNA
<213> ORGANISM: Homo sapiens

<400> SEQUENCE: 638
cggguagaga gggcaguggg agguaa 26

<210> SEQ ID NO 639
<211> LENGTH: 15
<212> TYPE: RNA
<213> ORGANISM: Homo sapiens

<400> SEQUENCE: 639
cggguagaga gggca 15

<210> SEQ ID NO 640
<211> LENGTH: 22
<212> TYPE: RNA
<213> ORGANISM: Homo sapiens

<400> SEQUENCE: 640
ucccccggcc ugcucauccc cc 22

<210> SEQ ID NO 641
<211> LENGTH: 24
<212> TYPE: RNA
<213> ORGANISM: Homo sapiens

<400> SEQUENCE: 641
cccggggcag auugguguag ggug 24

<210> SEQ ID NO 642
<211> LENGTH: 17
<212> TYPE: RNA
<213> ORGANISM: Homo sapiens

<400> SEQUENCE: 642
cggggcagau uggugua 17

<210> SEQ ID NO 643
<211> LENGTH: 17
<212> TYPE: RNA
<213> ORGANISM: Homo sapiens

<400> SEQUENCE: 643
uccuagucac ggcacca 17

<210> SEQ ID NO 644
<211> LENGTH: 30
<212> TYPE: RNA
<213> ORGANISM: Homo sapiens

<400> SEQUENCE: 644
gcugggcugg gacggacacc cggccuccac 30

<210> SEQ ID NO 645
<211> LENGTH: 19
<212> TYPE: RNA
<213> ORGANISM: Homo sapiens

<400> SEQUENCE: 645
gaggcugggc ugggacgga 19

<210> SEQ ID NO 646
<211> LENGTH: 22
<212> TYPE: RNA
<213> ORGANISM: Homo sapiens

<400> SEQUENCE: 646
aggagcaagg cggcaucucu cu 22

<210> SEQ ID NO 647
<211> LENGTH: 18
<212> TYPE: RNA
<213> ORGANISM: Homo sapiens

<400> SEQUENCE: 647
gagcaaggcg gcaucucu 18

<210> SEQ ID NO 648
<211> LENGTH: 20
<212> TYPE: RNA
<213> ORGANISM: Homo sapiens

<400> SEQUENCE: 648
ggcuggucag augggagugg 20

<210> SEQ ID NO 649
<211> LENGTH: 24
<212> TYPE: RNA
<213> ORGANISM: Homo sapiens

<400> SEQUENCE: 649
agcagggcug gggauugcag uauc 24

<210> SEQ ID NO 650
<211> LENGTH: 19
<212> TYPE: RNA
<213> ORGANISM: Homo sapiens

<400> SEQUENCE: 650
ugcugcuccc aguccugcc 19

<210> SEQ ID NO 651
<211> LENGTH: 25
<212> TYPE: RNA
<213> ORGANISM: Homo sapiens

<400> SEQUENCE: 651
gcugcgggcu gcggucaggg cgauc 25

<210> SEQ ID NO 652
<211> LENGTH: 20
<212> TYPE: RNA
<213> ORGANISM: Homo sapiens

<400> SEQUENCE: 652
gcugcgggcu gcggucaggg 20

<210> SEQ ID NO 653
<211> LENGTH: 22
<212> TYPE: RNA
<213> ORGANISM: Homo sapiens

<400> SEQUENCE: 653
agcucugcug cucacuggca gu 22

<210> SEQ ID NO 654
<211> LENGTH: 20
<212> TYPE: RNA
<213> ORGANISM: Homo sapiens

<400> SEQUENCE: 654
agcucugcug cucacuggca 20

<210> SEQ ID NO 655
<211> LENGTH: 16
<212> TYPE: RNA
<213> ORGANISM: Homo sapiens

<400> SEQUENCE: 655
ggcgcggagg gcggac 16

<210> SEQ ID NO 656
<211> LENGTH: 15
<212> TYPE: RNA
<213> ORGANISM: Homo sapiens

<400> SEQUENCE: 656
ggcgcggagg gcgga 15

<210> SEQ ID NO 657
<211> LENGTH: 23
<212> TYPE: RNA
<213> ORGANISM: Homo sapiens

<400> SEQUENCE: 657
agcagaggca gagaggcuca ggg 23

<210> SEQ ID NO 658
<211> LENGTH: 15
<212> TYPE: RNA
<213> ORGANISM: Homo sapiens

<400> SEQUENCE: 658
agcagaggca gagag 15

<210> SEQ ID NO 659
<211> LENGTH: 22
<212> TYPE: RNA
<213> ORGANISM: Homo sapiens

<400> SEQUENCE: 659
ugggagggga gaggcagcaa gc 22

<210> SEQ ID NO 660
<211> LENGTH: 16
<212> TYPE: RNA
<213> ORGANISM: Homo sapiens

<400> SEQUENCE: 660
accagccugg ggcauc 16

<210> SEQ ID NO 661
<211> LENGTH: 22
<212> TYPE: RNA
<213> ORGANISM: Homo sapiens

<400> SEQUENCE: 661
aaaagcuggg cugagaggcg ac 22

<210> SEQ ID NO 662
<211> LENGTH: 15
<212> TYPE: RNA
<213> ORGANISM: Homo sapiens

<400> SEQUENCE: 662
aaagcugggc ugaga 15

<210> SEQ ID NO 663
<211> LENGTH: 25
<212> TYPE: RNA
<213> ORGANISM: Homo sapiens

<400> SEQUENCE: 663
caggaaggau uuagggacag gcuuu 25

<210> SEQ ID NO 664
<211> LENGTH: 19
<212> TYPE: RNA
<213> ORGANISM: Homo sapiens

<400> SEQUENCE: 664
caggaaggau uuagggaca 19

<210> SEQ ID NO 665
<211> LENGTH: 23
<212> TYPE: RNA
<213> ORGANISM: Homo sapiens

<400> SEQUENCE: 665
uggugcggag agggcccaca gug 23

<210> SEQ ID NO 666
<211> LENGTH: 15
<212> TYPE: RNA
<213> ORGANISM: Homo sapiens

<400> SEQUENCE: 666
gggucuggug cggag 15

<210> SEQ ID NO 667
<211> LENGTH: 16
<212> TYPE: RNA
<213> ORGANISM: Homo sapiens

<400> SEQUENCE: 667
ggacccaggg agagac 16

<210> SEQ ID NO 668
<211> LENGTH: 22
<212> TYPE: RNA
<213> ORGANISM: Homo sapiens

<400> SEQUENCE: 668
cgcggcgggg acggcgauug gu 22

<210> SEQ ID NO 669
<211> LENGTH: 17
<212> TYPE: RNA
<213> ORGANISM: Homo sapiens

<400> SEQUENCE: 669
cggcggggac ggcgauu 17

<210> SEQ ID NO 670
<211> LENGTH: 22
<212> TYPE: RNA
<213> ORGANISM: Homo sapiens

<400> SEQUENCE: 670
ccggcagagg aggcugcaga gg 22

<210> SEQ ID NO 671
<211> LENGTH: 19
<212> TYPE: RNA
<213> ORGANISM: Homo sapiens

<400> SEQUENCE: 671
ccggcagagg aggcugcag 19

<210> SEQ ID NO 672
<211> LENGTH: 29
<212> TYPE: RNA
<213> ORGANISM: Homo sapiens

<400> SEQUENCE: 672
gggagccgcg gggaucgccg agggccggu 29

<210> SEQ ID NO 673
<211> LENGTH: 15
<212> TYPE: RNA
<213> ORGANISM: Homo sapiens

<400> SEQUENCE: 673
ggcggcggug guggg 15

<210> SEQ ID NO 674
<211> LENGTH: 23
<212> TYPE: RNA
<213> ORGANISM: Homo sapiens

<400> SEQUENCE: 674
uguagagcag ggagcaggaa gcu 23

<210> SEQ ID NO 675
<211> LENGTH: 15
<212> TYPE: RNA
<213> ORGANISM: Homo sapiens

<400> SEQUENCE: 675
cagggagcag gaagc 15

<210> SEQ ID NO 676
<211> LENGTH: 21
<212> TYPE: RNA
<213> ORGANISM: Homo sapiens

<400> SEQUENCE: 676
ggcgggggug gcggcggcau c 21

<210> SEQ ID NO 677
<211> LENGTH: 15
<212> TYPE: RNA
<213> ORGANISM: Homo sapiens

<400> SEQUENCE: 677
gguggcggcg gcauc 15

<210> SEQ ID NO 678
<211> LENGTH: 29
<212> TYPE: RNA

<213> ORGANISM: Homo sapiens

<400> SEQUENCE: 678
ggucaggcgg cucggacuga gcagguggg 29

<210> SEQ ID NO 679
<211> LENGTH: 15
<212> TYPE: RNA
<213> ORGANISM: Homo sapiens

<400> SEQUENCE: 679
agaguguggu caggc 15

<210> SEQ ID NO 680
<211> LENGTH: 28
<212> TYPE: RNA
<213> ORGANISM: Homo sapiens

<400> SEQUENCE: 680
cagccuccca aaaugcuggg auuacagg 28

<210> SEQ ID NO 681
<211> LENGTH: 15
<212> TYPE: RNA
<213> ORGANISM: Homo sapiens

<400> SEQUENCE: 681
gcccaccuca gccuc 15

<210> SEQ ID NO 682
<211> LENGTH: 28
<212> TYPE: RNA
<213> ORGANISM: Homo sapiens

<400> SEQUENCE: 682
aggggugcua ucugugauug agggacau 28

<210> SEQ ID NO 683
<211> LENGTH: 15
<212> TYPE: RNA
<213> ORGANISM: Homo sapiens

<400> SEQUENCE: 683
gcuaucugug auuga 15

<210> SEQ ID NO 684
<211> LENGTH: 19
<212> TYPE: RNA
<213> ORGANISM: Homo sapiens

<400> SEQUENCE: 684
cgucccaccc cccacuccu 19

<210> SEQ ID NO 685
<211> LENGTH: 23
<212> TYPE: RNA
<213> ORGANISM: Homo sapiens

<400> SEQUENCE: 685
gccccggcgc gggcggguuc ugg 23

<210> SEQ ID NO 686
<211> LENGTH: 16

<212> TYPE: RNA
<213> ORGANISM: Homo sapiens

<400> SEQUENCE: 686
ggagccccgg cgcggg 16

<210> SEQ ID NO 687
<211> LENGTH: 22
<212> TYPE: RNA
<213> ORGANISM: Homo sapiens

<400> SEQUENCE: 687
accaggaggc ugaggccccu ca 22

<210> SEQ ID NO 688
<211> LENGTH: 15
<212> TYPE: RNA
<213> ORGANISM: Homo sapiens

<400> SEQUENCE: 688
accaggaggc ugagg 15

<210> SEQ ID NO 689
<211> LENGTH: 25
<212> TYPE: RNA
<213> ORGANISM: Homo sapiens

<400> SEQUENCE: 689
ugcaggcaga aguggggcug acagg 25

<210> SEQ ID NO 690
<211> LENGTH: 20
<212> TYPE: RNA
<213> ORGANISM: Homo sapiens

<400> SEQUENCE: 690
cugcaggcag aaguggggcu 20

<210> SEQ ID NO 691
<211> LENGTH: 22
<212> TYPE: RNA
<213> ORGANISM: Homo sapiens

<400> SEQUENCE: 691
auggccagag cucacacaga gg 22

<210> SEQ ID NO 692
<211> LENGTH: 21
<212> TYPE: RNA
<213> ORGANISM: Homo sapiens

<400> SEQUENCE: 692
auggccagag cucacacaga g 21

<210> SEQ ID NO 693
<211> LENGTH: 15
<212> TYPE: RNA
<213> ORGANISM: Homo sapiens

<400> SEQUENCE: 693
ggcgcgcggc ggcuc 15

<210> SEQ ID NO 694

-continued

<211> LENGTH: 20
<212> TYPE: RNA
<213> ORGANISM: Homo sapiens

<400> SEQUENCE: 694
aucccaccuc ugccaccaaa 20

<210> SEQ ID NO 695
<211> LENGTH: 15
<212> TYPE: RNA
<213> ORGANISM: Homo sapiens

<400> SEQUENCE: 695
aucccaccuc ugcca 15

<210> SEQ ID NO 696
<211> LENGTH: 25
<212> TYPE: RNA
<213> ORGANISM: Homo sapiens

<400> SEQUENCE: 696
ugggcagggg cuuauuguag gaguc 25

<210> SEQ ID NO 697
<211> LENGTH: 19
<212> TYPE: RNA
<213> ORGANISM: Homo sapiens

<400> SEQUENCE: 697
ugggcagggg cuuauugua 19

<210> SEQ ID NO 698
<211> LENGTH: 23
<212> TYPE: RNA
<213> ORGANISM: Homo sapiens

<400> SEQUENCE: 698
acaggagugg gggugggaca uaa 23

<210> SEQ ID NO 699
<211> LENGTH: 20
<212> TYPE: RNA
<213> ORGANISM: Homo sapiens

<400> SEQUENCE: 699
acaggagugg gggugggaca 20

<210> SEQ ID NO 700
<211> LENGTH: 18
<212> TYPE: RNA
<213> ORGANISM: Homo sapiens

<400> SEQUENCE: 700
gaggcugaag gaagaugg 18

<210> SEQ ID NO 701
<211> LENGTH: 15
<212> TYPE: RNA
<213> ORGANISM: Homo sapiens

<400> SEQUENCE: 701
gaggcugaag gaaga 15

<210> SEQ ID NO 702
<211> LENGTH: 22
<212> TYPE: RNA
<213> ORGANISM: Homo sapiens

<400> SEQUENCE: 702
cugggcucgg gacgcgcggc uc 22

<210> SEQ ID NO 703
<211> LENGTH: 19
<212> TYPE: RNA
<213> ORGANISM: Homo sapiens

<400> SEQUENCE: 703
cugggcucgg gacgcgcgg 19

<210> SEQ ID NO 704
<211> LENGTH: 18
<212> TYPE: RNA
<213> ORGANISM: Homo sapiens

<400> SEQUENCE: 704 ucuaggugg gagacuga 18

<210> SEQ ID NO 705
<211> LENGTH: 16
<212> TYPE: RNA
<213> ORGANISM: Homo sapiens

<400> SEQUENCE: 705
guggggagac ugacgg 16

<210> SEQ ID NO 706
<211> LENGTH: 15
<212> TYPE: RNA
<213> ORGANISM: Homo sapiens

<400> SEQUENCE: 706
ggcggcgggc ccggg 15

<210> SEQ ID NO 707
<211> LENGTH: 21
<212> TYPE: RNA
<213> ORGANISM: Homo sapiens

<400> SEQUENCE: 707
gaggcgaugu ggggauguag a 21

<210> SEQ ID NO 708
<211> LENGTH: 20
<212> TYPE: RNA
<213> ORGANISM: Homo sapiens

<400> SEQUENCE: 708
cccagucuca uuuccucauc 20

<210> SEQ ID NO 709
<211> LENGTH: 23
<212> TYPE: RNA
<213> ORGANISM: Homo sapiens

<400> SEQUENCE: 709
ucggcucugg gucugugggg agc 23

<210> SEQ ID NO 710
<211> LENGTH: 15
<212> TYPE: RNA
<213> ORGANISM: Homo sapiens

<400> SEQUENCE: 710
gcccggauac cucag 15

<210> SEQ ID NO 711
<211> LENGTH: 23
<212> TYPE: RNA
<213> ORGANISM: Homo sapiens

<400> SEQUENCE: 711
gggaugguag accggugacg ugc 23

<210> SEQ ID NO 712
<211> LENGTH: 21
<212> TYPE: RNA
<213> ORGANISM: Homo sapiens

<400> SEQUENCE: 712
uaggucaccc guuugacuau c 21

<210> SEQ ID NO 713
<211> LENGTH: 15
<212> TYPE: RNA
<213> ORGANISM: Homo sapiens

<400> SEQUENCE: 713
aggaggagga ggcag 15

<210> SEQ ID NO 714
<211> LENGTH: 24
<212> TYPE: RNA
<213> ORGANISM: Homo sapiens

<400> SEQUENCE: 714
cgcucgggcg gaggugguug agug 24

<210> SEQ ID NO 715
<211> LENGTH: 17
<212> TYPE: RNA
<213> ORGANISM: Homo sapiens

<400> SEQUENCE: 715
ucgggcggag gugguug 17

<210> SEQ ID NO 716
<211> LENGTH: 15
<212> TYPE: RNA
<213> ORGANISM: Homo sapiens

<400> SEQUENCE: 716
accucuccug gcauc 15

<210> SEQ ID NO 717
<211> LENGTH: 23
<212> TYPE: RNA
<213> ORGANISM: Homo sapiens

<400> SEQUENCE: 717
ggcaggaggg cugugccagg uug 23

<210> SEQ ID NO 718
<211> LENGTH: 17
<212> TYPE: RNA
<213> ORGANISM: Homo sapiens

<400> SEQUENCE: 718
ggcaggaggg cugugcc 17

<210> SEQ ID NO 719
<211> LENGTH: 22
<212> TYPE: RNA
<213> ORGANISM: Homo sapiens

<400> SEQUENCE: 719
uggggauuug gagaaguggu ga 22

<210> SEQ ID NO 720
<211> LENGTH: 27
<212> TYPE: RNA
<213> ORGANISM: Homo sapiens

<400> SEQUENCE: 720
ugagggacuu uugggggcag auguguu 27

<210> SEQ ID NO 721
<211> LENGTH: 17
<212> TYPE: RNA
<213> ORGANISM: Homo sapiens

<400> SEQUENCE: 721
ggacuuuugg gggcaga 17

<210> SEQ ID NO 722
<211> LENGTH: 23
<212> TYPE: RNA
<213> ORGANISM: Homo sapiens

<400> SEQUENCE: 722
uuucaagcca gggggcguuu uuc 23

<210> SEQ ID NO 723
<211> LENGTH: 18
<212> TYPE: RNA
<213> ORGANISM: Homo sapiens

<400> SEQUENCE: 723
uuucaagcca gggggcgu 18

<210> SEQ ID NO 724
<211> LENGTH: 15
<212> TYPE: RNA
<213> ORGANISM: Homo sapiens

<400> SEQUENCE: 724
cccgcgggac gcgcc 15

<210> SEQ ID NO 725
<211> LENGTH: 22
<212> TYPE: RNA
<213> ORGANISM: Homo sapiens

<400> SEQUENCE: 725
ccgggaacgu cgagacugga gc 22

<210> SEQ ID NO 726
<211> LENGTH: 15
<212> TYPE: RNA
<213> ORGANISM: Homo sapiens

<400> SEQUENCE: 726
cgggaacguc gagac 15

<210> SEQ ID NO 727
<211> LENGTH: 25
<212> TYPE: RNA
<213> ORGANISM: Homo sapiens

<400> SEQUENCE: 727
gggacgaggg uuggggaaca ggugg 25

<210> SEQ ID NO 728
<211> LENGTH: 15
<212> TYPE: RNA
<213> ORGANISM: Homo sapiens

<400> SEQUENCE: 728
uggggaacag guggu 15

<210> SEQ ID NO 729
<211> LENGTH: 24
<212> TYPE: RNA
<213> ORGANISM: Homo sapiens

<400> SEQUENCE: 729
cugguacagg ccugggggac aggg 24

<210> SEQ ID NO 730
<211> LENGTH: 18
<212> TYPE: RNA
<213> ORGANISM: Homo sapiens

<400> SEQUENCE: 730
cugguacagg ccuggggg 18

<210> SEQ ID NO 731
<211> LENGTH: 21
<212> TYPE: RNA
<213> ORGANISM: Homo sapiens

<400> SEQUENCE: 731
cccaggcugg agcgagugca g 21

<210> SEQ ID NO 732
<211> LENGTH: 15
<212> TYPE: RNA
<213> ORGANISM: Homo sapiens

<400> SEQUENCE: 732
agcucacugc agccu 15

<210> SEQ ID NO 733
<211> LENGTH: 24
<212> TYPE: RNA
<213> ORGANISM: Homo sapiens

<400> SEQUENCE: 733
ucgaggacug guggaagggc cuuu 24

<210> SEQ ID NO 734
<211> LENGTH: 16
<212> TYPE: RNA
<213> ORGANISM: Homo sapiens

<400> SEQUENCE: 734
ucgaggacug guggaa 16

<210> SEQ ID NO 735
<211> LENGTH: 17
<212> TYPE: RNA
<213> ORGANISM: Homo sapiens

<400> SEQUENCE: 735
ggugagcgcu cgcuggc 17

<210> SEQ ID NO 736
<211> LENGTH: 15
<212> TYPE: RNA
<213> ORGANISM: Homo sapiens

<400> SEQUENCE: 736
cggugagcgc ucgcu 15

<210> SEQ ID NO 737
<211> LENGTH: 21
<212> TYPE: RNA
<213> ORGANISM: Homo sapiens

<400> SEQUENCE: 737
cagcagggga gagagaggag u 21

<210> SEQ ID NO 738
<211> LENGTH: 20
<212> TYPE: RNA
<213> ORGANISM: Homo sapiens

<400> SEQUENCE: 738
cagcagggga gagagaggag 20

<210> SEQ ID NO 739
<211> LENGTH: 22
<212> TYPE: RNA
<213> ORGANISM: Homo sapiens

<400> SEQUENCE: 739
gggagugcag ggcaggguuu cc 22

<210> SEQ ID NO 740
<211> LENGTH: 18
<212> TYPE: RNA
<213> ORGANISM: Homo sapiens

<400> SEQUENCE: 740
agggagugca gggcaggg 18

<210> SEQ ID NO 741
<211> LENGTH: 25
<212> TYPE: RNA
<213> ORGANISM: Homo sapiens

<400> SEQUENCE: 741
aggaagcccu ggaggggcug gaggu 25

<210> SEQ ID NO 742
<211> LENGTH: 15
<212> TYPE: RNA
<213> ORGANISM: Homo sapiens

<400> SEQUENCE: 742
aggaagagga ggaag 15

<210> SEQ ID NO 743
<211> LENGTH: 24
<212> TYPE: RNA
<213> ORGANISM: Homo sapiens

<400> SEQUENCE: 743
ugacugggga gcagaaggag aacc 24

<210> SEQ ID NO 744
<211> LENGTH: 15
<212> TYPE: RNA
<213> ORGANISM: Homo sapiens

<400> SEQUENCE: 744
gacuggggag cagaa 15

<210> SEQ ID NO 745
<211> LENGTH: 19
<212> TYPE: RNA
<213> ORGANISM: Homo sapiens

<400> SEQUENCE: 745
gaggcuggag ugagcggag 19

<210> SEQ ID NO 746
<211> LENGTH: 15
<212> TYPE: RNA
<213> ORGANISM: Homo sapiens

<400> SEQUENCE: 746
aggcuggagu gagcg 15

<210> SEQ ID NO 747
<211> LENGTH: 17
<212> TYPE: RNA
<213> ORGANISM: Homo sapiens

<400> SEQUENCE: 747
ggggcggggg cgggggc 17

<210> SEQ ID NO 748
<211> LENGTH: 15
<212> TYPE: RNA
<213> ORGANISM: Homo sapiens

<400> SEQUENCE: 748
cgcgccgggc ccggg 15

<210> SEQ ID NO 749
<211> LENGTH: 23
<212> TYPE: RNA
<213> ORGANISM: Homo sapiens

<400> SEQUENCE: 749
ugaggauaug gcagggaagg gga 23

<210> SEQ ID NO 750
<211> LENGTH: 19
<212> TYPE: RNA
<213> ORGANISM: Homo sapiens

<400> SEQUENCE: 750
ugaggauaug gcagggaag 19

<210> SEQ ID NO 751
<211> LENGTH: 22
<212> TYPE: RNA
<213> ORGANISM: Homo sapiens

<400> SEQUENCE: 751
auuggagggu guggaagaca uc 22

<210> SEQ ID NO 752
<211> LENGTH: 16
<212> TYPE: RNA
<213> ORGANISM: Homo sapiens

<400> SEQUENCE: 752
uuggagggug uggaag 16

<210> SEQ ID NO 753
<211> LENGTH: 19
<212> TYPE: RNA
<213> ORGANISM: Homo sapiens

<400> SEQUENCE: 753
cggcgcgacc ggcccgggg 19

<210> SEQ ID NO 754
<211> LENGTH: 23
<212> TYPE: RNA
<213> ORGANISM: Homo sapiens

<400> SEQUENCE: 754
ggcuacaaca caggacccgg gcg 23

<210> SEQ ID NO 755
<211> LENGTH: 21
<212> TYPE: RNA
<213> ORGANISM: Homo sapiens

<400> SEQUENCE: 755
ggcuacaaca caggacccgg g 21

<210> SEQ ID NO 756
<211> LENGTH: 21
<212> TYPE: RNA
<213> ORGANISM: Homo sapiens

<400> SEQUENCE: 756
ccggccgccg gcuccgcccc g 21

<210> SEQ ID NO 757
<211> LENGTH: 17
<212> TYPE: RNA

<213> ORGANISM: Homo sapiens

<400> SEQUENCE: 757
ccggccgccg gcuccgc 17

<210> SEQ ID NO 758
<211> LENGTH: 26
<212> TYPE: RNA
<213> ORGANISM: Homo sapiens

<400> SEQUENCE: 758
caagauggug gacuacagcg uguggg 26

<210> SEQ ID NO 759
<211> LENGTH: 15
<212> TYPE: RNA
<213> ORGANISM: Homo sapiens

<400> SEQUENCE: 759
aggcaagaug gugga 15

<210> SEQ ID NO 760
<211> LENGTH: 24
<212> TYPE: RNA
<213> ORGANISM: Homo sapiens

<400> SEQUENCE: 760
cagggggaug gcagagcaaa auuc 24

<210> SEQ ID NO 761
<211> LENGTH: 17
<212> TYPE: RNA
<213> ORGANISM: Homo sapiens

<400> SEQUENCE: 761
agggggaugg cagagca 17

<210> SEQ ID NO 762
<211> LENGTH: 18
<212> TYPE: RNA
<213> ORGANISM: Homo sapiens

<400> SEQUENCE: 762
aaaaggaagg gggaggag 18

<210> SEQ ID NO 763
<211> LENGTH: 16
<212> TYPE: RNA
<213> ORGANISM: Homo sapiens

<400> SEQUENCE: 763
aaggaagggg gaggag 16

<210> SEQ ID NO 764
<211> LENGTH: 26
<212> TYPE: RNA
<213> ORGANISM: Homo sapiens

<400> SEQUENCE: 764
aggagggagg agaugggcca aguucc 26

<210> SEQ ID NO 765
<211> LENGTH: 15

<212> TYPE: RNA
<213> ORGANISM: Homo sapiens

<400> SEQUENCE: 765
gggaggaggg aggag 15

<210> SEQ ID NO 766
<211> LENGTH: 25
<212> TYPE: RNA
<213> ORGANISM: Homo sapiens

<400> SEQUENCE: 766
cugcaggcag aaguggggcu gacag 25

<210> SEQ ID NO 767
<211> LENGTH: 19
<212> TYPE: RNA
<213> ORGANISM: Homo sapiens

<400> SEQUENCE: 767
caggcagaag uggggcuga 19

<210> SEQ ID NO 768
<211> LENGTH: 27
<212> TYPE: RNA
<213> ORGANISM: Homo sapiens

<400> SEQUENCE: 768
agccuggaag cuggagccug cagugaa 27

<210> SEQ ID NO 769
<211> LENGTH: 15
<212> TYPE: RNA
<213> ORGANISM: Homo sapiens

<400> SEQUENCE: 769
ggugggagga uugcu 15

<210> SEQ ID NO 770
<211> LENGTH: 22
<212> TYPE: RNA
<213> ORGANISM: Homo sapiens

<400> SEQUENCE: 770
auagugggaa gcuggcagau uc 22

<210> SEQ ID NO 771
<211> LENGTH: 19
<212> TYPE: RNA
<213> ORGANISM: Homo sapiens

<400> SEQUENCE: 771
auagugggaa gcuggcaga 19

<210> SEQ ID NO 772
<211> LENGTH: 22
<212> TYPE: RNA
<213> ORGANISM: Homo sapiens

<400> SEQUENCE: 772
uaauuuuaga ucuggucugc uu 22

<210> SEQ ID NO 773

<211> LENGTH: 19
<212> TYPE: RNA
<213> ORGANISM: Homo sapiens

<400> SEQUENCE: 773
aauuuuagau cuggucugc 19

<210> SEQ ID NO 774
<211> LENGTH: 22
<212> TYPE: RNA
<213> ORGANISM: Homo sapiens

<400> SEQUENCE: 774
caggcacggg agcucaggug ag 22

<210> SEQ ID NO 775
<211> LENGTH: 17
<212> TYPE: RNA
<213> ORGANISM: Homo sapiens

<400> SEQUENCE: 775
caggcacggg agcucag 17

<210> SEQ ID NO 776
<211> LENGTH: 20
<212> TYPE: RNA
<213> ORGANISM: Homo sapiens

<400> SEQUENCE: 776
uggcuguugg agggggcagg 20

<210> SEQ ID NO 777
<211> LENGTH: 15
<212> TYPE: RNA
<213> ORGANISM: Homo sapiens

<400> SEQUENCE: 777
ggagggggca ggcuc 15

<210> SEQ ID NO 778
<211> LENGTH: 19
<212> TYPE: RNA
<213> ORGANISM: Homo sapiens

<400> SEQUENCE: 778
gagggcgggu ggaggagga 19

<210> SEQ ID NO 779
<211> LENGTH: 15
<212> TYPE: RNA
<213> ORGANISM: Homo sapiens

<400> SEQUENCE: 779
gcggguggag gagga 15

<210> SEQ ID NO 780
<211> LENGTH: 23
<212> TYPE: RNA
<213> ORGANISM: Homo sapiens

<400> SEQUENCE: 780
agggaguaga agggugggga gca 23

<210> SEQ ID NO 781
<211> LENGTH: 16
<212> TYPE: RNA
<213> ORGANISM: Homo sapiens

<400> SEQUENCE: 781
uagggaguag aagggu 16

<210> SEQ ID NO 782
<211> LENGTH: 16
<212> TYPE: RNA
<213> ORGANISM: Homo sapiens

<400> SEQUENCE: 782
ugggggggaa gaaaag 16

<210> SEQ ID NO 783
<211> LENGTH: 23
<212> TYPE: RNA
<213> ORGANISM: Homo sapiens

<400> SEQUENCE: 783
agggucgggg cagggagggc agg 23

<210> SEQ ID NO 784
<211> LENGTH: 15
<212> TYPE: RNA
<213> ORGANISM: Homo sapiens

<400> SEQUENCE: 784
gggagaaggg ucggg 15

<210> SEQ ID NO 785
<211> LENGTH: 23
<212> TYPE: RNA
<213> ORGANISM: Homo sapiens

<400> SEQUENCE: 785
ggugggugag gucgggcccc aag 23

<210> SEQ ID NO 786
<211> LENGTH: 20
<212> TYPE: RNA
<213> ORGANISM: Homo sapiens

<400> SEQUENCE: 786
cggggugggu gaggucgggc 20

<210> SEQ ID NO 787
<211> LENGTH: 23
<212> TYPE: RNA
<213> ORGANISM: Homo sapiens

<400> SEQUENCE: 787
uggggaaggc gucagugucg ggu 23

<210> SEQ ID NO 788
<211> LENGTH: 16
<212> TYPE: RNA
<213> ORGANISM: Homo sapiens

<400> SEQUENCE: 788
uggggaaggc gucagu 16

<210> SEQ ID NO 789
<211> LENGTH: 23
<212> TYPE: RNA
<213> ORGANISM: Homo sapiens

<400> SEQUENCE: 789
cuaguggaag aagauggcgg aag 23

<210> SEQ ID NO 790
<211> LENGTH: 15
<212> TYPE: RNA
<213> ORGANISM: Homo sapiens

<400> SEQUENCE: 790
uaguggaaga agaug 15

<210> SEQ ID NO 791
<211> LENGTH: 27
<212> TYPE: RNA
<213> ORGANISM: Homo sapiens

<400> SEQUENCE: 791
gaaaagcugg guugagaggg cgaaaaa 27

<210> SEQ ID NO 792
<211> LENGTH: 15
<212> TYPE: RNA
<213> ORGANISM: Homo sapiens

<400> SEQUENCE: 792
cuucucuucc cgguu 15

<210> SEQ ID NO 793
<211> LENGTH: 26
<212> TYPE: RNA
<213> ORGANISM: Homo sapiens

<400> SEQUENCE: 793
cggugggauc ccgcggccgu guuuuc 26

<210> SEQ ID NO 794
<211> LENGTH: 15
<212> TYPE: RNA
<213> ORGANISM: Homo sapiens

<400> SEQUENCE: 794
ggggcgccgc gggac 15

<210> SEQ ID NO 795
<211> LENGTH: 22
<212> TYPE: RNA
<213> ORGANISM: Homo sapiens

<400> SEQUENCE: 795
ggggggcagg aggggcucag gg 22

<210> SEQ ID NO 796
<211> LENGTH: 16
<212> TYPE: RNA
<213> ORGANISM: Homo sapiens

<400> SEQUENCE: 796 guggggggc aggagg 16

<210> SEQ ID NO 797
<211> LENGTH: 20
<212> TYPE: RNA
<213> ORGANISM: Homo sapiens

<400> SEQUENCE: 797
aagacacauu uggagaggga 20

<210> SEQ ID NO 798
<211> LENGTH: 16
<212> TYPE: RNA
<213> ORGANISM: Homo sapiens

<400> SEQUENCE: 798
agacacauuu ggagag 16

<210> SEQ ID NO 799
<211> LENGTH: 23
<212> TYPE: RNA
<213> ORGANISM: Homo sapiens

<400> SEQUENCE: 799
gggggccgau acacuguacg aga 23

<210> SEQ ID NO 800
<211> LENGTH: 20
<212> TYPE: RNA
<213> ORGANISM: Homo sapiens

<400> SEQUENCE: 800
gggggccgau acacuguacg 20

<210> SEQ ID NO 801
<211> LENGTH: 23
<212> TYPE: RNA
<213> ORGANISM: Homo sapiens

<400> SEQUENCE: 801
cacaggugag guucuuggga gcc 23

<210> SEQ ID NO 802
<211> LENGTH: 15
<212> TYPE: RNA
<213> ORGANISM: Homo sapiens

<400> SEQUENCE: 802
acaggugagg uucuu 15

<210> SEQ ID NO 803
<211> LENGTH: 29
<212> TYPE: RNA
<213> ORGANISM: Homo sapiens

<400> SEQUENCE: 803
caacggaauc ccaaaagcag cuguugucu 29

<210> SEQ ID NO 804
<211> LENGTH: 15
<212> TYPE: RNA
<213> ORGANISM: Homo sapiens

<400> SEQUENCE: 804
caacggaauc ccaaa 15

<210> SEQ ID NO 805
<211> LENGTH: 26
<212> TYPE: RNA
<213> ORGANISM: Homo sapiens

<400> SEQUENCE: 805
agggacggga cgcggugcag uguugu 26

<210> SEQ ID NO 806
<211> LENGTH: 15
<212> TYPE: RNA
<213> ORGANISM: Homo sapiens

<400> SEQUENCE: 806
ggcgggcggg aggga 15

<210> SEQ ID NO 807
<211> LENGTH: 23
<212> TYPE: RNA
<213> ORGANISM: Homo sapiens

<400> SEQUENCE: 807
gagggccccc ccucaauccu guu 23

<210> SEQ ID NO 808
<211> LENGTH: 15
<212> TYPE: RNA
<213> ORGANISM: Homo sapiens

<400> SEQUENCE: 808
agggcccccc cucaa 15

<210> SEQ ID NO 809
<211> LENGTH: 21
<212> TYPE: RNA
<213> ORGANISM: Homo sapiens

<400> SEQUENCE: 809
gaauggauuu uuggagcagg a 21

<210> SEQ ID NO 810
<211> LENGTH: 15
<212> TYPE: RNA
<213> ORGANISM: Homo sapiens

<400> SEQUENCE: 810
gaauggauuu uugga 15

<210> SEQ ID NO 811
<211> LENGTH: 25
<212> TYPE: RNA
<213> ORGANISM: Homo sapiens

<400> SEQUENCE: 811 gggugggau uuguugcauu acuug 25

<210> SEQ ID NO 812
<211> LENGTH: 20
<212> TYPE: RNA
<213> ORGANISM: Homo sapiens

<400> SEQUENCE: 812 gggugggau uuguugcauu 20

<210> SEQ ID NO 813
<211> LENGTH: 23
<212> TYPE: RNA
<213> ORGANISM: Homo sapiens

<400> SEQUENCE: 813
cggggccgua gcacugucug aga 23

<210> SEQ ID NO 814
<211> LENGTH: 20
<212> TYPE: RNA
<213> ORGANISM: Homo sapiens

<400> SEQUENCE: 814
cggggccgua gcacugucug 20

<210> SEQ ID NO 815
<211> LENGTH: 20
<212> TYPE: RNA
<213> ORGANISM: Homo sapiens

<400> SEQUENCE: 815
ggauuuuugg aucagggaug 20

<210> SEQ ID NO 816
<211> LENGTH: 15
<212> TYPE: RNA
<213> ORGANISM: Homo sapiens

<400> SEQUENCE: 816
auuuuuggau caggg 15

<210> SEQ ID NO 817
<211> LENGTH: 22
<212> TYPE: RNA
<213> ORGANISM: Homo sapiens

<400> SEQUENCE: 817
ggcagggaca gcaaaggggu gc 22

<210> SEQ ID NO 818
<211> LENGTH: 18
<212> TYPE: RNA
<213> ORGANISM: Homo sapiens

<400> SEQUENCE: 818
gcagggacag caaagggg 18

<210> SEQ ID NO 819
<211> LENGTH: 25
<212> TYPE: RNA
<213> ORGANISM: Homo sapiens

<400> SEQUENCE: 819
ugcggggcua gggcuaacag caguc 25

<210> SEQ ID NO 820
<211> LENGTH: 15
<212> TYPE: RNA
<213> ORGANISM: Homo sapiens

<400> SEQUENCE: 820
ugcggggcua gggcu 15

<210> SEQ ID NO 821
<211> LENGTH: 22
<212> TYPE: RNA
<213> ORGANISM: Homo sapiens

<400> SEQUENCE: 821
auauagggau uggagccgug gc 22

<210> SEQ ID NO 822
<211> LENGTH: 20
<212> TYPE: RNA
<213> ORGANISM: Homo sapiens

<400> SEQUENCE: 822
auauagggau uggagccgug 20

<210> SEQ ID NO 823
<211> LENGTH: 27
<212> TYPE: RNA
<213> ORGANISM: Homo sapiens

<400> SEQUENCE: 823
aaaccguuac cauuacugag uuuagua 27

<210> SEQ ID NO 824
<211> LENGTH: 15
<212> TYPE: RNA
<213> ORGANISM: Homo sapiens

<400> SEQUENCE: 824
gaaaccguua ccauu 15

<210> SEQ ID NO 825
<211> LENGTH: 26
<212> TYPE: RNA
<213> ORGANISM: Homo sapiens

<400> SEQUENCE: 825
gacuauagaa cuuucccccu cauccc 26

<210> SEQ ID NO 826
<211> LENGTH: 15
<212> TYPE: RNA
<213> ORGANISM: Homo sapiens

<400> SEQUENCE: 826
aacuuucccc cucau 15

<210> SEQ ID NO 827
<211> LENGTH: 28
<212> TYPE: RNA
<213> ORGANISM: Homo sapiens

<400> SEQUENCE: 827
guaugguauu gcacuugucc cggccugu 28

<210> SEQ ID NO 828
<211> LENGTH: 15
<212> TYPE: RNA
<213> ORGANISM: Homo sapiens

<400> SEQUENCE: 828
uauugcacuu guccc 15

<210> SEQ ID NO 829
<211> LENGTH: 24
<212> TYPE: RNA
<213> ORGANISM: Homo sapiens

<400> SEQUENCE: 829
agacacauuu ggagagggaa ccuc 24

<210> SEQ ID NO 830
<211> LENGTH: 24
<212> TYPE: RNA
<213> ORGANISM: Homo sapiens

<400> SEQUENCE: 830
agacgggagg aaagaaggga gugg 24

<210> SEQ ID NO 831
<211> LENGTH: 15
<212> TYPE: RNA
<213> ORGANISM: Homo sapiens

<400> SEQUENCE: 831
aagacgggag gaaag 15

<210> SEQ ID NO 832
<211> LENGTH: 26
<212> TYPE: RNA
<213> ORGANISM: Homo sapiens

<400> SEQUENCE: 832
acaacccuag gagagggugc cauuca 26

<210> SEQ ID NO 833
<211> LENGTH: 15
<212> TYPE: RNA
<213> ORGANISM: Homo sapiens

<400> SEQUENCE: 833
acaacccuag gagag 15

<210> SEQ ID NO 834
<211> LENGTH: 24
<212> TYPE: RNA
<213> ORGANISM: Homo sapiens

<400> SEQUENCE: 834
acuggcucag uucagcagga acag 24

<210> SEQ ID NO 835
<211> LENGTH: 15
<212> TYPE: RNA
<213> ORGANISM: Homo sapiens

<400> SEQUENCE: 835
uggcucaguu cagca 15

<210> SEQ ID NO 836
<211> LENGTH: 26
<212> TYPE: RNA

-continued

```
<213> ORGANISM: Homo sapiens

<400> SEQUENCE: 836

aaaaucacau ugccagggau uaccac                                    26


<210> SEQ ID NO 837
<211> LENGTH: 15
<212> TYPE: RNA
<213> ORGANISM: Homo sapiens

<400> SEQUENCE: 837

aaucacauug ccagg                                                15


<210> SEQ ID NO 838
<211> LENGTH: 27
<212> TYPE: RNA
<213> ORGANISM: Homo sapiens

<400> SEQUENCE: 838

aucacauugc cagggauuuc caaccga                                   27


<210> SEQ ID NO 839
<211> LENGTH: 24
<212> TYPE: RNA
<213> ORGANISM: Homo sapiens

<400> SEQUENCE: 839

aauauugcac ucgucccggc cucc                                      24


<210> SEQ ID NO 840
<211> LENGTH: 15
<212> TYPE: RNA
<213> ORGANISM: Homo sapiens

<400> SEQUENCE: 840

uauugcacuc guccc                                                15


<210> SEQ ID NO 841
<211> LENGTH: 25
<212> TYPE: RNA
<213> ORGANISM: Homo sapiens

<400> SEQUENCE: 841

aagcugccag uugaagaacu guugc                                     25


<210> SEQ ID NO 842
<211> LENGTH: 15
<212> TYPE: RNA
<213> ORGANISM: Homo sapiens

<400> SEQUENCE: 842

aagcugccag uugaa                                                15
```